(12) United States Patent
Pfeiffer et al.

(10) Patent No.: US 12,215,174 B2
(45) Date of Patent: Feb. 4, 2025

(54) COMPOSITIONS OF HYDROXYPROPYL-β-CYCLODEXTRIN AND METHODS OF PURIFYING THE SAME

(71) Applicant: Beren Therapeutics P.B.C., West Hollywood, CA (US)

(72) Inventors: Steven Pfeiffer, West Hollywood, CA (US); Dustin McMinn, West Hollywood, CA (US); Gabor Benkovics, Budapest (HU)

(73) Assignee: BEREN THERAPEUTICS P.B.C., West Hollywood, CA (US)

( * ) Notice: Subject to any disclaimer, the term of this patent is extended or adjusted under 35 U.S.C. 154(b) by 0 days.

(21) Appl. No.: 18/633,063

(22) Filed: Apr. 11, 2024

(65) Prior Publication Data

US 2024/0270877 A1 Aug. 15, 2024

Related U.S. Application Data

(63) Continuation of application No. 18/384,643, filed on Oct. 27, 2023, which is a continuation of application No. 18/111,237, filed on Feb. 17, 2023, now Pat. No. 11,958,917.

(60) Provisional application No. 63/311,661, filed on Feb. 18, 2022.

(51) Int. Cl.
*C08B 37/16* (2006.01)

(52) U.S. Cl.
CPC .................... *C08B 37/0012* (2013.01)

(58) Field of Classification Search
CPC .................................................. C08B 37/0012
USPC ............................................................. 536/103
See application file for complete search history.

(56) References Cited

U.S. PATENT DOCUMENTS

| | | | |
|---|---|---|---|
| 4,727,064 A | 2/1988 | Pitha | |
| 4,877,778 A | 10/1989 | Carpenter et al. | |
| 5,262,404 A | 11/1993 | Weisz et al. | |
| 5,376,645 A | 12/1994 | Stella et al. | |
| 5,624,914 A | 4/1997 | Patel et al. | |
| 6,407,079 B1 | 6/2002 | Müller et al. | |
| 6,528,642 B1 | 3/2003 | Duval et al. | |
| 6,878,695 B2 | 4/2005 | Woo et al. | |
| 9,044,451 B2 | 6/2015 | Zheng et al. | |
| 9,675,634 B2 | 6/2017 | Machielse et al. | |
| 11,633,423 B2 | 4/2023 | Machielse et al. | |
| 11,744,848 B2 | 9/2023 | Machielse et al. | |
| 11,958,917 B2 * | 4/2024 | Pfeiffer | C08B 37/0012 |
| 2001/0056080 A1 | 12/2001 | Woo et al. | |
| 2004/0076591 A1 | 4/2004 | Nelson et al. | |
| 2006/0025380 A1 | 2/2006 | Thorsteinsson et al. | |
| 2009/0258001 A1 | 10/2009 | Ponath et al. | |
| 2011/0028432 A1 | 2/2011 | Cataldo et al. | |
| 2015/0065457 A1 | 3/2015 | Fornoni et al. | |
| 2015/0216895 A1 | 8/2015 | McKew et al. | |
| 2016/0361345 A1 | 12/2016 | Machielse et al. | |
| 2021/0253746 A1 | 8/2021 | Buffe et al. | |

FOREIGN PATENT DOCUMENTS

| | | |
|---|---|---|
| CN | 1073359 A | 6/1993 |
| CN | 102040675 A | 5/2011 |
| CN | 109675054 A | 4/2019 |
| JP | 2007504166 A | 3/2007 |
| TW | 491715 B | 6/2002 |
| WO | 2010138802 A2 | 12/2010 |
| WO | 2012012473 A1 | 1/2012 |
| WO | 2014022841 A1 | 2/2014 |
| WO | 2015087016 A1 | 6/2015 |
| WO | 2016201137 A1 | 12/2016 |
| WO | 2020092107 A1 | 5/2020 |
| WO | 2021050890 A1 | 3/2021 |

OTHER PUBLICATIONS

Malanga et al., Published Jun. 14, 2016, Journal of Pharmaceutical Sciences, vol. 105, pp. 2921-2931 (Year: 2016).*
Jiang H., et al., "Development and Validation of Sensitive LC-MS/MS Assays for Quantification of HP-CD in Human Plasma and CSF," Journal of Lipid Research, 2014, vol. 55, No. 7, pp. 1537-1548.
Jiang X., et al., "Development of a Bile Acid-Based Newborn Screen for Niemann-Pick C Disease," Science Translational Medicine, May 4, 2016, vol. 8, No. 337, 26 Pages.
Kali G., et al., "Cyclodextrins and Derivatives in Drug Delivery: New Developments, Relevant Clinical Trials, and Advanced Products," Carbohydrate Polymers, 2024, vol. 324, pp. 1-23.
King K., et al., "Auditory Phenotype of Niemann-Pick Disease, Type C1," Ear and Hearing, 2014, vol. 35, No. 1, 17 pages.
Ko D.C., et al., "Cell-Autonomous Death of Cerebellar Purkinje Neurons with Autophagy in Niemann-Pick Type C Disease," PLoS Genetics, Jul. 2005, vol. 1, No. 1, pp. 81-95.
Kondo Y., et al., "In Vitro Evaluation of 2-Hydroxyalkylated-Cyclodextrins as Potential Therapeutic Agents for Niemann-Pick Type C Disease," Molecular Genetics and Metabolism, 2016, vol. 118, pp. 214-219.
Lachmann R.H., et al., "Treatment with Miglustat Reverses the Lipid-Trafficking Defect in NiemannPick Disease Type C," Neurobiology of Disease, 2004, vol. 16, No. 3, pp. 654-658.
Leigh-Paffenroth E., et al., "Objective Measures of Ototoxicity," Hearing and Hearing Disorders: Research and Diagnostics, Sep. 2005, vol. 9, No. 1, 7 pages.
Liao G., et al., "Allopregnanolone Treatment Delays Cholesterol Accumulation and Reduces Autophagic/Lysosomal Dysfunction and Inflammation in Npc1-/- Mouse Brain," Brain Research, May 13, 2009, vol. 1270, 20 pages.
Lieberman A.P., et al., "Autophagy in Lysosomal Storage Disorders," Autophagy, 2012, vol. 8, No. 5, pp. 719-730.

(Continued)

*Primary Examiner* — Yih-Horng Shiao
*Assistant Examiner* — Jaret J Crews
(74) *Attorney, Agent, or Firm* — POLSINELLI PC

(57) ABSTRACT

The present disclosure relates to compositions comprising mixtures of hydroxypropyl-β-cyclodextrin, wherein the compositions may be isomerically purified. The disclosure also relates to methods of isomerically purifying a mixture of hydroxypropyl-β-cyclodextrins.

28 Claims, 68 Drawing Sheets

(56) References Cited

OTHER PUBLICATIONS

Liu B., et al., "Cyclodextrin Overcomes the Transport Defect in Nearly Every Organ of NPC1 Mice Leading to Excretion of Sequestered Cholesterol as Bile Acid," Journal of Lipid Research, 2010, vol. 51, pp. 933-944.

Liu B., et al., "Genetic Variations and Treatments that Affect the Lifespan of the NPC1 Mouse," Journal of Lipid Research, 2008, vol. 49, pp. 663-669.

Liu B., et al., "Reversal of Defective Lysosomal Transport in NPC Disease Ameliorates Liver Dysfunction and Neurodegeneration in the npc1-/- Mouse," Proceedings of the National Academy of Sciences (PNAS), Feb. 17, 2009, vol. 106, No. 7, pp. 2377-2382.

Liu B., "Therapeutic Potential of Cyclodextrins in the Treatment of NiemannPick Type C Disease," Clinical Lipidology, Jun. 2012, vol. 7, No. 3, pp. 289-301.

Loftsson T., et al., "Pharmaceutical Applications of Cyclodextrins: Basic Science and Product Development" Journal of Pharmacy and Pharmacology, 2010, vol. 62, pp. 1607-1621.

Lopez A. M., et al., "Systemic Administration of 2-Hydroxypropyl-Beta-Cyclodextrin to Symptomatic Npc1-Deficient Mice Slows Cholesterol Sequestration in the Major Organs and Improves Liver Function," Clinical and Experimental Pharmacology and Physiology, 2014, vol. 41, pp. 780-787.

Maarup T.J., et al., "Intrathecal 2-Hydroxypropyl-Beta-Cyclodextrin in a Single Patient with Niemann-Pick C1," Molecular Genetics Metabolism, 2015, vol. 116, 13 pages.

Machine Translation for CN102040675A, 2011, 12 pages.

Maetzel D., et al., "Genetic and Chemical Correction of Cholesterol Accumulation and Impaired Autophagy in Hepatic and Neural Cells Derived From Niemann-Pick Type C Patient-Specific iPS Cells," Stem Cell Reports, Jun. 3, 2014, vol. 2, pp. 866-880.

Mak I.W.Y., et al., "Lost in Translation: Animal Models and Clinical Trials in Cancer Treatment," American Journal of Translational Research, 2014, vol. 6, No. 2, pp. 114-118.

Malanga M., et al., "Back to the Future": A New Look at Hydroxypropyl Beta-Cyclodextrins, Journal of Pharmaceutical Sciences, 2016, vol. 105, No. 9, pp. 2921-2931.

Marcus A.D., "A Mom Brokers Treatment for Her Twins' Fatal Illness," The Wall Street Journal, Apr. 3, 2009, 4 pages, Retrieved from the Internet: URL: https://www.wsj.com/articles/SB123871183055784317.

Marcus A.D., "Small Biotech Gets Rights to Rare Disease Drug," Press Release, Jan. 7, 2015, 3 pages, Retrieved from the Internet: URL: http://www.wsj.com/articles/small-biotech-vtesse-gets-rights-to-rare-disease-drug-1420606861.

Matsuo M., et al., "Effects of Cyclodextrin in Two Patients with Niemann-Pick Type C Disease," Molecular Genetics and Metabolism, 2013, vol. 108, pp. 76-81.

Matsuo M., et al., "Effects of Intracerebroventricular Administration of 2-Hydroxypropyl-B-Cyclodextrin in a Patient with Niemann-Pick Type C Disease," Molecular Genetics and Metabolism Reports, 2014, vol. 1, pp. 391-400.

Maue R.A., et al., "A Novel Mouse Model of Niemann-Pick Type C Disease Carrying a D1005G-Npc1 Mutation Comparable to Commonly Observed Human Mutations," Human Molecular Genetics, 2012, vol. 21, No. 4, pp. 730-750.

Mccook A., "Twin Disorders," The Scientist, Nov. 1, 2008, 7 pages.

Mengel E., et al., "Niemann-Pick Disease Type C Symptomatology: An Expert-Based Clinical Description," Orphanet Journal of Rare Diseases, 2013, vol. 8, No. 166, 11 Pages.

Meske V., et al., "How To Reduce The Accumulation of Autophagic Vacuoles In NPC1-Deficient Neurons: A Comparison of Two Pharmacological Strategies," Neuropharmacology, 2015, vol. 89, pp. 282-289.

Meske V., et al., "The Autophagic Defect in Niemann-Pick Disease Type C Neurons Differs from Somatic Cells and Reduces Neuronal Viability," Neurobiology of Disease, 2014, vol. 64, pp. 88-97.

Millat G., et al., "Niemann-Pick C1 Disease: The 11061T Substitution is a Frequent Mutant Allele in Patients of Western European Descent and Correlates with a Classic Juvenile Phenotype," American Journal of Human Genetics, 1999, vol. 65, pp. 1321-1329.

Mller B.W., et al., "Solubilization of Drugs by Modified-Cyclodextrins," International Journal of Pharmaceutics, 1985, vol. 26, pp. 77-88.

Montecucco F., et al. "Treatment with Kleptose Crysmeb Reduces Mouse Atherogenesis by Impacting on Lipid Profile and Th1 Lymphocyte Response," Vascular Pharmacology, 2015, vol. 72, pp. 197-208.

Munkacsi A.B., et al., "An "Exacerbate-Reverse" Strategy in Yeast Identifies Histone Deacetylase Inhibition as a Correction for Cholesterol and Sphingolipid Transport Defects in Human Niemann-Pick Type C Disease," The Journal of Biological Chemistry, Jul. 8, 2011, vol. 286, No. 27, pp. 23842-23851.

Nah J., et al., "Autophagy in Neurodegenerative Diseases: From Mechanism to Therapeutic Approach," Molecules and Cells, 2015, vol. 38, No. 5, pp. 381-389.

Non Final Office action for U.S. Appl. No. 18/141,832, mailed on Sep. 14, 2023, 12 pages.

Non Final Office Action for U.S. Appl. No. 18/384,643, mailed on Mar. 14, 2024, 12 pages.

Non-Final Office Action for U.S. Appl. No. 18/111,237, mailed on Sep. 28, 2023, 44 pages.

Notice of Acceptance for Australian Application 2018202964 dated Aug. 8, 2019, 3 pages.

Notice of Allowance for U.S. Appl. No. 17/745,487, mailed on Sep. 8, 2022, 8 pages.

Notice of Allowance for U.S. Appl. No. 18/072,260, mailed on Jun. 30, 2023, 22 pages.

Notice of Allowance for U.S. Appl. No. 18/111,237, mailed on Nov. 24, 2023, 9 pages.

Notice of Allowance for U.S. Appl. No. 18/115,897, mailed on May 5, 2023, 10 pages.

Notice of Allowance for U.S. Appl. No. 18/115,898, mailed on Jun. 7, 2023, 49 pages.

Notice of Allowance for U.S. Appl. No. 18/115,901, mailed on Jun. 29, 2023, 55 pages.

Notice of Allowance for U.S. Appl. No. 18/130,132, mailed on Jul. 11, 2023, 09 pages.

Nunes M.J., et al., "Histone Deacetylase Inhibition Decreases Cholesterol Levels in Neuronal Cells by Modulating Key Genes in Cholesterol Synthesis, Uptake And Efflux," PLOS One, Jan. 2013, vol. 8, No. 1, 10 pages.

Office Action for Australian Application 13762617.2, dated Mar. 27, 2019, 4 pages.

Office Action for Australian Application No. 2018202964 dated Apr. 5, 2019, 9 pages.

Office Action for Canadian Application No. 2880880 dated Aug. 23, 2019, 5 pages.

Abi-Mosleh L., et al., "Cyclodextrin Overcomes Deficient Lysosome-To-Endoplasmic Reticulum Transport of Cholesterol in Niemann-Pick Type C Cells," Proceedings of the National Academy of Sciences, Nov. 17, 2009, vol. 106, No. 46, pp. 19316-19321.

Acucena R.W., "Defining a strategy for the Validation and Qualification of Sterile Filtration Processes of Investigational Medicinal Compounds," PDA Metro Chapter Dinner, Mar. 4, 2014, 45 pages.

Alvarez A.R., et al., "Imatinib Therapy Blocks Cerebellar Apoptosis and Improves Neurological Symptoms in A Mouse Model of Niemann-Pick Type C Disease," The FASEB Journal, Oct. 2008, vol. 22, pp. 3617-3627.

Aqul A., et al., "Unesterified Cholesterol Accumulation in Late Endosomes/Lysosomes Causes Neurodegeneration and Is Prevented by Driving Cholesterol Export from This Compartment," The Journal of Neuroscience, Jun. 22, 2011, vol. 31, No. 25, pp. 9404-9413.

Beers M.H., et al., "Hydroxypropyl Beta-Cyclodextrin Compositions and Methods," The Merck Manual of Diagnosis and Therapy, 1992, pp. 1049-1051.

Bhandari T., "Protein Linked to Alzheimer's, Strokes Cleared from Brain Blood Vessels," Washington University School of Medicine,

(56) References Cited

OTHER PUBLICATIONS

Feb. 17, 2021, 6 pages, Retrieved from the Internet: URL: https://medicine.wustl.edu/news/protein-linked-to-alzheimers-strokes-cleared-from-brain-blood-vessels/.

Boldrini R., et al., "Wolman Disease and Cholesteryl Ester Storage Disease Diagnosed by Histological and Ultrastructural Examination of Intestinal and Liver Biopsy," Pathology—Research and Practice, 2004, vol. 200, pp. 231-240.

Brewster M. E., et al., "An Intravenous Toxicity Study of 2-Hydroxypropyl-Cyclodextrin, a Useful Drug Solubilizer, in Rats and Monkeys," International Journal of Pharmaceutics, 1990, vol. 59, pp. 231-243.

Byun K., et al., "Alteration of the Glutamate and GABA Transporters in the Hippocampus of the Niemann-Pick Disease, Type C Mouse Using Proteomic Analysis," Proteomics, 2006, vol. 6, pp. 1230-1236.

Camargo F., et al., "Cyclodextrins in the Treatment of a Mouse Model of Niemann-Pick C Disease," Life Sciences, 2001, vol. 70, No. 2, pp. 131-142.

Cantz M., et al., Disorders of Glycoprotein Degradation, Journal of Inherited Metabolic Disease, 1990, vol. 13 pp. 523-537.

Carstea E.D., et al., "Niemann-Pick C1 Disease Gene: Homology to Mediators of Cholesterol Homeostasis," Science, Jul. 11, 1997, vol. 277, pp. 228-231.

Chen F.W., et al., "Cyclodextrin Induces Calcium-Dependent Lysosomal Exocytosis," PLOS One, Nov. 2010, vol. 5, No. 11, 7 Pages.

Chien Y.H., et al., "Long-Term Efficacy of Miglustat in Paediatric Patients with Niemann-Pick Disease Type C," Journal of Inherited Metabolic Disease, 2013, vol. 36, pp. 129-137.

Choi H.Y., et al., "Impaired ABCA1-Dependent Lipid Efflux and Hypoalphalipoproteinemia in Human Niemann-Pick Type C Disease," Journal of Biological Chemistry, Aug. 29, 2003, vol. 278, No. 35, pp. 32569-32577.

Cluzeau C.V.M., et al., "Microarray Expression Analysis and Identification of Serum Biomarkers for Niemann-Pick Disease, Type C1," Human Molecular Genetics, 2012, vol. 21, No. 16, pp. 3632-3646.

Cologna S.M., et al., "Quantitative Proteomic Analysis of Niemann-Pick Disease, Type C1 Cerebellum Identifies Protein Biomarkers and Provides Pathological Insight," PLOS One, Oct. 2012, vol. 7, No. 10, 13 pages.

Crumling M.A., et al., "Hearing Loss and Hair Cell Death in Mice Given the Cholesterol-Chelating Agent Hydroxypropyl-Cyclodextrin," PLoS One, Dec. 2012, vol. 7, No. 12, 8 pages.

Cruz-Pardos S., et al., "Treatment with Cyclodextrin for Niemann Pick's Disease," Farm Hospital, 2013, vol. 37, No. 3, pp. 263-272.

Davidson C., et al., "Chronic Cyclodextrin Administration Ameliorates Clinical Symptoms and Storage Accumulation in Niemann-Pick Type C1 Mice," Lysosomal Disease Network Annual Meeting, Feb. 18-20, 2009, 1 page.

Davidson C., et al., "Different Cyclodextrins for the Treatment of Niemann-Pick Disease Type C," Molecular Genetics and Metabolism, 2016, vol. 117, 1 page.

Davidson C.D., et al., "Chronic Cyclodextrin Treatment of Murine Niemann-Pick C Disease Ameliorates Neuronal Cholesterol and Glycosphingolipid Storage and Disease Progression," PLoS One, Sep. 2009, vol. 4, No. 9, 15 Pages.

Davidson C.D., et al., "Efficacy and Ototoxicity of Different Cyclodextrins in Niemann-Pick C Disease," Annals of Clinical and Translational Neurology, 2016, vol. 3, No. 5, pp. 366-380.

De Windt A., et al., "Gene Set Enrichment Analyses Revealed Several Affected Pathways in Niemann-Pick Disease Type C Fibroblasts," DNA and Cell Biology, 2007, vol. 26, No. 9, pp. 665-671.

Decroocq C., et al., "Cyclodextrin-Based Iminosugar Click Clusters: The First Examples of Multivalent Pharmacological Chaperones for the Treatment of Lysosomal Storage Disorders," ChemBioChem, 2012, vol. 13, No. 5, pp. 661-664.

Dekaban A.S., et al., "Changes in Brain Weights during the Span of Human Life: Relation of Brain Weights to Body Heights and Body Weights," Annals of Neurology, 1978, vol. 4, pp. 345-356.

Elrick M.J., et al., "Autophagic Dysfunction in a Lysosomal Storage Disorder Due To Impaired Proteolysis," Autophagy, Feb. 2013, vol. 9, No. 2, 2 pages.

European Medicines Agency, "Background Review for Cyclodextrins Used as Excipients," Committee for Human Medicinal Products (CHMP), Nov. 20, 2014, 17 pages, Retrieved from the Internet: URL: http://www.ema.europa.eu/docs/en_GB/document_library/Report/2014/12/WC500177936.pdf.

European Medicines Agency, "Background Review for the Excipient Propylene Glycol," Committee for Human Medicinal Products (CHMP), Nov. 20, 2014, 96 pages.

Fenyvesi F., et al., "Fluorescently Labeled Methyl-Beta-Cyclodextrin Enters Intestinal Epithelial Caco-2 Cells By Fluid-Phase Endocytosis," PLoS One, Jan. 2014, vol. 9, No. 1, 11 pages.

First Examination Report for Australian Application No. 2013296170, mailed on May 5, 2017, 4 pages.

Fromming K.H., et al., "Pharmacokinetics and Toxicology of Cyclodextrins," Cyclodextrins in Pharmacy, Chapter 3, 1994, pp. 33-44.

Garcia-Robels A.A., et al., "Use of 2 Hydroxypropyl-Beta-Cyclodextrin Therapy in Two Adult Niemann Pick Type C Patients," Journal of the Neurological Sciences, 2016, vol. 366, pp. 65-67.

Gelsthorpe M.E., et al., "Niemann-Pick Type C1 11061T Mutant Encodes A Functional Protein That Is Selected For Endoplasmic Reticulum-Associated Degradation Due To Protein Misfolding," The Journal of Biological Chemistry, Mar. 28, 2008, vol. 283, No. 13, pp. 8229-8236.

Ginocchio V.M., et al., "Efficacy of Miglustat in NiemannPick C Disease: A Single Centre Experience," Molecular Genetics and Metabolism, 2013, vol. 110, No. 3, pp. 329-335.

Gould S., et al., "2-Hydroxypropyl-Cyclodextrin (HP-CD): A Toxicology Review," Food and Chemical Toxicology, 2005, vol. 43, pp. 1451-1459.

Hackam D.G., et al., "Translation of Research Evidence From Animals to Humans," Journal of the American Medical Association (JAMA), Oct. 11, 2006, vol. 296, No. 14, pp. 1731-1732.

Hempel C., "Dear British Media—Feel Free to Call or Email!," Mar. 26, 2009, 2 pages, Retrieved from the Internet: URL: http://addiandcassi.com/dear-british-media/.

Hempel C., "Dr. Caroline Hastings Submission Letter to FDA: Investigational New Drug Application," May 2009, 23 pages, Retrieved from the Internet: URL: http://addiandcassi.com/wordpress/wp-content/uploads/2009/09/FDA-Caroline-Hastings-Submission-Letter-May 2009.pdf, on Sep. 16, 2016.

Heron B., et al., "Miglustat Therapy in the French Cohort of Paediatric Patients with Niemann-Pick Disease Type C," Orphanet Journal of Rare Diseases, 2012, vol. 7, No. 36, 14 Pages.

Herrmann H.C., et al., "Inhibition of Smooth Muscle Cell Proliferation and Experimental Angioplasty Restenosis by Beta-Cyclodextrin Tetradecasulfate," Arteriosclerosis and Thrombosis, Jun. 1993, vol. 13, No. 6, pp. 924-931.

Hospira, "0.9% Sodium Chloride Injection," USP, May 2014, 13 pages.

"Hydroxypropyl Beta Cyclodextrin for Niemann-Pick Type C1 Disease," Dec. 10, 2012, retrieved from the Internet: URL: http://clinicaltrials.gov/archive/NCTO1747135/2012_12_10, 6 pages.

International Preliminary Report on Patentability for Application No. PCT/US2013/053527, mailed on Feb. 3, 2015, 10 Pages.

International Preliminary Report on Patentability for International Application No. PCT/US2016/036753, mailed Dec. 21, 2017, 09 Pages.

International Search Report and Written Opinion for Application No. PCT/US2013/053527, mailed on Oct. 16, 2013, 14 Pages.

International Search Report and Written Opinion for International Application No. PCT/US2016/036753, mailed Aug. 30, 2016, 11 Pages.

International Search Report and Written Opinion in PCT/IB2023/051462 mailed on May 4, 2023, 10 pages.

Irie T., et al., "Hydroxypropylcyclodextrins in Parenteral Use. II: Effects on Transport and Disposition of Lipids in Rabbit and Humans," Journal of Pharmaceutical Sciences, Jun. 1992, vol. 81, No. 6, pp. 524-528.

(56) References Cited

OTHER PUBLICATIONS

Irie T., et al., "Pharmaceutical Applications of Cyclodextrins. III. Toxicological Issues and Safety Evaluation," Journal of Pharmaceutical Sciences, Feb. 1997, vol. 86, No. 2, pp. 147-162.
Yanjanin N.M., et al., "Linear Clinical Progression, Independent of Age of Onset, in NiemannPick Disease, Type C," American Journal of Medical Genetics Part B: Neuropsychiatric Genetics, Jan. 5, 2010, vol. 153B, No. 1, 17 pages.
Yergey A.L., et al., "Characterization of Hydroxypropyl-Beta-Cyclodextrins by ESI Ion Mobility Mass Spectrometry," Michael, Marcia, and Christa Parseghian Scientific Conference for Niemann-Pick Type C Research, 2016, 1 page.
Yergey A.L., et al., "Characterization of Hydroxypropyl-Beta-Cyclodextrins Used in the Treatment of Niemann-Pick Disease Type C1," PLOS One, Apr. 17, 2017, vol. 12, No. 4, pp. 1-13.
Yu D., et al., "NiemannPick Disease Type C: Induced Pluripotent Stem CellDerived Neuronal Cells for Modeling Neural Disease and Evaluating Drug Efficacy," Journal of Biomolecular Screening, 2014, vol. 19, No. 8, pp. 1164-1173.
Yuan C., et al., "Characterization of Hydroxypropyl-Cyclodextrins with Different Substitution Patterns via FTIR, GCMS, and TGDTA," Carbohydrate Polymers, 2015, vol. 118, pp. 36-40.
Zervas M., et al., "Critical Role for Glycosphingolipids in Niemann-Pick Disease Type C," Current Biology, 2001, vol. 11, No. 16, pp. 1283-1287.
Zimmer S., et al., "Cyclodextrin Promotes Atherosclerosis Regression via Macrophage Reprogramming," Science Translational Medicine, 2016, vol. 8, No. 333, pp. 1-31.
Office Action for Chinese Application No. 201380052023.0, mailed on Jul. 28, 2016, 14 Pages.
Office action for Chinese Application No. 201680041193.2, mailed on Jul. 11, 2019, 12 pages.
Office Action for Chinese Application No. 201711057517.4 dated Jul. 1, 2020, 9 pages.
Office action for Eurasian Application No. 201792487/28, mailed on Nov. 29, 2018, 2 pages.
Office action for European Application No. 16808313.7, mailed on Feb. 8, 2019, 4 pages.
Office action for European Application No. 16808313.7, mailed on May 29, 2018, 10 pages.
Office action for Israell Application No. 255991, mailed on Jun. 3, 2019, 6 pages.
Office Action for Japanese Application No. 2018-116666 dated Jun. 10, 2019, 5 pages.
Office Action for Japanese Application No. 2018-116666 dated Oct. 23, 2019, 2 pages.
Office action for Singapore Application No. 11201710032U, mailed on Dec. 13, 2018, 10 pages.
Office Action for U.S. Appl. No. 14/419,471, mailed on Apr. 19, 2016, 18 Pages.
Office Action for U.S. Appl. No. 14/419,471, mailed on Dec. 12, 2016, 16 Pages.
Office action for U.S. Appl. No. 16/134,028, mailed on Nov. 16, 2018, 10 pages.
Office action for U.S. Appl. No. 16/372,899, mailed on Nov. 21, 2019, 6 pages.
Office action for U.S. Appl. No. 16/430,664, mailed on Feb. 18, 2020, 9 pages.
Office Action for U.S. Appl. No. 17/985,762, mailed on Mar. 13, 2023, 14 pages.
Office Action for U.S. Appl. No. 18/072,260, mailed on Apr. 18, 2023, 26 pages.
Office Action for Venezuela Application No. 2016000260, mailed on Dec. 1, 2022, 4 pages.
Ordonez M.P., et al., "Disruption and Therapeutic Rescue of Autophagy in a Human Neuronal Model of Niemann Pick Type C1," Human Molecular Genetics, 2012, vol. 21, No. 12, pp. 2651-2662.
Ottinger E.A., et al., "Collaborative Development of 2-Hydroxypropyl-Cyclodextrin for the Treatment of Niemann-Pick Type C1 Disease," Current Topics in Medicinal Chemistry, 2014, vol. 14, No. 3, 20 pages.
Pacheco C.D., et al., "Autophagy in NiemannPick C Disease is Dependent Upon Beclin-1 and Responsive to Lipid Trafficking Defects," Human Molecular Genetics, 2007, vol. 16, No. 12, pp. 1495-1503.
Papandreou A., et al., "Diagnostic Workup and Management of C Patients with Suspected Niemann-Pick Type C Disease," Therapeutic Advances in Neurological Disorders, 2016, vol. 9, No. 3, pp. 216-229.
Patterson M., "Niemann-Pick Disease Type C," GeneReviews [Online], 2000, 24 pages, Retrieved from the Internet: URL: https://www.ncbi.nlm.nih.gov/books/NBK1296/.
Patterson M.C., et al., "Long-Term Miglustat Therapy in Children With Niemann-Pick Disease Type C," Journal of Child Neurology, Mar. 2010, vol. 25, No. 3, pp. 300-305.
Patterson M.C., et al., "Recommendations for the Diagnosis and Management of Niemann-Pick Disease Type C: An Update," Molecular Genetics and Metabolism, 2012, vol. 106, No. 3, 15 pages.
Patterson M.C., "Miglustat for Treatment of Niemann-Pick C Disease: A Randomised Controlled Study," The Lancet Neurology, 2007, vol. 6, 8 pages.
Peake K.B., et al., "Defective Cholesterol Trafficking in Niemann-Pick C-Deficient Cells," FEBS Letters, vol. 584, No. 13, Jul. 2, 2010, pp. 2731-2739.
Peake K.B., et al., "Normalization of Cholesterol Homeostasis by 2-Hydroxypropyl-cyclodextrin in Neurons and Glia from Niemann-Pick C1 (NPC1)-deficient Mice," The Journal of Biological Chemistry, Mar. 16, 2012, vol. 287, No. 12, pp. 9290-9298.
Perlman R.L., "Mouse Models of Human Disease: An Evolutionary Perspective," Evolution, Medicine, and Public Health, 2016, vol. 2016, No. 01, pp. 170-176.
Pillai B.K., et al., "Fast Diffusion of Very Long Chain Saturated Fatty Acids across a Bilayer Membrane and Their Rapid Extraction by Cyclodextrins: Implications for Adrenoleukodystrophy," The Journal of Biological Chemistry, Nov. 27, 2009, vol. 284, No. 48, pp. 33296-33304.
Pipalia N.H., et al., "Histone Deacetylase Inhibitor Treatment Dramatically Reduces Cholesterol Accumulation in Niemann-Pick Type C1 Mutant Human Fibroblasts," Proceedings of the National Academy of Sciences (PNAS), Apr. 5, 2011, vol. 108, No. 14, pp. 5620-5625.
Pitha J., et al., "Distribution of Substituents in Hydroxypropyl Ethers of Cyclomaltoheptaose," Carbohydrate Research, 1990, vol. 200, pp. 429-435.
Pitha J., et al., "Drug Solubilizers to Aid Pharmacologists: Amorphous Cylodextrin Derivatives," Life Sciences, 1988, vol. 43, No. 6, pp. 493-502.
Pitha J., et al., "Hydroxypropyl-Cyclodextrin: Preparation and Characterization; Effects on Solubility of Drugs," International Journal of Pharmaceutics, 1986, vol. 29, No. 1, pp. 73-82.
Pontikis C.C., et al., "Cyclodextrin Alleviates Neuronal Storage of Cholesterol in Niemann-Pick C Disease Without Evidence of Detectable Blood-Brain Barrier Permeability," Journal of Inherited Metabolic Disease, May 2013, vol. 36, No. 3, 14 pages.
Porter F.D., et al., "Phase 1/2 Evaluation of Intrathecal 2-Hydroxypropyl-Cyclodextrin for the Treatment of Niemann-Pick Disease Type C1," Molecular Genetics and Metabolism, 2016, vol. 117, 1 page.
Puskas I., et al, "Aggregation Behavior of Cyclodextrin and Cholesterol in Simulated Human Cerebrospinal Fluid," Bioactive Carbohydrates and Dietary Fibre, 2013, vol. 2, No. 2, pp. 157-163.
Ramirez C.M., et al., "Quantitative Role of LAL, NPC2, and NPC1 in Lysosomal Cholesterol Processing Defined by Genetic and Pharmacological Manipulations," Journal of Lipid Research, 2011, vol. 52, No. 4, pp. 688-698.
Ramirez C.M., et al., "Weekly Cyclodextrin Administration Normalizes Cholesterol Metabolism in Nearly Every Organ of the Niemann-Pick Type C1 Mouse and Markedly Prolongs Life," Pediatric Research, 2010, vol. 68, No. 4, pp. 309-315.
Rao C.T., et al., "Distribution of Substituents in O-(2-hydroxypropyl) Derivatives of Cyclomalto-oligosaccharides

(56) References Cited

OTHER PUBLICATIONS

Cyclodextrins): Influence of Increasing Substitution, of the Base Used in the Preparation, and of Macrocyclic Size," Carbohydrate Research, 1992, vol. 223, pp. 99-107.

Rao C.T., et al., "Substitution in Beta-Cyclodextrin Directed by Basicity: Preparation of 2-O-and 6-O-[(R)-and (S)-2-hydroxypropyl] Derivatives," The Journal of Organic Chemistry, 1991, vol. 56, No. 1, pp. 1327-1329.

Rao T.C., et al., "Pharmaceutical Usefulness of Hydroxypropylcyclodextrins: "E Pluribus Unum" Is an Essential Feature," Pharmaceutical Research, 1990, vol. 7, No. 6, 4 pages.

Rauniyar N., et al., "Quantitative Proteomics of Human Fibroblasts with 11061T Mutation in NiemannPick C1 (NPC1) Protein Provides Insights into the Disease Pathogenesis," Molecular Cellular Proteomics, 2015, vol. 14, No. 7, pp. 1734-1749.

Reagan J.W., et al., "Posttranslational Regulation of Acid Sphingomyelinase in Niemann-Pick Type C1 Fibroblasts and Free Cholesterol-enriched Chinese Hamster Ovary Cells," The Journal of Biological Chemistry, Dec. 1, 2000, vol. 275, No. 48, pp. 38104-38110.

Reddy J.V., et al., "Clues to Neuro-Degeneration in Niemann-Pick Type C Disease from Global Gene Expression Profiling," PLoS One, Dec. 2006, vol. 1, No. 1, 7 pages.

Rodal S.K., et al., "Extraction of Cholesterol with Methyl-Cyclodextrin Perturbs Formation of Clathrin-Coated Endocytic Vesicles," Molecular Biology of the Cell, Apr. 1999, vol. 10, pp. 961-974.

Rosenbaum A.I., et al., "Endocytosis of Beta-Cyclodextrins is Responsible for Cholesterol Reduction in Niemann-Pick Type C Mutant Cells," Proceedings of the National Academy of Sciences, Mar. 23, 2010, vol. 107, No. 12, pp. 5477-5482.

Rosenbaum A.I., et al., "Niemann-Pick Type C Disease: Molecular Mechanisms and Potential Therapeutic Approaches," Journal of Neurochemistry, 2011, vol. 116, No. 5, pp. 789-795.

Rosseels M.L.A., et al., "Hydroxypropyl-Cyclodextrin Impacts Renal and Systemic Hemodynamics in the Anesthetized Dog," Regulatory Toxicology and Pharmacology, 2013, vol. 67, No. 3, pp. 1-9.

Sarkar S., et al., "Impaired Autophagy in the Lipid-Storage Disorder Niemann-Pick Type C1 Disease," Cell Reports, Dec. 12, 2013, vol. 5, pp. 1302-1315.

Sarkar S., et al., "Restarting Stalled Autophagy a Potential Therapeutic Approach for the Lipid Storage Disorder, Niemann-Pick Type C1 Disease," Autophagy, Jun. 2014, vol. 10, No. 6, pp. 1137-1140.

Schonbeck C., et al., "Hydroxypropyl-Substituted Beta-Cydodextrins: Influence Of Degree of Substitution on the Thermodynamics of Complexation with Tauroconjugated and Glycoconjugated Bile Salts," Langmuir, 2010, vol. 26, No. 23, pp. 17949-17957.

Schultz M.L., et al., "Clarifying Lysosomal Storage Diseases," Trends in Neurosciences, Aug. 2011, vol. 34, No. 8, 20 pages.

Soga M., et al., HPGCD Outperforms HPBCD as a Potential Treatment for Niemann-Pick Disease Type C During Disease Modeling with iPS Cells, Stem Cells, 2015, vol. 33, pp. 1075-1088.

Song W., et al., "2-Hydroxypropyl-Cyclodextrin Promotes Transcription Factor EB-Mediated Activation of Autophagy," The Journal of Biological Chemistry, Apr. 4, 2014, vol. 289, No. 14, pp. 10211-10222.

Stella V., et al., "Cyclodextrins," Toxicologic Pathology, 2008, vol. 36, pp. 30-42.

Stern W.C., et al., "Cyclodextrin-Based Drug Delivery," Drug News and Perspectives, Oct. 1989, vol. 2, No. 7, pp. 410-415.

Study NCT01747135, Clinical Trials, Comparison of Dec. 8, 2012 version and Apr. 2, 2014 version, retrieved from the internet: URL: https://clinicaltrials.gov/ct2/history/NCT01747135?A=1B=19C-Side-by-Side, 18 pages.

Sun D., et al., "Effect of the Platelet-Activating Factor Antagonist BN 50739 and Its Diluents on Mitochondrial Respiration and Membrane Lipids During and Following Cerebral Ischemia," Journal of Neurochemistry, 1994, vol. 62, No. 5, pp. 1929-1938.

Swaroop M., et al., "Evaluation of Cholesterol Reduction Activity of Methyl-cyclodextrin Using Differentiated Human Neurons and Astrocytes," Journal of Biomolecular Screening, 2012, vol. 17, No. 9, pp. 1243-1251.

Szejtli J_, "Medicinal Applications of Cyclodextrins," Medicinal Research Reviews, 1994, vol. 14, No. 3, pp. 353-386.

Tamura A., et al., "-Cyclodextrin-Threaded Biocleavable Polyrotaxanes Ameliorate Impaired Autophagic Flux in Niemann-Pick Type C Disease," The Journal of Biological Chemistry, Apr. 10, 2015, vol. 290, No. 15, pp. 9442-9454.

Tanaka Y., et al., "Efficacy of 2-Hydroxypropyl-p-cyclodextrin in Niemann-Pick Disease Type C Model Mice and Its Pharmacokinetic Analysis in a Patient with the Disease," Biological and Pharmaceutical Bulletin, 2015, vol. 38, No. 6, pp. 844-851.

Thackaberry E.A., et al., "Comprehensive Investigation of Hydroxypropyl Methylcellulose, Propylene Glycol, Polysorbate 80, and Hydroxypropyl-Beta-Cyclodextrin for use in General Toxicology Studies," Toxicological Sciences, 2010, vol. 117, No. 2, pp. 485-492.

Thein P., et al., "In Vitro Assessment of Antiretroviral Drugs Demonstrates Potential for Ototoxicity," Hearing Research, Apr. 2014, vol. 310, 19 pages.

Tortelli B., et al., "Cholesterol Homeostatic Responses Provide Biomarkers for Monitoring Treatment for the Neurodegenerative Disease NiemannPick C1 (NPC1)," Human Molecular Genetics, 2014, vol. 23, No. 22, pp. 6022-6033.

Vance J.E., et al., "Function of the NiemannPick type C proteins and their bypass by cyclodextrin," Current Opinion in Lipidology, 2011, vol. 22, pp. 204-209.

Vance J.E., et al., "Niemann-Pick C Disease and Mobilization of Lysosomal Cholesterol by Cyclodextrin," Journal of Lipid Research, 2014, vol. 55, pp. 1609-1621.

Vanier M.T., et al., "NiemannPick disease type C," Clinical Genetics, 2003, vol. 64, pp. 269-281.

Vanier M.T., "Niemann-Pick Disease Type C," Orphanet Journal of Rare Diseases, 2010, vol. 5, No. 16, 18 pages.

Vazquez M.C., et al., "Alteration of Gene Expression Profile in Niemann-Pick Type C Mice Correlates with Tissue Damage and Oxidative Stress," PLoS One, Dec. 2011, vol. 6, No. 12, 9 pages.

Vite C.H., et al., "Clinical, Electrophysiological, and Serum Biochemical Measures of Progressive Neurological and Hepatic Dysfunction in Feline Niemann-Pick Type C Disease," Pediatric Research, 2008, vol. 64, No. 5, pp. 544-549.

Vite C.H., et al., "Intracisternal Cyclodextrin Prevents Cerebellar Dysfunction and Purkinje Cell Death in Feline Niemann-Pick Type C1 Disease," Science Translational Medicine, Feb. 25, 2015, vol. 7, No. 276, 35 pages.

Vite C.H., et al., "Intrathecal Cyclodextrin Therapy of Feline Niemann-pick Type C Disease," Molecular Genetics and Metabolism, 2011, vol. 102, 4 pages.

Vtesse Inc., "Leading Life Science Syndicate Commits $25 Million to Series A Funding to Launch Vtesse, Inc., the First Rare Disease Company Spun Out of Cydan Development, Inc.," Press Release, Jan. 7, 2015, 5 pages.

Vtesse Inc., "NIH Teams with Industry to Develop Treatments for Niemann-pick Type C Disease.," Press Release, Jan. 7, 2015, 4 pages, Retrieved from the Internet: URL: https://www.nih.gov/news-events/news-releases/nih-teams-industry-develop-treatments-niemann-pick-type-c-disease.

Vtesse Inc., "Vtesse Advances Phase 2b/3 Clinical Trial of VTS-270 in Niemann-Pick Type C1 Disease with Dose Selection for Evaluation in Second and Final Portion of Trial and Expansion into Europe," Press Release, May 23, 2016, 3 pages.

Vtesse Inc., "Vtesse, Inc. Announces FDA's Granting of Breakthrough Therapy Designation for VTS-270 in Niemann-Pick Type C1 Disease," Press Release, Jan. 6, 2016, 4 pages.

Vtesse Inc., "Vtesse, Inc. Announces Phase 1/2 Clinical Data Showing Slowing of Disease Progression from VTS-270 Treatment for Niemann-Pick Type C1 Disease," Press Release, Mar. 4, 2016, 3 pages.

Vtesse Inc., "Vtesse, Inc. Announces Preliminary Data from Ongoing Phase 1 Study of VTS-270 for Treatment of Niemann-Pick Disease Type C," Press Release, Aug. 6, 2015, 4 pages.

(56) References Cited

OTHER PUBLICATIONS

Vtesse Inc., "Vtesse, Inc. Expands Scientific Advisory Board and Appoints New VP of Clinical Operations to Support Late-Stage Clinical Study of Lead Drug Candidate VTS-270," Press Release, Oct. 22, 2015, 4 pages.

Vtesse Inc., "Vtesse, Inc. Expands Scientific Advisory Board, Fills Key Patient Advocacy Position to Prepare for Further Clinical Development of VTS-270 in Niemann-Pick Disease Type C (NPC)," Press Release, Jun. 15, 2015, 4 pages.

Vtesse Inc., "Vtesse, Inc. Forms Scientific Advisory Board," Press Release, Mar. 25, 2015, 3 pages.

Vtesse Inc., "Vtesse, Inc. Initiates Phase 2b/3 Clinical Trial of VTS-270 for Treatment of Niemann-Pick Type C1 (Npc) Disease," Press Release, Sep. 28, 2015, 4 pages.

Vtesse Inc., "Vtesse Secures Additional $17 Million in Series A Extension to Support Further Product Development and Expand the Ongoing Clinical Trial of VTS-270 for the Treatment of Niemann-Pick Type C1 Disease," Press Release, Jul. 25, 2016, 4 pages.

Walenbergh S.M.A, et al., "Weekly Treatment of 2-Hydroxypropyl-cyclodextrin Improves Intracellular Cholesterol Levels in LDL Receptor Knockout Mice," International Journal of Molecular Sciences, 2015, vol. 16, No. 9, pp. 21056-21069.

Walkley S., et al., "141. Cyclodextrin Treatment Not Only Delays but also Reduces Established Intraneuronal Storage in Niemann-Pick Type C Disease," Molecular Genetics and Metabolism, 2010, vol. 99, No. 2, 1 page.

Walkley S.U., "Cellular Pathology of Lysosomal Storage Disorders," Brain Pathology, 1998, vol. 8, pp. 175-193.

Walkley S.U., et al., "Consequences of NPC1 and NPC2 Loss of Function in Mammalian Neurons," Biochimica et Biophysica Acta (BBA)—Molecular and Cell Biology of Lipids, 2004, vol. 1685, No. 1-3, pp. 48-62.

Walkley S.U., et al., "Gangliosides as Modulators of Dendritogenesis in Normal and Storage Disease-affected Pyramidal Neurons," Cerebral Cortex, Oct. 2000, vol. 10, No. 10, pp. 1028-1037.

Walkley S.U., et al., "Lysosomal Compromise and Brain Dysfunction: Examining the Role of Neuroaxonal Dystrophy," Biochemical Society Transactions, Dec. 2010, vol. 38, No. 6, 13 pages.

Walpole S.C., et al., "The Weight of Nations: An Estimation of Adult Human Biomass," BMC Public Health, 2012, vol. 12, No. 439, 6 pages.

Wang M.L., et al., "Identification of Surface Residues on Niemann-Pick C2 Essential for Hydrophobic Handoff of Cholesterol to NPC1 in Lysosomes," Cell Metabolism, Aug. 4, 2010, vol. 12, No. 2, pp. 166-173.

Ward S., et al., "2-hydroxypropyl-beta-Cyclodextrin Raises Hearing Threshold in Normal Cats and in Cats with Niemann-pick Type C Disease," Pediatric Research, 2010, vol. 68, No. 1, pp. 52-56.

Wehrmann Z.T., et al., "Quantitative Comparison of the Efficacy of Various Compounds in Lowering Intracellular Cholesterol Levels in Niemann-Pick Type C Fibroblasts," PLoS One, Oct. 2012, vol. 7, No. 10, 9 pages.

Wistrand L.G., et al., "A Method for Removal of Endotoxin from Pharmaceutical Formulation," BioPharm Interntional, Nov. 1, 2012, vol. 25, No. 9, 26 pages.

Wraith J.E., et al., "Miglustat in Adult and Juvenile Patients with NiemannPick Disease Type C: Long-term Data from a Clinical Trial," Molecular Genetics and Metabolism, 2009, 7 pages.

Xu M., et al., "A Phenotypic Compound Screening Assay for Lysosomal Storage Diseases," Journal of Biomolecular Screening, 2014, vol. 19, No. 1, pp. 168-175.

Xu M., et al., "-Tocopherol Reduces Lipid Accumulation in Niemann-Pick Type C1 and Wolman Cholesterol Storage Disorders," The Journal of Biological Chemistry, Nov. 16, 2012, vol. 287, No. 47, pp. 39349-39360.

Coisne C., et al., "Cyclodextrins as Emerging Therapeutic Tools in the Treatment of Cholesterol-Associated Vascular and Neurodegenerative Diseases," Molecules, Dec. 20, 2016, vol. 21, No. 12, pp. 1-22, XP055548026, DOI: 10.3390/molecules21121748.

Ozkok A., "Cholesterol-Embolization Syndrome: Current Perspectives," Vascular Health and Risk Management [Online], Jul. 2019, vol. 15, pp. 209-220, XP093169720, DOI: 10.2147/VHRM.S175150, Retrieved from the Internet: URL: https://www.dovepress.com/getfile.php?fileID=51025.

Mendelsohn A.R., et al., "Preclinical Reversal of Atherosclerosis by FDA-Approved Compound that Transforms Cholesterol into an Anti-Inflammatory "Prodrug"," Rejuvenation Research, Jun. 20, 2016 [Published Online], vol. 19, No. 3, pp. 1-9.

Pharmacopeia Online, "Hydroxypropyl Betadex," USP32-NF27 p. 1250, Pharmacopeial Forum: vol. No. 32(5) p. 1481, 4 pages, date retrieved from the internet—Oct. 19, 2023. [Retrieved from the Internet URL: http://www.uspbpep.com/usp32/pub/data/v32270/usp32nf27s0_m39130.html].

International Preliminary Report on Patentability for Application No. PCT/IB2023/051462, mailed on Aug. 29, 2024, 5 pages.

Non-Final Office Action for U.S. Appl. No. 18/633,087 dated Jul. 15, 2024, 23 pages.

Notice of Allowance for U.S. Appl. No. 18/384,643 dated Aug. 14, 2024, 12 pages.

\* cited by examiner

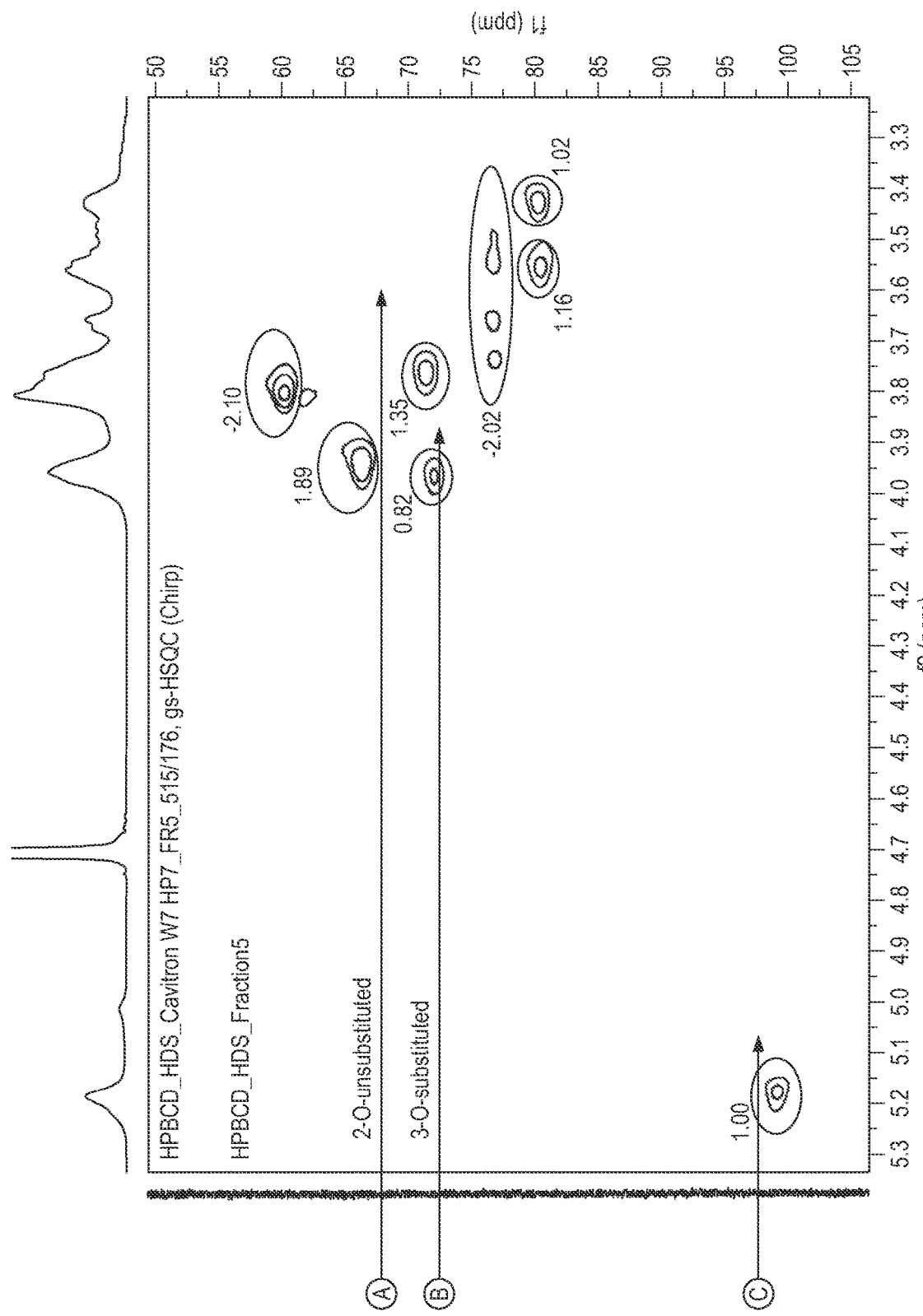
FIG. 38 (contd.)

COMPOSITIONS OF HYDROXYPROPYL-β-CYCLODEXTRIN AND METHODS OF PURIFYING THE SAME

CROSS-REFERENCE TO RELATED APPLICATIONS

This application is a continuation of U.S. application Ser. No. 18/384,643 titled "COMPOSITIONS OF HYDROXYPROPYL-BETA-CYCLODEXTRIN AND METHODS OF PURIFYING THE SAME", filed Oct. 27, 2023, which is a continuation of U.S. application Ser. No. 18/111,237 titled "COMPOSITIONS OF HYDROXYPROPYL-BETA-CYCLODEXTRIN AND METHODS OF PURIFYING THE SAME", filed Feb. 17, 2023, which claims priority to U.S. Provisional Application No. 63/311,661 titled "COMPOSITIONS OF HYDROXYPROPYL-BETA-CYCLODEXTRIN AND METHODS OF PURIFYING THE SAME", filed Feb. 18, 2022, the entire content of which is incorporated by reference herein.

FIELD OF THE DISCLOSURE

The present disclosure relates to mixtures of beta-cyclodextrin molecules. The present disclosure also relates to compositions comprising mixtures of beta-cyclodextrin molecules. Accordingly, the disclosure is related to the fields of chemistry and pharmacy.

BACKGROUND

Hydroxypropyl-B-cyclodextrin ("HPBCD") is a common organic molecule having various industrial applications. Such applications include pharmaceutical excipients, polymers, solubilizing agents, chelating agents, drug delivery vehicles and various other uses. HPBCD is manufactured commercially on a large scale. HPBCD is usually manufactured by subjecting B-cyclodextrin to propylene oxide in the presence of a base in order to alkylate the cyclodextrin ring with hydroxypropyl groups. The alkylation, (or addition of hydroxypropyl groups) can potentially occur at any available site where there is an alcohol on the cyclodextrin ring. On an industrial scale, this alkylation process is largely uncontrolled and the resulting HPBCD product is usually a gross mixture of HPBCD molecules that range from a single hydroxyl substituent to an exhaustively alkylated molecule with all 21 possible alkylation sites occupied by a hydroxypropyl group, and every possible substitution combination in between. Moreover, subsequent alkylation can occur at any or all of the 21 available hydroxy sites on the cyclodextrin structure, leading to an extremely large set of possible substitution patterns. In fact, it has been determined that there are 117,655 possible isomeric configurations that can result on the primary face of the cyclodextrin ring structure alone. See, i.e., Liu, Jiang & Wang, Bo & Przybylski, Cédric & Bistri, Olivia & Ménand, Mickaël & Zhang, Yongmin & Sollogoub, Matthieu. (2021). Programmed Synthesis of Hepta-Differentiated β-Cyclodextrin: 1 out of 117655 Arrangements. Angewandte Chemie (International ed. in English). 60. 10.1002/anie.202102182. Even more striking, the number of possible substitution patterns taking into account the full 21 positions is exponentially larger.

In most applications for HPBCD, the commercially available gross mixture is acceptable for its intended purpose, and there is generally no technical or economic reason to expend resources to isolate or isomerically purify the mixture into more concise groups or individual compounds. However, there are certain applications of HPBCD that do require a more refined mixture or even single isomers. For example, there may be a need to selectively solubilize or chelate a specific guest molecule that is found within a mixture of many substituents in a solution or suspension such as cholesterol in blood or spinal fluid. While the gross HPBCD mixture in the presence of the guest molecule might solubilize the guest molecule, it may also solubilize certain spectator molecules that are not desirable for solubilization or chelation. Conversely, there may also be a need to selectively solubilize or deliver a guest molecule (such as a pharmaceutical agent) to a specific environment or internal organ. While a gross mixture of HPBCD may very well be capable of carrying a guest molecule, it may not be capable of selectively delivering or releasing the guest molecule to a specific environment or organ. On the other hand, a specific HPBCD isomer or group of isomers may be capable of selectively solubilizing or delivering the desired guest molecule to the desired environment or organ. Alternatively, if one could identify, isolate and/or enrich a concise group of HPBCD isomers or an individual compound that could selectively solubilize, chelate, deliver or sequester a particular guest molecule of interest at the expense of other components in a mixture, then one could amplify and employ those unique chemical qualities that would not ordinarily be available from the use of the HPBCD gross mixture. The particular guest molecule of interest may be cholesterol. The particular guest molecule of interest may be one or more lipids.

Therefore, in view of the shortcomings described above relating to the gross mixture of commercially available HPBCD, there is a need in certain applications to fine-tune the selectivity of HPBCD in order to sequester, deliver or solubilize guest or target molecules with specific HPBCD molecules or concise groups of HPBCD isomers that may be isolated from the gross commercial HPBCD mixture. The concise groups of HPBCD isomers may comprise similar HPBCD molecules which are isolated in groups such as by molecular weight, alkylation or substitution patterns, or some other chemical property or characteristic.

The present invention provides for the isolation and use of a range of specific like isomers of HPBCD for use as selective solubilizing or chelation agents that allow for finely tuned selectively. These isolated groups of HPBCD molecules, which have similar chemical properties, can then be used for very specific purposes. Where the gross mixture might provide some generalized result, the use of isomerically similar groups of HPBCD molecules could be employed to a more precise pharmacological or chemical result. For example, the present invention provides for the isolation and use of specific mixtures of HPBCD molecules to selectively solubilize or chelate cholesterol. The improved affinity towards cholesterol exhibited by the mixtures of the present invention is advantageous for the treatment or prevention of diseases or conditions such as Niemann-Pick disease Type C, liver disease, cardiovascular disease, familial hypercholesterolemia, and cholesterol deposits.

Previously applied preparative chromatography approaches for purification of hydroxypropyl-β-cyclodextrin molecules and related materials applied direct phase silica gel, which separates the main hydroxypropyl-β-cyclodextrin components based on hydrophilic interactions between OH groups of the silica gel and the OH groups of the hydroxypropyl-β-cyclodextrin components. This approach, however, fails to separate the different isomers of hydroxypropyl-β-cyclodextrin. One reason for this is that the size and molecular weight distribution of the different isomers may be distributed across a very narrow range. Hydroxypropylation of the β-cyclodextrin molecules does not add an OH group to the β-cyclodextrin molecule; rather, it only replaces an OH group of the β-cyclodextrin with an OH group of the hydroxypropyl side chain. The net charge of the molecule is not changed, since no ionic group is added to the β-cyclodextrin molecule. These afore-mentioned technical factors make isomeric separation through conventional chromatography means (e.g., ion-exchange, size-exclusion, reversed phase or normal phase silica gels) technically infeasible and/or economically impractical.

SUMMARY OF THE DISCLOSURE

Provided herein is a composition comprising a mixture of beta-cyclodextrin molecules substituted at one or more hydroxyl positions by hydroxypropyl groups, wherein: the mixture comprises less than 0.05% unsubstituted beta-cyclodextrin ("DS-0") and less than 0.05% beta-cyclodextrin substituted with one hydroxypropyl group ("DS-1"), the composition comprising an average degree of substitution of 6.02-7.98, wherein the composition is suitable for intrathecal, intravenous, oral, or intracerebroventricular administration to a patient in need thereof. In some embodiments, the composition has a pH of between 6.0 and 7.9. In some embodiments, the true density of the composition is about 1.096-1.098 g/cm$^3$. In some embodiments, the osmolality of the composition is about 635-695 mOs/kg. In some embodiments, the composition further comprises a container and non-visible particulate matter, and the non-visible particulate matter with a size 25 microns is in an amount ≤600/container. In some embodiments, the composition comprises no more than 10 ppb of propylene glycol as measured by HPLC. In some embodiment, the composition comprises no more than 10 ppb propylene glycol as measured by gas chromatography. In some embodiments, the composition comprises no more than 10 ppb propylene glycol as measured by PG/EG-ratio of propylene glycol to ethylene glycol. In some embodiments, the composition comprises no more than 1 ppm propylene oxide.

In certain embodiments, the pharmaceutical composition comprises no more than ("NMT") 5 EU/g beta-cyclodextrin mixture, NMT 4 EU/g beta-cyclodextrin mixture, NMT3 EU/g beta-cyclodextrin mixture, or no more than 2 EU/g beta-cyclodextrin mixture. In preferred embodiments, the pharmaceutical composition comprises NMT 1.5 EU/g beta cyclodextrin mixture. In certain embodiments, the pharmaceutical composition comprises NMT 1.4 EU/g beta-cyclodextrin mixture, NMT 1.3 EU/g beta-cyclodextrin mixture, NMT 1.2 EU/g beta-cyclodextrin mixture, NMT 1.1 EU/g beta-cyclodextrin mixture, or NMT 1.0 EU/g beta-cyclodextrin mixture.

In some embodiments, the total amount of other unspecified impurities is less than or equal to 0.05% as measured by HPLC. In some embodiments, the composition has a concentration of about 10 mg/mL to about 200 mg/mL. In some embodiments, the composition has a concentration of the mixture of β-cyclodextrin molecules of about 10 mg/mL to about 200 mg/mL. In some embodiments, the composition exhibits a lower toxicity than Trappsol® Cyclo. In some embodiments, the composition has a conductivity of about ≤200 µS/cm. In some embodiments, the composition is stable for at least 6 months. In some embodiments, the composition further comprises at least one of a pharmaceutical excipient, a carrier, a pharmaceutically acceptable diluent, a pH adjusting agent, and a buffer. In some aspects, the pH adjusting agent is sodium hydroxide. In some aspects, the buffer comprises monobasic sodium phosphate and dibasic sodium phosphate.

Further provided herein is a method of preparing a purified mixture of beta-cyclodextrin suitable for intrathecal, intravenous, oral, or intracerebroventricular administration to a patient in need thereof, the method comprising nanofiltrating a beta-cyclodextrin to achieve a purified mixture of beta-cyclodextrin molecules substituted at one or more hydroxyl positions by hydroxypropyl groups, wherein the mixture comprises less than 0.05% unsubstituted beta-cyclodextrin ("DS-0") and less than 0.05% beta-cyclodextrin substituted with one hydroxypropyl group ("DS-1"), and wherein the average degree of substitution of 6.02-7.98, and adjusting the pH of the nanofiltrated purified mixture of beta-cyclodextrin to achieve a pH of 6.0 to 7.8. In some embodiments, the pH is adjusted with 0.1 M sodium hydroxide.

Further provided herein is a method of treating Niemann-Pick disease Type C, the method comprising administering to a patient in need thereof a therapeutically effective amount of a composition comprising a mixture of beta-cyclodextrin molecules substituted at one or more hydroxyl positions by hydroxypropyl groups, wherein: the mixture comprises less than 0.05% unsubstituted beta-cyclodextrin ("DS-0") and less than 0.05% beta-cyclodextrin substituted with one hydroxypropyl group ("DS-1"), the composition comprising an average degree of substitution of 6.02-7.98, wherein the composition is suitable for intrathecal, intravenous, oral, or intracerebroventricular administration to a patient in need thereof. Also provided herein is a composition for use in a method of treating Niemann-Pick disease Type C, the method comprising administering to a patient in need thereof a therapeutically effective amount of the composition, wherein the composition comprises a mixture of beta-cyclodextrin molecules substituted at one or more hydroxyl positions by hydroxypropyl groups, and wherein: the mixture comprises less than 0.05% unsubstituted beta-cyclodextrin ("DS-0") and less than 0.05% beta-cyclodextrin substituted with one hydroxypropyl group ("DS-1"), the composition comprising an average degree of substitution of 6.02-7.98, wherein the composition is suitable for intrathecal, intravenous, oral, or intracerebroventricular administration to a patient in need thereof. Alternatively, said methods may be methods of treating liver disease, cardiovascular disease, familial hypercholesterolemia, or cholesterol deposits. In some embodiments, the method comprises administering about 50 mg to about 2000 mg of the beta-cyclodextrin mixture to the patient. In some examples, about 50 mg to about 300 mg of the beta-cyclodextrin mixture is administered. In some embodiments, the method comprises administering the composition at 1-day, 2-day, or 3-day intervals. In some embodiments, the method comprises administering the composition once every week. In some embodiments, the composition is administered once every two weeks. In some embodiments, the administering comprises intravenously administering about 200 mg/kg to about 4100 mg/kg of the beta-cyclodextrin mixture to the patient. In some embodiments, the administration results in the lowering of one or more lipids (e.g. one or more LDLs (low-density lipoproteins) and/or triglycerides) by 75%±5%, 80%±5%, 85%±5%, 90%±5%, or 95%±5%. In some embodiments, the administration prevents progression of NPC as compared with no administration or administration of a placebo. In some embodiments, the administration is sufficient to maintain or reduce one or more domain scores of the NPC Severity Scale selected from: ambulation, fine motor skills, cognition, speech, swallowing, eye movement, memory, hearing, and seizures. In some embodiments, the administration occurs within 4 hours. In some embodiments, the duration of the administration (which is preferably intravenous administration) is about 4 hours or less.

Further provided herein is a composition comprising a mixture of β-cyclodextrin molecules, wherein the mixture of β-cyclodextrin molecules comprises β-cyclodextrin substituted with four hydroxypropyl groups ("DS-4"); β-cyclodextrin substituted with five hydroxypropyl groups ("DS-5"); β-cyclodextrin substituted with six hydroxypropyl groups ("DS-6"); β-cyclodextrin substituted with seven hydroxypropyl groups ("DS-7"); β-cyclodextrin substituted with eight hydroxypropyl groups ("DS-8"); β-cyclodextrin substituted with nine hydroxypropyl groups ("DS-9"); β-cyclodextrin substituted with ten hydroxypropyl groups ("DS-10"); β-cyclodextrin substituted with eleven hydroxypropyl groups ("DS-11"); β-cyclodextrin substituted with twelve hydroxypropyl groups ("DS-12"); β-cyclodextrin substituted with thirteen hydroxypropyl groups ("DS-13"); and β-cyclodextrin substituted with fourteen hydroxypropyl groups ("DS-14"); and wherein the mixture of β-cyclodextrin molecules comprises less than 1% DS-4. In some embodiments, the composition has an HPLC-CAD chromatogram of FIG. 4. In some embodiments, the HPLC-CAD mean retention time of the mixture of isomerically-purified hydroxypropyl β-cyclodextrin molecules is about 13.5 minutes. In some embodiments, the mixture of β-cyclodextrin molecules has a DEPT-edited HSQC spectrum of FIG. 3. In some embodiments, the mixture of β-cyclodextrin molecules comprises about 0.5% w/w to about 1% w/w DS-4. In some embodiments, the mixture of β-cyclodextrin molecules comprises about 2% w/w to about 5% w/w DS-5. In some embodiments, the mixture of β-cyclodextrin molecules comprises about 7% w/w to about 13% w/w DS-6. In some embodiments, the mixture of β-cyclodextrin molecules comprises about 21% w/w to about 27% w/w DS-7. In some embodiments, the mixture of β-cyclodextrin molecules comprises about 23% w/w to about 29% w/w DS-8. In some embodiments, the mixture of β-cyclodextrin molecules comprises about 15% w/w to about 21% w/w DS-9. In some embodiments, the mixture of β-cyclodextrin molecules comprises about 6% w/w to about 12% w/w DS-10. In some embodiments, the mixture of β-cyclodextrin molecules comprises about 2% w/w to about 6% w/w DS-11. In some embodiments, the mixture of β-cyclodextrin molecules comprises about 0.5% w/w to about 4% w/w DS-12. In some embodiments, the mixture of β-cyclodextrin molecules comprises less than about 1% w/w DS-13. In some embodiments, the composition is free of DS-0, DS-1, DS-2, and/or DS-3. In some embodiments, the mixture of β-cyclodextrin molecules is suitable for intravenous, intrathecal, or intracerebroventricular administration. In some embodiments, the composition is suitable for intravenous, intrathecal, or intracerebroventricular administration. In some embodiments, the amount of DS-1, DS-2, DS-3, DS-4, DS-5, DS-6, DS-7, DS-8, DS-9, DS-10, DS-11, DS-12, and DS-13 in the mixture of β-cyclodextrin molecules is determined by MALDI-TOF-MS. In some embodiments, DS-8 has the highest concentration in the mixture of β-cyclodextrin molecules as compared to the concentrations of DS-1, DS-2, DS-3, DS-4, DS-5, DS-6, DS-7, DS-9, DS-10, DS-11, DS-12, and DS-13. In some embodiments, the β-cyclodextrin molecules are substituted at the 2-O— position at a rate of 35-55%, the 3-O— position at a rate of 45-65%, and the 6-O— position at a rate of 0-20%. In some embodiments, the rate of substitution at the 2-O—, 3-O—, and 6-O positions is determined via DEPT-ed HSQC. These positions (2-O—, 3-O— and 6-O—) on each glucose-unit of the β-cyclodextrin are confirmed below. In some embodiments, the composition has an average degree of substitution of between about 7 to about 9. In an exemplary embodiment, the composition has an average degree of substitution of about 7.7. In some embodiments, the composition has a MALDI-TOF spectrum of FIG. 1. In some embodiments, the composition has a true density of about 1.095 g/cm$^3$ to about 1.100 g/cm$^3$. In some embodiments, the composition has an osmolality of about 600 mOs/kg to about 750 mOs/kg. In some embodiments, the composition is a clear and colorless solution. In some embodiments, the composition has a pH of about 4.0 to about 6.0. In some embodiments, the composition has a viscosity of 1.5 cP to about 3.0 cP at 20° C. In some embodiments, the composition comprises less than or equal to about 0.05% impurities. In some embodiments, the composition comprises less than 600 particles per container having a diameter of greater than or equal to 25 microns. In some embodiments, the composition comprises less than 6000 particles per container having a diameter of greater than or equal to 10 microns.

Further provided herein is a composition comprising a mixture of β-cyclodextrin molecules, the composition having a $^1$H-NMR spectrum comprising at least one peak at about 5.0-5.4 ppm corresponding to anomeric protons of the β-cyclodextrin molecules; at least one peak at about 3.2-4.2 ppm corresponding to protons within a core region of the β-cyclodextrin molecules; and at least one peak at about 1.0-1.2 ppm corresponding to methyl protons of side chains of the β-cyclodextrin molecules. In some embodiments, the composition may have a $^1$H-NMR of FIG. 2.

Fraction 1 Mixture

Further provided herein is a composition comprising a mixture of isomerically-purified hydroxypropyl-β-cyclodextrin molecules comprising less than 1% β-cyclodextrin substituted with four hydroxypropyl groups ("DS-4"). In some embodiments, the hydroxypropyl β-cyclodextrin percentage is based upon area percentage from a MALDI-TOF-MS spectrum. In some embodiments, the hydroxypropyl β-cyclodextrin percentage is based upon weight percentage. In some embodiments, the composition comprises less than 1% β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1"). In some embodiments, the mixture of isomerically-purified hydroxypropyl β-cyclodextrin molecules comprises about 1% to about 5% of β-cyclodextrin substituted with five hydroxypropyl groups ("DS-5"). In some embodiments, the mixture of isomerically-purified hydroxypropyl β-cyclodextrin comprises about 7% to about 13% of β-cyclodextrin substituted with six hydroxypropyl groups ("DS-6"). In some aspects, the mixture of isomerically-purified hydroxypropyl β-cyclodextrin comprises about 8% to about 12% of DS-6. In some embodiments, the mixture of isomerically-purified hydroxypropyl β-cyclodextrin comprises about 16% to about 22% of β-cyclodextrin substituted with seven hydroxypropyl groups ("DS-7"). In some aspects, the mixture of isomerically-purified hydroxypropyl β-cyclodextrin comprises about 17% to about 21% of DS-7. In some embodiments, the mixture of isomerically-purified hydroxypropyl β-cyclodextrin comprises about 26% to about 32% of β-cyclodextrin substituted with eight hydroxypropyl groups ("DS-8"). In some aspects, the mixture of isomerically-purified hydroxypropyl β-cyclodextrin comprises about 27% to about 31% of DS-8. In some embodiments, the mixture of isomerically-purified hydroxypropyl β-cyclodextrin comprises about 22% to about 28% of β-cyclodextrin substituted with nine hydroxypropyl groups ("DS-9"). In some aspects, the mixture of isomerically-purified hydroxypropyl β-cyclodextrin comprises about 23% to about 27% of DS-9. In some embodiments, the mixture of isomerically-purified hydroxypropyl β-cyclodextrin comprises about 11% to about 17% of β-cyclodextrin substituted with ten hydroxypropyl groups ("DS-10"). In some aspects, the mixture of isomerically-purified hydroxypropyl β-cyclodextrin comprises about 12% to about 16% of DS-10. In some embodiments, mixture of isomerically-purified hydroxypropyl β-cyclodextrin molecules comprising less than 1% β-cyclodextrin substituted with eleven hydroxypropyl groups ("DS-11"). In some embodiments, the mixture of isomerically-purified hydroxypropyl β-cyclodextrin molecules comprising less than 1% β-cyclodextrin substituted with twelve hydroxypropyl groups ("DS-12"), β-cyclodextrin substituted with thirteen hydroxypropyl groups ("DS-13"), and β-cyclodextrin substituted with fourteen hydroxypropyl groups ("DS-14"). In some embodiments, the average degree of substitution of the mixture of isomerically-purified hydroxypropyl β-cyclodextrin is about 6.4 to about 7.0. In an exemplary embodiment, the average degree of substitution is about 6.69. In some embodiments, about 52% to about 58% of the hydroxypropyl substitutions in the hydroxypropyl β-cyclodextrin molecules are located at the 3-O— position. In some aspects, about 55% to about 56% of the hydroxypropyl substitutions in the β-cyclodextrin molecules are located at the 3-O— position. In some embodiments, about 41% to about 47% of the hydroxypropyl substitutions in the hydroxypropyl β-cyclodextrin molecules are located at the 2-O— position. In some aspects, about 43% to about 45% of the hydroxypropyl substitutions in the hydroxypropyl β-cyclodextrin molecules are located at the 2-O— position. In some embodiments, the concentration of the composition does not substantially change the time required for nanofiltration. In some aspects, the length of time to nanofilter the composition ranges from 1.04 to 1.20 hours per diafiltration volume (kg soln/m2-hr/L soln). In some embodiments, the composition has no substantial difference observed in HPLC-ELSD after nanofiltration as compared to before nanofiltration. In some embodiments, the composition has no substantial difference observed in NMR after nanofiltration as compared to before nanofiltration. In some embodiments, the composition has a conductivity between 0 and 8.0 μS/cm, 0 and 4.5 μS/cm, 0 and 3 μS/cm, or between 0 and 1.5 μS/cm. In some embodiments, the composition has an osmolality of about 600 mOs/kg to about 750 mOs/kg. In some embodiments, the composition has a true density of about 1.095 g/cm$^3$ to about 1.100 g/cm$^3$. In some embodiments, the composition has a pH of about 4.0 to about 8.0. In some embodiments, the composition has a viscosity of about 1.5 cP to about 10,000 cP at 20° C.

Further provided herein is a composition comprising a mixture of isomerically-purified hydroxypropyl β-cyclodextrin molecules comprising: β-cyclodextrin substituted with five hydroxypropyl groups ("DS-5"); β-cyclodextrin substituted with six hydroxypropyl groups ("DS-6"); β-cyclodextrin substituted with seven hydroxypropyl groups ("DS-7"); β-cyclodextrin substituted with eight hydroxypropyl groups ("DS-8"); β-cyclodextrin substituted with nine hydroxypropyl groups ("DS-9"); and β-cyclodextrin substituted with ten hydroxypropyl groups ("DS-10"), wherein the composition comprises less than 1% β-cyclodextrin substituted with four hydroxypropyl groups ("DS-4") and less than 1% β-cyclodextrin substituted with eleven hydroxypropyl groups ("DS-11"). In some embodiments, the composition comprises 0.0 to 1.0% β-cyclodextrin substituted with three hydroxypropyl groups ("DS-3"), 0.0 to 1.0% β-cyclodextrin substituted with two hydroxypropyl groups ("DS-2"), and 0.0 to 1.0% β-cyclodextrin substituted with one hydroxypropyl group ("DS-1"). In some embodiments, the composition comprises less than 1% β-cyclodextrin substituted with twelve hydroxypropyl groups ("DS-12"), β-cyclodextrin substituted with thirteen hydroxypropyl groups ("DS-13"), and β-cyclodextrin substituted with fourteen hydroxypropyl groups ("DS-14"). In some embodiments, the DS-8 has the highest concentration in the mixture of isomerically-purified hydroxypropyl β-cyclodextrin molecules as compared to DS-5, DS-6, DS-7, DS-9, and DS-10. In some embodiments, the mixture of isomerically-purified hydroxypropyl β-cyclodextrin molecules comprises about 1% to about 5% of DS-5. In some embodiments, the mixture of isomerically-purified hydroxypropyl β-cyclodextrin comprises about 7% to about 13% of DS-6. In some embodiments, the mixture of isomerically-purified hydroxypropyl β-cyclodextrin comprises about 16% to about 22% of DS-7. In some embodiments, the mixture of isomerically-purified hydroxypropyl β-cyclodextrin comprises about 26% to about 32% of DS-8. In some embodiments, the mixture of isomerically-purified hydroxypropyl β-cyclodextrin comprises about 22% to about 28% of DS-9. In some embodiments, the mixture of isomerically-purified hydroxypropyl β-cyclodextrin comprises about 11% to about 17% of DS-10. In some embodiments, the average degree of substitution of the mixture of isomerically-purified hydroxypropyl β-cyclodextrin is about 6.4 to about 7.0. In an exemplary embodiment, the average degree of substitution is about 6.69. In some embodiments, about 52% to about 58% of the hydroxypropyl substitutions in the hydroxypropyl β-cyclodextrin molecules are located at the 3-O— position. In some embodiments, about 41% to about 47% of the hydroxypropyl substitutions in the hydroxypropyl β-cyclodextrin molecules are located at the 2-O— position. In an exemplary embodiment, the composition has an HPLC-CAD chromatogram of FIG. 8. In an exemplary embodiment, the HPLC-CAD mean retention time of the mixture of isomerically-purified hydroxypropyl β-cyclodextrin molecules is about 10.1 minutes. In some embodiments, the composition has a –ESI-MS spectrum with peaks at about 653 m/z, about 682 m/z, about 711 m/z, about 741 m/z, about 769 m/z, about 799 m/z, about 828 m/z, and about 857 m/z, and a +ESI-MS spectrum with peaks at about 686 m/z, about 715 m/z, about 744 m/z, about 773 m/z, about 802 m/z, about 832 m/z, about 861 m/z, and about 890 m/z. In an exemplary embodiment, the composition has a ESI-MS spectra of FIG. 9. In some embodiments, the composition has a MALDI-TOF spectrum with peaks at about 1436 m/z, about 1495 m/z, about 1555 m/z, about 1614 m/z, about 1674 m/z, and about 1733 m/z. In an exemplary embodiment, the composition has a MALDI-TOF spectrum of FIG. 10. In an exemplary embodiment, the composition has a $^1$H-NMR spectrum of FIG. 6. In an exemplary embodiment, the composition has a DEPT-edited HSQC spectrum of FIG. 7. In some embodiments, the osmolality of the composition is about 635-695 mOs/kg. In some embodiments, the true density of the composition is about 1.096-1.098 g/cm$^3$. In some embodiments, the composition has a conductivity between 0 and 8.0 μS/cm. In some embodiments, the composition has a pH of about 4.0 to about 8.0. In some embodiments, the composition has a viscosity of about 1.5 cP to about 10,000 cP at 20° C. In some embodiments, the composition comprises no more than 10 ppb of propylene glycol as measured by HPLC. In some embodiments, the composition comprises no more than 1 ppm propylene oxide. In some embodiments, the total amount of other unspecified impurities is less than or equal to 0.05% as measured by HPLC. In some embodiments, the composition further comprises between 0 and 10 ppm chloride. In some embodiments, the composition is nanofiltered. In some embodiments, the nanofiltered composition has no substantial difference observed in HPLC-ELSD after nanofiltration as compared to before nanofiltration. In some embodiments, the nanofiltered composition has no substantial difference observed in NMR after nanofiltration as compared to before nanofiltration.

Fraction 2 Mixture

Further provided herein is a composition comprising a mixture of isomerically-purified hydroxypropyl β-cyclodextrin molecules comprising less than 1% hydroxypropyl β-cyclodextrin with five hydroxypropyl groups ("DS-5"). In some embodiments, the hydroxypropyl β-cyclodextrin percentage is based upon area percentage from a MALDI-TOF-MS spectrum. In some embodiments, the hydroxypropyl β-cyclodextrin percentage is based upon weight percentage. In some embodiments, the composition comprises less than 1% β-cyclodextrin substituted with four hydroxypropyl groups ("DS-4"), β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1"). In some embodiments, the mixture of isomerically-purified hydroxypropyl β-cyclodextrin molecules is free of DS-1, DS-2, DS-3, and/or DS-4. In some embodiments, the mixture of isomerically-purified hydroxypropyl β-cyclodextrin comprises about 0% to about 6% of hydroxypropyl β-cyclodextrin substituted with six hydroxypropyl groups ("DS-6"). In some aspects, the mixture of isomerically-purified β-hydroxypropyl cyclodextrin molecules comprises about 1% to about 5% of DS-6. In some embodiments, the mixture of isomerically-purified hydroxypropyl β-cyclodextrin molecules comprises about 8% to about 14% of hydroxypropyl β-cyclodextrin substituted with seven hydroxypropyl groups ("DS-7"). In some aspects, the mixture of isomerically-purified hydroxypropyl β-cyclodextrin molecules comprises about 9% to about 13% of DS-7. In some embodiments, the mixture of isomerically-purified p-hydroxypropyl cyclodextrin molecules comprises about 19% to about 25% of hydroxypropyl β-cyclodextrin substituted with eight hydroxypropyl groups ("DS-8"). In some aspects, the mixture of isomerically-purified hydroxypropyl β-cyclodextrin molecules comprises about 20% to about 24% of DS-8. In some embodiments, the mixture of isomerically-purified β-hydroxypropyl cyclodextrin molecules comprises about 23% to about 29% hydroxypropyl β-cyclodextrin substituted with nine hydroxypropyl groups ("DS-9"). In some aspects, the mixture of isomerically-purified hydroxypropyl β-cyclodextrin molecules comprises about 24% to about 28% of DS-9. In some embodiments, the mixture of isomerically-purified hydroxypropyl β-cyclodextrin molecules comprises about 17% to about 23% of hydroxypropyl β-cyclodextrin substituted with ten hydroxypropyl groups ("DS-10). In some aspects, the mixture of isomerically-purified β-hydroxypropyl cyclodextrin molecules comprises about 18% to about 22% of DS-10. In some embodiments, the mixture of isomerically-purified β-hydroxypropyl cyclodextrin molecules comprises about 9% to about 15% of hydroxypropyl β-cyclodextrin substituted with eleven hydroxypropyl groups ("DS-11"). In some aspects, the mixture of isomerically-purified β-cyclodextrin molecules comprises about 10% to about 14% of DS-11. In some embodiments, the mixture of isomerically-purified β-cyclodextrin molecules comprises about 2% to about 8% hydroxypropyl β-cyclodextrin substituted with twelve hydroxypropyl groups ("DS-12"). In some aspects, the mixture of isomerically-purified β-cyclodextrin molecules comprises about 3% to about 7% DS-12. In some embodiments, the mixture of isomerically-purified β-cyclodextrin molecules comprises less than 1% hydroxypropyl β-cyclodextrin substituted with thirteen hydroxypropyl groups ("DS-13"), and/or less than 1% hydroxypropyl β-cyclodextrin substituted with fourteen hydroxypropyl groups ("DS-14"). In some embodiments, the mixture of isomerically-purified hydroxypropyl β-cyclodextrin molecules is free of DS-13 and/or DS-14. In some embodiments, the mixture of isomerically-purified β-cyclodextrin molecules has an average degree of substitution of about 7 to about 8. In an exemplary embodiment, the average degree of substitution is about 7.42. In some embodiments, about 36% to about 42% of the hydroxypropyl substitutions in the hydroxypropyl β-cyclodextrin molecules are located at the 3-O-position. In some aspects, about 37% to about 41% of the hydroxypropyl substitutions in the hydroxypropyl β-cyclodextrin molecules are located at the 3-O— position. In some embodiments, about 58% to about 64% of the hydroxypropyl substitutions in the hydroxypropyl β-cyclodextrin molecules are located at the 2-O— position. In some aspects, about 59% to about 63% of the hydroxypropyl substitutions in the hydroxypropyl β-cyclodextrin molecules are located at the 2-O— position. In some embodiments, the concentration of the composition does not substantially change the time required for nanofiltration. In some aspects, the length of time to nanofilter the composition ranges from 1.04 to 1.20 hours per diafiltration volume (kg soln/m2-hr/L soln). In some embodiments, the composition has no substantial difference observed in HPLC-ELSD after nanofiltration as compared to before nanofiltration. In some embodiments, wherein the composition has no substantial difference observed in NMR after nanofiltration as compared to before nanofiltration. In some embodiments, the composition has a conductivity between 0 and 8.0 μS/cm, 0 and 4.5 μS/cm, 0 and 3 μS/cm, or between 0 and 1.5 μS/cm. In some embodiments, the composition has a pH of about 4.0 to about 8.0. In some embodiments, the composition has a viscosity of about 1.5 cP to about 10,000 cP at 20° C.

Further provided herein is a composition comprising a mixture of isomerically-purified hydroxypropyl β-cyclodextrin molecules comprising: β-cyclodextrin substituted with six hydroxypropyl groups ("DS-6"); β-cyclodextrin substituted with seven hydroxypropyl groups ("DS-7"); β-cyclodextrin substituted with eight hydroxypropyl groups ("DS-8"); β-cyclodextrin substituted with nine hydroxypropyl groups ("DS-9"); β-cyclodextrin substituted with ten hydroxypropyl groups ("DS-10"); β-cyclodextrin substituted with eleven hydroxypropyl groups ("DS-11"); and β-cyclodextrin substituted with twelve hydroxypropyl groups ("DS-12"), wherein the composition comprises less than 1% β-cyclodextrin substituted with five hydroxypropyl groups ("DS-5") and the composition comprises less than 1% I β-cyclodextrin substituted with thirteen hydroxypropyl groups ("DS-13"). In some embodiments, the composition comprises less than 1% β-cyclodextrin substituted with four hydroxypropyl groups ("DS-4"), β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1"). In some embodiments, the composition comprises less than 1% β-cyclodextrin substituted with thirteen hydroxypropyl groups ("DS-13") and hydroxypropyl β-cyclodextrin substituted with fourteen hydroxypropyl groups ("DS-14"). In some embodiments, the composition is free of DS-1, DS-2, DS-3, DS-4, and/or DS-14. In some embodiments, the DS-9 has the highest concentration in the composition as compared to DS-6, DS-7, DS-8, DS-10, DS-11, and DS-12. In some embodiments, the mixture of isomerically-purified hydroxypropyl β-cyclodextrin molecules comprises about 0% to about 6% of DS-6. In some embodiments, the mixture of isomerically-purified hydroxypropyl β-cyclodextrin molecules comprises about 8% to about 14% of DS-7. In some embodiments, the mixture of isomerically-purified hydroxypropyl β-cyclodextrin molecules comprises about 19% to about 25% of DS-8. In some embodiments, the mixture of isomerically-purified hydroxypropyl β-cyclodextrin molecules comprises about 23% to about 29% of DS-9. In some embodiments, the mixture of isomerically-purified hydroxypropyl β-cyclodextrin molecules comprises about 17% to about 23% of DS-10. In some embodiments, the mixture of isomerically-purified hydroxypropyl β-cyclodextrin molecules comprises about 9% to about 15% of DS-11. In some embodiments, the mixture of isomerically-purified hydroxypropyl β-cyclodextrin molecules comprises about 2% to about 8% DS-12. In some embodiments, the mixture of isomerically-purified hydroxypropyl β-cyclodextrin molecules has an average degree of substitution of about 7 to about 8. In some embodiments, about 36% to about 42% of the hydroxypropyl substitutions in the hydroxypropyl β-cyclodextrin molecules are located at the 3-O-position. In some embodiments, about 58% to about 64% of the hydroxypropyl substitutions in the hydroxypropyl β-cyclodextrin molecules are located at the 2-O-position. In an exemplary embodiment, the composition has an HPLC-CAD chromatogram of FIG. 13. In an exemplary embodiment, the HPLC-CAD mean retention time of the mixture of isomerically-purified hydroxypropyl β-cyclodextrin molecules is about 11.9 minutes. In some embodiments, the composition has a −ESI-MS spectrum with peaks at about 682 m/z, about 712 m/z, about 740 m/z, about 770 m/z, about 798 m/z, about 828 m/z, about 856 m/z, and about 886 m/z, and a +ESI-MS spectrum with peaks at about 744 m/z, about 773 m/z, about 803 m/z, about 832 m/z, about 860 m/z, about 889 m/z, and about 919 m/z. In some embodiments, the composition has a MALDI-TOF-MS spectrum with peaks at about 1497 m/z, about 1557 m/z, about 1616 m/z, about 1675 m/z, about 1734 m/z, about 1794 m/z, and about 1914 m/z. In an exemplary embodiment, the composition has a MALDI-TOF-MS spectrum of FIG. 15. In an exemplary embodiment, the composition has a $^1$H-NMR spectrum of FIG. 11. In an exemplary embodiment, the composition has a DEPT-edited HSQC spectrum of FIG. 12. In an exemplary embodiment, the mixture of isomerically-purified hydroxypropyl β-cyclodextrin molecules has an ESI-MS spectrum of FIG. 14. In some embodiments, the osmolality of the composition is about 635-695 mOs/kg. In some embodiments, the true density of the composition is about 1.096-1.098 g/cm$^3$. In some embodiments, the composition comprises no more than 10 ppb of propylene glycol as measured by HPLC. In some embodiments, the composition comprises no more than 1 ppm propylene oxide. In some embodiments, the total amount of other unspecified impurities is less than or equal to 0.05% as measured by HPLC. In some embodiments, the composition comprises between 0 and 10 ppm chloride. In some embodiments, the composition has a conductivity between 0 and 8 μS/cm. In some embodiments, the composition is nanofiltered. In some embodiments, the nanofiltered composition has no substantial difference observed in HPLC-ELSD after nanofiltration as compared to before nanofiltration. In some embodiments, the nanofiltered composition has no substantial difference observed in NMR after nanofiltration as compared to before nanofiltration.

Fraction 3 Mixture

Further provided herein is a composition comprising a mixture of isomerically-purified hydroxypropyl β-cyclodextrin molecules comprising less than 1% hydroxypropyl β-cyclodextrin with six hydroxypropyl groups ("DS-6") and less than 1% β-cyclodextrin substituted with fourteen hydroxypropyl groups ("DS-14"). In some embodiments, the hydroxypropyl β-cyclodextrin percentage is based upon area percentage from a MALDI-TOF-MS spectrum. In some embodiments, the hydroxypropyl β-cyclodextrin percentage is based upon weight percentage. In some embodiments, the composition comprises less than 1% β-cyclodextrin substituted with five hydroxypropyl groups ("DS-5"), β-cyclodextrin substituted with four hydroxypropyl groups ("DS-4"), β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1"). In some embodiments, the mixture of isomerically-purified hydroxypropyl β-cyclodextrin molecules is free of DS-1, DS-2, DS-3, DS-4, and/or DS-5. In some embodiments, the mixture of isomerically-purified hydroxypropyl β-cyclodextrin molecules comprises about 1% to about 7% of β-cyclodextrin substituted with seven hydroxypropyl groups ("DS-7"). In some aspects, the mixture of isomerically-purified hydroxypropyl β-cyclodextrin molecules comprises about 2% to about 6% of DS-7. In some embodiments, the mixture of isomerically-purified hydroxypropyl β-cyclodextrin molecules comprises about 16% to about 22% of β-cyclodextrin substituted with eight hydroxypropyl groups ("DS-8"). In some aspects, the mixture of isomerically-purified hydroxypropyl β-cyclodextrin molecules comprises about 17% to about 21% of DS-8. In some embodiments, the mixture of isomerically-purified hydroxypropyl β-cyclodextrin molecules comprises about 22% to about 28% of β-cyclodextrin substituted with nine hydroxypropyl groups ("DS-9"). In some aspects, the mixture of isomerically-purified hydroxypropyl β-cyclodextrin molecules comprises about 23% to about 27% of DS-9. In some embodiments, the mixture of isomerically-purified hydroxypropyl β-cyclodextrin molecules comprises about 19% to about 25% of β-cyclodextrin substituted with ten hydroxypropyl groups ("DS-10"). In some aspects, the mixture of isomerically-purified hydroxypropyl β-cyclodextrin molecules comprises about 20% to about 24% of DS-10. In some embodiments, the mixture of isomerically-purified hydroxypropyl β-cyclodextrin molecules comprises about 14% to about 20% of β-cyclodextrin substituted with eleven hydroxypropyl groups ("DS-11"). In some aspects, the mixture of isomerically-purified hydroxypropyl β-cyclodextrin molecules comprises about 15% to about 19% of DS-11. In some embodiments, the mixture of isomerically-purified hydroxypropyl β-cyclodextrin molecules comprises about 5% to about 11% of β-cyclodextrin substituted with twelve hydroxypropyl groups ("DS-12"). In some aspects, the mixture of isomerically-purified hydroxypropyl β-cyclodextrin molecules comprises about 6% to about 10% of DS-12. In some embodiments, the mixture of isomerically-purified hydroxypropyl β-cyclodextrin molecules comprises about 1% to about 7% of β-cyclodextrin substituted with thirteen hydroxypropyl groups ("DS-13"). In some aspects, the mixture of isomerically-purified hydroxypropyl β-cyclodextrin molecules comprises about 2% to about 6% of DS-13. In some embodiments, the average degree of substitution of the mixture of isomerically-purified hydroxypropyl β-cyclodextrin is about 8 to about 9. In an exemplary embodiment, the average degree of substitution of the mixture of isomerically-purified hydroxypropyl β-cyclodextrin is about 8.53. In some embodiments, about 26% to about 32% of the hydroxypropyl substitutions in the hydroxypropyl β-cyclodextrin molecules are located at the 3-O— position. In some aspects, about 27% to about 31% of the hydroxypropyl substitutions in the hydroxypropyl β-cyclodextrin molecules are located at the 3-O— position. In some embodiments, about 68% to about 74% of the hydroxypropyl substitutions in the hydroxypropyl β-cyclodextrin molecules are located at the 2-O-position. In some aspects, about 69% to about 73% of the hydroxypropyl substitutions in the hydroxypropyl β-cyclodextrin molecules are located at the 2-O— position. In some embodiments, the concentration of the composition does not substantially change the time required for nanofiltration. In some aspects, the length of time to nanofilter the composition ranges from 1.04 to 1.20 hours per diafiltration volume (kg soln/m²-hr/L soln). In some embodiments, the composition has no substantial difference observed in HPLC-ELSD after nanofiltration as compared to before nanofiltration. In some embodiments, the composition has no substantial difference observed in NMR after nanofiltration as compared to before nanofiltration. In some embodiments, the composition has a conductivity between 0 and 8.0 μS/cm, 0 and 4.5 μS/cm, 0 and 3 μS/cm, or between 0 and 1.5 μS/cm. In some embodiments, the composition has a pH of about 4.0 to about 8.0. In some embodiments, the composition has a viscosity of about 1.5 cP to about 10,000 cP at 20° C.

Further provided herein is composition comprising a mixture of isomerically-purified hydroxypropyl β-cyclodextrin molecules comprising: β-cyclodextrin substituted with seven hydroxypropyl groups ("DS-7"); β-cyclodextrin substituted with eight hydroxypropyl groups ("DS-8"); β-cyclodextrin substituted with nine hydroxypropyl groups ("DS-9"); β-cyclodextrin substituted with ten hydroxypropyl groups ("DS-10"); β-cyclodextrin substituted with eleven hydroxypropyl groups ("DS-11"); β-cyclodextrin substituted with twelve hydroxypropyl groups ("DS-12"); and β-cyclodextrin substituted with thirteen hydroxypropyl groups ("DS-13"), wherein the composition comprises less than 1% β-cyclodextrin substituted with six hydroxypropyl groups ("DS-6") and less than 1% β-cyclodextrin substituted with fourteen hydroxypropyl groups ("DS-14"). In some embodiments, the composition comprises less than 1% β-cyclodextrin substituted with five hydroxypropyl groups ("DS-5"), β-cyclodextrin substituted with four hydroxypropyl groups ("DS-4"), β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1"). In some embodiments, the DS-9 has the highest concentration in the mixture of isomerically-purified hydroxypropyl β-cyclodextrin molecules as compared to DS-6, DS-7, DS-8, DS-10, DS-11, DS-12, and DS-13. In some embodiments, the mixture of isomerically-purified hydroxypropyl β-cyclodextrin molecules comprises about 1% to about 7% of DS-7. In some embodiments, the mixture of isomerically-purified hydroxypropyl β-cyclodextrin molecules comprises about 16% to about 22% of DS-8. In some embodiments, the mixture of isomerically-purified hydroxypropyl β-cyclodextrin molecules comprises about 22% to about 28% of DS-9. In some embodiments, the mixture of isomerically-purified hydroxypropyl β-cyclodextrin molecules comprises about 19% to about 25% of DS-10. In some embodiments, the mixture of isomerically-purified hydroxypropyl β-cyclodextrin molecules comprises about 14% to about 20% of DS-11. In some embodiments, the mixture of isomerically-purified hydroxypropyl β-cyclodextrin molecules comprises about 5% to about 11% of DS-12. In some embodiments, the mixture of isomerically-purified hydroxypropyl β-cyclodextrin molecules comprises about 1% to about 7% of DS-13. In some embodiments, the average degree of substitution of the mixture of isomerically-purified hydroxypropyl β-cyclodextrin is about 8 to about 9. In an exemplary embodiment, the average degree of substitution of the mixture of isomerically-purified hydroxypropyl β-cyclodextrin is about 8.53. In some embodiments, about 26% to about 32% of the hydroxypropyl substitutions in the β-cyclodextrin molecules are located at the 3-O-position. In some embodiments, about 68% to about 74% of the hydroxypropyl substitutions in the β-cyclodextrin molecules are located at the 2-O— position. In an exemplary embodiment, the composition has a HPLC-CAD chromatogram of FIG. 18. In an exemplary embodiment, the HPLC-CAD mean retention time of the composition is about 13.5 minutes. In some embodiments, the composition has a −ESI-MS spectrum with peaks at about 741 m/z, about 769 m/z, about 799 m/z, about 828 m/z, about 856 m/z, about 886 m/z, and a +ESI-MS spectrum with peaks at about 773 m/z, about 803 m/z, about 833 m/z, about 860 m/z, about 889 m/z, and about 920 m/z. In some embodiments, the mixture of isomerically-purified hydroxypropyl β-cyclodextrin molecules has an ESI-MS spectrum of FIG. 19. In some embodiments, the composition has a MALDI-TOF spectrum with peaks at about 1557 m/z, about 1617 m/z, about 1676 m/z, about 1736 m/z, about 1795 m/z, about 1855 m/z, and about 1915 m/z. In an exemplary embodiment, the composition has a MALDI-TOF spectrum of FIG. 20. In an exemplary embodiment, the composition has a DEPT-edited HSQC spectrum of FIG. 17. In an exemplary embodiment, the mixture of isomerically-purified hydroxypropyl β-cyclodextrin molecules has a $^1$H NMR spectrum of FIG. 16. In some embodiments, the osmolality of the composition is about 635-695 mOs/kg. In some embodiments, the true density of the composition is about 1.096-1.098 g/cm³. In some embodiments, the composition comprises no more than 10 ppb of propylene glycol as measured by HPLC. In some embodiments, the composition comprises no more than 1 ppm propylene oxide. In some embodiments, the total amount of other unspecified impurities is less than or equal to 0.05% as measured by HPLC. In some embodiments, the composition comprises between 0 and 10 ppm chloride. In some embodiments, the composition comprises between 0 and 1 ppm chloride. In some embodiments, the composition has a conductivity between 0 and 8 μS/cm. In some embodiments, the composition is nanofiltered. In some embodiments, the nanofiltered composition has no substantial difference observed in HPLC-ELSD after nanofiltration as compared to before nanofiltration. In some embodiments, wherein the nanofiltered composition has no substantial difference observed in NMR after nanofiltration as compared to before nanofiltration.

Fraction 4 Mixture

Further provided herein is a composition comprising a mixture of isomerically-purified hydroxypropyl β-cyclodextrin molecules comprising less than 1% hydroxypropyl β-cyclodextrin with six hydroxypropyl groups ("DS-6"). In some embodiments, the hydroxypropyl β-cyclodextrin percentage is based upon area percentage from a MALDI-TOF-MS spectrum. In some embodiments, the hydroxypropyl β-cyclodextrin percentage is based upon weight percentage.

In some embodiments, the composition comprises less than 1% β-cyclodextrin substituted with five hydroxypropyl groups ("DS-5"), β-cyclodextrin substituted with four hydroxypropyl groups ("DS-4"), β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1"). In some embodiments, the mixture of isomerically-purified hydroxypropyl β-cyclodextrin molecules is free of DS-1, DS-2, DS-3, DS-4, and/or DS-5. In some embodiments, the mixture of isomerically-purified hydroxypropyl β-cyclodextrin molecules comprises about 0% to about 6% of β-cyclodextrin substituted with seven hydroxypropyl groups ("DS-7"). In some aspects, the mixture of isomerically-purified hydroxypropyl β-cyclodextrin molecules comprises about 1% to about 5% of DS-7. In some embodiments, the mixture of isomerically-purified hydroxypropyl β-cyclodextrin molecules comprises about 13% to about 19% of β-cyclodextrin substituted with eight hydroxypropyl groups ("DS-8"). In some embodiments, the mixture of isomerically-purified hydroxypropyl β-cyclodextrin molecules comprises about 14% to about 18% of DS-8. In some embodiments, the mixture of isomerically-purified hydroxypropyl β-cyclodextrin molecules comprises about 22% to about 28% of β-cyclodextrin substituted with nine hydroxypropyl groups ("DS-9"). In some aspects, the mixture of isomerically-purified hydroxypropyl β-cyclodextrin molecules comprises about 23% to about 27% of DS-9. In some embodiments, the mixture of isomerically-purified hydroxypropyl β-cyclodextrin molecules comprises about 23% to about 29% of β-cyclodextrin substituted with ten hydroxypropyl groups ("DS-10"). In some aspects, the mixture of isomerically-purified hydroxypropyl β-cyclodextrin molecules comprises about 24% to about 28% of DS-10. In some embodiments, the mixture of isomerically-purified hydroxypropyl β-cyclodextrin molecules comprises about 12% to about 18% of β-cyclodextrin substituted with eleven hydroxypropyl groups ("DS-11"). In some aspects, the mixture of isomerically-purified hydroxypropyl β-cyclodextrin molecules comprises about 13% to about 17% of DS-11. In some embodiments, the mixture of isomerically-purified hydroxypropyl β-cyclodextrin molecules comprises about 7% to about 13% of β-cyclodextrin substituted with twelve hydroxypropyl groups ("DS-12"). In some aspects, the mixture of isomerically-purified hydroxypropyl β-cyclodextrin molecules comprises about 8% to about 12% of DS-12. In some embodiments, the mixture of isomerically-purified hydroxypropyl β-cyclodextrin molecules comprises about 2% to about 8% of β-cyclodextrin substituted with thirteen hydroxypropyl groups ("DS-13"). In some aspects, the mixture of isomerically-purified hydroxypropyl β-cyclodextrin molecules comprises about 3% to about 7% of DS-13. In some embodiments, the mixture of isomerically-purified hydroxypropyl β-cyclodextrin molecules comprises about 0% to about 6% of β-cyclodextrin substituted with fourteen hydroxypropyl groups ("DS-14"). In some aspects, the mixture of isomerically-purified hydroxypropyl β-cyclodextrin molecules comprises about 1% to about 5% of DS-14. In some embodiments, the average degree of substitution of the mixture of isomerically-purified hydroxypropyl β-cyclodextrin is about 7.5 to about 8.5. In an exemplary embodiment, the average degree of substitution of the mixture of isomerically-purified hydroxypropyl β-cyclodextrin is about 8.08. In some embodiments, about 22% to about 28% of the hydroxypropyl substitutions in the hydroxypropyl β-cyclodextrin molecules are located at the 3-O— position. In some aspects, about 23% to about 27% of the hydroxypropyl substitutions in the hydroxypropyl β-cyclodextrin molecules are located at the 3-O— position. In some embodiments, about 72% to about 78% of the hydroxypropyl substitutions in the hydroxypropyl β-cyclodextrin molecules are located at the 2-O— position. In some aspects, about 73% to about 77% of the hydroxypropyl substations in the hydroxypropyl β-cyclodextrin molecules are located at the 2-O— position. In some embodiments, the concentration of the composition does not substantially change the time required for nanofiltration. In some aspects, the length of time to nanofilter the composition ranges from 1.04 to 1.20 hours per diafiltration volume (kg soln/m²-hr/L soln). In some embodiments, the nanofiltrated composition has no substantial difference observed in HPLC-ELSD after nanofiltration as compared to before nanofiltration. In some embodiments, the nanofiltrated composition has no substantial difference observed in NMR after nanofiltration as compared to before nanofiltration. In some embodiments, the composition has a conductivity between 0 and 8.0 µS/cm, 0 and 4.5 µS/cm, 0 and 3 µS/cm, or between 0 and 1.5 µS/cm. In some embodiments, the composition has a pH of about 4.0 to about 8.0. In some embodiments, the composition has a viscosity of about 1.5 cP to about 10,000 cP at 20° C.

Further provided herein is a composition comprising a mixture of isomerically-purified hydroxypropyl β-cyclodextrin molecules comprising: β-cyclodextrin substituted with seven hydroxypropyl groups ("DS-7"); β-cyclodextrin substituted with eight hydroxypropyl groups ("DS-8"); β-cyclodextrin substituted with nine hydroxypropyl groups ("DS-9"); β-cyclodextrin substituted with ten hydroxypropyl groups ("DS-10"); β-cyclodextrin substituted with eleven hydroxypropyl groups ("DS-11"); β-cyclodextrin substituted with twelve hydroxypropyl groups ("DS-12"); β-cyclodextrin substituted with thirteen hydroxypropyl groups ("DS-13"); and β-cyclodextrin substituted with fourteen hydroxypropyl groups ("DS-14"), wherein the composition comprises less than 1% β-cyclodextrin substituted with six hydroxypropyl groups ("DS-6"). In some embodiments, the composition comprises less than 1% β-cyclodextrin substituted with five hydroxypropyl groups ("DS-5"), β-cyclodextrin substituted with four hydroxypropyl groups ("DS-4"), β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1"). In some embodiments, the mixture of isomerically-purified hydroxypropyl β-cyclodextrin molecules are free of DS-1, DS-2, DS-3, DS-4, and/or DS-5. In some embodiments, the DS-9 and DS-10 each have higher concentrations in the mixture of isomerically-purified hydroxypropyl β-cyclodextrin molecules as compared to DS-7, DS-8, DS-11, DS-12, DS-13, and DS-14. In some embodiments, the DS-9 has the highest concentration in the mixture of isomerically-purified hydroxypropyl β-cyclodextrin molecules as compared to DS-7, DS-8, DS-10, DS-11, DS-12, DS-13, and DS-14. In some embodiments, the DS-10 has the highest concentration in the mixture of isomerically-purified hydroxypropyl β-cyclodextrin molecules as compared to DS-7, DS-8, DS-10, DS-11, DS-12, DS-13, and DS-14. In some embodiments, the mixture of isomerically-purified hydroxypropyl β-cyclodextrin molecules comprises about 0% to about 6% DS-7. In some embodiments, the mixture of isomerically-purified hydroxypropyl β-cyclodextrin molecules comprises about 13% to about 19% DS-8. In some embodiments, the mixture of isomerically-purified hydroxypropyl β-cyclodextrin molecules comprises about 22% to about 28% DS-9. In some embodiments, the mixture of isomerically-purified hydroxypropyl β-cyclodextrin molecules comprises about 23% to about 29% DS-10. In some embodiments, the mixture of isomerically-purified hydroxypropyl β-cyclodextrin molecules comprises about 12% to about 18% DS-11. In some embodiments, the mixture of isomerically-purified hydroxypropyl β-cyclodextrin molecules comprises about 7% to about 13% DS-12. In some embodiments, the mixture of isomerically-purified hydroxypropyl β-cyclodextrin molecules comprises about 2% to about 8% DS-13. In some embodiments, the mixture of isomerically-purified hydroxypropyl β-cyclodextrin molecules comprises about 0% to about 6% DS-14. In some embodiments, the average degree of substitution of the mixture of isomerically-purified hydroxypropyl β-cyclodextrin is about 7.5 to about 8.5. In some embodiments, about 22% to about 28% of the hydroxypropyl substitutions in the hydroxypropyl β-cyclodextrin molecules are located at the 3-O— position. In some embodiments, about 72% to about 78% of the hydroxypropyl substitutions in the β-cyclodextrin molecules are located at the 2-O— position. In an exemplary embodiment, the composition has an HPLC-CAD chromatogram of FIG. 23. In some embodiments, the HPLC-CAD mean retention time of the mixture of isomerically-purified hydroxypropyl β-cyclodextrin molecules is about 14.3 minutes. In some embodiments, the composition has a –ESI-MS spectrum with peaks at about 740 m/z, about 770 m/z, about 798 m/z, about 828 m/z, and about 857 m/z, and a +ESI-MS spectrum with peaks at about 803 m/z, about 831 m/z, about 861 m/z, about 889 m/z, and about 919 m/z. In some embodiments, the composition has a ESI-MS spectra of FIG. 24. In some embodiments, the composition has a MALDI-TOF spectrum with peaks at about 1559 m/z, about 1618 m/z, about 1678 m/z, about 1737 m/z, about 1796 m/z, about 1857 m/z, and about 1916 m/z. In an exemplary embodiment, the mixture of isomerically-purified hydroxypropyl β-cyclodextrin molecules has a MALDI-TOF-MS spectrum of FIG. 25. In an exemplary embodiment, the composition has a DEPT-edited HSQC spectrum of FIG. 22. In an exemplary embodiment, the mixture of isomerically-purified hydroxypropyl β-cyclodextrin molecules has a $^1$H NMR spectrum of FIG. 21. In some embodiments, the osmolality of the composition is about 635-695 mOs/kg. In some embodiments, the true density of the composition is about 1.096-1.098 g/cm$^3$. In some embodiments, the composition comprises no more than 10 ppb of propylene glycol as measured by HPLC. In some embodiments, the composition comprises no more than 1 ppm propylene oxide. In some embodiments, the total amount of other unspecified impurities is less than or equal to 0.05% as measured by HPLC. In some embodiments, the composition comprises between 0 and 10 ppm chloride. In some embodiments, the composition has a conductivity between 0 and 8 µS/cm. In some embodiments, the composition is nanofiltered. In some embodiments, the nanofiltrated composition has no substantial difference observed in HPLC-ELSD after nanofiltration as compared to before nanofiltration. In some embodiments, the nanofiltrated composition has no substantial difference observed in NMR after nanofiltration as compared to before nanofiltration.

Fraction 5 Mixture

Further provided herein is a composition comprising a mixture of isomerically-purified hydroxypropyl β-cyclodextrin molecules comprising less than 1% hydroxypropyl β-cyclodextrin with seven hydroxypropyl groups ("DS-7"). In some embodiments, the hydroxypropyl β-cyclodextrin percentage is based upon area percentage from a MALDI-TOF-MS spectrum. In some embodiments, the hydroxypropyl β-cyclodextrin percentage is based upon weight percentage. In some embodiments, the composition comprises less than 1% β-cyclodextrin substituted with six hydroxypropyl groups ("DS-6"), β-cyclodextrin substituted with five hydroxypropyl groups ("DS-5"), β-cyclodextrin substituted with four hydroxypropyl groups ("DS-4"), β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1"). In some embodiments, the mixture of isomerically-purified hydroxypropyl β-cyclodextrin molecules is free of DS-1, DS-2, DS-3, DS-4, DS-5, DS-5, and/or DS-6. In some embodiments, the mixture of isomerically-purified hydroxypropyl β-cyclodextrin molecules comprises about 6% to about 12% of β-cyclodextrin substituted with eight hydroxypropyl groups ("DS-8"). In some aspects, the mixture of isomerically-purified hydroxypropyl β-cyclodextrin molecules comprises about 7% to about 11% of DS-8. In some embodiments, the mixture of isomerically-purified hydroxypropyl β-cyclodextrin molecules comprises about 18% to about 24% of β-cyclodextrin substituted with nine hydroxypropyl groups ("DS-9"). In some aspects, the mixture of isomerically-purified hydroxypropyl β-cyclodextrin molecules comprises about 19% to about 23% of DS-9. In some embodiments, the mixture of isomerically-purified hydroxypropyl β-cyclodextrin molecules comprises about 24% to about 30% of β-cyclodextrin substituted with ten hydroxypropyl groups ("DS-10). In some aspects, the mixture of isomerically-purified hydroxypropyl β-cyclodextrin molecules comprises about 25% to about 29% of DS-10. In some embodiments, the mixture of isomerically-purified hydroxypropyl β-cyclodextrin molecules comprises about 18% to about 24% of β-cyclodextrin substituted with eleven hydroxypropyl groups ("DS-11"). In some aspects, the mixture of isomerically-purified hydroxypropyl β-cyclodextrin molecules comprises about 19% to about 23% of DS-11. In some embodiments, the mixture of isomerically-purified hydroxypropyl β-cyclodextrin molecules comprises about 10% to about 16% of β-cyclodextrin substituted with twelve hydroxypropyl groups ("DS-12"). In some aspects, the mixture of isomerically-purified hydroxypropyl β-cyclodextrin molecules comprises about 11% to about 15% of DS-12. In some embodiments, the mixture of isomerically-purified hydroxypropyl β-cyclodextrin molecules comprises about 4% to about 10% of β-cyclodextrin substituted with thirteen hydroxypropyl groups ("DS-13"). In some aspects, the mixture of isomerically-purified hydroxypropyl β-cyclodextrin molecules comprises about 5% to about 9% of DS-13. In some embodiments, the mixture of isomerically-purified hydroxypropyl β-cyclodextrin molecules comprises about 0% to about 6% of β-cyclodextrin substituted with fourteen hydroxypropyl groups ("DS-14"). In some aspects, the mixture of isomerically-purified hydroxypropyl β-cyclodextrin molecules comprises about 1% to about 5% of DS-14. In some embodiments, the average degree of substitution of the mixture of isomerically-purified hydroxypropyl β-cyclodextrin is about 9 to about 10. In an exemplary embodiment, the average degree of substitution of the mixture of isomerically-purified hydroxypropyl β-cyclodextrin is about 9.65. In some embodiments, about 15% to about 21% of the hydroxypropyl substitutions in the hydroxypropyl β-cyclodextrin molecules are located at the 3-O— position. In some aspects, about 16% to about 20% of the hydroxypropyl substitutions in the hydroxypropyl β-cyclodextrin molecules are located at the 3-O— position. In some embodiments, about 79% to about 85% of the hydroxypropyl substitutions in the hydroxypropyl β-cyclodextrin molecules are located at the 2-O-position. In some aspects, about 80% to about 84% of the hydroxypropyl substitutions in the hydroxypropyl β-cyclodextrin molecules are located at the 2-O— position. In some embodiments, the concentration of the composition does not substantially change the time required for nanofiltration. In some embodiments, the length of time to nanofilter the composition ranges from 1.04 to 1.20 hours per diafiltration volume (kg soln/m²·hr/L soln). In some embodiments, the composition has no substantial difference observed in HPLC-ELSD after nanofiltration as compared to before nanofiltration. In some embodiments, the composition has no substantial difference observed in NMR after nanofiltration as compared to before nanofiltration. In some embodiments, the composition has a conductivity between 0 and 8.0 μS/cm, 0 and 4.5 μS/cm, 0 and 3 μS/cm, or between 0 and 1.5 μS/cm. In some embodiments, the composition has a pH of about 4.0 to about 8.0. In some embodiments, the composition has a viscosity of about 1.5 cP to about 10,000 cP at 20° C.

Further provided herein is a composition comprising a mixture of isomerically-purified hydroxypropyl β-cyclodextrin molecules comprising: β-cyclodextrin substituted with eight hydroxypropyl groups ("DS-8"); β-cyclodextrin substituted with nine hydroxypropyl groups ("DS-9"); β-cyclodextrin substituted with ten hydroxypropyl groups ("DS-10"); β-cyclodextrin substituted with eleven hydroxypropyl groups ("DS-11"); β-cyclodextrin substituted with twelve hydroxypropyl groups ("DS-12"); β-cyclodextrin substituted with thirteen hydroxypropyl groups ("DS-13"); and β-cyclodextrin substituted with fourteen hydroxypropyl groups ("DS-14"), wherein the composition comprises less than 1% β-cyclodextrin substituted with seven hydroxypropyl groups ("DS-7"). In some embodiments, the composition comprises less than 1% β-cyclodextrin substituted with six hydroxypropyl groups ("DS-6"), 1% β-cyclodextrin substituted with five hydroxypropyl groups ("DS-5"), β-cyclodextrin substituted with four hydroxypropyl groups ("DS-4"), β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1"). In some embodiments, the mixture of isomerically-purified hydroxypropyl β-cyclodextrin molecules is free of DS-1, DS-2, DS-3, DS-4, DS-5, and/or DS-6. In some embodiments, the DS-10 has the highest concentration in the mixture of isomerically-purified hydroxypropyl β-cyclodextrin molecules as compared to DS-8, DS-9, DS-11, DS-12, DS-13, and DS-14. In some embodiments, the mixture of isomerically-purified hydroxypropyl β-cyclodextrin molecules comprises about 6% to about 12% DS-8. In some embodiments, the mixture of isomerically-purified hydroxypropyl β-cyclodextrin molecules comprises about 18% to about 24% DS-9. In some embodiments, the mixture of isomerically-purified hydroxypropyl β-cyclodextrin molecules comprises about 24% to about 30% DS-10. In some embodiments, the mixture of isomerically-purified hydroxypropyl β-cyclodextrin molecules comprises about 18% to about 24% DS-11. In some embodiments, the mixture of isomerically-purified hydroxypropyl β-cyclodextrin molecules comprises about 10% to about 16% DS-12. In some embodiments, the mixture of isomerically-purified hydroxypropyl β-cyclodextrin molecules comprises about 4% to about 10% DS-13. In some embodiments, the mixture of isomerically-purified hydroxypropyl β-cyclodextrin molecules comprises about 0% to about 6% DS-14. In some embodiments, the average degree of substitution of the mixture of isomerically-purified hydroxypropyl β-cyclodextrin is about 9 to about 10. In some embodiments, about 15% to about 21% of the hydroxypropyl substitutions in the hydroxypropyl β-cyclodextrin molecules are located at the 3-O— position. In some embodiments, about 79% to about 85% of the hydroxypropyl substitutions in the hydroxypropyl β-cyclodextrin molecules are located at the 2-O— position. In an exemplary embodiment, the composition has an HPLC-CAD chromatogram of FIG. 28. In an exemplary embodiment, the HPLC-CAD mean retention time of the mixture of isomerically-purified hydroxypropyl β-cyclodextrin molecules is about 15.4 minutes. In some embodiments, the composition has a −ESI-MS spectrum with peaks at about 770 m/z, about 798 m/z, about 828 m/z, about 857 m/z, about 885 m/z, and a +ESI-MS spectrum with peaks at about 803 m/z, about 831 m/z, about 861 m/z, about 889 m/z, and about 919 m/z. In an exemplary embodiment, the composition has a ESI-MS spectra of FIG. 29. In some embodiments, the composition has a MALDI-TOF spectrum with peaks at about 1614 m/z, about 1673 m/z, about 1733 m/z, about 1792 m/z, about 1852 m/z, about 1912 m/z, and about 1971 m/z. In an exemplary embodiment, the composition has a MALDI-TOF spectrum of FIG. 30. In an exemplary embodiment, the composition has a $^1$H-NMR spectrum of FIG. 26. In an exemplary embodiment, the composition has a DEPT-edited HSQC spectrum of FIG. 27. In some embodiments, the osmolality of the composition is about 635-695 mOs/kg. In some embodiments, the true density of the composition is about 1.096-1.098 g/cm³. In some embodiments, the composition comprises no more than 10 ppb of propylene glycol as measured by HPLC. In some embodiments, the composition comprises no more than 1 ppm propylene oxide. In some embodiments, the total amount of other unspecified impurities is less than or equal to 0.05% as measured by HPLC. In some embodiments, the composition comprises between 0 and 10 ppm chloride. In some embodiments, the composition has a conductivity between 0 and 8 μS/cm. In some embodiments, the composition is nanofiltered. In some embodiments, the nanofiltrated composition has no substantial difference observed in HPLC-ELSD after nanofiltration as compared to before nanofiltration. In some embodiments, the nanofiltrated composition has no substantial difference observed in NMR after nanofiltration as compared to before nanofiltration.

Compositions and Mixtures of the Invention

Further provided herein is an isomerically-purified composition comprising a mixture of hydroxypropyl-β-cyclodextrin molecules having the general subunit structure:

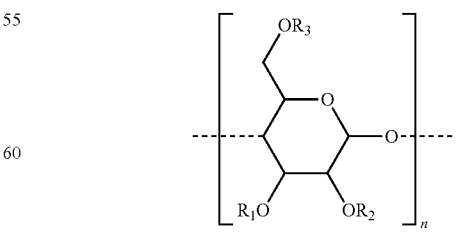

wherein n=7=m+k+y+z; m=0-7; k=0-7; y=0-7; z=0-7; $R_1$, $R_2$, and $R_3$ are each independently H, hydroxypropyl, or

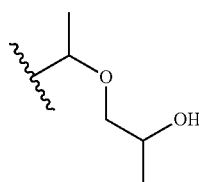

wherein m refers to the number of subunits wherein $R_1$ is not H, $R_2$ is H, and $R_3$ is H; wherein k refers to the number of subunits wherein $R_1$ is H, $R_2$ is not H, and $R_3$ is H; wherein y refers to the number of subunits wherein $R_1$ is H, $R_2$ is H, and $R_3$ is not H; wherein z refers to the number of subunits wherein $R_1$ is H, $R_2$ is H, and $R_3$ is H; and wherein $R_3$=H in at least 80% of the subunits. Those having skill in the art will appreciate that $R_1$ is located at the 3-O— position, $R_2$ is located at the 2-O— position, and $R_3$ is located at the 6-O— position of the subunit structure. In some embodiments, $R_3$=H in at least 80% of the subunits, 90% of the subunits, 95% of the subunits, 99% of the subunits, or at 100% of the subunits. In some embodiments, y=0. In some embodiments, z=0. In some embodiments, $R_1$ is not H in at least 35% of the subunits, or at least 40% of the subunits. In some embodiments, $R_1$ is not H in about 50% to about 70% of the subunits. In some embodiments, $R_1$ is not H in about 60% to about 80% of the subunits. In some embodiments, $R_1$ is not H in about 65% to about 85% of the subunits. In some embodiments, $R_1$ is not H in about 70% to about 80% of the subunits. In some embodiments, $R_2$ is not H in no more than 65% of the subunits. In some embodiments, $R_2$ is not H in about 35% to about 55% of the subunits. In some embodiments, $R_2$ is not H in about 10% to about 30% of the subunits. In some embodiments, the general subunit structure has the following stereochemistry:

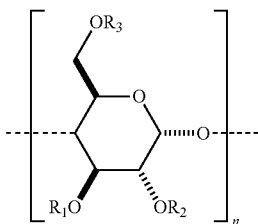

Further provided herein is an isomerically-purified composition comprising a mixture of hydroxypropyl-β-cyclodextrin molecules, wherein 0% to 5% of the hydroxypropyl-β-cyclodextrin subunits are substituted at the 6-O— position.

Further provided herein is an isomerically-purified composition comprising a mixture of hydroxypropyl-β-cyclodextrin molecules, wherein 80% to 100% of the hydroxypropyl-β-cyclodextrin subunits are substituted at the 2-O— position, the 3-O— position, or a combination thereof.

Further provided herein is an isomerically-purified composition comprising a mixture of hydroxypropyl-β-cyclodextrin molecules eluted from a Cholester HPLC column.

Further provided herein is an isomerically-purified composition comprising a 5% (w/w) mixture of hydroxypropyl-β-cyclodextrin HDS (high degree of substitution) molecules in aqueous media that yields an equilibrium solubility of cholesterol between about 0.2500 to about 0.6000 mg/ml at a temperature of 37° C. In some embodiments, the composition yields an equilibrium solubility of cholesterol between about 0.2500 to 0.2700 mg/ml at a temperature of 37° C. In some embodiments, the composition yields an equilibrium solubility of cholesterol between about 0.4000 to 0.4200 mg/ml at a temperature of 37° C. In some embodiments, the composition yields an equilibrium solubility of cholesterol between about 0.5000 to 0.5200 mg/ml at a temperature of 37° C. In some embodiments, the composition yields an equilibrium solubility of cholesterol between about 0.5400 to 0.5600 mg/ml at a temperature of 37° C. In some embodiments, the composition yields an equilibrium solubility of cholesterol between about 0.3600 to 0.3800 mg/ml at a temperature of 37° C.

Further provided herein is an isomerically-purified composition comprising a 5% (w/w) mixture of hydroxypropyl-β-cyclodextrin HDS molecules in aqueous media, wherein the mixture of hydroxypropyl-β-cyclodextrin HDS molecules is insoluble in water (e.g. insoluble at room temperature (20-25 degrees centigrade)).

Further provided herein is an isomerically-purified composition comprising a 5% (w/w) mixture of hydroxypropyl-β-cyclodextrin LDS (low degree of substitution) molecules in aqueous media that yields an equilibrium solubility of cholesterol between about 0.1700 to about 0.3200 mg/ml at a temperature of 37° C. In some embodiments, the composition yields an equilibrium solubility of cholesterol between about 0.1800 to 0.2000 mg/ml at a temperature of 37° C. In some embodiments, the composition yields an equilibrium solubility of cholesterol between about 0.1700 to 0.1900 mg/ml at a temperature of 37° C. In some embodiments, the composition yields an equilibrium solubility of cholesterol between about 0.2000 to 0.2200 mg/ml at a temperature of 37° C. In some embodiments, the composition yields an equilibrium solubility of cholesterol between about 0.2200 to 0.2400 mg/ml at a temperature of 37° C. In some embodiments, the composition yields an equilibrium solubility of cholesterol between about 0.3100 to 0.3300 mg/ml at a temperature of 37° C.

Further provided herein is an isomerically-purified composition comprising a 20% (w/w) mixture of hydroxypropyl-β-cyclodextrin molecules in aqueous media that yields an equilibrium solubility of cholesterol between about 3.2500 to about 3.7500 mg/ml at a temperature of 37° C.

Nanofiltration

Further provided herein is a composition comprising a purified mixture of β-cyclodextrin molecules substituted at one or more hydroxyl positions by hydroxypropyl groups, wherein the unpurified mixture of β-cyclodextrin molecules comprises propylene oxide monomers, propylene oxide dimers, propylene oxide trimers, and/or propylene oxide tetramers, as well as propylene glycol, and sodium chloride, and wherein at least 90% of the propylene oxide monomers, propylene oxide dimers, propylene oxide trimers, and/or propylene oxide tetramers, as well as propylene glycol, and sodium chloride content is removed after purification.

In some aspects, at least 95% of the propylene oxide monomers, propylene oxide dimers, propylene oxide trimers, and/or propylene oxide tetramers, as well as propylene glycol, and sodium chloride content is removed after purification. In some additional aspects, at least 96% to at least 99% of the propylene oxide monomers, propylene oxide dimers, propylene oxide trimers, and/or propylene oxide tetramers, as well as propylene glycol, and sodium chloride content is removed after purification.

In some aspects, at least 90% of the propylene oxide dimer and propylene oxide trimer content is removed after purification. In some additional aspects, at least 95% of the propylene oxide dimer and propylene oxide trimer content is removed after purification. In still further aspects, at least 96% to at least 99% of the propylene oxide dimer and propylene oxide trimer content is removed after purification.

In some aspects, at least 90% to at least 95% of the propylene oxide tetramer content is removed.

In preferred embodiments, the purified composition comprises no detectable amount of propylene oxide monomers, propylene oxide dimers, propylene oxide trimers, and/or propylene oxide tetramers. In other preferred embodiments, the purified composition comprises no detectable amount of propylene glycol.

In some embodiments, the purified mixture of β-cyclodextrin molecules has a solution concentration of about 25.0 wt % solids to about 35.0 wt % solids. In some aspects, the purified mixture of β-cyclodextrin molecules has a solution concentration of about 27.5 wt % solids to about 32.5 wt % solids. In preferred embodiments, the purified mixture of β-cyclodextrin molecules has a solution concentration of about 29.0 wt % solids to about 31.0 wt % solids.

Further provided herein is a method of purifying a mixture of β-cyclodextrin molecules substituted at one or more hydroxyl positions by hydroxypropyl groups, the method comprising: diluting the mixture of β-cyclodextrin molecules with water; and nanofiltering the mixture at least three times; wherein the removal efficiency (RE) of propylene oxide monomers, propylene oxide dimers, propylene oxide trimers, and/or propylene oxide tetramers, as well as propylene glycol, and sodium chloride content in the mixture of β-cyclodextrin molecules is at least 90%.

In some embodiments, the method further comprises isolating a purified mixture of β-cyclodextrin molecules having a solution concentration from about 25.0 wt % solids to about 35.0 wt % solids. In some aspects, the method further comprises isolating a purified mixture of β-cyclodextrin molecules having a solution concentration from about 27.5 wt % solids to about 32.5 wt % solids. In preferred embodiments, the method further comprises isolating a purified mixture of β-cyclodextrin molecules having a solution concentration from about 29.0 wt % solids to about 31.0 wt % solids.

In some embodiments, the mixture is nanofiltered at least four times. In some preferred embodiments, the mixture is nanofiltered at least five times.

In some embodiments, the mixture is nanofiltered at least once at a temperature from at least about 40° C. to about 50° C. In some aspects, the mixture is nanofiltered at least once at a temperature from at least about 42.5° C. to about 47.5° C. In preferred embodiments, the mixture is nanofiltered at least once at a temperature of about 45° C.

In some embodiments, the removal efficiency of propylene oxide monomers, propylene oxide dimers, propylene oxide trimers, and/or propylene oxide tetramers, as well as propylene glycol, and sodium chloride content in the purified mixture of β-cyclodextrin molecules is at least 95%. In preferred embodiments, the removal efficiency of propylene oxide monomers, propylene oxide dimers, propylene oxide trimers, and/or propylene oxide tetramers, as well as propylene glycol, and sodium chloride content in the purified mixture of β-cyclodextrin molecules is at least 96% to at least 99%.

In some embodiments, the removal efficiency of propylene oxide dimer and propylene oxide trimer content in the mixture of β-cyclodextrin molecules is at least 90%. In some aspects, the removal efficiency of propylene oxide dimer and propylene oxide trimer content in the mixture of β-cyclodextrin molecules is at least 95%. In preferred embodiments, the removal efficiency of propylene oxide dimer and propylene oxide trimer content in the mixture of β-cyclodextrin molecules is from at least 96% to at least 99%. In some embodiments, the removal efficiency of propylene oxide tetramer content in the mixture of β-cyclodextrin molecules is from at least 90% to at least 95%.

In some embodiments, the water is deionized water or 18.2 MΩ water.

In some embodiments, the nanofiltering occurs at a membrane having a surface area of at least 100 cm$^2$.

In some embodiments, the nanofiltering occurs at a pressure of about psig to about 500 psig. In some aspects, the nanofiltering occurs at a pressure of about 100 psig to about 300 psig. In some additional aspects, the nanofiltering occurs at a pressure of about 100 psig to about 200 psig. In further aspects, the nanofiltering occurs at a pressure of about 100 psig to about 150 psig. In still further aspects, the nanofiltering occurs at a pressure of about 150 psig to about 200 psig. In still further aspects, the nanofiltering occurs at a pressure of about 200 psig to about 250 psig.

In some embodiments, the nanofiltering occurs at an operating pressure effective to maintain a flux of about 200 g/(m$^2$·min) to about 250 g/(m$^2$·min). In some aspects, the nanofiltering occurs at an operating pressure effective to maintain a flux of about 200 g/(m$^2$·min) to about 225 g/(m$^2$·min). In an exemplary embodiment, the nanofiltering occurs at an operating pressure effective to maintain a flux of about 217 g/(m$^2$·min).

In some embodiments, the nanofiltering occurs at an operating pressure effective to maintain a mass flow rate of about 400 g/min to about 600 g/min. In some aspects, the nanofiltering occurs at an operating pressure effective to maintain a mass flow rate of about 450 g/min to about 550 g/min.

In some embodiments, the nanofiltering comprises a permeate generation rate of about 600 kg/hour to about 1800 kg/hour. In some aspects, the nanofiltering comprises a permeate generation rate of about 900 kg/hour to about 1500 kg/hour. In still further aspects, the nanofiltering comprises a permeate generation rate of about 1200 kg/hour to about 1500 kg/hour.

In some embodiments, the nanofiltering is accomplished with a Trisep XN45 membrane, a spiral wound membrane a flatsheet membrane, or a combination thereof. In some aspects, the Trisep XN45 membrane is selected from the group consisting of #1812, #2540, #4040, #8040, and combinations thereof.

In some embodiments, the method further comprises recirculating the permeate for nanofiltering.

In some embodiments, the method further comprises upconcentrating the mixture of β-cyclodextrin molecules after nanofiltering.

Further provided herein is a method of purifying a mixture of β-cyclodextrin molecules substituted at one or more hydroxyl positions by hydroxypropyl groups, the method comprising: diluting the mixture of hydroxypropyl beta-cyclodextrin molecules with water and nanofiltering the mixture at least three times, wherein there is no detectable amount of β-cyclodextrin molecules in the permeate following nanofiltering, and the removal efficiency (RE) of propylene oxide monomers, propylene oxide dimers, propylene oxide trimers, and/or propylene oxide tetramers, as well as propylene glycol, and sodium chloride content in the mixture of β-cyclodextrin molecules after nanofiltering the mixture at least three times is at least 90%.

In some embodiments, the composition is nanofiltered at a temperature from about 40° C. to about 50° C. and a pressure from about 100 psig to about 300 psig. In some aspects, the composition is nanofiltered at a temperature from about 42.5° C. to about 47.5° C. and a pressure from about 150 psig to about 250 psig.

In some embodiments, the composition is nanofiltered at a diafiltration flux from about 15 kg/(m²·hr) to about 35 kg/(m²·hr). In some aspects, the composition is nanofiltered at a diafiltration flux from about 20 kg/(m²·hr) to about 30 kg/(m²·hr). In some additional aspects, the composition is nanofiltered at a diafiltration flux of about 22.5 kg/(m²·hr) to about 27.5 kg/(m²·hr).

BRIEF DESCRIPTION OF THE FIGURES

FIG. 34A shows the overlaid MALDI-TOF spectra for HDS fractions 1-3, and FIG. 34B shows the overlaid MALDI-TOF spectra for HDS fractions 3-5.

DETAILED DESCRIPTION

Figure 1:
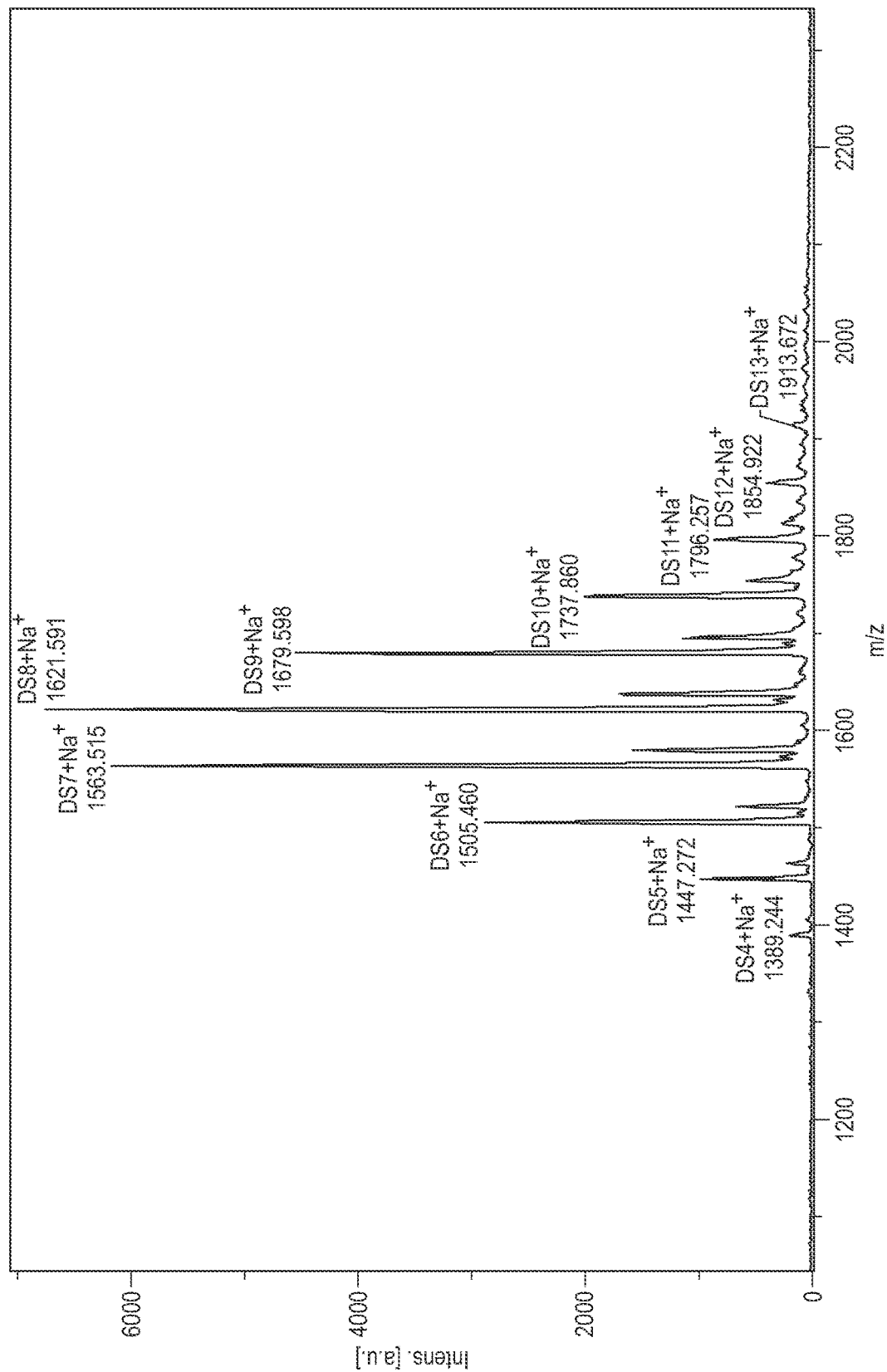
FIG. 1 is a MALDI-TOF-MS spectrum of an unfractionated mixture of hydroxypropyl-β-cyclodextrins of the present disclosure, showing the distribution of hydroxypropyl-β-cyclodextrin components with different degrees of substitution.

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure. Thus, the following description and drawings are illustrative and are not to be construed as limiting. Numerous specific details are described to provide a thorough understanding of the disclosure. However, in certain instances, well-known or conventional details are not described in order to avoid obscuring the description.

Reference to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Thus, references to one or an embodiment in the present disclosure may be references to the same embodiment or any embodiment; and such references mean at least one of the embodiments.

The terms used in this specification generally have their ordinary meanings in the art, within the context of the disclosure, and in the specific context where each term is used. Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms. The use of examples anywhere in this specification including examples of any terms discussed herein is illustrative only and is not intended to further limit the scope and meaning of the disclosure or of any example term. Likewise, the disclosure is not limited to various embodiments given in this specification.

Concentrations, amounts, and other numerical data may be expressed or presented herein in a range format. It is to be understood that such a range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 2 to about 50" should be interpreted to include not only the explicitly recited values of 2 to 50, but also include all individual values and sub-ranges within the indicated range. Thus, included in this numerical range are individual values such as 2, 2.4, 3, 3.7, 4, 5.5, 10, 10.1, 14, 15, 15.98, 20, 20.13, 23, 25.06, 30, 35.1, 38.0, 40, 44, 44.6, 45, 48, and sub-ranges such as from 1-3, from 2-4, from 5-10, from 5-20, from 5-25, from 5-30, from 5-35, from 5-40, from 5-50, from 2-10, from 2-20, from 2-30, from 2-40, from 2-50, etc. This same principle applies to ranges reciting only one numerical value as a minimum or a maximum. Furthermore, such an interpretation should apply regardless of the breadth of the range or the characteristics being described.

As used herein, the terms "a," "an," and "the" are understood to encompass the plural as well as the singular. Thus, the term "a mixture thereof" also relates to "mixtures thereof" and the term "a component" also refers to "components."

As used herein, the term "about" is used to provide flexibility to a numerical range endpoint by providing that a given value may be "a little above" or "a little below" the endpoint. For example, the endpoint may be within 10%, 8%, 5%, 3%, 2%, or 1% of the listed value. Further, for the sake of convenience and brevity, a numerical range of "about 50 mg/mL to about 80 mg/mL" should also be understood to provide support for the range of "50 mg/mL to 80 mg/mL." The endpoint may also be based on the variability allowed by an appropriate regulatory body, such as the FDA, USP, etc.

In this disclosure, "comprises," "comprising," "containing," and "having" and the like may have the meaning ascribed to them in U.S. Patent Law and may mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the composition's nature or characteristics would be permissible if present under the "consisting essentially of" language, even though not expressly recited in a list of items following such terminology. In this specification when using an open ended term, like "comprising" or "including," it is understood that direct support should be afforded also to "consisting essentially of" language as well as "consisting of" language as if stated explicitly and vice versa.

In this disclosure, when referring to methods of treatment comprising administering a product, it is understood that direct support should be afforded also to the product for use in such methods of treatment and to uses of the product in such methods of treatment, as if stated explicitly.

Additional features and advantages of the disclosure will be set forth in the description which follows, and in part will be obvious from the description, or may be learned by practice of the herein disclosed principles. The features and advantages of the disclosure may be realized and obtained by means of the instruments and combinations particularly pointed out in the appended claims. These and other features of the disclosure will become more fully apparent from the following description and appended claims or may be learned by the practice of the principles set forth herein.

In one aspect, the invention provided herein is a composition comprising a mixture of β-cyclodextrin molecules. The β-cyclodextrin molecules have a degree of substitution (DS) depending on the number of functional groups bound to the β-cyclodextrin molecule or on hydroxypropyl side chains of the β-cyclodextrin molecule. To be more specific, described herein is a composition comprising a mixture of hydroxypropyl-β-cyclodextrin molecules. The hydroxypropyl-β-cyclodextrin molecules may be substituted with one or more hydroxypropyl groups. As used herein, the term "β-cyclodextrin molecules" necessarily provides express support for "hydroxypropyl-β-cyclodextrin molecules" and therefore may be optionally substituted with the term "hydroxypropyl-β-cyclodextrin molecules" anywhere that "β-cyclodextrin molecules" is recited. As used herein, the notation "DS-N" is used to refer to a β-cyclodextrin molecule with N degrees of substitution. Thus, as a non-limiting example, DS-1 refers to a β-cyclodextrin molecule having 1 degree of substitution, such as a hydroxypropyl-β-cyclodextrin molecule substituted with one hydroxypropyl group.

The degree of substitution (e.g., the average degree of substitution) of the mixture of β-cyclodextrin molecules may be determined via matrix-assisted laser desorption/ionization-time of flight mass spectrometry (MALDI-TOF-MS). The average degree of substitution may be calculated by determining the average number of substituent groups bound to the cyclodextrin molecules in the compositions described herein. Systems and methods for performing MALDI-TOF-MS and interpreting the resultant spectra are generally known to those having ordinary skill in the art. In some embodiments, the hydroxypropyl-β-cyclodextrin percent is based upon an area percentage from a MALDI-TOF-MS spectrum. In some embodiments, the area percentage from a MALDI-TOF-MS spectrum correlates to concentration percentage (e.g., molar percentage). In some embodiments, the hydroxypropyl-β-cyclodextrin concentration percentage may be expressed as a molar percentage, weight percentage (w/w), or a volume percentage. In an exemplary embodiment, the hydroxypropyl-β-cyclodextrin percentage is a weight percentage.

General Description of the Compositions Provided Herein

Any of the compositions described herein may have the physical and chemical properties, features, or ingredients provided below, unless stated otherwise. For example, any of the compositions described herein comprising any of Fractions 1 to 5 may have the physical and chemical properties, features, or ingredients provided below, unless stated otherwise.

In some embodiments, the composition may have a true density of about 1.095 g/cm$^3$ to about 1.100 g/cm$^3$. In some aspects, the composition may have a true density of about 1.095 g/cm$^3$ to about 1.096 g/cm$^3$, about 1.096 g/cm$^3$ to about 1.097 g/cm$^3$, about 1.097 g/cm$^3$ to about 1.098 g/cm$^3$, about 1.098 g/cm$^3$ to about 1.099 g/cm$^3$, about 1.099 g/cm$^3$ to about 1.100 g/cm$^3$, about 1.095 g/cm$^3$ to about 1.097 g/cm$^3$, about 1.095 g/cm$^3$ to about 1.098 g/cm$^3$, about 1.095 g/cm$^3$ to about 1.099 g/cm$^3$, about 1.096 g/cm$^3$ to about 1.100 g/cm$^3$, about 1.097 g/cm$^3$ to about 1.100 g/cm$^3$, about 1.098 g/cm$^3$ to about 1.100 g/cm$^3$, about 1.096 g/cm$^3$ to about 1.098 g/cm$^3$, or about 1.096 g/cm$^3$ to about 1.099 g/cm$^3$. In some additional aspects, the composition may have a true density of about 1.095 g/cm$^3$, 1.096 g/cm$^3$, 1.097 g/cm$^3$, 1.098 g/cm$^3$, 1.099 g/cm$^3$, or about 1.100 g/cm$^3$. In an exemplary embodiment, the composition has a true density of about 1.096 g/cm$^3$ to about 1.098 g/cm$^3$.

In some embodiments, the composition may have an osmolality of about 600 mOs/kg to about 750 mOs/kg. In some aspects, the composition may have an osmolality of about 600 mOs/kg to about 625 mOs/kg, about 625 mOs/kg to about 650 mOs/kg, about 650 mOs/kg to about 675 mOs/kg, about 675 mOs/kg to about 700 mOs/kg, about 700 mOs/kg to about 725 mOs/kg, or about 725 mOs/kg to about 750 mOs/kg. In some additional aspects, the composition may have an osmolality of about 600 mOs/kg to about 650 mOs/kg, about 600 mOs/kg to about 675 mOs/kg, about 600 mOs/kg to about 700 mOs/kg, about 600 mOs/kg to about 725 mOs/kg, about 625 mOs/kg to about 750 mOs/kg, about 650 mOs/kg to about 750 mOs/kg, about 675 mOs/kg to about 750 mOs/kg, about 700 mOs/kg to about 750 mOs/kg, about 625 mOs/kg to about 725 mOs/kg, or about 650 mOs/kg to about 700 mOs/kg. In still further embodiments, the composition may have an osmolality of about 600 mOs/kg, 610 mOs/kg, 620 mOs/kg, 630 mOs/kg, 640 mOs/kg, 650 mOs/kg, 660 mOs/kg, 670 mOs/kg, 680 mOs/kg, 690 mOs/kg, 700 mOs/kg, 710 mOs/kg, 720 mOs/kg, 730 mOs/kg, 740 mOs/kg, or about 750 mOs/kg. In an exemplary embodiment, the composition has an osmolality of about 635 mOs/kg to about 695 mOs/kg.

In some embodiments, the composition may have a conductivity between about 0 and about 8 µS/cm. In some aspects, the composition may have a conductivity between about 0 µS/cm and about 1 µS/cm, about 1 µS/cm and about 2 µS/cm, about 3 µS/cm and about 4 µS/cm, about 4 µS/cm and about 5 µS/cm, about 5 µS/cm and about 6 µS/cm, about 6 µS/cm and about 7 µS/cm, or between about 7 µS/cm and about 8 µS/cm. In some additional embodiments, the composition may have a conductivity between about 0 µS/cm and about 1.5 µS/cm, about 0 µS/cm and about 2 µS/cm, about 0 µS/cm and about 2.5 µS/cm, about 0 µS/cm and about 3 µS/cm, about 0 and about 3.5 µS/cm, about 0 µS/cm and about 4 µS/cm, about 0 and about 4.5 µS/cm, about 0 µS/cm and about 5 µS/cm, about 0 and about 5.5 µS/cm, about 0 µS/cm and about 6 µS/cm, about 0 and about 6.5, about 0 µS/cm and about 7 µS/cm, about 0 and about 7.5, about 1 µS/cm and about 8 µS/cm, about 1.5 µS/cm and about 8 µS/cm, about 2 µS/cm and about 8 µS/cm, about 2.5 µS/cm and about 8 µS/cm, about 3 µS/cm and about 8 µS/cm, about 3.5 µS/cm and about 8 µS/cm, about 4 µS/cm and about 8 µS/cm, about 4.5 µS/cm and about 8 µS/cm, about 5 µS/cm and about 8 µS/cm, about 5.5 µS/cm and about 8 µS/cm, about 6 µS/cm and about 8 µS/cm, about 6.5 µS/cm and about 8 µS/cm, about 1 µS/cm and about 7 µS/cm, about 2 µS/cm and about 6 µS/cm, or about 3 µS/cm and about 5 µS/cm. In still further aspects, the composition may have a conductivity of about 0.5 µS/cm, 1.0 µS/cm, 1.5 µS/cm, 2.0 µS/cm, 2.5 µS/cm, 3.0 µS/cm, 3.5 µS/cm, 4.0 µS/cm, 4.5 µS/cm, 5.0 µS/cm, 5.5 µS/cm, 6.0 µS/cm, 6.5 µS/cm, 7.0 µS/cm, 7.5 µS/cm, or about 8.0 µS/cm.

In some embodiments, the composition may have a pH of about 4.0 to about 8.0; for example, the composition may have a pH of about 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, or about 8.0. The composition may have a pH in a range or sub-range comprising any of the afore-mentioned numbers, including but not limited to a pH about 4.0 to about 4.5, about 4.5 to about 5.0, about 5.0 to about 5.5, about 5.5 to about 6.0, about 6.0 to about 6.5, about 6.5 to about 7.0, about 7.0 to about 7.5, or about 7.5 to about 8.0. In some embodiments, the composition may further comprise a pH adjusting agent, such as hydrochloric acid or sodium hydroxide, to adjust the pH to a desired level. In some embodiments, the composition may further comprise a buffer. In some embodiments, the buffer may include monobasic sodium phosphate and dibasic sodium phosphate.

In some embodiments, the composition may have a viscosity measured in centipoises (cP) at 20° C. For example, the composition may have a viscosity of about 1.5 cP to about 3.0 cP at 20° C. In some embodiments, the composition may have a viscosity of about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or about 10.0 cP at 20° C. In other embodiments, the composition may have a viscosity of about 3.0 cP to about 5.0 cP, about 5.0 cP to about 10.0 cP, about 10 to about 15 cP, about 15 to about 20 cP, about 20 cP to about 25 cP, about 25 cP to about 50 cP, about 50 cP to about 80 cP, about 80 cP to about 150 cP, about 150 cP to about 250 cP, about 250 cP to about 500 cP, about 500 cP to about 1,000 cP, about 1,000 cP to about 2,000 cP, about 2,000 cP to about 3,000 cP, about 3,000 cP to about 5,000 cP, or about 5,000 cP to about 10,000 cP at 20° C.

The composition may be substantially free of impurities. Impurities include particles having a diameter of greater than or equal to 25 microns, particles having a diameter of greater than or equal to 10 microns, chloride, propylene glycol, propylene oxide, and other unspecified impurities. In some embodiments, the composition may include less than or equal to about 0.05% impurities; for example, the composition may include less than or equal to about 0.05%, 0.04%, 0.03%, 0.02%, or less than or equal to about 0.01% impurities.

In some embodiments, the composition may further comprise a container and non-visible particulate matter. In some embodiments, the composition may be provided in a container. In some embodiments, the composition may further comprise non-visible particulate matter.

In some embodiments, the composition may include less than 600 particles per container having a diameter of greater than or equal to 25 microns. In some aspects, the composition may include less than 500, less than 400, less than 300, less than 200, or less than 100 particles per container having a diameter greater than or equal to 25 microns.

In some embodiments, the composition may include less than 6000 particles per container having a diameter of greater than or equal to 10 microns. In some aspects, the composition may include less than 5000, less than 4000, less than 3000, less than 2000, less than 1000, less than 500, or less than 100 particles per container having a diameter greater than or equal to 10 microns. In another aspect, the composition may include less than 5000, less than 4000, less than 3000, less than 2000, less than 1000, less than 500, or less than 100 particles per container having a diameter greater than or equal to 10 microns, wherein the container is: 100 mL. In another aspect, the composition may include less than 5000, less than 4000, less than 3000, less than 2000, less than 1000, less than 500, less than 100, less than 50, less than 25, less than 10, less than 5, or less than 3 particles per container having a diameter greater than or equal to 10 microns, wherein the container is ≤100 mL.

In some embodiments, the composition may include no more than 10 ppb of propylene glycol. In some aspects, the composition may include no more than 9 ppb, 8 ppb, 7 ppb, 6 ppb, 5 ppb, 4 ppb, 3 ppb, 2 ppb, or no more than 1 ppb propylene glycol. In some aspects, the amount of propylene glycol in the composition may be determined by HPLC. In some additional aspects, the amount of propylene glycol in the composition may be determined by gas chromatography. In still further aspects, the amount of propylene glycol in the composition may be determined by measuring the PG/EG-ratio of propylene glycol to ethylene glycol.

In some embodiments, the composition may include no more than 1 ppm propylene oxide. In some aspects, the composition may include no more than 0.9 ppm, 0.8 ppm, 0.7 ppm, 0.6 ppm, 0.5 ppm, 0.4 ppm, 0.3 ppm, 0.2 ppm, or 0.1 ppm propylene oxide. In some aspects, the amount of propylene oxide in the composition may be determined by HPLC. In some additional aspects, the amount of propylene oxide in the composition may be determined by gas chromatography.

In some embodiments, the composition may include between about 0 ppm to about 10 ppm chloride (e.g., Cl⁻ ions). In some aspects, the composition may include about 0 ppm chloride to about 2 ppm chloride, about 2 ppm chloride to about 4 ppm chloride, about 4 ppm chloride to about 6 ppm chloride, about 6 ppm chloride to about 8 ppm chloride, or about 8 to about 10 ppm chloride. In some additional aspects, the composition may include about 0 ppm chloride to about 4 ppm chloride, about 0 ppm chloride to about 6 ppm chloride, about 0 ppm chloride to about 8 ppm chloride, about 2 ppm chloride to about 1 ppm chloride, about 4 ppm chloride to about 1 ppm chloride, or about 6 ppm chloride to about 1 ppm chloride. In still further aspects, the composition may include about 0 ppm, 1 ppm, 2 ppm, 3 ppm, 4 ppm, 5 ppm, 6 ppm, 7 ppm, 8 ppm, 9 ppm, or about 10 ppm chloride. In an exemplary embodiment, the composition may include between about 0 ppm to about 1 ppm chloride.

In some embodiments, the composition may include between about 0 ppm to about 10 ppm sodium (e.g., Na⁺ ions). In some aspects, the composition may include about 0 ppm sodium to about 2 ppm sodium, about 2 ppm sodium to about 4 ppm sodium, about 4 ppm sodium to about 6 ppm sodium, about 6 ppm sodium to about 8 ppm sodium, or about 8 to about 10 ppm sodium. In some additional aspects, the composition may include about 0 ppm sodium to about 4 ppm sodium, about 0 ppm sodium to about 6 ppm sodium, about 0 ppm sodium to about 8 ppm sodium, about 2 ppm sodium to about 1 ppm sodium, about 4 ppm sodium to about 1 ppm sodium, or about 6 ppm sodium to about 1 ppm sodium. In still further aspects, the composition may include about 0 ppm, 1 ppm, 2 ppm, 3 ppm, 4 ppm, 5 ppm, 6 ppm, 7 ppm, 8 ppm, 9 ppm, or about 10 ppm sodium. In an exemplary embodiment, the composition may include between about 0 ppm to about 1 ppm sodium.

In some embodiments, the composition may include less than or equal to 0.05% of other unspecified impurities; for example, the composition may include less than or equal to 0.05%, 0.04%, 0.03%, 0.02%, or less than or equal to 0.01% of other unspecified impurities.

In some embodiments, the composition may be stable for at least 6 months. For example, the composition may be stable for at least 3 months, 6 months, at least 7 months, at least 8 months, at least 9 months, at least 10 months, at least 11 months, at least 12 months, at least 13 months, at least 14 months, at least 15 months, at least 16 months, at least 17 months, at least 18 months, at least 24 months, or at least 36 months.

The composition may be nanofiltered. In some embodiments, the concentration of the composition does not substantially change the time required for nanofiltration. Thus, the time for nanofiltration does not increase or decrease as the concentration of the mixture of β-cyclodextrin molecules increases or decreases in the composition. In some aspects, the length of time to nanofilter the composition ranges from about 1.04 to about 1.20 hours per diafiltration volume (kg soln/m²·hr/L soln). In some aspects, the nanofiltered composition has no substantial difference observed in HPLC-ELSD after nanofiltration as compared to before nanofiltration. In some embodiments, the composition has no substantial difference observed in NMR after nanofiltration as compared to before nanofiltration.

In some embodiments, the composition may be terminally sterilized. Methods of terminal sterilization are generally well-known in the art. In some embodiments, the pH of the composition may be adjusted after terminal sterilization.

In some embodiments, the composition may include less than or equal to 10.0% w/w of water. For example, the composition may include less than or equal to 10.0% w/w, 9.5% w/w, 9.0% w/w, 8.5% w/w, 8.0% w/w, 7.5% w/w, 7.0% w/w, 6.5% w/w, 6.0% w/w, 5.5% w/w, 5.0% w/w, 4.5% w/w, 4.0% w/w, 3.5% w/w, 3.0% w/w, 2.5% w/w, 2.0% w/w, 1.5% w/w, 1.0% w/w, 0.5% w/w, or less than or equal to 0.1% w/w water.

In some embodiments, the composition may be packaged in a vial suitable for injection to a human subject in need thereof. The vial may be glass, plastic, or any other material known in the pharmaceutical art. The vial may be coated with a material such as silicon dioxide to prevent leaching from the vial into the composition.

In some embodiments, the composition may be suitable for administration to a patient in need thereof. In some embodiments, the composition may be suitable for intrathecal administration, intravenous administration, oral administration, intracerebroventricular administration, or a combination thereof (e.g., intravenous and intrathecal administration), to a patient in need thereof. In some aspects, the patient may a human, such as an adult patient or a pediatric patient. In some examples, the human patient may be an infant (e.g., less than 6 months of age) or a neonate (e.g., less than 4 weeks of age).

In some embodiments, the composition may be efficacious in treating Niemann-Pick disease. In some embodiments, the composition may be efficacious in treating Niemann-Pick disease Type C. In some embodiments, the composition may be efficacious in treating liver disease. In some embodiments, the composition may be efficacious in treating cardiovascular disease. In some embodiments, the composition may be efficacious in treating familial hypercholesterolemia. In some embodiments, the composition may be efficacious in treating cholesterol deposits.

In some embodiments, the composition may further comprise a pharmaceutical excipient or carrier. In some embodiments, the composition may further comprise a pharmaceutically acceptable diluent. Examples of pharmaceutical excipients, carriers, and diluents are well known to those having skill in the art.

In some embodiments, the composition may exhibit a lower toxicity than Trappsol® Cyclo or Kleptose®. In some embodiments, the composition may exhibit a substantially lower ototoxicity than Trappsol® Cyclo or Kleptose®. In some embodiments, the composition may exhibit substantially no ototoxicity.

Unpurified Composition

Provided herein is a composition comprising a mixture of β-cyclodextrin, wherein the composition has not been isomerically-purified. In some embodiments, the composition includes a mixture of β-cyclodextrin molecules, wherein the mixture of β-cyclodextrin molecules may include β-cyclodextrin substituted with four hydroxypropyl groups ("DS-4"), β-cyclodextrin substituted with five hydroxypropyl groups ("DS-5"), β-cyclodextrin substituted with six hydroxypropyl groups ("DS-6"), β-cyclodextrin substituted with seven hydroxypropyl groups ("DS-7"), β-cyclodextrin substituted with eight hydroxypropyl groups ("DS-8"), β-cyclodextrin substituted with nine hydroxypropyl groups ("DS-9"), β-cyclodextrin substituted with ten hydroxypropyl groups ("DS-10"), β-cyclodextrin substituted with eleven hydroxypropyl groups ("DS-11"), β-cyclodextrin substituted with twelve hydroxypropyl groups ("DS-12"), β-cyclodextrin substituted with thirteen hydroxypropyl groups ("DS-13"), and β-cyclodextrin substituted with fourteen hydroxypropyl groups ("DS-14"). In some embodiments, the composition is a clear and colorless solution.

The degree of substitution of the mixture of β-cyclodextrin molecules may be determined MALDI-TOF-MS. An exemplary MALDI-TOF-MS spectrum for a composition of the present disclosure is shown in FIG. 1. In some embodiments, the MALDI-TOF-MS spectra may include peaks at about 1389 m/z, 1447 m/z, 1505 m/z, 1564 m/z, 1622 m/z, 1680 m/z, 1738 m/z, 1796 m/z, 1855 m/z, and 1914 m/z. In an exemplary embodiment, the composition has a MALDI-TOF-MS spectrum wherein the area of DS-4 is 0.73%, DS-5 is 3.49%, the area of DS-6 is 10.66%, the area of DS-7 is 24.10%, the area of DS-8 is 26.43%, the area of DS-9 is 18.09%, the area of DS-10 is 9.39%, the area of DS-11 is 4.58%, the area of DS-12 is 1.84%, and the area of DS-13 is 0.70%.

In some embodiments, the composition may have an average degree of substitution of between about 7 to about 9; for example, the average degree of substitution may be about 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or about 9.0. In an exemplary embodiment, the average degree of substitution of the mixture of β-cyclodextrin molecules is about 7.7.

In some embodiments, the mixture of β-cyclodextrin molecules may include less than 1% of DS-4; for example, the mixture of β-cyclodextrin molecules may include about 0.9% of DS-4, about 0.8% of DS-4, about 0.7% of DS-4, about 0.6% of DS-4, about 0.5% of DS-4, about 0.4% of DS-4, about 0.3% of DS-4, about 0.2% of DS-4, or about 0.1% of DS-4. In some aspects, the mixture of β-cyclodextrin molecules may include less than 1% to about 0.9% of DS-4, about 0.9% to about 0.8% of DS-4, about 0.8% to about 0.7% of DS-4, about 0.7% to about 0.6% of DS-4, about 0.7% to about 0.6% of DS-4, about 0.6% to about 0.5% of DS-4, about 0.5% to about 0.4% of DS-4, about 0.4% to about 0.3% of DS-4, about 0.3% to about 0.2% of DS-4, about 0.2% to about 0.1% of DS-4, or less than 0.1% of DS-4. In some additional aspects, the mixture of β-cyclodextrin molecules may include less than 1% to about 0.8% of DS-4, less than 1% to about 0.7% of DS-4, less than 1% to about 0.6% of DS-4, less than 1% to about 0.5% of DS-4, less than 1% to about 0.4% of DS-4, less than 1% to about 0.3% of DS-4, less than 1% to about 0.2% of DS-4, less than 1% to about 0.1% of DS-4, about 0.9% to about 0.1% of DS-4, about 0.8% to about 0.1% of DS-4, about 0.7% to about 0.1% of DS-4, about 0.6% to about 0.1% of DS-4, about 0.5% to about 0.1% of DS-4, about 0.4% to about 0.1% of DS-4, or about 0.3% to about 0.1% of DS-4. In still further aspects, the mixture of β-cyclodextrin may include less than 1% of DS-4, less than 0.9% of DS-4, less than 0.8% of DS-4, less than 0.7% of DS-4, less than 0.6% of DS-4, less than 0.5% of DS-4, less than 0.4% of DS-4, less than 0.3% of DS-4, less than 0.2% of DS-4, or less than 0.1% of DS-4. In still further aspects, the mixture of β-cyclodextrin molecules may include about 0.001%, 0.01%, 0.05%, 0.1%, 0.2%, 0.3%, 0.4%, 0.5%, 0.6%, 0.7%, 0.8%, 0.9%, or about 1% of DS-4. In some embodiments, the amount of DS-4 in the mixture of β-cyclodextrin molecules may be determined by MALDI-TOF-MS. In an exemplary embodiment, the area of DS-4 in the MALDI-TOF-MS spectrum is 0.73%.

In some embodiments, the mixture of β-cyclodextrin molecules may include about 2% to about 5% of DS-5. In some aspects, the mixture of β-cyclodextrin molecules may include about 2% to about 2.5% of DS-5, about 2.5% to about 3% of DS-5, about 3% to about 3.5% of DS-5, about 3.5% to about 4% of DS-5, about 4% to about 4.5% of DS-5, or about 4.5% to about 5% of DS-5. In some additional aspects, the mixture of β-cyclodextrin molecules may include about 2% to about 3% of DS-5, about 2% to about 3.5% of DS-5, about 2% to about 4% of DS-5, about 2% to about 4.5% of DS-5, about 2.5% to about 5% of DS-5, about 3% t about 5% of DS-5, about 3.5% to about 5% of DS-5, about 4% of DS-5 to about 5% of DS-5, or about 3% to about 4% of DS-5. In still further aspects, the mixture of β-cyclodextrin molecules may include about 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, or about 5.0% of DS-5. In some embodiments, the amount of DS-5 in the mixture of β-cyclodextrin molecules may be determined by MALDI-TOF-MS. In an exemplary embodiment, the area of DS-5 in the MALDI-TOF-MS spectrum is 3.49%.

In some embodiments, the mixture of β-cyclodextrin molecules may include about 7% to about 13% of DS-6. In some aspects, the mixture of β-cyclodextrin molecules may include about 7% to about 7.5% of DS-6, about 7.5% to about 8% of DS-6, about 8% to about 8.5% of DS-6, about 8.5% to about 9% of DS-6, about 9% to about 9.5% of DS-6, about 9.5% to about 10% of DS-6, about 10% of DS-6 to about 10.5% of DS-6, about 10.5% to about 11% of DS-6, about 11% of DS-6 to about 11.5% of DS-6, about 11.5% to about 12% of DS-6, about 12% to about 12.5% of DS-6, or about 12.5% to about 13% of DS-6. In some additional aspects, the mixture of β-cyclodextrin molecules may include about 7% to about 8% of DS-6, about 7% to about 8.5% of DS-6, about 7% to about 9% of DS-6, about 7% to about 9.5% of DS-6, about 7% to about 10% of DS-6, about 7% to about 10.5% of DS-6, about 7% to about 11% of DS-6, about 7% to about 11.5% of DS-6, about 7% to about 12% of DS-6, about 7% to about 12.5% of DS-6, about 7.5% to about 13% of DS-6, about 8% to about 13% of DS-6, about 8.5% to about 13% of DS-6, about 9% to about 13% of DS-6, about 9.5% to about 13% of DS-6, about 10% to about 13% of DS-6, about 10.5% to about 13% of DS-6, about 11% to about 13% of DS-6, about 11.5% to about 13% of DS-6, about 12% to about 13% of DS-6, about 8% to about 12% of DS-6, or about 9% to about 11% of DS-6. In still further aspects, the mixture of β-cyclodextrin molecules may include about 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10.0%, 10.1%, 10.2%, 10.3%, 10.4%, 10.5%, 10.6%, 10.7%, 10.8%, 10.9%, 11.0%, 11.1%, 11.2%, 11.3%, 11.4%, 11.5%, 11.6%, 11.7%, 11.8%, 11.9%, 12.0%, 12.1%, 12.2%, 12.3%, 12.4%, 12.5%, 12.6%, 12.7%, 12.8%, 12.9%, or about 13.0% of DS-6. In some embodiments, the amount of DS-6 in the mixture of β-cyclodextrin molecules may be determined by MALDI-TOF-MS. In an exemplary embodiment, the area of DS-6 in the MALDI-TOF-MS spectrum is 10.66%.

In some embodiments, the mixture of β-cyclodextrin molecules may include about 21% to about 27% of DS-7. In some aspects, the mixture of β-cyclodextrin molecules may include about 21% to about 21.5% of DS-7, about 21.5% to about 22% of DS-7, about 22% to about 22.5% of DS-7, about 22.5% to about 23% of DS-7, about 23% to about 23.5% of DS-7, about 23.5% of DS-7 to about 24% of DS-7, about 24% to about 24.5% of DS-7, about 24.5% to about 25% of DS-7, about 25% to about 25.5% of DS-7, about 25.5% to about 26% of DS-7, about 26% to about 26.5% of DS-7, or about 26.5% to about 27% of DS-7. In some additional aspects, the mixture of β-cyclodextrin molecules may include about 21% to about 22% of DS-7, about 21% to about 22.5% of DS-7, about 21% to about 23% of DS-7, about 21% to about 23.5% of DS-7, about 21% to about 24% of DS-7, about 21% to about 24.5% of DS-7, about 21% to about 25% of DS-7, about 21% to about 25.5% of DS-7, about 21% to about 26% of DS-7, about 21% to about 26.5% of DS-7, about 21.5% to about 27% of DS-7, about 22% to about 27% of DS-7, 22.5% to about 27% of DS-7, about 23% to about 27% of DS-7, about 23.5% to about 27% of DS-7, about 24% to about 27% of DS-7, about 24.5% to about 27% of DS-7, about 25% to about 27% of DS-7, about 25.5% to about 27% of DS-7, about 26% to about 27% of DS-7, about 22% to about 26% of DS-7, or about 23% to about 25% of DS-7. In still further aspects, the mixture of β-cyclodextrin molecules may include about 21.0%, 21.1%, 21.2%, 21.3%, 21.4%, 21.5%, 21.6%, 21.7%, 21.8%, 21.9%, 22.0%, 22.1%, 22.2%, 22.3%, 22.4%, 22.5%, 22.6%, 22.7%, 22.8%, 22.9%, 23.0%, 23.1%, 23.2%, 23.3%, 23.4%, 23.5%, 23.6%, 23.7%, 23.8%, 23.9%, 24.0%, 24.1%, 24.2%, 24.3%, 24.4%, 24.5%, 24.6%, 24.7%, 24.8%, 24.9%, 25.0%, 25.1%, 25.2%, 25.3%, 25.4%, 25.5%, 25.6%, 25.7%, 25.8%, 25.9%, 26.0%, 26.1%, 26.2%, 26.3%, 26.4%, 26.5%, 26.6%, 26.7%, 26.8%, 26.9%, or about 27.0% of DS-7. In some embodiments, the amount of DS-7 may be determined by MALDI-TOF-MS. In an exemplary embodiment, the area of DS-7 in the MALDI-TOF-MS spectrum is 24.10%.

In some embodiments, the mixture of β-cyclodextrin molecules may include about 23% to about 29% of DS-8. In some aspects, the mixture of β-cyclodextrin molecules may include about 23% to about 23.5% of DS-8, about 23.5% to about 24% of DS-8, about 24% to about 24.5% of DS-8, about 24.5% to about 25% of DS-8, about 25% to about 25.5% of DS-8, about 25.5% to about 26% of DS-8, about 26% to about 26.5% of DS-8, about 26.5% to about 27% of DS-8, about 27% to about 27.5% of DS-8, about 27.5% to about 28% of DS-8, about 28% to about 28.5% of DS-8, or about 28.5% to about 29% of DS-8. In some additional aspects, the mixture of β-cyclodextrin molecules may include about 23% to about 24% of DS-8, about 23% to about 24.5% of DS-8, about 23% to about 25% of DS-8, about 23% to about 25.5% of DS-8, about 23% to about 26% of DS-8, about 23% to about 26.5% of DS-8, about 23% to about 27% of DS-8, about 23% to about 27.5% of DS-8, about 23% to about 28% of DS-8, about 23% to about 28.5% of DS-8, about 23.5% to about 29% of DS-8, about 24% to about 29% of DS-8, about 24.5% to about 29% of DS-8, about % to about 29% of DS-8, about 25% to about 29% of DS-8, about 25.5% to about 29% of DS-8, about 26% to about 29% of DS-8, about 26.5% to about 29% of DS-8, about 27% to about 29% of DS-8, about 27.5% to about 29% of DS-8, about 28% to about 29% of DS-8, about 24% to about 28% of DS-8, or about 25% to about 27% of DS-8. In still further aspects, the mixture of β-cyclodextrin molecules may include about 23.0%, 23.1%, 23.2%, 23.3%, 23.4%, 23.5%, 23.6%, 23.7%, 23.8%, 23.9%, 24.0%, 24.1%, 24.2%, 24.3%, 24.4%, 24.5%, 24.6%, 24.7%, 24.8%, 24.9%, 25.0%, 25.1%, 25.2%, 25.3%, 25.4%, 25.5%, 25.6%, 25.7%, 25.8%, 25.9%, 26.0%, 26.1%, 26.2%, 26.3%, 26.4%, 26.5%, 26.6%, 26.7%, 26.8%, 26.9%, 27.0%, 27.1%, 27.2%, 27.3%, 27.4%, 27.5%, 27.6%, 27.7%, 27.8%, 27.9%, 28.0%, 28.1%, 28.2%, 28.3%, 28.4%, 28.5%, 28.6%, 28.7%, 28.8%, 28.9%, or about 29.0%. In some embodiments, the amount of DS-8 in the composition may be determined by MALDI-TOF-MS. In an exemplary embodiment, the area of DS-8 in the MALDI-TOF-MS spectrum is 26.43%.

In some embodiments, the mixture of β-cyclodextrin molecules may include about 15% to about 21% of DS-9. In some aspects, the mixture of β-cyclodextrin molecules may include about 15% to about 15.5% of DS-9, about 15.5% to about 16% of DS-9, about 16% to about 16.5% of DS-9, about 16.5% to about 17% of DS-9, about 17% to about 17.5% of DS-9, about 17.5% to about 18% of DS-9, about 18% to about 18.5% of DS-9, about 18.5% to about 19% of DS-9, about 19% to about 19.5% of DS-9, about 19.5% to about 20% of DS-9, about 20% to about 20.5% of DS-9, or about 20.5% to about 21% of DS-9. In some additional aspects, the mixture of β-cyclodextrin molecules may include about 15% to about 16% of DS-9, about 15% to about 16.5% of DS-9, about 15% to about 17% of DS-9, about 15% to about 17.5% of DS-9, about 15% to about 18% of DS-9, about 15% to about 18.5% of DS-9, about 15% to about 19% of DS-9, about 15% to about 19.5% of DS-9, about 15% to about 20% of DS-9, about 15% to about 20.5% of DS-9, about 15.5% to about 21% of DS-9, about 16% to about 21% of DS-9, about 16.5% to about 21% of DS-9, about 17% to about 21% of DS-9, about 17.5% to about 21% of DS-9, about 18% to about 21% of DS-9, about 18.5% to about 21% of DS-9, about 19% to about 21% of DS-9, about 19.5% to about 21% of DS-9, about 20% to about 21% of DS-9, about 16% to about 20% of DS-9, or about 17% to about 19% of DS-9. In still further aspects, the mixture of β-cyclodextrin molecules may include about 15.0%, 15.1%, 15.2%, 15.3%, 15.4%, 15.5%, 15.6%, 15.7%, 15.8%, 15.9%, 16.0%, 16.1%, 16.2%, 16.3%, 16.4%, 16.5%, 16.6%, 16.7%, 16.8%, 16.9%, 17.0%, 17.1%, 17.2%, 17.3%, 17.4%, 17.5%, 17.6%, 17.7%, 17.8%, 17.9%, 18.0%, 18.1%, 18.2%, 18.3%, 18.4%, 18.5%, 18.6%, 18.7%, 18.8%, 18.9%, 19.0%, 19.1%, 19.2%, 19.3%, 19.4%, 19.5%, 19.6%, 19.7%, 19.8%, 19.9%, 20.0%, 20.1%, 20.2%, 20.3%, 20.4%, 20.5%, 20.6%, 20.7%, 20.8%, 20.9%, or about 21.0% of DS-9. In some embodiments, the amount of DS-9 in the composition may be determined by MALDI-TOF-MS. In an exemplary embodiment, the area of DS-9 in the MALDI-TOF-MS spectrum is 18.09%.

In some embodiments, the mixture of β-cyclodextrin molecules may include about 6% to about 12% of DS-10. In some aspects, the mixture of β-cyclodextrin molecules may include about 6% to about 6.5% of DS-10, about 6.5% to about 7% of DS-10, about 7% to about 7.5% of DS-10, about 7.5% to about 8% of DS-10, about 8% to about 8.5% of DS-10, about 8.5% to about 9% of DS-10, about 9% to about 9.5% of DS-10, about 9.5% to about 10% of DS-10, about 10% to about 10.5% of DS-10, about 10.5% to about 11% of DS-10, about 11% to about 11.5% of DS-10, or about 11.5% to about 12% of DS-10. In some additional aspects, the mixture of β-cyclodextrin molecules may include about 6% to about 7% of DS-10, about 6% to about 7.5% of DS-10, about 6% to about 8% of DS-10, about 6% to about 8.5% of DS-10, about 6% to about 9% of DS-10, about 6% to about 9.5% of DS-10, about 6% to about 10% of DS-10, about 6% to about 10.5% of DS-10, about 6% to about 11% of DS-10, about 6% to about 11.5% of DS-10, about 6.5% to about 12% of DS-10, about 7% to about 12% of DS-10, about 7.5% to about 12% of DS-10, about 8% to about 12% of DS-10, about 8.5% to about 12% of DS-10, about 9% to about 12% of DS-10, about 9.5% to about 12% of DS-10, about 10% to about 12% of DS-10, about 10.5% to about 12% of DS-10, about 11% to about 12% of DS-10, about 7% to about 11% of DS-10, or about 8% to about 10% of DS-10. In still further aspects, the mixture of β-cyclodextrin molecules may include about 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10.0%, 10.1%, 10.2%, 10.3%, 10.4%, 10.5%, 10.6%, 10.7%, 10.8%, 10.9%, 11.0%, 11.1%, 11.2%, 11.3%, 11.4%, 11.5%, 11.6%, 11.7%, 11.8%, 11.9%, or about 12.0% of DS-10. In some embodiments, the amount of DS-10 in the mixture of β-cyclodextrin molecules may be determined by MALDI-TOF-MS. In an exemplary embodiment, the area of DS-10 in the MALDI-TOF-MS spectrum is 9.39%.

In some embodiments, the mixture of β-cyclodextrin molecules may include about 2% to about 6% of DS-11. In some aspects, the mixture of β-cyclodextrin molecules may include about 2% to about 2.5% of DS-11, about 2.5% to about 3% of DS-11, about 3% to about 3.5% of DS-11, about 3.5% to about 4% of DS-11, about 4% to about 4.5% of DS-11, about 4.5% to about 5% of DS-11, about 5% to about 5.5% of DS-11, or about 5.5% to about 6% of DS-11. In some additional aspects, the mixture of β-cyclodextrin molecules may include about 2% to about 3% of DS-11, about 2% to about 3.5% of DS-11, about 2% to about 4% of DS-11, about 2% to about 4.5% of DS-11, about 2% to about 5% of DS-11, about 2% to about 5.5% of DS-11, about 2.5% to about 6% of DS-11, about 3% to about 6% of DS-11, about 3.5% to about 6% of DS-11, about 4% to about 6% of DS-11, about 4.5% to about 6% of DS-11, about 5% to about 6% of DS-11, or about 3% to about 5% of DS-11. In still additional aspects, the mixture of β-cyclodextrin molecules may include about 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, or about 6.0% of DS-11. In some embodiments, the amount of DS-11 in the mixture of β-cyclodextrin molecules may be determined by MALDI-TOF-MS. In an exemplary embodiment, the area of DS-11 in the MALDI-TOF-MS spectrum is 4.58%.

In some embodiments, the mixture of β-cyclodextrin molecules may include about 0.5% to about 4% of DS-12. In some aspects, the mixture of β-cyclodextrin molecules may include about 0.5% to about 1% of DS-12, about 1% to about 1.5% of DS-12, about 1.5% of DS-12 to about 2% of DS-12, about 2% to about 2.5% of DS-12, about 2.5% of DS-12 to about 3% of DS-12, about 3% to about 3.5% of DS-12, or about 3.5% of DS-12 to about 4% of DS-12. In some additional aspects, the mixture of β-cyclodextrin molecules may include about 0.5% to about 1.5% of DS-12, about 0.5% to about 2% of DS-12, about 0.5% to about 2.5% of DS-12, about 0.5% to about 3% of DS-12, about 0.5% to about 3.5% of DS-12, about 1% to about 4% of DS-12, about 1.5% to about 4% of DS-12, about 2% to about 4% of DS-12, about 2.5% to about 4% of DS-12, about 3% to about 4% of DS-12, or about 1% to about 3% of DS-12. In still further aspects, the mixture of β-cyclodextrin molecules may include about 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, or about 4.0%. In some embodiments, the amount of DS-12 in the mixture of β-cyclodextrin molecules may be determined by MALDI-TOF-MS. In an exemplary embodiment, the area of DS-12 in the MALDI-TOF-MS spectrum is 1.84%.

In some embodiments, the mixture of β-cyclodextrin molecules may include less than 1% of DS-13; for example, the mixture of β-cyclodextrin molecules may include about 0.9% of DS-13, about 0.8% of DS-13, about 0.7% of DS-13, about 0.6% of DS-13, about 0.5% of DS-13, about 0.4% of DS-13, about 0.3% of DS-13, about 0.2% of DS-13, or about 0.1% of DS-13. In some aspects, the mixture of β-cyclodextrin molecules may include less than 1% to about 0.9% of DS-13, about 0.9% to about 0.8% of DS-13, about 0.8% to about 0.7% of DS-13, about 0.7% to about 0.6% of DS-13, about 0.7% to about 0.6% of DS-13, about 0.6% to about 0.5% of DS-13, about 0.5% to about 0.4% of DS-13, about 0.4% to about 0.3% of DS-13, about 0.3% to about 0.2% of DS-13, about 0.2% to about 0.1% of DS-13, or less than 0.1% of DS-13. In some additional aspects, the mixture of β-cyclodextrin molecules may include less than 1% to about 0.8% of DS-13, less than 1% to about 0.7% of DS-13, less than 1% to about 0.6% of DS-13, less than 1% to about 0.5% of DS-13, less than 1% to about 0.4% of DS-13, less than 1% to about 0.3% of DS-13, less than 1% to about 0.2% of DS-13, less than 1% to about 0.1% of DS-13, about 0.9% to about 0.1% of DS-13, about 0.8% to about 0.1% of DS-13, about 0.7% to about 0.1% of DS-13, about 0.6% to about 0.1% of DS-13, about 0.5% to about 0.1% of DS-13, about 0.4% to about 0.1% of DS-13, or about 0.3% to about 0.1% of DS-13. In still further aspects, the mixture of β-cyclodextrin may include less than 1% of DS-13, less than 0.9% of DS-13, less than 0.8% of DS-13, less than 0.7% of DS-13, less than 0.6% of DS-13, less than 0.5% of DS-13, less than 0.4% of DS-13, less than 0.3% of DS-13, less than 0.2% of DS-13, or less than 0.1% of DS-13. In some embodiments, the amount of DS-13 in the mixture of β-cyclodextrin molecules may be determined by MALDI-TOF-MS. In an exemplary embodiment, the area of DS-13 in the MALDI-TOF-MS spectrum is 0.70%.

In some embodiments, the composition may include less than than 1% of DS-14; for example, the mixture of β-cyclodextrin molecules may include about 0.9% of DS-14, about 0.8% of DS-14, about 0.7% of DS-14, about 0.6% of DS-14, about 0.5% of DS-14, about 0.4% of DS-14, about 0.3% of DS-14, about 0.2% of DS-14, or about 0.1% of DS-14. In some aspects, the mixture of β-cyclodextrin molecules may include less than 1% to about 0.9% of DS-14, about 0.9% to about 0.8% of DS-14, about 0.8% to about 0.7% of DS-14, about 0.7% to about 0.6% of DS-14, about 0.7% to about 0.6% of DS-14, about 0.6% to about 0.5% of DS-14, about 0.5% to about 0.4% of DS-14, about 0.4% to about 0.3% of DS-14, about 0.3% to about 0.2% of DS-14, about 0.2% to about 0.1% of DS-14, or less than 0.1% of DS-14. In some additional aspects, the mixture of β-cyclodextrin molecules may include less than 1% to about 0.8% of DS-14, less than 1% to about 0.7% of DS-14, less than 1% to about 0.6% of DS-14, less than 1% to about 0.5% of DS-14, less than 1% to about 0.4% of DS-14, less than 1% to about 0.3% of DS-14, less than 1% to about 0.2% of DS-14, less than 1% to about 0.1% of DS-14, about 0.9% to about 0.1% of DS-14, about 0.8% to about 0.1% of DS-14, about 0.7% to about 0.1% of DS-14, about 0.6% to about 0.1% of DS-14, about 0.5% to about 0.1% of DS-14, about 0.4% to about 0.1% of DS-14, or about 0.3% to about 0.1% of DS-14. In still further aspects, the mixture of β-cyclodextrin may optionally include less than 1% of DS-14, less than 0.9% of DS-14, less than 0.8% of DS-14, less than 0.7% of DS-14, less than 0.6% of DS-14, less than 0.5% of DS-14, less than 0.4% of DS-14, less than 0.3% of DS-14, less than 0.2% of DS-14, or less than 0.1% of DS-4. In still further aspects, the mixture of β-cyclodextrin molecules may optionally include about 0.001%, 0.01%, 0.05%, 0.1%, 0.2%, 0.3%, 0.4%, 0.5%, 0.6%, 0.7%, 0.8%, 0.9%, or about 1% of DS-14. In some embodiments, the amount of DS-14 in the mixture of β-cyclodextrin molecules may be determined by MALDI-TOF-MS. In some embodiments, DS-14 is absent from the composition.

In an exemplary embodiment, the composition includes a mixture of β-cyclodextrin molecules, wherein the mixture of β-cyclodextrin molecules includes DS-4, DS-5, DS-6, DS-7, DS-8, DS-9, DS-10, DS-11, DS-12, DS-13, and DS-14, wherein the mixture of β-cyclodextrin molecules includes less than 1% of DS-1, DS-2, DS-3, and DS-4.

The mixture of β-cyclodextrin molecules may be characterized using proton nuclear magnetic resonance spectroscopy ($^1$H-NMR). Methods of performing $^1$H-NMR and interpreting the resultant spectra are generally well-known to those having ordinary skill in the art. In some embodiments, the composition may have a $^1$H-NMR spectrum that includes at least one peak at about 5.0-5.4 ppm corresponding to anomeric protons of the β-cyclodextrin molecules, at least one peak at about 3.2-4.2 ppm corresponding to protons within a core region of the β-cyclodextrin molecules, and at least one peak at about 1.0-1.2 ppm corresponding to methyl protons of side chains of the β-cyclodextrin molecules. An exemplary $^1$H-NMR spectrum is provided in FIG. 2.

Figure 3:
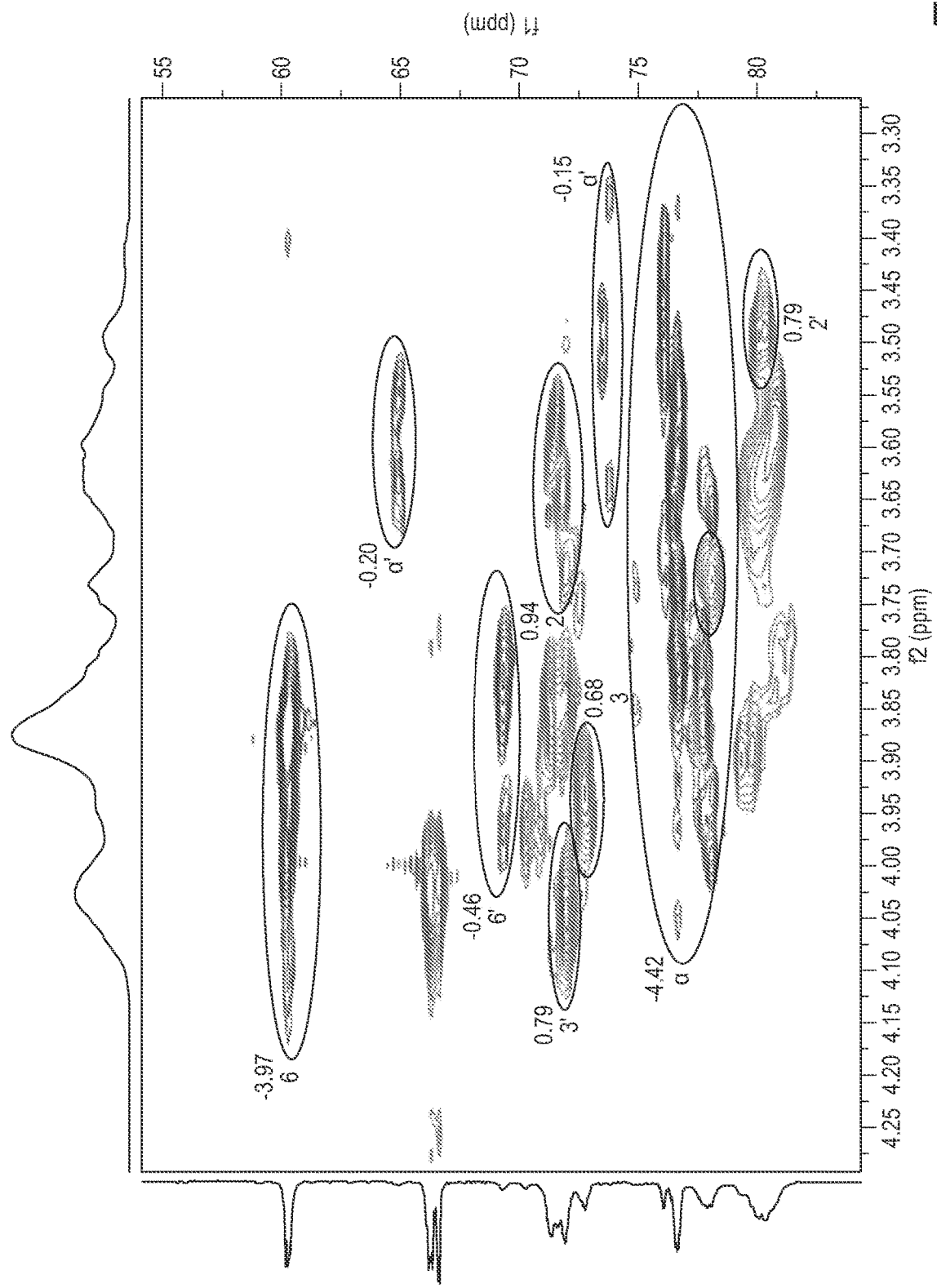
FIG. 3 is a DEPT-ed HSQC spectrum of an unfractionated mixture of hydroxypropyl-β-cyclodextrins of the present disclosure.

The mixture of β-cyclodextrin molecules may be substituted at one or more of the 2-O— position, the 3-O— position, or at the 6-O— position on each of the cyclodextrin subunits. Additionally, the mixture of β-cyclodextrin molecules may be substituted on one side chains emanating from one or more of the above positions. This pattern of substitution may be qualitatively determined using DEPT-ed heteronuclear single quantum coherence (DEPT-ed HSQC). Methods of performing DEPT-ed HSQC and interpreting the resultant spectra are generally well-known to those having ordinary skill in the art. An exemplary DEPT-ed HSQC spectrum for the mixture of β-cyclodextrins of the present disclosure is provided in FIG. 3.

In some embodiments, the mixture of β-cyclodextrin molecules may be substituted at the 2-O— position at a rate of about 35% to about 55%; that is, about 35% to about 55% of the 2-O— positions in the β-cyclodextrin molecules are substituted. In some aspects, the mixture of β-cyclodextrin molecules may be substituted at the 2-O-position at a rate of about 35% to about 40%, about 40% to about 45%, about 45% to about 50%, or about 50% to about 55%. In some additional aspects, the mixture of β-cyclodextrin molecules may be substituted at the 2-O— position at a rate of about 35% to about 45%, about 35% to about 50%, about 40% to about 55%, about 45% to about 55%, or about 40% to about 50%. In still further aspects, the mixture of β-cyclodextrin molecules may be substituted at the 2-O— position at a rate of about 35%, 36%, 37%, 38%, 39%, 40%, 41%, 42%, 43%, 44%, 45%, 46%, 47%, 48%, 49%, 50%, 51%, 52%, 53%, 54%, or about 55%. In some embodiments, the mixture of β-cyclodextrin molecules may be substituted at the 2-O— position at a rate of about 46%.

In some embodiments, the mixture of β-cyclodextrin molecules may be substituted at the 3-O— position at a rate of about 45% to about 65%. In some aspects, the mixture of β-cyclodextrin molecules may be substituted at the 3-O— position at a rate of about 45% to about 50%, about 50% to about 55%, about 55% to about 60%, or about 60% to about 65%. In some additional aspects, the mixture of β-cyclodextrin molecules may be substituted at the 3-O— position at a rate of about 45% to about 55%, about 45% to about 60%, about 50% to about 65%, about 55% to about 65%, or about 50% to about 60%. In still further embodiments, the mixture of β-cyclodextrin molecules may be substituted at the 3-O— position at a rate of about 45%, 46%, 47%, 48%, 49%, 50%, 51%, 52%, 53%, 54%, 55%, 56%, 57%, 58%, 59%, 60%, 61%, 62%, 63%, 64%, or about 65%. In some embodiments, the mixture of β-cyclodextrin molecules may be substituted at the 3-O— position at a rate of about 54%.

In some embodiments, the mixture of β-cyclodextrin molecules may be substituted at the 6-O— position at a rate of about 0% to about 20%. In some aspects, the mixture of β-cyclodextrin molecules may be substituted at the 6-O— position at a rate of about 0% to about 5%, about 5% to about 10%, about 10% to about 15%, or about 15% to about 20%. In some additional aspects, the β-cyclodextrin molecules may be substituted at the 6-O— position at a rate of about 0% to about 10%, about 0% to about 15%, about 5% to about 20%, about 10% to about 20%, or about 5% to about 15%. In still further aspects, the β-cyclodextrin molecules may be substituted at the 6-O— position at a rate of about 0%, 1%, 2%, 3%, 4%, 5%, 6%, 7%, 8%, 9%, 10%, 11%, 12%, 13%, 14%, 15%, 16%, 17%, 18%, 19%, or about 20%. In some embodiments, the β-cyclodextrin molecules may be substituted at the 6-O— position at a rate of about 10%.

In some embodiments, about 4-10% of the hydroxypropyl substituents are in an oligomerized state. For example, hydroxypropyl substituents in an oligomerized state may have the following formula:

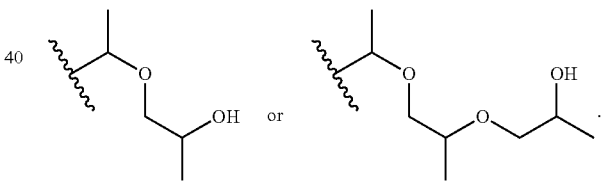

In some aspects, the percentage of hydroxypropyl substituents in an oligomerized state may be about 4% to about 5%, about 5% to about 6%, about 6% to about 7%, about 7% to about 8%, about 8% to about 9%, or about 9% to about 10%. In some additional aspects, the percentage of hydroxypropyl substituents in an oligomerized state may be about 4% to about 6%, about 4% to about 7%, about 4% to about 8%, about 4% to about 9%, about 5% to about 10%, about 6% to about 10%, about 7% to about 10%, about 8% to about 10%, about 5% to about 9%, or about 6% to about 8%. In an exemplary embodiment, about 7% of the hydroxypropyl substituents are in an oligomerized state.

Figure 4:
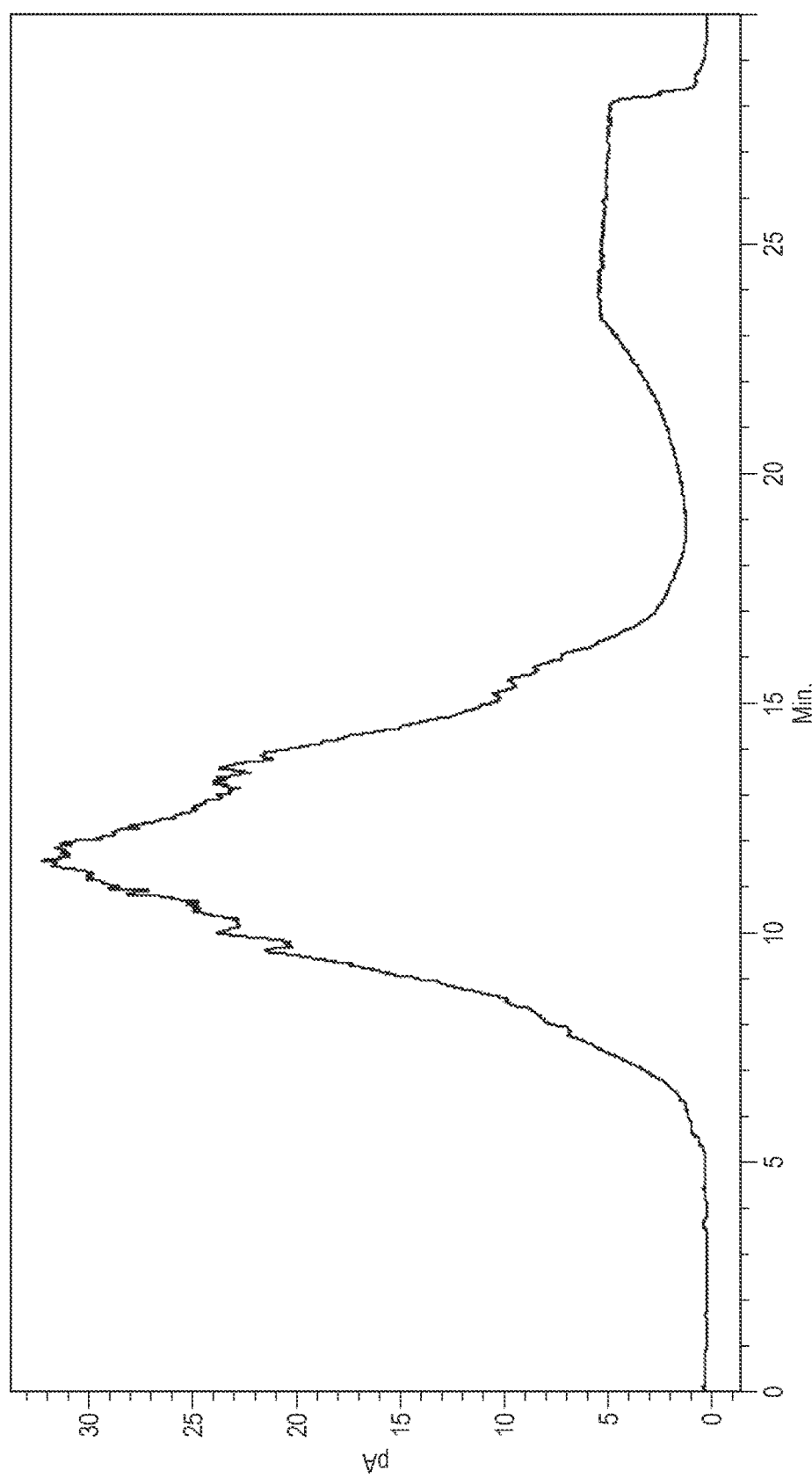
FIG. 4 is an HPLC-CAD chromatogram of an unfractionated mixture of hydroxypropyl-β-cyclodextrins of the present disclosure.

The composition may be characterized via HPLC-CAD by using methods known in the art. An exemplary HPLC-CAD chromatogram is shown in FIG. 4. In some embodiments, the mean retention time of the composition may be about 11 minutes to about 13 minutes; for example, the mean retention time may be about 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, or about 13.0 minutes. In an exemplary embodiment, the mean retention time is about 12 minutes.

Further provided herein is a composition comprising a mixture of beta-cyclodextrin molecules substituted at one or more hydroxyl positions by hydroxypropyl groups, wherein: the mixture comprises less than 0.05% unsubstituted beta-cyclodextrin ("DS-0") and less than 0.05% DS-1. In some embodiments, the composition has an average degree of substitution of about 6.02 to about 7.98. The average degree of substitution may be determined by $^1$H-NMR. In some embodiments, the amount of DS-0 and DS-1 is determined by the peak height of an electrospray MS spectrum.

In some embodiments, the composition may have a pH of between about 6.0 and about 7.9. In some aspects, the composition may have a pH of about 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, or about 7.9. Preferably, the composition has a pH of between about 7.1 and 7.7, more preferably between about 7.3 and 7.5.

In some embodiments, the composition may be purified by absorption chromatography alumina, solvent precipitation, or a combination thereof or by other methods known to those having ordinary skill in the art.

Further provided herein is a method of preparing a purified mixture of β-cyclodextrin suitable for intrathecal, intravenous, oral, or intracerebroventricular to a patient in need thereof. The method includes nanofiltrating a β-cyclodextrin to achieve a purified mixture of β-cyclodextrin molecules substituted at one or more hydroxyl positions by hydroxypropyl groups, and then adjusting the pH of the nanofiltrated purified mixture of β-cyclodextrin to achieve a pH of about 6.0 to about 7.8. The mixture may include less than 0.05% DS-0 and less than 0.05% DS-1. The mixture may have an average degree of substitution of about 6.02-7.98. The pH may be adjusted with sodium hydroxide, such as 0.1 M sodium hydroxide.

Further provided herein is a method of treating Niemann-Pick disease comprising administering to a patient in need thereof a therapeutically effective amount of a composition comprising a mixture of β-cyclodextrin molecules substituted at one or more hydroxyl positions by hydroxypropyl groups, wherein: the mixture comprises less than 0.05% unsubstituted beta-cyclodextrin ("DS-0") and less than 0.05% DS-1. Further provided herein is a composition comprising a mixture of β-cyclodextrin molecules substituted at one or more hydroxyl positions by hydroxypropyl groups for use in a method of treating Niemann-Pick disease comprising administering to a patient in need thereof a therapeutically effective amount of the composition, wherein the mixture comprises less than 0.05% unsubstituted beta-cyclodextrin ("DS-0") and less than 0.05% DS-1.

Further provided herein is a method of treating Niemann-Pick disease Type C comprising administering to a patient in need thereof a therapeutically effective amount of a composition comprising a mixture of β-cyclodextrin molecules substituted at one or more hydroxyl positions by hydroxypropyl groups, wherein: the mixture comprises less than 0.05% unsubstituted beta-cyclodextrin ("DS-0") and less than 0.05% DS-1. Further provided herein is a composition comprising a mixture of β-cyclodextrin molecules substituted at one or more hydroxyl positions by hydroxypropyl groups for use in a method of treating Niemann-Pick disease Type C comprising administering to a patient in need thereof a therapeutically effective amount of the composition, wherein the mixture comprises less than 0.05% unsubstituted beta-cyclodextrin ("DS-0") and less than 0.05% DS-1.

Further provided herein is a method of treating liver disease comprising administering to a patient in need thereof a therapeutically effective amount of a composition comprising a mixture of β-cyclodextrin molecules substituted at one or more hydroxyl positions by hydroxypropyl groups, wherein: the mixture comprises less than 0.05% unsubstituted beta-cyclodextrin ("DS-0") and less than 0.05% DS-1. Further provided herein is a composition comprising a mixture of β-cyclodextrin molecules substituted at one or more hydroxyl positions by hydroxypropyl groups for use in a method of treating liver disease comprising administering to a patient in need thereof a therapeutically effective amount of the composition, wherein the mixture comprises less than 0.05% unsubstituted beta-cyclodextrin ("DS-0") and less than 0.05% DS-1.

Further provided herein is a method of treating cardiovascular disease comprising administering to a patient in need thereof a therapeutically effective amount of a composition comprising a mixture of β-cyclodextrin molecules substituted at one or more hydroxyl positions by hydroxypropyl groups, wherein: the mixture comprises less than 0.05% unsubstituted beta-cyclodextrin ("DS-0") and less than 0.05% DS-1. Further provided herein is a composition comprising a mixture of β-cyclodextrin molecules substituted at one or more hydroxyl positions by hydroxypropyl groups for use in a method of treating cardiovascular disease comprising administering to a patient in need thereof a therapeutically effective amount of the composition, wherein the mixture comprises less than 0.05% unsubstituted beta-cyclodextrin ("DS-0") and less than 0.05% DS-1.

Further provided herein is a method of treating familial hypercholesterolemia comprising administering to a patient in need thereof a therapeutically effective amount of a composition comprising a mixture of β-cyclodextrin molecules substituted at one or more hydroxyl positions by hydroxypropyl groups, wherein: the mixture comprises less than 0.05% unsubstituted beta-cyclodextrin ("DS-0") and less than 0.05% DS-1. Further provided herein is a composition comprising a mixture of β-cyclodextrin molecules substituted at one or more hydroxyl positions by hydroxypropyl groups for use in a method of treating familial hypercholesterolemia comprising administering to a patient in need thereof a therapeutically effective amount of the composition, wherein the mixture comprises less than 0.05% unsubstituted beta-cyclodextrin ("DS-0") and less than 0.05% DS-1.

Further provided herein is a method of treating cholesterol deposits comprising administering to a patient in need thereof a therapeutically effective amount of a composition comprising a mixture of β-cyclodextrin molecules substituted at one or more hydroxyl positions by hydroxypropyl groups, wherein: the mixture comprises less than 0.05% unsubstituted beta-cyclodextrin ("DS-0") and less than 0.05% DS-1. Further provided herein is a composition comprising a mixture of β-cyclodextrin molecules substituted at one or more hydroxyl positions by hydroxypropyl groups for use in a method of treating cholesterol deposits comprising administering to a patient in need thereof a therapeutically effective amount of the composition, wherein the mixture comprises less than 0.05% unsubstituted beta-cyclodextrin ("DS-0") and less than 0.05% DS-1.

In some embodiments, the method may include administering about 50 mg to about 2000 mg of the β-cyclodextrin to the patient. In some aspects, the method may include administering about 50 mg to about 100 mg, about 100 mg to about 250 mg, about 250 mg to about 500 mg, about 500 mg to about 750 mg, about 750 mg to about 1000 mg, about 1000 mg to about 1250 mg, about 1250 mg to about 1500 mg, about 1500 mg to about 1750 mg, or about 1750 mg to about 2000 mg of the β-cyclodextrin to the patient. In some additional aspects, the method may include administering about 50 mg to about 250 mg, about 50 mg to about 500 mg, about 50 mg to about 750 mg, about 50 mg to about 1000 mg, about 50 mg to about 1250 mg, about 50 mg to about 1500 mg, about 50 mg to about 1750 mg, about 100 mg to about 2000 mg, about 250 mg to about 2000 mg, about 500 mg to about 2000 mg, about 750 mg to about 2000 mg, about 1000 mg to about 2000 mg, about 1250 mg to about 2000 mg, or about 1500 mg to about 2000 mg of the β-cyclodextrin to the patient. In an exemplary embodiment, the method includes administering about 50 mg to about 300 mg of the β-cyclodextrin to the patient.

In some embodiments, the method may include administering the composition at 1-day, 2-day, or 3-day intervals. In other embodiments, the method may include administering the composition at least once every week. In still further embodiments, the method may include administering the composition once every two weeks.

In some embodiments, the method includes intravenously administering about 200 mg/kg to about 4100 mg/kg of the β-cyclodextrin to the patient. In some aspects, the method includes intravenously administering about 200 mg/kg to about 500 mg/kg, about 500 mg/kg to about 1000 mg/kg, about 1000 mg/kg to about 1500 mg/kg, about 1500 mg/kg to about 2000 mg/kg, about 2000 mg/kg to about 2500 mg/kg, about 2500 mg/kg to about 3000 mg/kg, about 3000 mg/kg to about 3500 mg/kg, or about 3500 mg/kg to about 4100 mg/kg. In some additional aspects, the method includes intravenously administering about 200 mg/kg to about 1000 mg/kg, about 200 mg/kg to about 1500 mg/kg, about 200 mg/kg to about 2000 mg/kg, about 200 mg/kg to about 2500 mg/kg, about 200 mg/kg to about 3000 mg/kg, about 200 mg/kg to about 3500 mg/kg, about 500 mg/kg to about 4100 mg/kg, about 1000 mg/kg to about 4100 mg/kg, about 1500 mg/kg to about 4100 mg/kg, about 2000 mg/kg to about 4100 mg/kg, about 2500 mg/kg to about 4100 mg/kg, or about 3000 mg/kg to about 4100 mg/kg.

In some embodiments, the administration may occur within about 4 hours. For example, the administration may occur within 4 hours, within 3 hours, within 2 hours, within 1 hour, or within 30 minutes. In some embodiments, the duration of the administration (preferably the intravenous administration) may be about 4 hours or less. For example, the duration of the administration be about 4 hours or less, about 3 hours or less, about 2 hours or less, about 1 hour or less, or about 30 minutes or less.

In some embodiments, the administration may result in the lowering of one or more lipids by 75%±5%, 80%±5%, 85%±5%, 90%±5%, or 95%±5%. In some embodiments, the administration may be sufficient to modulate the level in plasma of one or more of 7-ketocholesterol, 7β-hydroxycholesterol, 24S-hydroxycholesterol, 25-hydroxycholesterol, 27-hydroxycholesterol, and cholestane-3β,5α,6β-triol.

In some embodiments, the administration may be sufficient to maintain or reduce one or more domain scores of the NPC Severity Scale selected from: ambulation, fine motor skills, cognition, speech, swallowing, eye movement, memory, hearing, and seizures. The NPC Severity Scale and methods of using the same are known to those having ordinary skill in the art.

In some embodiments, the administration may prevent the progression of NPC as compared with no administration or with administration of a placebo.

Fractionation

The unfractionated composition described above may be isomerically purified by the purification methods described below.

Without being bound by theory, isomers of hydroxypropyl-β-cyclodextrin differ from each other, their starting materials (β-cyclodextrin), and their coproduct (propylene glycol) by their ability to form non-covalent inclusion complexes with hydrophobic complexes. Thus, the inventors created an inclusion-assisted HPLC method to separate the isomers of hydroxypropyl-β-cyclodextrin and to separate other components from the composition. Inclusion-assisted HPLC methods are generally known and described in the art. In the inclusion-assisted HPLC methods of the present invention, hydrophobic species may be grafted to a silica surface in the stationary phase of the HPLC. Components which are unable to form inclusion complexes (e.g., propylene glycol and hydroxypropyl-β-cyclodextrin degradation products) or are only able to form weak inclusion complexes (e.g., unsubstituted β-cyclodextrin or DS-1) with the silica-grafted species elute with no retention or low retention times. Components forming stronger inclusion complexes elute with a higher retention time (DS-2, DS-3, DS-4, etc.).

Provided herein is a method for isomerically purifying a mixture of hydroxypropyl-β-cyclodextrin molecules, wherein the method includes separating the hydroxypropyl-β-cyclodextrin molecules through high performance liquid chromatography (HPLC). The columns used to isomerically purify the mixture of hydroxypropyl-β-cyclodextrin molecules are chromatography columns having cholesteryl moieties immobilized on the surface of the silica gel (also referred to herein as "Cholester HPLC" columns). This allows for inclusion-type interactions between the immobilized cholesteryl moieties and the cyclodextrin cavities, resulting in the separation of β-cyclodextrin and propylene glycol from hydroxypropyl-β-cyclodextrin isomers into subfractions. The cholesteryl moieties immobilized on the surface of the silica gel (the stationary phase of the "Cholester HPLC" column) may include the following:

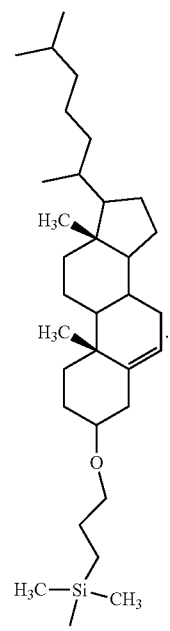 [SMILES: CC(C)CCCC(C)C1CCC2C3CC=C4CC(OCCC[Si](C)(C)C)CC[C@]4(C)C3CC[C@]12C]

Figure 5:
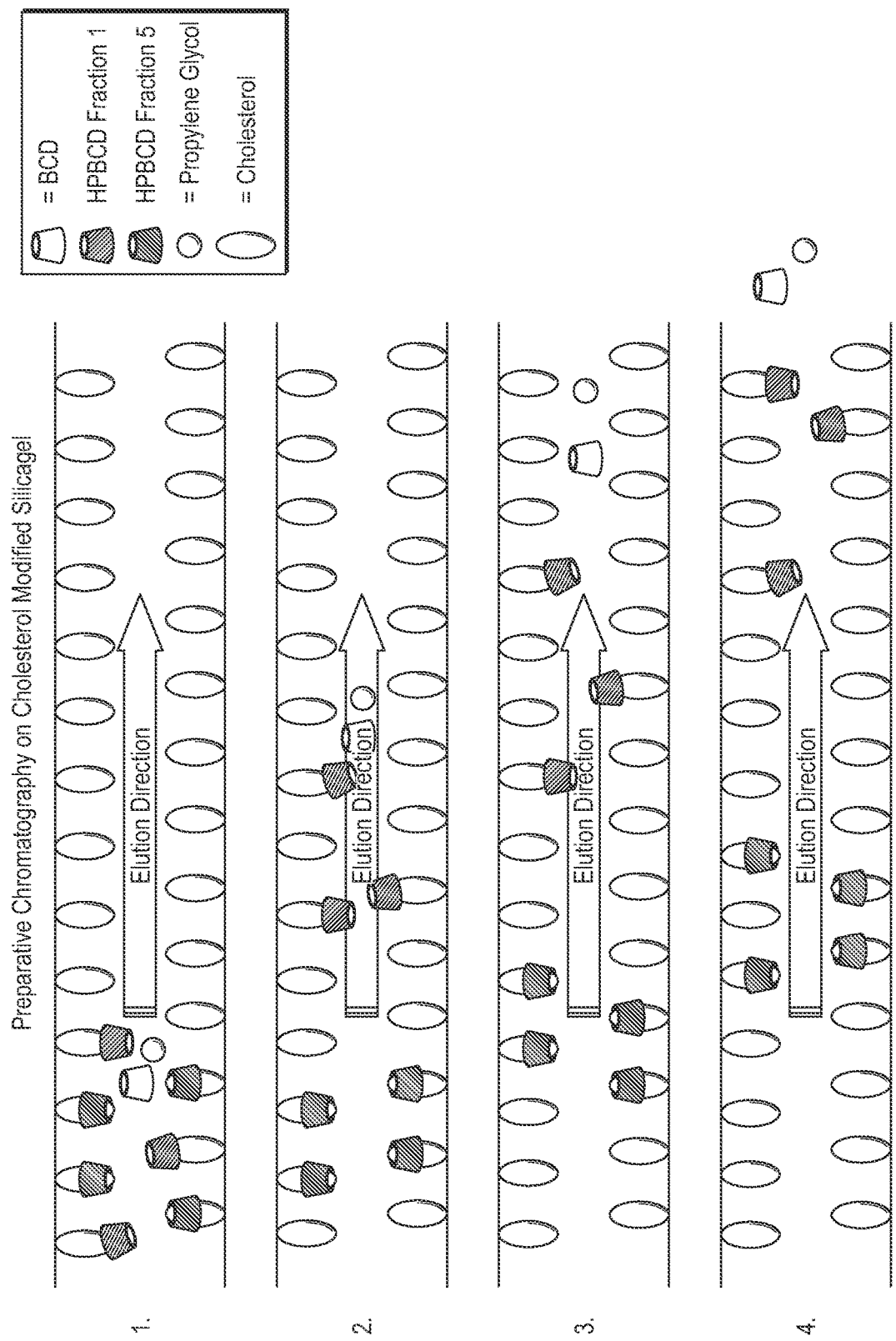
FIG. 5 is a schematic representation of the isomeric purification of a mixture of hydroxypropyl-β-cyclodextrin an HPLC Cholester column.

A schematic representation of the separation mechanism is provided in FIG. 5.

Further provided herein is an isomerically-purified composition comprising a mixture of hydroxypropyl-β-cyclodextrin molecules eluted from a Cholester HPLC column. The mixture of hydroxypropyl-β-cyclodextrin molecules may have a low degree of substitution (LDS) or a high degree of substitution (HDS). In some embodiments, about five mixtures of LDS hydroxypropyl-β-cyclodextrin and about five mixtures of HDS hydroxypropyl-β-cyclodextrin may elute from the Cholester HPLC column. Each of the mixtures is referred to herein as a "fraction."

Further provided herein is an isomerically-purified composition comprising a 5% (w/w) mixture of hydroxypropyl-β-cyclodextrin HDS molecules in aqueous media that yields an equilibrium solubility of cholesterol between about 0.2500 to about 0.6000 mg/mL at a temperature of 37° C. In some aspects, the composition may yield an equilibrium solubility of about 0.2500 mg/mL to about 0.3000 mg/mL, about 0.3000 mg/mL to about 0.3500 mg/mL, about 0.3500 mg/mL to about 0.4000 mg/mL, about 0.4000 mg/mL to about 0.4500 mg/mL, about 0.4500 mg/mL to about 0.5000 mg/mL, about 0.5000 mg/mL to about 0.5500 mg/mL, or about 0.6000 mg/mL at a temperature of 37° C. In some additional aspects, the composition may yield an equilibrium solubility of about 0.2500 mg/mL to about 0.3500 mg/mL, about 0.2500 mg/mL to about 0.4000 mg/mL, about 0.2500 mg/mL to about 0.4500 mg/mL, about 0.2500 mg/mL to about 0.5000 mg/mL, about 0.2500 mg/mL to about 0.5500 mg/mL, about 0.3000 mg/mL to about 0.6000 mg/mL, about 0.3500 mg/mL to about 0.6000 mg/mL, about 0.4000 mg/mL to about 0.6000 mg/mL, about 0.4500 mg/mL to about 0.6000 mg/mL, about 0.5000 mg/mL to about 0.6000 mg/mL, about 0.3000 mg/mL to about 0.5500 mg/mL, or about 0.3500 mg/mL to about 0.5000 mg/mL at a temperature of 37° C.

In some embodiments, the composition may yield an equilibrium solubility of cholesterol between about 0.4000 to 0.4200 mg/ml at a temperature of 37° C.

In some embodiments, the composition may yield an equilibrium solubility of cholesterol between about 0.5000 to 0.5200 mg/ml at a temperature of 37° C.

In some embodiments, the composition may yield an equilibrium solubility of cholesterol between about 0.5400 to 0.5600 mg/ml at a temperature of 37° C.

In some embodiments, the composition may yield an equilibrium solubility of cholesterol between about 0.3600 to 0.3800 mg/ml at a temperature of 37° C.

In some embodiments, the composition may yield an equilibrium solubility of cholesterol between about 0.2400 to about 0.2600 mg/ml at a temperature of 37° C. In an exemplary embodiment, the composition is HDS Fraction 1 and it yields an equilibrium solubility of cholesterol between about 0.2400 to about 0.2600 mg/ml at a temperature of 37° C. For example, the composition may yield an equilibrium solubility of cholesterol between about 0.2400 to about 0.2450 mg/ml, about 0.2400 to about 0.2500 mg/ml, about 0.2400 to about 0.2550 mg/ml, about 0.2400 to about 0.2600 mg/ml, about 0.2450 to about 0.2600 mg/ml, about 0.2500 to about 0.2600 mg/ml, about 0.2550 to about 0.2600 mg/ml. In additional embodiments, the HDS Fraction 1 may yield an equilibrium solubility of cholesterol between about 0.2400 to about 0.2450 mg/ml, about 0.2400 to about 0.2500 mg/ml, about 0.2400 to about 0.2550 mg/ml, about 0.2400 to about 0.2600 mg/ml, about 0.2450 to about 0.2600 mg/ml, about 0.2500 to about 0.2600 mg/ml, about 0.2550 to about 0.2600 mg/ml. In still additional embodiments, the composition may yield an equilibrium solubility of cholesterol of about 0.2400, 0.2410, 0.2420, 0.2430, 0.2440, 0.2450, 0.2460, 0.2470, 0.2480, 0.2490, 0.2500, 0.2510, 0.2520, 0.2530, 0.2540, 0.2550, 0.2560, 0.2570, 0.2580, 0.2590, or about 0.2600 mg/ml. In still additional embodiments, HDS Fraction 1 may yield an equilibrium solubility of cholesterol of about 0.2400, 0.2410, 0.2420, 0.2430, 0.2440, 0.2450, 0.2460, 0.2470, 0.2480, 0.2490, 0.2500, 0.2510, 0.2520, 0.2530, 0.2540, 0.2550, 0.2560, 0.2570, 0.2580, 0.2590, or about 0.2600 mg/ml.

In some embodiments, the composition may yield an equilibrium solubility of cholesterol between about 0.4000 to about 0.4200 mg/ml at a temperature of 37° C. In an exemplary embodiment, the composition is HDS Fraction 2 and it yields an equilibrium solubility of cholesterol between about 0.4000 to about 0.4200 mg/ml at a temperature of 37° C. For example, the composition may yield an equilibrium solubility of cholesterol between about 0.4000 to about 0.4050 mg/ml, about 0.4000 to about 0.4100 mg/ml, about 0.4000 to about 0.4150 mg/ml, about 0.4000 to about 0.4200 mg/ml, about 0.4050 to about 0.4200 mg/ml, about 0.4100 to about 0.4200 mg/ml, about 0.4150 to about 0.4200 mg/ml. In additional embodiments, the HDS Fraction 2 may yield an equilibrium solubility of cholesterol between about 0.4000 to about 0.4050 mg/ml, about 0.4000 to about 0.4100 mg/ml, about 0.4000 to about 0.4150 mg/ml, about 0.4000 to about 0.4200 mg/ml, about 0.4050 to about 0.4200 mg/ml, about 0.4100 to about 0.4200 mg/ml, about 0.4150 to about 0.4200 mg/ml. In still additional embodiments, the composition may yield an equilibrium solubility of cholesterol of about 0.4000, 0.4010, 0.4020, 0.4030, 0.4040, 0.4050, 0.4060, 0.4070, 0.4080, 0.4090, 0.4100, 0.4110, 0.4120, 0.4130, 0.4140, 0.4150, 0.4160, 0.4170, 0.4180, 0.4190, or about 0.4200 mg/ml. In still additional embodiments, HDS Fraction 2 may yield an equilibrium solubility of cholesterol of about 0.4000, 0.4010, 0.4020, 0.4030, 0.4040, 0.4050, 0.4060, 0.4070, 0.4080, 0.4090, 0.4100, 0.4110, 0.4120, 0.4130, 0.4140, 0.4150, 0.4160, 0.4170, 0.4180, 0.4190, or about 0.4200 mg/ml.

In some embodiments, the composition may yield an equilibrium solubility of cholesterol between about 0.5000 to about 0.5200 mg/ml at a temperature of 37° C. In an exemplary embodiment, the composition is HDS Fraction 3 and it yields an equilibrium solubility of cholesterol between about 0.5000 to about 0.5200 mg/ml at a temperature of 37° C. For example, the composition may yield an equilibrium solubility of cholesterol between about 0.5000 to about 0.5050 mg/ml, about 0.5000 to about 0.5100 mg/ml, about 0.5000 to about 0.5150 mg/ml, about 0.5000 to about 0.5200 mg/ml, about 0.5050 to about 0.5200 mg/ml, about 0.5100 to about 0.5200 mg/ml, about 0.5150 to about 0.5200 mg/ml. In additional embodiments, the HDS Fraction 3 may yield an equilibrium solubility of cholesterol between about 0.5000 to about 0.5050 mg/ml, about 0.5000 to about 0.5100 mg/ml, about 0.5000 to about 0.5150 mg/ml, about 0.5000 to about 0.5200 mg/ml, about 0.5050 to about 0.5200 mg/ml, about 0.5100 to about 0.5200 mg/ml, about 0.5150 to about 0.5200 mg/ml. In still additional embodiments, the composition may yield an equilibrium solubility of cholesterol of about 0.5000, 0.5010, 0.5020, 0.5030, 0.5040, 0.5050, 0.5060, 0.5070, 0.5080, 0.5090, 0.5100, 0.5110, 0.5120, 0.5130, 0.5140, 0.5150, 0.5160, 0.5170, 0.5180, 0.5190, or about 0.5200 mg/ml. In still additional embodiments, the HDS Fraction 3 may yield an equilibrium solubility of cholesterol of about 0.5000, 0.5010, 0.5020, 0.5030, 0.5040, 0.5050, 0.5060, 0.5070, 0.5080, 0.5090, 0.5100, 0.5110, 0.5120, 0.5130, 0.5140, 0.5150, 0.5160, 0.5170, 0.5180, 0.5190, or about 0.5200 mg/ml.

In some embodiments, the composition may yield an equilibrium solubility of cholesterol from about 0.5400 to about 0.5600 mg/ml at a temperature of 37° C. In an exemplary embodiment, the composition is HDS Fraction 4 and it yields an equilibrium solubility of cholesterol between about 0.5400 to about 0.5600 mg/ml at a temperature of 37° C. For example, the composition may yield an equilibrium solubility of cholesterol between about 0.5400 to about 0.5450 mg/ml, about 0.5400 to about 0.5500 mg/ml, about 0.5400 to about 0.5550 mg/ml, about 0.5400 to about 0.5600 mg/ml, about 0.5450 to about 0.5600 mg/ml, about 0.5500 to about 0.5600 mg/ml, about 0.5550 to about 0.5600 mg/ml. In some additional embodiments, the HDS Fraction 4 may yield an equilibrium solubility of cholesterol between about 0.5400 to about 0.5450 mg/ml, about 0.5400 to about 0.5500 mg/ml, about 0.5400 to about 0.5550 mg/ml, about 0.5400 to about 0.5600 mg/ml, about 0.5450 to about 0.5600 mg/ml, about 0.5500 to about 0.5600 mg/ml, about 0.5550 to about 0.5600 mg/ml. In still additional embodiments, the composition may yield an equilibrium solubility of cholesterol of about 0.5400, 0.5410, 0.5420, 0.5430, 0.5440, 0.5450, 0.5460, 0.5470, 0.5480, 0.5490, 0.5500, 0.5510, 0.5520, 0.5530, 0.5540, 0.5550, 0.5560, 0.5570, 0.5580, 0.5590, or about 0.5600 mg/ml. In still additional embodiments, the HDS Fraction 4 may yield an equilibrium solubility of cholesterol of about 0.5400, 0.5410, 0.5420, 0.5430, 0.5440, 0.5450, 0.5460, 0.5470, 0.5480, 0.5490, 0.5500, 0.5510, 0.5520, 0.5530, 0.5540, 0.5550, 0.5560, 0.5570, 0.5580, 0.5590, or about 0.5600 mg/ml.

In some embodiments, the composition may yield an equilibrium solubility of cholesterol between about 0.3600 to about 0.3800 mg/ml at a temperature of 37° C. In an exemplary embodiment, the composition is HDS Fraction 5 and it yields an equilibrium solubility of cholesterol between about 0.3600 to about 0.3800 mg/ml at a temperature of 37° C. For example, the composition may yield an equilibrium solubility of cholesterol between about 0.3600 to about 0.3650 mg/ml, about 0.3600 to about 0.3700 mg/ml, about 0.3600 to about 0.3750 mg/ml, about 0.3600 to about 0.3800 mg/ml, about 0.3650 to about 0.3800 mg/ml, about 0.3700 to about 0.3800 mg/ml, about 0.3750 to about 0.3800 mg/ml. In some additional embodiments, the HDS Fraction 5 may yield an equilibrium solubility of cholesterol between about 0.3600 to about 0.3650 mg/ml, about 0.3600 to about 0.3700 mg/ml, about 0.3600 to about 0.3750 mg/ml, about 0.3600 to about 0.3800 mg/ml, about 0.3650 to about 0.3800 mg/ml, about 0.3700 to about 0.3800 mg/ml, about 0.3750 to about 0.3800 mg/ml. In still additional embodiments, the composition may yield an equilibrium solubility of cholesterol of about 0.3600, 0.3610, 0.3620, 0.3630, 0.3640, 0.3650, 0.3660, 0.3670, 0.3680, 0.3690, 0.3700, 0.3710, 0.3720, 0.3730, 0.3740, 0.3750, 0.3760, 0.3770, 0.3780, 0.3790, or about 0.3800 mg/ml. In still additional embodiments, the HDS Fraction 5 may yield an equilibrium solubility of cholesterol of about 0.3600, 0.3610, 0.3620, 0.3630, 0.3640, 0.3650, 0.3660, 0.3670, 0.3680, 0.3690, 0.3700, 0.3710, 0.3720, 0.3730, 0.3740, 0.3750, 0.3760, 0.3770, 0.3780, 0.3790, or about 0.3800 mg/ml.

Further provided herein is an isomerically-purified composition comprising a 5% (w/w) mixture of hydroxypropyl-β-cyclodextrin HDS molecules in aqueous media, wherein the mixture of hydroxypropyl-β-cyclodextrin HDS molecules is insoluble in water. In some aspects, the mixture of hydroxypropyl-β-cyclodextrin HDS molecules may become soluble in water in the presence of cholesterol (e.g. soluble at room temperature (20-25 degrees centigrade)).

Further provided herein is an isomerically-purified composition comprising a 5% (w/w) mixture of hydroxypropyl-β-cyclodextrin LDS molecules in an aqueous media that yields an equilibrium solubility of cholesterol between about 0.1700 to about 0.3200 mg/mL at a temperature of 37° C. In some aspects, the composition may yield an equilibrium solubility of cholesterol between about 0.1700 mg/mL to about 0.2200 mg/mL, about 0.2200 mg/mL to about 0.2700 mg/mL, or about 0.2700 to about 0.3200 mg/mL at a temperature of 37° C. In some additional aspects, the composition may yield an equilibrium solubility of cholesterol between about 0.1700 mg/mL to about 0.2700 mg/mL or about 0.2200 mg/mL to about 0.3200 mg/mL at a temperature of 37° C.

In some embodiments, the composition may yield an equilibrium solubility of cholesterol between about 0.1800 to about 0.2000 mg/ml at a temperature of 37° C.

In some embodiments, the composition may yield an equilibrium solubility of cholesterol between about 0.1700 to about 0.1900 mg/ml at a temperature of 37° C.

In some embodiments, the composition may yield an equilibrium solubility of cholesterol between about 0.2000 to about 0.2200 mg/ml at a temperature of 37° C.

In some embodiments, the composition may yield an equilibrium solubility of cholesterol between about 0.2200 to about 0.2400 mg/ml at a temperature of 37° C.

In some embodiments, the composition may yield an equilibrium solubility of cholesterol between about 0.3100 to about 0.3300 mg/ml at a temperature of 37° C.

In some embodiments, the composition may yield an equilibrium solubility of cholesterol between about 0.1800 to about 0.2000 mg/ml at a temperature of 37° C. In an exemplary embodiment, the composition is LDS Fraction 1 yielding an equilibrium solubility of cholesterol between about 0.1800 to about 0.2000 mg/ml at a temperature of 37° C. For example, the composition may yield an equilibrium solubility of cholesterol between about 0.1800 to about 0.1850 mg/ml, about 0.1800 to about 0.1900 mg/ml, about 0.1800 to about 0.1950 mg/ml, about 0.1800 to about 0.2000 mg/ml, about 0.1850 to about 0.2000 mg/ml, about 0.1900 to about 0.2000 mg/ml, about 0.1950 to about 0.2000 mg/ml. In additional embodiments, the LDS Fraction 1 may yield an equilibrium solubility of cholesterol between about 0.1800 to about 0.1850 mg/ml, about 0.1800 to about 0.1900 mg/ml, about 0.1800 to about 0.1950 mg/ml, about 0.1800 to about 0.2000 mg/ml, about 0.1850 to about 0.2000 mg/ml, about 0.1900 to about 0.2000 mg/ml, about 0.1950 to about 0.2000 mg/ml. In still additional embodiments, the composition may yield an equilibrium solubility of cholesterol of about 0.1800, 0.1810, 0.1820, 0.1830, 0.1840, 0.1850, 0.1860, 0.1870, 0.1880, 0.1890, 0.1900, 0.1910, 0.1920, 0.1930, 0.1940, 0.1950, 0.1960, 0.1970, 0.1980, 0.1990, or about 0.2000 mg/ml. In still additional embodiments, the LDS Fraction 1 may yield an equilibrium solubility of cholesterol of about 0.1800, 0.1810, 0.1820, 0.1830, 0.1840, 0.1850, 0.1860, 0.1870, 0.1880, 0.1890, 0.1900, 0.1910, 0.1920, 0.1930, 0.1940, 0.1950, 0.1960, 0.1970, 0.1980, 0.1990, or about 0.2000 mg/ml.

In some embodiments, the composition may yield an equilibrium solubility of cholesterol between about 0.1700 to about 0.1900 mg/ml, such as between about 0.1700 to about 0.1790 mg/ml, at a temperature of 37° C. In an exemplary embodiment, the composition is LDS Fraction 2 and it yields an equilibrium solubility of cholesterol between about 0.1700 to about 0.1900 mg/ml, such as between about 0.1700 to about 0.1790 mg/ml, at a temperature of 37° C. For example, the composition may yield an equilibrium solubility of cholesterol between about 0.1700 to about 0.1750 mg/ml, about 0.1700 to about 0.1800 mg/ml, about 0.1700 to about 0.1850 mg/ml, about 0.1700 to about 0.1900 mg/ml, about 0.1750 to about 0.1900 mg/ml, about 0.1800 to about 0.1900 mg/ml, about 0.1850 to about 0.1900 mg/ml. In additional embodiments, the LDS Fraction 2 may yield an equilibrium solubility of cholesterol between about 0.1700 to about 0.1750 mg/ml, about 0.1700 to about 0.1800 mg/ml, about 0.1700 to about 0.1850 mg/ml, about 0.1700 to about 0.1900 mg/ml, about 0.1750 to about 0.1900 mg/ml, about 0.1800 to about 0.1900 mg/ml, about 0.1850 to about 0.1900 mg/ml. In still additional embodiments, the composition may yield an equilibrium solubility of cholesterol of about 0.1700, 0.1710, 0.1720, 0.1730, 0.1740, 0.1750, 0.1760, 0.1770, 0.1780, 0.1790, 0.1800, 0.1810, 0.1820, 0.1830, 0.1840, 0.1850, 0.1860, 0.1870, 0.1880, 0.1890, or about 0.1900 mg/ml. In still additional embodiments, the LDS Fraction 2 may yield an equilibrium solubility of cholesterol of about 0.1700, 0.1710, 0.1720, 0.1730, 0.1740, 0.1750, 0.1760, 0.1770, 0.1780, 0.1790, 0.1800, 0.1810, 0.1820, 0.1830, 0.1840, 0.1850, 0.1860, 0.1870, 0.1880, 0.1890, or about 0.1900 mg/ml.

In some embodiments, the composition may yield an equilibrium solubility of cholesterol between about 0.2000 to about 0.2200 mg/ml at a temperature of 37° C. In an exemplary embodiment, the composition is LDS Fraction 3 and it yields an equilibrium solubility of cholesterol between about 0.2000 to about 0.2200 mg/ml at a temperature of 37° C. For example, the composition may yield an equilibrium solubility of cholesterol between about 0.2000 to about 0.2050 mg/ml, about 0.2000 to about 0.2100 mg/ml, about 0.2000 to about 0.2150 mg/ml, about 0.2000 to about 0.2200 mg/ml, about 0.2050 to about 0.2200 mg/ml, about 0.2100 to about 0.2200 mg/ml, about 0.2150 to about 0.2200 mg/ml. In additional embodiments, the LDS Fraction 3 may yield an equilibrium solubility of cholesterol between about 0.2000 to about 0.2050 mg/ml, about 0.2000 to about 0.2100 mg/ml, about 0.2000 to about 0.2150 mg/ml, about 0.2000 to about 0.2200 mg/ml, about 0.2050 to about 0.2200 mg/ml, about 0.2100 to about 0.2200 mg/ml, about 0.2150 to about 0.2200 mg/ml. In still additional embodiments, the composition may yield an equilibrium solubility of cholesterol of about 0.2000, 0.2010, 0.2020, 0.2030, 0.2040, 0.2050, 0.2060, 0.2070, 0.2080, 0.2090, 0.2100, 0.2110, 0.2120, 0.2130, 0.2140, 0.2150, 0.2160, 0.2170, 0.2180, 0.2190, or about 0.2200 mg/ml. In still additional embodiments, the LDS Fraction 3 may yield an equilibrium solubility of cholesterol of about 0.2000, 0.2010, 0.2020, 0.2030, 0.2040, 0.2050, 0.2060, 0.2070, 0.2080, 0.2090, 0.2100, 0.2110, 0.2120, 0.2130, 0.2140, 0.2150, 0.2160, 0.2170, 0.2180, 0.2190, or about 0.2200 mg/ml.

In some embodiments, the composition may yield an equilibrium solubility of cholesterol between about 0.2200 to about 0.2400 mg/ml at a temperature of 37° C. In an exemplary embodiment, the composition is LDS Fraction 4 and it yields an equilibrium solubility of cholesterol between about 0.2200 to about 0.2400 mg/ml at a temperature of 37° C. For example, the composition may yield an equilibrium solubility of cholesterol between about 0.2200 to about 0.2250 mg/ml, about 0.2200 to about 0.2300 mg/ml, about 0.2200 to about 0.2350 mg/ml, about 0.2200 to about 0.2400 mg/ml, about 0.2250 to about 0.2400 mg/ml, about 0.2300 to about 0.2400 mg/ml, about 0.2350 to about 0.2400 mg/ml. In additional embodiments, the LDS Fraction 4 may yield an equilibrium solubility of cholesterol between about 0.2200 to about 0.2250 mg/ml, about 0.2200 to about 0.2300 mg/ml, about 0.2200 to about 0.2350 mg/ml, about 0.2200 to about 0.2400 mg/ml, about 0.2250 to about 0.2400 mg/ml, about 0.2300 to about 0.2400 mg/ml, about 0.2350 to about 0.2400 mg/ml. In still additional embodiments, the composition may yield an equilibrium solubility of cholesterol of about 0.2200, 0.2210, 0.2220, 0.2230, 0.2240, 0.2250, 0.2260, 0.2270, 0.2280, 0.2290, 0.2300, 0.2310, 0.2320, 0.2330, 0.2340, 0.2350, 0.2360, 0.2370, 0.2380, 0.2390, or about 0.2400 mg/ml. In still additional embodiments, the LDS Fraction 4 may yield an equilibrium solubility of cholesterol of about 0.2200, 0.2210, 0.2220, 0.2230, 0.2240, 0.2250, 0.2260, 0.2270, 0.2280, 0.2290, 0.2300, 0.2310, 0.2320, 0.2330, 0.2340, 0.2350, 0.2360, 0.2370, 0.2380, 0.2390, or about 0.2400 mg/ml.

In some embodiments, the composition may yield an equilibrium solubility of cholesterol between about 0.3100 to about 0.3300 mg/ml at a temperature of 37° C. In an exemplary embodiment, the composition is LDS Fraction 5 and it yields an equilibrium solubility of cholesterol from about 0.3100 to about 0.3300 mg/ml at a temperature of 37° C. For example, the composition may yield an equilibrium solubility of cholesterol between about 0.3100 to about 0.3150 mg/ml, about 0.3100 to about 0.3200 mg/ml, about 0.3100 to about 0.3250 mg/ml, about 0.3100 to about 0.3300 mg/ml, about 0.3150 to about 0.3300 mg/ml, about 0.3200 to about 0.3300 mg/ml, about 0.3250 to about 0.3300 mg/ml. In some additional embodiments, the LDS Fraction 5 may yield an equilibrium solubility of cholesterol between about 0.3100 to about 0.3150 mg/ml, about 0.3100 to about 0.3200 mg/ml, about 0.3100 to about 0.3250 mg/ml, about 0.3100 to about 0.3300 mg/ml, about 0.3150 to about 0.3300 mg/ml, about 0.3200 to about 0.3300 mg/ml, about 0.3250 to about 0.3300 mg/ml. In still additional embodiments, the composition may yield an equilibrium solubility of cholesterol of about 0.3100, 0.3110, 0.3120, 0.3130, 0.3140, 0.3150, 0.3160, 0.3170, 0.3180, 0.3190, 0.3200, 0.3210, 0.3220, 0.3230, 0.3240, 0.3250, 0.3260, 0.3270, 0.3280, 0.3290, or about 0.3300 mg/ml. In still additional embodiments, the LDS Fraction 5 may yield an equilibrium solubility of cholesterol of about 0.3100, 0.3110, 0.3120, 0.3130, 0.3140, 0.3150, 0.3160, 0.3170, 0.3180, 0.3190, 0.3200, 0.3210, 0.3220, 0.3230, 0.3240, 0.3250, 0.3260, 0.3270, 0.3280, 0.3290, or about 0.3300 mg/ml.

Further provided herein is an isomerically-purified composition comprising a 20% (w/w) mixture of hydroxypropyl-β-cyclodextrin molecules in an aqueous media that yields an equilibrium solubility of cholesterol between about 3.2500 mg/mL to about 3.7500 mg/mL at a temperature of 37° C. In some aspects, the composition may yield an equilibrium solubility of cholesterol between about 3.2500 mg/mL to about 3.3500 mg/mL, about 3.3500 mg/mL to about 3.4500 mg/mL, about 3.4500 mg/mL to about 3.5500 mg/mL, about 3.5500 mg/mL to about 3.6500 mg/mL, or about 3.6500 mg/mL to about 3.7500 mg/mL. In some additional aspects, the composition may yield an equilibrium solubility of cholesterol between about 3.2500 mg/mL to about 3.4500 mg/mL, about 3.2500 mg/mL to about 3.5500 mg/mL, about 3.2500 mg/mL to about 3.6500 mg/mL, about 3.3500 mg/mL to about 3.7500 mg/mL, about 3.4500 mg/mL to about 3.7500 mg/mL, or about 3.5500 mg/mL to about 3.7500 mg/mL.

Further provided herein is a method of increasing the solubility (e.g., at 37° C.) of a mixture of hydroxypropyl β-cyclodextrin molecules in water by increasing the substitution at the 2-O— positions of the hydroxypropyl β-cyclodextrin molecules. Also provided herein is a method of increasing the solubility (e.g., at 37° C.) of a mixture of hydroxypropyl β-cyclodextrin molecules in water by increasing the substitution at the 2-O— positions of the hydroxypropyl β-cyclodextrin molecules, without increasing the hydroxypropyl substitution at other positions of the hydroxypropyl β-cyclodextrin molecules. Further provided herein is a method of increasing the solubility (e.g., at 37° C.) of a mixture of hydroxypropyl β-cyclodextrin molecules in water by increasing the substitution at the 2-O— positions of the hydroxypropyl β-cyclodextrin molecules, while maintaining the hydroxypropyl substitution at other positions (e.g., 3-O position and/or 6-O position) of the hydroxypropyl β-cyclodextrin molecules at less than or equal to 1% by weight, 5% by weight, 10% by weight, 15% by weight, 20% by weight, 25% by weight, 30% by weight, 40% by weight, or 50% by weight. In yet another embodiment provided herein is a method of increasing the solubility (e.g., at 37° C.) of a mixture of hydroxypropyl β-cyclodextrin molecules in water by increasing the substitution at the 2-O— positions of the hydroxypropyl β-cyclodextrin molecules, without substantially increasing the hydroxypropyl substitution at the 3-0 position. Without wishing to be bound by theory, the solubility of hydroxypropyl β-cyclodextrin may be influenced in large part by interactions between hydroxyl groups of the molecule and the hydroxyl groups in the water. When the hydroxypropyl groups are substituted at the 3-O— position, the water hydroxyl groups may be sterically hindered from interacting with the hydroxyl groups of the hydroxypropyl moieties; accordingly, water solubility may decrease. When the hydroxypropyl groups are substituted at the 2-O— position, the water hydroxyl groups are no longer sterically hindered form interacting with the hydroxyl groups of the hydroxypropyl moieties; accordingly, water solubility may increase.

Without wishing to be bound by theory, the increased solubility of Fraction 5 in water with the addition of cholesterol is believed to be caused by conformational changes in the hydroxypropyl β-cyclodextrin molecules that form inclusion complexes with the cholesterol molecules. When the hydroxypropyl β-cyclodextrin molecules have oligomerized side chains at the 2-O— position, the hydroxyl groups in the oligomerized side chains may form self-inclusion complexes and are thus unable to interact with hydroxyl groups of water molecules. When the cholesterol is added to the solution the cholesterol molecules interact with the hydroxypropyl β-cyclodextrin molecules, causing conformational changes in the hydroxypropyl β-cyclodextrin molecules. This frees up the hydroxyl groups of the side chains to interact with the hydroxyl groups of the water molecules; accordingly the solubility of Fraction 5 increases.

Further provided herein are compositions comprising a mixture of hydroxypropyl β-cyclodextrin molecules and cholesterol, wherein the mixture of hydroxypropyl β-cyclodextrin molecules is present in a molar equivalent or in molar excess as compared to the cholesterol. The compositions may include a solvent, such as water. The mixture of hydroxypropyl β-cyclodextrin molecules may have a concentration in the composition of about 5% to about 20% by weight. In some embodiments, the mixture of hydroxypropyl β-cyclodextrin molecules may have a concentration of about 5% to about 10%, about 10% to about 15%, about 10% to about 20%, or about 15% to about 20% by weight (wherein the % by weight may, in some embodiments be the % by weight of the composition). In some embodiments, the presence of cholesterol substantially increases the solubility of the mixture of hydroxypropyl β-cyclodextrin molecules. In some embodiments, the presence of cholesterol substantially increases the solubility of the mixture of hydroxypropyl β-cyclodextrin molecules in water. Surprisingly, in some embodiments, the aqueous solubility (e.g., at 37° C.) of the hydroxypropyl β-cyclodextrin increases by about 2.5% to about 200%, such as by about 10% to about 100% in the presence of cholesterol. As such, one aspect of the current invention is a composition comprising a mixture of hydroxypropyl β-cyclodextrin molecules and cholesterol, wherein the solubility (e.g., at 37° C.) of the hydroxypropyl β-cyclodextrin molecules increases by about 2.5% to about 200%, such as by about 10% to about 100% in the presence of cholesterol. Another aspect of the current invention is a composition comprising a mixture of hydroxypropyl β-cyclodextrin molecules and cholesterol, wherein the aqueous solubility (e.g., at 37° C.) of the hydroxypropyl β-cyclodextrin increases by about 2.5% to about 200%, such as by about 10% to about 100% in the presence of cholesterol due to a conformational change in the hydroxypropyl β-cyclodextrin molecules bound and/or complexed to the cholesterol. In some embodiments, the presence of cholesterol substantially increases the aqueous solubility (e.g., at 37° C.) of the mixture of hydroxypropyl β-cyclodextrin molecules by about 2.5% to about 5%, 5% to about 10%, by about 10% to about 15%, by about 15% to about 25%, by about 25% to about 50%, by about 50% to about 75%, by about 75% to about 100%, by about 100% to about 150%, by about 150% to about 200%.

In some embodiments, the hydroxypropyl β-cyclodextrin may be present in the composition in molar ratio to cholesterol of about 100:1 to about 1:1. In some aspects, the hydroxypropyl β-cyclodextrin may be present in the composition in molar ratio to cholesterol of about 1:1 to about 25:1, about 25:1 to about 50:1, about 50:1 to about 75:1, or about 75:1 to about 100:1. In some embodiments, the solubility of the hydroxypropyl β-cyclodextrin increases by about 10% to about 100% in the presence of cholesterol and a molar excess of a mixture of hydroxypropyl β-cyclodextrin molecules (e.g., Fraction 5)

In other embodiments, the hydroxypropyl β-cyclodextrin may be present in the composition in molar ratio to cholesterol of about 1:1 to about 1:100 (i.e., a molar excess). In some aspects, the hydroxypropyl β-cyclodextrin may be present in the composition in molar ratio to cholesterol of about 1:1 to about 1:25, about 1:25 to about 1:50, about 1:50 to about 1:75, or about 1:75 to about 1:100.

Further provided herein are compositions comprising a mixture of hydroxypropyl β-cyclodextrin molecules, wherein the substitutions at the 3-O— positions are dimerized. Without wishing to be bound by theory, in molecules of hydroxypropyl β-cyclodextrin having two or more substitutions at the 3-O— position, the hydroxyl groups of the hydroxypropyl moieties may react to form hydroxypropyl dimers. In these molecules, the hydroxyl groups at the 3-O— positions become inaccessible to water, and thus have lower solubility in water.

Further provided herein are compositions comprising a mixture of hydroxypropyl β-cyclodextrin molecules, wherein the substitutions at the 3-O— positions form self-inclusion complexes. Without wishing to be bound by theory, in molecules of hydroxypropyl β-cyclodextrin having two or more substitutions at the 3-O— position, the hydroxyl groups of the hydroxypropyl moieties may interact to form self-inclusion complexes. In these molecules, the hydroxyl groups at the 3-O— positions become inaccessible to water, and thus have lower solubility in water.

Further provided herein is a method of increasing the surface polarity of a hydroxypropyl β-cyclodextrin molecule, the method comprising increasing the number of substitutions at the 2-O— position. In some embodiments, the method may further comprise increasing the number of substitutions at the 3-O— position of the hydroxypropyl β-cyclodextrin molecule.

Fraction 1 HDS

Provided herein is a composition comprising a mixture of isomerically-purified hydroxypropyl-β-cyclodextrin molecules that includes less than 1% of DS-4. In some embodiments, the hydroxypropyl-β-cyclodextrin percent is based upon an area percentage from a MALDI-TOF-MS spectrum. In some embodiments, the hydroxypropyl-β-cyclodextrin percentage may be a weight percentage, a mol percentage, or a volume percentage. In an exemplary embodiment, the hydroxypropyl-β-cyclodextrin percentage is a weight percentage.

In some embodiments, the mixture of isomerically-purified hydroxypropyl-β-cyclodextrin molecules may include less than 1% of DS-3, DS-2, and DS-1. In some aspects, the mixture of isomerically-purified hydroxypropyl-β-cyclodextrin molecules may include less than 1%, less than 0.9%, less than 0.8%, less than 0.7%, less than 0.6%, less than 0.5%, less than 0.4%, less than 0.3%, less than 0.2%, or less than 0.1% of DS-3, DS-2, and DS-1. In some aspects, the mixture of isomerically-purified hydroxypropyl-β-cyclodextrin molecules may include less than 1%, less than 0.9%, less than 0.8%, less than 0.7%, less than 0.6%, less than 0.5%, less than 0.4%, less than 0.3%, less than 0.2%, or less than 0.1% of DS-4, DS-3, DS-2, and/or DS-1. In some embodiments, the mixture of isomerically-purified hydroxypropyl-β-cyclodextrin molecules is free of DS-3, DS-2, and/or DS-1.

In some embodiments, the mixture of hydroxypropyl-β-cyclodextrin molecules may include less than 1% of DS-12, DS-13, and DS-14. In some aspects, the mixture of isomerically-purified hydroxypropyl-β-cyclodextrin molecules may include less than 1%, less than 0.9%, less than 0.8%, less than 0.7%, less than 0.6%, less than 0.5%, less than 0.4%, less than 0.3%, less than 0.2%, or less than 0.1% of DS-12, DS-13, and DS-14. In some aspects, the mixture of isomerically-purified hydroxypropyl-β-cyclodextrin molecules may include less than 1%, less than 0.9%, less than 0.8%, less than 0.7%, less than 0.6%, less than 0.5%, less than 0.4%, less than 0.3%, less than 0.2%, or less than 0.1% of DS-12, DS-13, and/or DS-14. In some embodiments, the mixture of isomerically-purified hydroxypropyl-β-cyclodextrin molecules is free of DS-12, DS-13 and/or DS-14.

In some embodiments, the mixture of isomerically-purified hydroxypropyl-β-cyclodextrin molecules comprises about 1% to about 5% of DS-5. In some aspects, the mixture of isomerically-purified hydroxypropyl-β-cyclodextrin molecules includes about 1% to about 1.5% of DS-5, about 1.5% to about 2% of DS-5, about 2% to about 2.5% of DS-5, about 2.5% to about 3% of DS-5, about 3% of DS-5 to about 3.5% of DS-5, about 3.5% to about 4% of DS-5, about 4% to about 4.5% of DS-5, or about 4.5% to about 5% of DS-5. In some additional aspects, the mixture of isomerically-purified β-cyclodextrin molecules includes about 1% to about 2% of DS-5, about 1% to about 2.5% of DS-5, about 1% to about 3% of DS-5, about 1% to about 3.5% of DS-5, about 1% to about 4% of DS-5, about 1% to about 4.5% of DS-5, about 1.5% to about 5% of DS-5, about 2% to about 5% of DS-5, about 2.5% to about 5% of DS-5, about 3% to about 5% of DS-5, about 3.5% to about 5% of DS-5, about 4% to about 5% of DS-5, about 1.5% to about 4.5% of DS-5, about 2% to about 4% of DS-5, or about 2.5% to about 3.5% of DS-5. In still further embodiments, the mixture of isomerically-purified hydroxypropyl-β-cyclodextrin molecules may include about 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, or about 5.0% of DS-5. In an exemplary embodiment, the area of DS-5 in a MALDI-TOF-MS spectrum is 2.83%.

In some embodiments, the mixture of isomerically-purified hydroxypropyl-β-cyclodextrin molecules includes about 7% to about 13% of DS-6. In some aspects, the mixture of isomerically-purified hydroxypropyl-β-cyclodextrin molecules may include about 7% to about 7.5% of DS-6, about 7.5% to about 8% of DS-6, about 8% to about 8.5% of DS-6, about 8.5% to about 9% of DS-6, about 9% to about 9.5% of DS-6, about 9.5% to about 10% of DS-6, about 10% to about 10.5% of DS-6, about 10.5% to about 11% of DS-6, about 11% to about 11.5% of DS-6, about 11.5% to about 12% of DS-6, about 12% to about 12.5% of DS-6, or about 12.5% to about 13% of DS-6. In some additional aspects, the mixture of isomerically-purified hydroxypropyl-β-cyclodextrin molecules may include about 7% to about 8% of DS-6, about 7% to about 8.5% of DS-6, about 7% to about 9% of DS-6, about 7% to about 9.5% of DS-6, about 7% to about 10% of DS-6, about 7% to about 10.5% of DS-6, about 7% to about 11% of DS-6, about 7% to about 11.5% of DS-6, about 7% to about 12% of DS-6, about 7% to about 12.5% of DS-6, about 7.5% to about 13% of DS-6, about 8% to about 13% of DS-6, about 8.5% to about 13% of DS-6, about 9% to about 13% of DS-6, about 9.5% to about 13% of DS-6, about 10% to about 13% of DS-6, about 10.5% to about 13% of DS-6, about 11% to about 13% of DS-6, about 11.5% to about 13% of DS-6, about 12% to about 13% of DS-6, about 7.5% to about 12.5% of DS-6, about 8% to about 12% of DS-6, about 8.5% to about 11.5% of DS-6, about 9% to about 11% of DS-6, or about 9.5% to about 10.5% of DS-6. In still additional aspects, the mixture of isomerically-purified hydroxypropyl-β-cyclodextrin molecules may include about 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10.0%, 10.1%, 10.2%, 10.3%, 10.4%, 10.5%, 10.6%, 10.7%, 10.8%, 10.9%, 11.0%, 11.1%, 11.2%, 11.3%, 11.4%, 11.5%, 11.6%, 11.7%, 11.8%, 11.9%, 12.0%, 12.1%, 12.2%, 12.3%, 12.4%, 12.5%, 12.6%, 12.7%, 12.8%, 12.9%, or about 13.0% of DS-6. In an exemplary embodiment, the area of DS-6 in a MALDI-TOF-MS spectrum is 10.64%.

In some embodiments, the mixture of hydroxypropyl-β-cyclodextrin molecules may include about 16% to about 22% of DS-7. In some aspects, the mixture of hydroxypropyl-β-cyclodextrin molecules may include about 16% to about 16.5% of DS-7, about 16.5% to about 17% of DS-7, about 17% to about 17.5% of DS-7, about 17.5% to about 18% of DS-7, about 18% to about 18.5% of DS-7, about 18.5% to about 19% of DS-7, about 19% to about 19.5% of DS-7, about 19.5% to about 20% of DS-7, about 20% to about 20.5% of DS-7, about 20.5% to about 21% of DS-7, about 21% to about 21.5% of DS-7, or about 21.5% to about 22% of DS-7. In some additional aspects, the mixture of hydroxypropyl-β-cyclodextrin molecules may include about 16% to about 17% of DS-7, about 16% to about 17.5% of DS-7, about 16% to about 18% of DS-7, about 16% to about 18.5% of DS-7, about 16% to about 19% of DS-7, about 16% to about 19.5% of DS-7, about 16% to about 20% of DS-7, about 16% to about 20.5% of DS-7, about 16% to about 21% of DS-7, about 16% to about 21.5% of DS-7, about 16.5% to about 22% of DS-7, about 17% to about 22% of DS-7, about 17.5% to about 22% of DS-7, about 18% to about 22% of DS-7, about 18.5% to about 22% of DS-7, about 19% to about 22% of DS-7, about 19.5% to about 22% of DS-7, about 20% to about 22% of DS-7, about 20.5% to about 22% of DS-7, about 21% to about 22% of DS-7, about 16.5% to about 21.5% of DS-7, about 17% to about 21% of DS-7, about 17.5% to about 20.5% of DS-7, about 18% to about 20% of DS-7, or about 18.5% to about 19.5% of DS-7. In still further aspects, the mixture of hydroxypropyl-β-cyclodextrin molecules may include about 16.0%, 16.1%, 16.2%, 16.3%, 16.4%, 16.5%, 16.6%, 16.7%, 16.8%, 16.9%, 17.0%, 17.1%, 17.2%, 17.3%, 17.4%, 17.5%, 17.6%, 17.7%, 17.8%, 17.9%, 18.0%, 18.1%, 18.2%, 18.3%, 18.4%, 18.5%, 18.6%, 18.7%, 18.8%, 18.9%, 19.0%, 19.1%, 19.2%, 19.3%, 19.4%, 19.5%, 19.6%, 19.7%, 19.8%, 19.9%, 20.0%, 20.1%, 20.2%, 20.3%, 20.4%, 20.5%, 20.6%, 20.7%, 20.8%, 20.9%, 21.0%, 21.1%, 21.2%, 21.3%, 21.4%, 21.5%, 21.6%, 21.7%, 21.8%, 21.9%, or about 22.0% of DS-7. In an exemplary embodiment, the area of DS-7 in a MALDI-TOF-MS spectrum is 19.30%.

In some embodiments, the mixture of isomerically-purified hydroxypropyl-β-cyclodextrin molecules may include about 26% to about 32% of DS-8. In some aspects, the mixture of isomerically-purified hydroxypropyl-β-cyclodextrin molecules may include about 26% to about 26.5% of DS-8, about 26.5% to about 27% of DS-8, about 27% to about 27.5% of DS-8, about 27.5% to about 28% of DS-8, about 28% to about 28.5% of DS-8, about 28.5% to about 29% of DS-8, about 29% to about 29.5% of DS-8, about 29.5% to about 30% of DS-8, about 30% to about 30.5% of DS-8, about 30.5% to about 31% of DS-8, about 31% to about 31.5% of DS-8, or about 31.5% to about 32% of DS-8. In some additional aspects, the mixture of isomerically-purified β-cyclodextrin may include about 26% to about 27% of DS-8, about 26% to about 27.5% of DS-8, about 26% to about 28% of DS-8, about 26% to about 28.5% of DS-8, about 26% to about 29% of DS-8, about 26% to about 29.5% of DS-8, about 26% to about 30% of DS-8, about 26% to about 30.5% of DS-8, about 26% to about 31% of DS-8, about 26% to about 31.5% of DS-8, about 26.5% to about 32% of DS-8, about 27% to about 32% of DS-8, about 27.5% to about 32% of DS-8, about 28% to about 32% of DS-8, about 28.5% to about 32% of DS-8, about 29% to about 32% of DS-8, about 29.5% to about 32% of DS-8, about 30% to about 32% of DS-8, about 30.5% to about 32% of DS-8, about 31% to about 32% of DS-8, about 26.5% to about 31.5% of DS-8, about 27% to about 31% of DS-8, about 27.5% to about 30.5% of DS-8, about 28% to about 30% of DS-8, or about 28.5% to about 29.5% of DS-8. In still further aspects, the mixture of isomerically-purified β-cyclodextrin molecules may include about 26.0%, 26.1%, 26.2%, 26.3%, 26.4%, 26.5%, 26.6%, 26.7%, 26.8%, 26.9%, 27.0%, 27.1%, 27.2%, 27.3%, 27.4%, 27.5%, 27.6%, 27.7%, 27.8%, 27.9%, 28.0%, 28.1%, 28.2%, 28.3%, 28.4%, 28.5%, 28.6%, 28.7%, 28.8%, 28.9%, 29.0%, 29.1%, 29.2%, 29.3%, 29.4%, 29.5%, 29.6%, 29.7%, 29.8%, 29.9%, 30.0%, 30.1%, 30.2%, 30.3%, 30.4%, 30.5%, 30.6%, 30.7%, 30.8%, 30.9%, 31.0%, 31.1%, 31.2%, 31.3%, 31.4%, 31.5%, 31.6%, 31.7%, 31.8%, 31.9%, or about 32.0% of DS-8. In an exemplary embodiment, the area of DS-8 in a MALDI-TOF-MS spectrum is 29.30%.

In some embodiments, the mixture of isomerically-purified hydroxypropyl-β-cyclodextrin molecules may include about 22% to about 28% of DS-9. In some aspects, the mixture of isomerically-purified β-cyclodextrin molecules includes about 22% to about 22.5% of DS-9, about 22.5% to about 23% of DS-9, about 23% to about 23.5% of DS-9, about 23.5% to about 24% of DS-9, about 24% to about 24.5% to about 25% of DS-9, about 25% to about 25.5% of DS-9, about 25.5% to about 26% of DS-9, about 26% to about 26.5% of DS-9, about 26.5% to about 27% of DS-9, about 27% to about 27.5% of DS-9, or about 27.5% to about 28% of DS-9. In some additional aspects, the mixture of isomerically-purified β-cyclodextrin may include about 22% to about 23% of DS-9, about 22% to about 23.5% of DS-9, about 22% to about 24% of DS-9, about 22% to about 24.5% of DS-9, about 22% to about 25% of DS-9, about 22% to about 25.5% of DS-9, about 22% to about 26% of DS-9, about 22% to about 26.5% of DS-9, about 22% to about 27% of DS-9, about 22% to about 27.5% of DS-9, about 22.5% to about 28% of DS-9, about 23% to about 28% of DS-9, about 23.5% to about 28% of DS-9, about 24% to about 28% of DS-9, about 24.5% to about 28% of DS-9, about 25% to about 28% of DS-9, about 25.5% to about 28% of DS-9, about 26% to about 28% of DS-9, about 26.5% to about 28% of DS-9, about 27% to about 28% of DS-9, about 22.5% to about 27.5% of DS-9, about 23% to about 27% of DS-9, about 23.5% to about 26.5% of DS-9, about 24% to about 26% of DS-9, or about 24.5% to about 25.5% of DS-9. In still further aspects, the mixture of isomerically-purified β-cyclodextrin molecules may include about 22.0%, 22.1%, 22.2%, 22.3%, 22.4%, 22.5%, 22.6%, 22.7%, 22.8%, 22.9%, 23.0%, 23.1%, 23.2%, 23.3%, 23.4%, 23.5%, 23.6%, 23.7%, 23.8%, 23.9%, 24.0%, 24.1%, 24.2%, 24.3%, 24.4%, 24.5%, 24.6%, 24.7%, 24.8%, 24.9%, 25.0%, 25.1%, 25.2%, 25.3%, 25.4%, 25.5%, 25.6%, 25.7%, 25.8%, 25.9%, 26.0%, 26.1%, 26.2%, 26.3%, 26.4%, 26.5%, 26.6%, 26.7%, 26.8%, 26.9%, 27.0%, 27.1%, 27.2%, 27.3%, 27.4%, 27.5%, 27.6%, 27.7%, 27.8%, 27.9%, or about 28.0% of DS-9. In an exemplary embodiment, the area of DS-9 in a MALDI-TOF-MS spectrum is 25.30%.

In some embodiments, the mixture of isomerically-purified hydroxypropyl-β-cyclodextrin molecules may include about 11% to about 17% of DS-10. In some aspects, the mixture of isomerically-purified hydroxypropyl-β-cyclodextrin molecules may include about 11% to about 11.5% of DS-10, about 11.5% to about 12% of DS-10, about 12% to about 12.5% of DS-10, about 12.5% to about 13% of DS-10, about 13% to about 13.5% of DS-10, about 13.5% to about 14% of DS-10, about 14% to about 14.5% of DS-10, about 14.5% to about 15% of DS-10, about 15% to about 15.5% of DS-10, about 15.5% to about 16% of DS-10, about 16% to about 16.5% of DS-10, or about 16.5% to about 17% of DS-10. In some additional aspects, the mixture of isomerically-purified hydroxypropyl-β-cyclodextrin molecules may include about 11% to about 12% of DS-10, about 11% to about 12.5% of DS-10, about 11% to about 13% of DS-10, about 11% to about 13.5% of DS-10, about 11% to about 14% of DS-10, about 11% to about 14.5% of DS-10, about 11% to about 15% of DS-10, about 11% to about 15.5% of DS-10, about 11% to about 16% of DS-10, about 11% to about 16.5% of DS-10, about 11.5% to about 17% of DS-10, about 12% to about 17% of DS-10, about 12.5% to about 17% of DS-10, about 13% to about 17% of DS-10, about 13.5% to about 17% of DS-10, about 14% to about 17% of DS-10, about 14.5% to about 17% of DS-10, about 15% to about 17% of DS-10, about 15.5% to about 17% of DS-10, about 16% to about 17% of DS-10, about 11.5% to about 16.5% of DS-10, about 12% to about 16% of DS-10, about 12.5% to about 15.5% of DS-10, about 13% to about 15% of DS-10, or about 13.5% to about 14.5% of DS-10. In still further aspects, the mixture of isomerically-purified hydroxypropyl-β-cyclodextrin molecules may include about 11.0%, 11.1%, 11.2%, 11.3%, 11.4%, 11.5%, 11.6%, 11.7%, 11.8%, 11.9%, 12.0%, 12.1%, 12.2% 12.3%, 12.4%, 12.5%, 12.6%, 12.7%, 12.8%, 12.9%, 13.0%, 13.1%, 13.2%, 13.3%, 13.4%, 13.5%, 13.6%, 13.7%, 13.8%, 13.9%, 14.0%, 14.1%, 14.2%, 14.3%, 14.4%, 14.5%, 14.6%, 14.7%, 14.8%, 14.9%, 15.0%, 15.1%, 15.2%, 15.3%, 15.4%, 15.5%, 15.6%, 15.7%, 15.8%, 15.9%, 16.0%, 16.1%, 16.2%, 16.3%, 16.4%, 16.5%, 16.6%, 16.7%, 16.8%, 16.9%, or about 17.0% of DS-10. In an exemplary embodiment, the area of DS-10 in a MALDI-TOF-MS spectrum is 14.30%.

In an exemplary embodiment, the mixture of isomerically-purified hydroxypropyl-β-cyclodextrin molecules may include about 1% to about 5% of DS-5, about 7% to about 13% of DS-6, about 16% to about 22% of DS-7, about 26% to about 32% of DS-8, about 22% to about 28% of DS-9, and about 11% to about 17% of DS-10.

Further provided herein is a composition comprising a mixture of isomerically-purified hydroxypropyl-β-cyclodextrin molecules including DS-5, DS-6, DS-7, DS-8, DS-9, and DS-10. In some embodiments, the composition includes less than 1% of DS-4. In some additional embodiments, the composition includes less than 1% of DS-11. In some embodiments, the DS-8 may have the highest concentration in the composition as compared to DS-5, DS-6, DS-7, DS-9, and DS-10.

In some embodiments, the mixture of isomerically-purified hydroxypropyl-β-cyclodextrin molecules comprises about 1% to about 5% of DS-5. In some aspects, the mixture of isomerically-purified hydroxypropyl-β-cyclodextrin molecules includes about 1% to about 1.5% of DS-5, about 1.5% to about 2% of DS-5, about 2% to about 2.5% of DS-5, about 2.5% to about 3% of DS-5, about 3% of DS-5 to about 3.5% of DS-5, about 3.5% to about 4% of DS-5, about 4% to about 4.5% of DS-5, or about 4.5% to about 5% of DS-5. In some additional aspects, the mixture of isomerically-purified β-cyclodextrin molecules includes about 1% to about 2% of DS-5, about 1% to about 2.5% of DS-5, about 1% to about 3% of DS-5, about 1% to about 3.5% of DS-5, about 1% to about 4% of DS-5, about 1% to about 4.5% of DS-5, about 1.5% to about 5% of DS-5, about 2% to about 5% of DS-5, about 2.5% to about 5% of DS-5, about 3% to about 5% of DS-5, about 3.5% to about 5% of DS-5, about 4% to about 5% of DS-5, about 1.5% to about 4.5% of DS-5, about 2% to about 4% of DS-5, or about 2.5% to about 3.5% of DS-5. In still further embodiments, the mixture of isomerically-purified hydroxypropyl-β-cyclodextrin molecules may include about 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, or about 5.0% of DS-5. In an exemplary embodiment, the area of DS-5 in a MALDI-TOF-MS spectrum is 2.83%.

In some embodiments, the mixture of isomerically-purified hydroxypropyl-β-cyclodextrin molecules includes about 7% to about 13% of DS-6. In some aspects, the mixture of isomerically-purified hydroxypropyl-β-cyclodextrin molecules may include about 7% to about 7.5% of DS-6, about 7.5% to about 8% of DS-6, about 8% to about 8.5% of DS-6, about 8.5% to about 9% of DS-6, about 9% to about 9.5% of DS-6, about 9.5% to about 10% of DS-6, about 10% to about 10.5% of DS-6, about 10.5% to about 11% of DS-6, about 11% to about 11.5% of DS-6, about 11.5% to about 12% of DS-6, about 12% to about 12.5% of DS-6, or about 12.5% to about 13% of DS-6. In some additional aspects, the mixture of isomerically-purified hydroxypropyl-β-cyclodextrin molecules may include about 7% to about 8% of DS-6, about 7% to about 8.5% of DS-6, about 7% to about 9% of DS-6, about 7% to about 9.5% of DS-6, about 7% to about 10% of DS-6, about 7% to about 10.5% of DS-6, about 7% to about 11% of DS-6, about 7% to about 11.5% of DS-6, about 7% to about 12% of DS-6, about 7% to about 12.5% of DS-6, about 7.5% to about 13% of DS-6, about 8% to about 13% of DS-6, about 8.5% to about 13% of DS-6, about 9% to about 13% of DS-6, about 9.5% to about 13% of DS-6, about 10% to about 13% of DS-6, about 10.5% to about 13% of DS-6, about 11% to about 13% of DS-6, about 11.5% to about 13% of DS-6, about 12% to about 13% of DS-6, about 7.5% to about 12.5% of DS-6, about 8% to about 12% of DS-6, about 8.5% to about 11.5% of DS-6, about 9% to about 11% of DS-6, or about 9.5% to about 10.5% of DS-6. In still additional aspects, the mixture of isomerically-purified hydroxypropyl-β-cyclodextrin molecules may include about 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10.0%, 10.1%, 10.2%, 10.3%, 10.4%, 10.5%, 10.6%, 10.7%, 10.8%, 10.9%, 11.0%, 11.1%, 11.2%, 11.3%, 11.4%, 11.5%, 11.6%, 11.7%, 11.8%, 11.9%, 12.0%, 12.1%, 12.2%, 12.3%, 12.4%, 12.5%, 12.6%, 12.7%, 12.8%, 12.9%, or about 13.0% of DS-6. In an exemplary embodiment, the area of DS-6 in a MALDI-TOF-MS spectrum is 10.64%.

In some embodiments, the mixture of hydroxypropyl-β-cyclodextrin molecules may include about 16% to about 22% of DS-7. In some aspects, the mixture of hydroxypropyl-β-cyclodextrin molecules may include about 16% to about 16.5% of DS-7, about 16.5% to about 17% of DS-7, about 17% to about 17.5% of DS-7, about 17.5% to about 18% of DS-7, about 18% to about 18.5% of DS-7, about 18.5% to about 19% of DS-7, about 19% to about 19.5% of DS-7, about 19.5% to about 20% of DS-7, about 20% to about 20.5% of DS-7, about 20.5% to about 21% of DS-7, about 21% to about 21.5% of DS-7, or about 21.5% to about 22% of DS-7. In some additional aspects, the mixture of hydroxypropyl-β-cyclodextrin molecules may include about 16% to about 17% of DS-7, about 16% to about 17.5% of DS-7, about 16% to about 18% of DS-7, about 16% to about 18.5% of DS-7, about 16% to about 19% of DS-7, about 16% to about 19.5% of DS-7, about 16% to about 20% of DS-7, about 16% to about 20.5% of DS-7, about 16% to about 21% of DS-7, about 16% to about 21.5% of DS-7, about 16.5% to about 22% of DS-7, about 17% to about 22% of DS-7, about 17.5% to about 22% of DS-7, about 18% to about 22% of DS-7, about 18.5% to about 22% of DS-7, about 19% to about 22% of DS-7, about 19.5% to about 22% of DS-7, about 20% to about 22% of DS-7, about 20.5% to about 22% of DS-7, about 21% to about 22% of DS-7, about 16.5% to about 21.5% of DS-7, about 17% to about 21% of DS-7, about 17.5% to about 20.5% of DS-7, about 18% to about 20% of DS-7, or about 18.5% to about 19.5% of DS-7. In still further aspects, the mixture of hydroxypropyl-β-cyclodextrin molecules may include about 16.0%, 16.1%, 16.2%, 16.3%, 16.4%, 16.5%, 16.6%, 16.7%, 16.8%, 16.9%, 17.0%, 17.1%, 17.2%, 17.3%, 17.4%, 17.5%, 17.6%, 17.7%, 17.8%, 17.9%, 18.0%, 18.1%, 18.2%, 18.3%, 18.4%, 18.5%, 18.6%, 18.7%, 18.8%, 18.9%, 19.0%, 19.1%, 19.2%, 19.3%, 19.4%, 19.5%, 19.6%, 19.7%, 19.8%, 19.9%, 20.0%, 20.1%, 20.2%, 20.3%, 20.4%, 20.5%, 20.6%, 20.7%, 20.8%, 20.9%, 21.0%, 21.1%, 21.2%, 21.3%, 21.4%, 21.5%, 21.6%, 21.7%, 21.8%, 21.9%, or about 22.0% of DS-7. In an exemplary embodiment, the area of DS-7 in a MALDI-TOF-MS spectrum is 19.30%.

In some embodiments, the mixture of isomerically-purified hydroxypropyl-β-cyclodextrin molecules may include about 26% to about 32% of DS-8. In some aspects, the mixture of isomerically-purified hydroxypropyl-β-cyclodextrin molecules may include about 26% to about 26.5% of DS-8, about 26.5% to about 27% of DS-8, about 27% to about 27.5% of DS-8, about 27.5% to about 28% of DS-8, about 28% to about 28.5% of DS-8, about 28.5% to about 29% of DS-8, about 29% to about 29.5% of DS-8, about 29.5% to about 30% of DS-8, about 30% to about 30.5% of DS-8, about 30.5% to about 31% of DS-8, about 31% to about 31.5% of DS-8, or about 31.5% to about 32% of DS-8. In some additional aspects, the mixture of isomerically-purified β-cyclodextrin may include about 26% to about 27% of DS-8, about 26% to about 27.5% of DS-8, about 26% to about 28% of DS-8, about 26% to about 28.5% of DS-8, about 26% to about 29% of DS-8, about 26% to about 29.5% of DS-8, about 26% to about 30% of DS-8, about 26% to about 30.5% of DS-8, about 26% to about 31% of DS-8, about 26% to about 31.5% of DS-8, about 26.5% to about 32% of DS-8, about 27% to about 32% of DS-8, about 27.5% to about 32% of DS-8, about 28% to about 32% of DS-8, about 28.5% to about 32% of DS-8, about 29% to about 32% of DS-8, about 29.5% to about 32% of DS-8, about 30% to about 32% of DS-8, about 30.5% to about 32% of DS-8, about 31% to about 32% of DS-8, about 26.5% to about 31.5% of DS-8, about 27% to about 31% of DS-8, about 27.5% to about 30.5% of DS-8, about 28% to about 30% of DS-8, or about 28.5% to about 29.5% of DS-8. In still further aspects, the mixture of isomerically-purified β-cyclodextrin molecules may include about 26.0%, 26.1%, 26.2%, 26.3%, 26.4%, 26.5%, 26.6%, 26.7%, 26.8%, 26.9%, 27.0%, 27.1%, 27.2%, 27.3%, 27.4%, 27.5%, 27.6%, 27.7%, 27.8%, 27.9%, 28.0%, 28.1%, 28.2%, 28.3%, 28.4%, 28.5%, 28.6%, 28.7%, 28.8%, 28.9%, 29.0%, 29.1%, 29.2%, 29.3%, 29.4%, 29.5%, 29.6%, 29.7%, 29.8%, 29.9%, 30.0%, 30.1%, 30.2%, 30.3%, 30.4%, 30.5%, 30.6%, 30.7%, 30.8%, 30.9%, 31.0%, 31.1%, 31.2%, 31.3%, 31.4%, 31.5%, 31.6%, 31.7%, 31.8%, 31.9%, or about 32.0% of DS-8. In an exemplary embodiment, the area of DS-8 in a MALDI-TOF-MS spectrum is 29.30%.

In some embodiments, the mixture of isomerically-purified hydroxypropyl-β-cyclodextrin molecules may include about 22% to about 28% of DS-9. In some aspects, the mixture of isomerically-purified β-cyclodextrin molecules includes about 22% to about 22.5% of DS-9, about 22.5% to about 23% of DS-9, about 23% to about 23.5% of DS-9, about 23.5% to about 24% of DS-9, about 24% to about 24.5% to about 25% of DS-9, about 25% to about 25.5% of DS-9, about 25.5% to about 26% of DS-9, about 26% to about 26.5% of DS-9, about 26.5% to about 27% of DS-9, about 27% to about 27.5% of DS-9, or about 27.5% to about 28% of DS-9. In some additional aspects, the mixture of isomerically-purified β-cyclodextrin may include about 22% to about 23% of DS-9, about 22% to about 23.5% of DS-9, about 22% to about 24% of DS-9, about 22% to about 24.5% of DS-9, about 22% to about 25% of DS-9, about 22% to about 25.5% of DS-9, about 22% to about 26% of DS-9, about 22% to about 26.5% of DS-9, about 22% to about 27% of DS-9, about 22% to about 27.5% of DS-9, about 22.5% to about 28% of DS-9, about 23% to about 28% of DS-9, about 23.5% to about 28% of DS-9, about 24% to about 28% of DS-9, about 24.5% to about 28% of DS-9, about 25% to about 28% of DS-9, about 25.5% to about 28% of DS-9, about 26% to about 28% of DS-9, about 26.5% to about 28% of DS-9, about 27% to about 28% of DS-9, about 22.5% to about 27.5% of DS-9, about 23% to about 27% of DS-9, about 23.5% to about 26.5% of DS-9, about 24% to about 26% of DS-9, or about 24.5% to about 25.5% of DS-9. In still further aspects, the mixture of isomerically-purified β-cyclodextrin molecules may include about 22.0%, 22.1%, 22.2%, 22.3%, 22.4%, 22.5%, 22.6%, 22.7%, 22.8%, 22.9%, 23.0%, 23.1%, 23.2%, 23.3%, 23.4%, 23.5%, 23.6%, 23.7%, 23.8%, 23.9%, 24.0%, 24.1%, 24.2%, 24.3%, 24.4%, 24.5%, 24.6%, 24.7%, 24.8%, 24.9%, 25.0%, 25.1%, 25.2%, 25.3%, 25.4%, 25.5%, 25.6%, 25.7%, 25.8%, 25.9%, 26.0%, 26.1%, 26.2%, 26.3%, 26.4%, 26.5%, 26.6%, 26.7%, 26.8%, 26.9%, 27.0%, 27.1%, 27.2%, 27.3%, 27.4%, 27.5%, 27.6%, 27.7%, 27.8%, 27.9%, or about 28.0% of DS-9. In an exemplary embodiment, the area of DS-9 in a MALDI-TOF-MS spectrum is 25.30%.

In some embodiments, the mixture of isomerically-purified hydroxypropyl-β-cyclodextrin molecules may include about 11% to about 17% of DS-10. In some aspects, the mixture of isomerically-purified hydroxypropyl-β-cyclodextrin molecules may include about 11% to about 11.5% of DS-10, about 11.5% to about 12% of DS-10, about 12% to about 12.5% of DS-10, about 12.5% to about 13% of DS-10, about 13% to about 13.5% of DS-10, about 13.5% to about 14% of DS-10, about 14% to about 14.5% of DS-10, about 14.5% to about 15% of DS-10, about 15% to about 15.5% of DS-10, about 15.5% to about 16% of DS-10, about 16% to about 16.5% of DS-10, or about 16.5% to about 17% of DS-10. In some additional aspects, the mixture of isomerically-purified hydroxypropyl-β-cyclodextrin molecules may include about 11% to about 12% of DS-10, about 11% to about 12.5% of DS-10, about 11% to about 13% of DS-10, about 11% to about 13.5% of DS-10, about 11% to about 14% of DS-10, about 11% to about 14.5% of DS-10, about 11% to about 15% of DS-10, about 11% to about 15.5% of DS-10, about 11% to about 16% of DS-10, about 11% to about 16.5% of DS-10, about 11.5% to about 17% of DS-10, about 12% to about 17% of DS-10, about 12.5% to about 17% of DS-10, about 13% to about 17% of DS-10, about 13.5% to about 17% of DS-10, about 14% to about 17% of DS-10, about 14.5% to about 17% of DS-10, about 15% to about 17% of DS-10, about 15.5% to about 17% of DS-10, about 16% to about 17% of DS-10, about 11.5% to about 16.5% of DS-10, about 12% to about 16% of DS-10, about 12.5% to about 15.5% of DS-10, about 13% to about 15% of DS-10, or about 13.5% to about 14.5% of DS-10. In still further aspects, the mixture of isomerically-purified hydroxypropyl-β-cyclodextrin molecules may include about 11.0%, 11.1%, 11.2%, 11.3%, 11.4%, 11.5%, 11.6%, 11.7%, 11.8%, 11.9%, 12.0%, 12.1%, 12.2% 12.3%, 12.4%, 12.5%, 12.6%, 12.7%, 12.8%, 12.9%, 13.0%, 13.1%, 13.2%, 13.3%, 13.4%, 13.5%, 13.6%, 13.7%, 13.8%, 13.9%, 14.0%, 14.1%, 14.2%, 14.3%, 14.4%, 14.5%, 14.6%, 14.7%, 14.8%, 14.9%, 15.0%, 15.1%, 15.2%, 15.3%, 15.4%, 15.5%, 15.6%, 15.7%, 15.8%, 15.9%, 16.0%, 16.1%, 16.2%, 16.3%, 16.4%, 16.5%, 16.6%, 16.7%, 16.8%, 16.9%, or about 17.0% of DS-10. In an exemplary embodiment, the area of DS-10 in a MALDI-TOF-MS spectrum is 14.30%.

In an exemplary embodiment, the mixture of isomerically-purified hydroxypropyl-β-cyclodextrin molecules may include about 1% to about 5% of DS-5, about 7% to about 13% of DS-6, about 16% to about 22% of DS-7, about 26% to about 32% of DS-8, about 22% to about 28% of DS-9, and about 11% to about 17% of DS-10.

In another exemplary embodiment, the mixture of isomerically-purified hydroxypropyl-β-cyclodextrin molecules includes DS-5, DS-6, DS-7, DS-8, DS-9, and DS-10; the composition includes less than 1% of DS-4, DS-3, DS-2, and DS-1; and the composition includes less than 1% of DS-11, DS-12, DS-13, and DS-14. In another exemplary embodiment, the mixture of isomerically-purified hydroxypropyl-β-cyclodextrin molecules includes DS-5, DS-6, DS-7, DS-8, DS-9, and DS-10 and the composition is free of DS-11, DS-12, DS-13, and/or DS-14. In another exemplary embodiment, the mixture of isomerically-purified hydroxypropyl-β-cyclodextrin molecules includes DS-5, DS-6, DS-7, DS-8, DS-9, and DS-10 and the composition is free of DS-4, DS-3, DS-2, and/or DS-1.

In some embodiments, the average degree of substitution of the mixture of isomerically-purified hydroxypropyl-β-cyclodextrin molecules may be about 6.4 to about 7.0. In some aspects, the average degree of substitution of the mixture of isomerically-purified hydroxypropyl-β-cyclodextrin molecules may be about 6.4, 6.5, 6.6, 6.7, 6.8, 6.9, or about 7.0. In an exemplary embodiment, the average degree of substitution of the mixture of hydroxypropyl-β-cyclodextrin molecules may be about 6.69.

Figure 6:
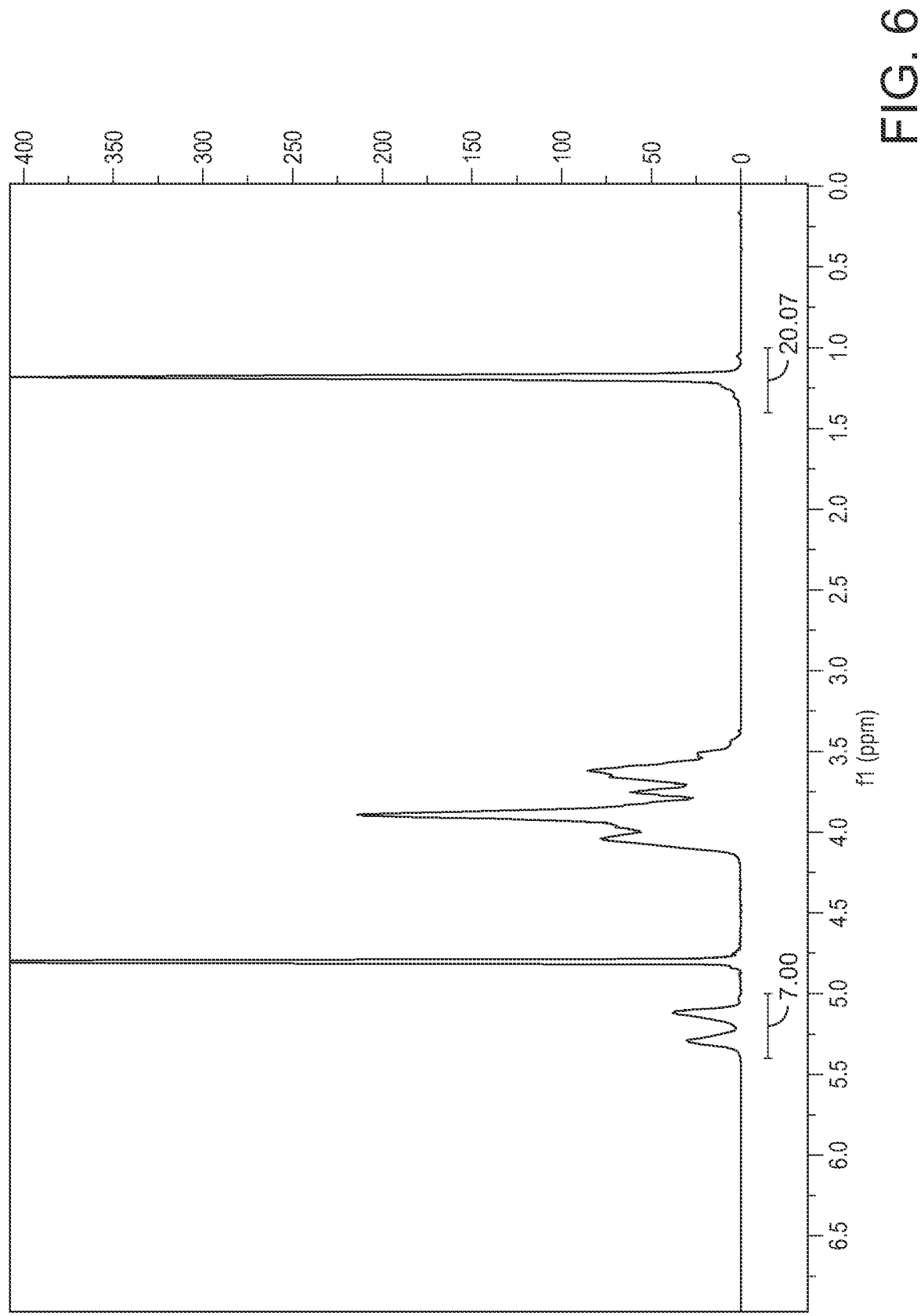
FIG. 6 is a ¹H NMR spectrum of the first HDS Fraction of a mixture of hydroxypropyl-β-cyclodextrins of the present disclosure.
Figure 7:
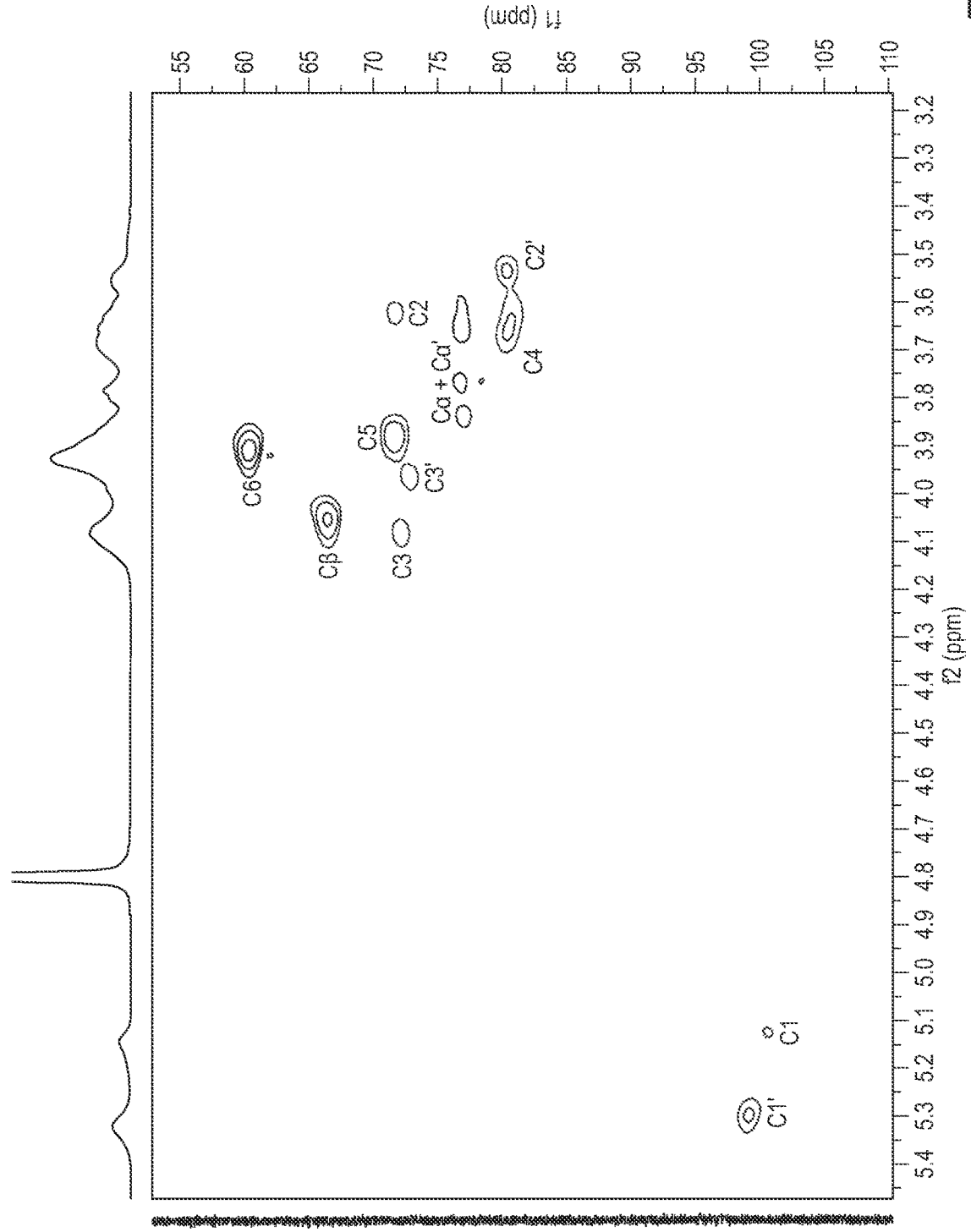
FIG. 7 is a DEPT-ed HSQC spectrum of the first HDS fraction of a mixture of hydroxypropyl-β-cyclodextrin of the present disclosure.

The position of the substitutions in the mixture isomerically-purified hydroxypropyl-β-cyclodextrin molecules of may be determined using methods known to those having a skill in the art. In some embodiments the composition may be characterized by $^1$H-NMR. In some aspects, $^1$H-NMR may be used to determine the degree of substitution of the composition. An exemplary $^1$H-NMR spectrum is provided in FIG. 6. In some embodiments, the composition may be characterized by DEPT-ed HSQC. An exemplary DEPT-ed HSQC spectrum is provided in FIG. 7.

In some embodiments, about 52% to about 58% of the hydroxypropyl substitutions in the hydroxypropyl-β-cyclodextrin molecules may be located at the 3-O-position. In some aspects, the percentage of substitutions in the mixture of the hydroxypropyl-β-cyclodextrin molecules at the 3-O— position may be about 52% to about 53%, about 53% to about 54%, about 54% to about 55%, about 55% to about 56%, about 56% to about 57%, or about 57% to about 58%. In some additional aspects, the percentage of substitutions in the mixture of hydroxypropyl-β-cyclodextrin molecules at the 3-O— position may be about 52% to about 54%, about 52% to about 55%, about 52% to about 56%, about 52% to about 57%, about 53% to about 58%, about 54% to about 58%, about 55% to about 58%, about 56% to about 58%, about 53% to about 57%, or about 54% to about 56%. In an exemplary embodiment, the percentage of substitutions in the mixture of hydroxypropyl-β-cyclodextrin molecules at the 3-O— position is about 55.43%.

In some embodiments, about 41% to about 47% of the hydroxypropyl substitutions in the hydroxypropyl-β-cyclodextrin molecules are located at the 2-O-position. In some aspects, the percentage of substitutions in the mixture of hydroxypropyl-β-cyclodextrin molecules at the 2-O— position is about 41% to about 42%, about 42% to about 43%, about 43% to about 44%, about 44% to about 45%, about 45% to about 46%, or about 46% to about 47%. In some additional aspects, the percentage of substitutions in the mixture of hydroxypropyl-β-cyclodextrin molecules at the 2-O— position is about 41% to about 43%, about 41% to about 44%, about 41% to about 45%, about 41% to about 46%, about 42% to about 47%, about 43% to about 47%, about 44% to about 47%, about 45% to about 47%, about 42% to about 46%, or about 43% to about 45%. In an exemplary embodiment, the percentage of substitutions in the mixture of hydroxypropyl-β-cyclodextrin molecules at the 2-O— position is about 44.57%.

In some embodiments, the percentage of substitutions in the mixture of hydroxypropyl-β-cyclodextrin molecules at the 6-O— position is about 0%.

Figure 8:
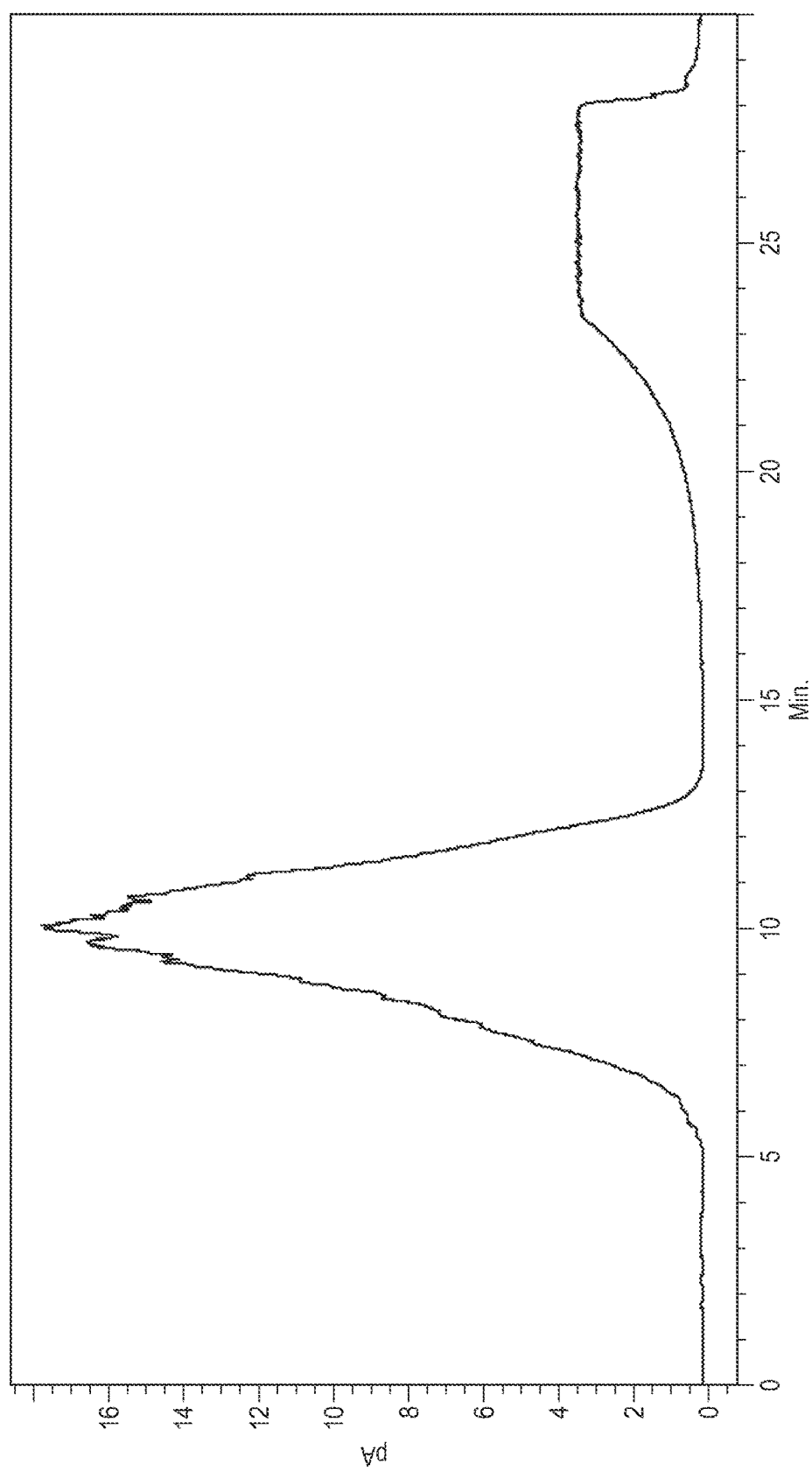
FIG. 8 is an HPLC-CAD chromatogram of the first HDS fraction of a mixture of hydroxypropyl-β-cyclodextrins of the present disclosure.

In some embodiments, the composition may have an HPLC-CAD chromatogram of FIG. 8. In some aspects, the mean retention time of the composition may be about 9 minutes to about 11 minutes as measured by HPLC-CAD. In some additional aspects, the mean retention time of the composition may be about 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, or about 11 minutes. In an exemplary embodiment, the mean retention time is about 10.1 minutes.

In some embodiments, the composition may have a −ESI-MS spectrum with peaks at about 653 m/z, about 682 m/z, about 711 m/z, about 741 m/z, about 769 m/z, about 799 m/z, about 828 m/z, and about 857 m/z. In some embodiments, the composition may have a +ESI-MS spectrum with peaks at about 686 m/z, about 715 m/z, about 744 m/z, about 773 m/z, about 802 m/z, about 832 m/z, about 861 m/z, and at about 890 m/z. In an exemplary embodiment, the composition has the ESI-MS spectra shown in FIG. 9.

The hydroxypropyl-β-cyclodextrin percent may be based upon an area percentage from a MALDI-TOF-MS spectrum. In some embodiments, the composition may have a MALDI-TOF-MS spectrum with peaks at about 1436 m/z, about 1495 m/z, about 1555 m/z, about 1614 m/z, about 1674 m/z, and at about 1733 m/z. In an exemplary embodiment, the composition has the MALDI-TOF-MS spectrum shown in FIG. 10. In an exemplary embodiment, the composition has a MALDI-TOF-MS spectrum wherein the area of DS-5 is 2.83%, the area of DS-6 is 10.64%, the area of DS-7 is 19.30%, the area of DS-8 is 29.30%, the area of DS-9 is 25.30%, and the area of DS-10 is 14.30%.

In some embodiments, the composition may have a true density of about 1.095 g/cm$^3$ to about 1.100 g/cm$^3$. In some aspects, the composition may have a true density of about 1.095 g/cm$^3$ to about 1.096 g/cm$^3$, about 1.096 g/cm$^3$ to about 1.097 g/cm$^3$, about 1.097 g/cm$^3$ to about 1.098 g/cm$^3$, about 1.098 g/cm$^3$ to about 1.099 g/cm$^3$, about 1.099 g/cm$^3$ to about 1.100 g/cm$^3$, about 1.095 g/cm$^3$ to about 1.097 g/cm$^3$, about 1.095 g/cm$^3$ to about 1.098 g/cm$^3$, about 1.095 g/cm$^3$ to about 1.099 g/cm$^3$, about 1.096 g/cm$^3$ to about 1.100 g/cm$^3$, about 1.097 g/cm$^3$ to about 1.100 g/cm$^3$, about 1.098 g/cm$^3$ to about 1.100 g/cm$^3$, about 1.096 g/cm$^3$ to about 1.098 g/cm$^3$, or about 1.096 g/cm$^3$ to about 1.099 g/cm$^3$. In some additional aspects, the composition may have a true density of about 1.095 g/cm$^3$, 1.096 g/cm$^3$, 1.097 g/cm$^3$, 1.098 g/cm$^3$, 1.099 g/cm$^3$, or about 1.100 g/cm$^3$. In an exemplary embodiment, the composition has a true density of about 1.096 g/cm$^3$ to about 1.098 g/cm$^3$.

In some embodiments, the composition may have an osmolality of about 600 mOs/kg to about 750 mOs/kg. In some aspects, the composition may have an osmolality of about 600 mOs/kg to about 625 mOs/kg, 625 mOs/kg to about 650 mOs/kg, about 650 mOs/kg to about 675 mOs/kg, about 675 mOs/kg to about 700 mOs/kg, about 700 mOs/kg to about 725 mOs/kg, or about 725 mOs/kg to about 750 mOs/kg. In some additional aspects, the composition may have an osmolality of about 600 mOs/kg to about 650 mOs/kg, about 600 mOs/kg to about 675 mOs/kg, about 600 mOs/kg to about 700 mOs/kg, about 600 mOs/kg to about 725 mOs/kg, about 625 mOs/kg to about 750 mOs/kg, about 650 mOs/kg to about 750 mOs/kg, about 675 mOs/kg to about 750 mOs/kg, about 700 mOs/kg to about 750 mOs/kg, about 625 mOs/kg to about 725 mOs/kg, or about 650 mOs/kg to about 700 mOs/kg. In still further embodiments, the composition may have an osmolality of about 600 mOs/kg, 610 mOs/kg, 620 mOs/kg, 630 mOs/kg, 640 mOs/kg, 650 mOs/kg, 660 mOs/kg, 670 mOs/kg, 680 mOs/kg, 690 mOs/kg, 700 mOs/kg, 710 mOs/kg, 720 mOs/kg, 730 mOs/kg, 740 mOs/kg, or about 750 mOs/kg. In an exemplary embodiment, the composition has an osmolality of about 635 mOs/kg to about 695 mOs/kg.

In some embodiments, the composition may have a conductivity between about 0 and about 8 µS/cm. In some aspects, the composition may have a conductivity between about 0 µS/cm and about 1 µS/cm, about 1 µS/cm and about 2 µS/cm, about 3 µS/cm and about 4 µS/cm, about 4 µS/cm and about 5 µS/cm, about 5 µS/cm and about 6 µS/cm, about 6 µS/cm and about 7 µS/cm, or between about 7 µS/cm and about 8 µS/cm. In some additional embodiments, the composition may have a conductivity between about 0 µS/cm and about 1.5 µS/cm, about 0 µS/cm and about 2 µS/cm, about 0 µS/cm and about 2.5 µS/cm, about 0 µS/cm and about 3 µS/cm, about 0 and about 3.5 µS/cm, about 0 µS/cm and about 4 µS/cm, about 0 and about 4.5 µS/cm, about 0 µS/cm and about 5 µS/cm, about 0 and about 5.5 µS/cm, about 0 µS/cm and about 6 µS/cm, about 0 and about 6.5, about 0 µS/cm and about 7 µS/cm, about 0 and about 7.5, about 1 µS/cm and about 8 µS/cm, about 1.5 µS/cm and about 8 µS/cm, about 2 µS/cm and about 8 µS/cm, about 2.5 µS/cm and about 8 µS/cm, about 3 µS/cm and about 8 µS/cm, about 3.5 µS/cm and about 8 µS/cm, about 4 µS/cm and about 8 µS/cm, about 4.5 µS/cm and about 8 µS/cm, about 5 µS/cm and about 8 µS/cm, about 5.5 µS/cm and about 8 µS/cm, about 6 µS/cm and about 8 µS/cm, about 6.5 µS/cm and about 8 µS/cm, about 1 µS/cm and about 7 µS/cm, about 2 µS/cm and about 6 µS/cm, or about 3 µS/cm and about 5 µS/cm. In still further aspects, the composition may have a conductivity of about 0.5 µS/cm, 1.0 µS/cm, 1.5 µS/cm, 2.0 µS/cm, 2.5 µS/cm, 3.0 µS/cm, 3.5 µS/cm, 4.0 µS/cm, 4.5 µS/cm, 5.0 µS/cm, 5.5 µS/cm, 6.0 µS/cm, 6.5 µS/cm, 7.0 µS/cm, 7.5 µS/cm, or about 8.0 µS/cm.

In some embodiments, the composition may have a pH of about 4.0 to about 8.0; for example, the composition may have a pH of about 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, or about 8.0. The composition may have a pH in a range or sub-range comprising any of the afore-mentioned numbers, including but not limited to a pH about 4.0 to about 4.5, about 4.5 to about 5.0, about 5.0 to about 5.5, about 5.5 to about 6.0, about 6.0 to about 6.5, about 6.5 to about 7.0, about 7.0 to about 7.5, or about 7.5 to about 8.0. In some embodiments, the composition may further comprise a pH adjusting agent, such as hydrochloric acid or sodium hydroxide, to adjust the pH to a desired level. In some embodiments, the composition may further comprise a buffer. In some embodiments, the buffer may include monobasic sodium phosphate and dibasic sodium phosphate.

In some embodiments, the composition may have a viscosity measured in centipoises (cP) at 20° C. For example, the composition may have a viscosity of about 1.5 cP to about 3.0 cP at 20° C. In some embodiments, the composition may have a viscosity of about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or about 10.0 cP at 20° C. In other embodiments, the composition may have a viscosity of about 3.0 cP to about 5.0 cP, about 5.0 cP to about 10.0 cP, about 10 to about 15 cP, about 15 to about 20 cP, about 20 cP to about 25 cP, about 25 cP to about 50 cP, about 50 cP to about 80 cP, about 80 cP to about 150 cP, about 150 cP to about 250 cP, about 250 cP to about 500 cP, about 500 cP to about 1,000 cP, about 1,000 cP to about 2,000 cP, about 2,000 cP to about 3,000 cP, about 3,000 cP to about 5,000 cP, or about 5,000 cP to about 10,000 cP at 20° C.

The composition may be substantially free of impurities. Impurities include particles having a diameter of greater than or equal to 25 microns, particles having a diameter of greater than or equal to 10 microns, chloride, propylene glycol, propylene oxide, and other unspecified impurities. In some embodiments, the composition may include less than or equal to about 0.05% impurities; for example, the composition may include less than or equal to about 0.05%, 0.04%, 0.03%, 0.02%, or less than or equal to about 0.01% impurities.

In some embodiments, the composition may further comprise a container and non-visible particulate matter. In some embodiments, the composition may be provided in a container. In some embodiments, the composition may further comprise non-visible particulate matter.

In some embodiments, the composition may include less than 600 particles per container having a diameter of greater than or equal to 25 microns. In some aspects, the composition may include less than 500, less than 400, less than 300, less than 200, or less than 100 particles per container having a diameter greater than or equal to 25 microns.

In some embodiments, the composition may include less than 6000 particles per container having a diameter of greater than or equal to 10 microns. In some aspects, the composition may include less than 5000, less than 4000, less than 3000, less than 2000, less than 1000, less than 500, or less than 100 particles per container having a diameter greater than or equal to 10 microns. In another aspect, the composition may include less than 5000, less than 4000, less than 3000, less than 2000, less than 1000, less than 500, or less than 100 particles per container having a diameter greater than or equal to 10 microns, wherein the container is: 100 mL. In another aspect, the composition may include less than 5000, less than 4000, less than 3000, less than 2000, less than 1000, less than 500, less than 100, less than 50, less than 25, less than 10, less than 5, or less than 3 particles per container having a diameter greater than or equal to 10 microns, wherein the container is >100 mL.

In some embodiments, the composition may include no more than 10 ppb of propylene glycol. In some aspects, the composition may include no more than 9 ppb, 8 ppb, 7 ppb, 6 ppb, 5 ppb, 4 ppb, 3 ppb, 2 ppb, or no more than 1 ppb propylene glycol. In some aspects, the amount of propylene glycol in the composition may be determined by HPLC. In some additional aspects, the amount of propylene glycol in the composition may be determined by gas chromatography. In still further aspects, the amount of propylene glycol in the composition may be determined by measuring the PG/EG-ratio of propylene glycol to ethylene glycol.

In some embodiments, the composition may include no more than 1 ppm propylene oxide. In some aspects, the composition may include no more than 0.9 ppm, 0.8 ppm, 0.7 ppm, 0.6 ppm, 0.5 ppm, 0.4 ppm, 0.3 ppm, 0.2 ppm, or 0.1 ppm propylene oxide. In some aspects, the amount of propylene oxide in the composition may be determined by HPLC. In some additional aspects, the amount of propylene oxide in the composition may be determined by gas chromatography.

In some embodiments, the composition may include between about 0 ppm to about 10 ppm chloride (e.g., Cl⁻ ions). In some aspects, the composition may include about 0 ppm chloride to about 2 ppm chloride, about 2 ppm chloride to about 4 ppm chloride, about 4 ppm chloride to about 6 ppm chloride, about 6 ppm chloride to about 8 ppm chloride, or about 8 to about 10 ppm chloride. In some additional aspects, the composition may include about 0 ppm chloride to about 4 ppm chloride, about 0 ppm chloride to about 6 ppm chloride, about 0 ppm chloride to about 8 ppm chloride, about 2 ppm chloride to about 1 ppm chloride, about 4 ppm chloride to about 1 ppm chloride, or about 6 ppm chloride to about 1 ppm chloride. In still further aspects, the composition may include about 0 ppm, 1 ppm, 2 ppm, 3 ppm, 4 ppm, 5 ppm, 6 ppm, 7 ppm, 8 ppm, 9 ppm, or about 10 ppm chloride. In an exemplary embodiment, the composition may include between about 0 ppm to about 1 ppm chloride.

In some embodiments, the composition may include between about 0 ppm to about 10 ppm sodium (e.g., Na⁺ ions). In some aspects, the composition may include about 0 ppm sodium to about 2 ppm sodium, about 2 ppm sodium to about 4 ppm sodium, about 4 ppm sodium to about 6 ppm sodium, about 6 ppm sodium to about 8 ppm sodium, or about 8 to about 10 ppm sodium. In some additional aspects, the composition may include about 0 ppm sodium to about 4 ppm sodium, about 0 ppm sodium to about 6 ppm sodium, about 0 ppm sodium to about 8 ppm sodium, about 2 ppm sodium to about 1 ppm sodium, about 4 ppm sodium to about 1 ppm sodium, or about 6 ppm sodium to about 1 ppm sodium. In still further aspects, the composition may include about 0 ppm, 1 ppm, 2 ppm, 3 ppm, 4 ppm, 5 ppm, 6 ppm, 7 ppm, 8 ppm, 9 ppm, or about 10 ppm sodium. In an exemplary embodiment, the composition may include between about 0 ppm to about 1 ppm sodium.

In some embodiments, the composition may include less than or equal to 0.05% of other unspecified impurities; for example, the composition may include less than or equal to 0.05%, 0.04%, 0.03%, 0.02%, or less than or equal to 0.01% of other unspecified impurities.

In some embodiments, the composition may be stable for at least 6 months. For example, the composition may be stable for at least 3 months, 6 months, at least 7 months, at least 8 months, at least 9 months, at least 10 months, at least 11 months, at least 12 months, at least 13 months, at least 14 months, at least 15 months, at least 16 months, at least 17 months, at least 18 months, at least 24 months, or at least 36 months.

The composition may be nanofiltered. In some embodiments, the concentration of the composition does not substantially change the time required for nanofiltration. Thus, the time for nanofiltration does not increase or decrease as the concentration of the mixture of β-cyclodextrin molecules increases or decreases in the composition. In some aspects, the length of time to nanofilter the composition ranges from about 1.04 to about 1.20 hours per diafiltration volume (kg soln/m²·hr/L soln). In some embodiments, the nanofiltered composition has no substantial difference observed in HPLC-ELSD after nanofiltration as compared to before nanofiltration. In some embodiments, the composition has no substantial difference observed in NMR after nanofiltration as compared to before nanofiltration.

In some embodiments, the composition may be terminally sterilized. Methods of terminal sterilization are generally well-known in the art. In some embodiments, the pH of the composition may be adjusted after terminal sterilization.

In some embodiments, the composition may include less than or equal to 10.0% w/w of water. For example, the composition may include less than or equal to 10.0% w/w, 9.5% w/w, 9.0% w/w, 8.5% w/w, 8.0% w/w, 7.5% w/w, 7.0% w/w, 6.5% w/w, 6.0% w/w, 5.5% w/w, 5.0% w/w, 4.5% w/w, 4.0% w/w, 3.5% w/w, 3.0% w/w, 2.5% w/w, 2.0% w/w, 1.5% w/w, 1.0% w/w, 0.5% w/w, or less than or equal to 0.1% w/w water.

In some embodiments, the composition may be packaged in a vial suitable for injection to a human subject in need thereof. The vial may be glass, plastic, or any other material known in the pharmaceutical art. The vial may be coated with a material such as silicon dioxide to prevent leaching from the vial into the composition.

In some embodiments, the composition may be suitable for administration to a patient in need thereof. In some embodiments, the composition may be suitable for intrathecal administration, intravenous administration, oral administration, intracerebroventricular administration, or a combination thereof (e.g., intravenous and intrathecal administration), to a patient in need thereof. In some aspects, the patient may a human, such as an adult patient or a pediatric patient. In some examples, the human patient may be an infant (e.g., less than 6 months of age) or a neonate (e.g., less than 4 weeks of age).

In some embodiments, the composition may be efficacious in treating Niemann-Pick disease. In some embodiments, the composition may be efficacious in treating Niemann-Pick disease Type C. In some embodiments, the composition may be efficacious in treating liver disease. In some embodiments, the composition may be efficacious in treating cardiovascular disease. In some embodiments, the composition may be efficacious in treating familial hypercholesterolemia. In some embodiments, the composition may be efficacious in treating cholesterol deposits.

In some embodiments, the composition may further comprise a pharmaceutical excipient or carrier. In some embodiments, the composition may further comprise a pharmaceutically acceptable diluent. Examples of pharmaceutical excipients, carriers, and diluents are well known to those having skill in the art.

In some embodiments, the composition may exhibit a lower toxicity than Trappsol® Cyclo or Kleptose®. In some embodiments, the composition may exhibit a substantially lower ototoxicity than Trappsol® Cyclo or Kleptose®. In some embodiments, the composition may exhibit substantially no ototoxicity.

Fraction 2 HDS

Provided herein is a composition comprising a mixture of isomerically-purified hydroxypropyl-β-cyclodextrin molecules that includes less than 1% of DS-5 and less than 1% of DS-13. In some embodiments, the mixture of isomerically-purified hydroxypropyl-β-cyclodextrin molecules may include less than 1% of DS-4, DS-3, DS-2, and DS-1. In some aspects, the mixture of isomerically-purified hydroxypropyl-β-cyclodextrin molecules may include less than 1%, less than 0.9%, less than 0.8%, less than 0.7%, less than 0.6%, less than 0.5%, less than 0.4%, less than 0.3%, less than 0.2%, or less than 0.1% of DS-4, DS-3, DS-2, and DS-1. In some aspects, the mixture of isomerically-purified hydroxypropyl-β-cyclodextrin molecules is free of DS-4, DS-3, DS-2, and/or DS-1.

In some embodiments, the mixture of hydroxypropyl-β-cyclodextrin molecules may include less than 1% of DS-13 and DS-14. In some aspects, the mixture of isomerically-purified hydroxypropyl-β-cyclodextrin molecules may include less than 1%, less than 0.9%, less than 0.8%, than 0.7%, less than 0.6%, less than 0.5%, less than 0.4%, less than 0.3%, less than 0.2%, or less than 0.1% of DS-13 and DS-14.

In some embodiments, the mixture of hydroxypropyl-β-cyclodextrin molecules may optionally include less than 1% of DS-13 and/or DS-14. In some aspects, the mixture of isomerically-purified hydroxypropyl-β-cyclodextrin molecules may optionally include less than 1%, less than 0.9%, less than 0.8%, less than 0.7%, less than 0.6%, less than 0.5%, less than 0.4%, less than 0.3%, less than 0.2%, or less than 0.1% of DS-13 and/or DS-14. In preferred embodiments, the mixture of isomerically-purified hydroxypropyl-β-cyclodextrin molecules is free DS-14.

In some embodiments, the mixture of isomerically-purified hydroxypropyl-β-cyclodextrin molecules includes about 0% to about 6% of DS-6. In some aspects, the mixture of isomerically-purified hydroxypropyl-β-cyclodextrin molecules may include about 0% to about 0.5% of DS-6, about 0.5% to about 1% of DS-6, about 1% to about 1.5% of DS-6, about 1.5% to about 2% of DS-6, about 2% to about 2.5% of DS-6, about 2.5% to about 3% of DS-6, about 3% to about 3.5% of DS-6, about 3.5% to about 4% of DS-6, about 4% to about 4.5% of DS-6, about 4.5% to about 5% of DS-6, about 5% to about 5.5% of DS-6, or about 5.5% to about 6% of DS-6. In some additional aspects, the mixture of isomerically-purified hydroxypropyl-β-cyclodextrin molecules may include about 0% to about 1% of DS-6, about 0% to about 1.5% of DS-6, about 0% to about 2% of DS-6, about 0% to about 2.5% of DS-6, about 0% to about 3% of DS-6, about 0% to about 3.5% of DS-6, about 0% to about 4% of DS-6, about 0% to about 4.5% of DS-6, about 0% to about 5% of DS-6, about 0% to about 5.5% of DS-6, about 0.5% to about 6% of DS-6, about 1% to about 6% of DS-6, about 1.5% to about 6% of DS-6, about 2% to about 6% of DS-6, about 2.5% to about 6% of DS-6, about 3% to about 6% of DS-6, about 3.5% to about 6% of DS-6, about 4% to about 6% of DS-6, about 4.5% to about 6% of DS-6, about 5% to about 6% of DS-6, about 0.5% to about 5.5% of DS-6, about 1% to about 5% of DS-6, about 1.5% to about 4.5% of DS-6, about 2% to about 4% of DS-6, or about 2.5% to about 3.5% of DS-6. In still additional aspects, the mixture of isomerically-purified hydroxypropyl-β-cyclodextrin molecules may include about 0.0%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, or about 6.0% of DS-6. In an exemplary embodiment, the area of DS-6 in a MALDI-TOF-MS spectrum is 2.91%.

In some embodiments, the mixture of hydroxypropyl-β-cyclodextrin molecules may include about 8% to about 14% of DS-7. In some aspects, the mixture of hydroxypropyl-β-cyclodextrin molecules may include about 8% to about 8.5% of DS-7, about 8.5% to about 9% of DS-7, about 9% to about 9.5% of DS-7, about 9.5% to about 10% of DS-7, about 10% to about 10.5% of DS-7, about 10.5% to about 11% of DS-7, about 11% to about 11.5% of DS-7, about 11.5% to about 12% of DS-7, about 12% to about 12.5% of DS-7, about 12.5% to about 13% of DS-7, about 13% to about 13.5% of DS-7, or about 13.5% to about 14% of DS-7. In some additional aspects, the mixture of hydroxypropyl-β-cyclodextrin molecules may include about 8% to about 9% of DS-7, about 8% to about 9.5% of DS-7, about 8% to about 10% of DS-7, about 8% to about 10.5% of DS-7, about 8% to about 11% of DS-7, about 8% to about 11.5% of DS-7, about 8% to about 12% of DS-7, about 8% to about 12.5% of DS-7, about 8% to about 13% of DS-7, about 8% to about 13.5% of DS-7, about 8.5% to about 14% of DS-7, about 9% to about 14% of DS-7, about 9.5% to about 14% of DS-7, about 10% to about 14% of DS-7, about 10.5% to about 14% of DS-7, about 11% to about 14% of DS-7, about 11.5% to about 14% of DS-7, about 12% to about 14% of DS-7, about 12.5% to about 14% of DS-7, about 13% to about 14% of DS-7, about 8.5% to about 13.5% of DS-7, about 9% to about 13% of DS-7, about 9.5% to about 12.5% of DS-7, about 10% to about 12% of DS-7, or about 10.5% to about 11.5% of DS-7. In still further aspects, the mixture of hydroxypropyl-β-cyclodextrin molecules may include about 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10.0%, 10.1%, 10.2%, 10.3%, 10.4%, 10.5%, 10.6%, 10.7%, 10.8%, 10.9%, 11.0%, 11.1%, 11.2%, 11.3%, 11.4%, 11.5%, 11.6%, 11.7%, 11.8%, 11.9%, 12.0%, 12.1%, 12.2%, 12.3%, 12.4%, 12.5%, 12.6%, 12.7%, 12.8%, 12.9%, 13.0%, 13.1%, 13.2%, 13.3%, 13.4%, 13.5%, 13.6%, 13.7%, 13.8%, 13.9%, or about 14.0% of DS-7. In an exemplary embodiment, the area of DS-7 in a MALDI-TOF-MS spectrum is 10.93%.

In some embodiments, the mixture of isomerically-purified hydroxypropyl-β-cyclodextrin molecules may include about 19% to about 25% of DS-8. In some aspects, the mixture of isomerically-purified hydroxypropyl-β-cyclodextrin molecules may include about 19% to about 19.5% of DS-8, about 19.5% to about 20% of DS-8, about 20% to about 20.5% of DS-8, about 20.5% to about 21% of DS-8, about 21% to about 21.5% of DS-8, about 21.5% to about 22% of DS-8, about 22% to about 22.5% of DS-8, about 22.5% to about 23% of DS-8, about 23% to about 23.5% of DS-8, about 23.5% to about 24% of DS-8, about 24% to about 24.5% of DS-8, or about 24.5% to about 25% of DS-8. In some additional aspects, the mixture of isomerically-purified β-cyclodextrin may include about 19% to about 20% of DS-8, about 19% to about 20.5% of DS-8, about 19% to about 21% of DS-8, about 19% to about 21.5% of DS-8, about 19% to about 22% of DS-8, about 19% to about 22.5% of DS-8, about 19% to about 23% of DS-8, about 19% to about 23.5% of DS-8, about 19% to about 24% of DS-8, about 19% to about 24.5% of DS-8, about 19.5% to about 25% of DS-8, about 20% to about 25% of DS-8, about 20.5% to about 25% of DS-8, about 21% to about 25% of DS-8, about 21.5% to about 25% of DS-8, about 22% to about 25% of DS-8, about 22.5% to about 25% of DS-8, about 23% to about 25% of DS-8, about 23.5% to about 25% of DS-8, about 24% to about 25% of DS-8, about 19.5% to about 24.5% of DS-8, about 20% to about 24% of DS-8, about 20.5% to about 23.5% of DS-8, about 21% to about 23% of DS-8, or about 21.5% to about 22.5% of DS-8. In still further aspects, the mixture of isomerically-purified β-cyclodextrin molecules may include about 19.0%, 19.1%, 19.2%, 19.3%, 19.4%, 19.5%, 19.6%, 19.7%, 19.8%, 19.9%, 20.0%, 20.1%, 20.2%, 20.3%, 20.4%, 20.5%, 20.6%, 20.7%, 20.8%, 20.9%, 21.0%, 21.1%, 21.2%, 21.3%, 21.4%, 21.5%, 21.6%, 21.7%, 21.8%, 21.9%, 22.0%, 22.1%, 22.2%, 22.3%, 22.4%, 22.5%, 22.6%, 22.7%, 22.8%, 22.9%, 23.0%, 23.1%, 23.2%, 23.3%, 23.4%, 23.5%, 23.6%, 23.7%, 23.8%, 23.9%, 24.0%, 24.1%, 24.2%, 24.3%, 24.4%, 24.5%, 24.6%, 24.7%, 24.8%, 24.9%, or about 25.0% of DS-8. In an exemplary embodiment, the area of DS-8 in a MALDI-TOF-MS spectrum is 22.52%.

In some embodiments, the mixture of isomerically-purified hydroxypropyl-β-cyclodextrin molecules may include about 23% to about 29% of DS-9. In some aspects, the mixture of isomerically-purified β-cyclodextrin molecules includes about 23% to about 23.5% of DS-9, about 23.5% to about 24% of DS-9, about 24% to about 24.5% to about 25% of DS-9, about 25% to about 25.5% of DS-9, about 25.5% to about 26% of DS-9, about 26% to about 26.5% of DS-9, about 26.5% to about 27% of DS-9, about 27% to about 27.5% of DS-9, about 27.5% to about 28% of DS-9, about 28% to about 28.5% of DS-9, or about 28.5% to about 29% of DS-9. In some additional aspects, the mixture of isomerically-purified β-cyclodextrin may include about 23% to about 24% of DS-9, about 23% to about 24.5% of DS-9, about 23% to about 25% of DS-9, about 23% to about 25.5% of DS-9, about 23% to about 26% of DS-9, about 23% to about 26.5% of DS-9, about 23% to about 27% of DS-9, about 23% to about 27.5% of DS-9, about 23% to about 28% of DS-9, about 23% to about 28.5% of DS-9, about 23.5% to about 29% of DS-9, about 24% to about 29% of DS-9, about 24.5% to about 29% of DS-9, about 25% to about 29% of DS-9, about 25.5% to about 29% of DS-9, about 26% to about 29% of DS-9, about 26.5% to about 29% of DS-9, about 27% to about 29% of DS-9, about 27.5% to about 29% of DS-9, about 28% to about 29% of DS-9, about 23.5% to about 28.5% of DS-9, about 24% to about 28% of DS-9, about 24.5% to about 27.5% of DS-9, about 25% to about 27% of DS-9, or about 25.5% to about 26.5% of DS-9. In still further aspects, the mixture of isomerically-purified β-cyclodextrin molecules may include about 23.0%, 23.1%, 23.2%, 23.3%, 23.4%, 23.5%, 23.6%, 23.7%, 23.8%, 23.9%, 24.0%, 24.1%, 24.2%, 24.3%, 24.4%, 24.5%, 24.6%, 24.7%, 24.8%, 24.9%, 25.0%, 25.1%, 25.2%, 25.3%, 25.4%, 25.5%, 25.6%, 25.7%, 25.8%, 25.9%, 26.0%, 26.1%, 26.2%, 26.3%, 26.4%, 26.5%, 26.6%, 26.7%, 26.8%, 26.9%, 27.0%, 27.1%, 27.2%, 27.3%, 27.4%, 27.5%, 27.6%, 27.7%, 27.8%, 27.9%, 28.0%, 28.1%, 28.2%, 28.3%, 28.4%, 28.5%, 28.6%, 28.7%, 28.8%, 28.9%, or about 29.0% of DS-9. In an exemplary embodiment, the area of DS-9 in a MALDI-TOF-MS spectrum is 26.42%.

In some embodiments, the mixture of isomerically-purified hydroxypropyl-β-cyclodextrin molecules may include about 17% to about 23% of DS-10. In some aspects, the mixture of isomerically-purified hydroxypropyl-β-cyclodextrin molecules may include about 17% to about 17.5% of DS-10, about 17.5% to about 18% of DS-10, about 18% to about 18.5% of DS-10, about 18.5% to about 19% of DS-10, about 19% to about 19.5% of DS-10, about 19.5% to about 20% of DS-10, about 20% to about 20.5% of DS-10, about 20.5% to about 21% of DS-10, about 21% to about 21.5% of DS-10, about 21.5% to about 22% of DS-10, about 22% to about 22.5% of DS-10, or about 22.5% to about 23% of DS-10. In some additional aspects, the mixture of isomerically-purified hydroxypropyl-β-cyclodextrin molecules may include about 17% to about 18% of DS-10, about 17% to about 18.5% of DS-10, about 17% to about 19% of DS-10, about 17% to about 19.5% of DS-10, about 17% to about 20% of DS-10, about 17% to about 20.5% of DS-10, about 17% to about 21% of DS-10, about 17% to about 21.5% of DS-10, about 17% to about 22% of DS-10, about 17% to about 22.5% of DS-10, about 17.5% to about 23% of DS-10, about 18% to about 23% of DS-10, about 18.5% to about 23% of DS-10, about 19% to about 23% of DS-10, about 19.5% to about 23% of DS-10, about 20% to about 23% of DS-10, about 20.5% to about 23% of DS-10, about 21% to about 23% of DS-10, about 21.5% to about 23% of DS-10, about 22% to about 23% of DS-10, about 17.5% to about 22.5% of DS-10, about 18% to about 22% of DS-10, about 18.5% to about 21.5% of DS-10, about 19% to about 21% of DS-10, or about 19.5% to about 20.5% of DS-10. In still further aspects, the mixture of isomerically-purified hydroxypropyl-β-cyclodextrin molecules may include about 17.0%, 17.1%, 17.2%, 17.3%, 17.4%, 17.5%, 17.6%, 17.7%, 17.8%, 17.9%, 18.0%, 18.1%, 18.2%, 18.3%, 18.4%, 18.5%, 18.6%, 18.7%, 18.8%, 18.9%, 19.0%, 19.1%, 19.2%, 19.3%, 19.4%, 19.5%, 19.6%, 19.7%, 19.8%, 19.9%, 20.0%, 20.1%, 20.2%, 20.3%, 20.4%, 20.5%, 20.6%, 20.7%, 20.8%, 20.9%, 21.0%, 21.1%, 21.2%, 21.3%, 21.4%, 21.5%, 21.6%, 21.7%, 21.8%, 21.9%, 22.0%, 22.1%, 22.2%, 22.3%, 22.4%, 22.5%, 22.6%, 22.7%, 22.8%, 22.9%, or about 23.0% of DS-10. In an exemplary embodiment, the area of DS-10 in a MALDI-TOF-MS spectrum is 20.35%.

In some embodiments, the mixture of isomerically-purified hydroxypropyl-β-cyclodextrin molecules may include about 9% to about 15% of DS-11. In some aspects, the mixture of isomerically-purified hydroxypropyl-β-cyclodextrin molecules may include about 9% to about 9.5% of DS-11, about 9.5% to about 10% DS-11, about 10% to about 10.5% of DS-11, about 10.5% to about 11% of DS-11, about 11% to about 11.5% of DS-11, about 11.5% to about 12% of DS-11, about 12% to about 12.5% of DS-11, about 12.5% to about 13% of DS-11, about 13% to about 13.5% of DS-11, about 13.5% to about 14% of DS-11, about 14% to about 14.5% of DS-11, or about 14.5% to about 15% of DS-11. In some additional aspects, the mixture of isomerically-purified hydroxypropyl-β-cyclodextrin molecules may include about 9% to about 10% of DS-11, about 9% to about 10.5% of DS-11, about 9% to about 11% of DS-11, about 9% to about 11.5% of DS-11, about 9% to about 12% of DS-11, about 9% to about 12.5% of DS-11, about 9% to about 13% of DS-11, about 9% to about 13.5% of DS-11, about 9% to about 14% of DS-11, about 9% to about 14.5% of DS-11, about 9.5% to about 15% of DS-11, about 10% to about 15% of DS-11, about 10.5% to about 15% of DS-11, about 11% to about 15% of DS-11, about 11.5% to about 15% of DS-11, about 12% to about 15% of DS-11, about 12.5% to about 15% of DS-11, about 13% to about 15% of DS-11, about 13.5% to about 15% of DS-11, about 14% to about 15% of DS-11, about 9.5% to about 14.5% of DS-11, about 10% to about 14% of DS-11, about 10.5% to about 13.5% of DS-11, about 11% to about 13% of DS-11, or about 11.5% to about 12.5% of DS-11. In still further aspects, the mixture of isomerically purified hydroxypropyl-β-cyclodextrin molecules may include about 9.0%, 9.1%, 9.2%, 9.3%, 9.4%, 9.5%, 9.6%, 9.7%, 9.8%, 9.9%, 10.0%, 10.1%, 10.2%, 10.3%, 10.4%, 10.5%, 10.6%, 10.7%, 10.8%, 10.9%, 11.0%, 11.1%, 11.2%, 11.3%, 11.4%, 11.5%, 11.6%, 11.7%, 11.8%, 11.9%, 12.0%, 12.1%, 12.2%, 12.3%, 12.4%, 12.5%, 12.6%, 12.7%, 12.8%, 12.9%, 13.0%, 13.1%, 13.2%, 13.3%, 13.4%, 13.5%, 13.6%, 13.7%, 13.8%, 13.9%, 14.0%, 14.1%, 14.2%, 14.3%, 14.4%, 14.5%, 14.6%, 14.7%, 14.8%, 14.9%, or about 15.0% of DS-11. In an exemplary embodiment, the area of DS-11 in a MALDI-TOF-MS spectrum is 12.02%.

In some embodiments, the mixture of isomerically-purified hydroxypropyl-β-cyclodextrin molecules may include about 2% to about 8% of DS-12. In some aspects, the mixture of isomerically-purified hydroxypropyl-β-cyclodextrin molecules may include about 2% to about 2.5% of DS-12, about 2.5% to about 3% of DS-12, about 3% to about 3.5% of DS-12, about 3.5% to about 4% of DS-12, about 4% to about 4.5% of DS-12, about 4.5% to about 5% of DS-12, about 5% to about 5.5% of DS-12, about 5.5% to about 6% of DS-12, about 6% to about 6.5% of DS-12, about 6.5% of to about 7% of DS-12, about 7% to about 7.5% of DS-12, or about 7.5% to about 8% of DS-12. In some additional aspects, the mixture of isomerically-purified hydroxypropyl-β-cyclodextrin molecules may include about 2% to about 3% of DS-12, about 2% to about 3.5% of DS-12, about 2% to about 4% of DS-12, about 2% to about 4.5% of DS-12, about 2% to about 5% of DS-12, about 2% to about 5.5% of DS-12, about 2% to about 6% of DS-12, about 2% to about 6.5% of DS-12, about 2% of about 7% of DS-12, about 2% of about 7.5% of DS-12, about 2.5% to about 8% of DS-12, about 3% to about 8% of DS-12, about 3.5% to about 8% of DS-12, about 4% to about 8% of DS-12, about 4.5% to about 8% of DS-12, about 5% to about 8% of DS-12, about 5.5% to about 8% of DS-12, about 6% to about 8% of DS-12, about 6.5% to about 8% of DS-12, about 7% to about 8% of DS-12, about 2.5% to about 7.5% of DS-12, about 3% to about 7% of DS-12, about 3.5% to about 6.5% of DS-12, about 4% to about 6% of DS-12, or about 4.5% to about 5.5% of DS-12. In still further aspects, the mixture of isomerically-purified hydroxypropyl-β-cyclodextrin molecules may include about 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, or about 8.0% of DS-12. In an exemplary embodiment, the area of DS-12 in a MALDI-TOF-MS spectrum is 4.85%.

Further provided herein is a composition comprising a mixture of isomerically-purified hydroxypropyl-β-cyclodextrin molecules including DS-6, DS-7, DS-8, DS-9, DS-10, DS-11, and DS-12. In some embodiments, the composition includes less than 1% of DS-5. In some additional embodiments, the composition includes less than 1% of DS-13. In some embodiments, the DS-9 may have the highest concentration in the composition as compared to DS-6, DS-7, DS-8, DS-10, DS-11, and DS-12.

In some embodiments, the mixture of isomerically-purified hydroxypropyl-β-cyclodextrin molecules includes about 0% to about 6% of DS-6. In some aspects, the mixture of isomerically-purified hydroxypropyl-β-cyclodextrin molecules may include about 0% to about 0.5% of DS-6, about 0.5% to about 1% of DS-6, about 1% to about 1.5% of DS-6, about 1.5% to about 2% of DS-6, about 2% to about 2.5% of DS-6, about 2.5% to about 3% of DS-6, about 3% to about 3.5% of DS-6, about 3.5% to about 4% of DS-6, about 4% to about 4.5% of DS-6, about 4.5% to about 5% of DS-6, about 5% to about 5.5% of DS-6, or about 5.5% to about 6% of DS-6. In some additional aspects, the mixture of isomerically-purified hydroxypropyl-β-cyclodextrin molecules may include about 0% to about 1% of DS-6, about 0% to about 1.5% of DS-6, about 0% to about 2% of DS-6, about 0% to about 2.5% of DS-6, about 0% to about 3% of DS-6, about 0% to about 3.5% of DS-6, about 0% to about 4% of DS-6, about 0% to about 4.5% of DS-6, about 0% to about 5% of DS-6, about 0% to about 5.5% of DS-6, about 0.5% to about 6% of DS-6, about 1% to about 6% of DS-6, about 1.5% to about 6% of DS-6, about 2% to about 6% of DS-6, about 2.5% to about 6% of DS-6, about 3% to about 6% of DS-6, about 3.5% to about 6% of DS-6, about 4% to about 6% of DS-6, about 4.5% to about 6% of DS-6, about 5% to about 6% of DS-6, about 0.5% to about 5.5% of DS-6, about 1% to about 5% of DS-6, about 1.5% to about 4.5% of DS-6, about 2% to about 4% of DS-6, or about 2.5% to about 3.5% of DS-6. In still additional aspects, the mixture of isomerically-purified hydroxypropyl-β-cyclodextrin molecules may include about 0.0%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, or about 6.0% of DS-6. In an exemplary embodiment, the area of DS-6 in a MALDI-TOF-MS spectrum is 2.91%.

In some embodiments, the mixture of hydroxypropyl-β-cyclodextrin molecules may include about 8% to about 14% of DS-7. In some aspects, the mixture of hydroxypropyl-β-cyclodextrin molecules may include about 8% to about 8.5% of DS-7, about 8.5% to about 9% of DS-7, about 9% to about 9.5% of DS-7, about 9.5% to about 10% of DS-7, about 10% to about 10.5% of DS-7, about 10.5% to about 11% of DS-7, about 11% to about 11.5% of DS-7, about 11.5% to about 12% of DS-7, about 12% to about 12.5% of DS-7, about 12.5% to about 13% of DS-7, about 13% to about 13.5% of DS-7, or about 13.5% to about 14% of DS-7. In some additional aspects, the mixture of hydroxypropyl-β-cyclodextrin molecules may include about 8% to about 9% of DS-7, about 8% to about 9.5% of DS-7, about 8% to about 10% of DS-7, about 8% to about 10.5% of DS-7, about 8% to about 11% of DS-7, about 8% to about 11.5% of DS-7, about 8% to about 12% of DS-7, about 8% to about 12.5% of DS-7, about 8% to about 13% of DS-7, about 8% to about 13.5% of DS-7, about 8.5% to about 14% of DS-7, about 9% to about 14% of DS-7, about 9.5% to about 14% of DS-7, about 10% to about 14% of DS-7, about 10.5% to about 14% of DS-7, about 11% to about 14% of DS-7, about 11.5% to about 14% of DS-7, about 12% to about 14% of DS-7, about 12.5% to about 14% of DS-7, about 13% to about 14% of DS-7, about 8.5% to about 13.5% of DS-7, about 9% to about 13% of DS-7, about 9.5% to about 12.5% of DS-7, about 10% to about 12% of DS-7, or about 10.5% to about 11.5% of DS-7. In still further aspects, the mixture of hydroxypropyl-β-cyclodextrin molecules may include about 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10.0%, 10.1%, 10.2%, 10.3%, 10.4%, 10.5%, 10.6%, 10.7%, 10.8%, 10.9%, 11.0%, 11.1%, 11.2%, 11.3%, 11.4%, 11.5%, 11.6%, 11.7%, 11.8%, 11.9%, 12.0%, 12.1%, 12.2%, 12.3%, 12.4%, 12.5%, 12.6%, 12.7%, 12.8%, 12.9%, 13.0%, 13.1%, 13.2%, 13.3%, 13.4%, 13.5%, 13.6%, 13.7%, 13.8%, 13.9%, or about 14.0% of DS-7. In an exemplary embodiment, the area of DS-7 in a MALDI-TOF-MS spectrum is 10.93%.

In some embodiments, the mixture of isomerically-purified hydroxypropyl-β-cyclodextrin molecules may include about 19% to about 25% of DS-8. In some aspects, the mixture of isomerically-purified hydroxypropyl-β-cyclodextrin molecules may include about 19% to about 19.5% of DS-8, about 19.5% to about 20% of DS-8, about 20% to about 20.5% of DS-8, about 20.5% to about 21% of DS-8, about 21% to about 21.5% of DS-8, about 21.5% to about 22% of DS-8, about 22% to about 22.5% of DS-8, about 22.5% to about 23% of DS-8, about 23% to about 23.5% of DS-8, about 23.5% to about 24% of DS-8, about 24% to about 24.5% of DS-8, or about 24.5% to about 25% of DS-8. In some additional aspects, the mixture of isomerically-purified β-cyclodextrin may include about 19% to about 20% of DS-8, about 19% to about 20.5% of DS-8, about 19% to about 21% of DS-8, about 19% to about 21.5% of DS-8, about 19% to about 22% of DS-8, about 19% to about 22.5% of DS-8, about 19% to about 23% of DS-8, about 19% to about 23.5% of DS-8, about 19% to about 24% of DS-8, about 19% to about 24.5% of DS-8, about 19.5% to about 25% of DS-8, about 20% to about 25% of DS-8, about 20.5% to about 25% of DS-8, about 21% to about 25% of DS-8, about 21.5% to about 25% of DS-8, about 22% to about 25% of DS-8, about 22.5% to about 25% of DS-8, about 23% to about 25% of DS-8, about 23.5% to about 25% of DS-8, about 24% to about 25% of DS-8, about 19.5% to about 24.5% of DS-8, about 20% to about 24% of DS-8, about 20.5% to about 23.5% of DS-8, about 21% to about 23% of DS-8, or about 21.5% to about 22.5% of DS-8. In still further aspects, the mixture of isomerically-purified β-cyclodextrin molecules may include about 19.0%, 19.1%, 19.2%, 19.3%, 19.4%, 19.5%, 19.6%, 19.7%, 19.8%, 19.9%, 20.0%, 20.1%, 20.2%, 20.3%, 20.4%, 20.5%, 20.6%, 20.7%, 20.8%, 20.9%, 21.0%, 21.1%, 21.2%, 21.3%, 21.4%, 21.5%, 21.6%, 21.7%, 21.8%, 21.9%, 22.0%, 22.1%, 22.2%, 22.3%, 22.4%, 22.5%, 22.6%, 22.7%, 22.8%, 22.9%, 23.0%, 23.1%, 23.2%, 23.3%, 23.4%, 23.5%, 23.6%, 23.7%, 23.8%, 23.9%, 24.0%, 24.1%, 24.2%, 24.3%, 24.4%, 24.5%, 24.6%, 24.7%, 24.8%, 24.9%, or about 25.0% of DS-8. In an exemplary embodiment, the area of DS-8 in a MALDI-TOF-MS spectrum is 22.52%.

In some embodiments, the mixture of isomerically-purified hydroxypropyl-β-cyclodextrin molecules may include about 23% to about 29% of DS-9. In some aspects, the mixture of isomerically-purified β-cyclodextrin molecules includes about 23% to about 23.5% of DS-9, about 23.5% to about 24% of DS-9, about 24% to about 24.5% to about 25% of DS-9, about 25% to about 25.5% of DS-9, about 25.5% to about 26% of DS-9, about 26% to about 26.5% of DS-9, about 26.5% to about 27% of DS-9, about 27% to about 27.5% of DS-9, about 27.5% to about 28% of DS-9, about 28% to about 28.5% of DS-9, or about 28.5% to about 29% of DS-9. In some additional aspects, the mixture of isomerically-purified β-cyclodextrin may include about 23% to about 24% of DS-9, about 23% to about 24.5% of DS-9, about 23% to about 25% of DS-9, about 23% to about 25.5% of DS-9, about 23% to about 26% of DS-9, about 23% to about 26.5% of DS-9, about 23% to about 27% of DS-9, about 23% to about 27.5% of DS-9, about 23% to about 28% of DS-9, about 23% to about 28.5% of DS-9, about 23.5% to about 29% of DS-9, about 24% to about 29% of DS-9, about 24.5% to about 29% of DS-9, about 25% to about 29% of DS-9, about 25.5% to about 29% of DS-9, about 26% to about 29% of DS-9, about 26.5% to about 29% of DS-9, about 27% to about 29% of DS-9, about 27.5% to about 29% of DS-9, about 28% to about 29% of DS-9, about 23.5% to about 28.5% of DS-9, about 24% to about 28% of DS-9, about 24.5% to about 27.5% of DS-9, about 25% to about 27% of DS-9, or about 25.5% to about 26.5% of DS-9. In still further aspects, the mixture of isomerically-purified β-cyclodextrin molecules may include about 23.0%, 23.1%, 23.2%, 23.3%, 23.4%, 23.5%, 23.6%, 23.7%, 23.8%, 23.9%, 24.0%, 24.1%, 24.2%, 24.3%, 24.4%, 24.5%, 24.6%, 24.7%, 24.8%, 24.9%, 25.0%, 25.1%, 25.2%, 25.3%, 25.4%, 25.5%, 25.6%, 25.7%, 25.8%, 25.9%, 26.0%, 26.1%, 26.2%, 26.3%, 26.4%, 26.5%, 26.6%, 26.7%, 26.8%, 26.9%, 27.0%, 27.1%, 27.2%, 27.3%, 27.4%, 27.5%, 27.6%, 27.7%, 27.8%, 27.9%, 28.0%, 28.1%, 28.2%, 28.3%, 28.4%, 28.5%, 28.6%, 28.7%, 28.8%, 28.9%, or about 29.0% of DS-9. In an exemplary embodiment, the area of DS-9 in a MALDI-TOF-MS spectrum is 26.42%.

In some embodiments, the mixture of isomerically-purified hydroxypropyl-β-cyclodextrin molecules may include about 17% to about 23% of DS-10. In some aspects, the mixture of isomerically-purified hydroxypropyl-β-cyclodextrin molecules may include about 17% to about 17.5% of DS-10, about 17.5% to about 18% of DS-10, about 18% to about 18.5% of DS-10, about 18.5% to about 19% of DS-10, about 19% to about 19.5% of DS-10, about 19.5% to about 20% of DS-10, about 20% to about 20.5% of DS-10, about 20.5% to about 21% of DS-10, about 21% to about 21.5% of DS-10, about 21.5% to about 22% of DS-10, about 22% to about 22.5% of DS-10, or about 22.5% to about 23% of DS-10. In some additional aspects, the mixture of isomerically-purified hydroxypropyl-β-cyclodextrin molecules may include about 17% to about 18% of DS-10, about 17% to about 18.5% of DS-10, about 17% to about 19% of DS-10, about 17% to about 19.5% of DS-10, about 17% to about 20% of DS-10, about 17% to about 20.5% of DS-10, about 17% to about 21% of DS-10, about 17% to about 21.5% of DS-10, about 17% to about 22% of DS-10, about 17% to about 22.5% of DS-10, about 17.5% to about 23% of DS-10, about 18% to about 23% of DS-10, about 18.5% to about 23% of DS-10, about 19% to about 23% of DS-10, about 19.5% to about 23% of DS-10, about 20% to about 23% of DS-10, about 20.5% to about 23% of DS-10, about 21% to about 23% of DS-10, about 21.5% to about 23% of DS-10, about 22% to about 23% of DS-10, about 17.5% to about 22.5% of DS-10, about 18% to about 22% of DS-10, about 18.5% to about 21.5% of DS-10, about 19% to about 21% of DS-10, or about 19.5% to about 20.5% of DS-10. In still further aspects, the mixture of isomerically-purified hydroxypropyl-β-cyclodextrin molecules may include about 17.0%, 17.1%, 17.2%, 17.3%, 17.4%, 17.5%, 17.6%, 17.7%, 17.8%, 17.9%, 18.0%, 18.1%, 18.2%, 18.3%, 18.4%, 18.5%, 18.6%, 18.7%, 18.8%, 18.9%, 19.0%, 19.1%, 19.2%, 19.3%, 19.4%, 19.5%, 19.6%, 19.7%, 19.8%, 19.9%, 20.0%, 20.1%, 20.2%, 20.3%, 20.4%, 20.5%, 20.6%, 20.7%, 20.8%, 20.9%, 21.0%, 21.1%, 21.2%, 21.3%, 21.4%, 21.5%, 21.6%, 21.7%, 21.8%, 21.9%, 22.0%, 22.1%, 22.2%, 22.3%, 22.4%, 22.5%, 22.6%, 22.7%, 22.8%, 22.9%, or about 23.0% of DS-10. In an exemplary embodiment, the area of DS-10 in a MALDI-TOF-MS spectrum is 20.35%.

In some embodiments, the mixture of isomerically-purified hydroxypropyl-β-cyclodextrin molecules may include about 9% to about 15% of DS-11. In some aspects, the mixture of isomerically-purified hydroxypropyl-β-cyclodextrin molecules may include about 9% to about 9.5% of DS-11, about 9.5% to about 10% DS-11, about 10% to about 10.5% of DS-11, about 10.5% to about 11% of DS-11, about 11% to about 11.5% of DS-11, about 11.5% to about 12% of DS-11, about 12% to about 12.5% of DS-11, about 12.5% to about 13% of DS-11, about 13% to about 13.5% of DS-11, about 13.5% to about 14% of DS-11, about 14% to about 14.5% of DS-11, or about 14.5% to about 15% of DS-11. In some additional aspects, the mixture of isomerically-purified hydroxypropyl-β-cyclodextrin molecules may include about 9% to about 10% of DS-11, about 9% to about 10.5% of DS-11, about 9% to about 11% of DS-11, about 9% to about 11.5% of DS-11, about 9% to about 12% of DS-11, about 9% to about 12.5% of DS-11, about 9% to about 13% of DS-11, about 9% to about 13.5% of DS-11, about 9% to about 14% of DS-11, about 9% to about 14.5% of DS-11, about 9.5% to about 15% of DS-11, about 10% to about 15% of DS-11, about 10.5% to about 15% of DS-11, about 11% to about 15% of DS-11, about 11.5% to about 15% of DS-11, about 12% to about 15% of DS-11, about 12.5% to about 15% of DS-11, about 13% to about 15% of DS-11, about 13.5% to about 15% of DS-11, about 14% to about 15% of DS-11, about 9.5% to about 14.5% of DS-11, about 10% to about 14% of DS-11, about 10.5% to about 13.5% of DS-11, about 11% to about 13% of DS-11, or about 11.5% to about 12.5% of DS-11. In still further aspects, the mixture of isomerically-purified hydroxypropyl-β-cyclodextrin molecules may include about 9.0%, 9.1%, 9.2%, 9.3%, 9.4%, 9.5%, 9.6%, 9.7%, 9.8%, 9.9%, 10.0%, 10.1%, 10.2%, 10.3%, 10.4%, 10.5%, 10.6%, 10.7%, 10.8%, 10.9%, 11.0%, 11.1%, 11.2%, 11.3%, 11.4%, 11.5%, 11.6%, 11.7%, 11.8%, 11.9%, 12.0%, 12.1%, 12.2%, 12.3%, 12.4%, 12.5%, 12.6%, 12.7%, 12.8%, 12.9%, 13.0%, 13.1%, 13.2%, 13.3%, 13.4%, 13.5%, 13.6%, 13.7%, 13.8%, 13.9%, 14.0%, 14.1%, 14.2%, 14.3%, 14.4%, 14.5%, 14.6%, 14.7%, 14.8%, 14.9%, or about 15.0% of DS-11. In an exemplary embodiment, the area of DS-11 in a MALDI-TOF-MS spectrum is 12.02%.

In some embodiments, the mixture of isomerically-purified hydroxypropyl-β-cyclodextrin molecules may include about 2% to about 8% of DS-12. In some aspects, the mixture of isomerically-purified hydroxypropyl-β-cyclodextrin molecules may include about 2% to about 2.5% of DS-12, about 2.5% to about 3% of DS-12, about 3% to about 3.5% of DS-12, about 3.5% to about 4% of DS-12, about 4% to about 4.5% of DS-12, about 4.5% to about 5% of DS-12, about 5% to about 5.5% of DS-12, about 5.5% to about 6% of DS-12, about 6% to about 6.5% of DS-12, about 6.5% of to about 7% of DS-12, about 7% to about 7.5% of DS-12, or about 7.5% to about 8% of DS-12. In some additional aspects, the mixture of isomerically-purified hydroxypropyl-β-cyclodextrin molecules may include about 2% to about 3% of DS-12, about 2% to about 3.5% of DS-12, about 2% to about 4% of DS-12, about 2% to about 4.5% of DS-12, about 2% to about 5% of DS-12, about 2% to about 5.5% of DS-12, about 2% to about 6% of DS-12, about 2% to about 6.5% of DS-12, about 2% of about 7% of DS-12, about 2% of about 7.5% of DS-12, about 2.5% to about 8% of DS-12, about 3% to about 8% of DS-12, about 3.5% to about 8% of DS-12, about 4% to about 8% of DS-12, about 4.5% to about 8% of DS-12, about 5% to about 8% of DS-12, about 5.5% to about 8% of DS-12, about 6% to about 8% of DS-12, about 6.5% to about 8% of DS-12, about 7% to about 8% of DS-12, about 2.5% to about 7.5% of DS-12, about 3% to about 7% of DS-12, about 3.5% to about 6.5% of DS-12, about 4% to about 6% of DS-12, or about 4.5% to about 5.5% of DS-12. In still further aspects, the mixture of isomerically-purified hydroxypropyl-β-cyclodextrin molecules may include about 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, or about 8.0% of DS-12. In an exemplary embodiment, the area of DS-12 in a MALDI-TOF-MS spectrum is 4.85%.

In an exemplary embodiment, the mixture of isomerically-purified hydroxypropyl-β-cyclodextrin molecules may include about 0.5% to about 6% of DS-6, about 8% to about 14% of DS-7, about 19% to about 25% of DS-8, about 23% to about 29% of DS-9, about 17% to about 23% of DS-10, about 9% to about 15% of DS-11, and about 2% to about 8% of DS-12.

In another exemplary embodiment, the mixture of isomerically-purified hydroxypropyl-β-cyclodextrin molecules may include DS-6, DS-7, DS-8, DS-9, DS-10, DS-11, and DS-12; wherein the mixture includes less than 1% DS-5, DS-4, DS-3, DS-2, and DS-1; and wherein the mixture includes less than 1% DS-13 and DS-14.

In some embodiments, the average degree of substitution of the mixture of isomerically-purified hydroxypropyl-β-cyclodextrin molecules may be about 7 to about 8. In some aspects, the average degree of substitution of the mixture of isomerically-purified hydroxypropyl-β-cyclodextrin molecules may be about 7.0, 7.1, 7.2, 7.3, 7.4, 7.5, 7.6, 7.7, 7.8, 7.9, or about 8.0. In an exemplary embodiment, the average degree of substitution of the mixture of hydroxypropyl-β-cyclodextrin molecules may be about 7.42.

Figure 11:
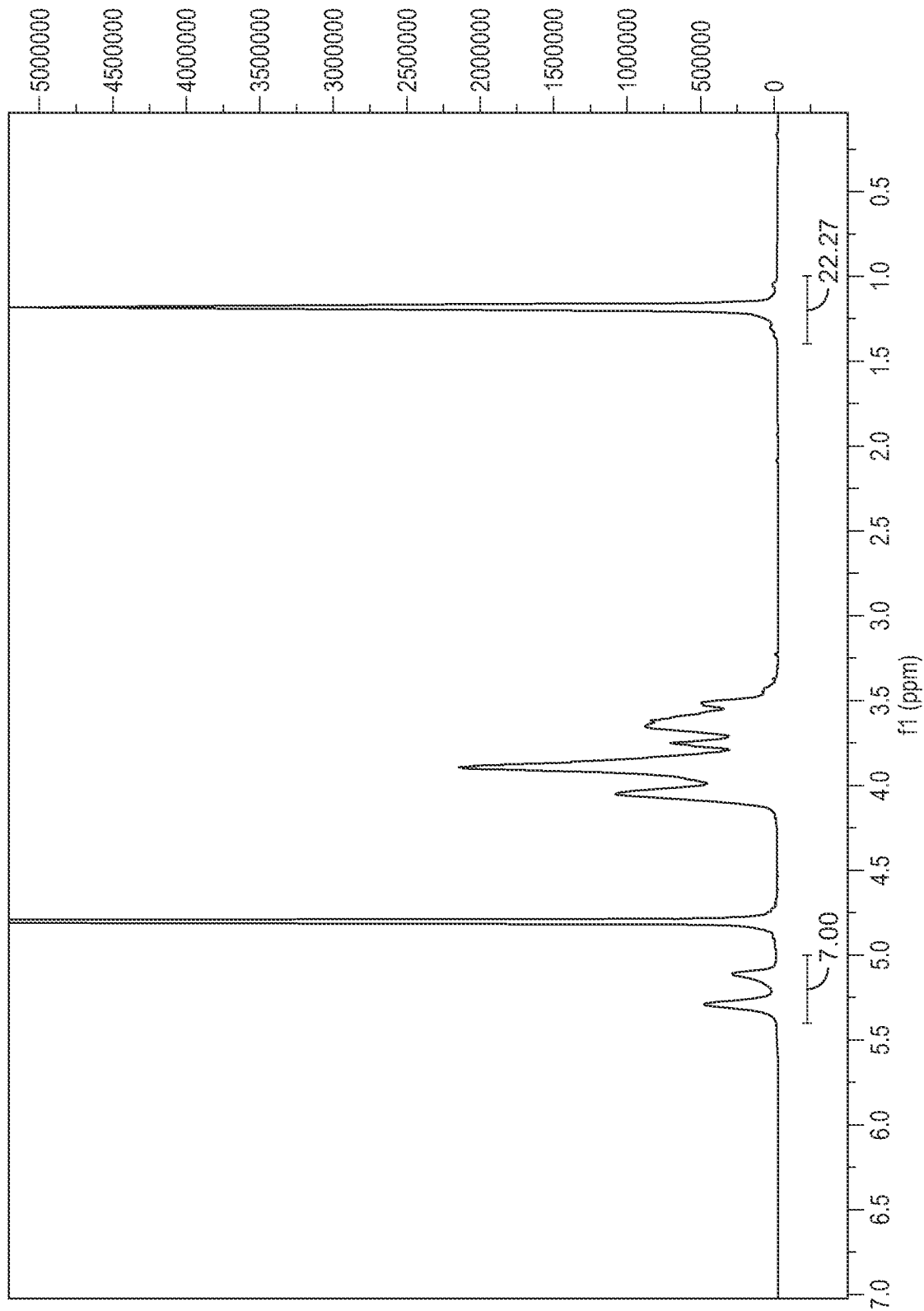
FIG. 11 is a ¹H NMR spectrum of the second HDS Fraction of a mixture of hydroxypropyl-β-cyclodextrins of the present disclosure.
Figure 12:
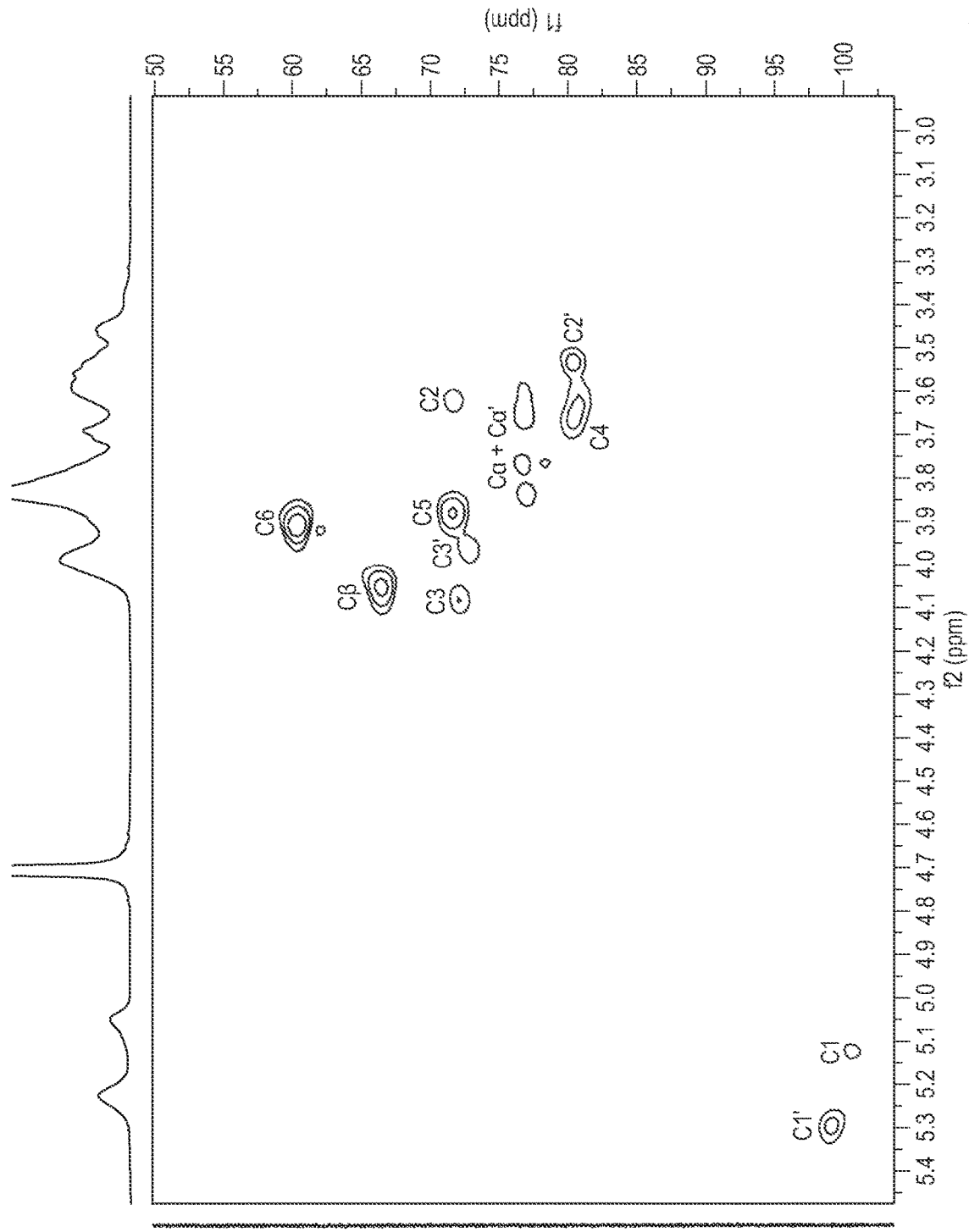
FIG. 12 is a DEPT-ed HSQC spectrum of the second HDS fraction of a mixture of hydroxypropyl-β-cyclodextrin of the present disclosure.

The position of the substitutions in the mixture isomerically-purified hydroxypropyl-β-cyclodextrin molecules of may be determined using methods known to those having skill in the art. In some embodiments the composition may be characterized by $^1$H-NMR. In some aspects, $^1$H-NMR may be used to determine the degree of substitution of the composition. An exemplary $^1$H-NMR spectrum is provided in FIG. 11. In some embodiments, the composition may be characterized by DEPT-ed HSQC. An exemplary DEPT-ed HSQC spectrum is provided in FIG. 12.

In some embodiments, about 36% to about 42% of the hydroxypropyl substitutions in the hydroxypropyl-β-cyclodextrin molecules may be located at the 3-O-position. In some aspects, the percentage of substitutions in the mixture of the hydroxypropyl-β-cyclodextrin molecules at the 3-O— position may be about 36% to about 37%, about 37% to about 38%, about 38% to about 39%, about 39% to about 40%, about 40% to about 41%, or about 41% to about 42%. In some additional aspects, the percentage of substitutions in the mixture of hydroxypropyl-β-cyclodextrin molecules at the 3-O— position may be about 36% to about 38%, about 36% to about 39%, about 36% to about 40%, about 36% to about 41%, about 37% to about 42%, about 38% to about 42%, about 39% to about 42%, about 40% to about 42%, about 37% to about 41%, or about 38% to about 40%. In an exemplary embodiment, the percentage of substitutions in the mixture of hydroxypropyl-β-cyclodextrin molecules at the 3-O— position is about 39.00%.

In some embodiments, about 58% to about 64% of the hydroxypropyl substitutions in the hydroxypropyl-β-cyclodextrin molecules are located at the 2-O-position. In some aspects, the percentage of substitutions in the mixture of hydroxypropyl-β-cyclodextrin molecules at the 2-O— position is about 58% to about 59%, about 59% to about 60%, about 60% to about 61%, about 61% to about 62%, about 62% to about 63%, or about 63% to about 64%. In some additional aspects, the percentage of substitutions in the mixture of hydroxypropyl-β-cyclodextrin molecules at the 2-O— position is about 58% to about 60%, about 58% to about 61%, about 58% to about 62%, about 58% to about 63%, about 59% to about 64%, about 60% to about 64%, about 61% to about 64%, about 62% to about 64%, about 59% to about 63%, or about 60% to about 62%. In an exemplary embodiment, the percentage of substitutions in the mixture of hydroxypropyl-β-cyclodextrin molecules at the 2-O— position is about 61.14%.

In some embodiments, the percentage of substitutions in the mixture of hydroxypropyl-β-cyclodextrin molecules at the 6-O— position is about 0%.

Figure 13:
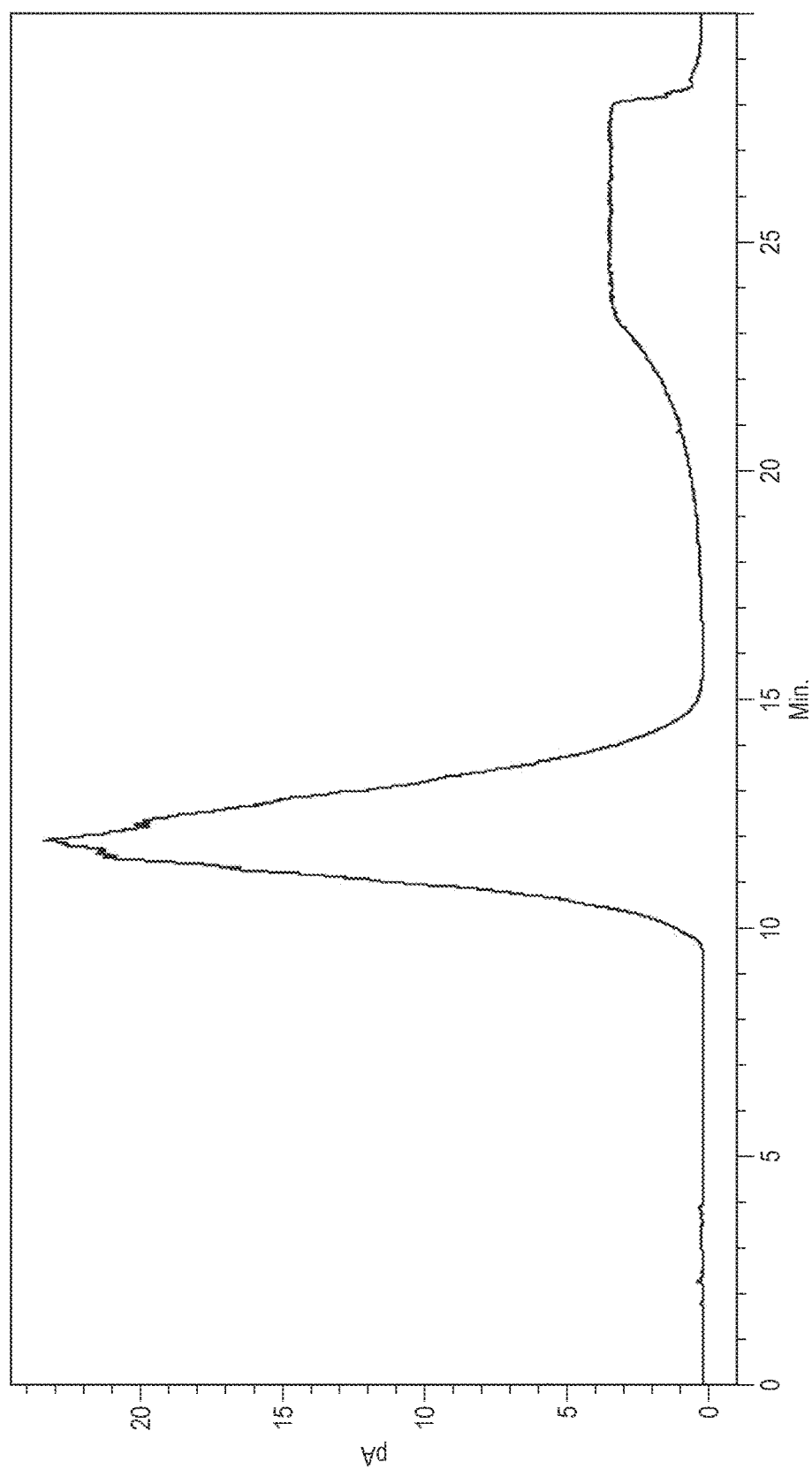
FIG. 13 is an HPLC-CAD chromatogram of the second HDS fraction of a mixture of hydroxypropyl-β-cyclodextrins of the present disclosure.

In some embodiments, the composition may have an HPLC-CAD chromatogram of FIG. 13. In some aspects, the mean retention time of the composition may be about 11 minutes to about 13 minutes as measured by HPLC-CAD. In some additional aspects, the mean retention time of the composition may be about 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, or about 13.0 minutes. In an exemplary embodiment, the mean retention time is about 11.9 minutes.

In some embodiments, the composition may have a −ESI-MS spectrum with peaks at about 682 m/z, about 712 m/z, about 740 m/z, about 770 m/z, about 798 m/z, about 828 m/z, about 856 m/z, and about 886 m/z. In some embodiments, the composition may have a +ESI-MS spectrum with peaks at about 744 m/z, about 773 m/z, about 803 m/z, about 832 m/z, about 860 m/z, about 889 m/z, and at about 919 m/z. In an exemplary embodiment, the composition has the ESI-MS spectra shown in FIG. 14.

The hydroxypropyl-β-cyclodextrin percent may be based upon an area percentage from a MALDI-TOF-MS spectrum. In some embodiments, the composition may have a MALDI-TOF-MS spectrum with peaks at about 1497 m/z, about 1557 m/z, about 1616 m/z, about 1675 m/z, about 1734 m/z, about 1794 m/z, and at about 1914 m/z. In an exemplary embodiment, the composition has the MALDI-TOF-MS spectrum shown in FIG. 15. In an exemplary embodiment, the composition has a MALDI-TOF-MS spectrum wherein the area of DS-6 is 2.91%, the area of DS-7 is 10.93%, the area of DS-8 is 22.52%, the area of DS-9 is 26.42%, the area of DS-10 is 20.35%, the area of DS-11 is 12.02%, and the area of DS-12 is 4.85%.

In some embodiments, the composition may have a true density of about 1.095 g/cm$^3$ to about 1.100 g/cm$^3$. In some aspects, the composition may have a true density of about 1.095 g/cm$^3$ to about 1.096 g/cm$^3$, about 1.096 g/cm$^3$ to about 1.097 g/cm$^3$, about 1.097 g/cm$^3$ to about 1.098 g/cm$^3$, about 1.098 g/cm$^3$ to about 1.099 g/cm$^3$, about 1.099 g/cm$^3$ to about 1.100 g/cm$^3$, about 1.095 g/cm$^3$ to about 1.097 g/cm$^3$, about 1.095 g/cm$^3$ to about 1.098 g/cm$^3$, about 1.095 g/cm$^3$ to about 1.099 g/cm$^3$, about 1.096 g/cm$^3$ to about 1.100 g/cm$^3$, about 1.097 g/cm$^3$ to about 1.100 g/cm$^3$, about 1.098 g/cm$^3$ to about 1.100 g/cm$^3$, about 1.096 g/cm$^3$ to about 1.098 g/cm$^3$, or about 1.096 g/cm$^3$ to about 1.099 g/cm$^3$. In some additional aspects, the composition may have a true density of about 1.095 g/cm$^3$, 1.096 g/cm$^3$, 1.097 g/cm$^3$, 1.098 g/cm$^3$, 1.099 g/cm$^3$, or about 1.100 g/cm$^3$. In an exemplary embodiment, the composition has a true density of about 1.096 g/cm$^3$ to about 1.098 g/cm$^3$.

In some embodiments, the composition may have an osmolality of about 600 mOs/kg to about 750 mOs/kg. In some aspects, the composition may have an osmolality of about 600 mOs/kg to about 625 mOs/kg, about 625 mOs/kg to about 650 mOs/kg, about 650 mOs/kg to about 675 mOs/kg, about 675 mOs/kg to about 700 mOs/kg, about 700 mOs/kg to about 725 mOs/kg, or about 725 mOs/kg to about 750 mOs/kg. In some additional aspects, the composition may have an osmolality of about 600 mOs/kg to about 650 mOs/kg, about 600 mOs/kg to about 675 mOs/kg, about 600 mOs/kg to about 700 mOs/kg, about 600 mOs/kg to about 725 mOs/kg, about 625 mOs/kg to about 750 mOs/kg, about 650 mOs/kg to about 750 mOs/kg, about 675 mOs/kg to about 750 mOs/kg, about 700 mOs/kg to about 750 mOs/kg, about 625 mOs/kg to about 725 mOs/kg, or about 650 mOs/kg to about 700 mOs/kg. In still further embodiments, the composition may have an osmolality of about 600 mOs/kg, 610 mOs/kg, 620 mOs/kg, 630 mOs/kg, 640 mOs/kg, 650 mOs/kg, 660 mOs/kg, 670 mOs/kg, 680 mOs/kg, 690 mOs/kg, 700 mOs/kg, 710 mOs/kg, 720 mOs/kg, 730 mOs/kg, 740 mOs/kg, or 750 mOs/kg. In an exemplary embodiment, the composition has an osmolality of about 635 mOs/kg to about 695 mOs/kg.

In some embodiments, the composition may have a conductivity between about 0 and about 8 μS/cm. In some aspects, the composition may have a conductivity between about 0 μS/cm and about 1 μS/cm, about 1 μS/cm and about 2 μS/cm, about 3 μS/cm and about 4 μS/cm, about 4 μS/cm and about 5 μS/cm, about 5 μS/cm and about 6 μS/cm, about 6 μS/cm and about 7 μS/cm, or between about 7 μS/cm and about 8 μS/cm. In some additional embodiments, the composition may have a conductivity between about 0 μS/cm and about 1.5 μS/cm, about 0 μS/cm and about 2 μS/cm, about 0 μS/cm and about 2.5 μS/cm, about 0 μS/cm and about 3 μS/cm, about 0 and about 3.5 μS/cm, about 0 μS/cm and about 4 μS/cm, about 0 and about 4.5 μS/cm, about 0 μS/cm and about 5 μS/cm, about 0 and about 5.5 μS/cm, about 0 μS/cm and about 6 μS/cm, about 0 and about 6.5, about 0 μS/cm and about 7 μS/cm, about 0 and about 7.5, about 1 μS/cm and about 8 μS/cm, about 1.5 μS/cm and about 8 μS/cm, about 2 μS/cm and about 8 μS/cm, about 2.5 μS/cm and about 8 μS/cm, about 3 μS/cm and about 8 μS/cm, about 3.5 μS/cm and about 8 μS/cm, about 4 μS/cm and about 8 μS/cm, about 4.5 μS/cm and about 8 μS/cm, about 5 μS/cm and about 8 μS/cm, about 5.5 μS/cm and about 8 μS/cm, about 6 μS/cm and about 8 μS/cm, about 6.5 μS/cm and about 8 μS/cm, about 1 μS/cm and about 7 μS/cm, about 2 μS/cm and about 6 μS/cm, or about 3 μS/cm and about 5 μS/cm. In still further aspects, the composition may have a conductivity of about 0.5 μS/cm, 1.0 μS/cm, 1.5 μS/cm, 2.0 μS/cm, 2.5 μS/cm, 3.0 μS/cm, 3.5 μS/cm, 4.0 μS/cm, 4.5 μS/cm, 5.0 μS/cm, 5.5 μS/cm, 6.0 μS/cm, 6.5 μS/cm, 7.0 μS/cm, 7.5 μS/cm, or about 8.0 μS/cm.

In some embodiments, the composition may have a pH of about 4.0 to about 8.0; for example, the composition may have a pH of about 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, or about 8.0. The composition may have a pH in a range or sub-range comprising any of the afore-mentioned numbers, including but not limited to a pH about 4.0 to about 4.5, about 4.5 to about 5.0, about 5.0 to about 5.5, about 5.5 to about 6.0, about 6.0 to about 6.5, about 6.5 to about 7.0, about 7.0 to about 7.5, or about 7.5 to about 8.0. In some embodiments, the composition may further comprise a pH adjusting agent, such as hydrochloric acid or sodium hydroxide, to adjust the pH to a desired level. In some embodiments, the composition may further comprise a buffer. In some embodiments, the buffer may include monobasic sodium phosphate and dibasic sodium phosphate.

In some embodiments, the composition may have a viscosity measured in centipoises (cP) at 20° C. For example, the composition may have a viscosity of about 1.5 cP to about 3.0 cP at 20° C. In some embodiments, the composition may have a viscosity of about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or about 10.0 cP at 20° C. In other embodiments, the composition may have a viscosity of about 3.0 cP to about 5.0 cP, about 5.0 cP to about 10.0 cP, about 10 to about 15 cP, about 15 to about 20 cP, about 20 cP to about 25 cP, about 25 cP to about 50 cP, about 50 cP to about 80 cP, about 80 cP to about 150 cP, about 150 cP to about 250 cP, about 250 cP to about 500 cP, about 500 cP to about 1,000 cP, about 1,000 cP to about 2,000 cP, about 2,000 cP to about 3,000 cP, about 3,000 cP to about 5,000 cP, or about 5,000 cP to about 10,000 cP at 20° C.

The composition may be substantially free of impurities. Impurities include particles having a diameter of greater than or equal to 25 microns, particles having a diameter of greater than or equal to 10 microns, chloride, propylene glycol, propylene oxide, and other unspecified impurities. In some embodiments, the composition may include less than or equal to about 0.05% impurities; for example, the composition may include less than or equal to about 0.05%, 0.04%, 0.03%, 0.02%, or less than or equal to about 0.01% impurities.

In some embodiments, the composition may further comprise a container and non-visible particulate matter. In some embodiments, the composition may be provided in a container. In some embodiments, the composition may further comprise non-visible particulate matter.

In some embodiments, the composition may include less than 600 particles per container having a diameter of greater than or equal to 25 microns. In some aspects, the composition may include less than 500, less than 400, less than 300, less than 200, or less than 100 particles per container having a diameter greater than or equal to 25 microns.

In some embodiments, the composition may include less than 6000 particles per container having a diameter of greater than or equal to 10 microns. In some aspects, the composition may include less than 5000, less than 4000, less than 3000, less than 2000, less than 1000, less than 500, or less than 100 particles per container having a diameter greater than or equal to 10 microns. In another aspect, the composition may include less than 5000, less than 4000, less than 3000, less than 2000, less than 1000, less than 500, or less than 100 particles per container having a diameter greater than or equal to 10 microns, wherein the container is ≤100 mL. In another aspect, the composition may include less than 5000, less than 4000, less than 3000, less than 2000, less than 1000, less than 500, less than 100, less than 50, less than 25, less than 10, less than 5, or less than 3 particles per container having a diameter greater than or equal to 10 microns, wherein the container is >100 mL.

In some embodiments, the composition may include no more than 10 ppb of propylene glycol. In some aspects, the composition may include no more than 9 ppb, 8 ppb, 7 ppb, 6 ppb, 5 ppb, 4 ppb, 3 ppb, 2 ppb, or no more than 1 ppb propylene glycol. In some aspects, the amount of propylene glycol in the composition may be determined by HPLC. In some additional aspects, the amount of propylene glycol in the composition may be determined by gas chromatography. In still further aspects, the amount of propylene glycol in the composition may be determined by measuring the PG/EG-ratio of propylene glycol to ethylene glycol.

In some embodiments, the composition may include no more than 1 ppm propylene oxide. In some aspects, the composition may include no more than 0.9 ppm, 0.8 ppm, 0.7 ppm, 0.6 ppm, 0.5 ppm, 0.4 ppm, 0.3 ppm, 0.2 ppm, or 0.1 ppm propylene oxide. In some aspects, the amount of propylene oxide in the composition may be determined by HPLC. In some additional aspects, the amount of propylene oxide in the composition may be determined by gas chromatography.

In some embodiments, the composition may include between about 0 ppm to about 10 ppm chloride (e.g., Cl$^-$ ions). In some aspects, the composition may include about 0 ppm chloride to about 2 ppm chloride, about 2 ppm chloride to about 4 ppm chloride, about 4 ppm chloride to about 6 ppm chloride, about 6 ppm chloride to about 8 ppm chloride, or about 8 to about 10 ppm chloride. In some additional aspects, the composition may include about 0 ppm chloride to about 4 ppm chloride, about 0 ppm chloride to about 6 ppm chloride, about 0 ppm chloride to about 8 ppm chloride, about 2 ppm chloride to about 1 ppm chloride, about 4 ppm chloride to about 1 ppm chloride, or about 6 ppm chloride to about 1 ppm chloride. In still further aspects, the composition may include about 0 ppm, 1 ppm, 2 ppm, 3 ppm, 4 ppm, 5 ppm, 6 ppm, 7 ppm, 8 ppm, 9 ppm, or about 10 ppm chloride. In an exemplary embodiment, the composition may include between about 0 ppm to about 1 ppm chloride.

In some embodiments, the composition may include between about 0 ppm to about 10 ppm sodium (e.g., Na$^+$ ions). In some aspects, the composition may include about 0 ppm sodium to about 2 ppm sodium, about 2 ppm sodium to about 4 ppm sodium, about 4 ppm sodium to about 6 ppm sodium, about 6 ppm sodium to about 8 ppm sodium, or about 8 to about 10 ppm sodium. In some additional aspects, the composition may include about 0 ppm sodium to about 4 ppm sodium, about 0 ppm sodium to about 6 ppm sodium, about 0 ppm sodium to about 8 ppm sodium, about 2 ppm sodium to about 1 ppm sodium, about 4 ppm sodium to about 1 ppm sodium, or about 6 ppm sodium to about 1 ppm sodium. In still further aspects, the composition may include about 0 ppm, 1 ppm, 2 ppm, 3 ppm, 4 ppm, 5 ppm, 6 ppm, 7 ppm, 8 ppm, 9 ppm, or about 10 ppm sodium. In an exemplary embodiment, the composition may include between about 0 ppm to about 1 ppm sodium.

In some embodiments, the composition may include less than or equal to 0.05% of other unspecified impurities; for example, the composition may include less than or equal to 0.05%, 0.04%, 0.03%, 0.02%, or less than or equal to 0.01% of other unspecified impurities.

In some embodiments, the composition may be stable for at least 6 months. For example, the composition may be stable for at least 3 months, 6 months, at least 7 months, at least 8 months, at least 9 months, at least 10 months, at least 11 months, at least 12 months, at least 13 months, at least 14 months, at least 15 months, at least 16 months, at least 17 months, at least 18 months, at least 24 months, or at least 36 months.

The composition may be nanofiltered. In some embodiments, the concentration of the composition does not substantially change the time required for nanofiltration. Thus, the time for nanofiltration does not increase or decrease as the concentration of the mixture of β-cyclodextrin molecules increases or decreases in the composition. In some aspects, the length of time to nanofilter the composition ranges from about 1.04 to about 1.20 hours per diafiltration volume (kg soln/m$^2$·hr/L soln). In some embodiments, the nanofiltered composition has no substantial difference observed in HPLC-ELSD after nanofiltration as compared to before nanofiltration. In some embodiments, the composition has no substantial difference observed in NMR after nanofiltration as compared to before nanofiltration.

In some embodiments, the composition may be terminally sterilized. Methods of terminal sterilization are generally well-known in the art. In some embodiments, the pH of the composition may be adjusted after terminal sterilization.

In some embodiments, the composition may include less than or equal to 10.0% w/w of water. For example, the composition may include less than or equal to 10.0% w/w, 9.5% w/w, 9.0% w/w, 8.5% w/w, 8.0% w/w, 7.5% w/w, 7.0% w/w, 6.5% w/w, 6.0% w/w, 5.5% w/w, 5.0% w/w, 4.5% w/w, 4.0% w/w, 3.5% w/w, 3.0% w/w, 2.5% w/w, 2.0% w/w, 1.5% w/w, 1.0% w/w, 0.5% w/w, or less than or equal to 0.1% w/w water.

In some embodiments, the composition may be packaged in a vial suitable for injection to a human subject in need thereof. The vial may be glass, plastic, or any other material known in the pharmaceutical art. The vial may be coated with a material such as silicon dioxide to prevent leaching from the vial into the composition.

In some embodiments, the composition may be efficacious in treating Niemann-Pick disease. In some embodiments, the composition may be efficacious in treating Niemann-Pick disease Type C. In some embodiments, the composition may be efficacious in treating liver disease. In some embodiments, the composition may be efficacious in treating cardiovascular disease. In some embodiments, the composition may be efficacious in treating familial hypercholesterolemia. In some embodiments, the composition may be efficacious in treating cholesterol deposits.

In some embodiments, the composition may further comprise a pharmaceutical excipient or carrier. In some embodiments, the composition may further comprise a pharmaceutically acceptable diluent. Examples of pharmaceutical excipients, carriers, and diluents are well known to those having skill in the art.

In some embodiments, the composition may exhibit a lower toxicity than Trappsol® Cyclo or Kleptose®. In some embodiments, the composition may exhibit a substantially lower ototoxicity than Trappsol® Cyclo or Kleptose®. In some embodiments, the composition may exhibit substantially no ototoxicity.

Fraction 3 HDS

Provided herein is a composition comprising a mixture of isomerically-purified hydroxypropyl-β-cyclodextrin molecules that includes less than 1% of DS-6 and less than 1% of DS-14. In some embodiments, the mixture of isomerically-purified hydroxypropyl-β-cyclodextrin molecules may include less than 1% of DS-5, DS-4, DS-3, DS-2, and DS-1. In some aspects, the mixture of isomerically-purified hydroxypropyl-β-cyclodextrin molecules may include less than 1%, less than 0.9%, less than 0.8%, less than 0.7%, less than 0.6%, less than 0.5%, less than 0.4%, less than 0.3%, less than 0.2%, or less than 0.1% of DS-5, DS-4, DS-3, DS-2, and DS-1. In some aspects, the mixture of isomerically-purified hydroxypropyl-β-cyclodextrin molecules may include less than 1%, less than 0.9%, less than 0.8%, less than 0.7%, less than 0.6%, less than 0.5%, less than 0.4%, less than 0.3%, less than 0.2%, or less than 0.1% of DS-6, DS-5, DS-4, DS-3, DS-2, and/or DS-1. In some embodiments, the mixture of hydroxypropyl-β-cyclodextrin molecules is free of DS-5, DS-4, DS-3, DS-2, and/or DS-1.

In some embodiments, the mixture of hydroxypropyl-β-cyclodextrin molecules may include less than 1% of DS-14. In some aspects, the mixture of isomerically-purified hydroxypropyl-β-cyclodextrin molecules may include less than 1%, less than 0.9%, less than 0.8%, less than 0.7%, less than 0.6%, less than 0.5%, less than 0.4%, less than 0.3%, less than 0.2%, or less than 0.1% of DS-14.

In some embodiments, the mixture of hydroxypropyl-β-cyclodextrin molecules may include about 1% to about 7% of DS-7. In some aspects, the mixture of hydroxypropyl-β-cyclodextrin molecules may include about 1% to about 1.5% of DS-7, about 1.5% to about 2% of DS-7, about 2% to about 2.5% of DS-7, about 2.5% to about 3% of DS-7, about 3% to about 3.5% of DS-7, about 3.5% to about 4% of DS-7, about 4% to about 4.5% of DS-7, about 4.5% to about 5% of DS-7, about 5% to about 5.5% of DS-7, about 5.5% to about 6% of DS-7, about 6% to about 6.5% of DS-7, or about 6.5% to about 7% of DS-7. In some additional aspects, the mixture of hydroxypropyl-β-cyclodextrin molecules may include about 1% to about 2% of DS-7, about 1% to about 2.5% of DS-7, about 1% to about 3% of DS-7, about 1% to about 3.5% of DS-7, about 1% to about 4% of DS-7, about 1% to about 4.5% of DS-7, about 1% to about 5% of DS-7, about 1% to about 5.5% of DS-7, about 1% to about 6% of DS-7, about 1% to about 6.5% of DS-7, about 1.5% to about 7% of DS-7, about 2% to about 7% of DS-7, about 2.5% to about 7% of DS-7, about 3% to about 7% of DS-7, about 3.5% to about 7% of DS-7, about 4% to about 7% of DS-7, about 4.5% to about 7% of DS-7, about 5% to about 7% of DS-7, about 5.5% to about 7% of DS-7, about 6% to about 7% of DS-7, about 1.5% to about 6.5% of DS-7, about 2% to about 6% of DS-7, about 2.5% to about 5.5% of DS-7, about 3% to about 5% of DS-7, or about 3.5% to about 4.5% of DS-7. In still further aspects, the mixture of hydroxypropyl-β-cyclodextrin molecules may include about 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, or about 7.0% of DS-7. In an exemplary embodiment, the area of DS-7 in a MALDI-TOF-MS spectrum is 3.92%.

In some embodiments, the mixture of isomerically-purified hydroxypropyl-β-cyclodextrin molecules may include about 16% to about 22% of DS-8. In some aspects, the mixture of isomerically-purified hydroxypropyl-β-cyclodextrin molecules may include about 16% to about 16.5% of DS-8, about 16.5% to about 17% of DS-8, about 17% to about 17.5% of DS-8, about 17.5% to about 18% of DS-8, about 18% to about 18.5% of DS-8, about 18.5% to about 19% of DS-8, about 19% to about 19.5% of DS-8, about 19.5% to about 20% of DS-8, about 20% to about 20.5% of DS-8, about 20.5% to about 21% of DS-8, about 21% to about 21.5% of DS-8, or about 21.5% to about 22% of DS-8. In some additional aspects, the mixture of isomerically-purified β-cyclodextrin may include about 16% to about 17% of DS-8, about 16% to about 17.5% of DS-8, about 16% to about 18% of DS-8, about 16% to about 18.5% of DS-8, about 16% to about 19% of DS-8, about 16% to about 19.5% of DS-8, about 16% to about 20% of DS-8, about 16% to about 20.5% of DS-8, about 16% to about 21% of DS-8, about 16% to about 21.5% of DS-8, about 16.5% to about 22% of DS-8, about 17% to about 22% of DS-8, about 17.5% to about 22% of DS-8, about 18% to about 22% of DS-8, about 18.5% to about 22% of DS-8, about 19% to about 22% of DS-8, about 19.5% to about 22% of DS-8, about 20% to about 22% of DS-8, about 20.5% to about 22% of DS-8, about 21% to about 22% of DS-8, about 16.5% to about 21.5% of DS-8, about 17% to about 21% of DS-8, about 17.5% to about 20.5% of DS-8, about 18% to about 20% of DS-8, or about 18.5% to about 19.5% of DS-8. In still further aspects, the mixture of isomerically-purified β-cyclodextrin molecules may include about 16.0%, 16.1%, 16.2%, 16.3%, 16.4%, 16.5%, 16.6%, 16.7%, 16.8%, 16.9%, 17.0%, 17.1%, 17.2%, 17.3%, 17.4%, 17.5%, 17.6%, 17.7%, 17.8%, 17.9%, 18.0%, 18.1%, 18.2%, 18.3%, 18.4%, 18.5%, 18.6%, 18.7%, 18.8%, 18.9%, 19.0%, 19.1%, 19.2%, 19.3%, 19.4%, 19.5%, 19.6%, 19.7%, 19.8%, 19.9%, 20.0%, 20.1%, 20.2%, 20.3%, 20.4%, 20.5%, 20.6%, 20.7%, 20.8%, 20.9%, 21.0%, 21.1%, 21.2%, 21.3%, 21.4%, 21.5%, 21.6%, 21.7%, 21.8%, 21.9%, or about 22.0% of DS-8. In an exemplary embodiment, the area of DS-8 in a MALDI-TOF-MS spectrum is 18.65%.

In some embodiments, the mixture of isomerically-purified hydroxypropyl-β-cyclodextrin molecules may include about 22% to about 28% of DS-9. In some aspects, the mixture of isomerically-purified β-cyclodextrin molecules includes about 22% to about 22.5% of DS-9, about 22.5% to about 23% of DS-9, about 23% to about 23.5% of DS-9, about 23.5% to about 24% of DS-9, about 24% to about 24.5% to about 25% of DS-9, about 25% to about 25.5% of DS-9, about 25.5% to about 26% of DS-9, about 26% to about 26.5% of DS-9, about 26.5% to about 27% of DS-9, about 27% to about 27.5% of DS-9, or about 27.5% to about 28% of DS-9. In some additional aspects, the mixture of isomerically-purified β-cyclodextrin may include about 22% to about 23% of DS-9, about 22% to about 23.5% of DS-9, about 22% to about 24% of DS-9, about 22% to about 24.5% of DS-9, about 22% to about 25% of DS-9, about 22% to about 25.5% of DS-9, about 22% to about 26% of DS-9, about 22% to about 26.5% of DS-9, about 22% to about 27% of DS-9, about 22% to about 27.5% of DS-9, about 22.5% to about 28% of DS-9, about 23% to about 28% of DS-9, about 23.5% to about 28% of DS-9, about 24% to about 28% of DS-9, about 24.5% to about 28% of DS-9, about 25% to about 28% of DS-9, about 25.5% to about 28% of DS-9, about 26% to about 28% of DS-9, about 26.5% to about 28% of DS-9, about 27% to about 28% of DS-9, about 22.5% to about 27.5% of DS-9, about 23% to about 27% of DS-9, about 23.5% to about 26.5% of DS-9, about 24% to about 26% of DS-9, or about 24.5% to about 25.5% of DS-9. In still further aspects, the mixture of isomerically-purified β-cyclodextrin molecules may include about 22.0%, 22.1%, 22.2%, 22.3%, 22.4%, 22.5%, 22.6%, 22.7%, 22.8%, 22.9%, 23.0%, 23.1%, 23.2%, 23.3%, 23.4%, 23.5%, 23.6%, 23.7%, 23.8%, 23.9%, 24.0%, 24.1%, 24.2%, 24.3%, 24.4%, 24.5%, 24.6%, 24.7%, 24.8%, 24.9%, 25.0%, 25.1%, 25.2%, 25.3%, 25.4%, 25.5%, 25.6%, 25.7%, 25.8%, 25.9%, 26.0%, 26.1%, 26.2%, 26.3%, 26.4%, 26.5%, 26.6%, 26.7%, 26.8%, 26.9%, 27.0%, 27.1%, 27.2%, 27.3%, 27.4%, 27.5%, 27.6%, 27.7%, 27.8%, 27.9%, or about 28.0% of DS-9. In an exemplary embodiment, the area of DS-9 in a MALDI-TOF-MS spectrum is 25.45%.

In some embodiments, the mixture of isomerically-purified hydroxypropyl-β-cyclodextrin molecules may include about 19% to about 25% of DS-10. In some aspects, the mixture of isomerically-purified hydroxypropyl-β-cyclodextrin molecules may include about 19% to about 19.5% of DS-10, about 19.5% to about 20% of DS-10, about 20% to about 20.5% of DS-10, about 20.5% to about 21% of DS-10, about 21% to about 21.5% of DS-10, about 21.5% to about 22% of DS-10, about 22% to about 22.5% of DS-10, about 22.5% to about 23% of DS-10, about 23% to about 23.5% of DS-10, about 23.5% to about 24% of DS-10, about 24% to about 24.5% of DS-10, or about 24.5% to about 25% of DS-10. In some additional aspects, the mixture of isomerically-purified hydroxypropyl-β-cyclodextrin molecules may include about 19% to about 20% of DS-10, about 19% to about 20.5% of DS-10, about 19% to about 21% of DS-10, about 19% to about 21.5% of DS-10, about 19% to about 22% of DS-10, about 19% to about 22.5% of DS-10, about 19% to about 23% of DS-10, about 19% to about 23.5% of DS-10, about 19% to about 24% of DS-10, about 19% to about 24.5% of DS-10, about 19.5% to about 25% of DS-10, about 20% to about 25% of DS-10, about 20.5% to about 25% of DS-10, about 21% to about 25% of DS-10, about 21.5% to about 25% of DS-10, about 22% to about 25% of DS-10, about 22.5% to about 25% of DS-10, about 23% to about 25% of DS-10, about 23.5% to about 25% of DS-10, about 24% to about 25% of DS-10, about 19.5% to about 24.5% of DS-10, about 20% to about 24% of DS-10, about 20.5% to about 23.5% of DS-10, about 21% to about 23% of DS-10, or about 21.5% to about 22.5% of DS-10. In still further aspects, the mixture of isomerically-purified hydroxypropyl-β-cyclodextrin molecules may include about 19.0%, 19.1%, 19.2%, 19.3%, 19.4%, 19.5%, 19.6%, 19.7%, 19.8%, 19.9%, 20.0%, 20.1%, 20.2%, 20.3%, 20.4%, 20.5%, 20.6%, 20.7%, 20.8%, 20.9%, 21.0%, 21.1%, 21.2%, 21.3%, 21.4%, 21.5%, 21.6%, 21.7%, 21.8%, 21.9%, 22.0%, 22.1%, 22.2%, 22.3%, 22.4%, 22.5%, 22.6%, 22.7%, 22.8%, 22.9%, 23.0%, 23.1%, 23.2%, 23.3%, 23.4%, 23.5%, 23.6%, 23.7%, 23.8%, 23.9%, 24.0%, 24.1%, 24.2%, 24.3%, 24.4%, 24.5%, 24.6%, 24.7%, 24.8%, 24.9%, or about 25.0% of DS-10. In an exemplary embodiment, the area of DS-10 in a MALDI-TOF-MS spectrum is 22.37%.

In some embodiments, the mixture of isomerically-purified hydroxypropyl-β-cyclodextrin molecules may include about 14% to about 20% of DS-11. In some aspects, the mixture of isomerically-purified hydroxypropyl-β-cyclodextrin molecules may include about 14% to about 14.5% of DS-11, about 14.5% to about 15% DS-11, about 15% to about 15.5% of DS-11, about 15.5% to about 16% of DS-11, about 16% to about 16.5% of DS-11, about 16.5% to about 17% of DS-11, about 17% to about 17.5% of DS-11, about 17.5% to about 18% of DS-11, about 18% to about 18.5% of DS-11, about 18.5% to about 19% of DS-11, about 19% to about 19.5% of DS-11, or about 19.5% to about 20% of DS-11. In some additional aspects, the mixture of isomerically-purified hydroxypropyl-β-cyclodextrin molecules may include about 14% to about 15% of DS-11, about 14% to about 15.5% of DS-11, about 14% to about 16% of DS-11, about 14% to about 16.5% of DS-11, about 14% to about 17% of DS-11, about 14% to about 17.5% of DS-11, about 14% to about 18% of DS-11, about 14% to about 18.5% of DS-11, about 14% to about 19% of DS-11, about 14% to about 19.5% of DS-11, about 14.5% to about 20% of DS-11, about 15% to about 20% of DS-11, about 15.5% to about 20% of DS-11, about 16% to about 20% of DS-11, about 16.5% to about 20% of DS-11, about 17% to about 20% of DS-11, about 17.5% to about 20% of DS-11, about 18% to about 20% of DS-11, about 18.5% to about 20% of DS-11, about 19% to about 20% of DS-11, about 14.5% to about 19.5% of DS-11, about 15% to about 19% of DS-11, about 15.5% to about 18.5% of DS-11, about 16% to about 18% of DS-11, or about 16.5% to about 17.5% of DS-11. In still further aspects, the mixture of isomerically purified hydroxypropyl-β-cyclodextrin molecules may include about 14.0%, 14.1%, 14.2%, 14.3%, 14.4%, 14.5%, 14.6%, 14.7%, 14.8%, 14.9%, 15.0%, 15.1%, 15.2%, 15.3%, 15.4%, 15.5%, 15.6%, 15.7%, 15.8%, 15.9%, 16.0%, 16.1%, 16.2%, 16.3%, 16.4%, 16.5%, 16.6%, 16.7%, 16.8%, 16.9%, 17.0%, 17.1%, 17.2%, 17.3%, 17.4%, 17.5%, 17.6%, 17.7%, 17.8%, 17.9%, 18.0%, 18.1%, 18.2%, 18.3%, 18.4%, 18.5%, 18.6%, 18.7%, 18.8%, 18.9%, 19.0%, 19.1%, 19.2%, 19.3%, 19.4%, 19.5%, 19.6%, 19.7%, 19.8%, 19.9%, or about 20.0% of DS-11. In an exemplary embodiment, the area of DS-11 in a MALDI-TOF-MS spectrum is 17.41%.

In some embodiments, the mixture of isomerically-purified hydroxypropyl-β-cyclodextrin molecules may include about 5% to about 11% of DS-12. In some aspects, the mixture of isomerically-purified hydroxypropyl-β-cyclodextrin molecules may include about 5% to about 5.5% of DS-12, about 5.5% to about 6% of DS-12, about 6% to about 6.5% of DS-12, about 6.5% of to about 7% of DS-12, about 7% to about 7.5% of DS-12, about 7.5% to about 8% of DS-12, about 8% to about 8.5% of DS-12, about 8.5% to about 9% of DS-12, about 9% to about 9.5% of DS-12, about 9.5% to about 10% of DS-12, about 10% to about 10.5% of DS-12, or about 10.5% to about 11% of DS-12. In some additional aspects, the mixture of isomerically-purified hydroxypropyl-β-cyclodextrin molecules may include about 5% to about 6% of DS-12, about 5% to about 6.5% of DS-12, about 5% to about 7% of DS-12, about 5% to about 7.5% of DS-12, about 5% to about 8% of DS-12, about 5% to about 8.5% of DS-12, about 5% to about 9% of DS-12, about 5% to about 9.5% of DS-12, about 5% of about 10% of DS-12, about 5% of about 10.5% of DS-12, about 5.5% to about 11% of DS-12, about 6% to about 11% of DS-12, about 6.5% to about 11% of DS-12, about 7% to about 11% of DS-12, about 7.5% to about 11% of DS-12, about 8% to about 11% of DS-12, about 8.5% to about 11% of DS-12, about 9% to about 11% of DS-12, about 9.5% to about 11% of DS-12, about 10% to about 11% of DS-12, about 5.5% to about 10.5% of DS-12, about 6% to about 10% of DS-12, about 6.5% to about 9.5% of DS-12, about 7% to about 9% of DS-12, or about 7.5% to about 8.5% of DS-12. In still further aspects, the mixture of isomerically-purified hydroxypropyl-β-cyclodextrin molecules may include about 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10.0%, 10.1%, 10.2%, 10.3%, 10.4%, 10.5%, 10.6%, 10.7%, 10.8%, 10.9%, or about 11.0% of DS-12. In an exemplary embodiment, the area of DS-12 in a MALDI-TOF-MS spectrum is 8.01%.

In some embodiments, the mixture of isomerically-purified hydroxypropyl-β-cyclodextrin molecules may include about 1% to about 7% of DS-13. In some aspects, the mixture of isomerically-purified hydroxypropyl-β-cyclodextrin molecules may include about 1% to about 1.5% of DS-13, about 1.5% to about 2% of DS-13, about 2% to about 2.5% of DS-13, about 2.5% to about 3% of DS-13, about 3% to about 3.5% of DS-13, about 3.5% to about 4% of DS-13, about 4% to about 4.5% of DS-13, about 4.5% to about 5% of DS-13, about 5% to about 5.5% of DS-13, about 5.5% to about 6% of DS-13, about 6% to about 6.5% of DS-13, or about 6.5% to about 7% of DS-13. In some additional aspects, the mixture of isomerically-purified hydroxypropyl-β-cyclodextrin molecules may include about 1% to about 2% of DS-13, about 1% to about 2.5% of DS-13, about 1% to about 3% of DS-13, about 1% to about 3.5% of DS-13, about 1% to about 4% of DS-13, about 1% to about 4.5% of DS-13, about 1% to about 5% of DS-13, about 1% to about 5.5% of DS-13, about 1% to about 6% of DS-13, about 1% to about 6.5% of DS-13, about 1.5% to about 7% of DS-13, about 2% to about 7% of DS-13, about 2.5% to about 7% of DS-13, about 3% to about 7% of DS-13, about 3.5% to about 7% of DS-13, about 4% to about 7% of DS-13, about 4.5% to about 7% of DS-13, about 5% to about 7% of DS-13, about 5.5% to about 7% of DS-13, about 6% to about 7% of DS-13, about 1.5% to about 6.5% of DS-13, about 2% to about 6% of DS-13, about 2.5% to about 5.5% of DS-13, about 3% to about 5% of DS-13, or about 3.5% to about 4.5% of DS-13. In still further aspects, the mixture of isomerically-purified hydroxypropyl-β-cyclodextrin molecules may include about 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, or about 7.0% of DS-13. In an exemplary embodiment, the area of DS-13 in a MALDI-TOF-MS spectrum is 4.20%.

Further provided herein is a composition comprising a mixture of isomerically-purified hydroxypropyl-β-cyclodextrin molecules including DS-6, DS-7, DS-8, DS-9, DS-10, DS-11, DS-12, and DS-13. In some embodiments, the composition includes less than 1% of DS-5. In some additional embodiments, the composition includes less than 1% of DS-14. In some embodiments, the DS-9 may have the highest concentration in the composition as compared to DS-6, DS-7, DS-8, DS-10, DS-11, DS-12, and DS-13.

In some embodiments, the mixture of hydroxypropyl-β-cyclodextrin molecules may include about 1% to about 7% of DS-7. In some aspects, the mixture of hydroxypropyl-β-cyclodextrin molecules may include about 1% to about 1.5% of DS-7, about 1.5% to about 2% of DS-7, about 2% to about 2.5% of DS-7, about 2.5% to about 3% of DS-7, about 3% to about 3.5% of DS-7, about 3.5% to about 4% of DS-7, about 4% to about 4.5% of DS-7, about 4.5% to about 5% of DS-7, about 5% to about 5.5% of DS-7, about 5.5% to about 6% of DS-7, about 6% to about 6.5% of DS-7, or about 6.5% to about 7% of DS-7. In some additional aspects, the mixture of hydroxypropyl-β-cyclodextrin molecules may include about 1% to about 2% of DS-7, about 1% to about 2.5% of DS-7, about 1% to about 3% of DS-7, about 1% to about 3.5% of DS-7, about 1% to about 4% of DS-7, about 1% to about 4.5% of DS-7, about 1% to about 5% of DS-7, about 1% to about 5.5% of DS-7, about 1% to about 6% of DS-7, about 1% to about 6.5% of DS-7, about 1.5% to about 7% of DS-7, about 2% to about 7% of DS-7, about 2.5% to about 7% of DS-7, about 3% to about 7% of DS-7, about 3.5% to about 7% of DS-7, about 4% to about 7% of DS-7, about 4.5% to about 7% of DS-7, about 5% to about 7% of DS-7, about 5.5% to about 7% of DS-7, about 6% to about 7% of DS-7, about 1.5% to about 6.5% of DS-7, about 2% to about 6% of DS-7, about 2.5% to about 5.5% of DS-7, about 3% to about 5% of DS-7, or about 3.5% to about 4.5% of DS-7. In still further aspects, the mixture of hydroxypropyl-β-cyclodextrin molecules may include about 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, or about 7.0% of DS-7. In an exemplary embodiment, the area of DS-7 in a MALDI-TOF-MS spectrum is 3.92%.

In some embodiments, the mixture of isomerically-purified hydroxypropyl-β-cyclodextrin molecules may include about 16% to about 22% of DS-8. In some aspects, the mixture of isomerically-purified hydroxypropyl-β-cyclodextrin molecules may include about 16% to about 16.5% of DS-8, about 16.5% to about 17% of DS-8, about 17% to about 17.5% of DS-8, about 17.5% to about 18% of DS-8, about 18% to about 18.5% of DS-8, about 18.5% to about 19% of DS-8, about 19% to about 19.5% of DS-8, about 19.5% to about 20% of DS-8, about 20% to about 20.5% of DS-8, about 20.5% to about 21% of DS-8, about 21% to about 21.5% of DS-8, or about 21.5% to about 22% of DS-8. In some additional aspects, the mixture of isomerically-purified β-cyclodextrin may include about 16% to about 17% of DS-8, about 16% to about 17.5% of DS-8, about 16% to about 18% of DS-8, about 16% to about 18.5% of DS-8, about 16% to about 19% of DS-8, about 16% to about 19.5% of DS-8, about 16% to about 20% of DS-8, about 16% to about 20.5% of DS-8, about 16% to about 21% of DS-8, about 16% to about 21.5% of DS-8, about 16.5% to about 22% of DS-8, about 17% to about 22% of DS-8, about 17.5% to about 22% of DS-8, about 18% to about 22% of DS-8, about 18.5% to about 22% of DS-8, about 19% to about 22% of DS-8, about 19.5% to about 22% of DS-8, about 20% to about 22% of DS-8, about 20.5% to about 22% of DS-8, about 21% to about 22% of DS-8, about 16.5% to about 21.5% of DS-8, about 17% to about 21% of DS-8, about 17.5% to about 20.5% of DS-8, about 18% to about 20% of DS-8, or about 18.5% to about 19.5% of DS-8. In still further aspects, the mixture of isomerically-purified β-cyclodextrin molecules may include about 16.0%, 16.1%, 16.2%, 16.3%, 16.4%, 16.5%, 16.6%, 16.7%, 16.8%, 16.9%, 17.0%, 17.1%, 17.2%, 17.3%, 17.4%, 17.5%, 17.6%, 17.7%, 17.8%, 17.9%, 18.0%, 18.1%, 18.2%, 18.3%, 18.4%, 18.5%, 18.6%, 18.7%, 18.8%, 18.9%, 19.0%, 19.1%, 19.2%, 19.3%, 19.4%, 19.5%, 19.6%, 19.7%, 19.8%, 19.9%, 20.0%, 20.1%, 20.2%, 20.3%, 20.4%, 20.5%, 20.6%, 20.7%, 20.8%, 20.9%, 21.0%, 21.1%, 21.2%, 21.3%, 21.4%, 21.5%, 21.6%, 21.7%, 21.8%, 21.9%, or about 22.0% of DS-8. In an exemplary embodiment, the area of DS-8 in a MALDI-TOF-MS spectrum is 18.65%.

In some embodiments, the mixture of isomerically-purified hydroxypropyl-β-cyclodextrin molecules may include about 22% to about 28% of DS-9. In some aspects, the mixture of isomerically-purified β-cyclodextrin molecules includes about 22% to about 22.5% of DS-9, about 22.5% to about 23% of DS-9, about 23% to about 23.5% of DS-9, about 23.5% to about 24% of DS-9, about 24% to about 24.5% to about 25% of DS-9, about 25% to about 25.5% of DS-9, about 25.5% to about 26% of DS-9, about 26% to about 26.5% of DS-9, about 26.5% to about 27% of DS-9, about 27% to about 27.5% of DS-9, or about 27.5% to about 28% of DS-9. In some additional aspects, the mixture of isomerically-purified β-cyclodextrin may include about 22% to about 23% of DS-9, about 22% to about 23.5% of DS-9, about 22% to about 24% of DS-9, about 22% to about 24.5% of DS-9, about 22% to about 25% of DS-9, about 22% to about 25.5% of DS-9, about 22% to about 26% of DS-9, about 22% to about 26.5% of DS-9, about 22% to about 27% of DS-9, about 22% to about 27.5% of DS-9, about 22.5% to about 28% of DS-9, about 23% to about 28% of DS-9, about 23.5% to about 28% of DS-9, about 24% to about 28% of DS-9, about 24.5% to about 28% of DS-9, about 25% to about 28% of DS-9, about 25.5% to about 28% of DS-9, about 26% to about 28% of DS-9, about 26.5% to about 28% of DS-9, about 27% to about 28% of DS-9, about 22.5% to about 27.5% of DS-9, about 23% to about 27% of DS-9, about 23.5% to about 26.5% of DS-9, about 24% to about 26% of DS-9, or about 24.5% to about 25.5% of DS-9. In still further aspects, the mixture of isomerically-purified β-cyclodextrin molecules may include about 22.0%, 22.1%, 22.2%, 22.3%, 22.4%, 22.5%, 22.6%, 22.7%, 22.8%, 22.9%, 23.0%, 23.1%, 23.2%, 23.3%, 23.4%, 23.5%, 23.6%, 23.7%, 23.8%, 23.9%, 24.0%, 24.1%, 24.2%, 24.3%, 24.4%, 24.5%, 24.6%, 24.7%, 24.8%, 24.9%, 25.0%, 25.1%, 25.2%, 25.3%, 25.4%, 25.5%, 25.6%, 25.7%, 25.8%, 25.9%, 26.0%, 26.1%, 26.2%, 26.3%, 26.4%, 26.5%, 26.6%, 26.7%, 26.8%, 26.9%, 27.0%, 27.1%, 27.2%, 27.3%, 27.4%, 27.5%, 27.6%, 27.7%, 27.8%, 27.9%, or about 28.0% of DS-9. In an exemplary embodiment, the area of DS-9 in a MALDI-TOF-MS spectrum is 25.45%.

In some embodiments, the mixture of isomerically-purified hydroxypropyl-β-cyclodextrin molecules may include about 19% to about 25% of DS-10. In some aspects, the mixture of isomerically-purified hydroxypropyl-β-cyclodextrin molecules may include about 19% to about 19.5% of DS-10, about 19.5% to about 20% of DS-10, about 20% to about 20.5% of DS-10, about 20.5% to about 21% of DS-10, about 21% to about 21.5% of DS-10, about 21.5% to about 22% of DS-10, about 22% to about 22.5% of DS-10, about 22.5% to about 23% of DS-10, about 23% to about 23.5% of DS-10, about 23.5% to about 24% of DS-10, about 24% to about 24.5% of DS-10, or about 24.5% to about 25% of DS-10. In some additional aspects, the mixture of isomerically-purified hydroxypropyl-β-cyclodextrin molecules may include about 19% to about 20% of DS-10, about 19% to about 20.5% of DS-10, about 19% to about 21% of DS-10, about 19% to about 21.5% of DS-10, about 19% to about 22% of DS-10, about 19% to about 22.5% of DS-10, about 19% to about 23% of DS-10, about 19% to about 23.5% of DS-10, about 19% to about 24% of DS-10, about 19% to about 24.5% of DS-10, about 19.5% to about 25% of DS-10, about 20% to about 25% of DS-10, about 20.5% to about 25% of DS-10, about 21% to about 25% of DS-10, about 21.5% to about 25% of DS-10, about 22% to about 25% of DS-10, about 22.5% to about 25% of DS-10, about 23% to about 25% of DS-10, about 23.5% to about 25% of DS-10, about 24% to about 25% of DS-10, about 19.5% to about 24.5% of DS-10, about 20% to about 24% of DS-10, about 20.5% to about 23.5% of DS-10, about 21% to about 23% of DS-10, or about 21.5% to about 22.5% of DS-10. In still further aspects, the mixture of isomerically-purified hydroxypropyl-β-cyclodextrin molecules may include about 19.0%, 19.1%, 19.2%, 19.3%, 19.4%, 19.5%, 19.6%, 19.7%, 19.8%, 19.9%, 20.0%, 20.1%, 20.2%, 20.3%, 20.4%, 20.5%, 20.6%, 20.7%, 20.8%, 20.9%, 21.0%, 21.1%, 21.2%, 21.3%, 21.4%, 21.5%, 21.6%, 21.7%, 21.8%, 21.9%, 22.0%, 22.1%, 22.2%, 22.3%, 22.4%, 22.5%, 22.6%, 22.7%, 22.8%, 22.9%, 23.0%, 23.1%, 23.2%, 23.3%, 23.4%, 23.5%, 23.6%, 23.7%, 23.8%, 23.9%, 24.0%, 24.1%, 24.2%, 24.3%, 24.4%, 24.5%, 24.6%, 24.7%, 24.8%, 24.9%, or about 25.0% of DS-10. In an exemplary embodiment, the area of DS-10 in a MALDI-TOF-MS spectrum is 22.37%.

In some embodiments, the mixture of isomerically-purified hydroxypropyl-β-cyclodextrin molecules may include about 14% to about 20% of DS-11. In some aspects, the mixture of isomerically-purified hydroxypropyl-β-cyclodextrin molecules may include about 14% to about 14.5% of DS-11, about 14.5% to about 15% DS-11, about 15% to about 15.5% of DS-11, about 15.5% to about 16% of DS-11, about 16% to about 16.5% of DS-11, about 16.5% to about 17% of DS-11, about 17% to about 17.5% of DS-11, about 17.5% to about 18% of DS-11, about 18% to about 18.5% of DS-11, about 18.5% to about 19% of DS-11, about 19% to about 19.5% of DS-11, or about 19.5% to about 20% of DS-11. In some additional aspects, the mixture of isomerically-purified hydroxypropyl-β-cyclodextrin molecules may include about 14% to about 15% of DS-11, about 14% to about 15.5% of DS-11, about 14% to about 16% of DS-11, about 14% to about 16.5% of DS-11, about 14% to about 17% of DS-11, about 14% to about 17.5% of DS-11, about 14% to about 18% of DS-11, about 14% to about 18.5% of DS-11, about 14% to about 19% of DS-11, about 14% to about 19.5% of DS-11, about 14.5% to about 20% of DS-11, about 15% to about 20% of DS-11, about 15.5% to about 20% of DS-11, about 16% to about 20% of DS-11, about 16.5% to about 20% of DS-11, about 17% to about 20% of DS-11, about 17.5% to about 20% of DS-11, about 18% to about 20% of DS-11, about 18.5% to about 20% of DS-11, about 19% to about 20% of DS-11, about 14.5% to about 19.5% of DS-11, about 15% to about 19% of DS-11, about 15.5% to about 18.5% of DS-11, about 16% to about 18% of DS-11, or about 16.5% to about 17.5% of DS-11. In still further aspects, the mixture of isomerically purified hydroxypropyl-β-cyclodextrin molecules may include about 14.0%, 14.1%, 14.2%, 14.3%, 14.4%, 14.5%, 14.6%, 14.7%, 14.8%, 14.9%, 15.0%, 15.1%, 15.2%, 15.3%, 15.4%, 15.5%, 15.6%, 15.7%, 15.8%, 15.9%, 16.0%, 16.1%, 16.2%, 16.3%, 16.4%, 16.5%, 16.6%, 16.7%, 16.8%, 16.9%, 17.0%, 17.1%, 17.2%, 17.3%, 17.4%, 17.5%, 17.6%, 17.7%, 17.8%, 17.9%, 18.0%, 18.1%, 18.2%, 18.3%, 18.4%, 18.5%, 18.6%, 18.7%, 18.8%, 18.9%, 19.0%, 19.1%, 19.2%, 19.3%, 19.4%, 19.5%, 19.6%, 19.7%, 19.8%, 19.9%, or about 20.0% of DS-11. In an exemplary embodiment, the area of DS-11 in a MALDI-TOF-MS spectrum is 17.41%.

In some embodiments, the mixture of isomerically-purified hydroxypropyl-β-cyclodextrin molecules may include about 5% to about 11% of DS-12. In some aspects, the mixture of isomerically-purified hydroxypropyl-β-cyclodextrin molecules may include about 5% to about 5.5% of DS-12, about 5.5% to about 6% of DS-12, about 6% to about 6.5% of DS-12, about 6.5% of to about 7% of DS-12, about 7% to about 7.5% of DS-12, about 7.5% to about 8% of DS-12, about 8% to about 8.5% of DS-12, about 8.5% to about 9% of DS-12, about 9% to about 9.5% of DS-12, about 9.5% to about 10% of DS-12, about 10% to about 10.5% of DS-12, or about 10.5% to about 11% of DS-12. In some additional aspects, the mixture of isomerically-purified hydroxypropyl-β-cyclodextrin molecules may include about 5% to about 6% of DS-12, about 5% to about 6.5% of DS-12, about 5% to about 7% of DS-12, about 5% to about 7.5% of DS-12, about 5% to about 8% of DS-12, about 5% to about 8.5% of DS-12, about 5% to about 9% of DS-12, about 5% to about 9.5% of DS-12, about 5% of about 10% of DS-12, about 5% of about 10.5% of DS-12, about 5.5% to about 11% of DS-12, about 6% to about 11% of DS-12, about 6.5% to about 11% of DS-12, about 7% to about 11% of DS-12, about 7.5% to about 11% of DS-12, about 8% to about 11% of DS-12, about 8.5% to about 11% of DS-12, about 9% to about 11% of DS-12, about 9.5% to about 11% of DS-12, about 10% to about 11% of DS-12, about 5.5% to about 10.5% of DS-12, about 6% to about 10% of DS-12, about 6.5% to about 9.5% of DS-12, about 7% to about 9% of DS-12, or about 7.5% to about 8.5% of DS-12. In still further aspects, the mixture of isomerically-purified hydroxypropyl-β-cyclodextrin molecules may include about 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10.0%, 10.1%, 10.2%, 10.3%, 10.4%, 10.5%, 10.6%, 10.7%, 10.8%, 10.9%, or about 11.0% of DS-12. In an exemplary embodiment, the area of DS-12 in a MALDI-TOF-MS spectrum is 8.01%.

In some embodiments, the mixture of isomerically-purified hydroxypropyl-β-cyclodextrin molecules may include about 1% to about 7% of DS-13. In some aspects, the mixture of isomerically-purified hydroxypropyl-β-cyclodextrin molecules may include about 1% to about 1.5% of DS-13, about 1.5% to about 2% of DS-13, about 2% to about 2.5% of DS-13, about 2.5% to about 3% of DS-13, about 3% to about 3.5% of DS-13, about 3.5% to about 4% of DS-13, about 4% to about 4.5% of DS-13, about 4.5% to about 5% of DS-13, about 5% to about 5.5% of DS-13, about 5.5% to about 6% of DS-13, about 6% to about 6.5% of DS-13, or about 6.5% to about 7% of DS-13. In some additional aspects, the mixture of isomerically-purified hydroxypropyl-β-cyclodextrin molecules may include about 1% to about 2% of DS-13, about 1% to about 2.5% of DS-13, about 1% to about 3% of DS-13, about 1% to about 3.5% of DS-13, about 1% to about 4% of DS-13, about 1% to about 4.5% of DS-13, about 1% to about 5% of DS-13, about 1% to about 5.5% of DS-13, about 1% to about 6% of DS-13, about 1% to about 6.5% of DS-13, about 1.5% to about 7% of DS-13, about 2% to about 7% of DS-13, about 2.5% to about 7% of DS-13, about 3% to about 7% of DS-13, about 3.5% to about 7% of DS-13, about 4% to about 7% of DS-13, about 4.5% to about 7% of DS-13, about 5% to about 7% of DS-13, about 5.5% to about 7% of DS-13, about 6% to about 7% of DS-13, about 1.5% to about 6.5% of DS-13, about 2% to about 6% of DS-13, about 2.5% to about 5.5% of DS-13, about 3% to about 5% of DS-13, or about 3.5% to about 4.5% of DS-13. In still further aspects, the mixture of isomerically-purified hydroxypropyl-β-cyclodextrin molecules may include about 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, or about 7.0% of DS-13. In an exemplary embodiment, the area of DS-13 in a MALDI-TOF-MS spectrum is 4.20%.

In an exemplary embodiment, the mixture of isomerically-purified hydroxypropyl-β-cyclodextrin molecules may include about 1% to about 7% of DS-7, about 16% to about 22% of DS-8, about 22% to about 28% of DS-9, about 19% to about 25% of DS-10, about 14% to about 20% of DS-11, about 5% to about 11% of DS-12, and about 1% to about 7% of DS-13.

In another exemplary embodiment, the mixture of isomerically-purified hydroxypropyl-β-cyclodextrin molecules may include DS-7, DS-8, DS-9, DS-10, DS-11, DS-12, and DS-13, wherein the mixture includes less than 1% of DS-6, DS-5, DS-4, DS-3, DS-2, and DS-1.

In some embodiments, the average degree of substitution of the mixture of isomerically-purified hydroxypropyl-β-cyclodextrin molecules may be about 8 to about 9. In some aspects, the average degree of substitution of the mixture of isomerically-purified hydroxypropyl-β-cyclodextrin molecules may be 8.0, 8.1, 8.2, 8.3, 8.4, 8.5, 8.6, 8.7, 8.8, 8.9, or about 9.0. In an exemplary embodiment, the average degree of substitution of the mixture of hydroxypropyl-β-cyclodextrin molecules may be about 8.53.

Figure 16:
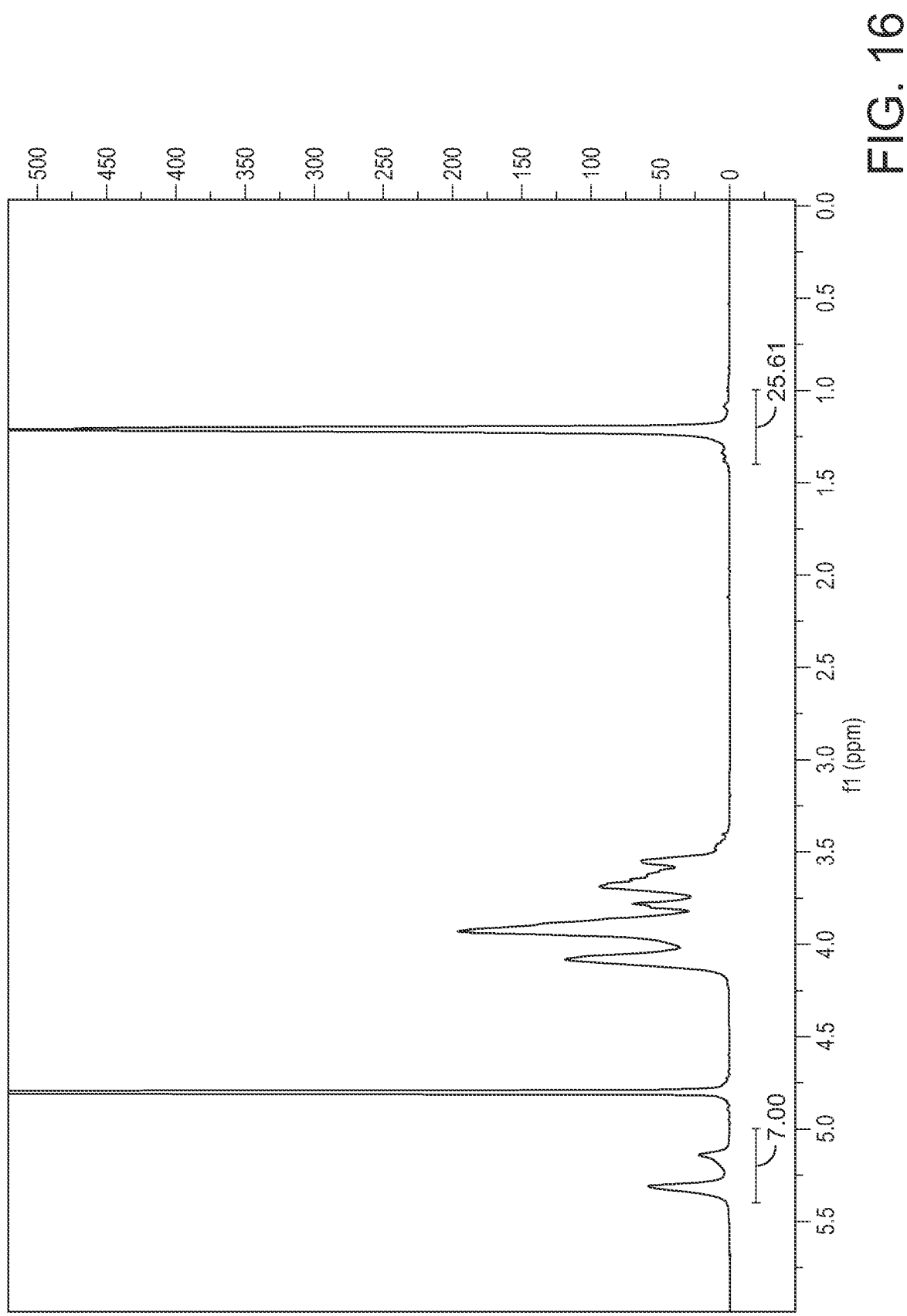
FIG. 16 is a ¹H NMR spectrum of the third HDS Fraction of a mixture of hydroxypropyl-β-cyclodextrins of the present disclosure.
Figure 17:
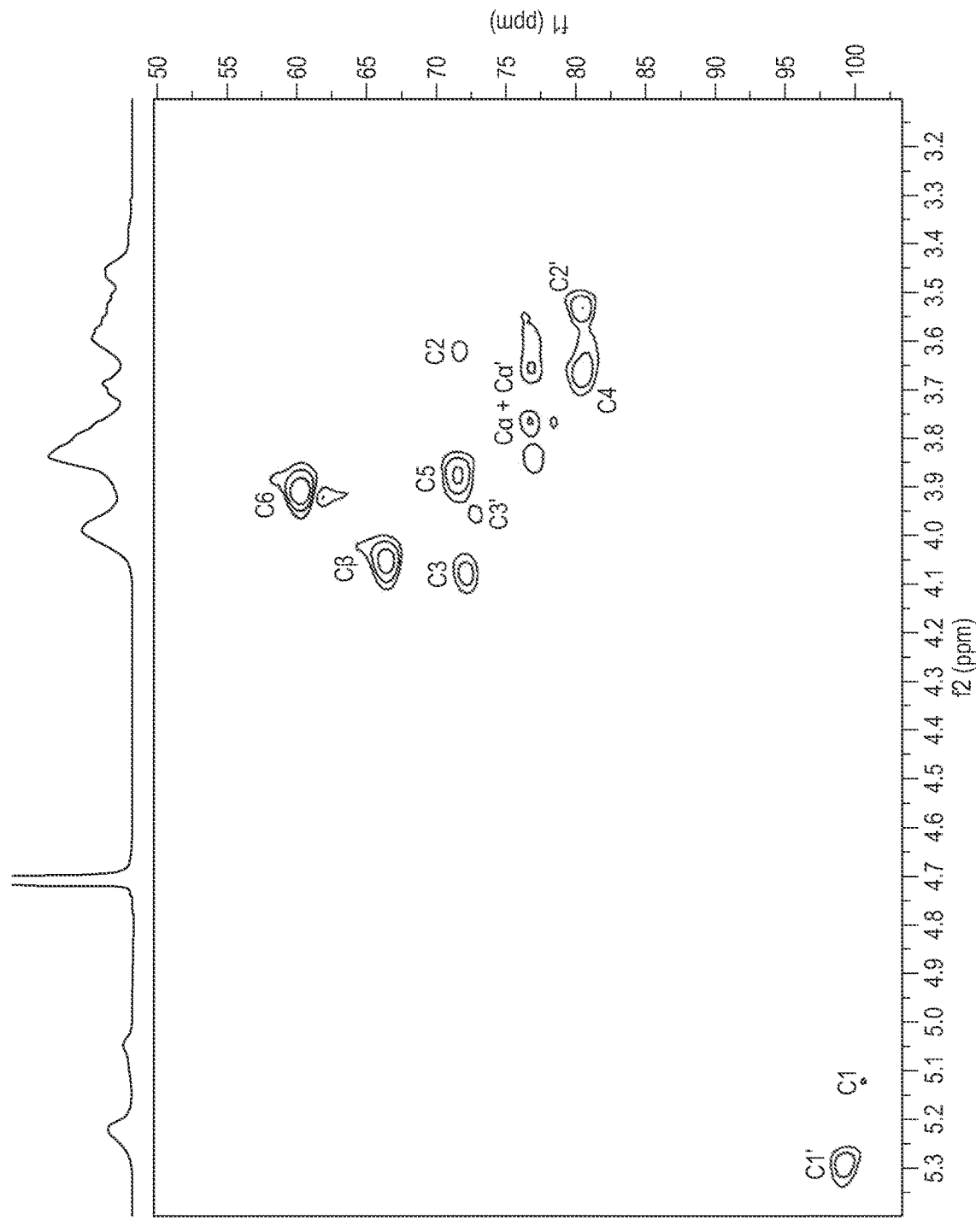
FIG. 17 is a DEPT-ed HSQC spectrum of the third HDS fraction of a mixture of hydroxypropyl-β-cyclodextrin of the present disclosure.

The position of the substitutions in the mixture isomerically-purified hydroxypropyl-β-cyclodextrin molecules of may be determined using methods known to those having skill in the art. In some embodiments the composition may be characterized by 1H-NMR. In some aspects, $^1$H-NMR may be used to determine the degree of substitution of the composition. An exemplary 1H-NMR spectrum is provided in FIG. 16. In some embodiments, the composition may be characterized by DEPT-ed HSQC. An exemplary DEPT-ed HSQC spectrum is provided in FIG. 17.

In some embodiments, about 26% to about 32% of the hydroxypropyl substitutions in the hydroxypropyl-β-cyclodextrin molecules may be located at the 3-O-position. In some aspects, the percentage of substitutions in the mixture of the hydroxypropyl-β-cyclodextrin molecules at the 3-O— position may be about 26% to about 27%, about 27% to about 28%, about 28% to about 29%, about 29% to about 30%, about 30% to about 31%, or about 31% to about 32%. In some additional aspects, the percentage of substitutions in the mixture of hydroxypropyl-β-cyclodextrin molecules at the 3-O— position may be about 26% to about 28%, about 26% to about 29%, about 26% to about 30%, about 26% to about 31%, about 27% to about 32%, about 28% to about 32%, about 29% to about 32%, about 30% to about 32%, about 27% to about 31%, or about 28% to about 30%. In an exemplary embodiment, the percentage of substitutions in the mixture of hydroxypropyl-β-cyclodextrin molecules at the 3-O— position is about 29.14%.

In some embodiments, about 68% to about 74% of the hydroxypropyl substitutions in the hydroxypropyl-β-cyclodextrin molecules are located at the 2-O-position. In some aspects, the percentage of substitutions in the mixture of hydroxypropyl-β-cyclodextrin molecules at the 2-O— position is about 68% to about 69%, about 69% to about 70%, about 70% to about 71%, about 71% to about 72%, about 72% to about 73%, or about 73% to about 74%. In some additional aspects, the percentage of substitutions in the mixture of hydroxypropyl-β-cyclodextrin molecules at the 2-O— position is about 68% to about 70%, about 68% to about 71%, about 68% to about 72%, about 68% to about 73%, about 69% to about 74%, about 70% to about 74%, about 71% to about 74%, about 72% to about 74%, about 69% to about 73%, or about 70% to about 72%. In an exemplary embodiment, the percentage of substitutions in the mixture of hydroxypropyl-β-cyclodextrin molecules at the 2-O— position is about 70.86%.

In some embodiments, the percentage of substitutions in the mixture of hydroxypropyl-β-cyclodextrin molecules at the 6-O— position is about 0%.

Figure 18:
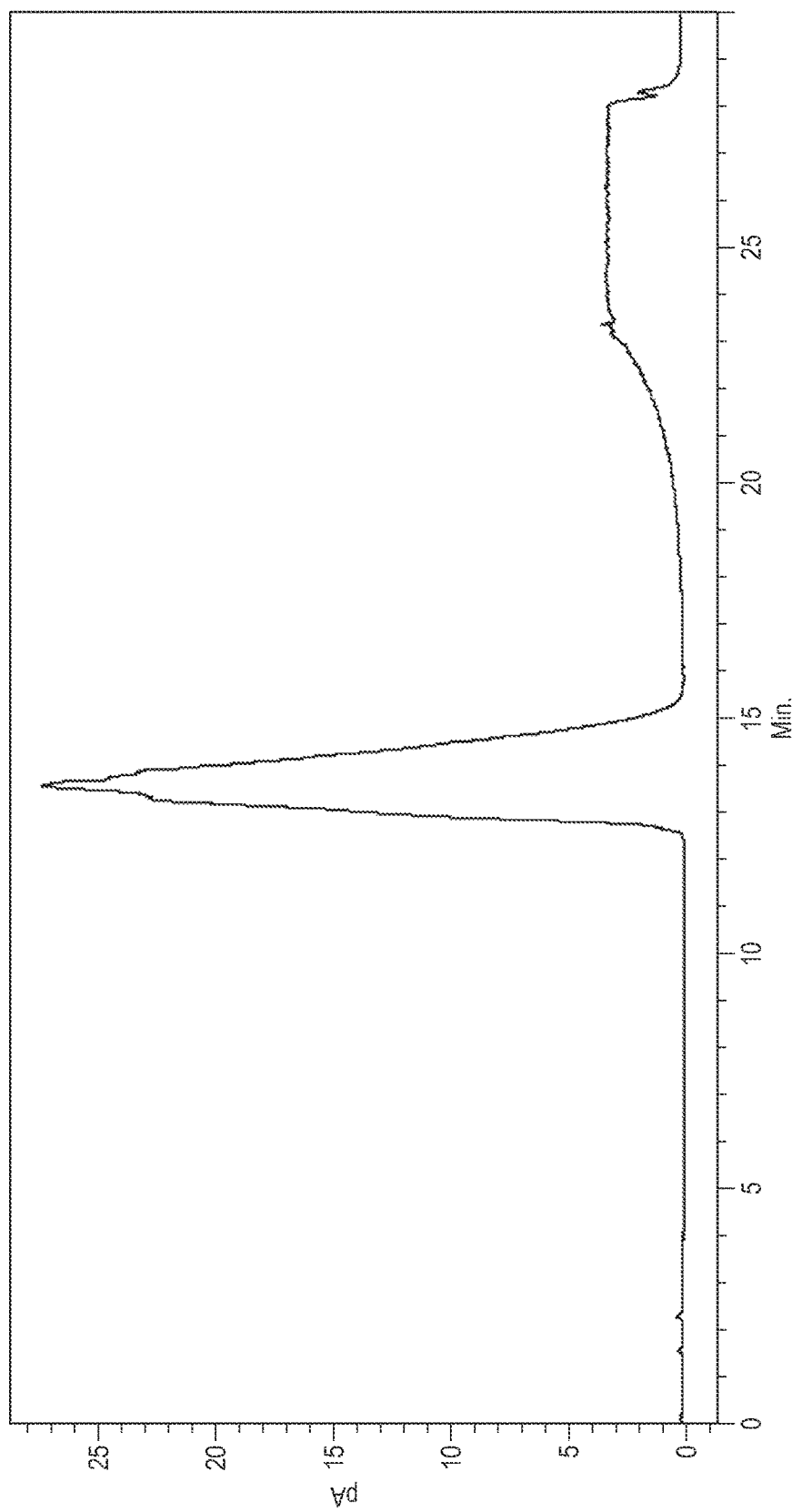
FIG. 18 is an HPLC-CAD chromatogram of the third HDS fraction of a mixture of hydroxypropyl-β-cyclodextrins of the present disclosure.

In some embodiments, the composition may have an HPLC-CAD chromatogram of FIG. 18. In some aspects, the mean retention time of the composition may be about 12.5 minutes to about 14.5 minutes as measured by HPLC-CAD. In some additional aspects, the mean retention time of the composition may be about 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, or about 14.5 minutes. In an exemplary embodiment, the mean retention time is about 13.5 minutes.

In some embodiments, the composition may have a −ESI-MS spectrum with peaks at about 741 m/z, about 769 m/z, about 799 m/z, about 828 m/z, about 856 m/z, and about 886 m/z. In some embodiments, the composition may have a +ESI-MS spectrum with peaks at about 773 m/z, about 803 m/z, about 833 m/z, about 860 m/z, about 889 m/z, and at about 920 m/z. In an exemplary embodiment, the composition has the ESI-MS spectra shown in FIG. 19.

The hydroxypropyl-β-cyclodextrin percent may be based upon an area percentage from a MALDI-TOF-MS spectrum. In some embodiments, the composition may have a MALDI-TOF-MS spectrum with peaks at about 1557 m/z, about 1617 m/z, about 1676 m/z, about 1736 m/z, about 1795 m/z, about 1855 m/z, and at about 1915 m/z. In an exemplary embodiment, the composition has the MALDI-TOF-MS spectrum shown in FIG. 20. In an exemplary embodiment, the composition has a MALDI-TOF-MS spectrum wherein the area of DS-7 is 3.92%, the area of DS-8 is 18.65%, the area of DS-9 is 25.45%, the area of DS-10 is 22.37%, the area of DS-11 is 17.41%, the area of DS-12 is 8.01%, and the area of DS-13 is 4.20%.

In some embodiments, the composition may have a true density of about 1.095 g/cm$^3$ to about 1.100 g/cm$^3$. In some aspects, the composition may have a true density of about 1.095 g/cm$^3$ to about 1.096 g/cm$^3$, about 1.096 g/cm$^3$ to about 1.097 g/cm$^3$, about 1.097 g/cm$^3$ to about 1.098 g/cm$^3$, about 1.098 g/cm$^3$ to about 1.099 g/cm$^3$, about 1.099 g/cm$^3$ to about 1.100 g/cm$^3$, about 1.095 g/cm$^3$ to about 1.097 g/cm$^3$, about 1.095 g/cm$^3$ to about 1.098 g/cm$^3$, about 1.095 g/cm$^3$ to about 1.099 g/cm$^3$, about 1.096 g/cm$^3$ to about 1.100 g/cm$^3$, about 1.097 g/cm$^3$ to about 1.100 g/cm$^3$, about 1.098 g/cm$^3$ to about 1.100 g/cm$^3$, about 1.096 g/cm$^3$ to about 1.098 g/cm$^3$, or about 1.096 g/cm$^3$ to about 1.099 g/cm$^3$. In some additional aspects, the composition may have a true density of about 1.095 g/cm$^3$, 1.096 g/cm$^3$, 1.097 g/cm$^3$, 1.098 g/cm$^3$, 1.099 g/cm$^3$, or about 1.100 g/cm$^3$. In an exemplary embodiment, the composition has a true density of about 1.096 g/cm$^3$ to about 1.098 g/cm$^3$.

In some embodiments, the composition may have an osmolality of about 600 mOs/kg to about 750 mOs/kg. In some aspects, the composition may have an osmolality of about 600 mOs/kg to about 625 mOs/kg, about 625 mOs/kg to about 650 mOs/kg, about 650 mOs/kg to about 675 mOs/kg, about 675 mOs/kg to about 700 mOs/kg, about 700 mOs/kg to about 725 mOs/kg, or about 725 mOs/kg to about 750 mOs/kg. In some additional aspects, the composition may have an osmolality of about 600 mOs/kg to about 650 mOs/kg, about 600 mOs/kg to about 675 mOs/kg, about 600 mOs/kg to about 700 mOs/kg, about 600 mOs/kg to about 725 mOs/kg, about 625 mOs/kg to about 750 mOs/kg, about 650 mOs/kg to about 750 mOs/kg, about 675 mOs/kg to about 750 mOs/kg, about 700 mOs/kg to about 750 mOs/kg, about 625 mOs/kg to about 725 mOs/kg, or about 650 mOs/kg to about 700 mOs/kg. In still further embodiments, the composition may have an osmolality of about 600 mOs/kg, 610 mOs/kg, 620 mOs/kg, 630 mOs/kg, 640 mOs/kg, 650 mOs/kg, 660 mOs/kg, 670 mOs/kg, 680 mOs/kg, 690 mOs/kg, 700 mOs/kg, 710 mOs/kg, 720 mOs/kg, 730 mOs/kg, 740 mOs/kg, or about 750 mOs/kg. In an exemplary embodiment, the composition has an osmolality of about 635 mOs/kg to about 695 mOs/kg.

In some embodiments, the composition may have a conductivity between about 0 and about 8 µS/cm. In some aspects, the composition may have a conductivity between about 0 µS/cm and about 1 µS/cm, about 1 µS/cm and about 2 µS/cm, about 3 µS/cm and about 4 µS/cm, about 4 µS/cm and about 5 µS/cm, about 5 µS/cm and about 6 µS/cm, about 6 µS/cm and about 7 µS/cm, or between about 7 µS/cm and about 8 µS/cm. In some additional embodiments, the composition may have a conductivity between about 0 µS/cm and about 1.5 µS/cm, about 0 µS/cm and about 2 µS/cm, about 0 µS/cm and about 2.5 µS/cm, about 0 µS/cm and about 3 µS/cm, about 0 and about 3.5 µS/cm, about 0 µS/cm and about 4 µS/cm, about 0 and about 4.5 µS/cm, about 0 µS/cm and about 5 µS/cm, about 0 and about 5.5 µS/cm, about 0 µS/cm and about 6 µS/cm, about 0 and about 6.5, about 0 µS/cm and about 7 µS/cm, about 0 and about 7.5, about 1 µS/cm and about 8 µS/cm, about 1.5 µS/cm and about 8 µS/cm, about 2 µS/cm and about 8 µS/cm, about 2.5 µS/cm and about 8 µS/cm, about 3 µS/cm and about 8 µS/cm, about 3.5 µS/cm and about 8 µS/cm, about 4 µS/cm and about 8 µS/cm, about 4.5 µS/cm and about 8 µS/cm, about 5 µS/cm and about 8 µS/cm, about 5.5 µS/cm and about 8 µS/cm, about 6 µS/cm and about 8 µS/cm, about 6.5 µS/cm and about 8 µS/cm, about 1 µS/cm and about 7 µS/cm, about 2 µS/cm and about 6 µS/cm, or about 3 µS/cm and about 5 µS/cm. In still further aspects, the composition may have a conductivity of about 0.5 µS/cm, 1.0 µS/cm, 1.5 µS/cm, 2.0 µS/cm, 2.5 µS/cm, 3.0 µS/cm, 3.5 µS/cm, 4.0 µS/cm, 4.5

µS/cm, 5.0 µS/cm, 5.5 µS/cm, 6.0 µS/cm, 6.5 µS/cm, 7.0 µS/cm, 7.5 µS/cm, or about 8.0 µS/cm.

In some embodiments, the composition may have a pH of about 4.0 to about 8.0; for example, the composition may have a pH of about 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, or about 8.0. The composition may have a pH in a range or sub-range comprising any of the afore-mentioned numbers, including but not limited to a pH about 4.0 to about 4.5, about 4.5 to about 5.0, about 5.0 to about 5.5, about 5.5 to about 6.0, about 6.0 to about 6.5, about 6.5 to about 7.0, about 7.0 to about 7.5, or about 7.5 to about 8.0. In some embodiments, the composition may further comprise a pH adjusting agent, such as hydrochloric acid or sodium hydroxide, to adjust the pH to a desired level. In some embodiments, the composition may further comprise a buffer. In some embodiments, the buffer may include monobasic sodium phosphate and dibasic sodium phosphate.

In some embodiments, the composition may have a viscosity measured in centipoises (cP) at 20° C. For example, the composition may have a viscosity of about 1.5 cP to about 3.0 cP at 20° C. In some embodiments, the composition may have a viscosity of about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or about 10.0 cP at 20° C. In other embodiments, the composition may have a viscosity of about 3.0 cP to about 5.0 cP, about 5.0 cP to about 10.0 cP, about 10 to about 15 cP, about 15 to about 20 cP, about 20 cP to about 25 cP, about 25 cP to about 50 cP, about 50 cP to about 80 cP, about 80 cP to about 150 cP, about 150 cP to about 250 cP, about 250 cP to about 500 cP, about 500 cP to about 1,000 cP, about 1,000 cP to about 2,000 cP, about 2,000 cP to about 3,000 cP, about 3,000 cP to about 5,000 cP, or about 5,000 cP to about 10,000 cP at 20° C.

The composition may be substantially free of impurities. Impurities include particles having a diameter of greater than or equal to 25 microns, particles having a diameter of greater than or equal to 10 microns, chloride, propylene glycol, propylene oxide, and other unspecified impurities. In some embodiments, the composition may include less than or equal to about 0.05% impurities; for example, the composition may include less than or equal to about 0.05%, 0.04%, 0.03%, 0.02%, or less than or equal to about 0.01% impurities.

In some embodiments, the composition may further comprise a container and non-visible particulate matter. In some embodiments, the composition may be provided in a container. In some embodiments, the composition may further comprise non-visible particulate matter.

In some embodiments, the composition may include less than 600 particles per container having a diameter of greater than or equal to 25 microns. In some aspects, the composition may include less than 500, less than 400, less than 300, less than 200, or less than 100 particles per container having a diameter greater than or equal to 25 microns.

In some embodiments, the composition may include less than 6000 particles per container having a diameter of greater than or equal to 10 microns. In some aspects, the composition may include less than 5000, less than 4000, less than 3000, less than 2000, less than 1000, less than 500, or less than 100 particles per container having a diameter greater than or equal to 10 microns. In another aspect, the composition may include less than 5000, less than 4000, less than 3000, less than 2000, less than 1000, less than 500, or less than 100 particles per container having a diameter greater than or equal to 10 microns, wherein the container is: 100 mL. In another aspect, the composition may include less than 5000, less than 4000, less than 3000, less than 2000, less than 1000, less than 500, less than 100, less than 50, less than 25, less than 10, less than 5, or less than 3 particles per container having a diameter greater than or equal to 10 microns, wherein the container is >100 mL.

In some embodiments, the composition may include no more than 10 ppb of propylene glycol. In some aspects, the composition may include no more than 9 ppb, 8 ppb, 7 ppb, 6 ppb, 5 ppb, 4 ppb, 3 ppb, 2 ppb, or no more than 1 ppb propylene glycol. In some aspects, the amount of propylene glycol in the composition may be determined by HPLC. In some additional aspects, the amount of propylene glycol in the composition may be determined by gas chromatography. In still further aspects, the amount of propylene glycol in the composition may be determined by measuring the PG/EG-ratio of propylene glycol to ethylene glycol.

In some embodiments, the composition may include no more than 1 ppm propylene oxide. In some aspects, the composition may include no more than 0.9 ppm, 0.8 ppm, 0.7 ppm, 0.6 ppm, 0.5 ppm, 0.4 ppm, 0.3 ppm, 0.2 ppm, or 0.1 ppm propylene oxide. In some aspects, the amount of propylene oxide in the composition may be determined by HPLC. In some additional aspects, the amount of propylene oxide in the composition may be determined by gas chromatography.

In some embodiments, the composition may include between about 0 ppm to about 10 ppm chloride (e.g., Cl⁻ ions). In some aspects, the composition may include about 0 ppm chloride to about 2 ppm chloride, about 2 ppm chloride to about 4 ppm chloride, about 4 ppm chloride to about 6 ppm chloride, about 6 ppm chloride to about 8 ppm chloride, or about 8 to about 10 ppm chloride. In some additional aspects, the composition may include about 0 ppm chloride to about 4 ppm chloride, about 0 ppm chloride to about 6 ppm chloride, about 0 ppm chloride to about 8 ppm chloride, about 2 ppm chloride to about 1 ppm chloride, about 4 ppm chloride to about 1 ppm chloride, or about 6 ppm chloride to about 1 ppm chloride. In still further aspects, the composition may include about 0 ppm, 1 ppm, 2 ppm, 3 ppm, 4 ppm, 5 ppm, 6 ppm, 7 ppm, 8 ppm, 9 ppm, or about 10 ppm chloride. In an exemplary embodiment, the composition may include between about 0 ppm to about 1 ppm chloride.

In some embodiments, the composition may include between about 0 ppm to about 10 ppm sodium (e.g., Na⁺ ions). In some aspects, the composition may include about 0 ppm sodium to about 2 ppm sodium, about 2 ppm sodium to about 4 ppm sodium, about 4 ppm sodium to about 6 ppm sodium, about 6 ppm sodium to about 8 ppm sodium, or about 8 to about 10 ppm sodium. In some additional aspects, the composition may include about 0 ppm sodium to about 4 ppm sodium, about 0 ppm sodium to about 6 ppm sodium, about 0 ppm sodium to about 8 ppm sodium, about 2 ppm sodium to about 1 ppm sodium, about 4 ppm sodium to about 1 ppm sodium, or about 6 ppm sodium to about 1 ppm sodium. In still further aspects, the composition may include about 0 ppm, 1 ppm, 2 ppm, 3 ppm, 4 ppm, 5 ppm, 6 ppm, 7 ppm, 8 ppm, 9 ppm, or about 10 ppm sodium. In an exemplary embodiment, the composition may include between about 0 ppm to about 1 ppm sodium.

In some embodiments, the composition may include less than or equal to 0.05% of other unspecified impurities; for example, the composition may include less than or equal to 0.05%, 0.04%, 0.03%, 0.02%, or less than or equal to 0.01% of other unspecified impurities.

In some embodiments, the composition may be stable for at least 6 months. For example, the composition may be stable for at least 3 months, 6 months, at least 7 months, at least 8 months, at least 9 months, at least 10 months, at least 11 months, at least 12 months, at least 13 months, at least 14 months, at least 15 months, at least 16 months, at least 17 months, at least 18 months, at least 24 months, or at least 36 months.

The composition may be nanofiltered. In some embodiments, the concentration of the composition does not substantially change the time required for nanofiltration. Thus, the time for nanofiltration does not increase or decrease as the concentration of the mixture of β-cyclodextrin molecules increases or decreases in the composition. In some aspects, the length of time to nanofilter the composition ranges from about 1.04 to about 1.20 hours per diafiltration volume (kg soln/m$^2$·hr/L soln). In some embodiments, the nanofiltered composition has no substantial difference observed in HPLC-ELSD after nanofiltration as compared to before nanofiltration. In some embodiments, the composition has no substantial difference observed in NMR after nanofiltration as compared to before nanofiltration.

In some embodiments, the composition may be terminally sterilized. Methods of terminal sterilization are generally well-known in the art. In some embodiments, the pH of the composition may be adjusted after terminal sterilization.

In some embodiments, the composition may include less than or equal to 10.0% w/w of water. For example, the composition may include less than or equal to 10.0% w/w, 9.5% w/w, 9.0% w/w, 8.5% w/w, 8.0% w/w, 7.5% w/w, 7.0% w/w, 6.5% w/w, 6.0% w/w, 5.5% w/w, 5.0% w/w, 4.5% w/w, 4.0% w/w, 3.5% w/w, 3.0% w/w, 2.5% w/w, 2.0% w/w, 1.5% w/w, 1.0% w/w, 0.5% w/w, or less than or equal to 0.1% w/w water.

In some embodiments, the composition may be packaged in a vial suitable for injection to a human subject in need thereof. The vial may be glass, plastic, or any other material known in the pharmaceutical art. The vial may be coated with a material such as silicon dioxide to prevent leaching from the vial into the composition.

In some embodiments, the composition may be efficacious in treating Niemann-Pick disease. In some embodiments, the composition may be efficacious in treating Niemann-Pick disease Type C. In some embodiments, the composition may be efficacious in treating liver disease. In some embodiments, the composition may be efficacious in treating cardiovascular disease. In some embodiments, the composition may be efficacious in treating familial hypercholesterolemia. In some embodiments, the composition may be efficacious in treating cholesterol deposits.

In some embodiments, the composition may further comprise a pharmaceutical excipient or carrier. In some embodiments, the composition may further comprise a pharmaceutically acceptable diluent. Examples of pharmaceutical excipients, carriers, and diluents are well known to those having skill in the art.

In some embodiments, the composition may exhibit a lower toxicity than Trappsol® Cyclo or Kleptose®. In some embodiments, the composition may exhibit a substantially lower ototoxicity than Trappsol® Cyclo or Kleptose®. In some embodiments, the composition may exhibit substantially no ototoxicity.

Fraction 4 HDS

Provided herein is a composition comprising a mixture of isomerically-purified hydroxypropyl-β-cyclodextrin molecules that includes less than 1% of DS-6. In some embodiments, the mixture of isomerically-purified hydroxypropyl-β-cyclodextrin molecules may include less than 1% of DS-5, DS-4, DS-3, DS-2, and DS-1. In some aspects, the mixture of isomerically-purified hydroxypropyl-β-cyclodextrin molecules may include less than 1%, less than 0.9%, less than 0.8%, less than 0.7%, less than 0.6%, less than 0.5%, less than 0.4%, less than 0.3%, less than 0.2%, or less than 0.1% of DS-5, DS-4, DS-3, DS-2, and DS-1.

In some embodiments, the mixture of hydroxypropyl-β-cyclodextrin molecules may include about 0% to about 6% of DS-7. In some aspects, the mixture of hydroxypropyl-β-cyclodextrin molecules may include about 0% to about 0.5% of DS-7, about 0.5% to about 1% of DS-7, about 1% to about 1.5% of DS-7, about 1.5% to about 2% of DS-7, about 2% to about 2.5% of DS-7, about 2.5% to about 3% of DS-7, about 3% to about 3.5% of DS-7, about 3.5% to about 4% of DS-7, about 4% to about 4.5% of DS-7, about 4.5% to about 5% of DS-7, about 5% to about 5.5% of DS-7, or about 5.5% to about 6% of DS-7. In some additional aspects, the mixture of hydroxypropyl-β-cyclodextrin molecules may include about 0% to about 1% of DS-7, about 0% to about 1.5% of DS-7, about 0% to about 2% of DS-7, about 0% to about 2.5% of DS-7, about 0% to about 3% of DS-7, about 0% to about 3.5% of DS-7, about 0% to about 4% of DS-7, about 0% to about 4.5% of DS-7, about 0% to about 5% of DS-7, about 0% to about 5.5% of DS-7, about 0.5% to about 6% of DS-7, about 1% to about 6% of DS-7, about 1.5% to about 6% of DS-7, about 2% to about 6% of DS-7, about 2.5% to about 6% of DS-7, about 3% to about 6% of DS-7, about 3.5% to about 6% of DS-7, about 4% to about 6% of DS-7, about 4.5% to about 6% of DS-7, about 5% to about 6% of DS-7, about 0.5% to about 5.5% of DS-7, about 1% to about 5% of DS-7, about 1.5% to about 4.5% of DS-7, about 2% to about 4% of DS-7, or about 2.5% to about 3.5% of DS-7. In still further aspects, the mixture of hydroxypropyl-β-cyclodextrin molecules may include about 0.0%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, or about 6.0% of DS-7. In an exemplary embodiment, the area of DS-7 in a MALDI-TOF-MS spectrum is 3.16%.

In some embodiments, the mixture of isomerically-purified hydroxypropyl-β-cyclodextrin molecules may include about 13% to about 19% of DS-8. In some aspects, the mixture of isomerically-purified hydroxypropyl-β-cyclodextrin molecules may include about 13% to about 13.5% of DS-8, about 13.5% to about 14% of DS-8, about 14% to about 14.5% of DS-8, about 14.5% to about 15% of DS-8, about 15% to about 15.5% of DS-8, about 15.5% to about 16% of DS-8, about 16% to about 16.5% of DS-8, about 16.5% to about 17% of DS-8, about 17% to about 17.5% of DS-8, about 17.5% to about 18% of DS-8, about 18% to about 18.5% of DS-8, or about 18.5% to about 19% of DS-8. In some additional aspects, the mixture of isomerically-purified β-cyclodextrin may include about 13% to about 14% of DS-8, about 13% to about 14.5% of DS-8, about 13% to about 15% of DS-8, about 13% to about 15.5% of DS-8, about 13% to about 16% of DS-8, about 13% to about 16.5% of DS-8, about 13% to about 17% of DS-8, about 13% to about 17.5% of DS-8, about 13% to about 18% of DS-8, about 13% to about 18.5% of DS-8, about 13.5% to about 19% of DS-8, about 14% to about 19% of DS-8, about 14.5% to about 19% of DS-8, about 15% to about 19% of DS-8, about 15.5% to about 19% of DS-8, about 16% to about 19% of DS-8, about 16.5% to about 19% of DS-8, about 17% to about 19% of DS-8, about 17.5% to about 19% of DS-8, about 18% to about 19% of DS-8, about 13.5% to about 18.5% of DS-8, about 14% to about 18% of DS-8, about 14.5% to about 17.5% of DS-8, about 15% to about 17% of DS-8, or about 15.5% to about 16.5% of DS-8. In still further aspects, the mixture of isomerically-purified β-cyclodextrin molecules may include about 13.0%, 13.1%, 13.2%, 13.3%, 13.4%, 13.5%, 13.6%, 13.7%, 13.8%, 13.9%, 14.0%, 14.1%, 14.2%, 14.3%, 14.4%, 14.5%, 14.6%, 14.7%, 14.8%, 14.9%, 15.0%, 15.1%, 15.2%, 15.3%, 15.4%, 15.5%, 15.6%, 15.7%, 15.8%, 15.9%, 16.0%, 16.1%, 16.2%, 16.3%, 16.4%, 16.5%, 16.6%, 16.7%, 16.8%, 16.9%, 17.0%, 17.1%, 17.2%, 17.3%, 17.4%, 17.5%, 17.6%, 17.7%, 17.8%, 17.9%, 18.0%, 18.1%, 18.2%, 18.3%, 18.4%, 18.5%, 18.6%, 18.7%, 18.8%, 18.9%, or about 19.0% of DS-8. In an exemplary embodiment, the area of DS-8 in a MALDI-TOF-MS spectrum is 16.44%.

In some embodiments, the mixture of isomerically-purified hydroxypropyl-β-cyclodextrin molecules may include about 22% to about 28% of DS-9. In some aspects, the mixture of isomerically-purified β-cyclodextrin molecules includes about 22% to about 22.5% of DS-9, about 22.5% to about 23% of DS-9, about 23% to about 23.5% of DS-9, about 23.5% to about 24% of DS-9, about 24% to about 24.5% to about 25% of DS-9, about 25% to about 25.5% of DS-9, about 25.5% to about 26% of DS-9, about 26% to about 26.5% of DS-9, about 26.5% to about 27% of DS-9, about 27% to about 27.5% of DS-9, or about 27.5% to about 28% of DS-9. In some additional aspects, the mixture of isomerically-purified β-cyclodextrin may include about 22% to about 23% of DS-9, about 22% to about 23.5% of DS-9, about 22% to about 24% of DS-9, about 22% to about 24.5% of DS-9, about 22% to about 25% of DS-9, about 22% to about 25.5% of DS-9, about 22% to about 26% of DS-9, about 22% to about 26.5% of DS-9, about 22% to about 27% of DS-9, about 22% to about 27.5% of DS-9, about 22.5% to about 28% of DS-9, about 23% to about 28% of DS-9, about 23.5% to about 28% of DS-9, about 24% to about 28% of DS-9, about 24.5% to about 28% of DS-9, about 25% to about 28% of DS-9, about 25.5% to about 28% of DS-9, about 26% to about 28% of DS-9, about 26.5% to about 28% of DS-9, about 27% to about 28% of DS-9, about 22.5% to about 27.5% of DS-9, about 23% to about 27% of DS-9, about 23.5% to about 26.5% of DS-9, about 24% to about 26% of DS-9, or about 24.5% to about 25.5% of DS-9. In still further aspects, the mixture of isomerically-purified β-cyclodextrin molecules may include about 22.0%, 22.1%, 22.2%, 22.3%, 22.4%, 22.5%, 22.6%, 22.7%, 22.8%, 22.9%, 23.0%, 23.1%, 23.2%, 23.3%, 23.4%, 23.5%, 23.6%, 23.7%, 23.8%, 23.9%, 24.0%, 24.1%, 24.2%, 24.3%, 24.4%, 24.5%, 24.6%, 24.7%, 24.8%, 24.9%, 25.0%, 25.1%, 25.2%, 25.3%, 25.4%, 25.5%, 25.6%, 25.7%, 25.8%, 25.9%, 26.0%, 26.1%, 26.2%, 26.3%, 26.4%, 26.5%, 26.6%, 26.7%, 26.8%, 26.9%, 27.0%, 27.1%, 27.2%, 27.3%, 27.4%, 27.5%, 27.6%, 27.7%, 27.8%, 27.9%, or about 28.0% of DS-9. In an exemplary embodiment, the area of DS-9 in a MALDI-TOF-MS spectrum is 25.24%.

In some embodiments, the mixture of isomerically-purified hydroxypropyl-β-cyclodextrin molecules may include about 23% to about 29% of DS-10. In some aspects, the mixture of isomerically-purified hydroxypropyl-β-cyclodextrin molecules may include about 23% to about 23.5% of DS-10, about 23.5% to about 24% of DS-10, about 24% to about 24.5% of DS-10, about 24.5% to about 25% of DS-10, about 25% to about 25.5% of DS-10, about 25.5% to about 26% of DS-10, about 26% to about 26.5% of DS-10, about 26.5% to about 27% of DS-10, about 27% to about 27.5% of DS-10, about 27.5% to about 28% of DS-10, about 28% to about 28.5% of DS-10, or about 28.5% to about 29% of DS-10. In some additional aspects, the mixture of isomerically-purified hydroxypropyl-β-cyclodextrin molecules may include about 23% to about 24% of DS-10, about 23% to about 24.5% of DS-10, about 23% to about 25% of DS-10, about 23% to about 25.5% of DS-10, about 23% to about 26% of DS-10, about 23% to about 26.5% of DS-10, about 23% to about 27% of DS-10, about 23% to about 27.5% of DS-10, about 23% to about 28% of DS-10, about 23% to about 28.5% of DS-10, about 23.5% to about 29% of DS-10, about 24% to about 29% of DS-10, about 24.5% to about 29% of DS-10, about 25% to about 29% of DS-10, about 25.5% to about 29% of DS-10, about 26% to about 29% of DS-10, about 26.5% to about 29% of DS-10, about 27% to about 29% of DS-10, about 27.5% to about 29% of DS-10, about 28% to about 29% of DS-10, about 23.5% to about 28.5% of DS-10, about 24% to about 28% of DS-10, about 24.5% to about 27.5% of DS-10, about 25% to about 27% of DS-10, or about 25.5% to about 26.5% of DS-10. In still further aspects, the mixture of isomerically-purified hydroxypropyl-β-cyclodextrin molecules may include about 23.0%, 23.1%, 23.2%, 23.3%, 23.4%, 23.5%, 23.6%, 23.7%, 23.8%, 23.9%, 24.0%, 24.1%, 24.2%, 24.3%, 24.4%, 24.5%, 24.6%, 24.7%, 24.8%, 24.9%, 25.0%, 25.1%, 25.2%, 25.3%, 25.4%, 25.5%, 25.6%, 25.7%, 25.8%, 25.9%, 26.0%, 26.1%, 26.2%, 26.3%, 26.4%, 26.5%, 26.6%, 26.7%, 26.8%, 26.9%, 27.0%, 27.1%, 27.2%, 27.3%, 27.4%, 27.5%, 27.6%, 27.7%, 27.8%, 27.9%, 28.0%, 28.1%, 28.2%, 28.3%, 28.4%, 28.5%, 28.6%, 28.7%, 28.8%, 28.9%, or about 29.0% of DS-10. In an exemplary embodiment, the area of DS-10 in a MALDI-TOF-MS spectrum is 25.52%.

In some embodiments, the mixture of isomerically-purified hydroxypropyl-β-cyclodextrin molecules may include about 12% to about 18% of DS-11. In some aspects, the mixture of isomerically-purified hydroxypropyl-β-cyclodextrin molecules may include about 12% to about 12.5% of DS-11, about 12.5% to about 13% of DS-11, about 13% to about 13.5% of DS-11, about 13.5% to about 14% of DS-11, about 14% to about 14.5% of DS-11, about 14.5% to about 15% DS-11, about 15% to about 15.5% of DS-11, about 15.5% to about 16% of DS-11, about 16% to about 16.5% of DS-11, about 16.5% to about 17% of DS-11, about 17% to about 17.5% of DS-11, or about 17.5% to about 18% of DS-11. In some additional aspects, the mixture of isomerically-purified hydroxypropyl-β-cyclodextrin molecules may include about 12% to about 13% of DS-11, about 12% to about 13.5% of DS-11, about 12% to about 14% of DS-11, about 12% to about 14.5% of DS-11, about 12% to about 15% of DS-11, about 12% to about 15.5% of DS-11, about 12% to about 16% of DS-11, about 12% to about 16.5% of DS-11, about 12% to about 17% of DS-11, about 12% to about 17.5% of DS-11, about 12.5% to about 18% of DS-11, about 13% to about 18% of DS-11, about 13.5% to about 18% of DS-11, about 14% to about 18% of DS-11, about 14.5% to about 18% of DS-11, about 15% to about 18% of DS-11, about 15.5% to about 18% of DS-11, about 16% to about 18% of DS-11, about 16.5% to about 18% of DS-11, about 17% to about 18% of DS-11, about 12.5% to about 17.5% of DS-11, about 13% to about 17% of DS-11, about 13.5% to about 16.5% of DS-11, about 14% to about 16% of DS-11, or about 14.5% to about 15.5% of DS-11. In still further aspects, the mixture of isomerically purified hydroxypropyl-β-cyclodextrin molecules may include about 12.0%, 12.1%, 12.2%, 12.3%, 12.4%, 12.5%, 12.6%, 12.7%, 12.8%, 12.9%, 13.0%, 13.1%, 13.2%, 13.3%, 13.4%, 13.5%, 13.6%, 13.7%, 13.8%, 13.9%, 14.0%, 14.1%, 14.2%, 14.3%, 14.4%, 14.5%, 14.6%, 14.7%, 14.8%, 14.9%, 15.0%, 15.1%, 15.2%, 15.3%, 15.4%, 15.5%, 15.6%, 15.7%, 15.8%, 15.9%, 16.0%, 16.1%, 16.2%, 16.3%, 16.4%, 16.5%, 16.6%, 16.7%, 16.8%, 16.9%, 17.0%, 17.1%, 17.2%, 17.3%, 17.4%, 17.5%, 17.6%, 17.7%, 17.8%, 17.9%, or about 18.0% of DS-11. In an exemplary embodiment, the area of DS-11 in a MALDI-TOF-MS spectrum is 15.10%.

In some embodiments, the mixture of isomerically-purified hydroxypropyl-β-cyclodextrin molecules may include about 7% to about 13% of DS-12. In some aspects, the mixture of isomerically-purified hydroxypropyl-β-cyclodextrin molecules may include about 7% to about 7.5% of DS-12, about 7.5% to about 8% of DS-12, about 8% to about 8.5% of DS-12, about 8.5% to about 9% of DS-12, about 9% to about 9.5% of DS-12, about 9.5% to about 10% of DS-12, about 10% to about 10.5% of DS-12, about 10.5% to about 11% of DS-12, about 11% to about 11.5% of DS-12, about 11.5% to about 12% of DS-12, about 12% to about 12.5% of DS-12, or about 12.5% to about 13% of DS-12. In some additional aspects, the mixture of isomerically-purified hydroxypropyl-β-cyclodextrin molecules may include about 7% to about 8% of DS-12, about 7% to about 8.5% of DS-12, about 7% to about 9% of DS-12, about 7% to about 9.5% of DS-12, about 7% to about 10% of DS-12, about 7% to about 10.5% of DS-12, about 7% to about 11% of DS-12, about 7% to about 11.5% of DS-12, about 7% of about 12% of DS-12, about 7% of about 12.5% of DS-12, about 7.5% to about 13% of DS-12, about 8% to about 13% of DS-12, about 8.5% to about 13% of DS-12, about 9% to about 13% of DS-12, about 9.5% to about 13% of DS-12, about 10% to about 13% of DS-12, about 10.5% to about 13% of DS-12, about 11% to about 13% of DS-12, about 11.5% to about 13% of DS-12, about 12% to about 13% of DS-12, about 7.5% to about 12.5% of DS-12, about 8% to about 12% of DS-12, about 8.5% to about 11.5% of DS-12, about 9% to about 11% of DS-12, or about 9.5% to about 10.5% of DS-12. In still further aspects, the mixture of isomerically-purified hydroxypropyl-β-cyclodextrin molecules may include about 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10.0%, 10.1%, 10.2%, 10.3%, 10.4%, 10.5%, 10.6%, 10.7%, 10.8%, 10.9%, 11.0%, 11.1%, 11.2%, 11.3%, 11.4%, 11.5%, 11.6%, 11.7%, 11.8%, 11.9%, 12.0%, 12.1%, 12.2%, 12.3%, 12.4%, 12.5%, 12.6%, 12.7%, 12.8%, 12.9%, or about 13.0% of DS-12. In an exemplary embodiment, the area of DS-12 in a MALDI-TOF-MS spectrum is 10.03%.

In some embodiments, the mixture of isomerically-purified hydroxypropyl-β-cyclodextrin molecules may include about 2% to about 8% of DS-13. In some aspects, the mixture of isomerically-purified hydroxypropyl-β-cyclodextrin molecules may include about 2% to about 2.5% of DS-13, about 2.5% to about 3% of DS-13, about 3% to about 3.5% of DS-13, about 3.5% to about 4% of DS-13, about 4% to about 4.5% of DS-13, about 4.5% to about 5% of DS-13, about 5% to about 5.5% of DS-13, about 5.5% to about 6% of DS-13, about 6% to about 6.5% of DS-13, about 6.5% to about 7% of DS-13, about 7% to about 7.5% of DS-13, or about 7.5% to about 8% of DS-13. In some additional aspects, the mixture of isomerically-purified hydroxypropyl-β-cyclodextrin molecules may include about 2% to about 3% of DS-13, about 2% to about 3.5% of DS-13, about 2% to about 4% of DS-13, about 2% to about 4.5% of DS-13, about 2% to about 5% of DS-13, about 2% to about 5.5% of DS-13, about 2% to about 6% of DS-13, about 2% to about 6.5% of DS-13, about 2% to about 7% of DS-13, about 2% to about 7.5% of DS-13, about 2.5% to about 8% of DS-13, about 3% to about 8% of DS-13, about 3.5% to about 8% of DS-13, about 4% to about 8% of DS-13, about 4.5% to about 8% of DS-13, about 5% to about 8% of DS-13, about 5.5% to about 8% of DS-13, about 6% to about 8% of DS-13, about 6.5% to about 8% of DS-13, about 7% to about 8% of DS-13, about 2.5% to about 7.5% of DS-13, about 3% to about 7% of DS-13, about 3.5% to about 6.5% of DS-13, about 4% to about 6% of DS-13, or about 4.5% to about 5.5% of DS-13. In still further aspects, the mixture of isomerically-purified hydroxypropyl-β-cyclodextrin molecules may include about 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, or about 8.0% of DS-13. In an exemplary embodiment, the area of DS-13 in a MALDI-TOF-MS spectrum is 4.50%.

In some embodiments, the mixture of isomerically-purified hydroxypropyl-β-cyclodextrin molecules may include about 0% to about 6% of DS-14. In some aspects, the mixture of isomerically-purified hydroxypropyl-β-cyclodextrin molecules may include about 0% to about 0.5% of DS-14, about 0.5% to about 1% of DS-14, about 1% to about 1.5% of DS-14, about 1.5% to about 2% of DS-14, about 2% to about 2.5% of DS-14, about 2.5% to about 3% of DS-14, about 3% to about 3.5% of DS-14, about 3.5% to about 4% of DS-14, about 4% to about 4.5% of DS-14, about 4.5% to about 5% of DS-14, about 5% to about 5.5% of DS-14, or about 5.5% to about 6% of DS-14. In some additional aspects, the mixture of isomerically-purified hydroxypropyl-β-cyclodextrin molecules may include about 0% to about 1% of DS-14, about 0% to about 1.5% of DS-14, about 0% to about 2% of DS-14, about 0% to about 2.5% of DS-14, about 0% to about 3% of DS-14, about 0% to about 3.5% of DS-14, about 0% to about 4% of DS-14, about 0% to about 4.5% of DS-14, about 0% to about 5% of DS-14, about 0% to about 5.5% of DS-14, about 0.5% to about 6% of DS-14, about 1% to about 6% of DS-14, about 1.5% to about 6% of DS-14, about 2% to about 6% of DS-14, about 2.5% to about 6% of DS-14, about 3% to about 6% of DS-14, about 3.5% to about 6% of DS-14, about 4% to about 6% of DS-14, about 4.5% to about 6% of DS-14, about 5% to about 6% of DS-14, about 0.5% to about 5.5% of DS-14, about 1% to about 5% of DS-14, about 1.5% to about 4.5% of DS-14, about 2% to about 4% of DS-14, or about 2.5% to about 3.5% of DS-14. In still further aspects, the mixture of isomerically-purified hydroxypropyl-β-cyclodextrin molecules may include about 0.0%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, or about 6.0% of DS-14. In an exemplary embodiment, the area of DS-14 in a MALDI-TOF-MS spectrum is 2.67%.

Further provided herein is a composition comprising a mixture of isomerically-purified hydroxypropyl-β-cyclodextrin molecules including DS-6, DS-7, DS-8, DS-9, DS-10, DS-11, DS-12, DS-13, and DS-14. In some embodiments, the composition includes less than 1% of DS-5. In some embodiments, the DS-9 may have the highest concentration in the composition as compared to DS-6, DS-7, DS-8, DS-10, DS-11, DS-12, DS-13, and DS-14. In other embodiments, the DS-10 may have the highest concentration in the composition as compared to DS-6, DS-7, DS-8, DS-9, DS-11, DS-12, DS-13, and DS-14.

In some embodiments, the mixture of hydroxypropyl-β-cyclodextrin molecules may include about 0% to about 6% of DS-7. In some aspects, the mixture of hydroxypropyl-β-cyclodextrin molecules may include about 0% to about 0.5% of DS-7, about 0.5% to about 1% of DS-7, about 1% to about 1.5% of DS-7, about 1.5% to about 2% of DS-7, about 2% to about 2.5% of DS-7, about 2.5% to about 3% of DS-7, about 3% to about 3.5% of DS-7, about 3.5% to about 4% of DS-7, about 4% to about 4.5% of DS-7, about 4.5% to about 5% of DS-7, about 5% to about 5.5% of DS-7, or about 5.5% to about 6% of DS-7. In some additional aspects, the mixture of hydroxypropyl-β-cyclodextrin molecules may include about 0% to about 1% of DS-7, about 0% to about 1.5% of DS-7, about 0% to about 2% of DS-7, about 0% to about 2.5% of DS-7, about 0% to about 3% of DS-7, about 0% to about 3.5% of DS-7, about 0% to about 4% of DS-7, about 0% to about 4.5% of DS-7, about 0% to about 5% of DS-7, about 0% to about 5.5% of DS-7, about 0.5% to about 6% of DS-7, about 1% to about 6% of DS-7, about 1.5% to about 6% of DS-7, about 2% to about 6% of DS-7, about 2.5% to about 6% of DS-7, about 3% to about 6% of DS-7, about 3.5% to about 6% of DS-7, about 4% to about 6% of DS-7, about 4.5% to about 6% of DS-7, about 5% to about 6% of DS-7, about 0.5% to about 5.5% of DS-7, about 1% to about 5% of DS-7, about 1.5% to about 4.5% of DS-7, about 2% to about 4% of DS-7, or about 2.5% to about 3.5% of DS-7. In still further aspects, the mixture of hydroxypropyl-β-cyclodextrin molecules may include about 0.0%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, or about 6.0% of DS-7. In an exemplary embodiment, the area of DS-7 in a MALDI-TOF-MS spectrum is 3.16%.

In some embodiments, the mixture of isomerically-purified hydroxypropyl-β-cyclodextrin molecules may include about 13% to about 19% of DS-8. In some aspects, the mixture of isomerically-purified hydroxypropyl-β-cyclodextrin molecules may include about 13% to about 13.5% of DS-8, about 13.5% to about 14% of DS-8, about 14% to about 14.5% of DS-8, about 14.5% to about 15% of DS-8, about 15% to about 15.5% of DS-8, about 15.5% to about 16% of DS-8, about 16% to about 16.5% of DS-8, about 16.5% to about 17% of DS-8, about 17% to about 17.5% of DS-8, about 17.5% to about 18% of DS-8, about 18% to about 18.5% of DS-8, or about 18.5% to about 19% of DS-8. In some additional aspects, the mixture of isomerically-purified β-cyclodextrin may include about 13% to about 14% of DS-8, about 13% to about 14.5% of DS-8, about 13% to about 15% of DS-8, about 13% to about 15.5% of DS-8, about 13% to about 16% of DS-8, about 13% to about 16.5% of DS-8, about 13% to about 17% of DS-8, about 13% to about 17.5% of DS-8, about 13% to about 18% of DS-8, about 13% to about 18.5% of DS-8, about 13.5% to about 19% of DS-8, about 14% to about 19% of DS-8, about 14.5% to about 19% of DS-8, about 15% to about 19% of DS-8, about 15.5% to about 19% of DS-8, about 16% to about 19% of DS-8, about 16.5% to about 19% of DS-8, about 17% to about 19% of DS-8, about 17.5% to about 19% of DS-8, about 18% to about 19% of DS-8, about 13.5% to about 18.5% of DS-8, about 14% to about 18% of DS-8, about 14.5% to about 17.5% of DS-8, about 15% to about 17% of DS-8, or about 15.5% to about 16.5% of DS-8. In still further aspects, the mixture of isomerically-purified β-cyclodextrin molecules may include about 13.0%, 13.1%, 13.2%, 13.3%, 13.4%, 13.5%, 13.6%, 13.7%, 13.8%, 13.9%, 14.0%, 14.1%, 14.2%, 14.3%, 14.4%, 14.5%, 14.6%, 14.7%, 14.8%, 14.9%, 15.0%, 15.1%, 15.2%, 15.3%, 15.4%, 15.5%, 15.6%, 15.7%, 15.8%, 15.9%, 16.0%, 16.1%, 16.2%, 16.3%, 16.4%, 16.5%, 16.6%, 16.7%, 16.8%, 16.9%, 17.0%, 17.1%, 17.2%, 17.3%, 17.4%, 17.5%, 17.6%, 17.7%, 17.8%, 17.9%, 18.0%, 18.1%, 18.2%, 18.3%, 18.4%, 18.5%, 18.6%, 18.7%, 18.8%, 18.9%, or about 19.0% of DS-8. In an exemplary embodiment, the area of DS-8 in a MALDI-TOF-MS spectrum is 16.44%.

In some embodiments, the mixture of isomerically-purified hydroxypropyl-β-cyclodextrin molecules may include about 22% to about 28% of DS-9. In some aspects, the mixture of isomerically-purified β-cyclodextrin molecules includes about 22% to about 22.5% of DS-9, about 22.5% to about 23% of DS-9, about 23% to about 23.5% of DS-9, about 23.5% to about 24% of DS-9, about 24% to about 24.5% to about 25% of DS-9, about 25% to about 25.5% of DS-9, about 25.5% to about 26% of DS-9, about 26% to about 26.5% of DS-9, about 26.5% to about 27% of DS-9, about 27% to about 27.5% of DS-9, or about 27.5% to about 28% of DS-9. In some additional aspects, the mixture of isomerically-purified β-cyclodextrin may include about 22% to about 23% of DS-9, about 22% to about 23.5% of DS-9, about 22% to about 24% of DS-9, about 22% to about 24.5% of DS-9, about 22% to about 25% of DS-9, about 22% to about 25.5% of DS-9, about 22% to about 26% of DS-9, about 22% to about 26.5% of DS-9, about 22% to about 27% of DS-9, about 22% to about 27.5% of DS-9, about 22.5% to about 28% of DS-9, about 23% to about 28% of DS-9, about 23.5% to about 28% of DS-9, about 24% to about 28% of DS-9, about 24.5% to about 28% of DS-9, about 25% to about 28% of DS-9, about 25.5% to about 28% of DS-9, about 26% to about 28% of DS-9, about 26.5% to about 28% of DS-9, about 27% to about 28% of DS-9, about 22.5% to about 27.5% of DS-9, about 23% to about 27% of DS-9, about 23.5% to about 26.5% of DS-9, about 24% to about 26% of DS-9, or about 24.5% to about 25.5% of DS-9. In still further aspects, the mixture of isomerically-purified β-cyclodextrin molecules may include about 22.0%, 22.1%, 22.2%, 22.3%, 22.4%, 22.5%, 22.6%, 22.7%, 22.8%, 22.9%, 23.0%, 23.1%, 23.2%, 23.3%, 23.4%, 23.5%, 23.6%, 23.7%, 23.8%, 23.9%, 24.0%, 24.1%, 24.2%, 24.3%, 24.4%, 24.5%, 24.6%, 24.7%, 24.8%, 24.9%, 25.0%, 25.1%, 25.2%, 25.3%, 25.4%, 25.5%, 25.6%, 25.7%, 25.8%, 25.9%, 26.0%, 26.1%, 26.2%, 26.3%, 26.4%, 26.5%, 26.6%, 26.7%, 26.8%, 26.9%, 27.0%, 27.1%, 27.2%, 27.3%, 27.4%, 27.5%, 27.6%, 27.7%, 27.8%, 27.9%, or about 28.0% of DS-9. In an exemplary embodiment, the area of DS-9 in a MALDI-TOF-MS spectrum is 25.24%.

In some embodiments, the mixture of isomerically-purified hydroxypropyl-β-cyclodextrin molecules may include about 23% to about 29% of DS-10. In some aspects, the mixture of isomerically-purified hydroxypropyl-β-cyclodextrin molecules may include about 23% to about 23.5% of DS-10, about 23.5% to about 24% of DS-10, about 24% to about 24.5% of DS-10, about 24.5% to about 25% of DS-10, about 25% to about 25.5% of DS-10, about 25.5% to about 26% of DS-10, about 26% to about 26.5% of DS-10, about 26.5% to about 27% of DS-10, about 27% to about 27.5% of DS-10, about 27.5% to about 28% of DS-10, about 28% to about 28.5% of DS-10, or about 28.5% to about 29% of DS-10. In some additional aspects, the mixture of isomerically-purified hydroxypropyl-β-cyclodextrin molecules may include about 23% to about 24% of DS-10, about 23% to about 24.5% of DS-10, about 23% to about 25% of DS-10, about 23% to about 25.5% of DS-10, about 23% to about 26% of DS-10, about 23% to about 26.5% of DS-10, about 23% to about 27% of DS-10, about 23% to about 27.5% of DS-10, about 23% to about 28% of DS-10, about 23% to about 28.5% of DS-10, about 23.5% to about 29% of DS-10, about 24% to about 29% of DS-10, about 24.5% to about 29% of DS-10, about 25% to about 29% of DS-10, about 25.5% to about 29% of DS-10, about 26% to about 29% of DS-10, about 26.5% to about 29% of DS-10, about 27% to about 29% of DS-10, about 27.5% to about 29% of DS-10, about 28% to about 29% of DS-10, about 23.5% to about 28.5% of DS-10, about 24% to about 28% of DS-10, about 24.5% to about 27.5% of DS-10, about 25% to about 27% of DS-10, or about 25.5% to about 26.5% of DS-10. In still further aspects, the mixture of isomerically-purified hydroxypropyl-β-cyclodextrin molecules may include about 23.0%, 23.1%, 23.2%, 23.3%, 23.4%, 23.5%, 23.6%, 23.7%, 23.8%, 23.9%, 24.0%, 24.1%, 24.2%, 24.3%, 24.4%, 24.5%, 24.6%, 24.7%, 24.8%, 24.9%, 25.0%, 25.1%, 25.2%, 25.3%, 25.4%, 25.5%, 25.6%, 25.7%, 25.8%, 25.9%, 26.0%, 26.1%, 26.2%, 26.3%, 26.4%, 26.5%, 26.6%, 26.7%, 26.8%, 26.9%, 27.0%, 27.1%, 27.2%, 27.3%, 27.4%, 27.5%, 27.6%, 27.7%, 27.8%, 27.9%, 28.0%, 28.1%, 28.2%, 28.3%, 28.4%, 28.5%, 28.6%, 28.7%, 28.8%, 28.9%, or about 29.0% of DS-10. In an exemplary embodiment, the area of DS-10 in a MALDI-TOF-MS spectrum is 25.52%.

In some embodiments, the mixture of isomerically-purified hydroxypropyl-β-cyclodextrin molecules may include about 12% to about 18% of DS-11. In some aspects, the mixture of isomerically-purified hydroxypropyl-β-cyclodextrin molecules may include about 12% to about 12.5% of DS-11, about 12.5% to about 13% of DS-11, about 13% to about 13.5% of DS-11, about 13.5% to about 14% of DS-11, about 14% to about 14.5% of DS-11, about 14.5% to about 15% DS-11, about 15% to about 15.5% of DS-11, about 15.5% to about 16% of DS-11, about 16% to about 16.5% of DS-11, about 16.5% to about 17% of DS-11, about 17% to about 17.5% of DS-11, or about 17.5% to about 18% of DS-11. In some additional aspects, the mixture of isomerically-purified hydroxypropyl-β-cyclodextrin molecules may include about 12% to about 13% of DS-11, about 12% to about 13.5% of DS-11, about 12% to about 14% of DS-11, about 12% to about 14.5% of DS-11, about 12% to about 15% of DS-11, about 12% to about 15.5% of DS-11, about 12% to about 16% of DS-11, about 12% to about 16.5% of DS-11, about 12% to about 17% of DS-11, about 12% to about 17.5% of DS-11, about 12.5% to about 18% of DS-11, about 13% to about 18% of DS-11, about 13.5% to about 18% of DS-11, about 14% to about 18% of DS-11, about 14.5% to about 18% of DS-11, about 15% to about 18% of DS-11, about 15.5% to about 18% of DS-11, about 16% to about 18% of DS-11, about 16.5% to about 18% of DS-11, about 17% to about 18% of DS-11, about 12.5% to about 17.5% of DS-11, about 13% to about 17% of DS-11, about 13.5% to about 16.5% of DS-11, about 14% to about 16% of DS-11, or about 14.5% to about 15.5% of DS-11. In still further aspects, the mixture of isomerically purified hydroxypropyl-β-cyclodextrin molecules may include about 12.0%, 12.1%, 12.2%, 12.3%, 12.4%, 12.5%, 12.6%, 12.7%, 12.8%, 12.9%, 13.0%, 13.1%, 13.2%, 13.3%, 13.4%, 13.5%, 13.6%, 13.7%, 13.8%, 13.9%, 14.0%, 14.1%, 14.2%, 14.3%, 14.4%, 14.5%, 14.6%, 14.7%, 14.8%, 14.9%, 15.0%, 15.1%, 15.2%, 15.3%, 15.4%, 15.5%, 15.6%, 15.7%, 15.8%, 15.9%, 16.0%, 16.1%, 16.2%, 16.3%, 16.4%, 16.5%, 16.6%, 16.7%, 16.8%, 16.9%, 17.0%, 17.1%, 17.2%, 17.3%, 17.4%, 17.5%, 17.6%, 17.7%, 17.8%, 17.9%, or about 18.0% of DS-11. In an exemplary embodiment, the area of DS-11 in a MALDI-TOF-MS spectrum is 15.10%.

In some embodiments, the mixture of isomerically-purified hydroxypropyl-β-cyclodextrin molecules may include about 7% to about 13% of DS-12. In some aspects, the mixture of isomerically-purified hydroxypropyl-β-cyclodextrin molecules may include about 7% to about 7.5% of DS-12, about 7.5% to about 8% of DS-12, about 8% to about 8.5% of DS-12, about 8.5% to about 9% of DS-12, about 9% to about 9.5% of DS-12, about 9.5% to about 10% of DS-12, about 10% to about 10.5% of DS-12, about 10.5% to about 11% of DS-12, about 11% to about 11.5% of DS-12, about 11.5% to about 12% of DS-12, about 12% to about 12.5% of DS-12, or about 12.5% to about 13% of DS-12. In some additional aspects, the mixture of isomerically-purified hydroxypropyl-β-cyclodextrin molecules may include about 7% to about 8% of DS-12, about 7% to about 8.5% of DS-12, about 7% to about 9% of DS-12, about 7% to about 9.5% of DS-12, about 7% to about 10% of DS-12, about 7% to about 10.5% of DS-12, about 7% to about 11% of DS-12, about 7% to about 11.5% of DS-12, about 7% of about 12% of DS-12, about 7% of about 12.5% of DS-12, about 7.5% to about 13% of DS-12, about 8% to about 13% of DS-12, about 8.5% to about 13% of DS-12, about 9% to about 13% of DS-12, about 9.5% to about 13% of DS-12, about 10% to about 13% of DS-12, about 10.5% to about 13% of DS-12, about 11% to about 13% of DS-12, about 11.5% to about 13% of DS-12, about 12% to about 13% of DS-12, about 7.5% to about 12.5% of DS-12, about 8% to about 12% of DS-12, about 8.5% to about 11.5% of DS-12, about 9% to about 11% of DS-12, or about 9.5% to about 10.5% of DS-12. In still further aspects, the mixture of isomerically-purified hydroxypropyl-β-cyclodextrin molecules may include about 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10.0%, 10.1%, 10.2%, 10.3%, 10.4%, 10.5%, 10.6%, 10.7%, 10.8%, 10.9%, 11.0%, 11.1%, 11.2%, 11.3%, 11.4%, 11.5%, 11.6%, 11.7%, 11.8%, 11.9%, 12.0%, 12.1%, 12.2%, 12.3%, 12.4%, 12.5%, 12.6%, 12.7%, 12.8%, 12.9%, or about 13.0% of DS-12. In an exemplary embodiment, the area of DS-12 in a MALDI-TOF-MS spectrum is 10.03%.

In some embodiments, the mixture of isomerically-purified hydroxypropyl-β-cyclodextrin molecules may include about 2% to about 8% of DS-13. In some aspects, the mixture of isomerically-purified hydroxypropyl-β-cyclodextrin molecules may include about 2% to about 2.5% of DS-13, about 2.5% to about 3% of DS-13, about 3% to about 3.5% of DS-13, about 3.5% to about 4% of DS-13, about 4% to about 4.5% of DS-13, about 4.5% to about 5% of DS-13, about 5% to about 5.5% of DS-13, about 5.5% to about 6% of DS-13, about 6% to about 6.5% of DS-13, about 6.5% to about 7% of DS-13, about 7% to about 7.5% of DS-13, or about 7.5% to about 8% of DS-13. In some additional aspects, the mixture of isomerically-purified hydroxypropyl-β-cyclodextrin molecules may include about 2% to about 3% of DS-13, about 2% to about 3.5% of DS-13, about 2% to about 4% of DS-13, about 2% to about 4.5% of DS-13, about 2% to about 5% of DS-13, about 2% to about 5.5% of DS-13, about 2% to about 6% of DS-13, about 2% to about 6.5% of DS-13, about 2% to about 7% of DS-13, about 2% to about 7.5% of DS-13, about 2.5% to about 8% of DS-13, about 3% to about 8% of DS-13, about 3.5% to about 8% of DS-13, about 4% to about 8% of DS-13, about 4.5% to about 8% of DS-13, about 5% to about 8% of DS-13, about 5.5% to about 8% of DS-13, about 6% to about 8% of DS-13, about 6.5% to about 8% of DS-13, about 7% to about 8% of DS-13, about 2.5% to about 7.5% of DS-13, about 3% to about 7% of DS-13, about 3.5% to about 6.5% of DS-13, about 4% to about 6% of DS-13, or about 4.5% to about 5.5% of DS-13. In still further aspects, the mixture of isomerically-purified hydroxypropyl-β-cyclodextrin molecules may include about 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, or about 8.0% of DS-13. In an exemplary embodiment, the area of DS-13 in a MALDI-TOF-MS spectrum is 4.50%.

In some embodiments, the mixture of isomerically-purified hydroxypropyl-β-cyclodextrin molecules may include about 0% to about 6% of DS-14. In some aspects, the mixture of isomerically-purified hydroxypropyl-β-cyclodextrin molecules may include about 0% to about 0.5% of DS-14, about 0.5% to about 1% of DS-14, about 1% to about 1.5% of DS-14, about 1.5% to about 2% of DS-14, about 2% to about 2.5% of DS-14, about 2.5% to about 3% of DS-14, about 3% to about 3.5% of DS-14, about 3.5% to about 4% of DS-14, about 4% to about 4.5% of DS-14, about 4.5% to about 5% of DS-14, about 5% to about 5.5% of DS-14, or about 5.5% to about 6% of DS-14. In some additional aspects, the mixture of isomerically-purified hydroxypropyl-β-cyclodextrin molecules may include about 0% to about 1% of DS-14, about 0% to about 1.5% of DS-14, about 0% to about 2% of DS-14, about 0% to about 2.5% of DS-14, about 0% to about 3% of DS-14, about 0% to about 3.5% of DS-14, about 0% to about 4% of DS-14, about 0% to about 4.5% of DS-14, about 0% to about 5% of DS-14, about 0% to about 5.5% of DS-14, about 0.5% to about 6% of DS-14, about 1% to about 6% of DS-14, about 1.5% to about 6% of DS-14, about 2% to about 6% of DS-14, about 2.5% to about 6% of DS-14, about 3% to about 6% of DS-14, about 3.5% to about 6% of DS-14, about 4% to about 6% of DS-14, about 4.5% to about 6% of DS-14, about 5% to about 6% of DS-14, about 0.5% to about 5.5% of DS-14, about 1% to about 5% of DS-14, about 1.5% to about 4.5% of DS-14, about 2% to about 4% of DS-14, or about 2.5% to about 3.5% of DS-14. In still further aspects, the mixture of isomerically-purified hydroxypropyl-β-cyclodextrin molecules may include about 0.0%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, or about 6.0% of DS-14. In an exemplary embodiment, the area of DS-14 in a MALDI-TOF-MS spectrum is 2.67%.

In an exemplary embodiment, the mixture of isomerically-purified hydroxypropyl-β-cyclodextrin molecules may include about 0% to about 6% of DS-7, about 13% to about 19% of DS-8, about 22% to about 28% of DS-9, about 23% to about 29% of DS-10, about 12% to about 18% of DS-11, about 7% to about 13% of DS-12, about 2% to about 8% of DS-13, and about 0% to about 6% of DS-14

In another exemplary embodiment, the mixture of isomerically-purified hydroxypropyl-β-cyclodextrin molecules may include DS-7, DS-8, DS-9, DS-10, DS-11, DS-12, DS-13, and DS-14 wherein the mixture includes less than 1% of DS-6, DS-5, DS-4, DS-3, DS-2, and DS-1. In another exemplary embodiment, the mixture of isomerically-purified hydroxypropyl-β-cyclodextrin molecules may include DS-7, DS-8, DS-9, DS-10, DS-11, DS-12, DS-13, and DS-14 wherein the mixture includes less than 1% of DS-6, DS-5, DS-4, DS-3, DS-2, and/or DS-1.

The inventors surprisingly found that the fourth fraction had a lower average degree of substitution as compared to the third fraction. In some embodiments, the average degree of substitution of the mixture of isomerically-purified hydroxypropyl-β-cyclodextrin molecules may be about 7.5 to about 8.5. In some aspects, the average degree of substitution of the mixture of isomerically-purified hydroxypropyl-β-cyclodextrin molecules may be 7.5, 7.6, 7.7, 7.8, 7.9, 8.0, 8.1, 8.2, 8.3, 8.4, or about 8.5. In an exemplary embodiment, the average degree of substitution of the mixture of hydroxypropyl-β-cyclodextrin molecules may be about 8.08.

Figure 21:
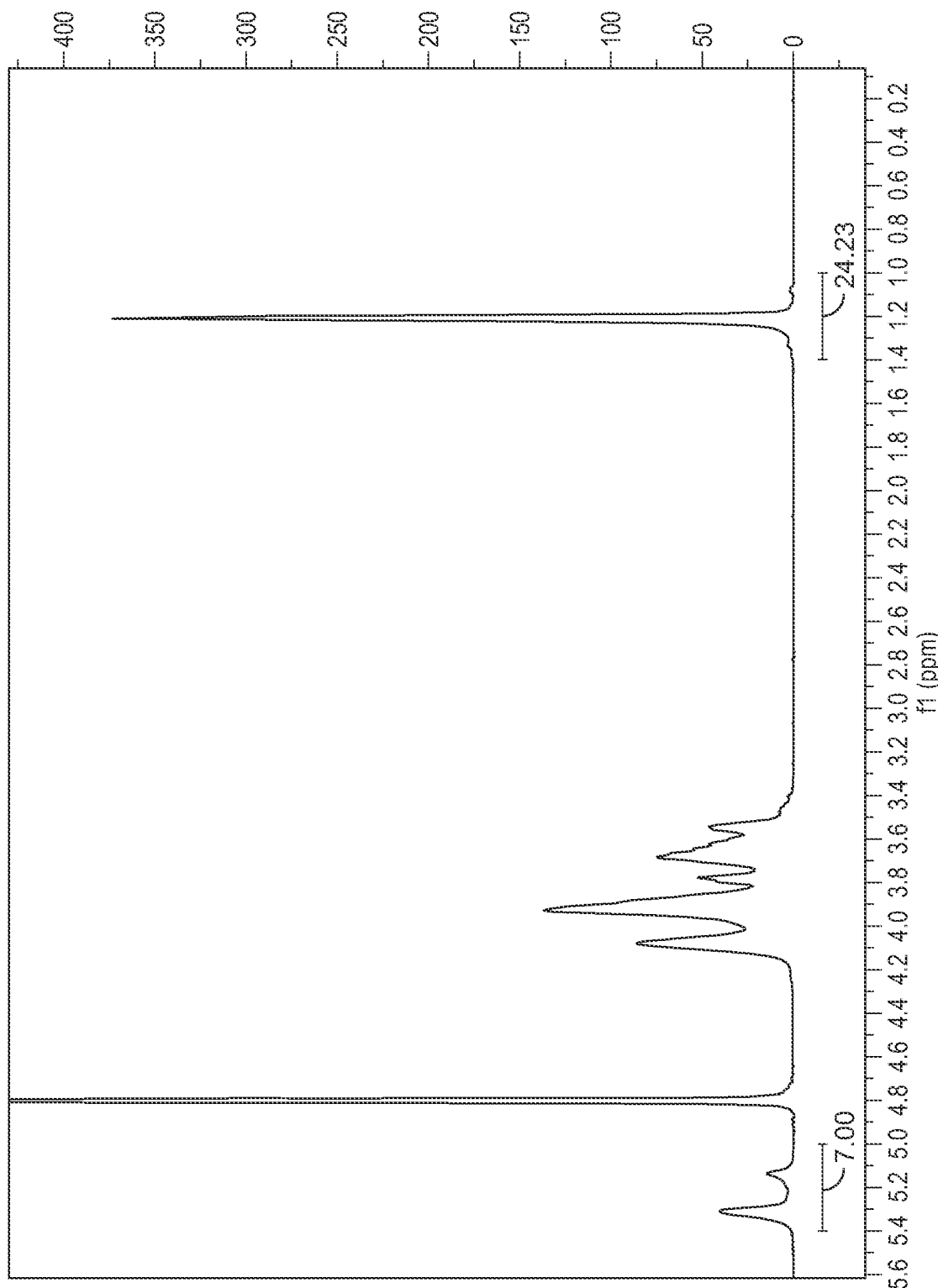
FIG. 21 is a H NMR spectrum of the fourth HDS Fraction of a mixture of hydroxypropyl-β-cyclodextrins of the present disclosure.
Figure 22:
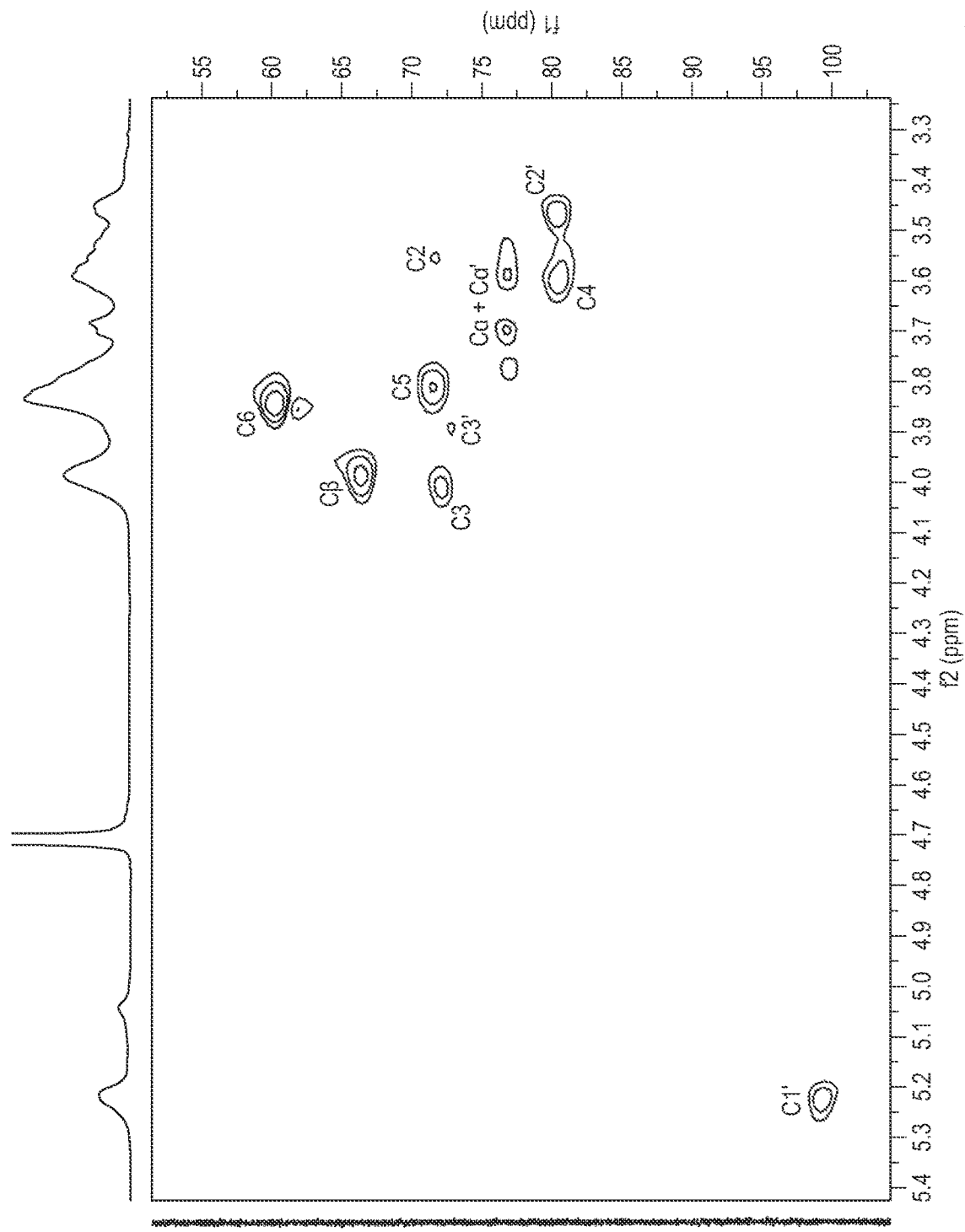
FIG. 22 is a DEPT-ed HSQC spectrum of the fourth HDS fraction of a mixture of hydroxypropyl-β-cyclodextrin of the present disclosure.

The position of the substitutions in the mixture isomerically-purified hydroxypropyl-β-cyclodextrin molecules of may be determined using methods known to those having skill in the art. In some embodiments the composition may be characterized by $^1$H-NMR. In some aspects, $^1$H-NMR may be used to determine the degree of substitution of the composition. An exemplary $^1$H-NMR spectrum is provided in FIG. 21. In some embodiments, the composition may be characterized by DEPT-ed HSQC. An exemplary DEPT-ed HSQC spectrum is provided in FIG. 22.

In some embodiments, about 22% to about 28% of the hydroxypropyl substitutions in the hydroxypropyl-β-cyclodextrin molecules may be located at the 3-O-position. In some aspects, the percentage of substitutions in the mixture of the hydroxypropyl-β-cyclodextrin molecules at the 3-O— position may be about 22% to about 23%, about 23% to about 24%, about 24% to about 25%, about 25% to about 26%, about 26% to about 27%, or about 27% to about 28%. In some additional aspects, the percentage of substitutions in the mixture of hydroxypropyl-β-cyclodextrin molecules at the 3-O— position may be about 22% to about 24%, about 22% to about 25%, about 22% to about 26%, about 22% to about 27%, about 23% to about 28%, about 24% to about 28%, about 25% to about 28%, about 26% to about 28%, about 23% to about 27%, or about 24% to about 26%. In an exemplary embodiment, the percentage of substitutions in the mixture of hydroxypropyl-β-cyclodextrin molecules at the 3-O— position is about 24.57%.

In some embodiments, about 72% to about 78% of the hydroxypropyl substitutions in the hydroxypropyl-β-cyclodextrin molecules are located at the 2-O-position. In some aspects, the percentage of substitutions in the mixture of hydroxypropyl-β-cyclodextrin molecules at the 2-O— position is about 72% to about 73%, about 73% to about 74%, about 74% to about 75%, about 75% to about 76%, about 76% to about 77%, or about 77% to about 78%. In some additional aspects, the percentage of substitutions in the mixture of hydroxypropyl-β-cyclodextrin molecules at the 2-O— position is about 72% to about 74%, about 72% to about 75%, about 72% to about 76%, about 72% to about 77%, about 73% to about 78%, about 74% to about 78%, about 75% to about 78%, about 76% to about 78%, about 73% to about 77%, or about 74% to about 76%. In an exemplary embodiment, the percentage of substitutions in the mixture of hydroxypropyl-β-cyclodextrin molecules at the 2-O— position is about 75.43%.

In some embodiments, the percentage of substitutions in the mixture of hydroxypropyl-β-cyclodextrin molecules at the 6-O— position is about 0%.

Figure 23:
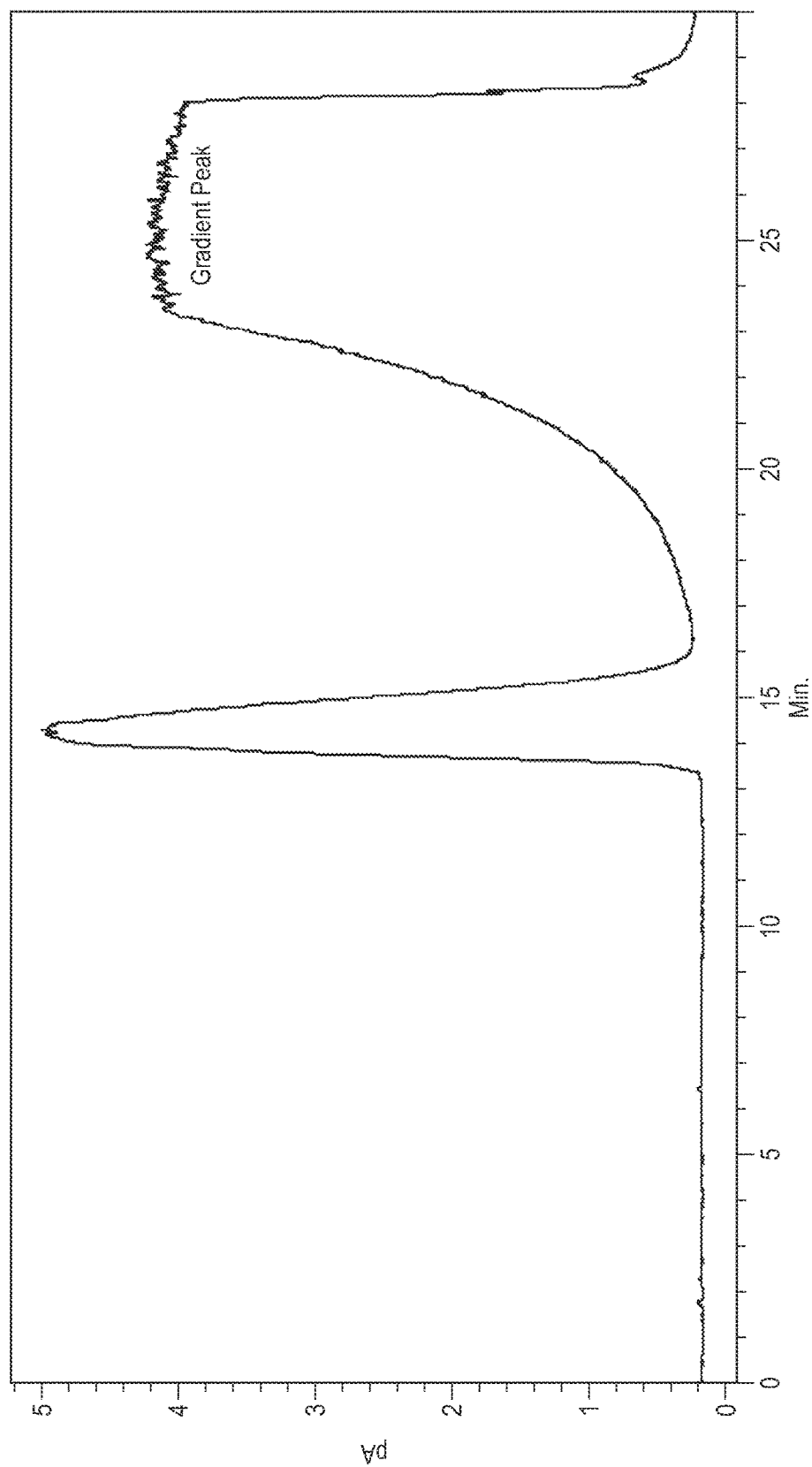
FIG. 23 is an HPLC-CAD chromatogram of the fourth HDS fraction of a mixture of hydroxypropyl-β-cyclodextrins of the present disclosure.

In some embodiments, the composition may have an HPLC-CAD chromatogram of FIG. 23. In some aspects, the mean retention time of the composition may be about 13.5 minutes to about 15.5 minutes as measured by HPLC-CAD. In some additional aspects, the mean retention time of the composition may be about 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5. In an exemplary embodiment, the mean retention time is about 14.3 minutes.

In some embodiments, the composition may have a −ESI-MS spectrum with peaks at about 740 m/z, about 770 m/z, about 798 m/z, about 828 m/z, and about 857 m/z. In some embodiments, the composition may have a +ESI-MS spectrum with peaks at about 803 m/z, about 831 m/z, about 861 m/z, about 889 m/z, and at about 919 m/z. In an exemplary embodiment, the composition has the ESI-MS spectra shown in FIG. 24.

The hydroxypropyl-β-cyclodextrin percent may be based upon an area percentage from a MALDI-TOF-MS spectrum. In some embodiments, the composition may have a MALDI-TOF-MS spectrum with peaks at about 1559 m/z, about 1618 m/z, about 1678 m/z, about 1737 m/z, about 1796 m/z, about 1857 m/z, and at about 1916 m/z. In an exemplary embodiment, the composition has the MALDI-TOF-MS spectrum shown in FIG. 25. In an exemplary embodiment, the composition has a MALDI-TOF-MS spectrum wherein the area of DS-7 is 3.16%, the area of DS-8 is 16.44%, the area of DS-9 is 25.24%, the area of DS-10 is 25.52%, the area of DS-11 is 15.10%, the area of DS-12 is 10.03%, the area of DS-13 is 4.50%, and the area of DS-14 is about 2.67%.

In some embodiments, the composition may have a true density of about 1.095 g/cm$^3$ to about 1.100 g/cm$^3$. In some aspects, the composition may have a true density of about 1.095 g/cm$^3$ to about 1.096 g/cm$^3$, about 1.096 g/cm$^3$ to about 1.097 g/cm$^3$, about 1.097 g/cm$^3$ to about 1.098 g/cm$^3$, about 1.098 g/cm$^3$ to about 1.099 g/cm$^3$, about 1.099 g/cm$^3$ to about 1.100 g/cm$^3$, about 1.095 g/cm$^3$ to about 1.097 g/cm$^3$, about 1.095 g/cm$^3$ to about 1.098 g/cm$^3$, about 1.095 g/cm$^3$ to about 1.099 g/cm$^3$, about 1.096 g/cm$^3$ to about 1.100 g/cm$^3$, about 1.097 g/cm$^3$ to about 1.100 g/cm$^3$, about 1.098 g/cm$^3$ to about 1.100 g/cm$^3$, about 1.096 g/cm$^3$ to about 1.098 g/cm$^3$, or about 1.096 g/cm$^3$ to about 1.099 g/cm$^3$. In some additional aspects, the composition may have a true density of about 1.095 g/cm$^3$, 1.096 g/cm$^3$, 1.097 g/cm$^3$, 1.098 g/cm$^3$, 1.099 g/cm$^3$, or about 1.100 g/cm$^3$. In an exemplary embodiment, the composition has a true density of about 1.096 g/cm$^3$ to about 1.098 g/cm$^3$.

In some embodiments, the composition may have an osmolality of about 600 mOs/kg to about 750 mOs/kg. In some aspects, the composition may have an osmolality of about 600 mOs/kg to about 625 mOs/kg, about 625 mOs/kg to about 650 mOs/kg, about 650 mOs/kg to about 675 mOs/kg, about 675 mOs/kg to about 700 mOs/kg, about 700 mOs/kg to about 725 mOs/kg, or about 725 mOs/kg to about 750 mOs/kg. In some additional aspects, the composition may have an osmolality of about 600 mOs/kg to about 650 mOs/kg, about 600 mOs/kg to about 675 mOs/kg, about 600 mOs/kg to about 700 mOs/kg, about 600 mOs/kg to about 725 mOs/kg, about 625 mOs/kg to about 750 mOs/kg, about 650 mOs/kg to about 750 mOs/kg, about 675 mOs/kg to about 750 mOs/kg, about 700 mOs/kg to about 750 mOs/kg, about 625 mOs/kg to about 725 mOs/kg, or about 650 mOs/kg to about 700 mOs/kg. In still further embodiments, the composition may have an osmolality of about 600 mOs/kg, 610 mOs/kg, 620 mOs/kg, 630 mOs/kg, 640 mOs/kg, 650 mOs/kg, 660 mOs/kg, 670 mOs/kg, 680 mOs/kg, 690 mOs/kg, 700 mOs/kg, 710 mOs/kg, 720 mOs/kg, 730 mOs/kg, 740 mOs/kg, or about 750 mOs/kg. In an exemplary embodiment, the composition has an osmolality of about 635 mOs/kg to about 695 mOs/kg.

In some embodiments, the composition may have a conductivity between about 0 and about 8 μS/cm. In some aspects, the composition may have a conductivity between about 0 μS/cm and about 1 μS/cm, about 1 μS/cm and about 2 μS/cm, about 3 μS/cm and about 4 μS/cm, about 4 μS/cm and about 5 μS/cm, about 5 μS/cm and about 6 μS/cm, about 6 μS/cm and about 7 μS/cm, or between about 7 μS/cm and about 8 μS/cm. In some additional embodiments, the composition may have a conductivity between about 0 μS/cm and about 1.5 μS/cm, about 0 μS/cm and about 2 μS/cm, about 0 μS/cm and about 2.5 μS/cm, about 0 μS/cm and about 3 μS/cm, about 0 and about 3.5 μS/cm, about 0 μS/cm and about 4 μS/cm, about 0 and about 4.5 μS/cm, about 0 μS/cm and about 5 μS/cm, about 0 and about 5.5 μS/cm, about 0 μS/cm and about 6 μS/cm, about 0 and about 6.5, about 0 μS/cm and about 7 μS/cm, about 0 and about 7.5, about 1 μS/cm and about 8 μS/cm, about 1.5 μS/cm and about 8 μS/cm, about 2 μS/cm and about 8 μS/cm, about 2.5 μS/cm and about 8 μS/cm, about 3 μS/cm and about 8 μS/cm, about 3.5 μS/cm and about 8 μS/cm, about 4 μS/cm and about 8 μS/cm, about 4.5 μS/cm and about 8 μS/cm, about 5 μS/cm and about 8 μS/cm, about 5.5 μS/cm and about 8 μS/cm, about 6 μS/cm and about 8 μS/cm, about 6.5 μS/cm and about 8 μS/cm, about 1 μS/cm and about 7 μS/cm, about 2 μS/cm and about 6 μS/cm, or about 3 μS/cm and about 5 μS/cm. In still further aspects, the composition may have a conductivity of about 0.5 μS/cm, 1.0 μS/cm, 1.5 μS/cm, 2.0 μS/cm, 2.5 μS/cm, 3.0 μS/cm, 3.5 μS/cm, 4.0 μS/cm, 4.5 μS/cm, 5.0 μS/cm, 5.5 μS/cm, 6.0 μS/cm, 6.5 μS/cm, 7.0 μS/cm, 7.5 μS/cm, or about 8.0 μS/cm.

In some embodiments, the composition may have a pH of about 4.0 to about 8.0; for example, the composition may have a pH of about 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, or about 8.0. The composition may have a pH in a range or sub-range comprising any of the afore-mentioned numbers, including but not limited to a pH about 4.0 to about 4.5, about 4.5 to about 5.0, about 5.0 to about 5.5, about 5.5 to about 6.0, about 6.0 to about 6.5, about 6.5 to about 7.0, about 7.0 to about 7.5, or about 7.5 to about 8.0. In some embodiments, the composition may further comprise a pH adjusting agent, such as hydrochloric acid or sodium hydroxide, to adjust the pH to a desired level. In some embodiments, the composition may further comprise a buffer. In some embodiments, the buffer may include monobasic sodium phosphate and dibasic sodium phosphate.

In some embodiments, the composition may have a viscosity measured in centipoises (cP) at 20° C. For example, the composition may have a viscosity of about 1.5 cP to about 3.0 cP at 20° C. In some embodiments, the composition may have a viscosity of about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or about 10.0 cP at 20° C. In other embodiments, the composition may have a viscosity of about 3.0 cP to about 5.0 cP, about 5.0 cP to about 10.0 cP, about 10 to about 15 cP, about 15 to about 20 cP, about 20 cP to about 25 cP, about 25 cP to about 50 cP, about 50 cP to about 80 cP, about 80 cP to about 150 cP, about 150 cP to about 250 cP, about 250 cP to about 500 cP, about 500 cP to about 1,000 cP, about 1,000 cP to about 2,000 cP, about 2,000 cP to about 3,000 cP, about 3,000 cP to about 5,000 cP, or about 5,000 cP to about 10,000 cP at 20° C.

The composition may be substantially free of impurities. Impurities include particles having a diameter of greater than or equal to 25 microns, particles having a diameter of greater than or equal to 10 microns, chloride, propylene glycol, propylene oxide, and other unspecified impurities. In some embodiments, the composition may include less than or equal to about 0.05% impurities; for example, the composition may include less than or equal to about 0.05%, 0.04%, 0.03%, 0.02%, or less than or equal to about 0.01% impurities.

In some embodiments, the composition may further comprise a container and non-visible particulate matter. In some embodiments, the composition may be provided in a container. In some embodiments, the composition may further comprise non-visible particulate matter.

In some embodiments, the composition may include less than 600 particles per container having a diameter of greater than or equal to 25 microns. In some aspects, the composition may include less than 500, less than 400, less than 300, less than 200, or less than 100 particles per container having a diameter greater than or equal to 25 microns.

In some embodiments, the composition may include less than 6000 particles per container having a diameter of greater than or equal to 10 microns. In some aspects, the composition may include less than 5000, less than 4000, less than 3000, less than 2000, less than 1000, less than 500, or less than 100 particles per container having a diameter greater than or equal to 10 microns. In another aspect, the composition may include less than 5000, less than 4000, less than 3000, less than 2000, less than 1000, less than 500, or less than 100 particles per container having a diameter greater than or equal to 10 microns, wherein the container is ≤100 mL. In another aspect, the composition may include less than 5000, less than 4000, less than 3000, less than 2000, less than 1000, less than 500, less than 100, less than 50, less than 25, less than 10, less than 5, or less than 3 particles per container having a diameter greater than or equal to 10 microns, wherein the container is >100 mL.

In some embodiments, the composition may include no more than 10 ppb of propylene glycol. In some aspects, the composition may include no more than 9 ppb, 8 ppb, 7 ppb, 6 ppb, 5 ppb, 4 ppb, 3 ppb, 2 ppb, or no more than 1 ppb propylene glycol. In some aspects, the amount of propylene glycol in the composition may be determined by HPLC. In some additional aspects, the amount of propylene glycol in the composition may be determined by gas chromatography. In still further aspects, the amount of propylene glycol in the composition may be determined by measuring the PG/EG-ratio of propylene glycol to ethylene glycol.

In some embodiments, the composition may include no more than 1 ppm propylene oxide. In some aspects, the composition may include no more than 0.9 ppm, 0.8 ppm, 0.7 ppm, 0.6 ppm, 0.5 ppm, 0.4 ppm, 0.3 ppm, 0.2 ppm, or 0.1 ppm propylene oxide. In some aspects, the amount of propylene oxide in the composition may be determined by HPLC. In some additional aspects, the amount of propylene oxide in the composition may be determined by gas chromatography.

In some embodiments, the composition may include between about 0 ppm to about 10 ppm chloride (e.g., Cl$^-$ ions). In some aspects, the composition may include about 0 ppm chloride to about 2 ppm chloride, about 2 ppm chloride to about 4 ppm chloride, about 4 ppm chloride to about 6 ppm chloride, about 6 ppm chloride to about 8 ppm chloride, or about 8 to about 10 ppm chloride. In some additional aspects, the composition may include about 0 ppm chloride to about 4 ppm chloride, about 0 ppm chloride to about 6 ppm chloride, about 0 ppm chloride to about 8 ppm chloride, about 2 ppm chloride to about 1 ppm chloride, about 4 ppm chloride to about 1 ppm chloride, or about 6 ppm chloride to about 1 ppm chloride. In still further aspects, the composition may include about 0 ppm, 1 ppm, 2 ppm, 3 ppm, 4 ppm, 5 ppm, 6 ppm, 7 ppm, 8 ppm, 9 ppm, or about 10 ppm chloride. In an exemplary embodiment, the composition may include between about 0 ppm to about 1 ppm chloride.

In some embodiments, the composition may include between about 0 ppm to about 10 ppm sodium (e.g., Na$^+$ ions). In some aspects, the composition may include about 0 ppm sodium to about 2 ppm sodium, about 2 ppm sodium to about 4 ppm sodium, about 4 ppm sodium to about 6 ppm sodium, about 6 ppm sodium to about 8 ppm sodium, or about 8 to about 10 ppm sodium. In some additional aspects, the composition may include about 0 ppm sodium to about 4 ppm sodium, about 0 ppm sodium to about 6 ppm sodium, about 0 ppm sodium to about 8 ppm sodium, about 2 ppm sodium to about 1 ppm sodium, about 4 ppm sodium to about 1 ppm sodium, or about 6 ppm sodium to about 1 ppm sodium. In still further aspects, the composition may include about 0 ppm, 1 ppm, 2 ppm, 3 ppm, 4 ppm, 5 ppm, 6 ppm, 7 ppm, 8 ppm, 9 ppm, or about 10 ppm sodium. In an exemplary embodiment, the composition may include between about 0 ppm to about 1 ppm sodium.

In some embodiments, the composition may include less than or equal to 0.05% of other unspecified impurities; for example, the composition may include less than or equal to 0.05%, 0.04%, 0.03%, 0.02%, or less than or equal to 0.01% of other unspecified impurities.

In some embodiments, the composition may be stable for at least 6 months. For example, the composition may be stable for at least 3 months, 6 months, at least 7 months, at least 8 months, at least 9 months, at least 10 months, at least 11 months, at least 12 months, at least 13 months, at least 14 months, at least 15 months, at least 16 months, at least 17 months, at least 18 months, at least 24 months, or at least 36 months.

The composition may be nanofiltered. In some embodiments, the concentration of the composition does not substantially change the time required for nanofiltration. Thus, the time for nanofiltration does not increase or decrease as the concentration of the mixture of β-cyclodextrin molecules increases or decreases in the composition. In some aspects, the length of time to nanofilter the composition ranges from about 1.04 to about 1.20 hours per diafiltration volume (kg soln/m$^2$·hr/L soln). In some embodiments, the nanofiltered composition has no substantial difference observed in HPLC-ELSD after nanofiltration as compared to before nanofiltration. In some embodiments, the composition has no substantial difference observed in NMR after nanofiltration as compared to before nanofiltration.

In some embodiments, the composition may be terminally sterilized. Methods of terminal sterilization are generally well-known in the art. In some embodiments, the pH of the composition may be adjusted after terminal sterilization.

In some embodiments, the composition may include less than or equal to 10.0% w/w of water. For example, the composition may include less than or equal to 10.0% w/w, 9.5% w/w, 9.0% w/w, 8.5% w/w, 8.0% w/w, 7.5% w/w, 7.0% w/w, 6.5% w/w, 6.0% w/w, 5.5% w/w, 5.0% w/w, 4.5% w/w, 4.0% w/w, 3.5% w/w, 3.0% w/w, 2.5% w/w, 2.0% w/w, 1.5% w/w, 1.0% w/w, 0.5% w/w, or less than or equal to 0.1% w/w water.

In some embodiments, the composition may be packaged in a vial suitable for injection to a human subject in need thereof. The vial may be glass, plastic, or any other material known in the pharmaceutical art. The vial may be coated with a material such as silicon dioxide to prevent leaching from the vial into the composition.

In some embodiments, the composition may be efficacious in treating Niemann-Pick disease. In some embodiments, the composition may be efficacious in treating Niemann-Pick disease Type C. In some embodiments, the composition may be efficacious in treating liver disease. In some embodiments, the composition may be efficacious in treating cardiovascular disease. In some embodiments, the composition may be efficacious in treating familial hypercholesterolemia. In some embodiments, the composition may be efficacious in treating cholesterol deposits.

In some embodiments, the composition may further comprise a pharmaceutical excipient or carrier. In some embodiments, the composition may further comprise a pharmaceutically acceptable diluent. Examples of pharmaceutical excipients, carriers, and diluents are well known to those having skill in the art.

In some embodiments, the composition may exhibit a lower toxicity than Trappsol® Cyclo or Kleptose®. In some embodiments, the composition may exhibit a substantially lower ototoxicity than Trappsol® Cyclo or Kleptose®. In some embodiments, the composition may exhibit substantially no ototoxicity.

Fraction 5 HDS

Provided herein is a composition comprising a mixture of isomerically-purified hydroxypropyl-β-cyclodextrin molecules that includes less than 1% of DS-7. In some embodiments, the mixture of isomerically-purified hydroxypropyl-β-cyclodextrin molecules may include less than 1% of DS-6, DS-5, DS-4, DS-3, DS-2, and DS-1. In some aspects, the mixture of isomerically-purified hydroxypropyl-β-cyclodextrin molecules may include less than 1%, less than 0.9%, less than 0.8%, less than 0.7%, less than 0.6%, less than 0.5%, less than 0.4%, less than 0.3%, less than 0.2%, or less than 0.1% of DS-6, DS-5, DS-4, DS-3, DS-2, and DS-1.

In some embodiments, the mixture of isomerically-purified hydroxypropyl-β-cyclodextrin molecules may include about 6% to about 12% of DS-8. In some aspects, the mixture of isomerically-purified hydroxypropyl-β-cyclodextrin molecules may include about 6% to about 6.5% of DS-8, about 6.5% to about 7% of DS-8, about 7% to about 7.5% of DS-8, about 7.5% to about 8% of DS-8, about 8% to about 8.5% of DS-8, about 8.5% to about 16% of DS-8, about 9% to about 9.5% of DS-8, about 9.5% to about 10% of DS-8, about 10% to about 10.5% of DS-8, about 10.5% to about 11% of DS-8, about 11% to about 11.5% of DS-8, or about 11.5% to about 12% of DS-8. In some additional aspects, the mixture of isomerically-purified β-cyclodextrin may include about 6% to about 7% of DS-8, about 6% to about 7.5% of DS-8, about 6% to about 8% of DS-8, about 6% to about 8.5% of DS-8, about 6% to about 9% of DS-8, about 6% to about 9.5% of DS-8, about 6% to about 10% of DS-8, about 6% to about 10.5% of DS-8, about 6% to about 11% of DS-8, about 6% to about 11.5% of DS-8, about 6.5% to about 12% of DS-8, about 7% to about 12% of DS-8, about 7.5% to about 12% of DS-8, about 8% to about 12% of DS-8, about 8.5% to about 12% of DS-8, about 9% to about 12% of DS-8, about 9.5% to about 12% of DS-8, about 10% to about 12% of DS-8, about 10.5% to about 12% of DS-8, about 11% to about 12% of DS-8, about 6.5% to about 11.5% of DS-8, about 7% to about 11% of DS-8, about 7.5% to about 10.5% of DS-8, about 8% to about 10% of DS-8, or about 8.5% to about 9.5% of DS-8. In still further aspects, the mixture of isomerically-purified β-cyclodextrin molecules may include about 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10.0%, 10.1%, 10.2%, 10.3%, 10.4%, 10.5%, 10.6%, 10.7%, 10.8%, 10.9%, 11.0%, 11.1%, 11.2%, 11.3%, 11.4%, 11.5%, 11.6%, 11.7%, 11.8%, 11.9%, or about 12.0% of DS-8. In an exemplary embodiment, the area of DS-8 in a MALDI-TOF-MS spectrum is 8.53%.

In some embodiments, the mixture of isomerically-purified hydroxypropyl-β-cyclodextrin molecules may include about 18% to about 24% of DS-9. In some aspects, the mixture of isomerically-purified β-cyclodextrin molecules includes about 18% to about 18.5% of DS-9, about 18.5% to about 19% of DS-9, about 19% to about 19.5% of DS-9, about 19.5% to about 20% of DS-9, about 20% to about 20.5% to about 21% of DS-9, about 21% to about 21.5% of DS-9, about 21.5% to about 22% of DS-9, about 22% to about 22.5% of DS-9, about 22.5% to about 23% of DS-9, about 23% to about 23.5% of DS-9, or about 23.5% to about 24% of DS-9. In some additional aspects, the mixture of isomerically-purified β-cyclodextrin may include about 18% to about 19% of DS-9, about 18% to about 19.5% of DS-9, about 18% to about 20% of DS-9, about 18% to about 20.5% of DS-9, about 18% to about 21% of DS-9, about 18% to about 21.5% of DS-9, about 18% to about 22% of DS-9, about 18% to about 22.5% of DS-9, about 18% to about 23% of DS-9, about 18% to about 23.5% of DS-9, about 18.5% to about 24% of DS-9, about 19% to about 24% of DS-9, about 19.5% to about 24% of DS-9, about 20% to about 24% of DS-9, about 20.5% to about 24% of DS-9, about 21% to about 24% of DS-9, about 21.5% to about 24% of DS-9, about 22% to about 24% of DS-9, about 22.5% to about 24% of DS-9, about 23% to about 24% of DS-9, about 18.5% to about 23.5% of DS-9, about 19% to about 23% of DS-9, about 19.5% to about 22.5% of DS-9, about 20% to about 22% of DS-9, or about 20.5% to about 21.5% of DS-9. In still further aspects, the mixture of isomerically-purified β-cyclodextrin molecules may include about 18.0%, 18.1%, 18.2%, 18.3%, 18.4%, 18.5%, 18.6%, 18.7%, 18.8%, 18.9%, 19.0%, 19.1%, 19.2%, 19.3%, 19.4%, 19.5%, 19.6%, 19.7%, 19.8%, 19.9%, 20.0%, 20.1%, 20.2%, 20.3%, 20.4%, 20.5%, 20.6%, 20.7%, 20.8%, 20.9%, 21.0%, 21.1%, 21.2%, 21.3%, 21.4%, 21.5%, 21.6%, 21.7%, 21.8%, 21.9%, 22.0%, 22.1%, 22.2%, 22.3%, 22.4%, 22.5%, 22.6%, 22.7%, 22.8%, 22.9%, 23.0%, 23.1%, 23.2%, 23.3%, 23.4%, 23.5%, 23.6%, 23.7%, 23.8%, 23.9%, or about 24.0% of DS-9. In an exemplary embodiment, the area of DS-9 in a MALDI-TOF-MS spectrum is 21.33%.

In some embodiments, the mixture of isomerically-purified hydroxypropyl-β-cyclodextrin molecules may include about 24% to about 30% of DS-10. In some aspects, the mixture of isomerically-purified hydroxypropyl-β-cyclodextrin molecules may include about 24% to about 24.5% of DS-10, about 24.5% to about 25% of DS-10, about 25% to about 25.5% of DS-10, about 25.5% to about 26% of DS-10, about 26% to about 26.5% of DS-10, about 26.5% to about 27% of DS-10, about 27% to about 27.5% of DS-10, about 27.5% to about 28% of DS-10, about 28% to about 28.5% of DS-10, about 28.5% to about 29% of DS-10, about 29% to about 29.5% of DS-10, or about 29.5% to about 30% of DS-10. In some additional aspects, the mixture of isomerically-purified hydroxypropyl-β-cyclodextrin molecules may include about 24% to about 25% of DS-10, about 24% to about 25.5% of DS-10, about 24% to about 26% of DS-10, about 24% to about 26.5% of DS-10, about 24% to about 27% of DS-10, about 24% to about 27.5% of DS-10, about 24% to about 28% of DS-10, about 24% to about 28.5% of DS-10, about 24% to about 29% of DS-10, about 24% to about 29.5% of DS-10, about 24.5% to about 30% of DS-10, about 25% to about 30% of DS-10, about 25.5% to about 30% of DS-10, about 26% to about 30% of DS-10, about 26.5% to about 30% of DS-10, about 27% to about 30% of DS-10, about 27.5% to about 30% of DS-10, about 28% to about 30% of DS-10, about 28.5% to about 30% of DS-10, about 29% to about 30% of DS-10, about 24.5% to about 29.5% of DS-10, about 25% to about 29% of DS-10, about 25.5% to about 28.5% of DS-10, about 26% to about 28% of DS-10, or about 26.5% to about 27.5% of DS-10. In still further aspects, the mixture of isomerically-purified hydroxypropyl-β-cyclodextrin molecules may include about 24.0%, 24.1%, 24.2%, 24.3%, 24.4%, 24.5%, 24.6%, 24.7%, 24.8%, 24.9%, 25.0%, 25.1%, 25.2%, 25.3%, 25.4%, 25.5%, 25.6%, 25.7%, 25.8%, 25.9%, 26.0%, 26.1%, 26.2%, 26.3%, 26.4%, 26.5%, 26.6%, 26.7%, 26.8%, 26.9%, 27.0%, 27.1%, 27.2%, 27.3%, 27.4%, 27.5%, 27.6%, 27.7%, 27.8%, 27.9%, 28.0%, 28.1%, 28.2%, 28.3%, 28.4%, 28.5%, 28.6%, 28.7%, 28.8%, 28.9%, 29.0%, 29.1%, 29.2%, 29.3%, 29.4%, 29.5%, 29.6%, 29.7%, 29.8%, 29.9%, or about 30.0% of DS-10. In an exemplary embodiment, the area of DS-10 in a MALDI-TOF-MS spectrum is 26.58%.

In some embodiments, the mixture of isomerically-purified hydroxypropyl-β-cyclodextrin molecules may include about 18% to about 24% of DS-11. In some aspects, the mixture of isomerically-purified hydroxypropyl-β-cyclodextrin molecules may include about 18% to about 18.5% of DS-11, about 18.5% to about 19% of DS-11, about 19% to about 19.5% of DS-11, about 19.5% to about 20% of DS-11, about 20% to about 20.5% of DS-11, about 20.5% to about 21% of DS-11, about 21% to about 21.5% of DS-11, about 21.5% to about 22% of DS-11, about 22% to about 22.5% of DS-11, about 22.5% to about 23% of DS-11, about 23% to about 23.5% of DS-11, or about 23.5% to about 24% of DS-11. In some additional aspects, the mixture of isomerically-purified hydroxypropyl-β-cyclodextrin molecules may include about 18% to about 19% of DS-11, about 18% to about 19.5% of DS-11, about 18% to about 20% of DS-11, about 18% to about 20.5% of DS-11, about 18% to about 21% of DS-11, about 18% to about 21.5% of DS-11, about 18% to about 22% of DS-11, about 18% to about 22.5% of DS-11, about 18% to about 23% of DS-11, about 18% to about 23.5% of DS-11, about 18.5% to about 24% of DS-11, about 19% to about 24% of DS-11, about 19.5% to about 24% of DS-11, about 20% to about 24% of DS-11, about 20.5% to about 24% of DS-11, about 21% to about 24% of DS-11, about 21.5% to about 24% of DS-11, about 22% to about 24% of DS-11, about 22.5% to about 24% of DS-11, about 23% to about 24% of DS-11, about 18.5% to about 23.5% of DS-11, about 19% to about 23% of DS-11, about 19.5% to about 22.5% of DS-11, about 20% to about 22% of DS-11, or about 20.5% to about 21.5% of DS-11. In still further aspects, the mixture of isomerically purified hydroxypropyl-β-cyclodextrin molecules may include about 18.0%, 18.1%, 18.2%, 18.3%, 18.4%, 18.5%, 18.6%, 18.7%, 18.8%, 18.9%, 19.0%, 19.1%, 19.2%, 19.3%, 19.4%, 19.5%, 19.6%, 19.7%, 19.8%, 19.9%, 20.0%, 20.1%, 20.2%, 20.3%, 20.4%, 20.5%, 20.6%, 20.7%, 20.8%, 20.9%, 21.0%, 21.1%, 21.2%, 21.3%, 21.4%, 21.5%, 21.6%, 21.7%, 21.8%, 21.9%, 22.0%, 22.1%, 22.2%, 22.3%, 22.4%, 22.5%, 22.6%, 22.7%, 22.8%, 22.9%, 23.0%, 23.1%, 23.2%, 23.3%, 23.4%, 23.5%, 23.6%, 23.7%, 23.8%, 23.9%, or about 24.0% of DS-11. In an exemplary embodiment, the area of DS-11 in a MALDI-TOF-MS spectrum is 20.90%.

In some embodiments, the mixture of isomerically-purified hydroxypropyl-β-cyclodextrin molecules may include about 10% to about 16% of DS-12. In some aspects, the mixture of isomerically-purified hydroxypropyl-β-cyclodextrin molecules may include about 10% to about 10.5% of DS-12, about 10.5% to about 11% of DS-12, about 11% to about 11.5% of DS-12, about 11.5% to about 12% of DS-12, about 12% to about 12.5% of DS-12, about 12.5% to about 13% of DS-12, about 13% to about 13.5% of DS-12, about 13.5% to about 14% of DS-12, about 14% to about 14.5% of DS-12, about 14.5% to about 15% of DS-12, about 15% to about 15.5% of DS-12, or about 15.5% to about 16% of DS-12. In some additional aspects, the mixture of isomerically-purified hydroxypropyl-β-cyclodextrin molecules may include about 10% to about 11% of DS-12, about 10% to about 11.5% of DS-12, about 10% to about 12% of DS-12, about 10% to about 12.5% of DS-12, about 10% to about 13% of DS-12, about 10% to about 13.5% of DS-12, about 10% to about 14% of DS-12, about 10% to about 14.5% of DS-12, about 10% of about 15% of DS-12, about 10% of about 15.5% of DS-12, about 10.5% to about 16% of DS-12, about 11% to about 16% of DS-12, about 11.5% to about 16% of DS-12, about 12% to about 16% of DS-12, about 12.5% to about 16% of DS-12, about 13% to about 16% of DS-12, about 13.5% to about 16% of DS-12, about 14% to about 16% of DS-12, about 14.5% to about 16% of DS-12, about 15% to about 16% of DS-12, about 10.5% to about 15.5% of DS-12, about 11% to about 15% of DS-12, about 11.5% to about 14.5% of DS-12, about 12% to about 14% of DS-12, or about 12.5% to about 13.5% of DS-12. In still further aspects, the mixture of isomerically-purified hydroxypropyl-β-cyclodextrin molecules may include about 10.0%, 10.1%, 10.2%, 10.3%, 10.4%, 10.5%, 10.6%, 10.7%, 10.8%, 10.9%, 11.0%, 11.1%, 11.2%, 11.3%, 11.4%, 11.5%, 11.6%, 11.7%, 11.8%, 11.9%, 12.0%, 12.1%, 12.2%, 12.3%, 12.4%, 12.5%, 12.6%, 12.7%, 12.8%, 12.9%, 13.0%, 13.1%, 13.2%, 13.3%, 13.4%, 13.5%, 13.6%, 13.7%, 13.8%, 13.9%, 14.0%, 14.1%, 14.2%, 14.3%, 14.4%, 14.5%, 14.6%, 14.7%, 14.8%, 14.9%, 15.0%, 15.1%, 15.2%, 15.3%, 15.4%, 15.5%, 15.6%, 15.7%, 15.8%, 15.9%, or about 16.0% of DS-12. In an exemplary embodiment, the area of DS-12 in a MALDI-TOF-MS spectrum is 13.31%.

In some embodiments, the mixture of isomerically-purified hydroxypropyl-β-cyclodextrin molecules may include about 4% to about 10% of DS-13. In some aspects, the mixture of isomerically-purified hydroxypropyl-β-cyclodextrin molecules may include about 4% to about 4.5% of DS-13, about 4.5% to about 5% of DS-13, about 5% to about 5.5% of DS-13, about 5.5% to about 6% of DS-13, about 6% to about 6.5% of DS-13, about 6.5% to about 7% of DS-13, about 7% to about 7.5% of DS-13, about 7.5% to about 8% of DS-13, about 8% to about 8.5% of DS-13, about 8.5% to about 9% of DS-13, about 9% to about 9.5% of DS-13, or about 9.5% to about 10% of DS-13. In some additional aspects, the mixture of isomerically-purified hydroxypropyl-β-cyclodextrin molecules may include about 4% to about 5% of DS-13, about 4% to about 5.5% of DS-13, about 4% to about 6% of DS-13, about 4% to about 6.5% of DS-13, about 4% to about 7% of DS-13, about 4% to about 7.5% of DS-13, about 4% to about 8% of DS-13, about 4% to about 8.5% of DS-13, about 4% to about 9% of DS-13, about 4% to about 9.5% of DS-13, about 4.5% to about 10% of DS-13, about 5% to about 10% of DS-13, about 5.5% to about 10% of DS-13, about 6% to about 10% of DS-13, about 6.5% to about 10% of DS-13, about 7% to about 10% of DS-13, about 7.5% to about 10% of DS-13, about 8% to about 10% of DS-13, about 8.5% to about 10% of DS-13, about 9% to about 10% of DS-13, about 4.5% to about 9.5% of DS-13, about 5% to about 9% of DS-13, about 5.5% to about 8.5% of DS-13, about 6% to about 8% of DS-13, or about 6.5% to about 7.5% of DS-13. In still further aspects, the mixture of isomerically-purified hydroxypropyl-β-cyclodextrin molecules may include about 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, or about 10.0% of DS-13. In an exemplary embodiment, the area of DS-13 in a MALDI-TOF-MS spectrum is 6.74%.

In some embodiments, the mixture of isomerically-purified hydroxypropyl-β-cyclodextrin molecules may include about 0% to about 6% of DS-14. In some aspects, the mixture of isomerically-purified hydroxypropyl-β-cyclodextrin molecules may include about 0% to about 0.5% of DS-14, about 0.5% to about 1% of DS-14, about 1% to about 1.5% of DS-14, about 1.5% to about 2% of DS-14, about 2% to about 2.5% of DS-14, about 2.5% to about 3% of DS-14, about 3% to about 3.5% of DS-14, about 3.5% to about 4% of DS-14, about 4% to about 4.5% of DS-14, about 4.5% to about 5% of DS-14, about 5% to about 5.5% of DS-14, or about 5.5% to about 6% of DS-14. In some additional aspects, the mixture of isomerically-purified hydroxypropyl-β-cyclodextrin molecules may include about 0% to about 1% of DS-14, about 0% to about 1.5% of DS-14, about 0% to about 2% of DS-14, about 0% to about 2.5% of DS-14, about 0% to about 3% of DS-14, about 0% to about 3.5% of DS-14, about 0% to about 4% of DS-14, about 0% to about 4.5% of DS-14, about 0% to about 5% of DS-14, about 0% to about 5.5% of DS-14, about 0.5% to about 6% of DS-14, about 1% to about 6% of DS-14, about 1.5% to about 6% of DS-14, about 2% to about 6% of DS-14, about 2.5% to about 6% of DS-14, about 3% to about 6% of DS-14, about 3.5% to about 6% of DS-14, about 4% to about 6% of DS-14, about 4.5% to about 6% of DS-14, about 5% to about 6% of DS-14, about 0.5% to about 5.5% of DS-14, about 1% to about 5% of DS-14, about 1.5% to about 4.5% of DS-14, about 2% to about 4% of DS-14, or about 2.5% to about 3.5% of DS-14. In still further aspects, the mixture of isomerically-purified hydroxypropyl-β-cyclodextrin molecules may include about 0.0%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, or about 6.0% of DS-14. In an exemplary embodiment, the area of DS-14 in a MALDI-TOF-MS spectrum is 2.60%.

Further provided herein is a composition comprising a mixture of isomerically-purified hydroxypropyl-β-cyclodextrin molecules including DS-8, DS-9, DS-10, DS-11, DS-12, DS-13, and DS-14. In some embodiments, the composition includes less than 1% of DS-7. In some embodiments, the DS-10 may have the highest concentration in the composition as compared to DS-8, DS-9, DS-11, DS-12, DS-13, and DS-14.

In some embodiments, the mixture of isomerically-purified hydroxypropyl-β-cyclodextrin molecules may include about 6% to about 12% of DS-8. In some aspects, the mixture of isomerically-purified hydroxypropyl-β-cyclodextrin molecules may include about 6% to about 6.5% of DS-8, about 6.5% to about 7% of DS-8, about 7% to about 7.5% of DS-8, about 7.5% to about 8% of DS-8, about 8% to about 8.5% of DS-8, about 8.5% to about 16% of DS-8, about 9% to about 9.5% of DS-8, about 9.5% to about 10% of DS-8, about 10% to about 10.5% of DS-8, about 10.5% to about 11% of DS-8, about 11% to about 11.5% of DS-8, or about 11.5% to about 12% of DS-8. In some additional aspects, the mixture of isomerically-purified β-cyclodextrin may include about 6% to about 7% of DS-8, about 6% to about 7.5% of DS-8, about 6% to about 8% of DS-8, about 6% to about 8.5% of DS-8, about 6% to about 9% of DS-8, about 6% to about 9.5% of DS-8, about 6% to about 10% of DS-8, about 6% to about 10.5% of DS-8, about 6% to about 11% of DS-8, about 6% to about 11.5% of DS-8, about 6.5% to about 12% of DS-8, about 7% to about 12% of DS-8, about 7.5% to about 12% of DS-8, about 8% to about 12% of DS-8, about 8.5% to about 12% of DS-8, about 9% to about 12% of DS-8, about 9.5% to about 12% of DS-8, about 10% to about 12% of DS-8, about 10.5% to about 12% of DS-8, about 11% to about 12% of DS-8, about 6.5% to about 11.5% of DS-8, about 7% to about 11% of DS-8, about 7.5% to about 10.5% of DS-8, about 8% to about 10% of DS-8, or about 8.5% to about 9.5% of DS-8. In still further aspects, the mixture of isomerically-purified β-cyclodextrin molecules may include about 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10.0%, 10.1%, 10.2%, 10.3%, 10.4%, 10.5%, 10.6%, 10.7%, 10.8%, 10.9%, 11.0%, 11.1%, 11.2%, 11.3%, 11.4%, 11.5%, 11.6%, 11.7%, 11.8%, 11.9%, or about 12.0% of DS-8. In an exemplary embodiment, the area of DS-8 in a MALDI-TOF-MS spectrum is 8.53%.

In some embodiments, the mixture of isomerically-purified hydroxypropyl-β-cyclodextrin molecules may include about 18% to about 24% of DS-9. In some aspects, the mixture of isomerically-purified β-cyclodextrin molecules includes about 18% to about 18.5% of DS-9, about 18.5% to about 19% of DS-9, about 19% to about 19.5% of DS-9, about 19.5% to about 20% of DS-9, about 20% to about 20.5% to about 21% of DS-9, about 21% to about 21.5% of DS-9, about 21.5% to about 22% of DS-9, about 22% to about 22.5% of DS-9, about 22.5% to about 23% of DS-9, about 23% to about 23.5% of DS-9, or about 23.5% to about 24% of DS-9. In some additional aspects, the mixture of isomerically-purified β-cyclodextrin may include about 18% to about 19% of DS-9, about 18% to about 19.5% of DS-9, about 18% to about 20% of DS-9, about 18% to about 20.5% of DS-9, about 18% to about 21% of DS-9, about 18% to about 21.5% of DS-9, about 18% to about 22% of DS-9, about 18% to about 22.5% of DS-9, about 18% to about 23% of DS-9, about 18% to about 23.5% of DS-9, about 18.5% to about 24% of DS-9, about 19% to about 24% of DS-9, about 19.5% to about 24% of DS-9, about 20% to about 24% of DS-9, about 20.5% to about 24% of DS-9, about 21% to about 24% of DS-9, about 21.5% to about 24% of DS-9, about 22% to about 24% of DS-9, about 22.5% to about 24% of DS-9, about 23% to about 24% of DS-9, about 18.5% to about 23.5% of DS-9, about 19% to about 23% of DS-9, about 19.5% to about 22.5% of DS-9, about 20% to about 22% of DS-9, or about 20.5% to about 21.5% of DS-9. In still further aspects, the mixture of isomerically-purified β-cyclodextrin molecules may include about 18.0%, 18.1%, 18.2%, 18.3%, 18.4%, 18.5%, 18.6%, 18.7%, 18.8%, 18.9%, 19.0%, 19.1%, 19.2%, 19.3%, 19.4%, 19.5%, 19.6%, 19.7%, 19.8%, 19.9%, 20.0%, 20.1%, 20.2%, 20.3%, 20.4%, 20.5%, 20.6%, 20.7%, 20.8%, 20.9%, 21.0%, 21.1%, 21.2%, 21.3%, 21.4%, 21.5%, 21.6%, 21.7%, 21.8%, 21.9%, 22.0%, 22.1%, 22.2%, 22.3%, 22.4%, 22.5%, 22.6%, 22.7%, 22.8%, 22.9%, 23.0%, 23.1%, 23.2%, 23.3%, 23.4%, 23.5%, 23.6%, 23.7%, 23.8%, 23.9%, or about 24.0% of DS-9. In an exemplary embodiment, the area of DS-9 in a MALDI-TOF-MS spectrum is 21.33%.

In some embodiments, the mixture of isomerically-purified hydroxypropyl-β-cyclodextrin molecules may include about 24% to about 30% of DS-10. In some aspects, the mixture of isomerically-purified hydroxypropyl-β-cyclodextrin molecules may include about 24% to about 24.5% of DS-10, about 24.5% to about 25% of DS-10, about 25% to about 25.5% of DS-10, about 25.5% to about 26% of DS-10, about 26% to about 26.5% of DS-10, about 26.5% to about 27% of DS-10, about 27% to about 27.5% of DS-10, about 27.5% to about 28% of DS-10, about 28% to about 28.5% of DS-10, about 28.5% to about 29% of DS-10, about 29% to about 29.5% of DS-10, or about 29.5% to about 30% of DS-10. In some additional aspects, the mixture of isomerically-purified hydroxypropyl-β-cyclodextrin molecules may include about 24% to about 25% of DS-10, about 24% to about 25.5% of DS-10, about 24% to about 26% of DS-10, about 24% to about 26.5% of DS-10, about 24% to about 27% of DS-10, about 24% to about 27.5% of DS-10, about 24% to about 28% of DS-10, about 24% to about 28.5% of DS-10, about 24% to about 29% of DS-10, about 24% to about 29.5% of DS-10, about 24.5% to about 30% of DS-10, about 25% to about 30% of DS-10, about 25.5% to about 30% of DS-10, about 26% to about 30% of DS-10, about 26.5% to about 30% of DS-10, about 27% to about 30% of DS-10, about 27.5% to about 30% of DS-10, about 28% to about 30% of DS-10, about 28.5% to about 30% of DS-10, about 29% to about 30% of DS-10, about 24.5% to about 29.5% of DS-10, about 25% to about 29% of DS-10, about 25.5% to about 28.5% of DS-10, about 26% to about 28% of DS-10, or about 26.5% to about 27.5% of DS-10. In still further aspects, the mixture of isomerically-purified hydroxypropyl-β-cyclodextrin molecules may include about 24.0%, 24.1%, 24.2%, 24.3%, 24.4%, 24.5%, 24.6%, 24.7%, 24.8%, 24.9%, 25.0%, 25.1%, 25.2%, 25.3%, 25.4%, 25.5%, 25.6%, 25.7%, 25.8%, 25.9%, 26.0%, 26.1%, 26.2%, 26.3%, 26.4%, 26.5%, 26.6%, 26.7%, 26.8%, 26.9%, 27.0%, 27.1%, 27.2%, 27.3%, 27.4%, 27.5%, 27.6%, 27.7%, 27.8%, 27.9%, 28.0%, 28.1%, 28.2%, 28.3%, 28.4%, 28.5%, 28.6%, 28.7%, 28.8%, 28.9%, 29.0%, 29.1%, 29.2%, 29.3%, 29.4%, 29.5%, 29.6%, 29.7%, 29.8%, 29.9%, or about 30.0% of DS-10. In an exemplary embodiment, the area of DS-10 in a MALDI-TOF-MS spectrum is 26.58%.

In some embodiments, the mixture of isomerically-purified hydroxypropyl-β-cyclodextrin molecules may include about 18% to about 24% of DS-11. In some aspects, the mixture of isomerically-purified hydroxypropyl-β-cyclodextrin molecules may include about 18% to about 18.5% of DS-11, about 18.5% to about 19% of DS-11, about 19% to about 19.5% of DS-11, about 19.5% to about 20% of DS-11, about 20% to about 20.5% of DS-11, about 20.5% to about 21% of DS-11, about 21% to about 21.5% of DS-11, about 21.5% to about 22% of DS-11, about 22% to about 22.5% of DS-11, about 22.5% to about 23% of DS-11, about 23% to about 23.5% of DS-11, or about 23.5% to about 24% of DS-11. In some additional aspects, the mixture of isomerically-purified hydroxypropyl-β-cyclodextrin molecules may include about 18% to about 19% of DS-11, about 18% to about 19.5% of DS-11, about 18% to about 20% of DS-11, about 18% to about 20.5% of DS-11, about 18% to about 21% of DS-11, about 18% to about 21.5% of DS-11, about 18% to about 22% of DS-11, about 18% to about 22.5% of DS-11, about 18% to about 23% of DS-11, about 18% to about 23.5% of DS-11, about 18.5% to about 24% of DS-11, about 19% to about 24% of DS-11, about 19.5% to about 24% of DS-11, about 20% to about 24% of DS-11, about 20.5% to about 24% of DS-11, about 21% to about 24% of DS-11, about 21.5% to about 24% of DS-11, about 22% to about 24% of DS-11, about 22.5% to about 24% of DS-11, about 23% to about 24% of DS-11, about 18.5% to about 23.5% of DS-11, about 19% to about 23% of DS-11, about 19.5% to about 22.5% of DS-11, about 20% to about 22% of DS-11, or about 20.5% to about 21.5% of DS-11. In still further aspects, the mixture of isomerically purified hydroxypropyl-β-cyclodextrin molecules may include about 18.0%, 18.1%, 18.2%, 18.3%, 18.4%, 18.5%, 18.6%, 18.7%, 18.8%, 18.9%, 19.0%, 19.1%, 19.2%, 19.3%, 19.4%, 19.5%, 19.6%, 19.7%, 19.8%, 19.9%, 20.0%, 20.1%, 20.2%, 20.3%, 20.4%, 20.5%, 20.6%, 20.7%, 20.8%, 20.9%, 21.0%, 21.1%, 21.2%, 21.3%, 21.4%, 21.5%, 21.6%, 21.7%, 21.8%, 21.9%, 22.0%, 22.1%, 22.2%, 22.3%, 22.4%, 22.5%, 22.6%, 22.7%, 22.8%, 22.9%, 23.0%, 23.1%, 23.2%, 23.3%, 23.4%, 23.5%, 23.6%, 23.7%, 23.8%, 23.9%, or about 24.0% of DS-11. In an exemplary embodiment, the area of DS-11 in a MALDI-TOF-MS spectrum is 20.90%.

In some embodiments, the mixture of isomerically-purified hydroxypropyl-β-cyclodextrin molecules may include about 10% to about 16% of DS-12. In some aspects, the mixture of isomerically-purified hydroxypropyl-β-cyclodextrin molecules may include about 10% to about 10.5% of DS-12, about 10.5% to about 11% of DS-12, about 11% to about 11.5% of DS-12, about 11.5% to about 12% of DS-12, about 12% to about 12.5% of DS-12, about 12.5% to about 13% of DS-12, about 13% to about 13.5% of DS-12, about 13.5% to about 14% of DS-12, about 14% to about 14.5% of DS-12, about 14.5% to about 15% of DS-12, about 15% to about 15.5% of DS-12, or about 15.5% to about 16% of DS-12. In some additional aspects, the mixture of isomerically-purified hydroxypropyl-β-cyclodextrin molecules may include about 10% to about 11% of DS-12, about 10% to about 11.5% of DS-12, about 10% to about 12% of DS-12, about 10% to about 12.5% of DS-12, about 10% to about 13% of DS-12, about 10% to about 13.5% of DS-12, about 10% to about 14% of DS-12, about 10% to about 14.5% of DS-12, about 10% of about 15% of DS-12, about 10% of about 15.5% of DS-12, about 10.5% to about 16% of DS-12, about 11% to about 16% of DS-12, about 11.5% to about 16% of DS-12, about 12% to about 16% of DS-12, about 12.5% to about 16% of DS-12, about 13% to about 16% of DS-12, about 13.5% to about 16% of DS-12, about 14% to about 16% of DS-12, about 14.5% to about 16% of DS-12, about 15% to about 16% of DS-12, about 10.5% to about 15.5% of DS-12, about 11% to about 15% of DS-12, about 11.5% to about 14.5% of DS-12, about 12% to about 14% of DS-12, or about 12.5% to about 13.5% of DS-12. In still further aspects, the mixture of isomerically-purified hydroxypropyl-β-cyclodextrin molecules may include about 10.0%, 10.1%, 10.2%, 10.3%, 10.4%, 10.5%, 10.6%, 10.7%, 10.8%, 10.9%, 11.0%, 11.1%, 11.2%, 11.3%, 11.4%, 11.5%, 11.6%, 11.7%, 11.8%, 11.9%, 12.0%, 12.1%, 12.2%, 12.3%, 12.4%, 12.5%, 12.6%, 12.7%, 12.8%, 12.9%, 13.0%, 13.1%, 13.2%, 13.3%, 13.4%, 13.5%, 13.6%, 13.7%, 13.8%, 13.9%, 14.0%, 14.1%, 14.2%, 14.3%, 14.4%, 14.5%, 14.6%, 14.7%, 14.8%, 14.9%, 15.0%, 15.1%, 15.2%, 15.3%, 15.4%, 15.5%, 15.6%, 15.7%, 15.8%, 15.9%, or about 16.0% of DS-12. In an exemplary embodiment, the area of DS-12 in a MALDI-TOF-MS spectrum is 13.31%.

In some embodiments, the mixture of isomerically-purified hydroxypropyl-β-cyclodextrin molecules may include about 4% to about 10% of DS-13. In some aspects, the mixture of isomerically-purified hydroxypropyl-β-cyclodextrin molecules may include about 4% to about 4.5% of DS-13, about 4.5% to about 5% of DS-13, about 5% to about 5.5% of DS-13, about 5.5% to about 6% of DS-13, about 6% to about 6.5% of DS-13, about 6.5% to about 7% of DS-13, about 7% to about 7.5% of DS-13, about 7.5% to about 8% of DS-13, about 8% to about 8.5% of DS-13, about 8.5% to about 9% of DS-13, about 9% to about 9.5% of DS-13, or about 9.5% to about 10% of DS-13. In some additional aspects, the mixture of isomerically-purified hydroxypropyl-β-cyclodextrin molecules may include about 4% to about 5% of DS-13, about 4% to about 5.5% of DS-13, about 4% to about 6% of DS-13, about 4% to about 6.5% of DS-13, about 4% to about 7% of DS-13, about 4% to about 7.5% of DS-13, about 4% to about 8% of DS-13, about 4% to about 8.5% of DS-13, about 4% to about 9% of DS-13, about 4% to about 9.5% of DS-13, about 4.5% to about 10% of DS-13, about 5% to about 10% of DS-13, about 5.5% to about 10% of DS-13, about 6% to about 10% of DS-13, about 6.5% to about 10% of DS-13, about 7% to about 10% of DS-13, about 7.5% to about 10% of DS-13, about 8% to about 10% of DS-13, about 8.5% to about 10% of DS-13, about 9% to about 10% of DS-13, about 4.5% to about 9.5% of DS-13, about 5% to about 9% of DS-13, about 5.5% to about 8.5% of DS-13, about 6% to about 8% of DS-13, or about 6.5% to about 7.5% of DS-13. In still further aspects, the mixture of isomerically-purified hydroxypropyl-β-cyclodextrin molecules may include about 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, or about 10.0% of DS-13. In an exemplary embodiment, the area of DS-13 in a MALDI-TOF-MS spectrum is 6.74%.

In some embodiments, the mixture of isomerically-purified hydroxypropyl-β-cyclodextrin molecules may include about 0% to about 6% of DS-14. In some aspects, the mixture of isomerically-purified hydroxypropyl-β-cyclodextrin molecules may include about 0% to about 0.5% of DS-14, about 0.5% to about 1% of DS-14, about 1% to about 1.5% of DS-14, about 1.5% to about 2% of DS-14, about 2% to about 2.5% of DS-14, about 2.5% to about 3% of DS-14, about 3% to about 3.5% of DS-14, about 3.5% to about 4% of DS-14, about 4% to about 4.5% of DS-14, about 4.5% to about 5% of DS-14, about 5% to about 5.5% of DS-14, or about 5.5% to about 6% of DS-14. In some additional aspects, the mixture of isomerically-purified hydroxypropyl-β-cyclodextrin molecules may include about 0% to about 1% of DS-14, about 0% to about 1.5% of DS-14, about 0% to about 2% of DS-14, about 0% to about 2.5% of DS-14, about 0% to about 3% of DS-14, about 0% to about 3.5% of DS-14, about 0% to about 4% of DS-14, about 0% to about 4.5% of DS-14, about 0% to about 5% of DS-14, about 0% to about 5.5% of DS-14, about 0.5% to about 6% of DS-14, about 1% to about 6% of DS-14, about 1.5% to about 6% of DS-14, about 2% to about 6% of DS-14, about 2.5% to about 6% of DS-14, about 3% to about 6% of DS-14, about 3.5% to about 6% of DS-14, about 4% to about 6% of DS-14, about 4.5% to about 6% of DS-14, about 5% to about 6% of DS-14, about 0.5% to about 5.5% of DS-14, about 1% to about 5% of DS-14, about 1.5% to about 4.5% of DS-14, about 2% to about 4% of DS-14, or about 2.5% to about 3.5% of DS-14. In still further aspects, the mixture of isomerically-purified hydroxypropyl-β-cyclodextrin molecules may include about 0.0%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, or about 6.0% of DS-14. In an exemplary embodiment, the area of DS-14 in a MALDI-TOF-MS spectrum is 2.60%.

In an exemplary embodiment, the mixture of isomerically-purified hydroxypropyl-β-cyclodextrin molecules may include about 6% to about 12% of DS-8, about 18% to about 24% of DS-9, about 24% to about 30% of DS-10, about 18% to about 24% of DS-11, about 10% to about 16% of DS-12, about 4% to about 10% of DS-13, and about 0% to about 6% of DS-14

In another exemplary embodiment, the mixture of isomerically-purified hydroxypropyl-β-cyclodextrin molecules may include DS-8, DS-9, DS-10, DS-11, DS-12, DS-13, and DS-14 wherein the mixture includes less than 1% of DS-7, DS-6, DS-5, DS-4, DS-3, DS-2, and DS-1.

In some embodiments, the average degree of substitution of the mixture of isomerically-purified hydroxypropyl-β-cyclodextrin molecules may be about 9 to about 10. In some aspects, the average degree of substitution of the mixture of isomerically-purified hydroxypropyl-β-cyclodextrin molecules may be 9.0, 9.1, 9.2, 9.3, 9.4, 9.5, 9.6, 9.7, 9.8, 9.9, or about 10.0. In an exemplary embodiment, the average degree of substitution of the mixture of hydroxypropyl-β-cyclodextrin molecules may be about 9.65.

Figure 26:
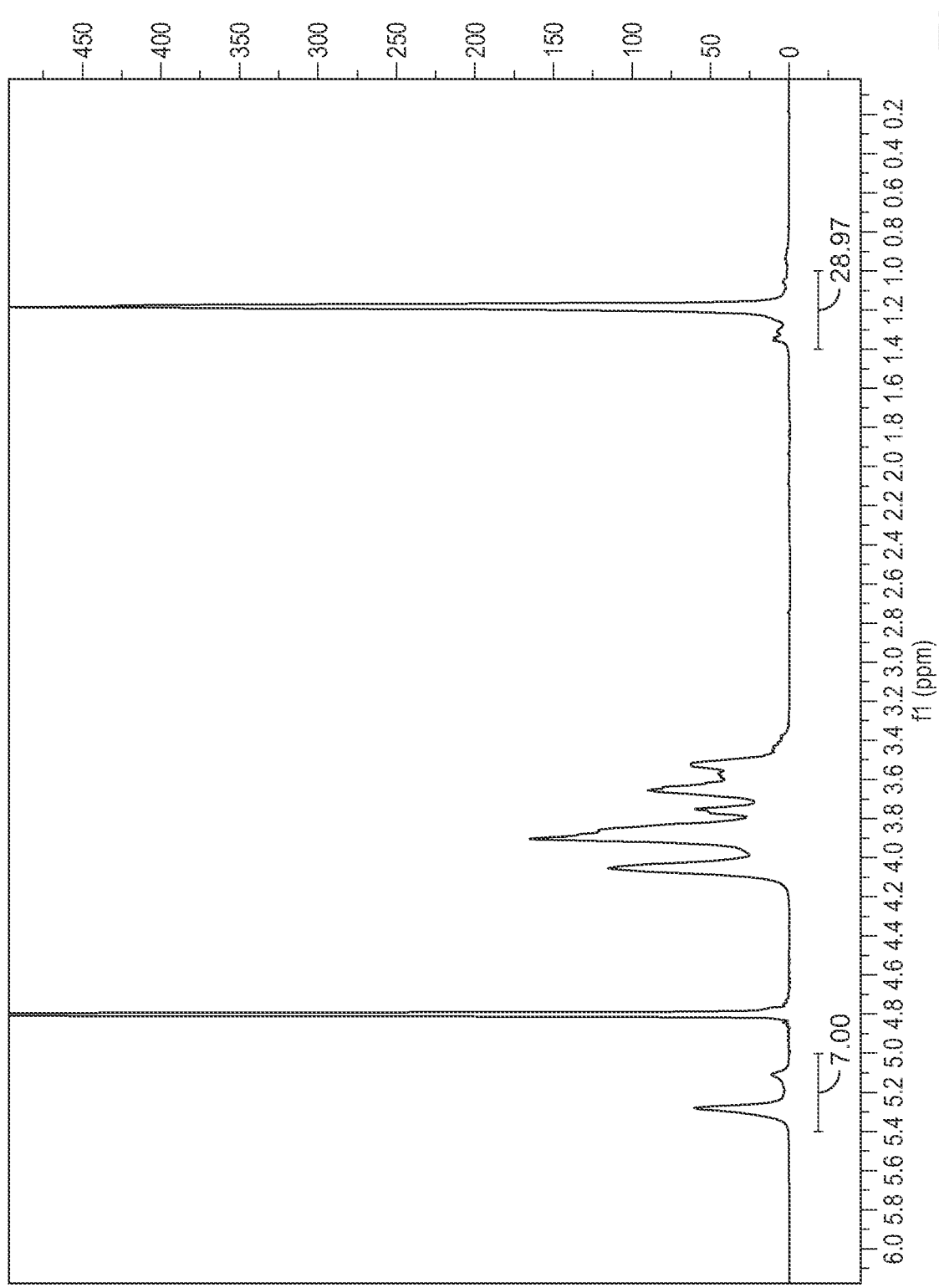
FIG. 26 is a ¹H NMR spectrum of the fifth HDS Fraction of a mixture of hydroxypropyl-β-cyclodextrins of the present disclosure.
Figure 27:
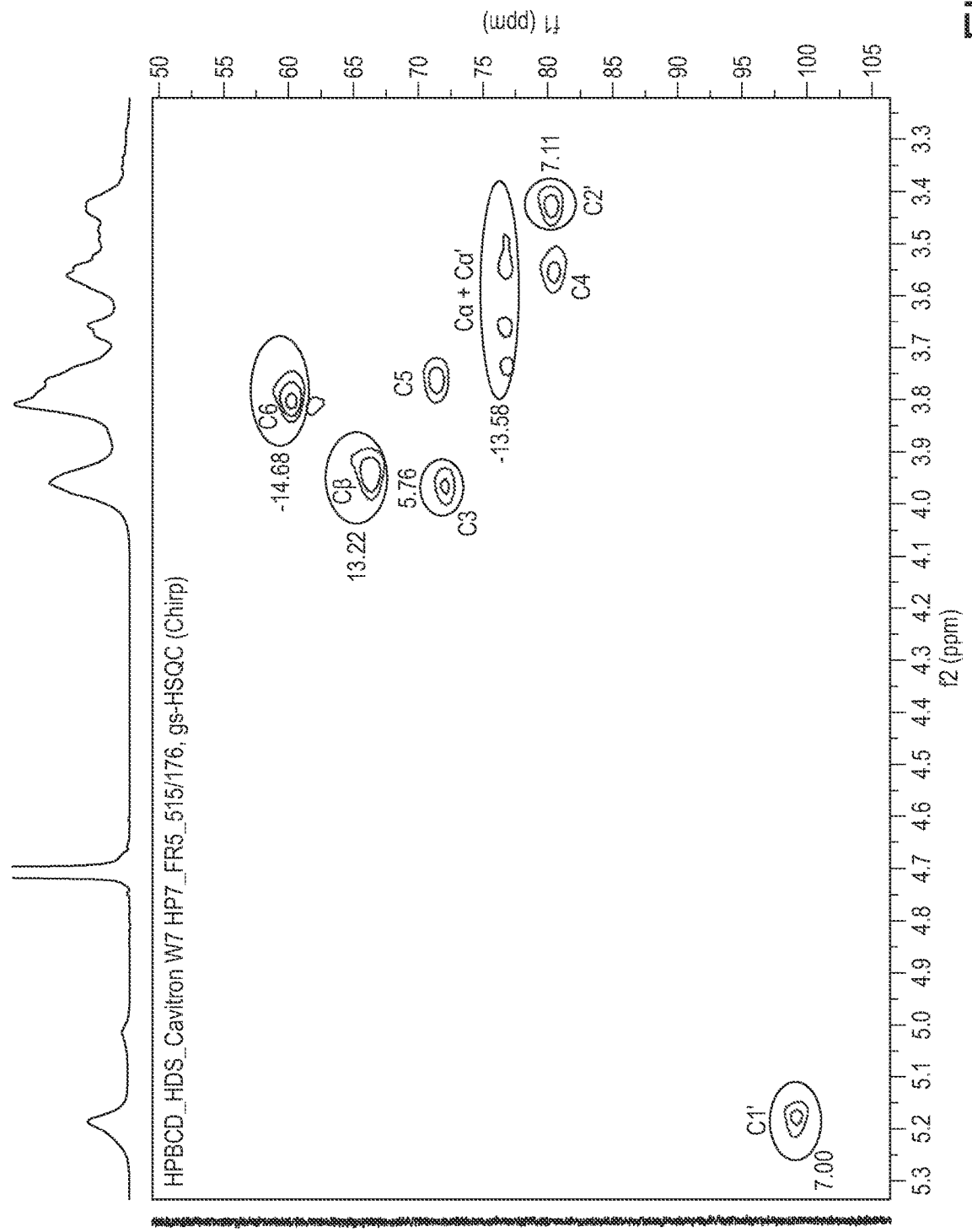
FIG. 27 is a DEPT-ed HSQC spectrum of the fifth HDS fraction of a mixture of hydroxypropyl-β-cyclodextrin of the present disclosure.

The position of the substitutions in the mixture isomerically-purified hydroxypropyl-β-cyclodextrin molecules of may be determined using methods known to those having skill in the art. In some embodiments the composition may be characterized by 1H-NMR. In some aspects, $^1$H-NMR may be used to determine the degree of substitution of the composition. An exemplary 1H-NMR spectrum is provided in FIG. 26. In some embodiments, the composition may be characterized by DEPT-ed HSQC. An exemplary DEPT-ed HSQC spectrum is provided in FIG. 27.

In some embodiments, about 15% to about 21% of the hydroxypropyl substitutions in the hydroxypropyl-β-cyclodextrin molecules may be located at the 3-O-position. In some aspects, the percentage of substitutions in the mixture of the hydroxypropyl-β-cyclodextrin molecules at the 3-O— position may be about 15% to about 16%, about 16% to about 17%, about 17% to about 18%, about 18% to about 19%, about 19% to about 20%, or about 20% to about 21%. In some additional aspects, the percentage of substitutions in the mixture of hydroxypropyl-β-cyclodextrin molecules at the 3-O— position may be about 15% to about 17%, about 15% to about 18%, about 15% to about 19%, about 15% to about 20%, about 16% to about 21%, about 17% to about 21%, about 18% to about 21%, about 19% to about 21%, about 16% to about 20%, or about 17% to about 19%. In an exemplary embodiment, the percentage of substitutions in the mixture of hydroxypropyl-β-cyclodextrin molecules at the 3-O— position is about 17.57%.

In some embodiments, about 79% to about 85% of the hydroxypropyl substitutions in the hydroxypropyl-β-cyclodextrin molecules are located at the 2-O-position. In some aspects, the percentage of substitutions in the mixture of hydroxypropyl-β-cyclodextrin molecules at the 2-O— position is about 79% to about 80%, about 80% to about 81%, about 81% to about 82%, about 82% to about 83%, about 83% to about 84%, or about 84% to about 85%. In some additional aspects, the percentage of substitutions in the mixture of hydroxypropyl-β-cyclodextrin molecules at the 2-O— position is about 79% to about 81%, about 79% to about 82%, about 79% to about 83%, about 79% to about 84%, about 80% to about 85%, about 81% to about 85%, about 82% to about 85%, about 83% to about 85%, about 80% to about 84%, or about 81% to about 83%. In an exemplary embodiment, the percentage of substitutions in the mixture of hydroxypropyl-β-cyclodextrin molecules at the 2-O— position is about 82.43%.

In some embodiments, the percentage of substitutions in the mixture of hydroxypropyl-β-cyclodextrin molecules at the 6-O— position is about 0%.

Figure 28:
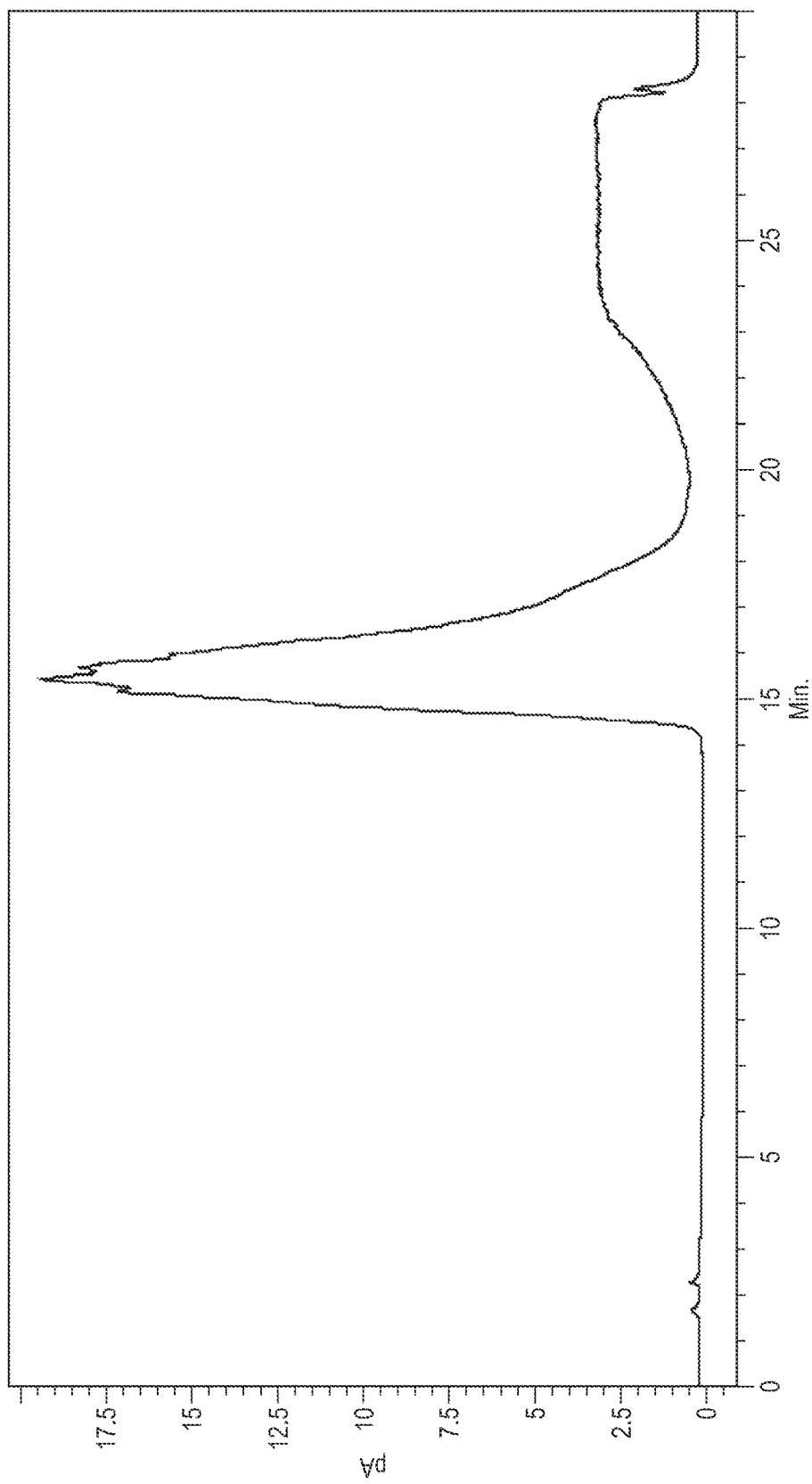
FIG. 28 is an HPLC-CAD chromatogram of the fifth HDS fraction of a mixture of hydroxypropyl-β-cyclodextrins of the present disclosure.

In some embodiments, the composition may have an HPLC-CAD chromatogram of FIG. 28. In some aspects, the mean retention time of the composition may be about 14.5 minutes to about 16.5 minutes as measured by HPLC-CAD. In some additional aspects, the mean retention time of the composition may be about 14.5, 14.6, 14.7, 14.8, 14.9, 15.0, 15.1, 15.2, 15.3, 15.4, 15.5, 15.6, 15.7, 15.8, 15.9, 16.0, 16.1, 16.2, 16.3, 16.4, or about 16.5 minutes. In an exemplary embodiment, the mean retention time is about 15.4 minutes.

In some embodiments, the composition may have a −ESI-MS spectrum with peaks at about 770 m/z, about 798 m/z, about 828 m/z, about 857 m/z, and about 885 m/z. In some embodiments, the composition may have a +ESI-MS spectrum with peaks at about 803 m/z, about 831 m/z, about 861 m/z, about 889 m/z, and at about 919 m/z. In an exemplary embodiment, the composition has the ESI-MS spectra shown in FIG. 29.

The hydroxypropyl-β-cyclodextrin percent may be based upon an area percentage from a MALDI-TOF-MS spectrum. In some embodiments, the composition may have a MALDI-TOF-MS spectrum with peaks at about 1614 m/z, about 1673 m/z, about 1733 m/z, about 1792 m/z, about 1852 m/z, about 1916 m/z, and at about 1971 m/z. In an exemplary embodiment, the composition has the MALDI-TOF-MS spectrum shown in FIG. 30. In an exemplary embodiment, the composition has a MALDI-TOF-MS spectrum wherein the area of DS-8 is 8.53%, the area of DS-9 is 21.33%, the area of DS-10 is 26.58%, the area of DS-11 is 20.90%, the area of DS-12 is 13.31%, the area of DS-13 is 6.74%, and the area of DS-14 is about 2.60%.

In some embodiments, when the degree of substitution is greater than 7, each of the 2-O— positions in the hydroxypropyl β-cyclodextrin may be substituted with a hydroxypropyl group or with an oligomerized side chain. As the degree of substitution increases from seven, the number of substitutions at the 3-O— position may increase and/or the hydroxypropyl groups already present at the 2-O— positions become oligomerized. In some aspects, each of the hydroxypropyl β-cyclodextrin molecules may be substituted exclusively at the 2-O— position when the degree of substitution is greater than 7 i.e., the 3-O— and 6-O— positions are unsubstituted.

In an exemplary embodiment, the mixture of hydroxypropyl β-cyclodextrin molecules comprises a molecule of Formula I:

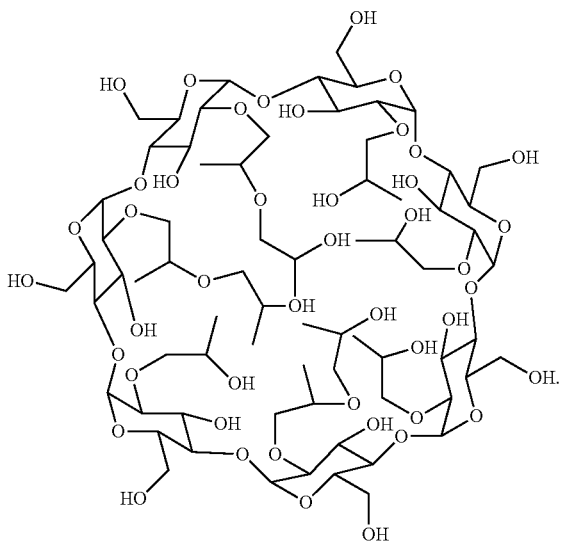

Formula I

As can be seen in the above Formula, the molecule of Formula I is substituted exclusively at the 2-O— position.

Without wishing to be bound by theory, the lower solubility of Fraction 5 as compared to unfractionated hydroxypropyl β-cyclodextrin may exhibit a longer half-life when administered to a subject. This may have benefits compared to administering unfractionated hydroxypropyl β-cyclodextrin because the Fraction 5 may be able to form inclusion complexes with more cholesterol molecules over a longer period of time as compared to unfractionated hydroxypropyl β-cyclodextrin.

In some embodiments, the half-life of Fraction 5 may be about 120% to about 300% of the half-life of unfractionated hydroxypropyl β-cyclodextrin. In some aspects, the half-life of Fraction 5 may be about 120% to about 150%, about 150% to about 200%, about 200% to about 250%, or about 250% to about 300% of the half-life of unfractionated hydroxypropyl β-cyclodextrin. In some additional aspects, the half-life of Fraction 5 may be about 120% to about 200%, about 120% to about 250%, about 150% to about 250%, about 150% to about 300%, or about 200% to about 300%, or about 300% to about 500% of the half-life of unfractionated hydroxypropyl β-cyclodextrin.

Regioisomers of Hydroxypropyl-β-Cyclodextrin

Further provided herein are isomerically-purified compositions comprising a mixture of hydroxypropyl-β-cyclodextrin molecules having the general subunit structure:

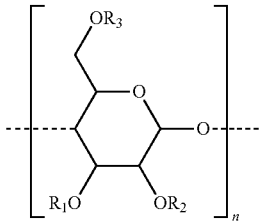

wherein n=7=m+k+y+z, m is a number between 0 to 7, k is a number between 0 to 7, y is a number between 0 to 7, and z is a number between 0 to 7, and wherein $R_1$, $R_2$, and $R_3$ are each independently hydrogen (H), hydroxypropyl, or an oligomerized hydroxypropyl group, such as the following structure:

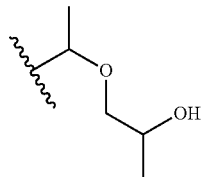 [SMILES: *C(C)OCC(C)O]

The letter m refers to the number of subunits in the mixture of hydroxypropyl-β-cyclodextrin molecules wherein $R_1$ is not H, $R_2$ is H, and $R_3$ is H. In other words, m refers to the number of subunits substituted at the 2-O— position of the subunit.

The letter k refers to the number of subunits in the mixture of hydroxypropyl-β-cyclodextrin molecules wherein $R_1$ is H, $R_2$ is not H, and $R_3$ is H. In other words, k refers to the number of subunits substituted at the 3-O— position of the subunit.

The letter y refers to the number of subunits in the mixture of hydroxypropyl-β-cyclodextrin molecules wherein $R_1$ is H, $R_2$ is H, and $R_3$ is not H. In other words, y refers to the number of subunits substituted at the 6-O— position of the subunit. In some embodiments, y may be 0.

The letter z refers to the number of subunits in the mixture of hydroxypropyl-β-cyclodextrin molecules wherein $R_1$ is H, $R_2$ is H, and $R_3$ is H. In other words, z refers to the number of subunits that are unsubstituted. In some embodiments, z may be 0, such as in a composition wherein the mixture of hydroxypropyl-β-cyclodextrin molecules has an average degree of substitution of 7 or greater.

In some embodiments, the subunit structure may have the following stereochemistry:

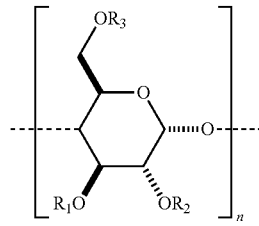

In some embodiments, $R_3$ may be H in at least 80% of the hydroxypropyl-β-cyclodextrin subunits. In some aspects, $R_3$ may be H in at least 80%, 81%, 82%, 83%, 84%, 85%, 86%, 87%, 88%, 89%, 90%, 91%, 92%, 93%, 94%, 95%, 96%, 97%, 98%, 99%, or at least 99.9% of the hydroxypropyl-β-cyclodextrin subunits. In an exemplary embodiment, $R_3$ may be H in 100% of the hydroxypropyl-β-cyclodextrin subunits.

In some embodiments, $R_1$ may not be H in at least 35% of the hydroxypropyl-β-cyclodextrin subunits. In some aspects, $R_1$ may not be H in at least 35%, 36%, 37%, 38%, 39%, or 40% of the hydroxypropyl-β-cyclodextrin subunits.

In some embodiments, $R_1$ may not be H in about 50% to about 70% of the hydroxypropyl-β-cyclodextrin subunits. In some aspects, $R_1$ may not be H in about 50% to about 55% of the subunits, about 55% to about 60% of the subunits, about 60% to about 65% of the subunits, or about 65% to about 70% of the subunits. In some additional aspects, $R_1$ may not be H in about 50% to about 60% of the subunits, about 50% to about 65% of the subunits, about 55% to about 65% of the subunits, about 55% to about 70% of the subunits, or about 60% to about 70% of the subunits.

In some embodiments, $R_1$ may not be H in about 60% to about 80% of the hydroxypropyl-β-cyclodextrin subunits. In some aspects, $R_1$ may not be H in about 60% to about 65% of the subunits, about 65% to about 70% of the subunits, about 70% to about 75% of the subunits, or about 75% to about 80% of the subunits. In some additional aspects, $R_1$ may not be H in about 60% to about 70% of the subunits, about 60% to about 75% of the subunits, about 65% to about 75% of the subunits, about 65% to about 80% of the subunits, or about 70% to about 80% of the subunits.

In some embodiments, $R_1$ may not be H in about 65% to about 85% of the hydroxypropyl-β-cyclodextrin subunits. In some aspects, $R_1$ may not be H in about 65% to about 70% of the subunits, about 70% to about 75% of the subunits, about 75% to about 80% of the subunits, or about 80% to about 85% of the subunits. In some additional aspects, $R_1$ may not be H in about 65% to about 75% of the subunits, about 65% to about 80% of the subunits, about 70% to about 80% of the subunits, about 70% to about 85% of the subunits, or about 75% to about 85% of the subunits.

In some embodiments, $R_1$ may not be H in about 70% to about 90% of the hydroxypropyl-β-cyclodextrin subunits. In some aspects, $R_1$ may not be H in about 70% to about 75% of the subunits, about 75% to about 80% of the subunits, about 80% to about 85% of the subunits, or about 85% to about 90% of the subunits. In some additional aspects, $R_1$ may not be H in about 70% to about 80% of the subunits, about 70% to about 85% of the subunits, about 75% to about 85% of the subunits, or about 80% to about 90% of the subunits.

In some embodiments, $R_2$ may not be H in no more than 65% of the hydroxypropyl-β-cyclodextrin subunits. In some aspects, $R_2$ may not be H in no more than 65%, 64%, 63%, 62%, 61%, or 60% of the hydroxypropyl-β-cyclodextrin subunits.

In some embodiments, $R_2$ may not be H in about 35% to about 55% of the hydroxypropyl-β-cyclodextrin subunits. In some aspects, $R_2$ may not be H in about 35% to about 40% of the subunits, about 40% to about 45% of the subunits, about 45% to about 50% of the subunits, or about 50% to about 55% of the subunits. In some additional aspects, $R_2$ may not be H in about 35% to about 45% of the subunits, about 35% to about 50% of the subunits, about 40% to about 50% of the subunits, about 40% to about 55% of subunits, or about 45% to about 55% of the subunits.

In some embodiments, $R_2$ may not be H in about 30% to about 50% of the hydroxypropyl-β-cyclodextrin subunits. In some aspects, $R_2$ may not be H in about 30% to about 35% of the subunits, about 35% to about 40% of the subunits, about 40% to about 45% of the subunits, or about 45% to about 50% of the subunits. In some additional aspects, $R_2$ may not be H in about 30% to about 40% of the subunits, about 30% to about 45% of the subunits, about 35% to about 45% of the subunits, about 35% to about 50% of the subunits, or about 40% to about 50% of the subunits.

In some embodiments, $R_2$ may not be H in about 20% to about 40% of the hydroxypropyl-β-cyclodextrin subunits. In some aspects, $R_2$ may not be H in about 20% to about 25% of the subunits, about 25% to about 30% of the subunits, about 30% to about 35% of the subunits, or about 35% to about 40% of the subunits. In some additional aspects, $R_2$ may not be H in about 20% to about 30% of the subunits, about 20% to about 35% of the subunits, about 25% to about 35% of the subunits, about 25% to about 40% of the subunits, or about 30% to about 40% of the subunits.

In some embodiments, $R_2$ may not be H in about 10% to about 30% of the hydroxypropyl-β-cyclodextrin subunits. In some aspects, $R_2$ may not be H in about 10% to about 15% of the subunits, about 15% to about 20% of the subunits, about 20% to about 25% of the subunits, or about 25% to about 30% of the subunits. In some additional aspects, $R_2$ may not be H in about 10% to about 20% of the subunits, about 10% to about 25% of the subunits, about 15% to about 25% of the subunits, about 15% to about 40% of the subunits, or about 20% to about 30% of the subunits.

Further, the subunit structure may have the following stereochemistry:

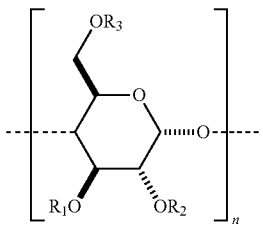

In some embodiments, $R_3$ may be H in at least 80% of the hydroxypropyl-β-cyclodextrin subunits. In some aspects, $R_3$ may be H in at least 80%, 81%, 82%, 83%, 84%, 85%, 86%, 87%, 88%, 89%, 90%, 91%, 92%, 93%, 94%, 95%, 96%, 97%, 98%, 99%, or at least 99.9% of the hydroxypropyl-β-cyclodextrin subunits. In an exemplary embodiment, $R_3$ may be H in 100% of the hydroxypropyl-β-cyclodextrin subunits.

In some embodiments, $R_2$ may not be H in at least 35% of the hydroxypropyl-β-cyclodextrin subunits. In some aspects, $R_2$ may not be H in at least 35%, 36%, 37%, 38%, 39%, or 40% of the hydroxypropyl-β-cyclodextrin subunits.

In some embodiments, $R_2$ may not be H in about 50% to about 70% of the hydroxypropyl-β-cyclodextrin subunits. In some aspects, $R_2$ may not be H in about 50% to about 55% of the subunits, about 55% to about 60% of the subunits, about 60% to about 65% of the subunits, or about 65% to about 70% of the subunits. In some additional aspects, $R_2$ may not be H in about 50% to about 60% of the subunits, about 50% to about 65% of the subunits, about 55% to about 65% of the subunits, about 55% to about 70% of the subunits, or about 60% to about 70% of the subunits.

In some embodiments, $R_2$ may not be H in about 60% to about 80% of the hydroxypropyl-β-cyclodextrin subunits. In some aspects, $R_2$ may not be H in about 60% to about 65% of the subunits, about 65% to about 70% of the subunits, about 70% to about 75% of the subunits, or about 75% to about 80% of the subunits. In some additional aspects, $R_2$ may not be H in about 60% to about 70% of the subunits, about 60% to about 75% of the subunits, about 65% to about 75% of the subunits, about 65% to about 80% of the subunits, or about 70% to about 80% of the subunits.

In some embodiments, $R_2$ may not be H in about 65% to about 85% of the hydroxypropyl-β-cyclodextrin subunits. In some aspects, $R_2$ may not be H in about 65% to about 70% of the subunits, about 70% to about 75% of the subunits, about 75% to about 80% of the subunits, or about 80% to about 85% of the subunits. In some additional aspects, $R_2$ may not be H in about 65% to about 75% of the subunits, about 65% to about 80% of the subunits, about 70% to about 80% of the subunits, about 70% to about 85% of the subunits, or about 75% to about 85% of the subunits.

In some embodiments, $R_2$ may not be H in about 70% to about 90% of the hydroxypropyl-β-cyclodextrin subunits. In some aspects, $R_2$ may not be H in about 70% to about 75% of the subunits, about 75% to about 80% of the subunits, about 80% to about 85% of the subunits, or about 85% to about 90% of the subunits. In some additional aspects, $R_2$ may not be H in about 70% to about 80% of the subunits, about 70% to about 85% of the subunits, about 75% to about 85% of the subunits, about 75% to about 90% of the subunits, or about 80% to about 90% of the subunits.

In some embodiments, $R_1$ may not be H in no more than 65% of the hydroxypropyl-β-cyclodextrin subunits. In some aspects, $R_1$ may not be H in no more than 65%, 64%, 63%, 62%, 61%, or 60% of the hydroxypropyl-β-cyclodextrin subunits.

In some embodiments, $R_1$ may not be H in about 35% to about 55% of the hydroxypropyl-β-cyclodextrin subunits. In some aspects, $R_1$ may not be H in about 35% to about 40% of the subunits, about 40% to about 45% of the subunits, about 45% to about 50% of the subunits, or about 50% to about 55% of the subunits. In some additional aspects, $R_1$ may not be H in about 35% to about 45% of the subunits, about 35% to about 50% of the subunits, about 40% to about 50% of the subunits, about 40% to about 55% of subunits, or about 45% to about 55% of the subunits.

In some embodiments, $R_1$ may not be H in about 30% to about 50% of the hydroxypropyl-β-cyclodextrin subunits. In some aspects, $R_1$ may not be H in about 30% to about 35% of the subunits, about 35% to about 40% of the subunits, about 40% to about 45% of the subunits, or about 45% to about 50% of the subunits. In some additional aspects, $R_1$ may not be H in about 30% to about 40% of the subunits, about 30% to about 45% of the subunits, about 35% to about 45% of the subunits, about 35% to about 50% of the subunits, or about 40% to about 50% of the subunits.

In some embodiments, $R_1$ may not be H in about 20% to about 40% of the hydroxypropyl-β-cyclodextrin subunits. In some aspects, $R_1$ may not be H in about 20% to about 25% of the subunits, about 25% to about 30% of the subunits, about 30% to about 35% of the subunits, or about 35% to about 40% of the subunits. In some additional aspects, $R_1$ may not be H in about 20% to about 30% of the subunits, about 20% to about 35% of the subunits, about 25% to about 35% of the subunits, about 25% to about 40% of the subunits, or about 30% to about 40% of the subunits.

In some embodiments, $R_1$ may not be H in about 10% to about 30% of the hydroxypropyl-β-cyclodextrin subunits. In some aspects, $R_1$ may not be H in about 10% to about 15% of the subunits, about 15% to about 20% of the subunits, about 20% to about 25% of the subunits, or about 25% to about 30% of the subunits. In some additional aspects, $R_1$ may not be H in about 10% to about 20% of the subunits, about 10% to about 25% of the subunits, about 15% to about 25% of the subunits, about 15% to about 40% of the subunits, or about 20% to about 30% of the subunits.

Further provided herein is an isomerically-purified composition including a mixture of hydroxypropyl-β-cyclodextrin molecules, wherein 0% to 5% of the hydroxypropyl-β-cyclodextrin subunits are substituted at the 6-O— position. In some aspects, the percentage of hydroxypropyl-β-cyclodextrin subunits substituted at the 6-O-position may be about 0% to about 1%, about 1% to about 2%, about 2% to about 3%, about 3% to about 4%, or about 4% to about 5%. In some additional aspects, the percentage of hydroxypropyl-β-cyclodextrin subunits substituted at the 6-O— position may be about 0% to about 2%, about 0% to about 3%, about 0% to about 4%, or about 0% to about 5%.

Further provided herein is an isomerically-purified composition including a mixture of hydroxypropyl-β-cyclodextrin molecules, wherein about 80% to about 100% of the hydroxypropyl-β-cyclodextrin subunits are substituted at the 2-O-position, the 3-O— position, or a combination thereof. In some aspects, the percentage of hydroxypropyl-β-cyclodextrin subunits substituted at the 2-O— position, the 3-O— position, or a combination thereof is about 80% to about 85%, about 85% to about 90%, about 90% to about 95%, or about 95% to about 100%. In some additional aspects, the percentage of hydroxypropyl-β-cyclodextrin subunits substituted at the 2-O— position, the 3-O— position, or a combination thereof is about 80% to about 90%, about 80% to about 95%, about 85% to about 95%, about 85% to about 100%, or about 90% to about 100%.

In some embodiments of the present invention, the isomerically-purified compositions including a mixture of hydroxypropyl-β-cyclodextrin molecules (e.g. regioisomers) have an increased ability to solubilize and/or dissolve cholesterol crystals. Surprisingly, for example, an isomerically-purified composition including a mixture of hydroxypropyl-β-cyclodextrin molecules, wherein about 80% to about 100% of the hydroxypropyl-β-cyclodextrin subunits are substituted at the 2-O— position, provides a substantially increased cholesterol solubilizing potential as compared to mixture of hydroxypropyl-β-cyclodextrin molecules having fewer substitutions at the 2-O— position (e.g., 50% or less). In addition, an isomerically-purified composition including a mixture of hydroxypropyl-β-cyclodextrin molecules, wherein about 80% to about 100% of the hydroxypropyl-β-cyclodextrin subunits are substituted at the 2-O— position provides a substantially increased cholesterol solubilizing potential as compared to mixture of hydroxypropyl-β-cyclodextrin molecules wherein about 80% to about 100% of the hydroxypropyl-β-cyclodextrin subunits are substituted at the 3-O— position, 6-O-position, or a combination thereof. Further, an isomerically-purified composition including a mixture of hydroxypropyl-β-cyclodextrin molecules, wherein about 80% to about 100% of the hydroxypropyl-β-cyclodextrin subunits are substituted at the 2-O— position, the 3-O-position, or a combination thereof, provides a substantially increased cholesterol solubilizing potential as compared to mixture of hydroxypropyl-β-cyclodextrin molecules having fewer substitutions at the 2-O— position, the 3-O— position, or a combination thereof. Likewise, an isomerically-purified composition including a mixture of hydroxypropyl-β-cyclodextrin molecules, wherein about 80% to about 100% of the hydroxypropyl-β-cyclodextrin subunits are substituted at the 2-O— position, the 3-O— position, or a combination thereof, provides a substantially increased cholesterol solubilizing potential as compared to mixture of hydroxypropyl-β-cyclodextrin molecules wherein about 80% to about 100% of the hydroxypropyl-β-cyclodextrin subunits are substituted at the 6-O-position. An isomerically-purified composition including a mixture of hydroxypropyl-β-cyclodextrin molecules, wherein about 80% to about 100% of the hydroxypropyl-β-cyclodextrin subunits are substituted at the 2-O— position, provides a substantially increased cholesterol solubilizing potential as compared to non-isomerically purified mixture of hydroxypropyl-β-cyclodextrin molecules. In yet another aspect, an isomerically-purified composition including a mixture of hydroxypropyl-β-cyclodextrin molecules, wherein about 80% to about 100% of the hydroxypropyl-β-cyclodextrin subunits are substituted at the 2-O— position, the 3-O— position, or a combination thereof, provides a substantially increased cholesterol solubilizing potential as compared to non-isomerically purified mixture of hydroxypropyl-β-cyclodextrin molecules. Examples of non-isomerically purified mixtures of hydroxypropyl-β-cyclodextrin molecules includes any selected from the group consisting of: Kleptose® HP Parenteral Grade, Kleptose® HPB Parenteral Grade, Kleptose® HPB-LB Parenteral Grade, Cavitron® W7 HP5 Pharma cyclodextrin, Cavitron® W7 HP7 Pharma cyclodextrin, Trappsol® Cyclo™, and VTS-270/adrabetadex, and combinations thereof. The substantially increased cholesterol solubilizing potential may be about 25% to about 500% greater, about 25% to about 50% greater, about 75% to about 100% greater, about 100% to about 150% greater, about 150% to about 200% greater, about 200% to about 300% greater, about 300% to about 400% greater, or about 400% to about 500% greater than the solubilizing potential of non-isomerically purified mixtures of hydroxypropyl-β-cyclodextrin molecules when measured in mg/mL at 37° C. The identification of specific regioisomers having increased ability to solubilize and/or dissolve cholesterol crystals of the individual is highly unexpected. Without being bound by theory, a mixture of hydroxypropyl-β-cyclodextrin molecules having the highest percentage of substitutions at the 2-O— position may have the greatest ability to solubilize and/or dissolve cholesterol crystals, followed by a mixture of hydroxypropyl-β-cyclodextrin molecules having the highest percentage of substitutions at a combination of the 2-O— position and 3-0 position. Therefore, in some aspects, the percentage of hydroxypropyl-β-cyclodextrin subunits substituted at the 2-O— position may be about 50% to about 100%. For example, the percentage of hydroxypropyl-β-cyclodextrin subunits substituted at the 2-O— position may be from about 50% to about 60%, about 50% to about 70%, about 50% to about 80%, about 50% to about 90%, about 50% to about 100%, about 60% to about 100%, about 70% to about 100%, about 80% to about 100%, or about 90% to about 100%. In some additional aspects, the percentage of hydroxypropyl-β-cyclodextrin subunits substituted at the 2-O— position may be about 50%, 55%, 60%, 65%, 70%, 75%, 80%, 85%, 90%, 95%, 99%, or about 100%.

In some aspects, the percentage of hydroxypropyl-β-cyclodextrin subunits substituted exclusively at the 2-O—position may be about 50% to about 100%. For example, the percentage of hydroxypropyl-β-cyclodextrin subunits substituted exclusively at the 2-O-position may be from about 50% to about 60%, about 50% to about 70%, about 50% to about 80%, about 50% to about 90%, about 50% to about 100%, about 60% to about 100%, about 70% to about 100%, about 80% to about 100%, or about 90% to about 100%. In some additional aspects, the percentage of hydroxypropyl-β-cyclodextrin subunits substituted exclusively at the 2-O— position may be about 50%, 55%, 60%, 65%, 70%, 75%, 80%, 85%, 90%, 95%, 99%, or about 100%

In some embodiments, the cholesterol solubility potential of an isomerically-purified composition including a mixture of hydroxypropyl-β-cyclodextrin molecules may range from about 0.10 mg/mL to about 1.00 mg/mL, from about 0.20 mg/mL to about 0.90 mg/mL, from about 0.25 mg/mL to about 0.75 mg/mL, from about 0.30 mg/mL to about 0.60 mg/mL, from about 0.35 mg/mL to about 0.55 mg/mL, from about 0.40 mg/mL to about 0.50 mg/mL at 37° C. In some embodiments, the cholesterol solubility potential of an isomerically-purified composition including a mixture of hydroxypropyl-β-cyclodextrin molecules may range from about 0.25 mg/mL to about 30 mg/mL, from about 0.30 mg/mL to about 0.35 mg/mL, from about 0.35 mg/mL to about 0.40 mg/mL, from about 0.40 mg/mL to about 0.45 mg/mL, from about 0.45 mg/mL to about 0.50 mg/mL, from about 0.50 mg/mL to about 0.55 mg/mL from about 0.55 mg/mL to about 0.60 mg/mL, from about 0.55 mg/mL to about 0.60 mg/mL at 37° C.

In a further embodiment, the solubility or other chemical properties of the novel mixtures of hydroxypropyl-β-cyclodextrin molecules (e.g. fractions) disclosed may be herein may be utilized to create combinations of the fractions to selectively dial-in affinity for specific guest molecules.

Nanofiltration

Any of the mixtures or compositions described herein may be purified via nanofiltration to remove one or more impurities. The nanofiltration may remove impurities including, but not limited to, propylene oxide monomers, propylene oxide dimers, propylene oxide trimers, and/or propylene oxide tetramers, propylene glycol, and sodium chloride. By removing these impurities, the number of side effects or adverse events that occur after administration of the compositions or mixtures to a subject in need thereof may be reduced as compared to the administration of an unfiltered composition or mixture.

Provided herein are compositions comprising a purified mixture of β-cyclodextrin molecules substituted at one or more hydroxyl positions by hydroxypropyl groups. Before the mixture is purified via nanofiltration, the mixture may include one or more impurities, including but not limited to propylene oxide monomers, propylene oxide dimers, propylene oxide trimers, and/or propylene oxide tetramers, propylene glycol, and sodium chloride. After purification, at least 90% of the propylene oxide monomers, propylene oxide dimers, propylene oxide trimers, and/or propylene oxide tetramers, propylene glycol, and sodium chloride content is removed. Thus, as a non-limiting example, if the mixture of β-cyclodextrin molecules originally contained 1 ppm propylene oxide monomer before purification, the mixture of β-cyclodextrin molecules will contain at most 0.1 ppm propylene oxide monomer after purification.

Figure 53:
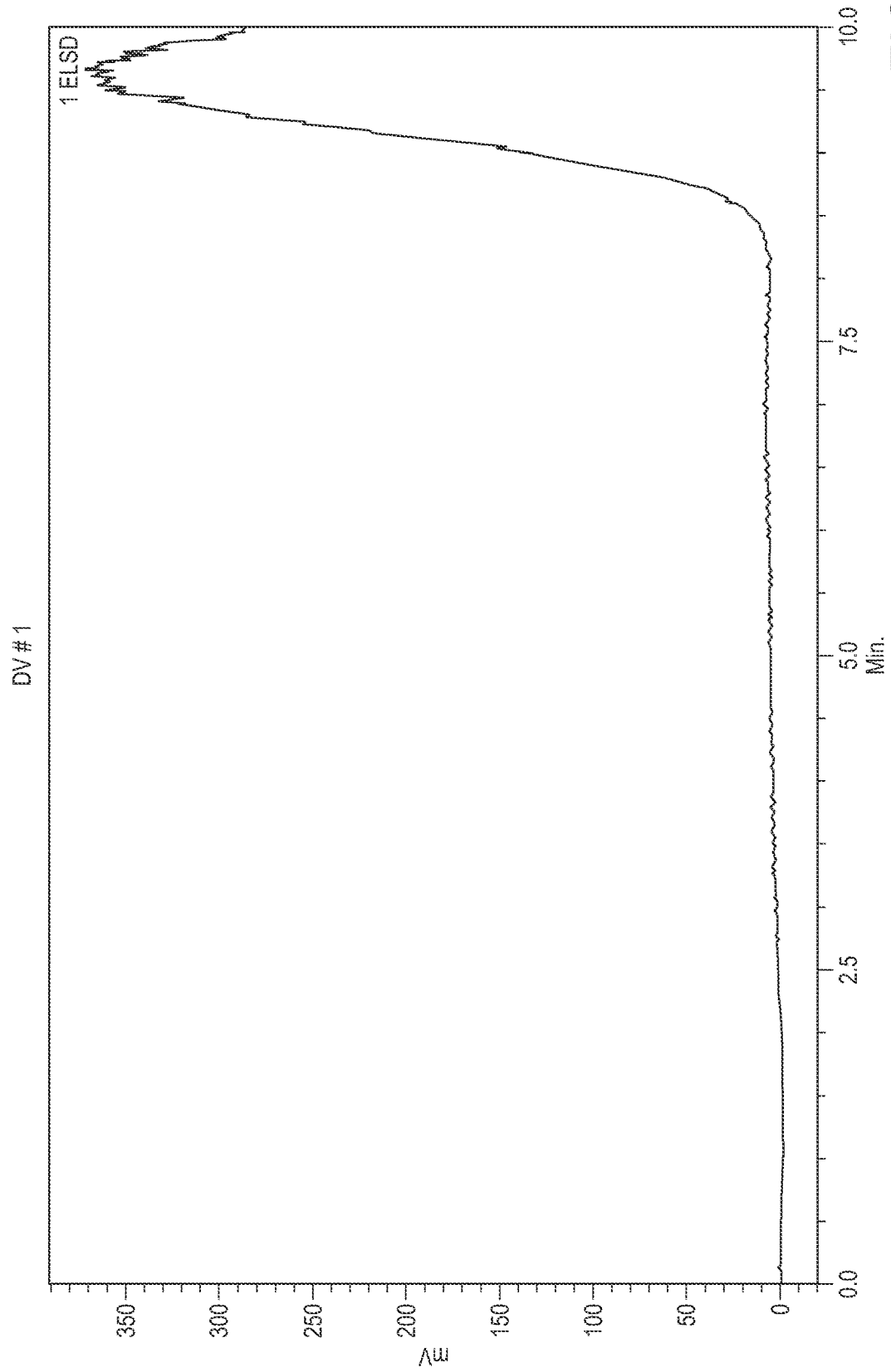
FIG. 53 shows a HPLC-ELSD spectrum of the retentate of the first diafiltration volume of Cavitron HP7.
Figure 54:
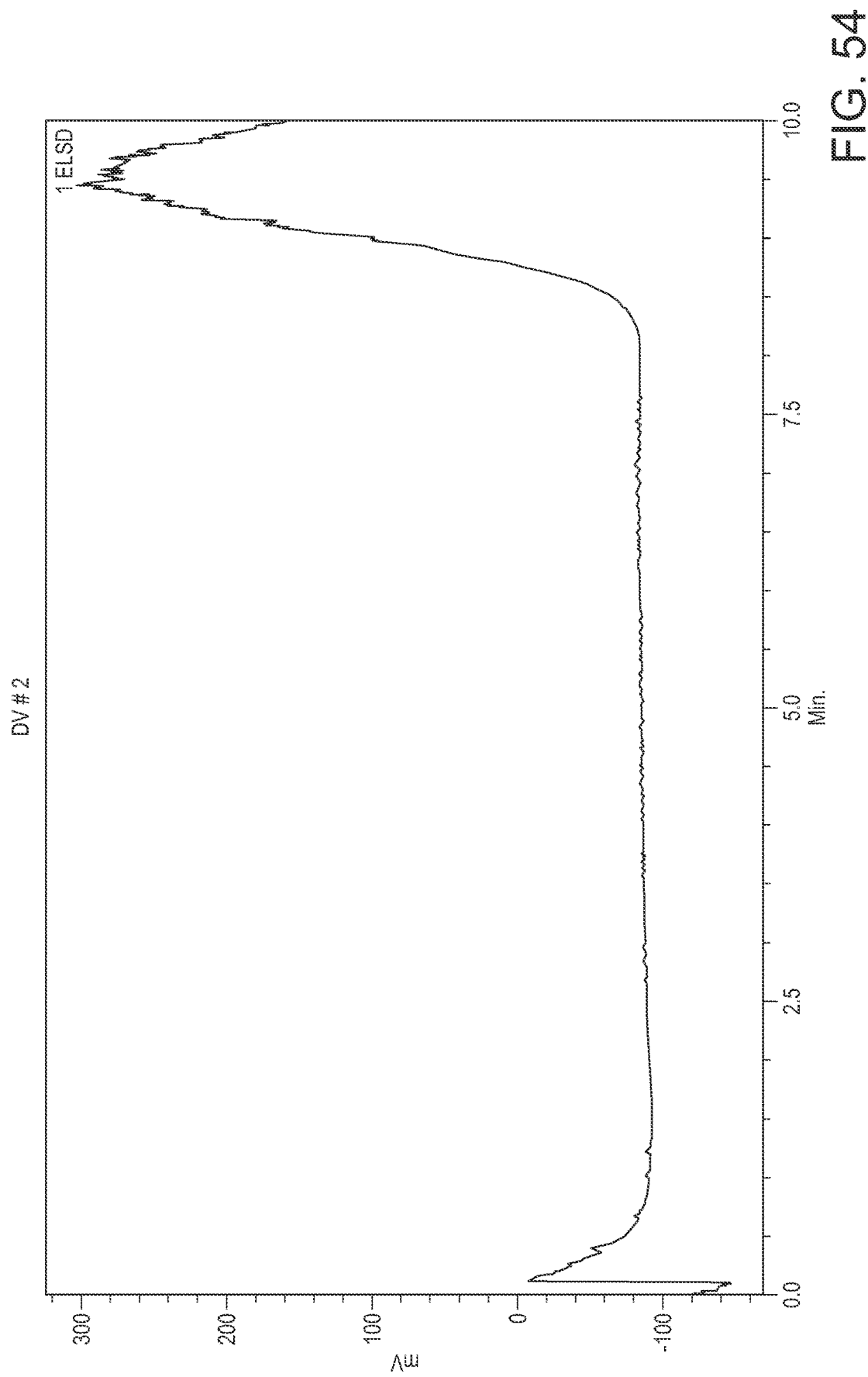
FIG. 54 shows a HPLC-ELSD spectrum of the retentate of the second diafiltration volume of Cavitron HP7.
Figure 55:
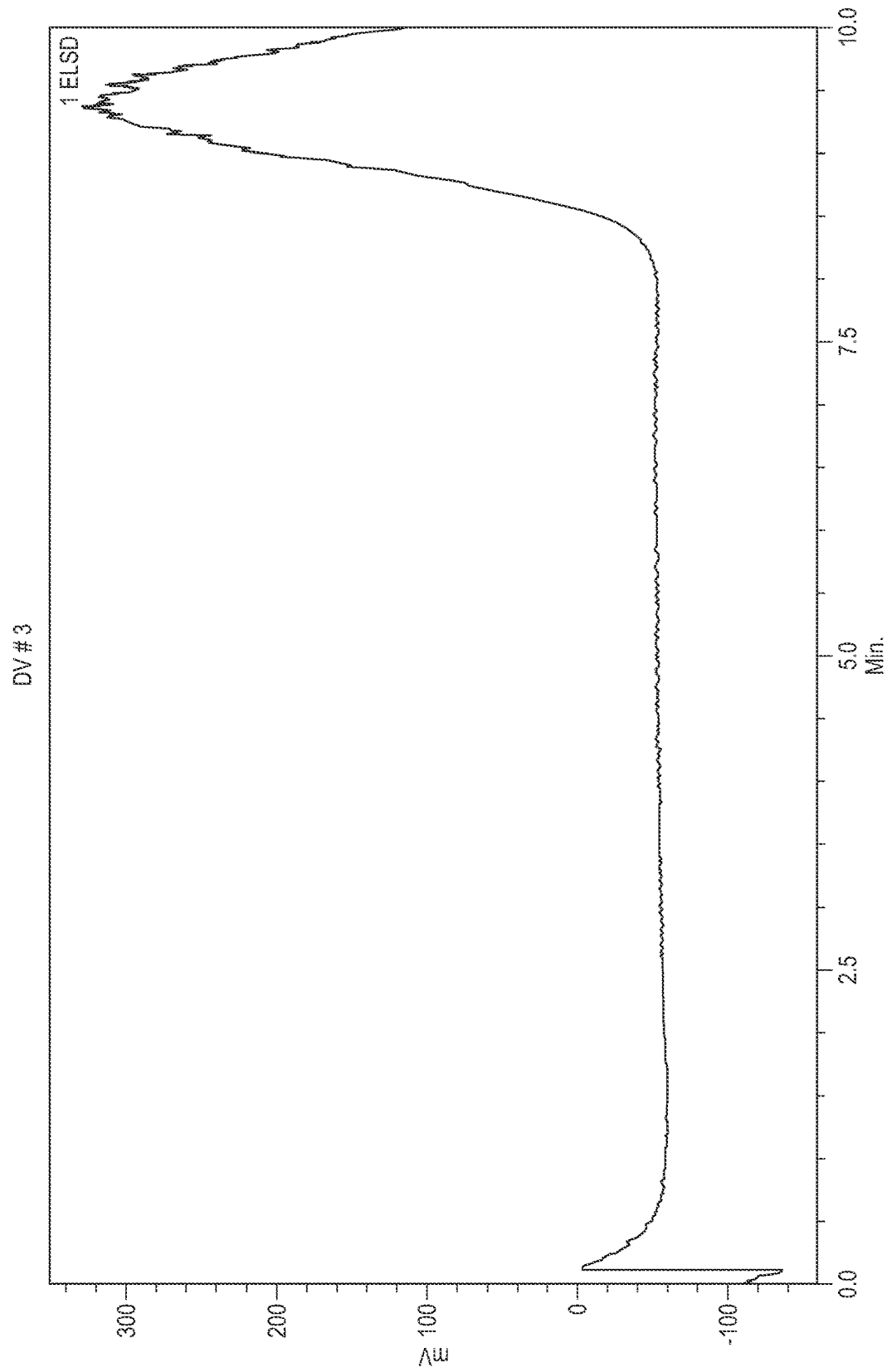
FIG. 55 shows a HPLC-ELSD spectrum of the retentate of the third diafiltration volume of Cavitron HP7.
Figure 56:
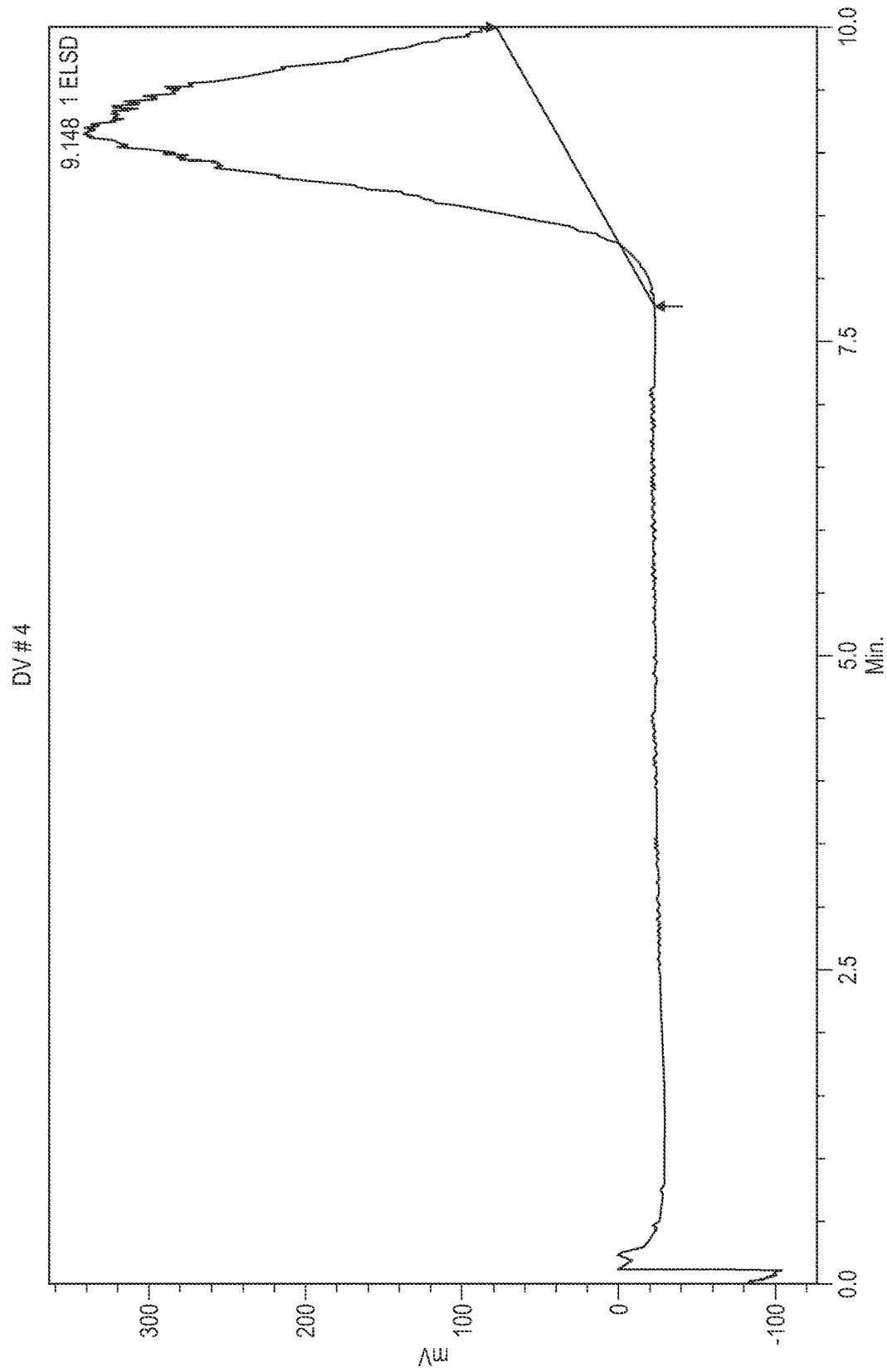
FIG. 56 shows a HPLC-ELSD spectrum of the retentate of the fourth diafiltration volume of Cavitron HP7.
Figure 57:
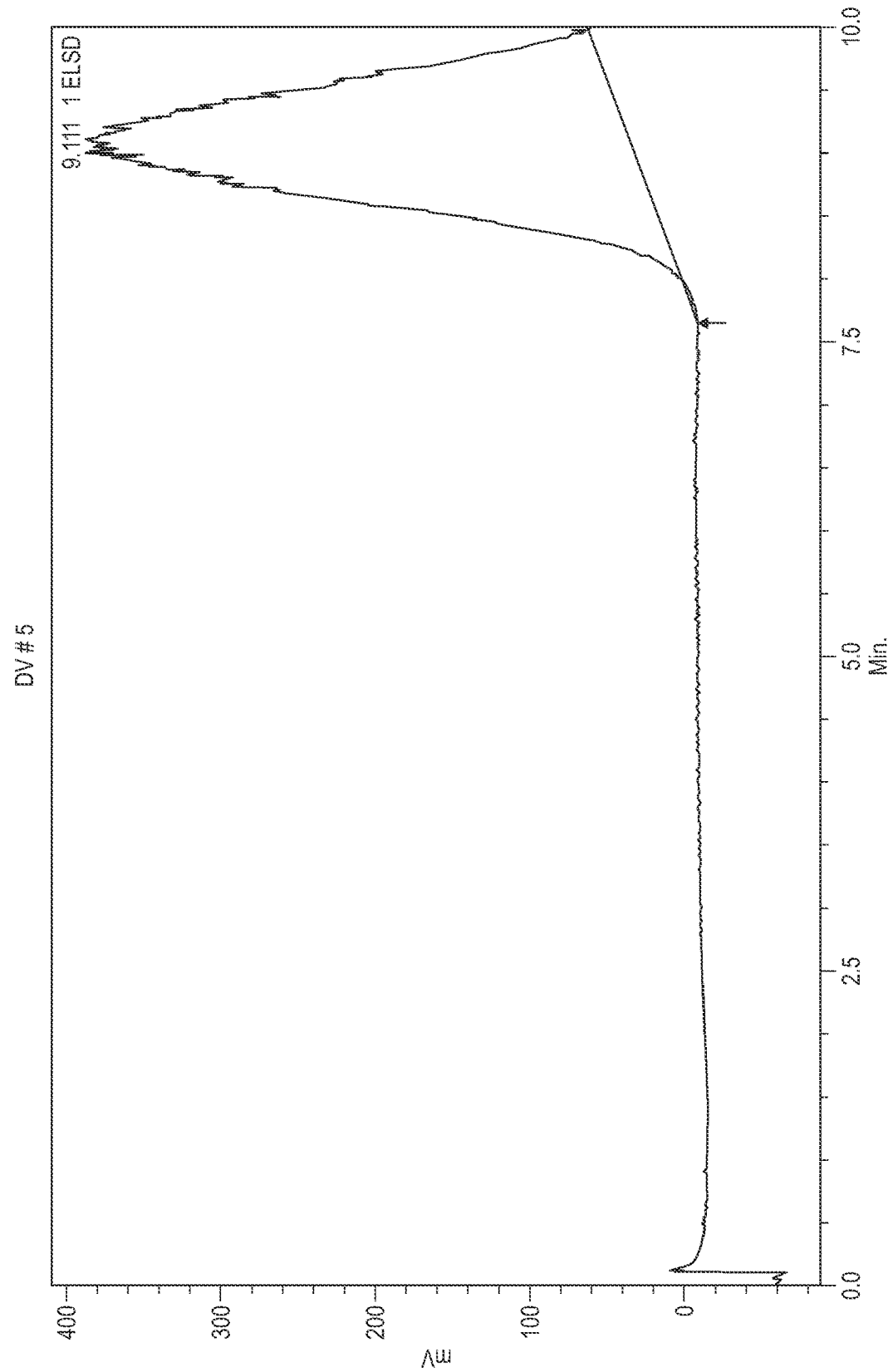
FIG. 57 shows a HPLC-ELSD spectrum of the retentate of the fifth diafiltration volume of Cavitron HP7.

In some embodiments, the mixture of β-cyclodextrin molecules that is purified may be one of the isomerically-purified mixtures of β-cyclodextrin molecules described herein above, including Fraction 1, Fraction 2, Fraction 3, Fraction 4, or Fraction 5 (e.g. HDS Fraction 1, 2, 3, 4, or 5). In embodiments wherein the mixture of β-cyclodextrin molecules that is purified is Fraction 1, the composition may have an HPLC-ELSD spectrum as depicted in FIG. 53. In embodiments wherein the mixture of β-cyclodextrin molecules that is purified is Fraction 2, the composition may have an HPLC-ELSD spectrum as depicted in FIG. 54. In embodiments wherein the mixture of β-cyclodextrin molecules that is purified is Fraction 3, the composition may have an HPLC-ELSD spectrum as depicted in FIG. 55. In embodiments wherein the mixture of β-cyclodextrin molecules that is purified is Fraction 4, the composition may have an HPLC-ELSD spectrum as depicted in FIG. 56. In embodiments wherein the mixture of β-cyclodextrin molecules that is purified is Fraction 5, the composition may have an HPLC-ELSD spectrum as depicted in FIG. 57.

Figure 47:
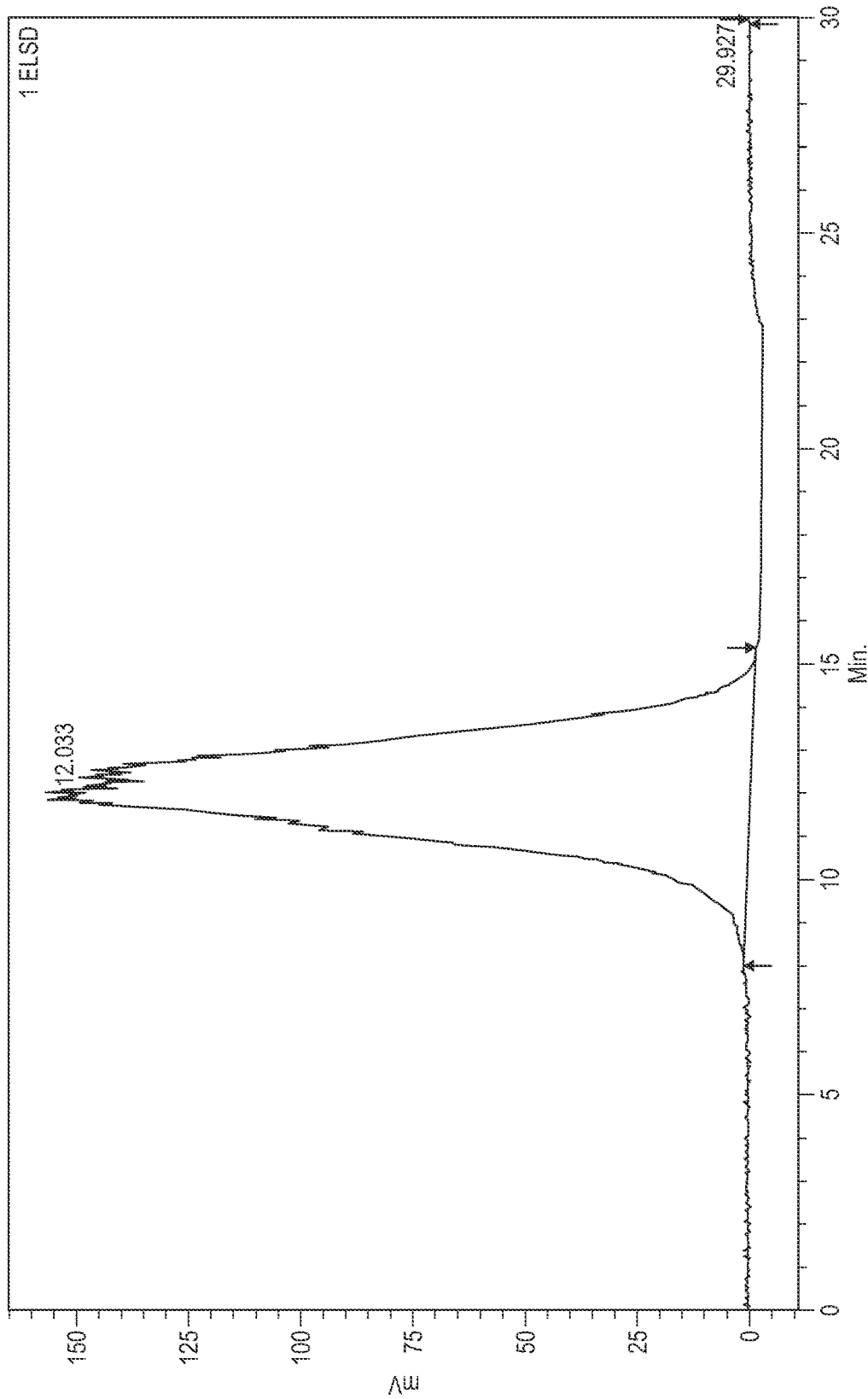
FIG. 47 shows a HPLC-ELSD spectrum of Cavitron HP7 after nanofiltration using the methods described herein.

In some embodiments, the mixture of β-cyclodextrin molecules that is purified may be a commercially-available mixture of β-cyclodextrin molecules substituted at one or more hydroxyl positions by hydroxypropyl groups. In some aspects, the commercially-available mixture of β-cyclodextrin molecules may have an average degree of substitution from about 4.0 to about 8.0, such as from about 4.0 to about 5.0, or from about 6.0 to about 8.0. In some examples, the commercially-available mixture of β-cyclodextrin molecules is Cavitron HP5, Cavitron HP7, and combinations thereof. In embodiments wherein the mixture of β-cyclodextrin molecules that is purified is Cavitron HP7, the composition may have an HPLC-ELSD spectrum substantially similar to the spectrum depicted in FIG. 47. As used herein "substantially similar" in reference to HPLC-ELSD spectra means that the mean retention time of the composition is ±15% the mean retention time of the spectrum provided herein. In embodiments wherein the mixture of β-cyclodextrin molecules that is purified is Cavitron HP5, the composition may have an HPLC-ELSD spectrum substantially similar to the spectra depicted in FIG. 62. In embodiments wherein the mixture of β-cyclodextrin molecules that is purified is Cavitron HP7, the composition may have a $^1$H-NMR spectrum substantially similar to the spectrum depicted in FIG. 48 as a product. As used herein "substantially similar" in reference to $^1$H-NMR spectra means that the mean retention time of the composition is ±15% the mean retention time of the spectrum provided herein. In embodiments wherein the mixture of β-cyclodextrin molecules that is purified is Cavitron HP5, the composition may have a $^1$H-NMR spectrum substantially similar to the spectrum depicted in FIG. 63 as a product. In other embodiments wherein the mixture of β-cyclodextrin molecules that is purified is Cavitron HP5, the composition may have a $^1$H-NMR spectrum substantially similar to the spectrum depicted in FIG. 64 as a product.

At least 90% of the propylene oxide monomers, propylene oxide dimers, propylene oxide trimers, and/or propylene oxide tetramers, propylene glycol, and sodium chloride content may be removed. In some embodiments, at least 91%, at least 92%, at least 93%, at least 94%, at least 95%, at least 96%, at least 97%, at least 98%, at least 99%, at least 99.5%, or at least 99.9% of the propylene oxide monomers, propylene oxide dimers, propylene oxide trimers, and/or propylene oxide tetramers, propylene glycol, and sodium chloride content may be removed. In a preferred embodiment, at least 95% of the propylene oxide monomers, propylene oxide dimers, propylene oxide trimers, and/or propylene oxide tetramers, propylene glycol, and sodium chloride content may be removed. In another preferred embodiment, at least 96% to at least 99% of the propylene oxide monomers, propylene oxide dimers, propylene oxide trimers, and/or propylene oxide tetramers, propylene glycol, and sodium chloride content is removed. In another preferred embodiment, at least 90% of the propylene oxide dimer content and at least 90% of the propylene oxide trimer content is removed. In another preferred embodiment, at least 96% to at least 99% of the propylene oxide dimer content and propylene oxide trimer content is removed. In another preferred embodiment, at least 90% to at least 95% of the propylene oxide tetramer content is removed.

In some embodiments, there is no detectable amount of propylene oxide monomers, propylene oxide dimers, propylene oxide trimers, and/or propylene oxide tetramers in the composition. In some embodiments, there is no detectable amount of propylene glycol in the composition.

In some embodiments, the purified mixture of β-cyclodextrin molecules has a solution concentration of about 25.0 wt % solids to about 35.0 wt % solids. In some aspects, the purified mixture of β-cyclodextrin molecules has a solution concentration from about 25.0 wt % solids to about 26.0 wt % solids, about 25.0 wt % solids to about 27.0 wt % solids, about 25.0 wt % solids to about 28.0 wt % solids, about 25.0 wt % solids to about 29.0 wt % solids, about 25.0 wt % solids to about 30.0 wt % solids, about 25.0 wt % solids to about 31.0 wt % solids, about 25.0 wt % solids to about 32.0 wt % solids, about 25.0 wt % solids to about 33.0 wt % solids, about 25.0 wt % solids to about 34.0 wt % solids, about 26.0 wt % solids to about 35.0 wt % solids, about 27.0 wt % solids to about 35.0 wt % solids, about 28.0 wt % solids to about 35.0 wt % solids, about 29.0 wt % solids to about 35.0 wt % solids, about 30.0 wt % solids to about 35.0 wt % solids, about 31.0 wt % solids to about 35.0 wt % solids, about 32.0 wt % solids to about 35.0 wt % solids, about 33.0 wt % solids to about 35.0 wt % solids, about 34.0 wt % solids to about 35.0 wt % solids, about 26.0 wt % solids to about 34.0 wt % solids, about 27.0 wt % solids to about 33.0 wt % solids, about 28.0 wt % solids to about 32.0 wt % solids, or about 29.0 wt % solids to about 31.0 wt % solids. In some additional aspects, the purified mixture of β-cyclodextrin molecules has a solution concentration of about 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, or about 35.0 wt % solids. In preferred embodiments, the purified mixture of β-cyclodextrin molecules has a solution concentration of about 25.0 wt % solids to about 35.0 wt % solids. In more preferred embodiments, the purified mixture of β-cyclodextrin molecules has a solution concentration of about 27.5 wt % solids to about 32.5 wt % solids. In even more preferred embodiments, the purified mixture of β-cyclodextrin molecules has a solution concentration of about 29.0 wt % solids to about 31.0 wt % solids.

In some embodiments, the composition may be nanofiltered at a temperature from about 40° C. to about 50° C. In some aspects, the composition may be nanofiltered at a temperature from about 40° C. to about 40.5° C., about 40° C. to about 41° C., about 40° C. to about 41.5° C., about 40° C. to about 42° C., about 40° C. to about 42.5° C., about 40° C. to about 43° C., about 40° C. to about 43.5° C., about 40° C. to about 44° C., about 40° C. to about 44.5° C., about 40° C. to about 45° C., about 40° C. to about 45.5° C., about 40° C. to about 46° C., about 40° C. to about 46.5° C., about 40° C. to about 47° C., about 40° C. to about 47.5° C., about 40° C. to about 48° C., about 40° C. to about 48.5° C., about 40° C. to about 49° C., about 40° C. to about 49.5° C., about 40.5° C. to about 50° C., about 41° C. to about 50° C., about 41.5° C. to about 50° C., about 42° C. to about 50° C., about 42.5° C. to about 50° C., about 43° C. to about 50° C., about 43.5° C. to about 50° C., about 44° C. to about 50° C., about 44.5° C. to about 50° C., about 45° C. to about 50° C., about 45.5° C. to about 50° C., about 46° C. to about 50° C., about 46.5° C. to about 50° C., about 47° C. to about 50° C., about 47.5° C. to about 50° C., about 48° C. to about 50° C., about 48.5° C. to about 50° C., about 49° C. to about 50° C., about 49.5° C. to about 50° C., about 41° C. to about 49° C., about 42° C. to about 48° C., about 43° C. to about 47° C., or about 44° C. to about 46° C. In some additional aspects, the composition may be nanofiltered at a temperature of about 40° C., 40.5° C., 41° C., 41.5° C., 42° C., 42.5° C., 43° C., 43.5° C., 44° C., 44.5° C., 45° C., 45.5° C., 46° C., 46.5° C., 47° C., 47.5° C., 48° C., 48.5° C., 49° C., 49.5° C., or about 50° C. In some preferred embodiments, the composition may be nanofiltered at least once at a temperature from about 40° C. to about 50° C., or more preferably about 42.5° C. to about 47.5° C., or even more preferably about 45° C.

In some embodiments, the composition is nanofiltered at a pressure from about 100 psig to about 500 psig. In some aspects, the composition is nanofiltered at a pressure from about 100 psig to about 150 psig, about 100 psig to about 200 psig, about 100 psig to about 250 psig, about 100 psig to about 300 psig, about 100 psig to about 350 psig, about 100 psig to about 350 psig, about 100 psig to about 400 psig, about 100 psig to about 450 psig, about 150 psig to about 500 psig, about 200 psig to about 500 psig, about 250 psig to about 500 psig, about 300 psig to about 500 psig, about 350 psig to about 500 psig, about 400 psig to about 500 psig, about 450 psig to about 500 psig, about 150 psig to about 450 psig, about 150 psig to about 400 psig, about 150 psig to about 350 psig, about 150 psig to about 300 psig, about 150 psig to about 200 psig, about 200 psig to about 400 psig, about 200 psig to about 350 psig, about 200 psig to about 300 psig, or about 200 psig to about 250 psig. In preferred embodiments, the composition is nanofiltered at a pressure from about 100 psig to about 300 psig, or more preferably from about 100 psig to about 200 psig, or even more preferably from about 100 psig to about 150 psig. In other preferred embodiments, the composition is nanofiltered at a pressure from about 150 psig to about 200 psig, or from about 200 psig to about 250 psig.

In some embodiments, the composition may be nanofiltered at a diafiltration flux from about 15 kg/m²·hr to about 35 kg/m²·hr. In some aspects, the composition may be nanofiltered at a diafiltration flux from about 15 kg/m²·hr to about 17.5 kg/m²·hr, about 15 kg/m²·hr to about 20 kg/m²·hr, about 15 kg/m²·hr to about 22.5 kg/m²·hr, about 15 kg/m²·hr to about 25 kg/m²·hr, about 15 kg/m²·hr to about 27.5 kg/m²·hr, about 15 kg/m²·hr to about 30 kg/m²·hr, about 15 kg/m²·hr to about 32.5 kg/m²·hr, about 17.5 kg/m²·hr to about 35 kg/m²·hr, about 20 kg/m²·hr to about 35 kg/m²·hr, about 22.5 kg/m²·hr to about 35 kg/m²·hr, about 25 kg/m²·hr to about 35 kg/m²·hr, about 27.5 kg/m²·hr to about 35 kg/m²·hr, about 30 kg/m²·hr to about 35 kg/m²·hr, about 32.5 kg/m²·hr to about 35 kg/m²·hr, about 17.5 kg/m²·hr to about 32.5 kg/m²·hr, about 20 kg/m²·hr to about 30 kg/m²·hr, or about 22.5 kg/m²·hr to about 27.5 kg/m²·hr. In some additional aspects, the composition may be nanofiltered at a diafiltration flux of about 15 kg/m²·hr, 17.5 kg/m²·hr, 20 kg/m²·hr, 22.5 kg/m²·hr, 25 kg/m²·hr, 27.5 kg/m²·hr, 30 kg/m²·hr, 32.5 kg/m²·hr, or about 35 kg/m²·hr. In some preferred embodiments, the composition may be nanofiltered at a diafiltration flux from about 20 kg/m²·hr to about 30 kg/m²·hr, or even more preferably from about 22.5 kg/m²·hr to about 27.5 kg/m²·hr.

In some embodiments, the composition may have an osmolality from about 600 to about 1200 mosmol/kg. In some aspects, the composition may have an osmolality from about 600 mosmol/kg to about 700 mosmol/kg, about 600 mosmol/kg to about 800 mosmol/kg, about 600 mosmol/kg to about 900 mosmol/kg, about 600 mosmol/kg to about 1000 mosmol/kg, about 600 mosmol/kg to about 1100 mosmol/kg, about 700 mosmol/kg to about 1200 mosmol/kg, about 800 mosmol/kg to about 1200 mosmol/kg, about 900 mosmol/kg to about 1200 mosmol/kg, about 1000 mosmol/kg to about 1200 mosmol/kg, about 1100 mosmol/kg to about 1200 mosmol/kg, about 700 mosmol/kg to about 1100 mosmol/kg, or about 800 mosmol/kg to about 1000 mosmol/kg. In some additional aspects, the composition may have an osmolality of about 600 mosmol/kg, 700 mosmol/kg, 800 mosmol/kg, 900 mosmol/kg, 1000 mosmol/kg, 1100 mosmol/kg, or about 1200 mosmol/kg.

In some embodiments, the composition may have a pH from about 6.0 to about 8.0. In some aspects, the composition may have a pH from about 6.0 to about 6.5, about 6.0 to about 7.0, about 6.0 to about 7.5, about 6.5 to about 7.0, about 6.5 to about 7.5, about 6.5 to about 8.0, about 7.0 to about 7.5, about 7.0 to about 8.0, or about 7.5 to about 8.0. In some additional aspects, the composition may have a pH of about 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, or about 8.0. In an exemplary embodiment, the composition has a pH from about 6.8 to about 7.5.

In some embodiments, the composition may further comprise saline.

In some embodiments, the composition further comprises a buffer. Those having ordinary skill in the art will appreciate that numerous buffer solutions are compatible with pharmaceutical applications and can be used in a composition of the present disclosure. In some embodiments, the buffer may be a potassium phosphate buffer (including monobasic potassium phosphate and dibasic potassium phosphate), a sodium phosphate buffer (including monobasic sodium phosphate and dibasic sodium phosphate), a citric acid buffer, an acetic acid buffer, a tromethamine (TRIS) buffer, a histidine buffer, a gluconic acid buffer, a lactic acid buffer, a tartaric acid buffer, an aspartic acid buffer, a glutamic acid buffer, or other buffers known in the art and combinations thereof. In particularly preferred embodiments, the buffer may be a potassium phosphate buffer, a sodium phosphate buffer, or a combination thereof. In an example, the buffer is a potassium phosphate buffer having a concentration of about 5 mM to about 10 mM. In another example, the buffer is a sodium phosphate buffer having a concentration of about 5 mM to about 10 mM.

In some embodiments, the composition may have a density from about 1.00 g/cm³ to about 1.20 g/cm³. In some aspects, the composition may have a density from about 1.00 g/cm³ to about 1.02 g/cm³, about 1.00 g/cm³ to about 1.04 g/cm³, about 1.00 g/cm³ to about 1.06 g/cm³, about 1.00 g/cm³ to about 1.08 g/cm³, about 1.00 g/cm³ to about 1.10 g/cm³, about 1.00 g/cm³ to about 1.12 g/cm³, about 1.00 g/cm³ to about 1.14 g/cm³, about 1.00 g/cm³ to about 1.16 g/cm³, about 1.00 g/cm³ to about 1.18 g/cm³, about 1.02 g/cm³ to about 1.20 g/cm³, about 1.04 g/cm³ to about 1.20 g/cm³, about 1.06 g/cm³ to about 1.20 g/cm³, about 1.08 g/cm³ to about 1.20 g/cm³, about 1.10 g/cm³ to about 1.20 g/cm³, about 1.12 g/cm³ to about 1.20 g/cm³, about 1.14 g/cm³ to about 1.20 g/cm³, about 1.16 g/cm³ to about 1.20 g/cm³, about 1.18 g/cm³ to about 1.20 g/cm³, about 1.02 g/cm³ to about 1.18 g/cm³, about 1.04 g/cm³ to about 1.16 g/cm³, about 1.06 g/cm³ to about 1.14 g/cm³, or about 1.08 g/cm³ to about 1.12 g/cm³. In some aspects, the composition may have a density of about 1.00 g/cm³, 1.01 g/cm³, 1.02 g/cm³, 1.03 g/cm³, 1.04 g/cm³, 1.05 g/cm³, 1.06 g/cm³, 1.07 g/cm³, 1.08 g/cm³, 1.09 g/cm³, 1.10 g/cm³, 1.11 g/cm³, 1.12 g/cm³, 1.13 g/cm³, 1.14 g/cm³, 1.15 g/cm³, 1.16 g/cm³, 1.17 g/cm³, 1.18 g/cm³, 1.19 g/cm³, or about 1.20 g/cm³.

In some embodiments, the composition may be contained in an intravenous bag. The intravenous bag may be any bag capable of holding a solution for intravenous administration known in the art.

In some embodiments, the composition may be contained in a vial. The vial may be any vial capable of holding a solution for pharmaceutical use. In some aspects, the vial may be single use. In some additional aspects, the vial may be multi-use.

Further provided herein is a method of purifying a mixture of β-cyclodextrin molecules substituted at one or more hydroxyl positions by hydroxypropyl groups. The method comprises diluting the mixture of hydroxypropyl β-cyclodextrin molecules with water and nanofiltering the mixture at least three times. As used herein, the terms "nanofiltering" and "diafiltering" are used interchangeably. In some aspects, the method may comprise nanofiltering the mixture at least four times. In some additional aspects, the method may comprise nanofiltering the mixture at least five times. In some embodiments, the method may further comprise recirculating the permeate for nanofiltering.

In some embodiments, the removal efficiency (RE) of propylene oxide monomers, propylene oxide dimers, propylene oxide trimers, and/or propylene oxide tetramers, propylene glycol, and sodium chloride content in the mixture of β-cyclodextrin molecules may be at least 90%; i.e., the removal efficiency of propylene oxide monomers, propylene oxide dimers, propylene oxide trimers, and/or propylene oxide tetramers, propylene glycol, and sodium chloride, individually or collectively, may be at least 90%. As used herein "removal efficiency" refers to the performance of a filtration device in terms of the ratio of the amount of an impurity removed from the solution to the total amount of impurity that enters the filtration device. In some aspects, the removal efficiency of propylene oxide monomers, propylene oxide dimers, propylene oxide trimers, and/or propylene oxide tetramers, propylene glycol, and sodium chloride content in the mixture of β-cyclodextrin molecules may be at least 90%, at least 91%, at least 92%, at least 93%, at least 94%, at least 95%, at least 96%, at least 97%, at least 98%, at least 99%, or at least 99.5%.

In some embodiments, the removal efficiency (RE) of propylene oxide dimer, propylene oxide trimer, and propylene oxide tetramer content in the mixture of β-cyclodextrin molecules may be at least 90%; i.e., the removal efficiency of propylene oxide dimer, propylene oxide trimer, and propylene oxide tetramer content individually or collectively, may be at least 90%. In some aspects, the removal efficiency of propylene oxide dimer, propylene oxide trimer, and propylene oxide tetramer content in the mixture of β-cyclodextrin molecules may be at least 90%, at least 91%, at least 92%, at least 93%, at least 94%, at least 95%, at least 96%, at least 97%, at least 98%, at least 99%, or at least 99.5%.

In some embodiments, the method may further comprise isolating a purified mixture of β-cyclodextrin molecules having a solution concentration from about 25.0 wt % solids to about 35.0 wt % solids. In some aspects, the method may comprise isolating a purified mixture of β-cyclodextrin molecules having a solution concentration of about 25.0 wt % solids to about 26.0 wt % solids, about 25.0 wt % solids to about 27.0 wt % solids, about 25.0 wt % solids to about 28.0 wt % solids, about 25.0 wt % solids to about 29.0 wt % solids, about 25.0 wt % solids to about 30.0 wt % solids, about 25.0 wt % solids to about 31.0 wt % solids, about 25.0 wt % solids to about 32.0 wt % solids, about 25.0 wt % solids to about 33.0 wt % solids, about 25.0 wt % solids to about 34.0 wt % solids, about 26.0 wt % solids to about 35.0 wt % solids, about 27.0 wt % solids to about 35.0 wt % solids, about 28.0 wt % solids to about 35.0 wt % solids, about 29.0 wt % solids to about 35.0 wt % solids, about 30.0 wt % solids to about 35.0 wt % solids, about 31.0 wt % solids to about 35.0 wt % solids, about 32.0 wt % solids to about 35.0 wt % solids, about 33.0 wt % solids to about 35.0 wt % solids, about 34.0 wt % solids to about 35.0 wt % solids, about 26.0 wt % solids to about 34.0 wt % solids, about 27.0 wt % solids to about 33.0 wt % solids, about 28.0 wt % solids to about 32.0 wt % solids, or about 29.0 wt % solids to about 31.0 wt % solids. In some additional aspects, the method may further comprise isolating a purified mixture of β-cyclodextrin molecules having a solution concentration from about 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, or about 35.0 wt % solids. In preferred embodiments, the method further comprises isolating a purified mixture of β-cyclodextrin molecules having a solution concentration from about 25.0 wt % solids to about 35.0 wt % solids. In more preferred embodiments, the method further comprises isolating a purified mixture of β-cyclodextrin molecules having a solution concentration from about 27.5 wt % solids to about 32.5 wt % solids. In even more preferred embodiments, the method further comprises isolating a purified mixture of β-cyclodextrin molecules having a solution concentration from about 29.0 wt % solids to about 31.0 wt % solids.

In some embodiments, the method may comprise nanofiltering the mixture of β-cyclodextrin molecules at a temperature from about 40° C. to about 50° C. In some aspects, the method may comprise nanofiltering the mixture of β-cyclodextrin molecules at a temperature from about 40° C. to about 40.5° C., about 40° C. to about 41° C., about 40° C. to about 41.5° C., about 40° C. to about 42° C., about 40° C. to about 42.5° C., about 40° C. to about 43° C., about 40° C. to about 43.5° C., about 40° C. to about 44° C., about 40° C. to about 44.5° C., about 40° C. to about 45° C., about 40° C. to about 45.5° C., about 40° C. to about 46° C., about 40° C. to about 46.5° C., about 40° C. to about 47° C., about 40° C. to about 47.5° C., about 40° C. to about 48° C., about 40° C. to about 48.5° C., about 40° C. to about 49° C., about 40° C. to about 49.5° C., about 40.5° C. to about 50° C., about 41° C. to about 50° C., about 41.5° C. to about 50° C., about 42° C. to about 50° C., about 42.5° C. to about 50° C., about 43° C. to about 50° C., about 43.5° C. to about 50° C., about 44° C. to about 50° C., about 44.5° C. to about 50° C., about 45° C. to about 50° C., about 45.5° C. to about 50° C., about 46° C. to about 50° C., about 46.5° C. to about 50° C., about 47° C. to about 50° C., about 47.5° C. to about 50° C., about 48° C. to about 50° C., about 48.5° C. to about 50° C., about 49° C. to about 50° C., about 49.5° C. to about 50° C., about 41° C. to about 49° C., about 42° C. to about 48° C., about 43° C. to about 47° C., or about 44° C. to about 46° C. In some additional aspects, the method may comprise nanofiltering the mixture of β-cyclodextrin molecules at a temperature of about 40° C., 40.5° C., 41° C., 41.5° C., 42° C., 42.5° C., 43° C., 43.5° C., 44° C., 44.5° C., 45° C., 45.5° C., 46° C., 46.5° C., 47° C., 47.5° C., 48° C., 48.5° C., 49° C., 49.5° C., or about 50° C. In some preferred embodiments, the mixture may be nanofiltered at least once at a temperature from about 40° C. to about 50° C., or more preferably about 42.5° C. to about 47.5° C., or even more preferably about 45° C.

In some embodiments, the water may be deionized water. In some additional embodiments, the water may have a conductivity of 18.2 MΩ (referred to herein as "18.2 MΩ water").

In some embodiments, the nanofiltering may occur at a membrane having a surface area of at least 100 cm$^2$. Those having ordinary skill in the art will appreciate, however, that the membrane surface area may be increased to accommodate increased production needs.

In some embodiments, the nanofiltering may occur at a pressure of about 100 psig to about 500 psig. In some aspects, the nanofiltering may occur at about 100 psig to about 150 psig, about 100 psig to about 200 psig, about 100 psig to about 250 psig, about 100 psig to about 300 psig, about 100 psig to about 350 psig, about 100 psig to about 350 psig, about 100 psig to about 400 psig, about 100 psig to about 450 psig, about 150 psig to about 500 psig, about 200 psig to about 500 psig, about 250 psig to about 500 psig, about 300 psig to about 500 psig, about 350 psig to about 500 psig, about 400 psig to about 500 psig, about 450 psig to about 500 psig, about 150 psig to about 450 psig, about 150 psig to about 400 psig, about 150 psig to about 350 psig, about 150 psig to about 300 psig, about 150 psig to about 200 psig, about 200 psig to about 400 psig, about 200 psig to about 350 psig, about 200 psig to about 300 psig, or about 200 psig to about 250 psig. In preferred embodiments, the nanofiltering occurs from about 100 psig to about 300 psig, or more preferably from about 100 psig to about 200 psig, or even more preferably from about 100 psig to about 150 psig. In other preferred embodiments, the nanofiltering occurs from about 150 psig to about 200 psig, or from about 200 psig to about 250 psig.

In some embodiments, the nanofiltering may occur at an operating pressure effective to maintain a flux from about 400 g/min to about 600 g/min when the membrane has an active area of about 2.3 m$^2$. In some aspects, the nanofiltering may occur at an operating pressure effective to maintain a flux from about 400 g/min to about 450 g/min, about 400 g/min to about 500 g/min, about 400 g/min to about 550 g/min, about 450 g/min to about 500 g/min, about 450 g/min to about 550 g/min, about 450 g/min to about 600 g/min, about 500 g/min to about 550 g/min, about 500 g/min to about 600 g/min, or about 550 g/min to about 600 g/min. In preferred embodiments, the nanofiltering occurs at an operating pressure effective to maintain a flux of about 450 g/min to about 550 g/min.

In some embodiments, the nanofiltering may occur at a pressure effective to maintain a flux of about 200 g/(m$^2$·min) to about 250 g/(m$^2$·min). In some aspects, the nanofiltering may occur at a pressure effective to maintain a flux of about 200 g/(m$^2$·min) to about 210 g/(m$^2$·min), about 200 g/(m$^2$·min) to about 220 g/(m$^2$·min), about 200 g/(m$^2$·min) to about 230 g/(m$^2$·min), about 200 g/(m$^2$·min) to about 240 g/(m$^2$·min), about 210 g/(m$^2$·min) to about 250 g/(m$^2$·min), about 220 g/(m$^2$·min) to about 250 g/(m$^2$·min), about 230 g/(m$^2$·min) to about 250 g/(m$^2$·min), about 240 g/(m$^2$·min) to about 250 g/(m$^2$·min), about 210 g/(m$^2$·min) to about 240 g/(m²·min), about 210 g/(m²·min) to about 230 g/(m²·min), or about 210 g/(m²·min) to about 220 g/(m²·min). In some additional aspects, the nanofiltering may occur at a pressure effective to maintain a flux of about 200 g/(m²·min), 205 g/(m²·min), 210 g/(m²·min), 215 g/(m²·min), 220 g/(m²·min), 225 g/(m²·min), 230 g/(m²·min), 235 g/(m²·min), 240 g/(m²·min), 245 g/(m²·min), or about 250 g/(m²·min).

In some embodiments, the nanofiltering may comprise a permeate generation rate of about 600 kg/hour to about 1800 kg/hour. As used herein, the "permeate generation rate" is the mass flow rate of the permeate produced by the nanofiltering. In some aspects, the nanofiltering may comprise a permeate generation rate from about 600 kg/hour to about 700 kg/hour, about 600 kg/hour to about 800 kg/hour, about 600 kg/hour to about 900 kg/hour, about 600 kg/hour to about 1000 kg/hour, about 600 kg/hour to about 1100 kg/hour, about 600 kg/hour to about 1200 kg/hour, about 600 kg/hour to about 1300 kg/hour, about 600 kg/hour to about 1400 kg/hour, about 600 kg/hour to about 1500 kg/hour, about 600 kg/hour to about 1600 kg/hour, about 600 kg/hour to about 1700 kg/hour, about 700 kg/hour to about 1800 kg/hour, about 800 kg/hour to about 1800 kg/hour, about 900 kg/hour to about 1800 kg/hour, about 1000 kg/hour to about 1800 kg/hour, about 1100 kg/hour to about 1800 kg/hour, about 1200 kg/hour to about 1800 kg/hour, about 1300 kg/hour to about 1800 kg/hour, about 1400 kg/hour to about 1800 kg/hour, about 1500 kg/hour to about 1800 kg/hour, about 1600 kg/hour to about 1800 kg/hour, or about 1700 kg/hour to about 1800 kg/hour. In preferred embodiments, the nanofiltering comprises a permeate generation rate from about 900 kg/hour to about 1500 kg/hour, or even more preferably from about 1200 kg/hour to about 1500 kg/hour.

In some embodiments, the nanofiltering may comprise a Trisep XN45 membrane, a spiral wound membrane, a flat-sheet membrane, or other membranes capable of nanofiltration known in the art and combinations thereof. In some aspects, the Trisep XN45 membrane may be selected from the group consisting of #1812, #2540, #4040, #8040, and combinations thereof.

In some embodiments, the method may further comprise upconcentrating the mixture of β-cyclodextrin molecules after nanofiltering. As used herein, the term "upconcentrating" refers to increasing a concentration. Methods of upconcentrating a pharmaceutical composition are generally well-known in the art.

In some embodiments, there may be no detectable amount of β-cyclodextrin in the permeate following the nanofiltering.

Methods of Treatment

In some embodiments, the present invention comprises a method of treatment comprising administering an isomerically purified mixture of hydroxypropyl-β-cyclodextrin molecules (i.e., 2-hydroxypropyl-beta-cyclodextrin) to a human subject in need thereof and reducing a size and/or an amount of circulating (e.g., blood, plasma, serum) cholesterol crystals (and/or clots comprising cholesterol crystals) in the subject. In some aspects, the size (e.g., average size, maximum size) of circulating (e.g., blood, serum, plasma) cholesterol crystals (and/or clots comprising cholesterol crystals) is reduced by at least about 10% (e.g., at least about 15%, at least about 20%, at least about 25%, at least about 30%, at least about 35%, at least about 40%, at least about 45%, at least about 50%, or greater) relative to the size (e.g., average size, maximum size) of circulating (e.g., blood, serum, plasma) cholesterol crystals (and/or clots comprising cholesterol crystals) prior to treatment with the 2-hydroxypropyl-beta-cyclodextrin. In some aspects, the amount (e.g., concentration) of circulating (e.g., blood, serum, plasma) cholesterol crystals (and/or clots comprising cholesterol crystals) is reduced by at least about 10% (e.g., at least about 15%, at least about 20%, at least about 25%, at least about 30%, at least about 35%, at least about 40%, at least about 45%, at least about 50%, or greater) relative to the amount (e.g., concentration) of circulating (e.g., blood, serum, plasma) cholesterol crystals (and/or clots comprising cholesterol crystals) prior to treatment with the 2-hydroxypropyl-beta-cyclodextrin. In some aspects, the treating results in a change in shape of circulating cholesterol crystals (and/or clots comprising cholesterol crystals). In some cases, the treating results in a decrease in inflammation (e.g., as measured by, e.g., cytokine protein and/or RNA levels) as compared to a level of inflammation prior to treatment with the 2-hydroxypropyl-beta-cyclodextrin. In some embodiments, the treatment increases renal and/or hepatogenic clearance of cholesterol or cholesterol derivates in the individual by at least about 10% (e.g., at least about 15%, at least about 20%, at least about 25%, at least about 30%, at least about 35%, at least about 40%, at least about 45%, at least about 50%, at least about 75%, at least about 100%, at least about 200%, at least about 300%, at least about 400%, at least about 500%, or greater) relative to the amount of cholesterol and/or cholesterol derivates cleared prior to the treatment.

In any one of the embodiments, the therapeutically effective amount of isomerically purified mixture of hydroxypropyl-β-cyclodextrin molecules is from about 50 mg/kg to about 8,000 mg/kg. In any one of the preceding aspects, the therapeutically effective amount is from about 4 g to about 250 g. In any one of the preceding aspects, the therapeutically effective amount is an amount sufficient to achieve a serum, plasma, and/or whole blood concentration of 2-hydroxypropyl-beta-cyclodextrin of about 0.01 mM to about 5 mM.

In any one of the aspects of the present invention, the human subject may be under 1, under 3, under 5 years old, or at least 5 (e.g., at least 10, at least 15, at least 20, at least 25, at least 30, at least 40) years old. In any one of the preceding aspects, the individual is a human. In any one of the preceding aspects, the administering further comprises: (i) administering, at a first time point, a therapeutically effective first dose of 2-hydroxypropyl-beta-cyclodextrin to the human subject; and (ii) administering, at a second time point, a therapeutically effective second dose of 2-hydroxypropyl-beta-cyclodextrin to the individual. In any one of the preceding aspects, the second time point is at least 4 hours, at least 6 hours, at least 8 hours, at least 12 hours, at least 1 day, at least 2 days, at least 3 three days, at least 4 days, at least 5 days, at least 6 days, at least 1 week, at least 2 weeks, at least 3 weeks, or at least 4 weeks after the first time point. In any one of the preceding aspects, the administering further comprises administering every 3 days, every 7 days, every 10 days, every 14 days, every 21 days, every 28 days, every 2 months, every 3 months, every 6 months, every 12 months. In any one of the preceding aspects, the administering is by parenteral methods including intravenous, intravascular, intramuscular, subcutaneous, intrathecal, depot, peristaltic pump administration and/or in conjunction to plasmapheresis.

As used herein, "subject" refers to a human. In some examples, the human subject may be an adult or pediatric patient (i.e., 18 years or younger). In some embodiments, the subject may be a human infant or neonate. In some aspects, the subject may be an infant (i.e., 0-6 months old). In some aspects, the subject may be a neonate (i.e., 0-4 weeks old). The subject may be less than 2 years old, less than 1 year old, less than 6 months old, less than 3 months old, less than 1 month old, less than 2 weeks old.

The terms "treat," "treating," or "treatment" as used herein, refer to both therapeutic treatment and prophylactic or preventative measures, wherein the object is to prevent or slow down (lessen) an undesired physiological change or disease/disorder. Beneficial or desired clinical results include, but are not limited to, alleviation of symptoms, diminishment of extent of disease, stabilized (i.e., not worsening) state of disease, a delay or slowing of disease progression, amelioration or palliation of the disease state, and remission (whether partial or total), whether detectable or undetectable. "Treatment" may also mean reducing the likelihood of a disease or condition occurring or recurring. "Treatment" may also mean prolonging survival as compared to expected survival if not receiving treatment (i.e., a reduction in mortality as compared to no treatment or a patient receiving placebo). Those in need of treatment include those already with the disease, condition, or disorder as well as those prone to have the disease, condition or disorder or those in which the disease, condition or disorder is to be prevented. Treatment also may include reduction of cholesterol esters, droplets, or crystals within the hepatocyte of a patient in need thereof or an increase in the amount of Kupffer cells and/or Kupffer cell activity of a patient in need thereof. Treatment also may include normalizing blood levels of bilirubin, improving the ratio of the serum concentration of AST:ALT, improving the serum concentration of lactate dehydrogenase (LDH), improving bile acid levels, or a combination thereof.

As used herein, the term "therapeutically effective quantity" means a quantity that leads to measurable and beneficial effects for the subject administered the substance, i.e., significant efficacy.

Further provided herein is a method of treating liver disease, the method comprising intravenously administering a therapeutically effective quantity of 2-hydroxypropyl-β-cyclodextrin (e.g., an isomerically purified mixture of hydroxypropyl-β-cyclodextrin molecules) to a human subject in need thereof, wherein the therapeutically effective quantity is about 500 mg/kg. In some embodiments, the therapeutically effective quantity is titrated to 1000 mg/kg. Also provided herein is a method of treating Niemann Pick disease, the method comprising intravenously administering a therapeutically effective quantity of 2-hydroxypropyl-β-cyclodextrin (e.g., an isomerically purified mixture of hydroxypropyl-β-cyclodextrin molecules) to a human subject in need thereof, wherein the therapeutically effective quantity is about 500 mg/kg. In some embodiments, the therapeutically effective quantity is titrated to 1000 mg/kg.

As used herein, "liver disease" refers generally to any disease, disorder, or condition that damages the liver and prevents the liver from functioning well. Generally, the term includes cirrhosis (scarring), fibrosis, ascites, esophageal varices, gastric varices, hepatomegaly, hepatosplenomegaly, fatty liver disease, hepatic steatosis, hepatosteatosis, hemolysis, hepatitis (e.g., hepatitis A, hepatitis B, hepatitis C, and autoimmune hepatitis), cholestasis (e.g., intrahepatic cholestasis and extrahepatic cholestasis), hyperbilirubinemia, cholangitis (e.g., primary biliary cholangitis and primary sclerosing cholangitis), galactosemia, non-alcoholic fatty liver disease (NAFLD), non-alcoholic steatohepatitis (NASH), Lysosomal acid lipase deficiency (LAL-D), NPC, jaundice (e.g., pre-hepatic, hepatocellular, and post-hepatic) hemochromatosis, hyperoxaluria, liver inflammation, Wilson's disease, alpha-1 antitrypsin deficiency, a reduction/deficiency in bile acids, liver cancer, bile duct cancer, liver cell adenoma, cholangiocarcinoma, hepatocellular carcinoma (HCT), and combinations thereof. Generally, the term also includes acute, progressive, chronic liver disease, and/or liver failure. The term liver disease may include any one of the afore-mentioned liver diseases, conditions, and combinations thereof.

In some embodiments the term "liver disease" refers to cirrhosis (scarring), fibrosis, ascites, esophageal varices, gastric varices, hepatomegaly, hepatosplenomegaly, fatty liver disease, hepatic steatosis, hepatosteatosis, hemolysis, hepatitis (e.g., hepatitis A, hepatitis B, hepatitis C, and autoimmune hepatitis), cholestasis (e.g., intrahepatic cholestasis and extrahepatic cholestasis), hyperbilirubinemia, cholangitis (e.g., primary biliary cholangitis and primary sclerosing cholangitis), galactosemia, non-alcoholic fatty liver disease (NAFLD), non-alcoholic steatohepatitis (NASH), Lysosomal acid lipase deficiency (LAL-D), jaundice (e.g., pre-hepatic, hepatocellular, and post-hepatic) hemochromatosis, hyperoxaluria, liver inflammation, Wilson's disease, alpha-1 antitrypsin deficiency, a reduction/deficiency in bile acids, liver cancer, bile duct cancer, liver cell adenoma, cholangiocarcinoma, hepatocellular carcinoma (HCT), and combinations thereof.

In some embodiments the term "liver disease" refers to cholestatic jaundice, hyperbilirubinemia, esophageal varices, gastric varices, primary sclerosing cholangitis, cirrhosis, nonalcoholic fatty liver disease (NAFLD), nonalcoholic steatohepatitis (NASH), or Wilson's disease.

In some embodiments the term liver disease also specifically includes any one of the afore-mentioned livers diseases, conditions, or combinations thereof, while also simultaneously excluding Niemann Pick disease (i.e., wherein the patient has liver disease but does not have Niemann Pick disease).

Further provided herein is a method of treating cardiovascular disease, the method comprising intravenously administering a therapeutically effective quantity of 2-hydroxypropyl-β-cyclodextrin (e.g., an isomerically purified mixture of hydroxypropyl-β-cyclodextrin molecules) to a human subject in need thereof, wherein the therapeutically effective quantity is about 500 mg/kg. In some embodiments, the therapeutically effective quantity is titrated to 1000 mg/kg. In one aspect, the term "cardiovascular disease" refers to atherosclerosis and/or atherosclerotic cardiovascular disease (e.g., coronary artery disease (CAD), peripheral artery disease (PAD), peripheral vascular disease (PVD), stroke, chronic kidney disease (CKD) caused by atherosclerosis, end-stage kidney disease (ESKD) caused by atherosclerosis, acute kidney failure caused by atherosclerosis, atherosclerotic renovascular disease (ARVD), renal artery stenosis, aortic aneurysm, idiopathic peripheral atrial hypertension, erectile dysfunction, intermittent claudication, post-surgical or iatrogenic arterial disease).

Further provided herein is a method of treating familial hypercholesterolemia, the method comprising intravenously administering a therapeutically effective quantity of 2-hydroxypropyl-β-cyclodextrin (e.g., an isomerically purified mixture of hydroxypropyl-β-cyclodextrin molecules) to a human subject in need thereof, wherein the therapeutically effective quantity is about 500 mg/kg. In some embodiments, the therapeutically effective quantity is titrated to 1000 mg/kg. In one aspect, the term "familial hypercholesterolemia" refers to homozygous familial hypercholesterolemia (HoFH) and/or heterozygous familial hypercholestolemia (HeFH).

Further provided is a method of treating cholesterol deposits in a human patient, the method comprising intravenously administering a therapeutically effective quantity of 2-hydroxypropyl-β-cyclodextrin (e.g., an isomerically purified mixture of hydroxypropyl-β-cyclodextrin molecules) to a human subject in need thereof, wherein the therapeutically effective quantity is about 500 mg/kg. In some embodiments, the therapeutically effective quantity is titrated to 1000 mg/kg. A decrease in a number or size of the cholesterol deposits may be observed after administering the composition. The cholesterol deposits may be in an organ or a tissue of the patient. For example, the cholesterol deposits may be in the skin, eye(s), arteries, veins, or other tissue of the patient. In an embodiment, the cholesterol deposits are xanthomas. The xanthomas may be under the surface of the skin in the patient's hand, nose, and/or eyelid. In another embodiment, the cholesterol deposits may be localized cholesterol deposits. In other embodiments, the cholesterol deposits may comprise an arcus senillis, a Hollen-horst plaque, or one or more myodesopsias. In some examples, the cholesterol deposits are in or around the patient's cornea or are in or around the patient's retina. For example, a portion of the cholesterol deposits may be floating within the patient's eye. In some embodiments, the cholesterol deposits may be free flowing plaque fragments. In an example, the free flowing plaque fragments may be fragments that have been dislodged during or after cardiac surgery on the patient. The administration of the composition to the patient may sequester free flowing plaque fragments.

Exemplary Embodiments List A

Embodiment 1: A composition comprising a mixture of β-cyclodextrin molecules, wherein the mixture of β-cyclodextrin molecules comprises:
  β-cyclodextrin substituted with four hydroxypropyl groups ("DS-4");
  β-cyclodextrin substituted with five hydroxypropyl groups ("DS-5");
  β-cyclodextrin substituted with six hydroxypropyl groups ("DS-6");
  β-cyclodextrin substituted with seven hydroxypropyl groups ("DS-7");
  β-cyclodextrin substituted with eight hydroxypropyl groups ("DS-8");
  β-cyclodextrin substituted with nine hydroxypropyl groups ("DS-9");
  β-cyclodextrin substituted with ten hydroxypropyl groups ("DS-10");
  β-cyclodextrin substituted with eleven hydroxypropyl groups ("DS-11");
  β-cyclodextrin substituted with twelve hydroxypropyl groups ("DS-12");
  β-cyclodextrin substituted with thirteen hydroxypropyl groups ("DS-13"); and
  β-cyclodextrin substituted with fourteen hydroxypropyl groups ("DS-14"); and
  wherein the mixture of β-cyclodextrin molecules comprises less than 1% DS-4.
Embodiment 2: The composition of embodiment 1 having a HPLC-CAD chromatogram of FIG. 4.
Embodiment 3: The composition of embodiment 1, wherein the mixture of β-cyclodextrin molecules comprises about 0.5% to about 1% DS-4.
Embodiment 4: The composition of embodiment 1, wherein the mixture of β-cyclodextrin molecules comprises about 2% to about 5% DS-5.
Embodiment 5: The composition of embodiment 4, wherein the mixture of β-cyclodextrin molecules comprises about 3% to about 4% DS-5.
Embodiment 6: The composition of embodiment 1, wherein the mixture of β-cyclodextrin molecules comprises about 7% to about 13% DS-6.
Embodiment 7: The composition of embodiment 6, wherein the mixture of β-cyclodextrin molecules comprises about 9% to about 11% DS-6.
Embodiment 8: The composition of embodiment 1, wherein the mixture of β-cyclodextrin molecules comprises about 21% to about 27% DS-7.
Embodiment 9: The composition of embodiment 8, wherein the mixture of β-cyclodextrin molecules comprises about 23% to about 25% DS-7.
Embodiment 10: The composition of embodiment 1, wherein the mixture of β-cyclodextrin molecules comprises about 23% to about 29% DS-8.
Embodiment 11: The composition of embodiment 10, wherein the mixture of β-cyclodextrin molecules comprises about 25% to about 27% DS-8.
Embodiment 12: The composition of embodiment 1, wherein the mixture of β-cyclodextrin molecules comprises about 15% to about 21% DS-9.
Embodiment 13: The composition of embodiment 12, wherein the mixture of β-cyclodextrin molecules comprises about 17% to about 19% DS-9.
Embodiment 14: The composition of embodiment 1, wherein the mixture of β-cyclodextrin molecules comprises about 6% to about 12% DS-10.
Embodiment 15: The composition of embodiment 14, wherein the mixture of β-cyclodextrin molecules comprises about 8% to about 10% DS-10.
Embodiment 16: The composition of embodiment 1, wherein the mixture of β-cyclodextrin molecules comprises about 2% to about 6% DS-11.
Embodiment 17: The composition of embodiment 16, wherein the mixture of β-cyclodextrin molecules comprises about 3% to about 5% DS-11.
Embodiment 18: The composition of embodiment 1, wherein the mixture of β-cyclodextrin molecules comprises about 0.5% to about 4% DS-12.
Embodiment 19: The composition of embodiment 18, wherein the mixture of β-cyclodextrin molecules comprises about 1% to about 3% DS-12.
Embodiment 20: The composition of embodiment 1, wherein the mixture of β-cyclodextrin molecules comprises less than about 1% DS-13.
Embodiment 21: The composition of embodiment 1, wherein the mixture of β-cyclodextrin molecules comprises about 0.5% to about 1% DS-13.
Embodiment 22: The composition of embodiment 1, wherein the mixture of β-cyclodextrin molecules is suitable for intravenous, intrathecal, or intracerebroventricular administration.
Embodiment 23: The composition of embodiment 1, wherein the amount of DS-1, DS-2, DS-3, DS-4, DS-5, DS-6, DS-7, DS-8, DS-9, DS-10, DS-11, DS-12, and DS-13 in the mixture of β-cyclodextrin molecules is determined by MALDI-TOF-MS.
Embodiment 24: The composition of embodiment 1, wherein DS-8 has the highest concentration in the mixture of β-cyclodextrin molecules as compared to the concentrations of DS-1, DS-2, DS-3, DS-4, DS-5, DS-6, DS-7, DS-9, DS-10, DS-11, DS-12, and DS-13.
Embodiment 25: The composition of embodiment 1, wherein the β-cyclodextrin molecules are substituted at the 2-O— position at a rate of 35-55%, the 3-O-position at a rate of 45-65%, and the 6-O— position at a rate of 0-20%.

Embodiment 26: The composition of embodiment 1, wherein the β-cyclodextrin molecules are substituted at the 2-O— position at a rate of about 46%, the 3-O— position at a rate of about 54%, and the 6-O— position at a rate of about 10%.

Embodiment 27: The composition of embodiment 25, wherein the rate of substitution at the 2-O—, 3-O—, and 6-0 positions is determined via DEPT-ed HSQC.

Embodiment 28: The composition of embodiment 1, wherein the HPLC peak retention time occurs at about 12 minutes.

Embodiment 29: The composition of embodiment 1, wherein the composition has an average degree of substitution of between about 7 to about 9.

Embodiment 30: The composition of embodiment 29, wherein the composition has an average degree of substitution of about 7.7.

Embodiment 31: A composition comprising a mixture of β-cyclodextrin molecules, the composition having a 1H-NMR spectrum comprising:
- at least one peak at about 5.0-5.4 ppm corresponding to anomeric protons of the β-cyclodextrin molecules;
- at least one peak at about 3.2-4.2 ppm corresponding to protons within a core region of the β-cyclodextrin molecules; and
- at least one peak at about 1.0-1.2 ppm corresponding to methyl protons of side chains of the β-cyclodextrin molecules.

Embodiment 32: The composition of embodiment 1, having the $^1$H-NMR spectrum of FIG. 2.

Embodiment 33: A composition comprising a mixture of β-cyclodextrin molecules, wherein the mixture of β-cyclodextrin molecules comprises:
- less than about 1% β-cyclodextrin substituted with four hydroxypropyl groups ("DS-4");
- about 1% to about 5% β-cyclodextrin substituted with five hydroxypropyl groups ("DS-5");
- about 7% to about 13% β-cyclodextrin substituted with six hydroxypropyl groups ("DS-6");
- about 21% to about 27% β-cyclodextrin substituted with seven hydroxypropyl groups ("DS-7");
- about 23% to about 29% β-cyclodextrin substituted with eight hydroxypropyl groups ("DS-8");
- about 15% to about 21% β-cyclodextrin substituted with nine hydroxypropyl groups ("DS-9");
- about 6% to about 12% β-cyclodextrin substituted with ten hydroxypropyl groups ("DS-10");
- about 1% to about 7% β-cyclodextrin substituted with eleven hydroxypropyl groups ("DS-11");
- about 0.5% to about 3% β-cyclodextrin substituted with twelve hydroxypropyl groups ("DS-12");
- less than about 1% β-cyclodextrin substituted with thirteen hydroxypropyl groups ("DS-13"); and
- less than about 1% β-cyclodextrin substituted with fourteen hydroxypropyl groups ("DS-14").

Embodiment 34: The composition of embodiment 1 having a MALDI-TOF spectrum of FIG. 1.

Embodiment 35: The composition of embodiment 34, wherein the area of DS-4 is 0.73%.

Embodiment 36: The composition of embodiment 34, wherein the area of DS-5 is 3.49%.

Embodiment 37: The composition of embodiment 34, wherein the area of DS-6 is 10.66%.

Embodiment 38: The composition of embodiment 34, wherein the area of DS-7 is 24.10%.

Embodiment 39: The composition of embodiment 34, wherein the area of DS-8 is 26.43%.

Embodiment 40: The composition of embodiment 34, wherein the area of DS-9 is 18.09%.

Embodiment 41: The composition of embodiment 34, wherein the area of DS-10 is 9.39%.

Embodiment 42: The composition of embodiment 34, wherein the area of DS-11 is 4.58%.

Embodiment 43: The composition of embodiment 34, wherein the area of DS-12 is 1.84%.

Embodiment 44: The composition of embodiment 34, wherein the area of DS-13 is 0.70%.

Embodiment 45: The composition of embodiment 1, wherein the composition has a true density of about 1.095 g/cm$^3$ to about 1.100 g/cm$^3$.

Embodiment 46: The composition of embodiment 45, wherein the composition has a true density of about 1.096 g/cm$^3$ to about 1.098 g/cm$^3$.

Embodiment 47: The composition of embodiment 1, wherein the composition has an osmolality of about 600 mOs/kg to about 750 mOs/kg.

Embodiment 48: The composition of embodiment 47, wherein the composition has an osmolality of about 635 mOs/kg to about 695 mOs/kg.

Embodiment 49: The composition of embodiment 1, wherein the composition is a clear and colorless solution.

Embodiment 50: The composition of embodiment 1, wherein the composition has a pH of about 4.0 to about 6.0.

Embodiment 51: The composition of embodiment 1, wherein the composition has a viscosity of 1.5 cP to about 3.0 cP at 20° C.

Embodiment 52: The composition of embodiment 1, wherein the composition comprises less than or equal to about 0.05% impurities.

Embodiment 53: The composition of embodiment 1, wherein the composition comprises less than 600 particles per container having a diameter of greater than or equal to 25 microns.

Embodiment 54: The composition of embodiment 1, wherein the composition comprises less than 6000 particles per container having a diameter of greater than or equal to 10 microns.

Embodiment 55: A composition comprising a mixture of β-cyclodextrin molecules, wherein the mixture of β-cyclodextrin molecules comprises:
- β-cyclodextrin substituted with four hydroxypropyl groups ("DS-4");
- β-cyclodextrin substituted with five hydroxypropyl groups ("DS-5");
- β-cyclodextrin substituted with six hydroxypropyl groups ("DS-6");
- β-cyclodextrin substituted with seven hydroxypropyl groups ("DS-7");
- β-cyclodextrin substituted with eight hydroxypropyl groups ("DS-8");
- β-cyclodextrin substituted with nine hydroxypropyl groups ("DS-9");
- β-cyclodextrin substituted with ten hydroxypropyl groups ("DS-10");
- β-cyclodextrin substituted with eleven hydroxypropyl groups ("DS-11");
- β-cyclodextrin substituted with twelve hydroxypropyl groups ("DS-12");
- β-cyclodextrin substituted with thirteen hydroxypropyl groups ("DS-13"); and
- β-cyclodextrin substituted with fourteen hydroxypropyl groups ("DS-14");

and wherein the mixture of β-cyclodextrin molecules comprises less than 1% w/w β-cyclodextrin substituted with one hydroxypropyl group ("DS-1"), β-cyclodextrin substituted with two hydroxypropyl groups ("DS-2"), β-cyclodextrin substituted with three hydroxypropyl groups ("DS-3"), and DS-4.

Embodiment 56: An isomerically-purified composition comprising a mixture of hydroxypropyl-β-cyclodextrin molecules eluted from a Cholester HPLC column.

Embodiment 57: An isomerically-purified composition comprising a 5% (w/w) mixture of hydroxypropyl-β-cyclodextrin HDS molecules in aqueous media that yields an equilibrium solubility of cholesterol between about 0.2500 to about 0.6000 mg/ml at a temperature of 37° C.

Embodiment 58: The composition of embodiment 57, wherein the composition yields an equilibrium solubility of cholesterol between about 0.2500 to 0.2700 mg/ml at a temperature of 37° C.

Embodiment 59: The composition of embodiment 57, wherein the composition yields an equilibrium solubility of cholesterol between about 0.4000 to 0.4200 mg/ml at a temperature of 37° C.

Embodiment 60: The composition of embodiment 57, wherein the composition yields an equilibrium solubility of cholesterol between about 0.5000 to 0.5200 mg/ml at a temperature of 37° C.

Embodiment 61: The composition of embodiment 57, wherein the composition yields an equilibrium solubility of cholesterol between about 0.5400 to 0.5600 mg/ml at a temperature of 37° C.

Embodiment 62: The composition of embodiment 57, wherein the composition yields an equilibrium solubility of cholesterol between about 0.3600 to 0.3800 mg/ml at a temperature of 37° C.

Embodiment 63: An isomerically-purified composition comprising a 5% (w/w) mixture of hydroxypropyl-β-cyclodextrin HDS molecules in aqueous media, wherein the mixture of hydroxypropyl-β-cyclodextrin HDS molecules is insoluble in water.

Embodiment 64: An isomerically-purified composition comprising a 5% (w/w) mixture of hydroxypropyl-β-cyclodextrin LDS molecules in aqueous media that yields an equilibrium solubility of cholesterol between about 0.1700 to about 0.3200 mg/ml at a temperature of 37° C.

Embodiment 65: The composition of embodiment 64, wherein the composition yields an equilibrium solubility of cholesterol between about 0.1800 to 0.2000 mg/ml at a temperature of 37° C.

Embodiment 66: The composition of embodiment 64, wherein the composition yields an equilibrium solubility of cholesterol between about 0.1700 to 0.1900 mg/ml at a temperature of 37° C.

Embodiment 67: The composition of embodiment 64, wherein the composition yields an equilibrium solubility of cholesterol between about 0.2000 to 0.2200 mg/ml at a temperature of 37° C.

Embodiment 68: The composition of embodiment 64, wherein the composition yields an equilibrium solubility of cholesterol between about 0.2200 to 0.2400 mg/ml at a temperature of 37° C.

Embodiment 69: The composition of embodiment 64, wherein the composition yields an equilibrium solubility of cholesterol between about 0.3100 to 0.3300 mg/ml at a temperature of 37° C.

Embodiment 70: An isomerically-purified composition comprising a 20% (w/w) mixture of hydroxypropyl-β-cyclodextrin molecules in aqueous media that yields an equilibrium solubility of cholesterol between about 3.2500 to about 3.7500 mg/ml at a temperature of 37° C.

Embodiment 71: A composition comprising a mixture of isomerically-purified hydroxypropyl β-cyclodextrin molecules comprising less than 1% β-cyclodextrin substituted with four hydroxypropyl groups ("DS-4").

Embodiment 72: The composition of embodiment 71, wherein the hydroxypropyl β-cyclodextrin percentage is based upon area percentage from a MALDI-TOF-MS spectrum.

Embodiment 73: The composition of embodiment 71, wherein the hydroxypropyl β-cyclodextrin percentage is based upon weight percentage.

Embodiment 74: The composition of embodiment 71, wherein the composition comprises less than 1% β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1").

Embodiment 75: The composition of embodiment 71, wherein the mixture of isomerically-purified hydroxypropyl β-cyclodextrin molecules comprises about 1% to about 5% of β-cyclodextrin substituted with five hydroxypropyl groups ("DS-5").

Embodiment 76: The composition of embodiment 71, wherein the mixture of isomerically-purified hydroxypropyl β-cyclodextrin comprises about 7% to about 13% of β-cyclodextrin substituted with six hydroxypropyl groups ("DS-6").

Embodiment 77: The composition of embodiment 76, wherein the mixture of isomerically-purified hydroxypropyl β-cyclodextrin comprises about 8% to about 12% of DS-6.

Embodiment 78: The composition of embodiment 71, wherein the mixture of isomerically-purified hydroxypropyl β-cyclodextrin comprises about 16% to about 22% of β-cyclodextrin substituted with seven hydroxypropyl groups ("DS-7").

Embodiment 79: The composition of embodiment 78, wherein the mixture of isomerically-purified hydroxypropyl β-cyclodextrin comprises about 17% to about 21% of DS-7.

Embodiment 80: The composition of embodiment 71, wherein the mixture of isomerically-purified hydroxypropyl β-cyclodextrin comprises about 26% to about 32% of β-cyclodextrin substituted with eight hydroxypropyl groups ("DS-8").

Embodiment 81: The composition of embodiment 80, wherein the mixture of isomerically-purified hydroxypropyl β-cyclodextrin comprises about 27% to about 31% of DS-8.

Embodiment 82: The composition of embodiment 71, wherein the mixture of isomerically-purified hydroxypropyl β-cyclodextrin comprises about 22% to about 28% of β-cyclodextrin substituted with nine hydroxypropyl groups ("DS-9").

Embodiment 83: The composition of embodiment 82, wherein the mixture of isomerically-purified hydroxypropyl β-cyclodextrin comprises about 23% to about 27% of DS-9.

Embodiment 84: The composition of embodiment 71, wherein the mixture of isomerically-purified hydroxypropyl β-cyclodextrin comprises about 11% to about 17% of β-cyclodextrin substituted with ten hydroxypropyl groups ("DS-10").

Embodiment 85: The composition of embodiment 84, wherein the mixture of isomerically-purified hydroxypropyl β-cyclodextrin comprises about 12% to about 16% of DS-10.

Embodiment 86: The composition of embodiment 71, wherein the mixture of isomerically-purified hydroxypropyl β-cyclodextrin molecules comprising less than 1% β-cyclodextrin substituted with eleven hydroxypropyl groups ("DS-11").

Embodiment 87: The composition of embodiment 71, wherein the mixture of isomerically-purified hydroxypropyl β-cyclodextrin molecules comprising less than 1% β-cyclodextrin substituted with twelve hydroxypropyl groups ("DS-12"), β-cyclodextrin substituted with thirteen hydroxypropyl groups ("DS-13"), and β-cyclodextrin substituted with fourteen hydroxypropyl groups ("DS-14").

Embodiment 88: The composition of embodiment 71, wherein the average degree of substitution of the mixture of isomerically-purified hydroxypropyl β-cyclodextrin is about 6.4 to about 7.0.

Embodiment 89: The composition of embodiment 88, wherein the average degree of substitution is about 6.69.

Embodiment 90: The composition of embodiment 71, wherein about 52% to about 58% of the hydroxypropyl substitutions in the hydroxypropyl β-cyclodextrin molecules are located at the 3-O— position.

Embodiment 91: The composition of embodiment 90, wherein about 55% to about 56% of the hydroxypropyl substitutions in the β-cyclodextrin molecules are located at the 3-O— position.

Embodiment 92: The composition of embodiment 71, wherein about 41% to about 47% of the hydroxypropyl substitutions in the hydroxypropyl β-cyclodextrin molecules are located at the 2-O— position.

Embodiment 93: The composition of embodiment 92, wherein about 43% to about 45% of the hydroxypropyl substitutions in the hydroxypropyl β-cyclodextrin molecules are located at the 2-O— position.

Embodiment 94: The composition of embodiment 91, wherein the concentration of the composition does not substantially change the time required for nanofiltration.

Embodiment 95: The composition of embodiment 94, wherein the length of time to nanofilter the composition ranges from 1.04 to 1.20 hours per diafiltration volume (kg soln/m²·hr/L soln).

Embodiment 96: The composition of embodiment 71, wherein the composition has a conductivity between 0 and 8.0 µS/cm.

Embodiment 97: The composition of embodiment 71, wherein the composition has a conductivity between 0 and 4.5 µS/cm.

Embodiment 98: The composition of embodiment 71, wherein the composition has a conductivity between 0 and 3 µS/cm.

Embodiment 99: The composition of embodiment 71, wherein the composition has a conductivity between 0 and 1.5 µS/cm.

Embodiment 100: A composition comprising a mixture of isomerically-purified hydroxypropyl β-cyclodextrin molecules comprising:
β-cyclodextrin substituted with five hydroxypropyl groups ("DS-5");
β-cyclodextrin substituted with six hydroxypropyl groups ("DS-6");
β-cyclodextrin substituted with seven hydroxypropyl groups ("DS-7");
β-cyclodextrin substituted with eight hydroxypropyl groups ("DS-8");
β-cyclodextrin substituted with nine hydroxypropyl groups ("DS-9"); and
β-cyclodextrin substituted with ten hydroxypropyl groups ("DS-10"),
wherein the composition comprises less than 1% β-cyclodextrin substituted with four hydroxypropyl groups ("DS-4") and less than 1% β-cyclodextrin substituted with eleven hydroxypropyl groups ("DS-11").

Embodiment 101: The composition of embodiment 100, wherein the composition comprises less than 1% β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1").

Embodiment 102: The composition of embodiment 100, wherein in the composition comprises less than 1% β-cyclodextrin substituted with twelve hydroxypropyl groups ("DS-12"), β-cyclodextrin substituted with thirteen hydroxypropyl groups ("DS-13"), and β-cyclodextrin substituted with fourteen hydroxypropyl groups ("DS-14").

Embodiment 103: The composition of embodiment 100, wherein the DS-8 has the highest concentration in the mixture of isomerically-purified hydroxypropyl β-cyclodextrin molecules as compared to DS-5, DS-6, DS-7, DS-9, and DS-10.

Embodiment 104: The composition of embodiment 100, wherein the mixture of isomerically-purified hydroxypropyl β-cyclodextrin molecules comprises about 1% to about 5% of DS-5.

Embodiment 105: The composition of embodiment 104, wherein the mixture of isomerically-purified hydroxypropyl β-cyclodextrin molecules comprises about 2% to about 4% of DS-5.

Embodiment 106: The composition of embodiment 100, wherein the mixture of isomerically-purified hydroxypropyl β-cyclodextrin comprises about 7% to about 13% of DS-6.

Embodiment 107: The composition of embodiment 106, wherein the mixture of isomerically-purified hydroxypropyl β-cyclodextrin comprises about 8% to about 12% of DS-6.

Embodiment 108: The composition of embodiment 100, wherein the mixture of isomerically-purified hydroxypropyl β-cyclodextrin comprises about 16% to about 22% of DS-7.

Embodiment 109: The composition of embodiment 108, wherein the mixture of isomerically-purified hydroxypropyl β-cyclodextrin comprises about 17% to about 21% of DS-7.

Embodiment 110: The composition of embodiment 100, wherein the mixture of isomerically-purified hydroxypropyl β-cyclodextrin comprises about 26% to about 32% of DS-8.

Embodiment 111: The composition of embodiment 110, wherein the mixture of isomerically-purified hydroxypropyl β-cyclodextrin comprises about 27% to about 31% of DS-8.

Embodiment 112: The composition of embodiment 100, wherein the mixture of isomerically-purified hydroxypropyl β-cyclodextrin comprises about 22% to about 28% of DS-9.

Embodiment 113: The composition of embodiment 112, wherein the mixture of isomerically-purified hydroxypropyl β-cyclodextrin comprises about 23% to about 27% of DS-9.

Embodiment 114: The composition of embodiment 100, wherein the mixture of isomerically-purified hydroxypropyl β-cyclodextrin comprises about 11% to about 17% of DS-10.

Embodiment 115: The composition of embodiment 114, wherein the mixture of isomerically-purified hydroxypropyl β-cyclodextrin comprises about 12% to about 16% of DS-10.

Embodiment 116: The composition of embodiment 100, wherein the average degree of substitution of the mixture of isomerically-purified hydroxypropyl β-cyclodextrin is about 6.4 to about 7.0.

Embodiment 117: The composition of embodiment 116, wherein the average degree of substitution is about 6.69.

Embodiment 118: The composition of embodiment 100, wherein about 52% to about 58% of the hydroxypropyl substitutions in the hydroxypropyl β-cyclodextrin molecules are located at the 3-O— position.

Embodiment 119: The composition of embodiment 118, wherein about 55% to about 57% of the hydroxypropyl substitutions in the hydroxypropyl β-cyclodextrin molecules are located at the 3-O— position.

Embodiment 120: The composition of embodiment 100, wherein about 41% to about 47% of the hydroxypropyl substitutions in the hydroxypropyl β-cyclodextrin molecules are located at the 2-O— position.

Embodiment 121: The composition of embodiment 120, wherein about 43% to about 45% of the hydroxypropyl substitutions in the hydroxypropyl β-cyclodextrin molecules are located at the 2-O— position.

Embodiment 122: The composition of embodiment 100, wherein the composition has an HPLC-CAD chromatogram of FIG. 8.

Embodiment 123: The composition of embodiment 122, wherein the composition has a mean retention time of about 10 minutes.

Embodiment 124: The composition of embodiment 100, wherein the composition has a −ESI-MS spectrum with peaks at about 653 m/z, about 682 m/z, about 711 m/z, about 741 m/z, about 769 m/z, about 799 m/z, about 828 m/z, and about 857 m/z.

Embodiment 125: The composition of embodiment 100, wherein the composition has a +ESI-MS spectrum with peaks at about 686 m/z, about 715 m/z, about 744 m/z, about 773 m/z, about 802 m/z, about 832 m/z, about 861 m/z, and about 890 m/z.

Embodiment 126: The composition of embodiment 100, wherein the composition has a ESI-MS spectra of FIG. 9.

Embodiment 127: The composition of embodiment 100, having a MALDI-TOF spectrum with peaks at about 1436 m/z, about 1495 m/z, about 1555 m/z, about 1614 m/z, about 1674 m/z, and about 1733 m/z.

Embodiment 128: The composition of embodiment 127, wherein the composition has a MALDI-TOF spectrum of FIG. 10.

Embodiment 129: The composition of embodiment 128, wherein the area of DS-5 is 2.83%.

Embodiment 130: The composition of embodiment 128, wherein the area of DS-6 is 10.64%.

Embodiment 131: The composition of embodiment 128, wherein the area of DS-7 is 19.30%.

Embodiment 132: The composition of embodiment 128, wherein the area of DS-8 is 29.30%.

Embodiment 133: The composition of embodiment 128, wherein the area of DS-9 is 25.30%.

Embodiment 134: The composition of embodiment 128, wherein the area of DS-10 is 14.30%.

Embodiment 135: The composition of embodiment 100 having a $^1$H-NMR spectrum of FIG. 6.

Embodiment 136: The composition of embodiment 100 having a DEPT-edited HSQC spectrum of FIG. 7.

Embodiment 137: The composition of embodiment 100, wherein the osmolality of the composition is about 635-695 mOs/kg.

Embodiment 138: The composition of embodiment 100, wherein the true density of the composition is about 1.096-1.098 g/cm$^3$.

Embodiment 139: The composition of embodiment 100, wherein the composition comprises no more than 10 ppb of propylene glycol as measured by HPLC.

Embodiment 140: The composition of embodiment 100, wherein the composition comprises no more than 10 ppb propylene glycol as measured by gas chromatography.

Embodiment 141: The composition of embodiment 100, wherein the composition comprises no more than 10 ppb propylene glycol as measured by PG/EG-ratio of propylene glycol to ethylene glycol.

Embodiment 142: The composition of embodiment 100, wherein the composition comprises no more than 1 ppm propylene oxide.

Embodiment 143: The composition of embodiment 100, wherein the total amount of other unspecified impurities is less than or equal to 0.05% as measured by HPLC.

Embodiment 144: The composition of embodiment 100, wherein the composition further comprises between 0 and 10 ppm chloride.

Embodiment 145: The composition of embodiment 144, wherein the composition comprises between 0 and 1 ppm chloride.

Embodiment 146: The composition of embodiment 100, wherein the composition has a conductivity between 0 and 8 µS/cm.

Embodiment 147: The composition of embodiment 146, wherein the composition has a conductivity between 0 and 4.5 µS/cm.

Embodiment 148: The composition of embodiment 147, wherein the composition has a conductivity between 0 and 3 µS/cm.

Embodiment 149: The composition of embodiment 148, wherein the composition has a conductivity between 0 and 1.5 µS/cm.

Embodiment 150: The composition of embodiment 100, wherein the composition is nanofiltered.

Embodiment 151: The composition of embodiment 150, wherein the nanofiltered composition has no substantial difference observed in HPLC-ELSD after nanofiltration as compared to before nanofiltration.

Embodiment 152: The composition of embodiment 151, wherein the nanofiltered composition has no substantial difference observed in NMR after nanofiltration as compared to before nanofiltration.

Embodiment 153: A composition comprising a mixture of isomerically-purified hydroxypropyl β-cyclodextrin molecules comprising:
  about 1% to about 5% β-cyclodextrin substituted with five hydroxypropyl groups ("DS-5");
  about 7% to about 13% β-cyclodextrin substituted with six hydroxypropyl groups ("DS-6");
  about 16% to about 22% β-cyclodextrin substituted with seven hydroxypropyl groups ("DS-7");
  about 26% to about 32% β-cyclodextrin substituted with eight hydroxypropyl groups ("DS-8");
  about 22% to about 28% β-cyclodextrin substituted with nine hydroxypropyl groups ("DS-9"); and about 11% to about 17% β-cyclodextrin substituted with ten hydroxypropyl groups ("DS-10").

Embodiment 154: A composition comprising a mixture of isomerically-purified hydroxypropyl β-cyclodextrin molecules comprising:
  β-cyclodextrin substituted with five hydroxypropyl groups ("DS-5");
  β-cyclodextrin substituted with six hydroxypropyl groups ("DS-6");
  β-cyclodextrin substituted with seven hydroxypropyl groups ("DS-7");
  β-cyclodextrin substituted with eight hydroxypropyl groups ("DS-8");

β-cyclodextrin substituted with nine hydroxypropyl groups ("DS-9"); and

β-cyclodextrin substituted with ten hydroxypropyl groups ("DS-10"), wherein the composition comprises less than 1% β-cyclodextrin substituted with four hydroxypropyl groups ("DS-4"), β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1"), and wherein the composition comprises less than 1% β-cyclodextrin substituted with eleven hydroxypropyl groups ("DS-11"), β-cyclodextrin substituted with twelve hydroxypropyl groups ("DS-12"), β-cyclodextrin substituted with thirteen hydroxypropyl groups ("DS-13"), and β-cyclodextrin substituted with fourteen hydroxypropyl groups ("DS-14").

Embodiment 155: A composition comprising a mixture of isomerically-purified hydroxypropyl β-cyclodextrin molecules comprising less than 1% hydroxypropyl β-cyclodextrin with five hydroxypropyl groups ("DS-5").

Embodiment 156: The composition of embodiment 155, wherein the hydroxypropyl β-cyclodextrin percentage is based upon area percentage from a MALDI-TOF-MS spectrum.

Embodiment 157: The composition of embodiment 155, wherein the hydroxypropyl β-cyclodextrin percentage is based upon weight percentage.

Embodiment 158: The composition of embodiment 155, wherein the composition comprises less than 1% β-cyclodextrin substituted with four hydroxypropyl groups ("DS-4"), β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1").

Embodiment 159: The composition of embodiment 155, wherein the mixture of isomerically-purified hydroxypropyl β-cyclodextrin comprises about 0% to about 6% of hydroxypropyl β-cyclodextrin substituted with six hydroxypropyl groups ("DS-6").

Embodiment 160: The composition of embodiment 159, wherein the mixture of isomerically-purified β-hydroxypropyl cyclodextrin molecules comprises about 1% to about 5% of DS-6.

Embodiment 161: The composition of embodiment 155, wherein the mixture of isomerically-purified hydroxypropyl β-cyclodextrin molecules comprises about 8% to about 14% of hydroxypropyl β-cyclodextrin substituted with seven hydroxypropyl groups ("DS-7").

Embodiment 162: The composition of embodiment 161, wherein the mixture of isomerically-purified hydroxypropyl β-cyclodextrin molecules comprises about 9% to about 13% of DS-7.

Embodiment 163: The composition of embodiment 155, wherein the mixture of isomerically-purified β-hydroxypropyl cyclodextrin molecules comprises about 19% to about 25% of hydroxypropyl β-cyclodextrin substituted with eight hydroxypropyl groups ("DS-8").

Embodiment 164: The composition of embodiment 163, wherein the mixture of isomerically-purified hydroxypropyl β-cyclodextrin molecules comprises about 20% to about 24% of DS-8.

Embodiment 165: The composition of embodiment 155, wherein the mixture of isomerically-purified β-hydroxypropyl cyclodextrin molecules comprises about 23% to about 29% hydroxypropyl β-cyclodextrin substituted with nine hydroxypropyl groups ("DS-9").

Embodiment 166: The composition of embodiment 165, wherein the mixture of isomerically-purified hydroxypropyl β-cyclodextrin molecules comprises about 24% to about 28% of DS-9.

Embodiment 167: The composition of embodiment 155, wherein the mixture of isomerically-purified hydroxypropyl β-cyclodextrin molecules comprises about 17% to about 23% of hydroxypropyl β-cyclodextrin substituted with ten hydroxypropyl groups ("DS-10).

Embodiment 168: The composition of embodiment 167, wherein the mixture of isomerically-purified β-hydroxypropyl cyclodextrin molecules comprises about 18% to about 22% of DS-10.

Embodiment 169: The composition of embodiment 155, wherein the mixture of isomerically-purified β-hydroxypropyl cyclodextrin molecules comprises about 9% to about 15% of hydroxypropyl β-cyclodextrin substituted with eleven hydroxypropyl groups ("DS-11").

Embodiment 170: The composition of embodiment 169, wherein the mixture of isomerically-purified β-cyclodextrin molecules comprises about 10% to about 14% of DS-11.

Embodiment 171: The composition of embodiment 155, wherein the mixture of isomerically-purified β-cyclodextrin molecules comprises about 2% to about 8% hydroxypropyl β-cyclodextrin substituted with twelve hydroxypropyl groups ("DS-12").

Embodiment 172: The composition of embodiment 171, wherein the mixture of isomerically-purified β-cyclodextrin molecules comprises about 3% to about 7% DS-12.

Embodiment 173: The composition of embodiment 155, wherein the mixture of isomerically-purified β-cyclodextrin molecules has an average degree of substitution of about 7 to about 8.

Embodiment 174: The composition of embodiment 173, wherein the average degree of substitution is about 7.42.

Embodiment 175: The composition of embodiment 155, wherein about 36% to about 42% of the hydroxypropyl substitutions in the hydroxypropyl β-cyclodextrin molecules are located at the 3-O— position.

Embodiment 176: The composition of embodiment 175, wherein about 37% to about 41% of the hydroxypropyl substitutions in the hydroxypropyl β-cyclodextrin molecules are located at the 3-O— position.

Embodiment 177: The composition of embodiment 155, wherein about 58% to about 64% of the hydroxypropyl substitutions in the hydroxypropyl β-cyclodextrin molecules are located at the 2-O— position.

Embodiment 178: The composition of embodiment 177, wherein about 59% to about 63% of the hydroxypropyl substitutions in the hydroxypropyl β-cyclodextrin molecules are located at the 2-O— position.

Embodiment 179: The composition of embodiment 155, wherein the concentration of the composition does not substantially change the time required for nanofiltration.

Embodiment 180: The composition of embodiment 179, wherein the length of time to nanofilter the composition ranges from 1.04 to 1.20 hours per diafiltration volume (kg soln/m2-hr/L soln).

Embodiment 181: The composition of embodiment 155, wherein the composition has no substantial difference observed in HPLC-ELSD after nanofiltration as compared to before nanofiltration.

Embodiment 182: The composition of embodiment 155, wherein the composition has no substantial difference observed in NMR after nanofiltration as compared to before nanofiltration.

Embodiment 183: The composition of embodiment 155, wherein the composition has a conductivity between 0 and 8.0 μS/cm.

Embodiment 184: The composition of embodiment 155, wherein the composition has a conductivity between 0 and 4.5 μS/cm.

Embodiment 185: A composition comprising a mixture of isomerically-purified hydroxypropyl β-cyclodextrin molecules comprising:
- β-cyclodextrin substituted with six hydroxypropyl groups ("DS-6");
- β-cyclodextrin substituted with seven hydroxypropyl groups ("DS-7");
- β-cyclodextrin substituted with eight hydroxypropyl groups ("DS-8");
- β-cyclodextrin substituted with nine hydroxypropyl groups ("DS-9");
- β-cyclodextrin substituted with ten hydroxypropyl groups ("DS-10");
- β-cyclodextrin substituted with eleven hydroxypropyl groups ("DS-11"); and
- β-cyclodextrin substituted with twelve hydroxypropyl groups ("DS-12"),
- wherein the composition comprises less than 1% β-cyclodextrin substituted with five hydroxypropyl groups ("DS-5") and the composition comprises less than 1% I β-cyclodextrin substituted with thirteen hydroxypropyl groups ("DS-13").

Embodiment 186: The composition of embodiment 185, wherein the composition comprises less than 1% β-cyclodextrin substituted with four hydroxypropyl groups ("DS-4"), β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1").

Embodiment 187: The composition of embodiment 185, wherein the composition comprises less than 1% β-cyclodextrin substituted with thirteen hydroxypropyl groups ("DS-13") and hydroxypropyl β-cyclodextrin substituted with fourteen hydroxypropyl groups ("DS-14").

Embodiment 188: The composition of embodiment 185, wherein the DS-9 has the highest concentration in the composition as compared to DS-6, DS-7, DS-8, DS-10, DS-11, and DS-12.

Embodiment 189: The composition of embodiment 185, wherein the mixture of isomerically-purified hydroxypropyl β-cyclodextrin molecules comprises about 0% to about 6% of DS-6.

Embodiment 190: The composition of embodiment 189, wherein the mixture of isomerically-purified hydroxypropyl β-cyclodextrin molecules comprises about 1% to about 5% of DS-6.

Embodiment 191: The composition of embodiment 185, wherein the mixture of isomerically-purified hydroxypropyl β-cyclodextrin molecules comprises about 8% to about 14% of DS-7.

Embodiment 192: The composition of embodiment 191, wherein the mixture of isomerically-purified hydroxypropyl β-cyclodextrin molecules comprises about 9% to about 13% of DS-7.

Embodiment 193: The composition of embodiment 185, wherein the mixture of isomerically-purified hydroxypropyl β-cyclodextrin molecules comprises about 19% to about 25% of DS-8.

Embodiment 194: The composition of embodiment 193, wherein the mixture of isomerically-purified hydroxypropyl β-cyclodextrin molecules comprises about 19% to about 25% of DS-8.

Embodiment 195: The composition of embodiment 185, wherein the mixture of isomerically-purified hydroxypropyl β-cyclodextrin molecules comprises about 23% to about 29% of DS-9.

Embodiment 196: The composition of embodiment 195, wherein the mixture of isomerically-purified hydroxypropyl β-cyclodextrin molecules comprises about 24% to about 28% of DS-9.

Embodiment 197: The composition of embodiment 185, wherein the mixture of isomerically-purified hydroxypropyl β-cyclodextrin molecules comprises about 17% to about 23% of DS-10.

Embodiment 198: The composition of embodiment 197, wherein the mixture of isomerically-purified hydroxypropyl β-cyclodextrin molecules comprises about 18% to about 22% of DS-10.

Embodiment 199: The composition of embodiment 185, wherein the mixture of isomerically-purified hydroxypropyl β-cyclodextrin molecules comprises about 9% to about 15% of DS-11.

Embodiment 200: The composition of embodiment 199, wherein the mixture of isomerically-purified hydroxypropyl β-cyclodextrin molecules comprises about 10% to about 14% of DS-11.

Embodiment 201: The composition of embodiment 185, wherein the mixture of isomerically-purified hydroxypropyl β-cyclodextrin molecules comprises about 2% to about 8% DS-12.

Embodiment 202: The composition of embodiment 201, wherein the mixture of isomerically-purified hydroxypropyl β-cyclodextrin molecules comprises about 3% to about 7% DS-12.

Embodiment 203: The composition of embodiment 185, wherein the mixture of isomerically-purified hydroxypropyl β-cyclodextrin molecules has an average degree of substitution of about 7 to about 8.

Embodiment 204: The composition of embodiment 203, wherein the average degree of substitution is about 7.42.

Embodiment 205: The composition of embodiment 185, wherein about 36% to about 42% of the hydroxypropyl substitutions in the hydroxypropyl β-cyclodextrin molecules are located at the 3-O— position.

Embodiment 206: The composition of embodiment 205, wherein about 37% to about 41% of the hydroxypropyl substitutions in the hydroxypropyl β-cyclodextrin molecules are located at the 3-O— position.

Embodiment 207: The composition of embodiment 185, wherein about 58% to about 64% of the hydroxypropyl substitutions in the hydroxypropyl β-cyclodextrin molecules are located at the 2-O— position.

Embodiment 208: The composition of embodiment 207, wherein about 59% to about 63% of the hydroxypropyl substitutions in the hydroxypropyl β-cyclodextrin molecules are located at the 2-O— position.

Embodiment 209: The composition of embodiment 185, having an HPLC-CAD chromatograph of FIG. 13.

Embodiment 210: The composition of embodiment 209, wherein the peak retention time is at about 11.9 minutes.

Embodiment 211: The composition of embodiment 185, wherein the composition has a −ESI-MS spectrum with peaks at about 682 m/z, about 712 m/z, about 740 m/z, about 770 m/z, about 798 m/z, about 828 m/z, about 856 m/z, and about 886 m/z.

Embodiment 212: The composition of embodiment 185, wherein the composition has a +ESI-MS spectrum with peaks at about 744 m/z, about 773 m/z, about 803 m/z, about 832 m/z, about 860 m/z, about 889 m/z, and about 919 m/z.

Embodiment 213: The composition of embodiment 185, having an ESI-MS spectrum of FIG. 14.

Embodiment 214: The composition of embodiment 185, having a MALDI-TOF-MS spectrum with peaks at about 1497 m/z, about 1557 m/z, about 1616 m/z, about 1675 m/z, about 1734 m/z, about 1794 m/z, and about 1914 m/z.

Embodiment 215: The composition of embodiment 214, having a MALDI-TOF-MS spectrum of FIG. 15.

Embodiment 216: The composition of embodiment 215, wherein the area of DS-6 is 2.91%.

Embodiment 217: The composition of embodiment 215, wherein the area of DS-7 is 10.93%.

Embodiment 218: The composition of embodiment 215, wherein the area of DS-8 is 22.52%.

Embodiment 219: The composition of embodiment 215, wherein the area of DS-9 is 26.42%.

Embodiment 220: The composition of embodiment 215, wherein the area of DS-10 is 20.35%.

Embodiment 221: The composition of embodiment 215, wherein the area of DS-11 is 12.02%.

Embodiment 222: The composition of embodiment 215, wherein the area of DS-12 is 4.85%.

Embodiment 223: The composition of embodiment 185, having a $^1$H-NMR spectrum of FIG. 16.

Embodiment 224: The composition of embodiment 185, having a DEPT-edited HSQC spectrum of FIG. 12.

Embodiment 225: The composition of embodiment 185, wherein the osmolality of the composition is about 635-695 mOs/kg.

Embodiment 226: The composition of embodiment 185, wherein the true density of the composition is about 1.096-1.098 g/cm$^3$.

Embodiment 227: The composition of embodiment 185, wherein the composition comprises no more than 10 ppb of propylene glycol as measured by HPLC.

Embodiment 228: The composition of embodiment 185, wherein the composition comprises no more than 10 ppb propylene glycol as measured by gas chromatography.

Embodiment 229: The composition of embodiment 185, wherein the composition comprises no more than 10 ppb propylene glycol as measured by PG/EG-ratio of propylene glycol to ethylene glycol.

Embodiment 230: The composition of embodiment 185, wherein the composition comprises no more than 1 ppm propylene oxide.

Embodiment 231: The composition of embodiment 185, wherein the total amount of other unspecified impurities is less than or equal to 0.05% as measured by HPLC.

Embodiment 232: The composition of embodiment 185, wherein the composition comprises between 0 and 10 ppm chloride.

Embodiment 233: The composition of embodiment 232, wherein the composition comprises between 0 and 1 ppm chloride.

Embodiment 234: The composition of embodiment 185, wherein the composition has a conductivity between 0 and 8 µS/cm.

Embodiment 235: The composition of embodiment 234, wherein the composition has a conductivity between 0 and 4.5 µS/cm.

Embodiment 236: The composition of embodiment 235, wherein the composition has a conductivity between 0 and 3 µS/cm.

Embodiment 237: The composition of embodiment 236, wherein the composition has a conductivity between 0 and 1.5 µS/cm.

Embodiment 238: The composition of embodiment 185, wherein the composition is nanofiltered.

Embodiment 239: The composition of embodiment 238, wherein the nanofiltered composition has no substantial difference observed in HPLC-ELSD after nanofiltration as compared to before nanofiltration.

Embodiment 240: The composition of embodiment 239, wherein the nanofiltered composition has no substantial difference observed in NMR after nanofiltration as compared to before nanofiltration.

Embodiment 241: A composition comprising a mixture of isomerically-purified hydroxypropyl β-cyclodextrin molecules comprising: about 0.5% to about 6% hydroxypropyl β-cyclodextrin substituted with six hydroxypropyl groups ("DS-6");

about 8% to about 14% hydroxypropyl β-cyclodextrin substituted with seven hydroxypropyl groups ("DS-7");

about 19% to about 25% hydroxypropyl β-cyclodextrin substituted with eight hydroxypropyl groups ("DS-8");

about 23% to about 29% hydroxypropyl β-cyclodextrin substituted with nine hydroxypropyl groups ("DS-9");

about 17% to about 23% hydroxypropyl β-cyclodextrin substituted with ten hydroxypropyl groups ("DS-10");

about 9% to about 15% hydroxypropyl β-cyclodextrin substituted with eleven hydroxypropyl groups ("DS-11"); and about 2% to about 8% hydroxypropyl β-cyclodextrin substituted with twelve hydroxypropyl groups ("DS-12").

Embodiment 242: A composition comprising a mixture of isomerically-purified hydroxypropyl β-cyclodextrin molecules comprising:

β-cyclodextrin substituted with six hydroxypropyl groups ("DS-6");

β-cyclodextrin substituted with seven hydroxypropyl groups ("DS-7");

β-cyclodextrin substituted with eight hydroxypropyl groups ("DS-8");

β-cyclodextrin substituted with nine hydroxypropyl groups ("DS-9");

β-cyclodextrin substituted with ten hydroxypropyl groups ("DS-10");

β-cyclodextrin substituted with eleven hydroxypropyl groups ("DS-11"), and

β-cyclodextrin substituted with twelve hydroxypropyl groups ("DS-12"), wherein the composition comprises less than 1% β-cyclodextrin substituted with five hydroxypropyl groups ("DS-5"), β-cyclodextrin substituted with four hydroxypropyl groups ("DS-4") β-cyclodextrin substituted with three hydroxypropyl groups ("DS-3") β-cyclodextrin substituted with two hydroxypropyl groups ("DS-2") β-cyclodextrin substituted with one hydroxypropyl group ("DS-1"), and wherein the composition comprises less than 1% β-cyclodextrin substituted with thirteen hydroxypropyl groups ("DS-13") and β-cyclodextrin substituted with fourteen hydroxypropyl groups ("DS-14").

Embodiment 243: A composition comprising a mixture of isomerically-purified hydroxypropyl β-cyclodextrin molecules comprising less than 1% hydroxypropyl β-cyclodextrin with six hydroxypropyl groups ("DS-6") and less than 1% β-cyclodextrin substituted with fourteen hydroxypropyl groups ("DS-14").

Embodiment 244: The composition of embodiment 243, wherein the hydroxypropyl β-cyclodextrin percentage is based upon area percentage from a MALDI-TOF-MS spectrum.

Embodiment 245: The composition of embodiment 243, wherein the hydroxypropyl β-cyclodextrin percentage is based upon weight percentage.

Embodiment 246: The composition of embodiment 243, wherein the composition comprises less than 1% β-cyclodextrin substituted with five hydroxypropyl groups ("DS-5"), β-cyclodextrin substituted with four hydroxypropyl groups ("DS-4"), β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1").

Embodiment 247: The composition of embodiment 243, wherein the mixture of isomerically-purified hydroxypropyl β-cyclodextrin molecules comprises about 1% to about 7% of β-cyclodextrin substituted with seven hydroxypropyl groups ("DS-7").

Embodiment 248: The composition of embodiment 247, wherein the mixture of isomerically-purified hydroxypropyl β-cyclodextrin molecules comprises about 2% to about 6% of DS-7.

Embodiment 249: The composition of embodiment 243, wherein the mixture of isomerically-purified hydroxypropyl β-cyclodextrin molecules comprises about 16% to about 22% of β-cyclodextrin substituted with eight hydroxypropyl groups ("DS-8").

Embodiment 250: The composition of embodiment 249, wherein the mixture of isomerically-purified hydroxypropyl β-cyclodextrin molecules comprises about 17% to about 21% of DS-8.

Embodiment 251: The composition of embodiment 243, wherein the mixture of isomerically-purified hydroxypropyl β-cyclodextrin molecules comprises about 22% to about 28% of β-cyclodextrin substituted with nine hydroxypropyl groups ("DS-9").

Embodiment 252: The composition of embodiment 251, wherein the mixture of isomerically-purified hydroxypropyl β-cyclodextrin molecules comprises about 23% to about 27% of DS-9.

Embodiment 253: The composition of embodiment 243, wherein the mixture of isomerically-purified hydroxypropyl β-cyclodextrin molecules comprises about 19% to about 25% of β-cyclodextrin substituted with ten hydroxypropyl groups ("DS-10).

Embodiment 254: The composition of embodiment 253, wherein the mixture of isomerically-purified hydroxypropyl β-cyclodextrin molecules comprises about 20% to about 24% of DS-10.

Embodiment 255: The composition of embodiment 243, wherein the mixture of isomerically-purified hydroxypropyl β-cyclodextrin molecules comprises about 14% to about 20% of β-cyclodextrin substituted with eleven hydroxypropyl groups ("DS-11").

Embodiment 256: The composition of embodiment 255, wherein the mixture of isomerically-purified hydroxypropyl β-cyclodextrin molecules comprises about 15% to about 19% of DS-11.

Embodiment 257: The composition of embodiment 243, wherein the mixture of isomerically-purified hydroxypropyl β-cyclodextrin molecules comprises about 5% to about 11% of β-cyclodextrin substituted with twelve hydroxypropyl groups ("DS-12").

Embodiment 258: The composition of embodiment 257, wherein the mixture of isomerically-purified hydroxypropyl β-cyclodextrin molecules comprises about 6% to about 10% of DS-12.

Embodiment 259: The composition of embodiment 243, wherein the mixture of isomerically-purified hydroxypropyl β-cyclodextrin molecules comprises about 1% to about 7% of β-cyclodextrin substituted with thirteen hydroxypropyl groups ("DS-13").

Embodiment 260: The composition of embodiment 259, wherein the mixture of isomerically-purified hydroxypropyl β-cyclodextrin molecules comprises about 2% to about 6% of DS-13.

Embodiment 261: The composition of embodiment 243, wherein the average degree of substitution of the mixture of isomerically-purified hydroxypropyl β-cyclodextrin is about 8 to about 9.

Embodiment 262: The composition of embodiment 261, wherein the average degree of substitution of the mixture of isomerically-purified hydroxypropyl β-cyclodextrin is about 8.53.

Embodiment 263: The composition of embodiment 243, wherein about 26% to about 32% of the hydroxypropyl substitutions in the hydroxypropyl β-cyclodextrin molecules are located at the 3-O— position.

Embodiment 264: The composition of embodiment 263, wherein about 27% to about 31% of the hydroxypropyl substitutions in the hydroxypropyl β-cyclodextrin molecules are located at the 3-O— position.

Embodiment 265: The composition of embodiment 243, wherein about 68% to about 74% of the hydroxypropyl substitutions in the hydroxypropyl β-cyclodextrin molecules are located at the 2-O— position.

Embodiment 266: The composition of embodiment 265, wherein about 69% to about 73% of the hydroxypropyl substitutions in the hydroxypropyl β-cyclodextrin molecules are located at the 2-O— position.

Embodiment 267: The composition of embodiment 243, wherein the concentration of the composition does not substantially change the time required for nanofiltration.

Embodiment 268: The composition of embodiment 267, wherein the length of time to nanofilter the composition ranges from 1.04 to 1.20 hours per diafiltration volume (kg soln/m$^2$·hr/L soln).

Embodiment 269: The composition of embodiment 243, wherein the composition has no substantial difference observed in HPLC-ELSD after nanofiltration as compared to before nanofiltration.

Embodiment 270: The composition of embodiment 243, wherein the composition has no substantial difference observed in NMR after nanofiltration as compared to before nanofiltration.

Embodiment 271: The composition of embodiment 243, wherein the composition has a conductivity between 0 and 8.0 μS/cm.

Embodiment 272: The composition of embodiment 243, wherein the composition has a conductivity between 0 and 4.5 μS/cm.

Embodiment 273: A composition comprising a mixture of isomerically-purified hydroxypropyl β-cyclodextrin molecules comprising:

β-cyclodextrin substituted with seven hydroxypropyl groups ("DS-7");

β-cyclodextrin substituted with eight hydroxypropyl groups ("DS-8");

β-cyclodextrin substituted with nine hydroxypropyl groups ("DS-9");

β-cyclodextrin substituted with ten hydroxypropyl groups ("DS-10");

β-cyclodextrin substituted with eleven hydroxypropyl groups ("DS-11");

β-cyclodextrin substituted with twelve hydroxypropyl groups ("DS-12"); and

β-cyclodextrin substituted with thirteen hydroxypropyl groups ("DS-13"), wherein the composition comprises less than 1% β-cyclodextrin substituted with six hydroxypropyl groups ("DS-6") and less than 1% β-cyclodextrin substituted with fourteen hydroxypropyl groups ("DS-14").

Embodiment 274: The composition of embodiment 273, wherein the composition comprises less than 1% β-cyclodextrin substituted with five hydroxypropyl groups ("DS-5"), β-cyclodextrin substituted with four hydroxypropyl groups ("DS-4"), β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1").

Embodiment 275: The composition of embodiment 273, wherein the DS-9 has the highest concentration in the mixture of isomerically-purified hydroxypropyl β-cyclodextrin molecules as compared to DS-6, DS-7, DS-8, DS-10, DS-11, DS-12, and DS-13.

Embodiment 276: The composition of embodiment 273, wherein the mixture of isomerically-purified hydroxypropyl β-cyclodextrin molecules comprises about 1% to about 7% of DS-7.

Embodiment 277: The composition of embodiment 276, wherein the mixture of isomerically-purified hydroxypropyl β-cyclodextrin molecules comprises about 2% to about 6% of DS-7.

Embodiment 278: The composition of embodiment 273, wherein the mixture of isomerically-purified hydroxypropyl β-cyclodextrin molecules comprises about 16% to about 22% of DS-8.

Embodiment 279: The composition of embodiment 279, wherein the mixture of isomerically-purified hydroxypropyl β-cyclodextrin molecules comprises about 17% to about 21% of DS-8.

Embodiment 280: The composition of embodiment 273, wherein the mixture of isomerically-purified hydroxypropyl β-cyclodextrin molecules comprises about 22% to about 28% of DS-9.

Embodiment 281: The composition of embodiment 280, wherein the mixture of isomerically-purified hydroxypropyl β-cyclodextrin molecules comprises about 23% to about 27% of DS-9.

Embodiment 282: The composition of embodiment 273, wherein the mixture of isomerically-purified hydroxypropyl β-cyclodextrin molecules comprises about 19% to about 25% of DS-10.

Embodiment 283: The composition of embodiment 282, wherein the mixture of isomerically-purified hydroxypropyl β-cyclodextrin molecules comprises about 20% to about 24% of DS-10.

Embodiment 284: The composition of embodiment 273, wherein the mixture of isomerically-purified hydroxypropyl β-cyclodextrin molecules comprises about 14% to about 20% of DS-11.

Embodiment 285: The composition of embodiment 284, wherein the mixture of isomerically-purified hydroxypropyl β-cyclodextrin molecules comprises about 15% to about 19% of DS-11.

Embodiment 286: The composition of embodiment 273, wherein the mixture of isomerically-purified hydroxypropyl β-cyclodextrin molecules comprises about 5% to about 11% of DS-12.

Embodiment 287: The composition of embodiment 286, wherein the mixture of isomerically-purified hydroxypropyl β-cyclodextrin molecules comprises about 6% to about 10% of DS-12.

Embodiment 288: The composition of embodiment 273, wherein the mixture of isomerically-purified hydroxypropyl β-cyclodextrin molecules comprises about 1% to about 7% of DS-13.

Embodiment 289: The composition of embodiment 288, wherein the mixture of isomerically-purified hydroxypropyl β-cyclodextrin molecules comprises about 2% to about 6% of DS-13.

Embodiment 290: The composition of embodiment 273, wherein the average degree of substitution of the mixture of isomerically-purified hydroxypropyl β-cyclodextrin is about 8 to about 9.

Embodiment 291: The composition of embodiment 290, wherein the average degree of substitution of the mixture of isomerically-purified hydroxypropyl β-cyclodextrin is about 8.53.

Embodiment 292: The composition of embodiment 273, wherein about 26% to about 32% of the hydroxypropyl substitutions in the β-cyclodextrin molecules are located at the 3-O— position.

Embodiment 293: The composition of embodiment 292, wherein about 27% to about 31% of the hydroxypropyl substitutions in the β-cyclodextrin molecules are located at the 3-O— position.

Embodiment 294: The composition of embodiment 273, wherein about 68% to about 74% of the hydroxypropyl substitutions in the β-cyclodextrin molecules are located at the 2-O— position.

Embodiment 295: The composition of embodiment 294, wherein about 69% to about 73% of the hydroxypropyl substitutions in the β-cyclodextrin molecules are located at the 2-O— position.

Embodiment 296: The composition of embodiment 273, wherein the composition has an HPLC-CAD chromatogram of FIG. 18.

Embodiment 297: The composition of embodiment 296, wherein the composition has a mean retention time of about 13.5 minutes.

Embodiment 298: The composition of embodiment 273, wherein the composition has a −ESI-MS spectrum with peaks at about 741 m/z, about 769 m/z, about 799 m/z, about 828 m/z, about 856 m/z, and about 886 m/z.

Embodiment 299: The composition of embodiment 273, wherein the composition has a +ESI-MS spectrum with peaks at about 773 m/z, about 803 m/z, about 833 m/z, about 860 m/z, about 889 m/z, and about 920 m/z.

Embodiment 300: The composition of embodiment 273, wherein the composition has a ESI-MS spectra of FIG. 19.

Embodiment 301: The composition of embodiment 273, having a MALDI-TOF spectrum with peaks at about 1557 m/z, about 1617 m/z, about 1676 m/z, about 1736 m/z, about 1795 m/z, about 1855 m/z, and about 1915 m/z.

Embodiment 302: The composition of embodiment 301, wherein the composition has a MALDI-TOF spectrum of FIG. 20.

Embodiment 303: The composition of embodiment 302, wherein the area of DS-7 is 3.92%.

Embodiment 304: The composition of embodiment 302, wherein the area of DS-8 is 18.65%.

Embodiment 305: The composition of embodiment 302, wherein the area of DS-9 is 25.45%.

Embodiment 306: The composition of embodiment 302, wherein the area of DS-10 is 22.37%.

Embodiment 307: The composition of embodiment 302, wherein the area of DS-11 is 17.41%.

Embodiment 308: The composition of embodiment 302, wherein the area of DS-12 is 8.01%.

Embodiment 309: The composition of embodiment 302, wherein the area of DS-13 is 4.20%.

Embodiment 310: The composition of embodiment 273 having a $^1$H-NMR spectrum of FIG. 16.

Embodiment 311: The composition of embodiment 273 having a DEPT-edited HSQC spectrum of FIG. 17.

Embodiment 312: The composition of embodiment 273, wherein the osmolality of the composition is about 635-695 mOs/kg.

Embodiment 313: The composition of embodiment 273, wherein the true density of the composition is about 1.096-1.098 g/cm3.

Embodiment 314: The composition of embodiment 273, wherein the composition comprises no more than 10 ppb of propylene glycol as measured by HPLC.

Embodiment 315: The composition of embodiment 273, wherein the composition comprises no more than 10 ppb propylene glycol as measured by gas chromatography.

Embodiment 316: The composition of embodiment 273, wherein the composition comprises no more than 10 ppb propylene glycol as measured by PG/EG-ratio of propylene glycol to ethylene glycol.

Embodiment 317: The composition of embodiment 273, wherein the composition comprises no more than 1 ppm propylene oxide.

Embodiment 318: The composition of embodiment 273, wherein the total amount of other unspecified impurities is less than or equal to 0.05% as measured by HPLC.

Embodiment 319: The composition of embodiment 273, wherein the composition comprises between 0 and 10 ppm chloride.

Embodiment 320: The composition of embodiment 319, wherein the composition comprises between 0 and 1 ppm chloride.

Embodiment 321: The composition of embodiment 273, wherein the composition has a conductivity between 0 and 8 µS/cm.

Embodiment 322: The composition of embodiment 321, wherein the composition has a conductivity between 0 and 4.5 µS/cm.

Embodiment 323: The composition of embodiment 322, wherein the composition has a conductivity between 0 and 3 µS/cm.

Embodiment 324: The composition of embodiment 323, wherein the composition has a conductivity between 0 and 1.5 µS/cm.

Embodiment 325: The composition of embodiment 273, wherein the composition is nanofiltered.

Embodiment 326: The composition of embodiment 325, wherein the nanofiltered composition has no substantial difference observed in HPLC-ELSD after nanofiltration as compared to before nanofiltration.

Embodiment 327: The composition of embodiment 325, wherein the nanofiltered composition has no substantial difference observed in NMR after nanofiltration as compared to before nanofiltration.

Embodiment 328: A composition comprising a mixture of isomerically-purified hydroxypropyl β-cyclodextrin molecules comprising:
- about 1% to about 7% β-cyclodextrin substituted with seven hydroxypropyl groups ("DS-7");
- about 16% to about 22% β-cyclodextrin substituted with eight hydroxypropyl groups ("DS-8");
- about 22% to about 28% β-cyclodextrin substituted with nine hydroxypropyl groups ("DS-9");
- about 19% to about 25% β-cyclodextrin substituted with ten hydroxypropyl groups ("DS-10");
- about 14% to about 20% β-cyclodextrin substituted with eleven hydroxypropyl groups ("DS-11");
- about 5% to about 11% β-cyclodextrin substituted with twelve hydroxypropyl groups ("DS-12"); and
- about 1% to about 7% β-cyclodextrin substituted with thirteen hydroxypropyl groups ("DS-13").

Embodiment 329: A composition comprising a mixture of isomerically-purified hydroxypropyl β-cyclodextrin molecules comprising:
- β-cyclodextrin substituted with seven hydroxypropyl groups ("DS-7");
- β-cyclodextrin substituted with eight hydroxypropyl groups ("DS-8");
- β-cyclodextrin substituted with nine hydroxypropyl groups ("DS-9");
- β-cyclodextrin substituted with ten hydroxypropyl groups ("DS-10");
- β-cyclodextrin substituted with eleven hydroxypropyl groups ("DS-11");
- β-cyclodextrin substituted with twelve hydroxypropyl groups ("DS-12"); and
- β-cyclodextrin substituted with thirteen hydroxypropyl groups ("DS-13"),
wherein the composition comprises less than 1% β-cyclodextrin substituted with six hydroxypropyl groups ("DS-6"), β-cyclodextrin substituted with five hydroxypropyl groups ("DS-5"), β-cyclodextrin substituted with four hydroxypropyl groups ("DS-4"), β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1").

Embodiment 330: A composition comprising a mixture of isomerically-purified hydroxypropyl β-cyclodextrin molecules comprising less than 1% hydroxypropyl β-cyclodextrin with six hydroxypropyl groups ("DS-6")

Embodiment 331: The composition of embodiment 330, wherein the hydroxypropyl β-cyclodextrin percentage is based upon area percentage from a MALDI-TOF-MS spectrum.

Embodiment 332: The composition of embodiment 330, wherein the hydroxypropyl β-cyclodextrin percentage is based upon weight percentage.

Embodiment 333: The composition of embodiment 330, wherein the composition comprises less than 1% β-cyclodextrin substituted with five hydroxypropyl groups ("DS-5"), β-cyclodextrin substituted with four hydroxypropyl groups ("DS-4"), β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1").

Embodiment 334: The composition of embodiment 330, wherein the mixture of isomerically-purified hydroxypropyl β-cyclodextrin molecules comprises about 0% to about 6% of β-cyclodextrin substituted with seven hydroxypropyl groups ("DS-7").

Embodiment 335: The composition of embodiment 334, wherein the mixture of isomerically-purified hydroxypropyl β-cyclodextrin molecules comprises about 1% to about 5% of DS-7.

Embodiment 336: The composition of embodiment 330, wherein the mixture of isomerically-purified hydroxypropyl β-cyclodextrin molecules comprises about 13% to about 19% of β-cyclodextrin substituted with eight hydroxypropyl groups ("DS-8").

Embodiment 337: The composition of embodiment 336, wherein the mixture of isomerically-purified hydroxypropyl β-cyclodextrin molecules comprises about 14% to about 18% of DS-8.

Embodiment 338: The composition of embodiment 330, wherein the mixture of isomerically-purified hydroxypropyl β-cyclodextrin molecules comprises about 22% to about 28% of β-cyclodextrin substituted with nine hydroxypropyl groups ("DS-9").

Embodiment 339: The composition of embodiment 338, wherein the mixture of isomerically-purified hydroxypropyl β-cyclodextrin molecules comprises about 23% to about 27% of DS-9.

Embodiment 340: The composition of embodiment 330, wherein the mixture of isomerically-purified hydroxypropyl β-cyclodextrin molecules comprises about 23% to about 29% of β-cyclodextrin substituted with ten hydroxypropyl groups ("DS-10).

Embodiment 341: The composition of embodiment 340, wherein the mixture of isomerically-purified hydroxypropyl β-cyclodextrin molecules comprises about 24% to about 28% of DS-10.

Embodiment 342: The composition of embodiment 330, wherein the mixture of isomerically-purified hydroxypropyl β-cyclodextrin molecules comprises about 12% to about 18% of β-cyclodextrin substituted with eleven hydroxypropyl groups ("DS-11").

Embodiment 343: The composition of embodiment 342, wherein the mixture of isomerically-purified hydroxypropyl β-cyclodextrin molecules comprises about 13% to about 17% of DS-11.

Embodiment 344: The composition of embodiment 330, wherein the mixture of isomerically-purified hydroxypropyl β-cyclodextrin molecules comprises about 7% to about 13% of β-cyclodextrin substituted with twelve hydroxypropyl groups ("DS-12").

Embodiment 345: The composition of embodiment 344, wherein the mixture of isomerically-purified hydroxypropyl β-cyclodextrin molecules comprises about 8% to about 12% of DS-12.

Embodiment 346: The composition of embodiment 330, wherein the mixture of isomerically-purified hydroxypropyl β-cyclodextrin molecules comprises about 2% to about 8% of β-cyclodextrin substituted with thirteen hydroxypropyl groups ("DS-13").

Embodiment 347: The composition of embodiment 346, wherein the mixture of isomerically-purified hydroxypropyl β-cyclodextrin molecules comprises about 3% to about 7% of DS-13.

Embodiment 348: The composition of embodiment 330, wherein the average degree of substitution of the mixture of isomerically-purified hydroxypropyl β-cyclodextrin is about 7.5 to about 8.5.

Embodiment 349: The composition of embodiment 348, wherein the average degree of substitution of the mixture of isomerically-purified hydroxypropyl β-cyclodextrin is about 8.08.

Embodiment 350: The composition of embodiment 330, wherein about 22% to about 28% of the hydroxypropyl substitutions in the hydroxypropyl β-cyclodextrin molecules are located at the 3-O— position.

Embodiment 351: The composition of embodiment 350, wherein about 23% to about 27% of the hydroxypropyl substitutions in the hydroxypropyl β-cyclodextrin molecules are located at the 3-O— position.

Embodiment 352: The composition of embodiment 330, wherein about 72% to about 78% of the hydroxypropyl substitutions in the hydroxypropyl β-cyclodextrin molecules are located at the 2-O— position.

Embodiment 353: The composition of embodiment 352, wherein about 73% to about 77% of the hydroxypropyl substations in the hydroxypropyl β-cyclodextrin molecules are located at the 2-O— position.

Embodiment 354: The composition of embodiment 330, wherein the concentration of the composition does not substantially change the time required for nanofiltration.

Embodiment 355: The composition of embodiment 354, wherein the length of time to nanofilter the composition ranges from 1.04 to 1.20 hours per diafiltration volume (kg soln/m2-hr/L soln).

Embodiment 356: The composition of embodiment 330, wherein the nanofiltrated composition has no substantial difference observed in HPLC-ELSD after nanofiltration as compared to before nanofiltration.

Embodiment 357: The composition of embodiment 330, wherein the nanofiltrated composition has no substantial difference observed in NMR after nanofiltration as compared to before nanofiltration.

Embodiment 358: The composition of embodiment 330, wherein the composition has a conductivity between 0 and 8.0 μS/cm.

Embodiment 359: The composition of embodiment 330, wherein the composition has a conductivity between 0 and 4.5 μS/cm.

Embodiment 360: A composition comprising a mixture of isomerically-purified hydroxypropyl β-cyclodextrin molecules comprising:
 β-cyclodextrin substituted with seven hydroxypropyl groups ("DS-7");
 β-cyclodextrin substituted with eight hydroxypropyl groups ("DS-8");
 β-cyclodextrin substituted with nine hydroxypropyl groups ("DS-9");
 β-cyclodextrin substituted with ten hydroxypropyl groups ("DS-10");
 β-cyclodextrin substituted with eleven hydroxypropyl groups ("DS-11");
 β-cyclodextrin substituted with twelve hydroxypropyl groups ("DS-12");
 β-cyclodextrin substituted with thirteen hydroxypropyl groups ("DS-13"); and
 β-cyclodextrin substituted with fourteen hydroxypropyl groups ("DS-14"),
 wherein the composition comprises less than 1% β-cyclodextrin substituted with six hydroxypropyl groups ("DS-6").

Embodiment 361: The composition of embodiment 360, wherein the composition comprises less than 1% β-cyclodextrin substituted with five hydroxypropyl groups ("DS-5"), β-cyclodextrin substituted with four hydroxypropyl groups ("DS-4"), β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1").

Embodiment 362: The composition of embodiment 360, wherein the DS-9 has the highest concentration in the mixture of isomerically-purified hydroxypropyl β-cyclodextrin molecules as compared to DS-7, DS-8, DS-10, DS-11, DS-12, DS-13, and DS-14.

Embodiment 363: The composition of embodiment 360, wherein the DS-10 has the highest concentration in the mixture of isomerically-purified hydroxypropyl β-cyclodextrin molecules as compared to DS-7, DS-8, DS-10, DS-11, DS-12, DS-13, and DS-14.

Embodiment 364: The composition of embodiment 360, wherein the mixture of isomerically-purified hydroxypropyl β-cyclodextrin molecules comprises about 0% to about 6% DS-7.

Embodiment 365: The composition of embodiment 364, wherein the mixture of isomerically-purified hydroxypropyl β-cyclodextrin molecules comprises about 1% to about 5% DS-7.

Embodiment 366: The composition of embodiment 360, wherein the mixture of isomerically-purified hydroxypropyl β-cyclodextrin molecules comprises about 13% to about 19% DS-8.

Embodiment 367: The composition of embodiment 366, wherein the mixture of isomerically-purified hydroxypropyl β-cyclodextrin molecules comprises about 14% to about 18% DS-8.

Embodiment 368: The composition of embodiment 360, wherein the mixture of isomerically-purified hydroxypropyl β-cyclodextrin molecules comprises about 22% to about 28% DS-9.

Embodiment 369: The composition of embodiment 368, wherein the mixture of isomerically-purified hydroxypropyl β-cyclodextrin molecules comprises about 23% to about 27% DS-9.

Embodiment 370: The composition of embodiment 360, wherein the mixture of isomerically-purified hydroxypropyl β-cyclodextrin molecules comprises about 23% to about 29% DS-10.

Embodiment 371: The composition of embodiment 370, wherein the mixture of isomerically-purified hydroxypropyl β-cyclodextrin molecules comprises about 24% to about 28% DS-10.

Embodiment 372: The composition of embodiment 360, wherein the mixture of isomerically-purified hydroxypropyl β-cyclodextrin molecules comprises about 12% to about 18% DS-11.

Embodiment 373: The composition of embodiment 372, wherein the mixture of isomerically-purified hydroxypropyl β-cyclodextrin molecules comprises about 13% to about 17% DS-11.

Embodiment 374: The composition of embodiment 360, wherein the mixture of isomerically-purified hydroxypropyl β-cyclodextrin molecules comprises about 7% to about 13% DS-12.

Embodiment 375: The composition of embodiment 374, wherein the mixture of isomerically-purified hydroxypropyl β-cyclodextrin molecules comprises about 8% to about 12% DS-12.

Embodiment 376: The composition of embodiment 360, wherein the mixture of isomerically-purified hydroxypropyl β-cyclodextrin molecules comprises about 2% to about 8% DS-13.

Embodiment 377: The composition of embodiment 376, wherein the mixture of isomerically-purified hydroxypropyl β-cyclodextrin molecules comprises about 3% to about 7% DS-13.

Embodiment 378: The composition of embodiment 360, wherein the mixture of isomerically-purified hydroxypropyl β-cyclodextrin molecules comprises about 0% to about 6% DS-14.

Embodiment 379: The composition of embodiment 378, wherein the mixture of isomerically-purified hydroxypropyl β-cyclodextrin molecules comprises about 1% to about 5% DS-14.

Embodiment 380: The composition of embodiment 360, wherein the average degree of substitution of the mixture of isomerically-purified hydroxypropyl β-cyclodextrin is about 7.5 to about 8.5.

Embodiment 381: The composition of embodiment 380, wherein the average degree of substitution of the mixture of isomerically-purified hydroxypropyl β-cyclodextrin is about 8.08.

Embodiment 382: The composition of embodiment 360, wherein about 22% to about 28% of the hydroxypropyl substitutions in the hydroxypropyl β-cyclodextrin molecules are located at the 3-O— position.

Embodiment 383: The composition of embodiment 360, wherein about 23% to about 27% of the hydroxypropyl substitutions in the hydroxypropyl β-cyclodextrin molecules are located at the 3-O— position.

Embodiment 384: The composition of embodiment 360, wherein about 72% to about 78% of the hydroxypropyl substitutions in the β-cyclodextrin molecules are located at the 2-O— position.

Embodiment 385: The composition of embodiment 360, wherein about 73% to about 77% of the hydroxypropyl substitutions in the β-cyclodextrin molecules are located at the 2-O— position.

Embodiment 386: The composition of embodiment 360, wherein the composition has an HPLC-CAD chromatogram of FIG. 23.

Embodiment 387: The composition of embodiment 386, wherein the composition has a mean retention time of about 14.3 minutes.

Embodiment 388: The composition of embodiment 360, wherein the composition has a −ESI-MS spectrum with peaks at about 740 m/z, about 770 m/z, about 798 m/z, about 828 m/z, and about 857 m/z.

Embodiment 389: The composition of embodiment 360, wherein the composition has a +ESI-MS spectrum with peaks at about 803 m/z, about 831 m/z, about 861 m/z, about 889 m/z, and about 919 m/z.

Embodiment 390: The composition of embodiment 360, wherein the composition has a ESI-MS spectra of FIG. 24.

Embodiment 391: The composition of embodiment 360, having a MALDI-TOF spectrum with peaks at about 1559 m/z, about 1618 m/z, about 1678 m/z, about 1737 m/z, about 1796 m/z, about 1857 m/z, and about 1916 m/z.

Embodiments 392: The composition of embodiment 391, wherein the composition has a MALDI-TOF spectrum of FIG. 25.

Embodiments 393: The composition of embodiment 392, wherein the area of DS-7 is 3.16%.

Embodiments 394: The composition of embodiment 392, wherein the area of DS-8 is 16.44%.

Embodiments 395: The composition of embodiment 392, wherein the area of DS-9 is 25.24%.

Embodiments 396: The composition of embodiment 392, wherein the area of DS-10 is 25.52%.

Embodiments 397: The composition of embodiment 392, wherein the area of DS-11 is 15.10%.

Embodiments 398: The composition of embodiment 392, wherein the area of DS-12 is 10.03%.

Embodiments 399: The composition of embodiment 392, wherein the area of DS-13 is 4.50%.

Embodiments 400: The composition of embodiment 392, wherein the area of DS-14 is 2.67%.

Embodiments 401: The composition of embodiment 360 having a $^1$H-NMR spectrum of FIG. 21.

Embodiment 402: The composition of embodiment 360 having a DEPT-edited HSQC spectrum of FIG. 22.

Embodiment 403: The composition of embodiment 360, wherein the osmolality of the composition is about 635-695 mOs/kg.

Embodiment 404: The composition of embodiment 360, wherein the true density of the composition is about 1.096-1.098 g/cm3.

Embodiment 405: The composition of embodiment 360, wherein the composition comprises no more than 10 ppb of propylene glycol as measured by HPLC.

Embodiment 406: The composition of embodiment 360, wherein the composition comprises no more than 10 ppb propylene glycol as measured by gas chromatography.

Embodiment 407: The composition of embodiment 360, wherein the composition comprises no more than 10 ppb propylene glycol as measured by PG/EG-ratio of propylene glycol to ethylene glycol.

Embodiment 408: The composition of embodiment 360, wherein the composition comprises no more than 1 ppm propylene oxide.

Embodiment 409: The composition of embodiment 360, wherein the total amount of other unspecified impurities is less than or equal to 0.05% as measured by HPLC.

Embodiment 410: The composition of embodiment 360, wherein the composition comprises between 0 and 10 ppm chloride.

Embodiment 411: The composition of embodiment 410, wherein the composition comprises between 0 and 1 ppm chloride.

Embodiment 412: The composition of embodiment 360, wherein the composition has a conductivity between 0 and 8 μS/cm.

Embodiment 413: The composition of embodiment 412, wherein the composition has a conductivity between 0 and 4.5 μS/cm.

Embodiment 414: The composition of embodiment 413, wherein the composition has a conductivity between 0 and 3 μS/cm.

Embodiment 415: The composition of embodiment 414, wherein the composition has a conductivity between 0 and 1.5 μS/cm.

Embodiment 416: The composition of embodiment 360, wherein the composition is nanofiltered.

Embodiment 417: The composition of embodiment 416, wherein the nanofiltrated composition has no substantial difference observed in HPLC-ELSD after nanofiltration as compared to before nanofiltration.

Embodiment 418: The composition of embodiment 417, wherein the nanofiltrated composition has no substantial difference observed in NMR after nanofiltration as compared to before nanofiltration.

Embodiment 419: A composition comprising a mixture of isomerically-purified hydroxypropyl β-cyclodextrin molecules comprising:

about 0% to about 6% β-cyclodextrin substituted with seven hydroxypropyl groups ("DS-7");

about 13% to about 19% β-cyclodextrin substituted with eight hydroxypropyl groups ("DS-8");

about 22% to about 28% β-cyclodextrin substituted with nine hydroxypropyl groups ("DS-9");

about 23% to about 29% β-cyclodextrin substituted with ten hydroxypropyl groups ("DS-10");

about 12% to about 18% β-cyclodextrin substituted with eleven hydroxypropyl groups ("DS-11");

about 7% to about 13% β-cyclodextrin substituted with twelve hydroxypropyl groups ("DS-12");

about 2% to about 8% β-cyclodextrin substituted with thirteen hydroxypropyl groups ("DS-13"); and about 0% to about 6% β-cyclodextrin substituted with fourteen hydroxypropyl groups ("DS-14").

Embodiment 420: A composition comprising a mixture of isomerically-purified hydroxypropyl β-cyclodextrin molecules comprising:

β-cyclodextrin substituted with seven hydroxypropyl groups ("DS-7");

β-cyclodextrin substituted with eight hydroxypropyl groups ("DS-8");

β-cyclodextrin substituted with nine hydroxypropyl groups ("DS-9");

β-cyclodextrin substituted with ten hydroxypropyl groups ("DS-10");

β-cyclodextrin substituted with eleven hydroxypropyl groups ("DS-11");

β-cyclodextrin substituted with twelve hydroxypropyl groups ("DS-12");

β-cyclodextrin substituted with thirteen hydroxypropyl groups ("DS-13"); and

β-cyclodextrin substituted with fourteen hydroxypropyl groups ("DS-14"), wherein the composition comprises less than 1% β-cyclodextrin substituted with six hydroxypropyl groups ("DS-6"), β-cyclodextrin substituted with five hydroxypropyl groups ("DS-5"), β-cyclodextrin substituted with four hydroxypropyl groups ("DS-4"), β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1").

Embodiment 421: A composition comprising a mixture of isomerically-purified hydroxypropyl β-cyclodextrin molecules comprising less than 1% hydroxypropyl β-cyclodextrin with seven hydroxypropyl groups ("DS-7").

Embodiment 422: The composition of embodiment 421, wherein the hydroxypropyl β-cyclodextrin percentage is based upon area percentage from a MALDI-TOF-MS spectrum.

Embodiment 423: The composition of embodiment 421, wherein the hydroxypropyl β-cyclodextrin percentage is based upon weight percentage.

Embodiment 424: The composition of embodiment 421, wherein the composition comprises less than 1% β-cyclodextrin substituted with six hydroxypropyl groups ("DS-6"), β-cyclodextrin substituted with five hydroxypropyl groups ("DS-5"), β-cyclodextrin substituted with four hydroxypropyl groups ("DS-4"), β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1").

Embodiment 425: The composition of embodiment 421, wherein the mixture of isomerically-purified hydroxypropyl β-cyclodextrin molecules comprises about 6% to about 12% of β-cyclodextrin substituted with eight hydroxypropyl groups ("DS-8").

Embodiment 426: The composition of embodiment 425, wherein the mixture of isomerically-purified hydroxypropyl β-cyclodextrin molecules comprises about 7% to about 11% of DS-8.

Embodiment 427: The composition of embodiment 421, wherein the mixture of isomerically-purified hydroxypropyl β-cyclodextrin molecules comprises about 18% to about 24% of β-cyclodextrin substituted with nine hydroxypropyl groups ("DS-9").

Embodiment 428: The composition of embodiment 427, wherein the mixture of isomerically-purified hydroxypropyl β-cyclodextrin molecules comprises about 19% to about 23% of DS-9.

Embodiment 429: The composition of embodiment 421, wherein the mixture of isomerically-purified hydroxypropyl β-cyclodextrin molecules comprises about 24% to about 30% of β-cyclodextrin substituted with ten hydroxypropyl groups ("DS-10).

Embodiment 430: The composition of embodiment 429, wherein the mixture of isomerically-purified hydroxypropyl β-cyclodextrin molecules comprises about 25% to about 29% of DS-10.

Embodiment 431: The composition of embodiment 421, wherein the mixture of isomerically-purified hydroxypropyl β-cyclodextrin molecules comprises about 18% to about 24% of β-cyclodextrin substituted with eleven hydroxypropyl groups ("DS-11").

Embodiment 432: The composition of embodiment 431, wherein the mixture of isomerically-purified hydroxypropyl β-cyclodextrin molecules comprises about 19% to about 23% of DS-11.

Embodiment 433: The composition of embodiment 421, wherein the mixture of isomerically-purified hydroxypropyl β-cyclodextrin molecules comprises about 10% to about 16% of β-cyclodextrin substituted with twelve hydroxypropyl groups ("DS-12").

Embodiment 434: The composition of embodiment 433, wherein the mixture of isomerically-purified hydroxypropyl β-cyclodextrin molecules comprises about 11% to about 15% of DS-12.

Embodiment 435: The composition of embodiment 421, wherein the mixture of isomerically-purified hydroxypropyl β-cyclodextrin molecules comprises about 4% to about 10% of β-cyclodextrin substituted with thirteen hydroxypropyl groups ("DS-13").

Embodiment 436: The composition of embodiment 435, wherein the mixture of isomerically-purified hydroxypropyl β-cyclodextrin molecules comprises about 5% to about 9% of DS-13.

Embodiment 437: The composition of embodiment 421, wherein the mixture of isomerically-purified hydroxypropyl β-cyclodextrin molecules comprises about 0% to about 6% of β-cyclodextrin substituted with fourteen hydroxypropyl groups ("DS-14").

Embodiment 438: The composition of embodiment 437, wherein the mixture of isomerically-purified hydroxypropyl β-cyclodextrin molecules comprises about 1% to about 5% of DS-14.

Embodiment 439: The composition of embodiment 421, wherein the average degree of substitution of the mixture of isomerically-purified hydroxypropyl β-cyclodextrin is about 9 to about 10.

Embodiment 440: The composition of embodiment 439, wherein the average degree of substitution of the mixture of isomerically-purified hydroxypropyl β-cyclodextrin is about 9.65.

Embodiment 441: The composition of embodiment 421, wherein about 15% to about 21% of the hydroxypropyl substitutions in the hydroxypropyl β-cyclodextrin molecules are located at the 3-O— position.

Embodiment 442: The composition of embodiment 441, wherein about 16% to about 20% of the hydroxypropyl substitutions in the hydroxypropyl β-cyclodextrin molecules are located at the 3-O— position.

Embodiment 443: The composition of embodiment 421, wherein about 79% to about 85% of the hydroxypropyl substitutions in the hydroxypropyl β-cyclodextrin molecules are located at the 2-O— position.

Embodiment 444: The composition of embodiment 443, wherein about 80% to about 84% of the hydroxypropyl substitutions in the hydroxypropyl β-cyclodextrin molecules are located at the 2-O— position.

Embodiment 445: The composition of embodiment 421, wherein the concentration of the composition does not substantially change the time required for nanofiltration.

Embodiment 446: The composition of embodiment 445, wherein the length of time to nanofilter the composition ranges from 1.04 to 1.20 hours per diafiltration volume (kg soln/m$^2$·hr/L soln).

Embodiment 447: The composition of embodiment 421, wherein the composition has no substantial difference observed in HPLC-ELSD after nanofiltration as compared to before nanofiltration.

Embodiment 448: The composition of embodiment 421, wherein the composition has no substantial difference observed in NMR after nanofiltration as compared to before nanofiltration.

Embodiment 449: The composition of embodiment 421, wherein the composition has a conductivity between 0 and 8.0 µS/cm.

Embodiment 450: The composition of embodiment 421, wherein the composition has a conductivity between 0 and 4.5 µS/cm.

Embodiment 451: A composition comprising a mixture of isomerically-purified hydroxypropyl β-cyclodextrin molecules comprising:

β-cyclodextrin substituted with eight hydroxypropyl groups ("DS-8");

β-cyclodextrin substituted with nine hydroxypropyl groups ("DS-9");

β-cyclodextrin substituted with ten hydroxypropyl groups ("DS-10");

β-cyclodextrin substituted with eleven hydroxypropyl groups ("DS-11");

β-cyclodextrin substituted with twelve hydroxypropyl groups ("DS-12");

β-cyclodextrin substituted with thirteen hydroxypropyl groups ("DS-13"); and

β-cyclodextrin substituted with fourteen hydroxypropyl groups ("DS-14"), wherein the composition comprises less than 1% β-cyclodextrin substituted with seven hydroxypropyl groups ("DS-7").

Embodiment 452: The composition of embodiment 451, wherein the composition comprises less than 1% β-cyclodextrin substituted with six hydroxypropyl groups ("DS-6"), 1% β-cyclodextrin substituted with five hydroxypropyl groups ("DS-5"), β-cyclodextrin substituted with four hydroxypropyl groups ("DS-4"), β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1").

Embodiment 453: The composition of embodiment 451, wherein the DS-10 has the highest concentration in the mixture of isomerically-purified hydroxypropyl β-cyclodextrin molecules as compared to DS-8, DS-9, DS-11, DS-12, DS-13, and DS-14.

Embodiment 454: The composition of embodiment 451, wherein the mixture of isomerically-purified hydroxypropyl β-cyclodextrin molecules comprises about 6% to about 12% DS-8.

Embodiment 455: The composition of embodiment 454, wherein the mixture of isomerically-purified hydroxypropyl β-cyclodextrin molecules comprises about 7% to about 11% DS-8.

Embodiment 456: The composition of embodiment 451, wherein the mixture of isomerically-purified hydroxypropyl β-cyclodextrin molecules comprises about 18% to about 24% DS-9.

Embodiment 457: The composition of embodiment 456, wherein the mixture of isomerically-purified hydroxypropyl β-cyclodextrin molecules comprises about 19% to about 23% DS-9.

Embodiment 458: The composition of embodiment 451, wherein the mixture of isomerically-purified hydroxypropyl β-cyclodextrin molecules comprises about 24% to about 30% DS-10.

Embodiment 459: The composition of embodiment 458, wherein the mixture of isomerically-purified hydroxypropyl β-cyclodextrin molecules comprises about 25% to about 29% DS-10.

Embodiment 460: The composition of embodiment 451, wherein the mixture of isomerically-purified hydroxypropyl β-cyclodextrin molecules comprises about 18% to about 24% DS-11.

Embodiment 461: The composition of embodiment 460, wherein the mixture of isomerically-purified hydroxypropyl β-cyclodextrin molecules comprises about 19% to about 23% DS-11.

Embodiment 462: The composition of embodiment 451, wherein the mixture of isomerically-purified hydroxypropyl β-cyclodextrin molecules comprises about 10% to about 16% DS-12.

Embodiment 463: The composition of embodiment 462, wherein the mixture of isomerically-purified hydroxypropyl β-cyclodextrin molecules comprises about 11% to about 15% DS-12.

Embodiment 464: The composition of embodiment 451, wherein the mixture of isomerically-purified hydroxypropyl β-cyclodextrin molecules comprises about 4% to about 10% DS-13.

Embodiment 465: The composition of embodiment 464, wherein the mixture of isomerically-purified hydroxypropyl β-cyclodextrin molecules comprises about 5% to about 9% DS-13.

Embodiment 466: The composition of embodiment 451, wherein the mixture of isomerically-purified hydroxypropyl β-cyclodextrin molecules comprises about 0% to about 6% DS-14.

Embodiment 467: The composition of embodiment 466, wherein the mixture of isomerically-purified hydroxypropyl β-cyclodextrin molecules comprises about 1% to about 5% DS-14.

Embodiment 468: The composition of embodiment 451, wherein the average degree of substitution of the mixture of isomerically-purified hydroxypropyl β-cyclodextrin is about 9 to about 10.

Embodiment 469: The composition of embodiment 468, wherein the average degree of substitution of the mixture of isomerically-purified hydroxypropyl β-cyclodextrin is about 9.65.

Embodiment 470: The composition of embodiment 451, wherein about 15% to about 21% of the hydroxypropyl substitutions in the hydroxypropyl β-cyclodextrin molecules are located at the 3-O— position.

Embodiment 471: The composition of embodiment 470, wherein about 16% to about 20% of the hydroxypropyl substitutions in the hydroxypropyl β-cyclodextrin molecules are located at the 3-O— position.

Embodiment 472: The composition of embodiment 451, wherein about 79% to about 85% of the hydroxypropyl substitutions in the hydroxypropyl β-cyclodextrin molecules are located at the 2-O— position.

Embodiment 473: The composition of embodiment 472, wherein about 80% to about 84% of the hydroxypropyl substitutions in the hydroxypropyl β-cyclodextrin molecules are located at the 2-O— position.

Embodiment 474: The composition of embodiment 451, wherein the composition has an HPLC-CAD chromatogram of FIG. 28.

Embodiment 475: The composition of embodiment 474, wherein the composition has a mean retention time of about 15.4 minutes.

Embodiment 476: The composition of embodiment 451, wherein the composition has a −ESI-MS spectrum with peaks at about 770 m/z, about 798 m/z, about 828 m/z, about 857 m/z, about 885 m/z.

Embodiment 477: The composition of embodiment 451, wherein the composition has a +ESI-MS spectrum with peaks at about 803 m/z, about 831 m/z, about 861 m/z, about 889 m/z, and about 919 m/z.

Embodiment 478: The composition of embodiment 451, wherein the composition has a ESI-MS spectra of FIG. 29.

Embodiment 479: The composition of embodiment 451, having a MALDI-TOF spectrum with peaks at about 1614 m/z, about 1673 m/z, about 1733 m/z, about 1792 m/z, about 1852 m/z, about 1912 m/z, and about 1971 m/z.

Embodiment 480: The composition of embodiment 479, having a MALDI-TOF spectrum of FIG. 30.

Embodiment 481: The composition of embodiment 480, wherein the area of DS-8 is 8.53%.

Embodiment 482: The composition of embodiment 480, wherein the area of DS-9 is 21.33%.

Embodiment 483: The composition of embodiment 480, wherein the area of DS-10 is 26.58%.

Embodiment 484: The composition of embodiment 480, wherein the area of DS-11 is 20.90%.

Embodiment 485: The composition of embodiment 480, wherein the area of DS-12 is 13.31%.

Embodiment 486: The composition of embodiment 480, wherein the area of DS-13 is 6.74%.

Embodiment 487: The composition of embodiment 480, wherein the area of DS-14 is 2.60%.

Embodiment 488: The composition of embodiment 451 having a 1H-NMR spectrum of FIG. 26.

Embodiment 489: The composition of embodiment 451 having a DEPT-edited HSQC spectrum of FIG. 27.

Embodiment 490: The composition of embodiment 451, wherein the osmolality of the composition is about 635-695 mOs/kg.

Embodiment 491: The composition of embodiment 451, wherein the true density of the composition is about 1.096-1.098 g/cm$^3$.

Embodiment 492: The composition of embodiment 451, wherein the composition comprises no more than 10 ppb of propylene glycol as measured by HPLC.

Embodiment 493: The composition of embodiment 451, wherein the composition comprises no more than 10 ppb propylene glycol as measured by gas chromatography.

Embodiment 494: The composition of embodiment 451, wherein the composition comprises no more than 10 ppb propylene glycol as measured by PG/EG-ratio of propylene glycol to ethylene glycol.

Embodiment 495: The composition of embodiment 451, wherein the composition comprises no more than 1 ppm propylene oxide.

Embodiment 496: The composition of embodiment 451, wherein the total amount of other unspecified impurities is less than or equal to 0.05% as measured by HPLC.

Embodiment 497: The composition of embodiment 451, wherein the composition comprises between 0 and 10 ppm chloride.

Embodiment 498: The composition of embodiment 497, wherein the composition comprises between 0 and 1 ppm chloride.

Embodiment 499: The composition of embodiment 451, wherein the composition has a conductivity between 0 and 8 µS/cm.

Embodiment 500: The composition of embodiment 499, wherein the composition has a conductivity between 0 and 4.5 µS/cm.

Embodiment 501: The composition of embodiment 500, wherein the composition has a conductivity between 0 and 3 µS/cm.

Embodiment 502: The composition of embodiment 501, wherein the composition has a conductivity between 0 and 1.5 µS/cm.

Embodiment 503: The composition of embodiment 451, wherein the composition is nanofiltered.

Embodiment 504: The composition of embodiment 503, wherein the nanofiltrated composition has no substantial difference observed in HPLC-ELSD after nanofiltration as compared to before nanofiltration.

Embodiment 505: The composition of embodiment 503, wherein the nanofiltrated composition has no substantial difference observed in NMR after nanofiltration as compared to before nanofiltration.

Embodiment 506: A composition comprising a mixture of isomerically-purified hydroxypropyl β-cyclodextrin molecules comprising:
- about 6% to about 12% β-cyclodextrin substituted with eight hydroxypropyl groups ("DS-8");
- about 18% to about 24% β-cyclodextrin substituted with nine hydroxypropyl groups ("DS-9");
- about 24% to about 30% β-cyclodextrin substituted with ten hydroxypropyl groups ("DS-10");
- about 18% to about 24% β-cyclodextrin substituted with eleven hydroxypropyl groups ("DS-11");
- about 10% to about 16% β-cyclodextrin substituted with twelve hydroxypropyl groups ("DS-12");
- about 4% to about 10% β-cyclodextrin substituted with thirteen hydroxypropyl groups ("DS-13"); and
- about 0% to about 6% β-cyclodextrin substituted with fourteen hydroxypropyl groups ("DS-14").

Embodiment 507: A composition comprising a mixture of isomerically-purified hydroxypropyl β-cyclodextrin molecules comprising:
- β-cyclodextrin substituted with eight hydroxypropyl groups ("DS-8");
- β-cyclodextrin substituted with nine hydroxypropyl groups ("DS-9");
- β-cyclodextrin substituted with ten hydroxypropyl groups ("DS-10");
- β-cyclodextrin substituted with eleven hydroxypropyl groups ("DS-11");
- β-cyclodextrin substituted with twelve hydroxypropyl groups ("DS-12");
- β-cyclodextrin substituted with thirteen hydroxypropyl groups ("DS-13"); and
- β-cyclodextrin substituted with fourteen hydroxypropyl groups ("DS-14"), wherein the composition comprises less than 1% β-cyclodextrin substituted with seven hydroxypropyl groups ("DS-7"), β-cyclodextrin substituted with six hydroxypropyl groups ("DS-6"), β-cyclodextrin substituted with five hydroxypropyl groups ("DS-5"), β-cyclodextrin substituted with four hydroxypropyl groups ("DS-4"), β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1").

Embodiment 508: An isomerically-purified composition comprising a mixture of hydroxypropyl-β-cyclodextrin molecules having the general subunit structure:

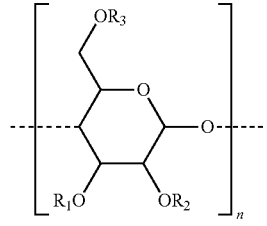

wherein $n=7=m+k+y+z$;
$m=0\text{-}7$;
$k=0\text{-}7$;
$y=0\text{-}7$;
$z=0\text{-}7$;
$R_1$, $R_2$, and $R_3$ are each independently H, hydroxypropyl, or

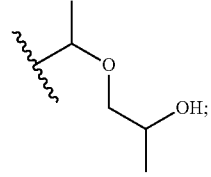 [SMILES: *C(C)OCC(C)O]

wherein m refers to the number of subunits wherein $R_1$ is not H, $R_2$ is H, and $R_3$ is H;
wherein k refers to the number of subunits wherein $R_1$ is H, $R_2$ is not H, and $R_3$ is H;
wherein y refers to the number of subunits wherein $R_1$ is H, $R_2$ is H, and $R_3$ is not H;
wherein z refers to the number of subunits wherein $R_1$ is H, $R_2$ is H, and $R_3$ is H; and
wherein $R_3$=H in at least 80% of the subunits.

Embodiment 509: The composition of embodiment 508, wherein $R_3$=H in at least 85% of the subunits.

Embodiment 510: The composition of embodiment 508, wherein $R_3$=H in at least 90% of the subunits.

Embodiment 511: The composition of embodiment 508, wherein $R_3$=H in at least 95% of the subunits.

Embodiment 512: The composition of embodiment 508, wherein $R_3$=H in at least 99% of the subunits.

Embodiment 513: The composition of embodiment 508, wherein $R_3$=H in 100% of the subunits.

Embodiment 514: The composition of embodiment 508, wherein y=0.

Embodiment 515: The composition of embodiment 508, wherein z=0.

Embodiment 516: The composition of embodiment 508, wherein $R_1$ is not H in at least 35% of the subunits.

Embodiment 517: The composition of embodiment 516, wherein $R_1$ is not H in at least 40% of the subunits.

Embodiment 518: The composition of embodiment 516, wherein $R_1$ is not H in about 50% to about 70% of the subunits.

Embodiment 519: The composition of embodiment 516, wherein $R_1$ is not H in about 60% to about 80% of the subunits.

Embodiment 520: The composition of embodiment 516, wherein $R_1$ is not H in about 65% to about 85% of the subunits.

Embodiment 521: The composition of embodiment 516, wherein $R_1$ is not H in about 70% to about 90% of the subunits.

Embodiment 522: The composition of embodiment 508, wherein $R_2$ is not H in no more than 65% of the subunits.

Embodiment 523: The composition of embodiment 522, wherein $R_2$ is not H in about 35% to about 55% of the subunits.

Embodiment 524: The composition of embodiment 522, wherein $R_2$ is not H in about 30% to about 50% of the subunits.

Embodiment 525: The composition of embodiment 522, wherein $R_2$ is not H in about 20% to about 40% of the subunits.

Embodiment 526: The composition of embodiment 522, wherein $R_2$ is not H in about 10% to about 30% of the subunits.

Embodiment 527: The composition of embodiment 508, wherein the general subunit structure is:

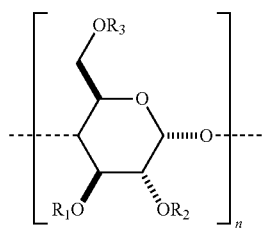

Embodiment 528: An isomerically-purified composition comprising a mixture of hydroxypropyl-β-cyclodextrin molecules, wherein 0% to 5% of the hydroxypropyl-β-cyclodextrin subunits are substituted at the 6-O— position.

Embodiment 529: An isomerically-purified composition comprising a mixture of hydroxypropyl-β-cyclodextrin molecules, wherein 80% to 100% of the hydroxypropyl-β-cyclodextrin subunits are substituted at the 2-O— position, the 3-O-position, or a combination thereof.

Embodiment 530: A composition comprising a mixture of beta-cyclodextrin molecules substituted at one or more hydroxyl positions by hydroxypropyl groups, wherein: the mixture comprises less than 0.05% unsubstituted beta-cyclodextrin ("DS-0") and less than 0.05% beta-cyclodextrin substituted with one hydroxypropyl group ("DS-1"), the composition comprising an average degree of substitution of 6.02-7.98, wherein the composition is suitable for intrathecal, intravenous, oral, or intracerebroventricular administration to a patient in need thereof.

Embodiment 531: The composition of embodiment 530, wherein the average degree of substitution is determined by $^1$H-NMR.

Embodiment 532: The composition of embodiment 530, wherein the amount of DS-0 and DS-1 is determined by peak height of an electrospray MS spectrum.

Embodiment 533: The composition of embodiment 530, wherein the pH of the composition is between 6.0 and 7.9.

Embodiment 534: The composition of embodiment 530, wherein the pH of the composition is between 7.1 and 7.7.

Embodiment 535: The composition of embodiment 530, wherein the pH of the composition is between 7.3-7.5.

Embodiment 536: The composition of embodiment 530, wherein the composition comprises at least one of a pharmaceutical excipient, a carrier, a pharmaceutically acceptable diluent, a pH adjusting agent, and a buffer.

Embodiment 537: The composition of embodiment 530, wherein the true density of the composition is about 1.096-1.098 g/cm$^3$.

Embodiment 538: The composition of embodiment 530, wherein the osmolality of the composition is about 635-695 mOs/kg.

Embodiment 539: The composition of embodiment 530, wherein composition further comprises a container and non-visible particulate matter, and the non-visible particulate matter with a size 25 microns is in an amount ≤600/container.

Embodiment 540: The composition of embodiment 530, wherein the composition comprises no more than 10 ppb of propylene glycol as measured by HPLC.

Embodiment 541: The composition of embodiment 530, wherein the composition comprises no more than 5 ppb of propylene glycol as measured by HPLC.

Embodiment 542: The composition of embodiment 530, wherein the composition comprises no more than 10 ppb propylene glycol as measured by PG/EG-ratio of propylene glycol to ethylene glycol.

Embodiment 543: The composition of embodiment 530, wherein the composition comprises no more than 5 ppb propylene glycol as measured by PG/EG-ratio of propylene glycol to ethylene glycol.

Embodiment 544: The composition of embodiment 530, wherein the composition purified by absorption chromatography alumina, solvent precipitation, or a combination thereof.

Embodiment 545: The composition of embodiment 530, wherein the composition comprises no more than 1 ppm propylene oxide.

Embodiment 546: The composition of embodiment 530, wherein the total amount of other unspecified impurities is less than or equal to 0.05% as measured by HPLC.

Embodiment 547: The composition of embodiment 530, wherein the composition has a concentration of about 10 mg/mL to about 200 mg/mL.

Embodiment 548: The composition of embodiment 530, wherein the composition is suitable for administration to a pediatric patient.

Embodiment 549: The composition of embodiment 530, wherein the composition is suitable for administration to an adult patient.

Embodiment 550: The composition of embodiment 530, further comprising a pharmaceutically acceptable diluent.

Embodiment 551: The composition of embodiment 530, wherein the composition exhibits a lower ototoxicity than Trappsol® Cyclo.

Embodiment 552: The composition of embodiment 530, wherein the composition has a conductivity of about ≤200 µS/cm.

Embodiment 553: The composition of embodiment 530, wherein the composition is stable for at least 6 months.

Embodiment 554: The composition of embodiment 553, wherein the composition is stable for at least 12 months.

Embodiment 555: The composition of embodiment 554, wherein the composition is stable for at least 18 months.

Embodiment 556: The composition of embodiment 530, further comprising a pH adjusting agent.

Embodiment 557: The composition of embodiment 556, wherein the pH adjusting agent is sodium hydroxide.

Embodiment 558: The composition of embodiment 530, further comprising a buffer.

Embodiment 559: The composition of embodiment 558, wherein the buffer comprises monobasic sodium phosphate and dibasic sodium phosphate.

Embodiment 560: The composition of embodiment 530, wherein the composition is packaged in a vial.

Embodiment 561: The composition of embodiment 530, wherein the composition is terminally sterilized.

Embodiment 562: The composition of embodiment 530, wherein the pH of the composition is adjusted after the terminal sterilization.

Embodiment 563: The composition of embodiment 530, wherein the composition contains ≤10.0% w/w/of water.

Embodiment 564: A method of preparing a purified mixture of beta-cyclodextrin suitable for intrathecal, intravenous, oral, or intracerebroventricular administration to a patient in need thereof, the method comprising:
nanofiltrating a beta-cyclodextrin to achieve a purified mixture of beta-cyclodextrin molecules substituted at one or more hydroxyl positions by hydroxypropyl groups, wherein the mixture comprises less than 0.05% unsubstituted beta-cyclodextrin ("DS-0") and less than 0.05% beta-cyclodextrin substituted with one hydroxypropyl group ("DS-1"), and wherein the average degree of substitution of 6.02-7.98, and adjusting the pH of the nanofiltrated purified mixture of beta-cyclodextrin to achieve a pH of 6.0 to 7.8.

Embodiment 565: The method of embodiment 564, wherein the pH is adjusted with 0.1 M sodium hydroxide.

Embodiment 566: A method of treating Niemann-Pick disease Type C, the method comprising administering to a patient in need thereof a therapeutically effective amount of the pharmaceutical composition of embodiment 530.

Embodiment 567: The method of embodiment 566, further comprising administering about 50 mg to about 2000 mg of the beta-cyclodextrin mixture to the patient.

Embodiment 568: The method of embodiment 567, wherein about 50 mg to about 300 mg of the beta-cyclodextrin mixture is administered.

Embodiment 569: The method of embodiment 566, further comprising administering the composition at 1-day, 2-day, or 3-day intervals.

Embodiment 570: The method of embodiment 566, further comprising administering the composition once every week.

Embodiment 571: The method of embodiment 566, further comprising administering the composition once every two weeks.

Embodiment 572: The method of embodiment 566, wherein the administering comprises intravenously administering about 200 mg/kg to about 4100 mg/kg of the beta-cyclodextrin mixture to the patient.

Embodiment 573: The method of embodiment 566, wherein administration results in the lowering of one or more lipids by 75%±5%, 80%±5%, 85%±5%, 90%±5%, or 95%±5%.

Embodiment 574: The method of embodiment 566, wherein administration prevents progression of NPC as compared with no administration or administration of a placebo.

Embodiment 575: The method of embodiment 566, wherein the administration is sufficient to modulate the level in plasma of one or more of 7-ketocholesterol, 7β-hydroxycholesterol, 24S-hydroxycholesterol, 25-hydroxycholesterol, 27-hydroxycholesterol, and cholestane-3β,5α,6β-triol.

Embodiment 576: The method of embodiment 566, wherein the administration is sufficient to maintain or reduce one or more domain scores of the NPC Severity Scale selected from: ambulation, fine motor skills, cognition, speech, swallowing, eye movement, memory, hearing, and seizures.

Embodiment 577: The method of embodiment 566, wherein the administration occurs within 4 hours.

Embodiment 578: The method of embodiment 566, wherein the administration occurs within 2 hours.

Exemplary Embodiments List B

Embodiment 1: A composition comprising a mixture of β-cyclodextrin molecules, wherein the mixture of β-cyclodextrin molecules comprises:
β-cyclodextrin substituted with four hydroxypropyl groups ("DS-4");
β-cyclodextrin substituted with five hydroxypropyl groups ("DS-5");
β-cyclodextrin substituted with six hydroxypropyl groups ("DS-6");
β-cyclodextrin substituted with seven hydroxypropyl groups ("DS-7");
β-cyclodextrin substituted with eight hydroxypropyl groups ("DS-8");
β-cyclodextrin substituted with nine hydroxypropyl groups ("DS-9");
β-cyclodextrin substituted with ten hydroxypropyl groups ("DS-10");
β-cyclodextrin substituted with eleven hydroxypropyl groups ("DS-11");
β-cyclodextrin substituted with twelve hydroxypropyl groups ("DS-12");
β-cyclodextrin substituted with thirteen hydroxypropyl groups ("DS-13"); and
β-cyclodextrin substituted with fourteen hydroxypropyl groups ("DS-14"); and
wherein the mixture of β-cyclodextrin molecules comprises less than 1% DS-4.

Embodiment 2: The composition of embodiment 1 having a HPLC-CAD chromatogram of FIG. 4.

Embodiment 3: The composition of embodiment 1 or embodiment 2, wherein the mixture of β-cyclodextrin molecules comprises about 0.5% to about 1% DS-4.

Embodiment 4: The composition of any one of embodiments 1-3, wherein the mixture of β-cyclodextrin molecules comprises about 2% to about 5% DS-5.

Embodiment 5: The composition of embodiment 4, wherein the mixture of β-cyclodextrin molecules comprises about 3% to about 4% DS-5.

Embodiment 6: The composition of any one of embodiments 1-5, wherein the mixture of β-cyclodextrin molecules comprises about 7% to about 13% DS-6.

Embodiment 7: The composition of embodiment 6, wherein the mixture of β-cyclodextrin molecules comprises about 9% to about 11% DS-6.

Embodiment 8: The composition of any one of embodiments 1-7, wherein the mixture of β-cyclodextrin molecules comprises about 21% to about 27% DS-7.

Embodiment 9: The composition of embodiment 8, wherein the mixture of β-cyclodextrin molecules comprises about 23% to about 25% DS-7.

Embodiment 10: The composition of any one of embodiments 1-9, wherein the mixture of β-cyclodextrin molecules comprises about 23% to about 29% DS-8.

Embodiment 11: The composition of embodiment 10, wherein the mixture of β-cyclodextrin molecules comprises about 25% to about 27% DS-8.

Embodiment 12: The composition of any one of embodiments 1-11, wherein the mixture of β-cyclodextrin molecules comprises about 15% to about 21% DS-9.

Embodiment 13: The composition of embodiment 12, wherein the mixture of β-cyclodextrin molecules comprises about 17% to about 19% DS-9.

Embodiment 14: The composition of any one of embodiments 1-13, wherein the mixture of β-cyclodextrin molecules comprises about 6% to about 12% DS-10.

Embodiment 15: The composition of embodiment 14, wherein the mixture of β-cyclodextrin molecules comprises about 8% to about 10% DS-10.

Embodiment 16: The composition of any one of embodiments 1-15, wherein the mixture of β-cyclodextrin molecules comprises about 2% to about 6% DS-11.

Embodiment 17: The composition of embodiment 16, wherein the mixture of β-cyclodextrin molecules comprises about 3% to about 5% DS-11.

Embodiment 18: The composition of any one of embodiments 1-17, wherein the mixture of β-cyclodextrin molecules comprises about 0.5% to about 4% DS-12.

Embodiment 19: The composition of embodiment 18, wherein the mixture of β-cyclodextrin molecules comprises about 1% to about 3% DS-12.

Embodiment 20: The composition of any one of embodiments 1-19, wherein the mixture of β-cyclodextrin molecules comprises less than about 1% DS-13.

Embodiment 21: The composition of any one of embodiments 1-20, wherein the mixture of β-cyclodextrin molecules comprises about 0.5% to about 1% DS-13.

Embodiment 22: The composition of any one of embodiments 1-21, wherein the mixture of β-cyclodextrin molecules is suitable for intravenous, intrathecal, or intracerebroventricular administration.

Embodiment 23: The composition of any one of embodiments 1-22, wherein the amount of DS-1, DS-2, DS-3, DS-4, DS-5, DS-6, DS-7, DS-8, DS-9, DS-10, DS-11, DS-12, and DS-13 in the mixture of β-cyclodextrin molecules is determined by MALDI-TOF-MS.

Embodiment 24: The composition of any one of embodiments 1-23, wherein DS-8 has the highest concentration in the mixture of β-cyclodextrin molecules as compared to the concentrations of DS-1, DS-2, DS-3, DS-4, DS-5, DS-6, DS-7, DS-9, DS-10, DS-11, DS-12, and DS-13.

Embodiment 25: The composition of any one of embodiments 1-24, wherein the β-cyclodextrin molecules are substituted at the 2-O— position at a rate of 35-55%, the 3-O— position at a rate of 45-65%, and the 6-O— position at a rate of 0-20%.

Embodiment 26: The composition of any one of embodiments 1-25, wherein the β-cyclodextrin molecules are substituted at the 2-O— position at a rate of about 46%, the 3-O— position at a rate of about 54%, and the 6-O— position at a rate of about 10%.

Embodiment 27: The composition of embodiment 25 or 26, wherein the rate of substitution at the 2-O—, 3-O—, and 6-0 positions is determined via DEPT-ed HSQC.

Embodiment 28: The composition of any one of embodiments 1-27, wherein the HPLC peak retention time occurs at about 12 minutes.

Embodiment 29: The composition of any one of embodiments 1-28, wherein the composition has an average degree of substitution of between about 7 to about 9.

Embodiment 30: The composition of embodiment 29, wherein the composition has an average degree of substitution of about 7.7.

Embodiment 31: A composition comprising a mixture of β-cyclodextrin molecules, the composition having a 1H-NMR spectrum comprising:
- at least one peak at about 5.0-5.4 ppm corresponding to anomeric protons of the β-cyclodextrin molecules;
- at least one peak at about 3.2-4.2 ppm corresponding to protons within a core region of the β-cyclodextrin molecules; and
- at least one peak at about 1.0-1.2 ppm corresponding to methyl protons of side chains of the β-cyclodextrin molecules.

Embodiment 32: The composition of any one of embodiments 1-31, having the $^1$H-NMR spectrum of FIG. 2.

Embodiment 33: A composition comprising a mixture of β-cyclodextrin molecules, wherein the mixture of β-cyclodextrin molecules comprises:
- less than about 1% β-cyclodextrin substituted with four hydroxypropyl groups ("DS-4");
- about 1% to about 5% β-cyclodextrin substituted with five hydroxypropyl groups ("DS-5");
- about 7% to about 13% β-cyclodextrin substituted with six hydroxypropyl groups ("DS-6");
- about 21% to about 27% β-cyclodextrin substituted with seven hydroxypropyl groups ("DS-7");
- about 23% to about 29% β-cyclodextrin substituted with eight hydroxypropyl groups ("DS-8");
- about 15% to about 21% β-cyclodextrin substituted with nine hydroxypropyl groups ("DS-9");
- about 6% to about 12% β-cyclodextrin substituted with ten hydroxypropyl groups ("DS-10");
- about 1% to about 7% β-cyclodextrin substituted with eleven hydroxypropyl groups ("DS-11");
- about 0.5% to about 3% β-cyclodextrin substituted with twelve hydroxypropyl groups ("DS-12");
- less than about 1% β-cyclodextrin substituted with thirteen hydroxypropyl groups ("DS-13"); and
- less than about 1% β-cyclodextrin substituted with fourteen hydroxypropyl groups ("DS-14").

Embodiment 34: The composition of any one of embodiments 1-33 having a MALDI-TOF spectrum of FIG. 1.

Embodiment 35: The composition of embodiment 34, wherein the area of DS-4 is 0.73%.

Embodiment 36: The composition of embodiment 34 or 35, wherein the area of DS-5 is 3.49%.

Embodiment 37: The composition of any one of embodiments 34 to 36, wherein the area of DS-6 is 10.66%.

Embodiment 38: The composition of any one of embodiments 34 to 37, wherein the area of DS-7 is 24.10%.

Embodiment 39: The composition of any one of embodiments 34 to 38, wherein the area of DS-8 is 26.43%.

Embodiment 40: The composition of any one of embodiments 34 to 39, wherein the area of DS-9 is 18.09%.

Embodiment 41: The composition of any one of embodiments 34 to 40, wherein the area of DS-10 is 9.39%.

Embodiment 42: The composition of any one of embodiments 34 to 41, wherein the area of DS-11 is 4.58%.

Embodiment 43: The composition of any one of embodiments 34 to 42, wherein the area of DS-12 is 1.84%.

Embodiment 44: The composition of any one of embodiments 34 to 43, wherein the area of DS-13 is 0.70%.

Embodiment 45: The composition of any one of embodiments 1-44, wherein the composition has a true density of about 1.095 g/cm$^3$ to about 1.100 g/cm$^3$.

Embodiment 46: The composition of embodiment 45, wherein the composition has a true density of about 1.096 g/cm$^3$ to about 1.098 g/cm$^3$.

Embodiment 47: The composition of any one of embodiments 1-46, wherein the composition has an osmolality of about 600 mOs/kg to about 750 mOs/kg.

Embodiment 48: The composition of embodiment 47, wherein the composition has an osmolality of about 635 mOs/kg to about 695 mOs/kg.

Embodiment 49: The composition of any one of embodiments 1-48, wherein the composition is a clear and colorless solution.

Embodiment 50: The composition of any one of embodiments 1-49, wherein the composition has a pH of about 4.0 to about 6.0.

Embodiment 51: The composition of any one of embodiments 1-50, wherein the composition has a viscosity of 1.5 cP to about 3.0 cP at 20° C.

Embodiment 52: The composition of any one of embodiments 1-51, wherein the composition comprises less than or equal to about 0.05% impurities.

Embodiment 53: The composition of any one of embodiments 1-52, wherein the composition comprises less than 600 particles per container having a diameter of greater than or equal to 25 microns.

Embodiment 54: The composition of any one of embodiments 1-52, wherein the composition comprises less than 6000 particles per container having a diameter of greater than or equal to 10 microns.

Embodiment 55: A composition comprising a mixture of β-cyclodextrin molecules, wherein the mixture of β-cyclodextrin molecules comprises:

β-cyclodextrin substituted with four hydroxypropyl groups ("DS-4");

β-cyclodextrin substituted with five hydroxypropyl groups ("DS-5");

β-cyclodextrin substituted with six hydroxypropyl groups ("DS-6");

β-cyclodextrin substituted with seven hydroxypropyl groups ("DS-7");

β-cyclodextrin substituted with eight hydroxypropyl groups ("DS-8");

β-cyclodextrin substituted with nine hydroxypropyl groups ("DS-9");

β-cyclodextrin substituted with ten hydroxypropyl groups ("DS-10");

β-cyclodextrin substituted with eleven hydroxypropyl groups ("DS-11");

β-cyclodextrin substituted with twelve hydroxypropyl groups ("DS-12");

β-cyclodextrin substituted with thirteen hydroxypropyl groups ("DS-13"); and

β-cyclodextrin substituted with fourteen hydroxypropyl groups ("DS-14");

and wherein the mixture of β-cyclodextrin molecules comprises less than 1% w/w β-cyclodextrin substituted with one hydroxypropyl group ("DS-1"), β-cyclodextrin substituted with two hydroxypropyl groups ("DS-2"), β-cyclodextrin substituted with three hydroxypropyl groups ("DS-3"), and DS-4.

Embodiment 56: An isomerically-purified composition comprising a mixture of hydroxypropyl-β-cyclodextrin molecules eluted from a Cholester HPLC column.

Embodiment 57: An isomerically-purified composition comprising a 5% (w/w) mixture of hydroxypropyl-β-cyclodextrin HDS molecules in aqueous media that yields an equilibrium solubility of cholesterol between about 0.2500 to about 0.6000 mg/ml at a temperature of 37° C.

Embodiment 58: The composition of embodiment 57, wherein the composition yields an equilibrium solubility of cholesterol between about 0.2500 to 0.2700 mg/ml at a temperature of 37° C.

Embodiment 59: The composition of embodiment 57, wherein the composition yields an equilibrium solubility of cholesterol between about 0.4000 to 0.4200 mg/ml at a temperature of 37° C.

Embodiment 60: The composition of embodiment 57, wherein the composition yields an equilibrium solubility of cholesterol between about 0.5000 to 0.5200 mg/ml at a temperature of 37° C.

Embodiment 61: The composition of embodiment 57, wherein the composition yields an equilibrium solubility of cholesterol between about 0.5400 to 0.5600 mg/ml at a temperature of 37° C.

Embodiment 62: The composition of embodiment 57, wherein the composition yields an equilibrium solubility of cholesterol between about 0.3600 to 0.3800 mg/ml at a temperature of 37° C.

Embodiment 63: An isomerically-purified composition comprising a 5% (w/w) mixture of hydroxypropyl-β-cyclodextrin HDS molecules in aqueous media, wherein the mixture of hydroxypropyl-β-cyclodextrin HDS molecules is insoluble in water.

Embodiment 64: An isomerically-purified composition comprising a 5% (w/w) mixture of hydroxypropyl-β-cyclodextrin LDS molecules in aqueous media that yields an equilibrium solubility of cholesterol between about 0.1700 to about 0.3200 mg/ml at a temperature of 37° C.

Embodiment 65: The composition of embodiment 64, wherein the composition yields an equilibrium solubility of cholesterol between about 0.1800 to 0.2000 mg/ml at a temperature of 37° C.

Embodiment 66: The composition of embodiment 64, wherein the composition yields an equilibrium solubility of cholesterol between about 0.1700 to 0.1900 mg/ml at a temperature of 37° C.

Embodiment 67: The composition of embodiment 64, wherein the composition yields an equilibrium solubility of cholesterol between about 0.2000 to 0.2200 mg/ml at a temperature of 37° C.

Embodiment 68: The composition of embodiment 64, wherein the composition yields an equilibrium solubility of cholesterol between about 0.2200 to 0.2400 mg/ml at a temperature of 37° C.

Embodiment 69: The composition of embodiment 64, wherein the composition yields an equilibrium solubility of cholesterol between about 0.3100 to 0.3300 mg/ml at a temperature of 37° C.

Embodiment 70: An isomerically-purified composition comprising a 20% (w/w) mixture of hydroxypropyl-β-cyclodextrin molecules in aqueous media that yields an equilibrium solubility of cholesterol between about 3.2500 to about 3.7500 mg/ml at a temperature of 37° C.

Embodiment 71: A composition comprising a mixture of isomerically-purified hydroxypropyl β-cyclodextrin molecules comprising less than 1% β-cyclodextrin substituted with four hydroxypropyl groups ("DS-4").

Embodiment 72: The composition of embodiment 71, wherein the hydroxypropyl β-cyclodextrin percentage is based upon area percentage from a MALDI-TOF-MS spectrum.

Embodiment 73: The composition of embodiment 71, wherein the hydroxypropyl β-cyclodextrin percentage is based upon weight percentage.

Embodiment 74: The composition of any one of embodiments 71 to 73, wherein the composition comprises less than 1% β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1").

Embodiment 75: The composition of any one of embodiments 71 to 74, wherein the mixture of isomerically-purified hydroxypropyl β-cyclodextrin molecules comprises about 1% to about 5% of β-cyclodextrin substituted with five hydroxypropyl groups ("DS-5").

Embodiment 76: The composition of any one of embodiments 71 to 75, wherein the mixture of isomerically-purified hydroxypropyl β-cyclodextrin comprises about 7% to about 13% of β-cyclodextrin substituted with six hydroxypropyl groups ("DS-6").

Embodiment 77: The composition of embodiment 76, wherein the mixture of isomerically-purified hydroxypropyl β-cyclodextrin comprises about 8% to about 12% of DS-6.

Embodiment 78: The composition of any one of embodiments 71 to 77, wherein the mixture of isomerically-purified hydroxypropyl β-cyclodextrin comprises about 16% to about 22% of β-cyclodextrin substituted with seven hydroxypropyl groups ("DS-7").

Embodiment 79: The composition of embodiment 78, wherein the mixture of isomerically-purified hydroxypropyl β-cyclodextrin comprises about 17% to about 21% of DS-7.

Embodiment 80: The composition of any one of embodiments 71 to 79, wherein the mixture of isomerically-purified hydroxypropyl β-cyclodextrin comprises about 26% to about 32% of β-cyclodextrin substituted with eight hydroxypropyl groups ("DS-8").

Embodiment 81: The composition of embodiment 80, wherein the mixture of isomerically-purified hydroxypropyl β-cyclodextrin comprises about 27% to about 31% of DS-8.

Embodiment 82: The composition of any one of embodiments 71 to 81, wherein the mixture of isomerically-purified hydroxypropyl β-cyclodextrin comprises about 22% to about 28% of β-cyclodextrin substituted with nine hydroxypropyl groups ("DS-9").

Embodiment 83: The composition of embodiment 82, wherein the mixture of isomerically-purified hydroxypropyl β-cyclodextrin comprises about 23% to about 27% of DS-9.

Embodiment 84: The composition of any one of embodiments 71 to 83, wherein the mixture of isomerically-purified hydroxypropyl β-cyclodextrin comprises about 11% to about 17% of β-cyclodextrin substituted with ten hydroxypropyl groups ("DS-10").

Embodiment 85: The composition of embodiment 84, wherein the mixture of isomerically-purified hydroxypropyl β-cyclodextrin comprises about 12% to about 16% of DS-10.

Embodiment 86: The composition of any one of embodiments 71 to 85, wherein the mixture of isomerically-purified hydroxypropyl β-cyclodextrin molecules comprising less than 1% β-cyclodextrin substituted with eleven hydroxypropyl groups ("DS-11").

Embodiment 87: The composition of any one of embodiments 71 to 86, wherein the mixture of isomerically-purified hydroxypropyl β-cyclodextrin molecules comprising less than 1% β-cyclodextrin substituted with twelve hydroxypropyl groups ("DS-12"), β-cyclodextrin substituted with thirteen hydroxypropyl groups ("DS-13"), and β-cyclodextrin substituted with fourteen hydroxypropyl groups ("DS-14").

Embodiment 88: The composition of any one of embodiments 71 to 87, wherein the average degree of substitution of the mixture of isomerically-purified hydroxypropyl β-cyclodextrin is about 6.4 to about 7.0.

Embodiment 89: The composition of embodiment 88, wherein the average degree of substitution is about 6.69.

Embodiment 90: The composition of any one of embodiments 71 to 89, wherein about 52% to about 58% of the hydroxypropyl substitutions in the hydroxypropyl β-cyclodextrin molecules are located at the 3-O— position.

Embodiment 91: The composition of embodiment 90, wherein about 55% to about 56% of the hydroxypropyl substitutions in the β-cyclodextrin molecules are located at the 3-O— position.

Embodiment 92: The composition of any one of embodiments 71 to 91, wherein about 41% to about 47% of the hydroxypropyl substitutions in the hydroxypropyl β-cyclodextrin molecules are located at the 2-O— position.

Embodiment 93: The composition of embodiment 92, wherein about 43% to about 45% of the hydroxypropyl substitutions in the hydroxypropyl β-cyclodextrin molecules are located at the 2-O— position.

Embodiment 94: The composition of any one of embodiments 71 to 91, wherein the concentration of the composition does not substantially change the time required for nanofiltration.

Embodiment 95: The composition of embodiment 94, wherein the length of time to nanofilter the composition ranges from 1.04 to 1.20 hours per diafiltration volume (kg soln/m²·hr/L soln).

Embodiment 96: The composition of any one of embodiments 71 to 95, wherein the composition has a conductivity between 0 and 8.0 µS/cm.

Embodiment 97: The composition of any one of embodiments 71 to 96, wherein the composition has a conductivity between 0 and 4.5 µS/cm.

Embodiment 98: The composition of any one of embodiments 71 to 97, wherein the composition has a conductivity between 0 and 3 µS/cm.

Embodiment 99: The composition of any one of embodiments 71 to 98, wherein the composition has a conductivity between 0 and 1.5 µS/cm.

Embodiment 100: A composition comprising a mixture of isomerically-purified hydroxypropyl β-cyclodextrin molecules comprising:

β-cyclodextrin substituted with five hydroxypropyl groups ("DS-5");

β-cyclodextrin substituted with six hydroxypropyl groups ("DS-6");

β-cyclodextrin substituted with seven hydroxypropyl groups ("DS-7");

β-cyclodextrin substituted with eight hydroxypropyl groups ("DS-8");

β-cyclodextrin substituted with nine hydroxypropyl groups ("DS-9"); and

β-cyclodextrin substituted with ten hydroxypropyl groups ("DS-10"), wherein the composition comprises less than 1% β-cyclodextrin substituted with four hydroxypropyl groups ("DS-4") and less than 1% β-cyclodextrin substituted with eleven hydroxypropyl groups ("DS-11").

Embodiment 101: The composition of embodiment 100, wherein the composition comprises less than 1% β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1").

Embodiment 102: The composition of embodiment 100 or 101, wherein in the composition comprises less than 1% β-cyclodextrin substituted with twelve hydroxypropyl groups ("DS-12"), β-cyclodextrin substituted with thirteen hydroxypropyl groups ("DS-13"), and β-cyclodextrin substituted with fourteen hydroxypropyl groups ("DS-14").

Embodiment 103: The composition of any one of embodiments 100 to 102, wherein the DS-8 has the highest concentration in the mixture of isomerically-purified hydroxypropyl β-cyclodextrin molecules as compared to DS-5, DS-6, DS-7, DS-9, and DS-10.

Embodiment 104: The composition of any one of embodiments 100 to 103, wherein the mixture of isomerically-purified hydroxypropyl β-cyclodextrin molecules comprises about 1% to about 5% of DS-5.

Embodiment 105: The composition of embodiment 104, wherein the mixture of isomerically-purified hydroxypropyl β-cyclodextrin molecules comprises about 2% to about 4% of DS-5.

Embodiment 106: The composition of any one of embodiments 100 to 105, wherein the mixture of isomerically-purified hydroxypropyl β-cyclodextrin comprises about 7% to about 13% of DS-6.

Embodiment 107: The composition of embodiment 106, wherein the mixture of isomerically-purified hydroxypropyl β-cyclodextrin comprises about 8% to about 12% of DS-6.

Embodiment 108: The composition of any one of embodiments 100 to 107, wherein the mixture of isomerically-purified hydroxypropyl β-cyclodextrin comprises about 16% to about 22% of DS-7.

Embodiment 109: The composition of embodiment 108, wherein the mixture of isomerically-purified hydroxypropyl β-cyclodextrin comprises about 17% to about 21% of DS-7.

Embodiment 110: The composition of any one of embodiments 100 to 109, wherein the mixture of isomerically-purified hydroxypropyl β-cyclodextrin comprises about 26% to about 32% of DS-8.

Embodiment 111: The composition of embodiment 110, wherein the mixture of isomerically-purified hydroxypropyl β-cyclodextrin comprises about 27% to about 31% of DS-8.

Embodiment 112: The composition of any one of embodiments 100 to 111, wherein the mixture of isomerically-purified hydroxypropyl β-cyclodextrin comprises about 22% to about 28% of DS-9.

Embodiment 113: The composition of embodiment 112, wherein the mixture of isomerically-purified hydroxypropyl β-cyclodextrin comprises about 23% to about 27% of DS-9.

Embodiment 114: The composition of any one of embodiments 100 to 113, wherein the mixture of isomerically-purified hydroxypropyl β-cyclodextrin comprises about 11% to about 17% of DS-10.

Embodiment 115: The composition of embodiment 114, wherein the mixture of isomerically-purified hydroxypropyl β-cyclodextrin comprises about 12% to about 16% of DS-10.

Embodiment 116: The composition of any one of embodiments 100 to 115, wherein the average degree of substitution of the mixture of isomerically-purified hydroxypropyl β-cyclodextrin is about 6.4 to about 7.0.

Embodiment 117: The composition of embodiment 116, wherein the average degree of substitution is about 6.69.

Embodiment 118: The composition of any one of embodiments 100 to 117, wherein about 52% to about 58% of the hydroxypropyl substitutions in the hydroxypropyl β-cyclodextrin molecules are located at the 3-O— position.

Embodiment 119: The composition of embodiment 118, wherein about 55% to about 57% of the hydroxypropyl substitutions in the hydroxypropyl β-cyclodextrin molecules are located at the 3-O— position.

Embodiment 120: The composition of any one of embodiments 100 to 119, wherein about 41% to about 47% of the hydroxypropyl substitutions in the hydroxypropyl β-cyclodextrin molecules are located at the 2-O— position.

Embodiment 121: The composition of embodiment 120, wherein about 43% to about 45% of the hydroxypropyl substitutions in the hydroxypropyl β-cyclodextrin molecules are located at the 2-O— position.

Embodiment 122: The composition of any one of embodiments 100 to 121, wherein the composition has an HPLC-CAD chromatogram of FIG. 8.

Embodiment 123: The composition of embodiment 122, wherein the composition has a mean retention time of about 10 minutes.

Embodiment 124: The composition of any one of embodiments 100 to 123, wherein the composition has a –ESI-MS spectrum with peaks at about 653 m/z, about 682 m/z, about 711 m/z, about 741 m/z, about 769 m/z, about 799 m/z, about 828 m/z, and about 857 m/z.

Embodiment 125: The composition of any one of embodiments 100 to 124, wherein the composition has a +ESI-MS spectrum with peaks at about 686 m/z, about 715 m/z, about 744 m/z, about 773 m/z, about 802 m/z, about 832 m/z, about 861 m/z, and about 890 m/z.

Embodiment 126: The composition of any one of embodiments 100 to 125, wherein the composition has a ESI-MS spectra of FIG. 9.

Embodiment 127: The composition of any one of embodiments 100 to 126, having a MALDI-TOF spectrum with peaks at about 1436 m/z, about 1495 m/z, about 1555 m/z, about 1614 m/z, about 1674 m/z, and about 1733 m/z.

Embodiment 128: The composition of embodiment 127, wherein the composition has a MALDI-TOF spectrum of FIG. 10.

Embodiment 129: The composition of embodiment 128, wherein the area of DS-5 is 2.83%.

Embodiment 130: The composition of embodiment 128 or 129, wherein the area of DS-6 is 10.64%.

Embodiment 131: The composition of any one of embodiments 128 to 130, wherein the area of DS-7 is 19.30%.

Embodiment 132: The composition of any one of embodiments 128 to 131, wherein the area of DS-8 is 29.30%.

Embodiment 133: The composition of any one of embodiments 128 to 132, wherein the area of DS-9 is 25.30%.

Embodiment 134: The composition of any one of embodiments 128 to 133, wherein the area of DS-10 is 14.30%.

Embodiment 135: The composition of any one of embodiments 100 to 134 having a $^1$H-NMR spectrum of FIG. 6.

Embodiment 136: The composition of any one of embodiments 100 to 135 having a DEPT-edited HSQC spectrum of FIG. 7.

Embodiment 137: The composition of any one of embodiments 100 to 136, wherein the osmolality of the composition is about 635-695 mOs/kg.

Embodiment 138: The composition of any one of embodiments 100 to 137, wherein the true density of the composition is about 1.096-1.098 g/cm$^3$.

Embodiment 139: The composition of any one of embodiments 100 to 138, wherein the composition comprises no more than 10 ppb of propylene glycol as measured by HPLC.

Embodiment 140: The composition of any one of embodiments 100 to 139, wherein the composition comprises no more than 10 ppb propylene glycol as measured by gas chromatography.

Embodiment 141: The composition of any one of embodiments 100 to 140, wherein the composition comprises no more than 10 ppb propylene glycol as measured by PG/EG-ratio of propylene glycol to ethylene glycol.

Embodiment 142: The composition of any one of embodiments 100 to 141, wherein the composition comprises no more than 1 ppm propylene oxide.

Embodiment 143: The composition of any one of embodiments 100 to 142, wherein the total amount of other unspecified impurities is less than or equal to 0.05% as measured by HPLC.

Embodiment 144: The composition of any one of embodiments 100 to 143, wherein the composition further comprises between 0 and 10 ppm chloride.

Embodiment 145: The composition of embodiment 144, wherein the composition comprises between 0 and 1 ppm chloride.

Embodiment 146: The composition of any one of embodiments 100 to 145, wherein the composition has a conductivity between 0 and 8 µS/cm.

Embodiment 147: The composition of embodiment 146, wherein the composition has a conductivity between 0 and 4.5 µS/cm.

Embodiment 148: The composition of embodiment 147, wherein the composition has a conductivity between 0 and 3 µS/cm.

Embodiment 149: The composition of embodiment 148, wherein the composition has a conductivity between 0 and 1.5 µS/cm.

Embodiment 150: The composition of any one of embodiments 100 to 149, wherein the composition is nanofiltered.

Embodiment 151: The composition of embodiment 150, wherein the nanofiltered composition has no substantial difference observed in HPLC-ELSD after nanofiltration as compared to before nanofiltration.

Embodiment 152: The composition of embodiment 151, wherein the nanofiltered composition has no substantial difference observed in NMR after nanofiltration as compared to before nanofiltration.

Embodiment 153: A composition comprising a mixture of isomerically-purified hydroxypropyl β-cyclodextrin molecules comprising:
about 1% to about 5% β-cyclodextrin substituted with five hydroxypropyl groups ("DS-5");
about 7% to about 13% β-cyclodextrin substituted with six hydroxypropyl groups ("DS-6");
about 16% to about 22% β-cyclodextrin substituted with seven hydroxypropyl groups ("DS-7");
about 26% to about 32% β-cyclodextrin substituted with eight hydroxypropyl groups ("DS-8");
about 22% to about 28% β-cyclodextrin substituted with nine hydroxypropyl groups ("DS-9"); and about 11% to about 17% β-cyclodextrin substituted with ten hydroxypropyl groups ("DS-10").

Embodiment 154: A composition comprising a mixture of isomerically-purified hydroxypropyl β-cyclodextrin molecules comprising:
β-cyclodextrin substituted with five hydroxypropyl groups ("DS-5");
β-cyclodextrin substituted with six hydroxypropyl groups ("DS-6");
β-cyclodextrin substituted with seven hydroxypropyl groups ("DS-7");
β-cyclodextrin substituted with eight hydroxypropyl groups ("DS-8");
β-cyclodextrin substituted with nine hydroxypropyl groups ("DS-9"); and
β-cyclodextrin substituted with ten hydroxypropyl groups ("DS-10"),
wherein the composition comprises less than 1% β-cyclodextrin substituted with four hydroxypropyl groups ("DS-4"), β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1"), and
wherein the composition comprises less than 1% β-cyclodextrin substituted with eleven hydroxypropyl groups ("DS-11"), β-cyclodextrin substituted with twelve hydroxypropyl groups ("DS-12"), β-cyclodextrin substituted with thirteen hydroxypropyl groups ("DS-13"), and β-cyclodextrin substituted with fourteen hydroxypropyl groups ("DS-14").

Embodiment 155: A composition comprising a mixture of isomerically-purified hydroxypropyl β-cyclodextrin molecules comprising less than 1% hydroxypropyl β-cyclodextrin with five hydroxypropyl groups ("DS-5").

Embodiment 156: The composition of embodiment 155, wherein the hydroxypropyl β-cyclodextrin percentage is based upon area percentage from a MALDI-TOF-MS spectrum.

Embodiment 157: The composition of embodiment 155, wherein the hydroxypropyl β-cyclodextrin percentage is based upon weight percentage.

Embodiment 158: The composition of any one of embodiments 155 to 157, wherein the composition comprises less than 1% β-cyclodextrin substituted with four hydroxypropyl groups ("DS-4"), β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1").

Embodiment 159: The composition of any one of embodiments 155 to 158, wherein the mixture of isomerically-purified hydroxypropyl β-cyclodextrin comprises about 0% to about 6% of hydroxypropyl β-cyclodextrin substituted with six hydroxypropyl groups ("DS-6").

Embodiment 160: The composition of embodiment 159, wherein the mixture of isomerically-purified β-hydroxypropyl cyclodextrin molecules comprises about 1% to about 5% of DS-6.

Embodiment 161: The composition of any one of embodiments 155 to 160, wherein the mixture of isomerically-purified hydroxypropyl β-cyclodextrin molecules comprises about 8% to about 14% of hydroxypropyl β-cyclodextrin substituted with seven hydroxypropyl groups ("DS-7").

Embodiment 162: The composition of embodiment 161, wherein the mixture of isomerically-purified hydroxypropyl β-cyclodextrin molecules comprises about 9% to about 13% of DS-7.

Embodiment 163: The composition of any one of embodiments 155 to 162, wherein the mixture of isomerically-purified β-hydroxypropyl cyclodextrin molecules comprises about 19% to about 25% of hydroxypropyl β-cyclodextrin substituted with eight hydroxypropyl groups ("DS-8").

Embodiment 164: The composition of embodiment 163, wherein the mixture of isomerically-purified hydroxypropyl β-cyclodextrin molecules comprises about 20% to about 24% of DS-8.

Embodiment 165: The composition of any one of embodiments 155 to 164, wherein the mixture of isomerically-purified β-hydroxypropyl cyclodextrin molecules comprises about 23% to about 29% hydroxypropyl β-cyclodextrin substituted with nine hydroxypropyl groups ("DS-9").

Embodiment 166: The composition of embodiment 165, wherein the mixture of isomerically-purified hydroxypropyl β-cyclodextrin molecules comprises about 24% to about 28% of DS-9.

Embodiment 167: The composition of any one of embodiments 155 to 166, wherein the mixture of isomerically-purified hydroxypropyl β-cyclodextrin molecules comprises about 17% to about 23% of hydroxypropyl β-cyclodextrin substituted with ten hydroxypropyl groups ("DS-10").

Embodiment 168: The composition of embodiment 167, wherein the mixture of isomerically-purified β-hydroxypropyl cyclodextrin molecules comprises about 18% to about 22% of DS-10.

Embodiment 169: The composition of any one of embodiments 155 to 168, wherein the mixture of isomerically-purified β-hydroxypropyl cyclodextrin molecules comprises about 9% to about 15% of hydroxypropyl β-cyclodextrin substituted with eleven hydroxypropyl groups ("DS-11").

Embodiment 170: The composition of embodiment 169, wherein the mixture of isomerically-purified β-cyclodextrin molecules comprises about 10% to about 14% of DS-11.

Embodiment 171: The composition of any one of embodiments 155 to 170, wherein the mixture of isomerically-purified β-cyclodextrin molecules comprises about 2% to about 8% hydroxypropyl β-cyclodextrin substituted with twelve hydroxypropyl groups ("DS-12").

Embodiment 172: The composition of embodiment 171, wherein the mixture of isomerically-purified β-cyclodextrin molecules comprises about 3% to about 7% DS-12.

Embodiment 173: The composition of any one of embodiments 155 to 172, wherein the mixture of isomerically-purified β-cyclodextrin molecules has an average degree of substitution of about 7 to about 8.

Embodiment 174: The composition of embodiment 173, wherein the average degree of substitution is about 7.42.

Embodiment 175: The composition of any one of embodiments 155 to 174, wherein about 36% to about 42% of the hydroxypropyl substitutions in the hydroxypropyl β-cyclodextrin molecules are located at the 3-O— position.

Embodiment 176: The composition of embodiment 175, wherein about 37% to about 41% of the hydroxypropyl substitutions in the hydroxypropyl β-cyclodextrin molecules are located at the 3-O— position.

Embodiment 177: The composition of any one of embodiments 155 to 176, wherein about 58% to about 64% of the hydroxypropyl substitutions in the hydroxypropyl β-cyclodextrin molecules are located at the 2-O— position.

Embodiment 178: The composition of embodiment 177, wherein about 59% to about 63% of the hydroxypropyl substitutions in the hydroxypropyl β-cyclodextrin molecules are located at the 2-O— position.

Embodiment 179: The composition of any one of embodiments 155 to 178, wherein the concentration of the composition does not substantially change the time required for nanofiltration.

Embodiment 180: The composition of embodiment 179, wherein the length of time to nanofilter the composition ranges from 1.04 to 1.20 hours per diafiltration volume (kg soln/m2-hr/L soln).

Embodiment 181: The composition of any one of embodiments 155 to 180, wherein the composition has no substantial difference observed in HPLC-ELSD after nanofiltration as compared to before nanofiltration.

Embodiment 182: The composition of any one of embodiments 155 to 181, wherein the composition has no substantial difference observed in NMR after nanofiltration as compared to before nanofiltration.

Embodiment 183: The composition of any one of embodiments 155 to 182, wherein the composition has a conductivity between 0 and 8.0 μS/cm.

Embodiment 184: The composition of any one of embodiments 155 to 183, wherein the composition has a conductivity between 0 and 4.5 μS/cm.

Embodiment 185: A composition comprising a mixture of isomerically-purified hydroxypropyl β-cyclodextrin molecules comprising:
  β-cyclodextrin substituted with six hydroxypropyl groups ("DS-6");
  β-cyclodextrin substituted with seven hydroxypropyl groups ("DS-7");
  β-cyclodextrin substituted with eight hydroxypropyl groups ("DS-8");
  β-cyclodextrin substituted with nine hydroxypropyl groups ("DS-9");
  β-cyclodextrin substituted with ten hydroxypropyl groups ("DS-10");
  β-cyclodextrin substituted with eleven hydroxypropyl groups ("DS-11"); and
  β-cyclodextrin substituted with twelve hydroxypropyl groups ("DS-12"),
  wherein the composition comprises less than 1% β-cyclodextrin substituted with five hydroxypropyl groups ("DS-5") and the composition comprises less than 1% I β-cyclodextrin substituted with thirteen hydroxypropyl groups ("DS-13").

Embodiment 186: The composition of embodiment 185, wherein the composition comprises less than 1% β-cyclodextrin substituted with four hydroxypropyl groups ("DS-4"), β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1").

Embodiment 187: The composition of embodiment 185 or 186, wherein the composition comprises less than 1% β-cyclodextrin substituted with thirteen hydroxypropyl groups ("DS-13") and hydroxypropyl β-cyclodextrin substituted with fourteen hydroxypropyl groups ("DS-14").

Embodiment 188: The composition of any one of embodiments 185 to 187, wherein the DS-9 has the highest concentration in the composition as compared to DS-6, DS-7, DS-8, DS-10, DS-11, and DS-12.

Embodiment 189: The composition of any one of embodiments 185 to 188, wherein the mixture of isomerically-purified hydroxypropyl β-cyclodextrin molecules comprises about 0% to about 6% of DS-6.

Embodiment 190: The composition of embodiment 189, wherein the mixture of isomerically-purified hydroxypropyl β-cyclodextrin molecules comprises about 1% to about 5% of DS-6.

Embodiment 191: The composition of any one of embodiments 185 to 190, wherein the mixture of isomerically-purified hydroxypropyl β-cyclodextrin molecules comprises about 8% to about 14% of DS-7.

Embodiment 192: The composition of embodiment 191, wherein the mixture of isomerically-purified hydroxypropyl β-cyclodextrin molecules comprises about 9% to about 13% of DS-7.

Embodiment 193: The composition of any one of embodiments 185 to 192, wherein the mixture of isomerically-purified hydroxypropyl β-cyclodextrin molecules comprises about 19% to about 25% of DS-8.

Embodiment 194: The composition of embodiment 193, wherein the mixture of isomerically-purified hydroxypropyl β-cyclodextrin molecules comprises about 19% to about 25% of DS-8.

Embodiment 195: The composition of any one of embodiments 185 to 194, wherein the mixture of isomerically-purified hydroxypropyl β-cyclodextrin molecules comprises about 23% to about 29% of DS-9.

Embodiment 196: The composition of embodiment 195, wherein the mixture of isomerically-purified hydroxypropyl β-cyclodextrin molecules comprises about 24% to about 28% of DS-9.

Embodiment 197: The composition of any one of embodiments 185 to 196, wherein the mixture of isomerically-purified hydroxypropyl β-cyclodextrin molecules comprises about 17% to about 23% of DS-10.

Embodiment 198: The composition of embodiment 197, wherein the mixture of isomerically-purified hydroxypropyl β-cyclodextrin molecules comprises about 18% to about 22% of DS-10.

Embodiment 199: The composition of any one of embodiments 185 to 198, wherein the mixture of isomerically-purified hydroxypropyl β-cyclodextrin molecules comprises about 9% to about 15% of DS-11.

Embodiment 200: The composition of embodiment 199, wherein the mixture of isomerically-purified hydroxypropyl β-cyclodextrin molecules comprises about 10% to about 14% of DS-11.

Embodiment 201: The composition of any one of embodiments 185 to 200, wherein the mixture of isomerically-purified hydroxypropyl β-cyclodextrin molecules comprises about 2% to about 8% DS-12.

Embodiment 202: The composition of embodiment 201, wherein the mixture of isomerically-purified hydroxypropyl β-cyclodextrin molecules comprises about 3% to about 7% DS-12.

Embodiment 203: The composition of any one of embodiments 185 to 202, wherein the mixture of isomerically-purified hydroxypropyl β-cyclodextrin molecules has an average degree of substitution of about 7 to about 8.

Embodiment 204: The composition of embodiment 203, wherein the average degree of substitution is about 7.42.

Embodiment 205: The composition of any one of embodiments 185 to 204, wherein about 36% to about 42% of the hydroxypropyl substitutions in the hydroxypropyl β-cyclodextrin molecules are located at the 3-O— position.

Embodiment 206: The composition of embodiment 205, wherein about 37% to about 41% of the hydroxypropyl substitutions in the hydroxypropyl β-cyclodextrin molecules are located at the 3-O— position.

Embodiment 207: The composition of any one of embodiments 185 to 206, wherein about 58% to about 64% of the hydroxypropyl substitutions in the hydroxypropyl β-cyclodextrin molecules are located at the 2-O— position.

Embodiment 208: The composition of embodiment 207, wherein about 59% to about 63% of the hydroxypropyl substitutions in the hydroxypropyl β-cyclodextrin molecules are located at the 2-O— position.

Embodiment 209: The composition of any one of embodiments 185 to 208, having an HPLC-CAD chromatograph of FIG. 13.

Embodiment 210: The composition of embodiment 209, wherein the peak retention time is at about 11.9 minutes.

Embodiment 211: The composition of any one of embodiments 185 to 210, wherein the composition has a –ESI-MS spectrum with peaks at about 682 m/z, about 712 m/z, about 740 m/z, about 770 m/z, about 798 m/z, about 828 m/z, about 856 m/z, and about 886 m/z.

Embodiment 212: The composition of any one of embodiments 185 to 211, wherein the composition has a +ESI-MS spectrum with peaks at about 744 m/z, about 773 m/z, about 803 m/z, about 832 m/z, about 860 m/z, about 889 m/z, and about 919 m/z.

Embodiment 213: The composition of any one of embodiments 185 to 212, having an ESI-MS spectrum of FIG. 14.

Embodiment 214: The composition of any one of embodiments 185 to 213, having a MALDI-TOF-MS spectrum with peaks at about 1497 m/z, about 1557 m/z, about 1616 m/z, about 1675 m/z, about 1734 m/z, about 1794 m/z, and about 1914 m/z.

Embodiment 215: The composition of embodiment 214, having a MALDI-TOF-MS spectrum of FIG. 15.

Embodiment 216: The composition of embodiment 215, wherein the area of DS-6 is 2.91%.

Embodiment 217: The composition of embodiment 215 or 216, wherein the area of DS-7 is 10.93%.

Embodiment 218: The composition of any one of embodiments 215 to 217, wherein the area of DS-8 is 22.52%.

Embodiment 219: The composition of any one of embodiments 215 to 218, wherein the area of DS-9 is 26.42%.

Embodiment 220: The composition of any one of embodiments 215 to 219, wherein the area of DS-10 is 20.35%.

Embodiment 221: The composition of any one of embodiments 215 to 220, wherein the area of DS-11 is 12.02%.

Embodiment 222: The composition of any one of embodiments 215 to 221, wherein the area of DS-12 is 4.85%.

Embodiment 223: The composition of any one of embodiments 185 to 222, having a $^1$H-NMR spectrum of FIG. 16.

Embodiment 224: The composition of any one of embodiments 185 to 223, having a DEPT-edited HSQC spectrum of FIG. 12.

Embodiment 225: The composition of any one of embodiments 185 to 224, wherein the osmolality of the composition is about 635-695 mOs/kg.

Embodiment 226: The composition of any one of embodiments 185 to 225, wherein the true density of the composition is about 1.096-1.098 g/cm$^3$.

Embodiment 227: The composition of any one of embodiments 185 to 226, wherein the composition comprises no more than 10 ppb of propylene glycol as measured by HPLC.

Embodiment 228: The composition of any one of embodiments 185 to 227, wherein the composition comprises no more than 10 ppb propylene glycol as measured by gas chromatography.

Embodiment 229: The composition of any one of embodiments 185 to 228, wherein the composition comprises no more than 10 ppb propylene glycol as measured by PG/EG-ratio of propylene glycol to ethylene glycol.

Embodiment 230: The composition of any one of embodiments 185 to 229, wherein the composition comprises no more than 1 ppm propylene oxide.

Embodiment 231: The composition of any one of embodiments 185 to 230, wherein the total amount of other unspecified impurities is less than or equal to 0.05% as measured by HPLC.

Embodiment 232: The composition of any one of embodiments 185 to 231, wherein the composition comprises between 0 and 10 ppm chloride.

Embodiment 233: The composition of embodiment 232, wherein the composition comprises between 0 and 1 ppm chloride.

Embodiment 234: The composition of any one of embodiments 185 to 233, wherein the composition has a conductivity between 0 and 8 μS/cm.

Embodiment 235: The composition of embodiment 234, wherein the composition has a conductivity between 0 and 4.5 μS/cm.

Embodiment 236: The composition of embodiment 235, wherein the composition has a conductivity between 0 and 3 μS/cm.

Embodiment 237: The composition of embodiment 236, wherein the composition has a conductivity between 0 and 1.5 μS/cm.

Embodiment 238: The composition of any one of embodiments 185 to 237, wherein the composition is nanofiltered.

Embodiment 239: The composition of embodiment 238, wherein the nanofiltered composition has no substantial difference observed in HPLC-ELSD after nanofiltration as compared to before nanofiltration.

Embodiment 240: The composition of embodiment 239, wherein the nanofiltered composition has no substantial difference observed in NMR after nanofiltration as compared to before nanofiltration.

Embodiment 241: A composition comprising a mixture of isomerically-purified hydroxypropyl β-cyclodextrin molecules comprising:
about 0.5% to about 6% hydroxypropyl β-cyclodextrin substituted with six hydroxypropyl groups ("DS-6");
about 8% to about 14% hydroxypropyl β-cyclodextrin substituted with seven hydroxypropyl groups ("DS-7");
about 19% to about 25% hydroxypropyl β-cyclodextrin substituted with eight hydroxypropyl groups ("DS-8");
about 23% to about 29% hydroxypropyl β-cyclodextrin substituted with nine hydroxypropyl groups ("DS-9");
about 17% to about 23% hydroxypropyl β-cyclodextrin substituted with ten hydroxypropyl groups ("DS-10");
about 9% to about 15% hydroxypropyl β-cyclodextrin substituted with eleven hydroxypropyl groups ("DS-11"); and
about 2% to about 8% hydroxypropyl β-cyclodextrin substituted with twelve hydroxypropyl groups ("DS-12").

Embodiment 242: A composition comprising a mixture of isomerically-purified hydroxypropyl β-cyclodextrin molecules comprising:
β-cyclodextrin substituted with six hydroxypropyl groups ("DS-6");
β-cyclodextrin substituted with seven hydroxypropyl groups ("DS-7");
β-cyclodextrin substituted with eight hydroxypropyl groups ("DS-8");
β-cyclodextrin substituted with nine hydroxypropyl groups ("DS-9");
β-cyclodextrin substituted with ten hydroxypropyl groups ("DS-10");
β-cyclodextrin substituted with eleven hydroxypropyl groups ("DS-11"); and
β-cyclodextrin substituted with twelve hydroxypropyl groups ("DS-12"),
wherein the composition comprises less than 1% β-cyclodextrin substituted with five hydroxypropyl groups ("DS-5"), β-cyclodextrin substituted with four hydroxypropyl groups ("DS-4") β-cyclodextrin substituted with three hydroxypropyl groups ("DS-3") β-cyclodextrin substituted with two hydroxypropyl groups ("DS-2") β-cyclodextrin substituted with one hydroxypropyl group ("DS-1"), and
wherein the composition comprises less than 1% β-cyclodextrin substituted with thirteen hydroxypropyl groups ("DS-13") and β-cyclodextrin substituted with fourteen hydroxypropyl groups ("DS-14").

Embodiment 243: A composition comprising a mixture of isomerically-purified hydroxypropyl β-cyclodextrin molecules comprising less than 1% hydroxypropyl β-cyclodextrin with six hydroxypropyl groups ("DS-6") and less than 1% β-cyclodextrin substituted with fourteen hydroxypropyl groups ("DS-14").

Embodiment 244: The composition of embodiment 243, wherein the hydroxypropyl β-cyclodextrin percentage is based upon area percentage from a MALDI-TOF-MS spectrum.

Embodiment 245: The composition of embodiment 243, wherein the hydroxypropyl β-cyclodextrin percentage is based upon weight percentage.

Embodiment 246: The composition of any one of embodiments 243 to 245, wherein the composition comprises less than 1% β-cyclodextrin substituted with five hydroxypropyl groups ("DS-5"), β-cyclodextrin substituted with four hydroxypropyl groups ("DS-4"), β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1").

Embodiment 247: The composition of any one of embodiments 243 to 246, wherein the mixture of isomerically-purified hydroxypropyl β-cyclodextrin molecules comprises about 1% to about 7% of β-cyclodextrin substituted with seven hydroxypropyl groups ("DS-7").

Embodiment 248: The composition of embodiment 247, wherein the mixture of isomerically-purified hydroxypropyl β-cyclodextrin molecules comprises about 2% to about 6% of DS-7.

Embodiment 249: The composition of any one of embodiments 243 to 248, wherein the mixture of isomerically-purified hydroxypropyl β-cyclodextrin molecules comprises about 16% to about 22% of β-cyclodextrin substituted with eight hydroxypropyl groups ("DS-8").

Embodiment 250: The composition of embodiment 249, wherein the mixture of isomerically-purified hydroxypropyl β-cyclodextrin molecules comprises about 17% to about 21% of DS-8.

Embodiment 251: The composition of any one of embodiments 243 to 250, wherein the mixture of isomerically-purified hydroxypropyl β-cyclodextrin molecules comprises about 22% to about 28% of β-cyclodextrin substituted with nine hydroxypropyl groups ("DS-9").

Embodiment 252: The composition of embodiment 251, wherein the mixture of isomerically-purified hydroxypropyl β-cyclodextrin molecules comprises about 23% to about 27% of DS-9.

Embodiment 253: The composition of any one of embodiments 243 to 252, wherein the mixture of isomerically-purified hydroxypropyl β-cyclodextrin molecules comprises about 19% to about 25% of β-cyclodextrin substituted with ten hydroxypropyl groups ("DS-10).

Embodiment 254: The composition of embodiment 253, wherein the mixture of isomerically-purified hydroxypropyl β-cyclodextrin molecules comprises about 20% to about 24% of DS-10.

Embodiment 255: The composition of any one of embodiments 243 to 254, wherein the mixture of isomerically-purified hydroxypropyl β-cyclodextrin molecules comprises about 14% to about 20% of β-cyclodextrin substituted with eleven hydroxypropyl groups ("DS-11").

Embodiment 256: The composition of embodiment 255, wherein the mixture of isomerically-purified hydroxypropyl β-cyclodextrin molecules comprises about 15% to about 19% of DS-11.

Embodiment 257: The composition of any one of embodiments 243 to 256, wherein the mixture of isomerically-purified hydroxypropyl β-cyclodextrin molecules comprises about 5% to about 11% of β-cyclodextrin substituted with twelve hydroxypropyl groups ("DS-12").

Embodiment 258: The composition of embodiment 257, wherein the mixture of isomerically-purified hydroxypropyl β-cyclodextrin molecules comprises about 6% to about 10% of DS-12.

Embodiment 259: The composition of any one of embodiments 243 to 258, wherein the mixture of isomerically-purified hydroxypropyl β-cyclodextrin molecules comprises about 1% to about 7% of β-cyclodextrin substituted with thirteen hydroxypropyl groups ("DS-13").

Embodiment 260: The composition of embodiment 259, wherein the mixture of isomerically-purified hydroxypropyl β-cyclodextrin molecules comprises about 2% to about 6% of DS-13.

Embodiment 261: The composition of any one of embodiments 243 to 260, wherein the average degree of substitution of the mixture of isomerically-purified hydroxypropyl β-cyclodextrin is about 8 to about 9.

Embodiment 262: The composition of embodiment 261, wherein the average degree of substitution of the mixture of isomerically-purified hydroxypropyl β-cyclodextrin is about 8.53.

Embodiment 263: The composition of any one of embodiments 243 to 262, wherein about 26% to about 32% of the hydroxypropyl substitutions in the hydroxypropyl β-cyclodextrin molecules are located at the 3-O— position.

Embodiment 264: The composition of embodiment 263, wherein about 27% to about 31% of the hydroxypropyl substitutions in the hydroxypropyl β-cyclodextrin molecules are located at the 3-O— position.

Embodiment 265: The composition of any one of embodiments 243 to 264, wherein about 68% to about 74% of the hydroxypropyl substitutions in the hydroxypropyl β-cyclodextrin molecules are located at the 2-O— position.

Embodiment 266: The composition of embodiment 265, wherein about 69% to about 73% of the hydroxypropyl substitutions in the hydroxypropyl β-cyclodextrin molecules are located at the 2-O— position.

Embodiment 267: The composition of any one of embodiments 243 to 266, wherein the concentration of the composition does not substantially change the time required for nanofiltration.

Embodiment 268: The composition of embodiment 267, wherein the length of time to nanofilter the composition ranges from 1.04 to 1.20 hours per diafiltration volume (kg soln/m²·hr/L soln).

Embodiment 269: The composition of any one of embodiments 243 to 268, wherein the composition has no substantial difference observed in HPLC-ELSD after nanofiltration as compared to before nanofiltration.

Embodiment 270: The composition of any one of embodiments 243 to 269, wherein the composition has no substantial difference observed in NMR after nanofiltration as compared to before nanofiltration.

Embodiment 271: The composition of any one of embodiments 243 to 270, wherein the composition has a conductivity between 0 and 8.0 µS/cm.

Embodiment 272: The composition of any one of embodiments 243 to 271, wherein the composition has a conductivity between 0 and 4.5 µS/cm.

Embodiment 273: A composition comprising a mixture of isomerically-purified hydroxypropyl β-cyclodextrin molecules comprising:
  β-cyclodextrin substituted with seven hydroxypropyl groups ("DS-7");
  β-cyclodextrin substituted with eight hydroxypropyl groups ("DS-8");
  β-cyclodextrin substituted with nine hydroxypropyl groups ("DS-9");
  β-cyclodextrin substituted with ten hydroxypropyl groups ("DS-10");
  β-cyclodextrin substituted with eleven hydroxypropyl groups ("DS-11");
  β-cyclodextrin substituted with twelve hydroxypropyl groups ("DS-12"); and
  β-cyclodextrin substituted with thirteen hydroxypropyl groups ("DS-13"),
  wherein the composition comprises less than 1% β-cyclodextrin substituted with six hydroxypropyl groups ("DS-6") and less than 1% β-cyclodextrin substituted with fourteen hydroxypropyl groups ("DS-14").

Embodiment 274: The composition of embodiment 273, wherein the composition comprises less than 1% β-cyclodextrin substituted with five hydroxypropyl groups ("DS-5"), β-cyclodextrin substituted with four hydroxypropyl groups ("DS-4"), β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1").

Embodiment 275: The composition of embodiment 273 or 274, wherein the DS-9 has the highest concentration in the mixture of isomerically-purified hydroxypropyl β-cyclodextrin molecules as compared to DS-6, DS-7, DS-8, DS-10, DS-11, DS-12, and DS-13.

Embodiment 276: The composition of any one of embodiments 273 to 275, wherein the mixture of isomerically-purified hydroxypropyl β-cyclodextrin molecules comprises about 1% to about 7% of DS-7.

Embodiment 277: The composition of embodiment 276, wherein the mixture of isomerically-purified hydroxypropyl β-cyclodextrin molecules comprises about 2% to about 6% of DS-7.

Embodiment 278: The composition of any one of embodiments 273 to 277, wherein the mixture of isomerically-purified hydroxypropyl β-cyclodextrin molecules comprises about 16% to about 22% of DS-8.

Embodiment 279: The composition of embodiment 278, wherein the mixture of isomerically-purified hydroxypropyl β-cyclodextrin molecules comprises about 17% to about 21% of DS-8.

Embodiment 280: The composition of any one of embodiments 273 to 279, wherein the mixture of isomerically-purified hydroxypropyl β-cyclodextrin molecules comprises about 22% to about 28% of DS-9.

Embodiment 281: The composition of embodiment 280, wherein the mixture of isomerically-purified hydroxypropyl β-cyclodextrin molecules comprises about 23% to about 27% of DS-9.

Embodiment 282: The composition of any one of embodiments 273 to 281, wherein the mixture of isomerically-purified hydroxypropyl β-cyclodextrin molecules comprises about 19% to about 25% of DS-10.

Embodiment 283: The composition of embodiment 282, wherein the mixture of isomerically-purified hydroxypropyl β-cyclodextrin molecules comprises about 20% to about 24% of DS-10.

Embodiment 284: The composition of any one of embodiments 273 to 283, wherein the mixture of isomerically-purified hydroxypropyl β-cyclodextrin molecules comprises about 14% to about 20% of DS-11.

Embodiment 285: The composition of embodiment 284, wherein the mixture of isomerically-purified hydroxypropyl β-cyclodextrin molecules comprises about 15% to about 19% of DS-11.

Embodiment 286: The composition of any one of embodiments 273 to 285, wherein the mixture of isomerically-purified hydroxypropyl β-cyclodextrin molecules comprises about 5% to about 11% of DS-12.

Embodiment 287: The composition of embodiment 286, wherein the mixture of isomerically-purified hydroxypropyl β-cyclodextrin molecules comprises about 6% to about 10% of DS-12.

Embodiment 288: The composition of any one of embodiments 273 to 287, wherein the mixture of isomerically-purified hydroxypropyl β-cyclodextrin molecules comprises about 1% to about 7% of DS-13.

Embodiment 289: The composition of embodiment 288, wherein the mixture of isomerically-purified hydroxypropyl β-cyclodextrin molecules comprises about 2% to about 6% of DS-13.

Embodiment 290: The composition of any one of embodiments 273 to 289, wherein the average degree of substitution of the mixture of isomerically-purified hydroxypropyl β-cyclodextrin is about 8 to about 9.

Embodiment 291: The composition of embodiment 290, wherein the average degree of substitution of the mixture of isomerically-purified hydroxypropyl β-cyclodextrin is about 8.53.

Embodiment 292: The composition of any one of embodiments 273 to 291, wherein about 26% to about 32% of the hydroxypropyl substitutions in the β-cyclodextrin molecules are located at the 3-O— position.

Embodiment 293: The composition of embodiment 292, wherein about 27% to about 31% of the hydroxypropyl substitutions in the β-cyclodextrin molecules are located at the 3-O— position.

Embodiment 294: The composition of any one of embodiments 273 to 293, wherein about 68% to about 74% of the hydroxypropyl substitutions in the β-cyclodextrin molecules are located at the 2-O— position.

Embodiment 295: The composition of embodiment 294, wherein about 69% to about 73% of the hydroxypropyl substitutions in the β-cyclodextrin molecules are located at the 2-O— position.

Embodiment 296: The composition of any one of embodiments 273 to 295, wherein the composition has an HPLC-CAD chromatogram of FIG. 18.

Embodiment 297: The composition of embodiment 296, wherein the composition has a mean retention time of about 13.5 minutes.

Embodiment 298: The composition of any one of embodiments 273 to 297, wherein the composition has a –ESI-MS spectrum with peaks at about 741 m/z, about 769 m/z, about 799 m/z, about 828 m/z, about 856 m/z, and about 886 m/z.

Embodiment 299: The composition of any one of embodiments 273 to 298, wherein the composition has a +ESI-MS spectrum with peaks at about 773 m/z, about 803 m/z, about 833 m/z, about 860 m/z, about 889 m/z, and about 920 m/z.

Embodiment 300: The composition of any one of embodiments 273 to 299, wherein the composition has a ESI-MS spectra of FIG. 19.

Embodiment 301: The composition of any one of embodiments 273 to 300, having a MALDI-TOF spectrum with peaks at about 1557 m/z, about 1617 m/z, about 1676 m/z, about 1736 m/z, about 1795 m/z, about 1855 m/z, and about 1915 m/z.

Embodiment 302: The composition of embodiment 301, wherein the composition has a MALDI-TOF spectrum of FIG. 20.

Embodiment 303: The composition of embodiment 302, wherein the area of DS-7 is 3.92%.

Embodiment 304: The composition of embodiment 302 or 303, wherein the area of DS-8 is 18.65%.

Embodiment 305: The composition of any one of embodiments 302 to 304, wherein the area of DS-9 is 25.45%.

Embodiment 306: The composition of any one of embodiments 302 to 305, wherein the area of DS-10 is 22.37%.

Embodiment 307: The composition of any one of embodiments 302 to 306, wherein the area of DS-11 is 17.41%.

Embodiment 308: The composition of any one of embodiments 302 to 307, wherein the area of DS-12 is 8.01%.

Embodiment 309: The composition of any one of embodiments 302 to 308, wherein the area of DS-13 is 4.20%.

Embodiment 310: The composition of any one of embodiments 273 to 309 having a $^1$H-NMR spectrum of FIG. 16.

Embodiment 311: The composition of any one of embodiments 273 to 310 having a DEPT-edited HSQC spectrum of FIG. 17.

Embodiment 312: The composition of any one of embodiments 273 to 311, wherein the osmolality of the composition is about 635-695 mOs/kg.

Embodiment 313: The composition of any one of embodiments 273 to 312, wherein the true density of the composition is about 1.096-1.098 g/cm3.

Embodiment 314: The composition of any one of embodiments 273 to 313, wherein the composition comprises no more than 10 ppb of propylene glycol as measured by HPLC.

Embodiment 315: The composition of any one of embodiments 273 to 314, wherein the composition comprises no more than 10 ppb propylene glycol as measured by gas chromatography.

Embodiment 316: The composition of any one of embodiments 273 to 315, wherein the composition comprises no more than 10 ppb propylene glycol as measured by PG/EG-ratio of propylene glycol to ethylene glycol.

Embodiment 317: The composition of any one of embodiments 273 to 316, wherein the composition comprises no more than 1 ppm propylene oxide.

Embodiment 318: The composition of any one of embodiments 273 to 317, wherein the total amount of other unspecified impurities is less than or equal to 0.05% as measured by HPLC.

Embodiment 319: The composition of any one of embodiments 273 to 318, wherein the composition comprises between 0 and 10 ppm chloride.

Embodiment 320: The composition of embodiment 319, wherein the composition comprises between 0 and 1 ppm chloride.

Embodiment 321: The composition of any one of embodiments 273 to 320, wherein the composition has a conductivity between 0 and 8 µS/cm.

Embodiment 322: The composition of embodiment 321, wherein the composition has a conductivity between 0 and 4.5 µS/cm.

Embodiment 323: The composition of embodiment 322, wherein the composition has a conductivity between 0 and 3 µS/cm.

Embodiment 324: The composition of embodiment 323, wherein the composition has a conductivity between 0 and 1.5 µS/cm.

Embodiment 325: The composition of any one of embodiments 273 to 324, wherein the composition is nanofiltered.

Embodiment 326: The composition of embodiment 325, wherein the nanofiltered composition has no substantial difference observed in HPLC-ELSD after nanofiltration as compared to before nanofiltration.

Embodiment 327: The composition of embodiment 325, wherein the nanofiltered composition has no substantial difference observed in NMR after nanofiltration as compared to before nanofiltration.

Embodiment 328: A composition comprising a mixture of isomerically-purified hydroxypropyl β-cyclodextrin molecules comprising:
  about 1% to about 7% β-cyclodextrin substituted with seven hydroxypropyl groups ("DS-7");
  about 16% to about 22% β-cyclodextrin substituted with eight hydroxypropyl groups ("DS-8");
  about 22% to about 28% β-cyclodextrin substituted with nine hydroxypropyl groups ("DS-9");
  about 19% to about 25% β-cyclodextrin substituted with ten hydroxypropyl groups ("DS-10");
  about 14% to about 20% β-cyclodextrin substituted with eleven hydroxypropyl groups ("DS-11");
  about 5% to about 11% β-cyclodextrin substituted with twelve hydroxypropyl groups ("DS-12"); and
  about 1% to about 7% β-cyclodextrin substituted with thirteen hydroxypropyl groups ("DS-13").

Embodiment 329: A composition comprising a mixture of isomerically-purified hydroxypropyl β-cyclodextrin molecules comprising:
  β-cyclodextrin substituted with seven hydroxypropyl groups ("DS-7");
  β-cyclodextrin substituted with eight hydroxypropyl groups ("DS-8");
  β-cyclodextrin substituted with nine hydroxypropyl groups ("DS-9");
  β-cyclodextrin substituted with ten hydroxypropyl groups ("DS-10");
  β-cyclodextrin substituted with eleven hydroxypropyl groups ("DS-11");
  β-cyclodextrin substituted with twelve hydroxypropyl groups ("DS-12"); and
  β-cyclodextrin substituted with thirteen hydroxypropyl groups ("DS-13"),
  wherein the composition comprises less than 1% β-cyclodextrin substituted with six hydroxypropyl groups ("DS-6"), β-cyclodextrin substituted with five hydroxypropyl groups ("DS-5"), β-cyclodextrin substituted with four hydroxypropyl groups ("DS-4"), β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1").

Embodiment 330: A composition comprising a mixture of isomerically-purified hydroxypropyl β-cyclodextrin molecules comprising less than 1% hydroxypropyl β-cyclodextrin with six hydroxypropyl groups ("DS-6")

Embodiment 331: The composition of embodiment 330, wherein the hydroxypropyl β-cyclodextrin percentage is based upon area percentage from a MALDI-TOF-MS spectrum.

Embodiment 332: The composition of embodiment 330, wherein the hydroxypropyl β-cyclodextrin percentage is based upon weight percentage.

Embodiment 333: The composition of any one of embodiments 330 to 332, wherein the composition comprises less than 1% β-cyclodextrin substituted with five hydroxypropyl groups ("DS-5"), β-cyclodextrin substituted with four hydroxypropyl groups ("DS-4"), β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1").

Embodiment 334: The composition of any one of embodiments 330 to 333, wherein the mixture of isomerically-purified hydroxypropyl β-cyclodextrin molecules comprises about 0% to about 6% of β-cyclodextrin substituted with seven hydroxypropyl groups ("DS-7").

Embodiment 335: The composition of embodiment 334, wherein the mixture of isomerically-purified hydroxypropyl β-cyclodextrin molecules comprises about 1% to about 5% of DS-7.

Embodiment 336: The composition of any one of embodiments 330 to 335, wherein the mixture of isomerically-purified hydroxypropyl β-cyclodextrin molecules comprises about 13% to about 19% of β-cyclodextrin substituted with eight hydroxypropyl groups ("DS-8").

Embodiment 337: The composition of embodiment 336, wherein the mixture of isomerically-purified hydroxypropyl β-cyclodextrin molecules comprises about 14% to about 18% of DS-8.

Embodiment 338: The composition of any one of embodiments 330 to 337, wherein the mixture of isomerically-purified hydroxypropyl β-cyclodextrin molecules comprises about 22% to about 28% of β-cyclodextrin substituted with nine hydroxypropyl groups ("DS-9").

Embodiment 339: The composition of embodiment 338, wherein the mixture of isomerically-purified hydroxypropyl β-cyclodextrin molecules comprises about 23% to about 27% of DS-9.

Embodiment 340: The composition of any one of embodiments 330 to 339, wherein the mixture of isomerically-purified hydroxypropyl β-cyclodextrin molecules comprises about 23% to about 29% of β-cyclodextrin substituted with ten hydroxypropyl groups ("DS-10).

Embodiment 341: The composition of embodiment 340, wherein the mixture of isomerically-purified hydroxypropyl β-cyclodextrin molecules comprises about 24% to about 28% of DS-10.

Embodiment 342: The composition of any one of embodiments 330 to 341, wherein the mixture of isomerically-purified hydroxypropyl β-cyclodextrin molecules comprises about 12% to about 18% of β-cyclodextrin substituted with eleven hydroxypropyl groups ("DS-11").

Embodiment 343: The composition of embodiment 342, wherein the mixture of isomerically-purified hydroxypropyl β-cyclodextrin molecules comprises about 13% to about 17% of DS-11.

Embodiment 344: The composition of any one of embodiments 330 to 343, wherein the mixture of isomerically-purified hydroxypropyl β-cyclodextrin molecules comprises about 7% to about 13% of β-cyclodextrin substituted with twelve hydroxypropyl groups ("DS-12").

Embodiment 345: The composition of embodiment 344, wherein the mixture of isomerically-purified hydroxypropyl β-cyclodextrin molecules comprises about 8% to about 12% of DS-12.

Embodiment 346: The composition of any one of embodiments 330 to 345, wherein the mixture of isomerically-purified hydroxypropyl β-cyclodextrin molecules comprises about 2% to about 8% of β-cyclodextrin substituted with thirteen hydroxypropyl groups ("DS-13").

Embodiment 347: The composition of embodiment 346, wherein the mixture of isomerically-purified hydroxypropyl β-cyclodextrin molecules comprises about 3% to about 7% of DS-13.

Embodiment 348: The composition of any one of embodiments 330 to 347, wherein the average degree of substitution of the mixture of isomerically-purified hydroxypropyl β-cyclodextrin is about 7.5 to about 8.5.

Embodiment 349: The composition of embodiment 348, wherein the average degree of substitution of the mixture of isomerically-purified hydroxypropyl β-cyclodextrin is about 8.08.

Embodiment 350: The composition of any one of embodiments 330 to 349, wherein about 22% to about 28% of the hydroxypropyl substitutions in the hydroxypropyl β-cyclodextrin molecules are located at the 3-O— position.

Embodiment 351: The composition of embodiment 350, wherein about 23% to about 27% of the hydroxypropyl substitutions in the hydroxypropyl β-cyclodextrin molecules are located at the 3-O— position.

Embodiment 352: The composition of any one of embodiments 330 to 351, wherein about 72% to about 78% of the hydroxypropyl substitutions in the hydroxypropyl β-cyclodextrin molecules are located at the 2-O— position.

Embodiment 353: The composition of embodiment 352, wherein about 73% to about 77% of the hydroxypropyl substations in the hydroxypropyl β-cyclodextrin molecules are located at the 2-O— position.

Embodiment 354: The composition of any one of embodiments 330 to 353, wherein the concentration of the composition does not substantially change the time required for nanofiltration.

Embodiment 355: The composition of embodiment 354, wherein the length of time to nanofilter the composition ranges from 1.04 to 1.20 hours per diafiltration volume (kg soln/m2-hr/L soln).

Embodiment 356: The composition of any one of embodiments 330 to 355, wherein the nanofiltrated composition has no substantial difference observed in HPLC-ELSD after nanofiltration as compared to before nanofiltration.

Embodiment 357: The composition of any one of embodiments 330 to 356, wherein the nanofiltrated composition has no substantial difference observed in NMR after nanofiltration as compared to before nanofiltration.

Embodiment 358: The composition of any one of embodiments 330 to 357, wherein the composition has a conductivity between 0 and 8.0 µS/cm.

Embodiment 359: The composition of any one of embodiments 330 to 358, wherein the composition has a conductivity between 0 and 4.5 µS/cm.

Embodiment 360: A composition comprising a mixture of isomerically-purified hydroxypropyl β-cyclodextrin molecules comprising:

β-cyclodextrin substituted with seven hydroxypropyl groups ("DS-7");

β-cyclodextrin substituted with eight hydroxypropyl groups ("DS-8");

β-cyclodextrin substituted with nine hydroxypropyl groups ("DS-9");

β-cyclodextrin substituted with ten hydroxypropyl groups ("DS-10");

β-cyclodextrin substituted with eleven hydroxypropyl groups ("DS-11");

β-cyclodextrin substituted with twelve hydroxypropyl groups ("DS-12");

β-cyclodextrin substituted with thirteen hydroxypropyl groups ("DS-13"); and

β-cyclodextrin substituted with fourteen hydroxypropyl groups ("DS-14"), wherein the composition comprises less than 1% β-cyclodextrin substituted with six hydroxypropyl groups ("DS-6").

Embodiment 361: The composition of embodiment 360, wherein the composition comprises less than 1% β-cyclodextrin substituted with five hydroxypropyl groups ("DS-5"), β-cyclodextrin substituted with four hydroxypropyl groups ("DS-4"), β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1").

Embodiment 362: The composition of embodiment 360 or 361, wherein the DS-9 has the highest concentration in the mixture of isomerically-purified hydroxypropyl β-cyclodextrin molecules as compared to DS-7, DS-8, DS-10, DS-11, DS-12, DS-13, and DS-14.

Embodiment 363: The composition of any one of embodiments 360 to 362, wherein the DS-10 has the highest concentration in the mixture of isomerically-purified hydroxypropyl β-cyclodextrin molecules as compared to DS-7, DS-8, DS-10, DS-11, DS-12, DS-13, and DS-14.

Embodiment 364: The composition of any one of embodiments 360 to 363, wherein the mixture of isomerically-purified hydroxypropyl β-cyclodextrin molecules comprises about 0% to about 6% DS-7.

Embodiment 365: The composition of embodiment 364, wherein the mixture of isomerically-purified hydroxypropyl β-cyclodextrin molecules comprises about 1% to about 5% DS-7.

Embodiment 366: The composition of any one of embodiments 360 to 365, wherein the mixture of isomerically-purified hydroxypropyl β-cyclodextrin molecules comprises about 13% to about 19% DS-8.

Embodiment 367: The composition of embodiment 366, wherein the mixture of isomerically-purified hydroxypropyl β-cyclodextrin molecules comprises about 14% to about 18% DS-8.

Embodiment 368: The composition of any one of embodiments 360 to 367, wherein the mixture of isomerically-purified hydroxypropyl β-cyclodextrin molecules comprises about 22% to about 28% DS-9.

Embodiment 369: The composition of embodiment 368, wherein the mixture of isomerically-purified hydroxypropyl β-cyclodextrin molecules comprises about 23% to about 27% DS-9.

Embodiment 370: The composition of any one of embodiments 360 to 369, wherein the mixture of isomerically-purified hydroxypropyl β-cyclodextrin molecules comprises about 23% to about 29% DS-10.

Embodiment 371: The composition of embodiment 370, wherein the mixture of isomerically-purified hydroxypropyl β-cyclodextrin molecules comprises about 24% to about 28% DS-10.

Embodiment 372: The composition of any one of embodiments 360 to 371, wherein the mixture of isomerically-purified hydroxypropyl β-cyclodextrin molecules comprises about 12% to about 18% DS-11.

Embodiment 373: The composition of embodiment 372, wherein the mixture of isomerically-purified hydroxypropyl β-cyclodextrin molecules comprises about 13% to about 17% DS-11.

Embodiment 374: The composition of any one of embodiments 360 to 373, wherein the mixture of isomerically-purified hydroxypropyl β-cyclodextrin molecules comprises about 7% to about 13% DS-12.

Embodiment 375: The composition of embodiment 374, wherein the mixture of isomerically-purified hydroxypropyl β-cyclodextrin molecules comprises about 8% to about 12% DS-12.

Embodiment 376: The composition of any one of embodiments 360 to 375, wherein the mixture of isomerically-purified hydroxypropyl β-cyclodextrin molecules comprises about 2% to about 8% DS-13.

Embodiment 377: The composition of embodiment 376, wherein the mixture of isomerically-purified hydroxypropyl β-cyclodextrin molecules comprises about 3% to about 7% DS-13.

Embodiment 378: The composition of any one of embodiments 360 to 377, wherein the mixture of isomerically-purified hydroxypropyl β-cyclodextrin molecules comprises about 0% to about 6% DS-14.

Embodiment 379: The composition of embodiment 378, wherein the mixture of isomerically-purified hydroxypropyl β-cyclodextrin molecules comprises about 1% to about 5% DS-14.

Embodiment 380: The composition of any one of embodiments 360 to 379, wherein the average degree of substitution of the mixture of isomerically-purified hydroxypropyl β-cyclodextrin is about 7.5 to about 8.5.

Embodiment 381: The composition of embodiment 380, wherein the average degree of substitution of the mixture of isomerically-purified hydroxypropyl β-cyclodextrin is about 8.08.

Embodiment 382: The composition of any one of embodiments 360 to 381, wherein about 22% to about 28% of the hydroxypropyl substitutions in the hydroxypropyl β-cyclodextrin molecules are located at the 3-O— position.

Embodiment 383: The composition of any one of embodiments 360 to 382, wherein about 23% to about 27% of the hydroxypropyl substitutions in the hydroxypropyl β-cyclodextrin molecules are located at the 3-O— position.

Embodiment 384: The composition of any one of embodiments 360 to 383, wherein about 72% to about 78% of the hydroxypropyl substitutions in the β-cyclodextrin molecules are located at the 2-O— position.

Embodiment 385: The composition of any one of embodiments 360 to 384, wherein about 73% to about 77% of the hydroxypropyl substitutions in the β-cyclodextrin molecules are located at the 2-O— position.

Embodiment 386: The composition of any one of embodiments 360 to 385, wherein the composition has an HPLC-CAD chromatogram of FIG. 23.

Embodiment 387: The composition of embodiment 386, wherein the composition has a mean retention time of about 14.3 minutes.

Embodiment 388: The composition of any one of embodiments 360 to 387, wherein the composition has a −ESI-MS spectrum with peaks at about 740 m/z, about 770 m/z, about 798 m/z, about 828 m/z, and about 857 m/z.

Embodiment 389: The composition of any one of embodiments 360 to 388, wherein the composition has a +ESI-MS spectrum with peaks at about 803 m/z, about 831 m/z, about 861 m/z, about 889 m/z, and about 919 m/z.

Embodiment 390: The composition of any one of embodiments 360 to 389, wherein the composition has a ESI-MS spectra of FIG. 24.

Embodiment 391: The composition of any one of embodiments 360 to 390, having a MALDI-TOF spectrum with peaks at about 1559 m/z, about 1618 m/z, about 1678 m/z, about 1737 m/z, about 1796 m/z, about 1857 m/z, and about 1916 m/z.

Embodiments 392: The composition of embodiment 391, wherein the composition has a MALDI-TOF spectrum of FIG. 25.

Embodiments 393: The composition of embodiment 392, wherein the area of DS-7 is 3.16%.

Embodiments 394: The composition of embodiment 392 or 393, wherein the area of DS-8 is 16.44%.

Embodiments 395: The composition of any one of embodiments 392 to 394, wherein the area of DS-9 is 25.24%.

Embodiments 396: The composition of any one of embodiments 392 to 395, wherein the area of DS-10 is 25.52%.

Embodiments 397: The composition of any one of embodiments 392 396, wherein the area of DS-11 is 15.10%.

Embodiments 398: The composition of any one of embodiments 392 to 397, wherein the area of DS-12 is 10.03%.

Embodiments 399: The composition of any one of embodiments 392 to 398, wherein the area of DS-13 is 4.50%.

Embodiments 400: The composition of any one of embodiments 392 to 399, wherein the area of DS-14 is 2.67%.

Embodiments 401: The composition of any one of embodiments 360 to 400 having a $^1$H-NMR spectrum of FIG. 21.

Embodiment 402: The composition of any one of embodiments 360 to 401 having a DEPT-edited HSQC spectrum of FIG. 22.

Embodiment 403: The composition of any one of embodiments 360 to 402, wherein the osmolality of the composition is about 635-695 mOs/kg.

Embodiment 404: The composition of any one of embodiments 360 to 403, wherein the true density of the composition is about 1.096-1.098 g/cm3.

Embodiment 405: The composition of any one of embodiments 360 to 404, wherein the composition comprises no more than 10 ppb of propylene glycol as measured by HPLC.

Embodiment 406: The composition of any one of embodiments 360 to 405, wherein the composition comprises no more than 10 ppb propylene glycol as measured by gas chromatography.

Embodiment 407: The composition of any one of embodiments 360 to 406, wherein the composition comprises no more than 10 ppb propylene glycol as measured by PG/EG-ratio of propylene glycol to ethylene glycol.

Embodiment 408: The composition of any one of embodiments 360 to 407, wherein the composition comprises no more than 1 ppm propylene oxide.

Embodiment 409: The composition of any one of embodiments 360 to 408, wherein the total amount of other unspecified impurities is less than or equal to 0.05% as measured by HPLC.

Embodiment 410: The composition of any one of embodiments 360 to 409, wherein the composition comprises between 0 and 10 ppm chloride.

Embodiment 411: The composition of embodiment 410, wherein the composition comprises between 0 and 1 ppm chloride.

Embodiment 412: The composition of any one of embodiments 360 to 411, wherein the composition has a conductivity between 0 and 8 µS/cm.

Embodiment 413: The composition of embodiment 412, wherein the composition has a conductivity between 0 and 4.5 µS/cm.

Embodiment 414: The composition of embodiment 413, wherein the composition has a conductivity between 0 and 3 µS/cm.

Embodiment 415: The composition of embodiment 414, wherein the composition has a conductivity between 0 and 1.5 µS/cm.

Embodiment 416: The composition of any one of embodiments 360 to 415, wherein the composition is nanofiltered.

Embodiment 417: The composition of embodiment 416, wherein the nanofiltrated composition has no substantial difference observed in HPLC-ELSD after nanofiltration as compared to before nanofiltration.

Embodiment 418: The composition of embodiment 416 or 417, wherein the nanofiltrated composition has no substantial difference observed in NMR after nanofiltration as compared to before nanofiltration.

Embodiment 419: A composition comprising a mixture of isomerically-purified hydroxypropyl β-cyclodextrin molecules comprising:
  about 0% to about 6% β-cyclodextrin substituted with seven hydroxypropyl groups ("DS-7");
  about 13% to about 19% β-cyclodextrin substituted with eight hydroxypropyl groups ("DS-8");
  about 22% to about 28% β-cyclodextrin substituted with nine hydroxypropyl groups ("DS-9");
  about 23% to about 29% β-cyclodextrin substituted with ten hydroxypropyl groups ("DS-10");
  about 12% to about 18% β-cyclodextrin substituted with eleven hydroxypropyl groups ("DS-11");
  about 7% to about 13% β-cyclodextrin substituted with twelve hydroxypropyl groups ("DS-12");
  about 2% to about 8% β-cyclodextrin substituted with thirteen hydroxypropyl groups ("DS-13"); and
  about 0% to about 6% β-cyclodextrin substituted with fourteen hydroxypropyl groups ("DS-14").

Embodiment 420: A composition comprising a mixture of isomerically-purified hydroxypropyl β-cyclodextrin molecules comprising:
  β-cyclodextrin substituted with seven hydroxypropyl groups ("DS-7");
  β-cyclodextrin substituted with eight hydroxypropyl groups ("DS-8");
  β-cyclodextrin substituted with nine hydroxypropyl groups ("DS-9");
  β-cyclodextrin substituted with ten hydroxypropyl groups ("DS-10");
  β-cyclodextrin substituted with eleven hydroxypropyl groups ("DS-11");
  β-cyclodextrin substituted with twelve hydroxypropyl groups ("DS-12");
  β-cyclodextrin substituted with thirteen hydroxypropyl groups ("DS-13"); and
  β-cyclodextrin substituted with fourteen hydroxypropyl groups ("DS-14"),
  wherein the composition comprises less than 1% β-cyclodextrin substituted with six hydroxypropyl groups ("DS-6"), β-cyclodextrin substituted with five hydroxypropyl groups ("DS-5"), β-cyclodextrin substituted with four hydroxypropyl groups ("DS-4"), β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1").

Embodiment 421: A composition comprising a mixture of isomerically-purified hydroxypropyl β-cyclodextrin molecules comprising less than 1% hydroxypropyl β-cyclodextrin with seven hydroxypropyl groups ("DS-7").

Embodiment 422: The composition of embodiment 421, wherein the hydroxypropyl β-cyclodextrin percentage is based upon area percentage from a MALDI-TOF-MS spectrum.

Embodiment 423: The composition of any one of embodiments 421 to 422, wherein the hydroxypropyl β-cyclodextrin percentage is based upon weight percentage.

Embodiment 424: The composition of any one of embodiments 421 to 423, wherein the composition comprises less than 1% β-cyclodextrin substituted with six hydroxypropyl groups ("DS-6"), β-cyclodextrin substituted with five hydroxypropyl groups ("DS-5"), β-cyclodextrin substituted with four hydroxypropyl groups ("DS-4"), β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1").

Embodiment 425: The composition of any one of embodiments 421 to 424, wherein the mixture of isomerically-purified hydroxypropyl β-cyclodextrin molecules comprises about 6% to about 12% of β-cyclodextrin substituted with eight hydroxypropyl groups ("DS-8").

Embodiment 426: The composition of embodiment 425, wherein the mixture of isomerically-purified hydroxypropyl β-cyclodextrin molecules comprises about 7% to about 11% of DS-8.

Embodiment 427: The composition of any one of embodiments 421 to 426, wherein the mixture of isomerically-purified hydroxypropyl β-cyclodextrin molecules comprises about 18% to about 24% of β-cyclodextrin substituted with nine hydroxypropyl groups ("DS-9").

Embodiment 428: The composition of embodiment 427, wherein the mixture of isomerically-purified hydroxypropyl β-cyclodextrin molecules comprises about 19% to about 23% of DS-9.

Embodiment 429: The composition of any one of embodiments 421 to 428, wherein the mixture of isomerically-purified hydroxypropyl β-cyclodextrin molecules comprises about 24% to about 30% of β-cyclodextrin substituted with ten hydroxypropyl groups ("DS-10").

Embodiment 430: The composition of embodiment 429, wherein the mixture of isomerically-purified hydroxypropyl β-cyclodextrin molecules comprises about 25% to about 29% of DS-10.

Embodiment 431: The composition of any one of embodiments 421 to 430, wherein the mixture of isomerically-purified hydroxypropyl β-cyclodextrin molecules comprises about 18% to about 24% of β-cyclodextrin substituted with eleven hydroxypropyl groups ("DS-11").

Embodiment 432: The composition of embodiment 431, wherein the mixture of isomerically-purified hydroxypropyl β-cyclodextrin molecules comprises about 19% to about 23% of DS-11.

Embodiment 433: The composition of any one of embodiments 421 to 432, wherein the mixture of isomerically-purified hydroxypropyl β-cyclodextrin molecules comprises about 10% to about 16% of β-cyclodextrin substituted with twelve hydroxypropyl groups ("DS-12").

Embodiment 434: The composition of embodiment 433, wherein the mixture of isomerically-purified hydroxypropyl β-cyclodextrin molecules comprises about 11% to about 15% of DS-12.

Embodiment 435: The composition of any one of embodiments 421 to 434, wherein the mixture of isomerically-purified hydroxypropyl β-cyclodextrin molecules comprises about 4% to about 10% of β-cyclodextrin substituted with thirteen hydroxypropyl groups ("DS-13").

Embodiment 436: The composition of embodiment 435, wherein the mixture of isomerically-purified hydroxypropyl β-cyclodextrin molecules comprises about 5% to about 9% of DS-13.

Embodiment 437: The composition of any one of embodiments 421 to 436, wherein the mixture of isomerically-purified hydroxypropyl β-cyclodextrin molecules comprises about 0% to about 6% of β-cyclodextrin substituted with fourteen hydroxypropyl groups ("DS-14").

Embodiment 438: The composition of embodiment 437, wherein the mixture of isomerically-purified hydroxypropyl β-cyclodextrin molecules comprises about 1% to about 5% of DS-14.

Embodiment 439: The composition of any one of embodiments 421 to 438, wherein the average degree of substitution of the mixture of isomerically-purified hydroxypropyl β-cyclodextrin is about 9 to about 10.

Embodiment 440: The composition of embodiment 439, wherein the average degree of substitution of the mixture of isomerically-purified hydroxypropyl β-cyclodextrin is about 9.65.

Embodiment 441: The composition of any one of embodiments 421 to 440, wherein about 15% to about 21% of the hydroxypropyl substitutions in the hydroxypropyl β-cyclodextrin molecules are located at the 3-O— position.

Embodiment 442: The composition of embodiment 441, wherein about 16% to about 20% of the hydroxypropyl substitutions in the hydroxypropyl β-cyclodextrin molecules are located at the 3-O— position.

Embodiment 443: The composition of any one of embodiments 421 to 442, wherein about 79% to about 85% of the hydroxypropyl substitutions in the hydroxypropyl β-cyclodextrin molecules are located at the 2-O— position.

Embodiment 444: The composition of embodiment 443, wherein about 80% to about 84% of the hydroxypropyl substitutions in the hydroxypropyl β-cyclodextrin molecules are located at the 2-O— position.

Embodiment 445: The composition of any one of embodiments 421 to 444, wherein the concentration of the composition does not substantially change the time required for nanofiltration.

Embodiment 446: The composition of embodiment 445, wherein the length of time to nanofilter the composition ranges from 1.04 to 1.20 hours per diafiltration volume (kg soln/m²-hr/L soln).

Embodiment 447: The composition of any one of embodiments 421 to 446, wherein the composition has no substantial difference observed in HPLC-ELSD after nanofiltration as compared to before nanofiltration.

Embodiment 448: The composition of any one of embodiments 421 to 447, wherein the composition has no substantial difference observed in NMR after nanofiltration as compared to before nanofiltration.

Embodiment 449: The composition of any one of embodiments 421 to 448, wherein the composition has a conductivity between 0 and 8.0 μS/cm.

Embodiment 450: The composition of any one of embodiments 421 to 449, wherein the composition has a conductivity between 0 and 4.5 μS/cm.

Embodiment 451: A composition comprising a mixture of isomerically-purified hydroxypropyl β-cyclodextrin molecules comprising:
- β-cyclodextrin substituted with eight hydroxypropyl groups ("DS-8");
- β-cyclodextrin substituted with nine hydroxypropyl groups ("DS-9");
- β-cyclodextrin substituted with ten hydroxypropyl groups ("DS-10");
- β-cyclodextrin substituted with eleven hydroxypropyl groups ("DS-11");
- β-cyclodextrin substituted with twelve hydroxypropyl groups ("DS-12");
- β-cyclodextrin substituted with thirteen hydroxypropyl groups ("DS-13"); and
- β-cyclodextrin substituted with fourteen hydroxypropyl groups ("DS-14"),
wherein the composition comprises less than 1% β-cyclodextrin substituted with seven hydroxypropyl groups ("DS-7").

Embodiment 452: The composition of embodiment 451, wherein the composition comprises less than 1% β-cyclodextrin substituted with six hydroxypropyl groups ("DS-6"), 1% β-cyclodextrin substituted with five hydroxypropyl groups ("DS-5"), β-cyclodextrin substituted with four hydroxypropyl groups ("DS-4"), β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1").

Embodiment 453: The composition of embodiment 451 or 452, wherein the DS-10 has the highest concentration in the mixture of isomerically-purified hydroxypropyl β-cyclodextrin molecules as compared to DS-8, DS-9, DS-11, DS-12, DS-13, and DS-14.

Embodiment 454: The composition of any one of embodiments 451 to 453, wherein the mixture of isomerically-purified hydroxypropyl β-cyclodextrin molecules comprises about 6% to about 12% DS-8.

Embodiment 455: The composition of embodiment 454, wherein the mixture of isomerically-purified hydroxypropyl β-cyclodextrin molecules comprises about 7% to about 11% DS-8.

Embodiment 456: The composition of any one of embodiments 451 to 455, wherein the mixture of isomerically-purified hydroxypropyl β-cyclodextrin molecules comprises about 18% to about 24% DS-9.

Embodiment 457: The composition of embodiment 456, wherein the mixture of isomerically-purified hydroxypropyl β-cyclodextrin molecules comprises about 19% to about 23% DS-9.

Embodiment 458: The composition of any one of embodiments 451 to 457, wherein the mixture of isomerically-purified hydroxypropyl β-cyclodextrin molecules comprises about 24% to about 30% DS-10.

Embodiment 459: The composition of embodiment 458, wherein the mixture of isomerically-purified hydroxypropyl β-cyclodextrin molecules comprises about 25% to about 29% DS-10.

Embodiment 460: The composition of any one of embodiments 451 to 459, wherein the mixture of isomerically-purified hydroxypropyl β-cyclodextrin molecules comprises about 18% to about 24% DS-11.

Embodiment 461: The composition of embodiment 460, wherein the mixture of isomerically-purified hydroxypropyl β-cyclodextrin molecules comprises about 19% to about 23% DS-11.

Embodiment 462: The composition of any one of embodiments 451 to 461, wherein the mixture of isomerically-purified hydroxypropyl β-cyclodextrin molecules comprises about 10% to about 16% DS-12.

Embodiment 463: The composition of embodiment 462, wherein the mixture of isomerically-purified hydroxypropyl β-cyclodextrin molecules comprises about 11% to about 15% DS-12.

Embodiment 464: The composition of any one of embodiments 451 to 463, wherein the mixture of isomerically-purified hydroxypropyl β-cyclodextrin molecules comprises about 4% to about 10% DS-13.

Embodiment 465: The composition of embodiment 464, wherein the mixture of isomerically-purified hydroxypropyl β-cyclodextrin molecules comprises about 5% to about 9% DS-13.

Embodiment 466: The composition of any one of embodiments 451 to 465, wherein the mixture of isomerically-purified hydroxypropyl β-cyclodextrin molecules comprises about 0% to about 6% DS-14.

Embodiment 467: The composition of embodiment 466, wherein the mixture of isomerically-purified hydroxypropyl β-cyclodextrin molecules comprises about 1% to about 5% DS-14.

Embodiment 468: The composition of any one of embodiments 451 to 467, wherein the average degree of substitution of the mixture of isomerically-purified hydroxypropyl β-cyclodextrin is about 9 to about 10.

Embodiment 469: The composition of embodiment 468, wherein the average degree of substitution of the mixture of isomerically-purified hydroxypropyl β-cyclodextrin is about 9.65.

Embodiment 470: The composition of any one of embodiments 451 to 469, wherein about 15% to about 21% of the hydroxypropyl substitutions in the hydroxypropyl β-cyclodextrin molecules are located at the 3-O— position.

Embodiment 471: The composition of embodiment 470, wherein about 16% to about 20% of the hydroxypropyl substitutions in the hydroxypropyl β-cyclodextrin molecules are located at the 3-O— position.

Embodiment 472: The composition of any one of embodiments 451 to 471, wherein about 79% to about 85% of the hydroxypropyl substitutions in the hydroxypropyl β-cyclodextrin molecules are located at the 2-O— position.

Embodiment 473: The composition of embodiment 472, wherein about 80% to about 84% of the hydroxypropyl substitutions in the hydroxypropyl β-cyclodextrin molecules are located at the 2-O— position.

Embodiment 474: The composition of any one of embodiments 451 to 473, wherein the composition has an HPLC-CAD chromatogram of FIG. 28.

Embodiment 475: The composition of embodiment 474, wherein the composition has a mean retention time of about 15.4 minutes.

Embodiment 476: The composition of any one of embodiments 451 to 475, wherein the composition has a −ESI-MS spectrum with peaks at about 770 m/z, about 798 m/z, about 828 m/z, about 857 m/z, about 885 m/z.

Embodiment 477: The composition of any one of embodiments 451 to 476, wherein the composition has a +ESI-MS spectrum with peaks at about 803 m/z, about 831 m/z, about 861 m/z, about 889 m/z, and about 919 m/z.

Embodiment 478: The composition of any one of embodiments 451 to 477, wherein the composition has a ESI-MS spectra of FIG. 29.

Embodiment 479: The composition of any one of embodiments 451 to 478, having a MALDI-TOF spectrum with peaks at about 1614 m/z, about 1673 m/z, about 1733 m/z, about 1792 m/z, about 1852 m/z, about 1912 m/z, and about 1971 m/z.

Embodiment 480: The composition of embodiment 479, having a MALDI-TOF spectrum of FIG. 30.

Embodiment 481: The composition of embodiment 480, wherein the area of DS-8 is 8.53%.

Embodiment 482: The composition of embodiment 480 or 481, wherein the area of DS-9 is 21.33%.

Embodiment 483: The composition of any one of embodiments 480 to 482, wherein the area of DS-10 is 26.58%.

Embodiment 484: The composition of any one of embodiments 480 to 483, wherein the area of DS-11 is 20.90%.

Embodiment 485: The composition of any one of embodiments 480 to 484, wherein the area of DS-12 is 13.31%.

Embodiment 486: The composition of any one of embodiments 480 to 485, wherein the area of DS-13 is 6.74%.

Embodiment 487: The composition of any one of embodiments 480 to 486, wherein the area of DS-14 is 2.60%.

Embodiment 488: The composition of any one of embodiments 451 to 487 having a 1H-NMR spectrum of FIG. 26.

Embodiment 489: The composition of any one of embodiments 451 to 488 having a DEPT-edited HSQC spectrum of FIG. 27.

Embodiment 490: The composition of any one of embodiments 451 to 489, wherein the osmolality of the composition is about 635-695 mOs/kg.

Embodiment 491: The composition of any one of embodiments 451 to 490, wherein the true density of the composition is about 1.096-1.098 g/cm$^3$.

Embodiment 492: The composition of any one of embodiments 451 to 491, wherein the composition comprises no more than 10 ppb of propylene glycol as measured by HPLC.

Embodiment 493: The composition of any one of embodiments 451 to 492, wherein the composition comprises no more than 10 ppb propylene glycol as measured by gas chromatography.

Embodiment 494: The composition of any one of embodiments 451 to 493, wherein the composition comprises no more than 10 ppb propylene glycol as measured by PG/EG-ratio of propylene glycol to ethylene glycol.

Embodiment 495: The composition of any one of embodiments 451 to 494, wherein the composition comprises no more than 1 ppm propylene oxide.

Embodiment 496: The composition of any one of embodiments 451 to 495, wherein the total amount of other unspecified impurities is less than or equal to 0.05% as measured by HPLC.

Embodiment 497: The composition of any one of embodiments 451 to 496, wherein the composition comprises between 0 and 10 ppm chloride.

Embodiment 498: The composition of embodiment 497, wherein the composition comprises between 0 and 1 ppm chloride.

Embodiment 499: The composition of any one of embodiments 451 to 498, wherein the composition has a conductivity between 0 and 8 µS/cm.

Embodiment 500: The composition of embodiment 499, wherein the composition has a conductivity between 0 and 4.5 µS/cm.

Embodiment 501: The composition of embodiment 500, wherein the composition has a conductivity between 0 and 3 µS/cm.

Embodiment 502: The composition of embodiment 501, wherein the composition has a conductivity between 0 and 1.5 µS/cm.

Embodiment 503: The composition of any one of embodiments 451 to 502, wherein the composition is nanofiltered.

Embodiment 504: The composition of embodiment 503, wherein the nanofiltrated composition has no substantial difference observed in HPLC-ELSD after nanofiltration as compared to before nanofiltration.

Embodiment 505: The composition of embodiment 503, wherein the nanofiltrated composition has no substantial difference observed in NMR after nanofiltration as compared to before nanofiltration.

Embodiment 506: A composition comprising a mixture of isomerically-purified hydroxypropyl β-cyclodextrin molecules comprising:
- about 6% to about 12% β-cyclodextrin substituted with eight hydroxypropyl groups ("DS-8");
- about 18% to about 24% β-cyclodextrin substituted with nine hydroxypropyl groups ("DS-9");
- about 24% to about 30% β-cyclodextrin substituted with ten hydroxypropyl groups ("DS-10");
- about 18% to about 24% β-cyclodextrin substituted with eleven hydroxypropyl groups ("DS-11");
- about 10% to about 16% β-cyclodextrin substituted with twelve hydroxypropyl groups ("DS-12");
- about 4% to about 10% β-cyclodextrin substituted with thirteen hydroxypropyl groups ("DS-13"); and
- about 0% to about 6% β-cyclodextrin substituted with fourteen hydroxypropyl groups ("DS-14").

Embodiment 507: A composition comprising a mixture of isomerically-purified hydroxypropyl β-cyclodextrin molecules comprising:
- β-cyclodextrin substituted with eight hydroxypropyl groups ("DS-8");
- β-cyclodextrin substituted with nine hydroxypropyl groups ("DS-9");
- β-cyclodextrin substituted with ten hydroxypropyl groups ("DS-10");
- β-cyclodextrin substituted with eleven hydroxypropyl groups ("DS-11");
- β-cyclodextrin substituted with twelve hydroxypropyl groups ("DS-12");
- β-cyclodextrin substituted with thirteen hydroxypropyl groups ("DS-13"); and
- β-cyclodextrin substituted with fourteen hydroxypropyl groups ("DS-14"), wherein the composition comprises less than 1% β-cyclodextrin substituted with seven hydroxypropyl groups ("DS-7"), β-cyclodextrin substituted with six hydroxypropyl groups ("DS-6"), β-cyclodextrin substituted with five hydroxypropyl groups ("DS-5"), β-cyclodextrin substituted with four hydroxypropyl groups ("DS-4"), β-cyclodextrin substituted with three hydroxypropyl groups ("DS-3"), β-cyclodextrin substituted with two hydroxypropyl groups ("DS-2"), and β-cyclodextrin substituted with one hydroxypropyl group ("DS-1").

Embodiment 508: An isomerically-purified composition comprising a mixture of hydroxypropyl-β-cyclodextrin molecules having the general subunit structure:

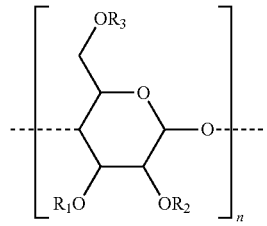

wherein $n=7=m+k+y+z$;
$m=0\text{-}7$;
$k=0\text{-}7$;
$y=0\text{-}7$;
$z=0\text{-}7$;
$R_1$, $R_2$, and $R_3$ are each independently H, hydroxypropyl, or

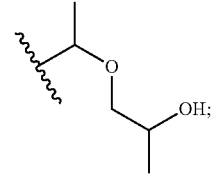 [SMILES: *C(C)OCC(C)O]

wherein m refers to the number of subunits wherein $R_1$ is not H, $R_2$ is H, and $R_3$ is H;
wherein k refers to the number of subunits wherein $R_1$ is H, $R_2$ is not H, and $R_3$ is H;
wherein y refers to the number of subunits wherein $R_1$ is H, $R_2$ is H, and $R_3$ is not H;
wherein z refers to the number of subunits wherein $R_1$ is H, $R_2$ is H, and $R_3$ is H; and
wherein $R_3$=H in at least 80% of the subunits.

Embodiment 509: The composition of embodiment 508, wherein $R_3$=H in at least 85% of the subunits.

Embodiment 510: The composition of embodiment 508 or 509, wherein $R_3$=H in at least 90% of the subunits.

Embodiment 511: The composition of any one of embodiments 508 to 510, wherein $R_3$=H in at least 95% of the subunits.

Embodiment 512: The composition of any one of embodiments 508 to 511, wherein $R_3$=H in at least 99% of the subunits.

Embodiment 513: The composition of any one of embodiments 508 to 512, wherein $R_3$=H in 100% of the subunits.

Embodiment 514: The composition of any one of embodiments 508 to 513, wherein y=0.

Embodiment 515: The composition of any one of embodiments 508 to 514, wherein z=0.

Embodiment 516: The composition of any one of embodiments 508 to 515, wherein $R_1$ is not H in at least 35% of the subunits.

Embodiment 517: The composition of embodiment 516, wherein $R_1$ is not H in at least 40% of the subunits.

Embodiment 518: The composition of embodiment 516, wherein $R_1$ is not H in about 50% to about 70% of the subunits.

Embodiment 519: The composition of embodiment 516, wherein $R_1$ is not H in about 60% to about 80% of the subunits.

Embodiment 520: The composition of embodiment 516, wherein $R_1$ is not H in about 65% to about 85% of the subunits.

Embodiment 521: The composition of embodiment 516, wherein $R_1$ is not H in about 70% to about 90% of the subunits.

Embodiment 522: The composition of embodiment 508, wherein $R_2$ is not H in no more than 65% of the subunits.

Embodiment 523: The composition of embodiment 522, wherein $R_2$ is not H in about 35% to about 55% of the subunits.

Embodiment 524: The composition of embodiment 522, wherein $R_2$ is not H in about 30% to about 50% of the subunits.

Embodiment 525: The composition of embodiment 522, wherein $R_2$ is not H in about 20% to about 40% of the subunits.

Embodiment 526: The composition of embodiment 522, wherein $R_2$ is not H in about 10% to about 30% of the subunits.

Embodiment 527: The composition of any one of embodiments 508 to 526, wherein the general subunit structure is:

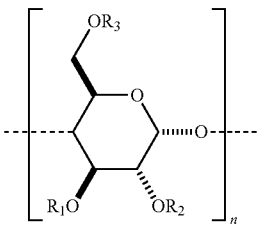

Embodiment 528: An isomerically-purified composition comprising a mixture of hydroxypropyl-β-cyclodextrin molecules, wherein 0% to 5% of the hydroxypropyl-β-cyclodextrin subunits are substituted at the 6-O— position.

Embodiment 529: An isomerically-purified composition comprising a mixture of hydroxypropyl-β-cyclodextrin molecules, wherein 80% to 100% of the hydroxypropyl-β-cyclodextrin subunits are substituted at the 2-O— position, the 3-O-position, or a combination thereof.

Embodiment 530: A composition comprising a mixture of beta-cyclodextrin molecules substituted at one or more hydroxyl positions by hydroxypropyl groups, wherein: the mixture comprises less than 0.05% unsubstituted beta-cyclodextrin ("DS-0") and less than 0.05% beta-cyclodextrin substituted with one hydroxypropyl group ("DS-1"), the composition comprising an average degree of substitution of 6.02-7.98, wherein the composition is suitable for intrathecal, intravenous, oral, or intracerebroventricular administration to a patient in need thereof.

Embodiment 531: The composition of embodiment 530, wherein the average degree of substitution is determined by $^1$H-NMR.

Embodiment 532: The composition of embodiment 530 or 531, wherein the amount of DS-0 and DS-1 is determined by peak height of an electrospray MS spectrum.

Embodiment 533: The composition of any one of embodiments 530 to 532, wherein the pH of the composition is between 6.0 and 7.9.

Embodiment 534: The composition of any one of embodiments 530 to 533, wherein the pH of the composition is between 7.1 and 7.7.

Embodiment 535: The composition of any one of embodiments 530 to 534, wherein the pH of the composition is between 7.3-7.5.

Embodiment 536: The composition of any one of embodiments 530 to 535, wherein the composition comprises at least one of a pharmaceutical excipient, a carrier, a pharmaceutically acceptable diluent, a pH adjusting agent, and a buffer.

Embodiment 537: The composition of any one of embodiments 530 to 536, wherein the true density of the composition is about 1.096-1.098 $g/cm^3$.

Embodiment 538: The composition of any one of embodiments 530 to 537, wherein the osmolality of the composition is about 635-695 mOs/kg.

Embodiment 539: The composition of any one of embodiments 530 to 538, wherein composition further comprises a container and non-visible particulate matter, and the non-visible particulate matter with a size ≥25 microns is in an amount ≤600/container.

Embodiment 540: The composition of any one of embodiments 530 to 539, wherein the composition comprises no more than 10 ppb of propylene glycol as measured by HPLC.

Embodiment 541: The composition of any one of embodiments 530 to 540, wherein the composition comprises no more than 5 ppb of propylene glycol as measured by HPLC.

Embodiment 542: The composition of any one of embodiments 530 to 541, wherein the composition comprises no more than 10 ppb propylene glycol as measured by PG/EG-ratio of propylene glycol to ethylene glycol.

Embodiment 543: The composition of any one of embodiments 530 to 542, wherein the composition comprises no more than 5 ppb propylene glycol as measured by PG/EG-ratio of propylene glycol to ethylene glycol.

Embodiment 544: The composition of any one of embodiments 530 to 543, wherein the composition purified by absorption chromatography alumina, solvent precipitation, or a combination thereof.

Embodiment 545: The composition of any one of embodiments 530 to 544, wherein the composition comprises no more than 1 ppm propylene oxide.

Embodiment 546: The composition of any one of embodiments 530 to 545, wherein the total amount of other unspecified impurities is less than or equal to 0.05% as measured by HPLC.

Embodiment 547: The composition of any one of embodiments 530 to 546, wherein the composition has a concentration of about 10 mg/mL to about 200 mg/mL.

Embodiment 548: The composition of any one of embodiments 1 to 547, wherein the composition is suitable for administration to a pediatric patient.

Embodiment 549: The composition of any one of embodiments 1 to 547, wherein the composition is suitable for administration to an adult patient.

Embodiment 550: The composition of any one of embodiments 1 to 549, further comprising a pharmaceutically acceptable diluent.

Embodiment 551: The composition of any one of embodiments 1 to 550, wherein the composition exhibits a lower ototoxicity than Trappsol® Cyclo.

Embodiment 552: The composition of any one of embodiments 1 to 551, wherein the composition has a conductivity of about ≤200 µS/cm.

Embodiment 553: The composition of any one of embodiments 1 to 552, wherein the composition is stable for at least 6 months.

Embodiment 554: The composition of any one of embodiments 1 to 553, wherein the composition is stable for at least 12 months.

Embodiment 555: The composition of any one of embodiments 1 to 554, wherein the composition is stable for at least 18 months.

Embodiment 556: The composition of any one of embodiments 1 to 555, further comprising a pH adjusting agent.

Embodiment 557: The composition of embodiment 556, wherein the pH adjusting agent is sodium hydroxide.

Embodiment 558: The composition of any one of embodiments 1 to 557, further comprising a buffer.

Embodiment 559: The composition of embodiment 558, wherein the buffer comprises monobasic sodium phosphate and dibasic sodium phosphate.

Embodiment 560: The composition of any one of embodiments 1 to 559, wherein the composition is packaged in a vial.

Embodiment 561: The composition of any one of embodiments 1 to 560, wherein the composition is terminally sterilized.

Embodiment 562: The composition of any one of embodiments 1 to 561, wherein the pH of the composition is adjusted after the terminal sterilization.

Embodiment 563: The composition of any one of embodiments 1 to 562, wherein the composition contains ≤10.0% w/w/ of water.

Embodiment 564: A method of preparing a purified mixture of beta-cyclodextrin suitable for intrathecal, intravenous, oral, or intracerebroventricular administration to a patient in need thereof, the method comprising:
nanofiltrating a beta-cyclodextrin to achieve a purified mixture of beta-cyclodextrin molecules substituted at one or more hydroxyl positions by hydroxypropyl groups, wherein the mixture comprises less than 0.05% unsubstituted beta-cyclodextrin ("DS-0") and less than 0.05% beta-cyclodextrin substituted with one hydroxypropyl group ("DS-1"), and wherein the average degree of substitution of 6.02-7.98, and
adjusting the pH of the nanofiltrated purified mixture of beta-cyclodextrin to achieve a pH of 6.0 to 7.8.

Embodiment 565: The method of embodiment 564, wherein the pH is adjusted with 0.1 M sodium hydroxide.

Embodiment 566: A method of treating Niemann-Pick disease Type C, liver disease, cardiovascular disease, familial hypercholesterolemia and/or cholesterol deposits, the method comprising administering to a patient in need thereof a therapeutically effective amount of the pharmaceutical composition of any one of embodiments 1 to 563.

Embodiment 567: The composition of any one of embodiments 1 to 563 for use in a method of treating Niemann-Pick disease Type C, liver disease, cardiovascular disease, familial hypercholesterolemia and/or cholesterol deposits, wherein the method comprises administering to a patient in need thereof a therapeutically effective amount of the pharmaceutical composition.

Embodiment 568: The method of embodiment 566, or the composition for use according to embodiment 567, wherein said method further comprises administering about 50 mg to about 2000 mg of the beta-cyclodextrin mixture to the patient.

Embodiment 569: The method or composition for use according to embodiment 568, wherein about 50 mg to about 300 mg of the beta-cyclodextrin mixture is administered.

Embodiment 570: The method of any one of embodiments 566 or 568 to 569, or the composition for use according to any one of embodiments 567 to 569, wherein said method further comprises administering the composition at 1-day, 2-day, or 3-day intervals.

Embodiment 571: The method of any one of embodiments 566 or 568 to 569, or the composition for use according to any one of embodiments 567 to 569, wherein said method further comprises administering the composition once every week.

Embodiment 572: The method of any one of embodiments 566 or 568 to 569, or the composition for use according to any one of embodiments 567 to 569, wherein said method further comprises administering the composition once every two weeks.

Embodiment 573: The method of any one of embodiments 566 or 568 to 572, or the composition for use according to any one of embodiments 567 to 572, wherein the administering comprises intravenously administering about 200 mg/kg to about 4100 mg/kg of the beta-cyclodextrin mixture to the patient.

Embodiment 574: The method of any one of embodiments 566 or 568 to 573, or the composition for use according to any one of embodiments 567 to 574, wherein administration results in the lowering of one or more lipids by 75%±5%, 80%±5%, 85%±5%, 90%±5%, or 95%±5%.

Embodiment 575: The method of any one of embodiments 566 or 568 to 574, or the composition for use according to any one of embodiments 567 to 574, wherein administration prevents progression of (i) NPC, or (ii) a disorder selected from liver disease, cardiovascular disease, familial hypercholesterolemia and/or cholesterol deposits, as compared with no administration or administration of a placebo.

Embodiment 576: The method of any one of embodiments 566 or 568 to 575, or the composition for use according to any one of embodiments 567 to 575, wherein the administration is sufficient to modulate the level in plasma of one or more of 7-ketocholesterol, 7β-hydroxycholesterol, 24S-hydroxycholesterol, 25-hydroxycholesterol, 27-hydroxycholesterol, and cholestane-3β,5α,6β-triol.

Embodiment 577: The method of any one of embodiments 566 or 568 to 576, or the composition for use according to any one of embodiments 567 to 576, wherein the administration is sufficient to maintain or reduce one or more domain scores of the NPC Severity Scale selected from: ambulation, fine motor skills, cognition, speech, swallowing, eye movement, memory, hearing, and seizures.

Embodiment 578: The method of any one of embodiments 566 or 568 to 577, or the composition for use according to any one of embodiments 567 to 577, wherein the duration of the administration is about 4 hours or less.

Embodiment 579: The method or composition for use according to embodiment 578, wherein the duration of the administration is about 2 hours or less.

EXAMPLES

Figure 31:
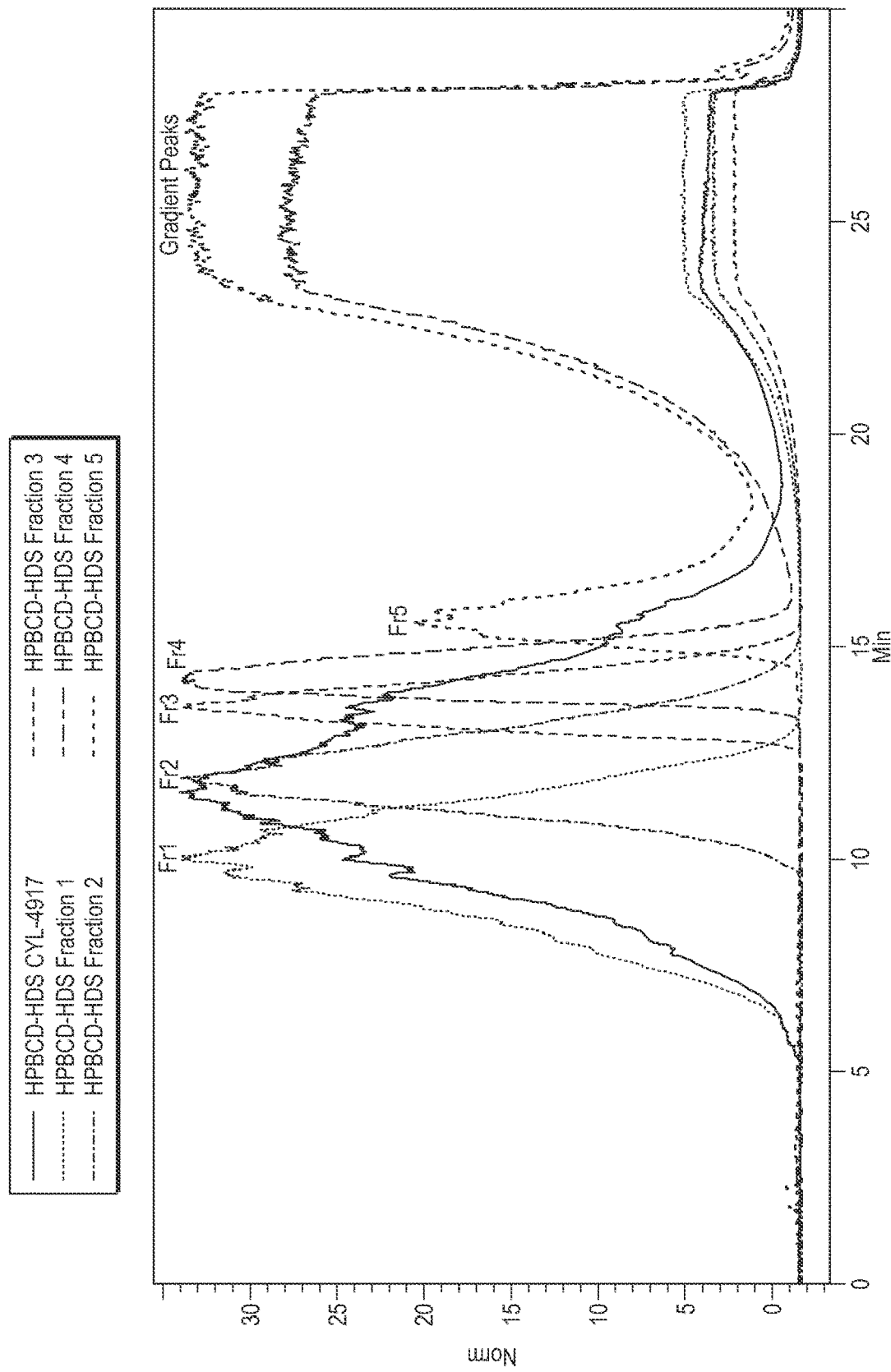
FIG. 31 is an HPLC chromatogram showing the HPLC chromatograms of HDS fractions 1-5 overlaid onto the HPLC chromatogram of the unfractionated mixture of hydroxypropyl-β-cyclodextrins.

Example 1: Fractionation of a Mixture of (2-Hydroxypropyl)-β-Cyclodextrin on a Cholester Column for Structural Analysis An analytical HPLC and semi-preparative HPLC method was developed, which was able to separate (2-hydroxypropyl)-β-cyclodextrin into five sub-fractions (i.e., five unique fractions of the unfractionated starting material). Representative overlaid HPLC-CAD chromatograms using the developed semi-preparative HPLC method with the labelled five fractions is shown in FIG. 31. The method uses a unique reversed phase stationary phase with immobilized, rigid cholesteryl structures and water/methanol gradient elution. Thus, it was anticipated that fractions having lower retention times (i.e., fractions 1-3 eluting first from the column) would have lower affinity toward cholesterol than the fractions with higher retention times (i.e., fractions 4-5, eluting last from the column).

After confirming the identity (molecular weight) of each separated hydroxypropyl-β-cyclodextrin fraction by HPLC-ESI-MS, the analytical method was transferred to the semi-preparative column. Method transfer involved adjustment of the flow rate, injection volume, and sample concentration. Each fraction was collected in 5 mg quantities.

It is important to note that none of the hydroxypropyl-β-cyclodextrin components are UV-active. Therefore, UV/diode array detector (DAD) is not applicable to follow the fractionation process, and the use of destructive detectors (e.g., evaporative light scattering detectors (ELSD) or charged aerosol detectors (CAD)) are necessary to confirm the identity and purity of the fractions. The identity of each isolated fraction was confirmed by comparing the given fraction elution profile with the unfractionated hydroxypropyl-β-cyclodextrin with the analytical method. Molecular weights of the isolated fractions were determined by HPLC-ESI-MS and also by matrix assisted laser desorption ionization time of flight mass spectrometry (MALDI-TOF).

To quantify the degree of substitution (DS) and to gain structural information about the separated sub-fractions, the structure of each fraction was elucidated by using 1 D and 2D NMR experiments.

Materials

The hydroxypropyl-β-cyclodextrin material investigated was a randomly substituted hydroxypropyl-β-cyclodextrin having an average degree of substitution of 7.7 (Cavitron W7 HP7 Pharma).

Analytical HPLC Method

The HPLC instrument used was HPLC-CAD-MS. The column used was a COSMOSIL Cholester colum (4.6ID×150 mm). Eluent channel A was purified water and eluent channel B was purified water:methanol (1:9). The HPLC gradient is described in Table 1 below. The column temperature was 30° C. The injection volume was 40 μL.

TABLE 1

Gradient profile for the analytical HPLC method

| Time (min) | B % | Flow (mL/min) |
|---|---|---|
| 0 | 25 | 0.7 |
| 20 | 90 | |

Stop time: 25 min
Post time: 7 min

Detection was performed using HPLC-CAD-ESI-MS. The HPLC was an Agilent 1260 HPLC equipped with Corona Veo™ CAD, coupled with Agilent G6135B LC/MSD XT with Agilent ESI source. The CAD evaporator temperature was 35° C. and the nitrogen gas pressure was 5 bar. The MS gas temperature was 350° C. and the nebulizer pressure was 60 psi. The MS gas flow was 13.0 L/min. The MS capillary voltage was +4000 V and the fragmentor voltage was 135 V. The MS acquisition was ±Scan 110-3000 m/z. The MS polarity was positive and negative.

A solid sample (combined, evaporated fractions or unfractionated hydroxypropyl-β-cyclodextrin) was dissolved in purified water at a concentration of 10 mg/mL. The collected fractions (liquid sample) from the preparative chromatograph were transferred to an HPLC for injection. The concentration of the chromatographed fractions was around 1 m/m %.

Semi-Preparative HPLC Method

The instrument used for the semi-preparative HPLC method was a HPLC-CAD-MS. The column was a COSMOSIL 15Cholester-PREP column (4.6ID×250 mm; Nacalai Tesque Inc.). The channel A eluent was purified water and the channel B eluent was purified water:methanol (1:9). The HPLC gradient is described in Table 2 below. The column temperature was 30° C. The injection volume was 100 μL.

TABLE 2

Gradient profile for the semi-preparative HPLC method

| Time (min) | B % | Flow (mL/min) |
|---|---|---|
| 0 | 0 | 1.5 |
| 50 | 0 | |
| 55 | 28 | |

Stop time: 60 min
Post time: 8 min

Figure 32:
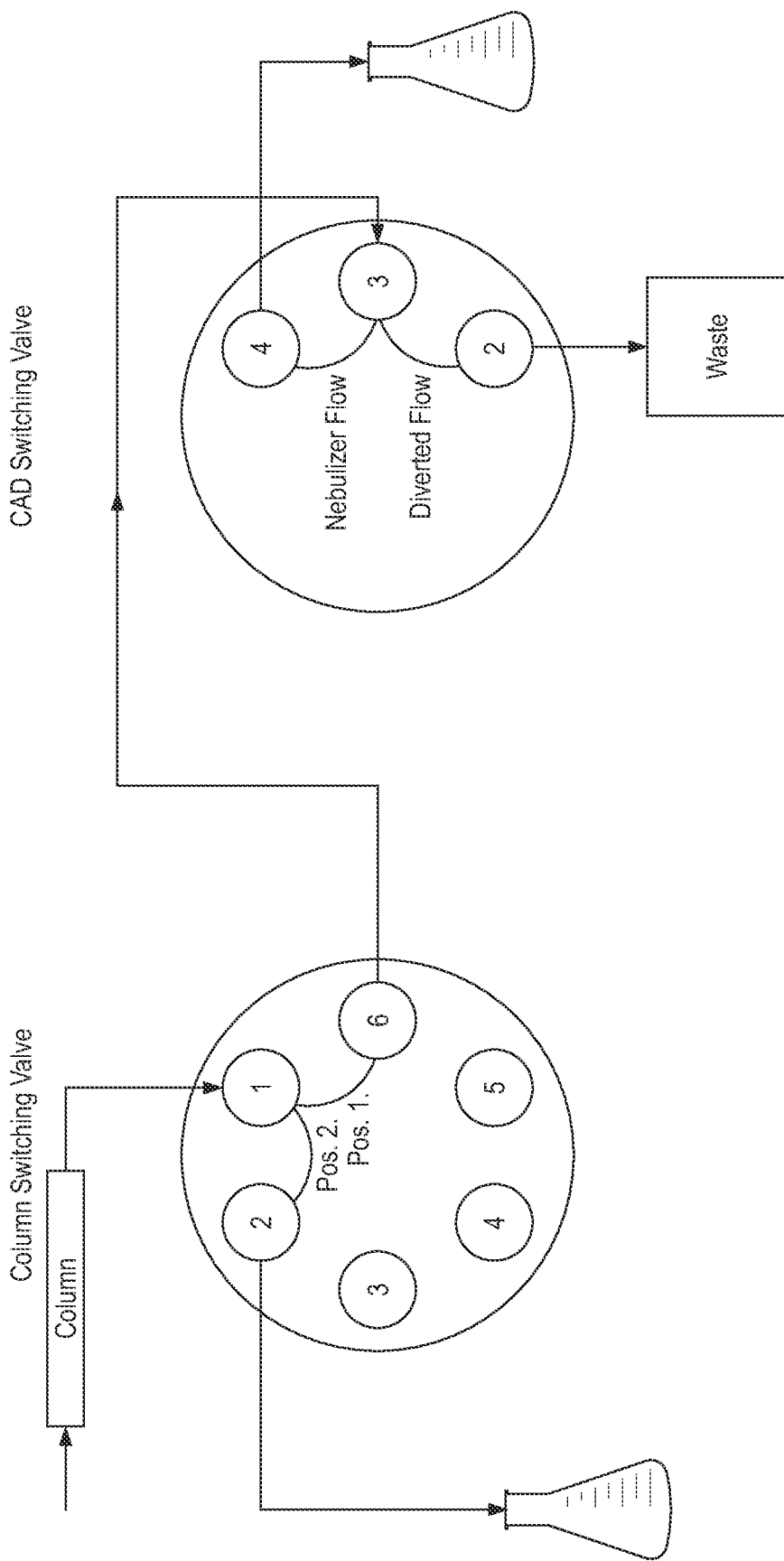
FIG. 32 is a schematic representation of the switching scheme for collecting fractions of hydroxypropyl-β-cyclodextrin.

Detection methods were labeled v01 to v05 and are described in Tables 3 and 4 below. A schematic representation of the semi-preparative HPLC instrument's switching valve connections is shown in FIG. 32. No detection was conducted for v02-v05 because both switching valves were used to collect the eluent.

TABLE 3

Timetables of the switching valve of CAD

| Method label | Time (min) | Event | Parameter | Collected fraction |
|---|---|---|---|---|
| v01 | | set nebulizer flow | on | No fraction collected |
| v02 | 0.01 | set divert | on | Fraction 5 |
| | 54.50 | set divert | off | |
| | 57.00 | set divert | on | |
| v03 | 0.01 | set divert | or | Fraction 5 |
| | 54.50 | set divert | off | |
| | 57.00 | set divert | on | |
| v04 | 0.01 | set divert | on | Fraction 1 |
| | 12.50 | set divert | off | |
| | 32.50 | set divert | on | |
| v05 | 0.01 | set divert | on | Fraction 2 |
| | 32.50 | set divert | off | |
| | 46.00 | set divert | on | |

TABLE 4

Timetables of the switching valve of the column thermostat

| Method label | Time (min) | Event | Parameter | Collected fraction |
|---|---|---|---|---|
| v01 | initial setting | — | Col. at Pos. 1 | No fraction collected |
| v02 | initial setting | — | Col. at Pos. 1 | Fraction 4 |
| | 52.10 | Change Valve Pos. | Col. at Pos. 2 | |
| | 54.50 | Change Valve Pos. | Col. at Pos. 1 | |
| v03 | initial setting | — | Col. at Pos. 1 | Fraction 3 |
| | 46.00 | Change Valve Pos. | Col. at Pos. 2 | |
| | 53.50 | Change Valve Pos. | Col. at Pos. 1 | |
| v04 | initial setting | — | Col. at Pos. 1 | Fraction 3 |
| | 46.00 | Change Valve Pos. | Col. at Pos. 2 | |
| | 53.50 | Change Valve Pos. | Col. at Pos. 1 | |
| v05 | initial setting | — | Col. at Pos. 1 | Fraction 2 |

To prepare the sample, solid material is dissolved in purified water at a concentration of 100 mg/mL.

Figure 33:
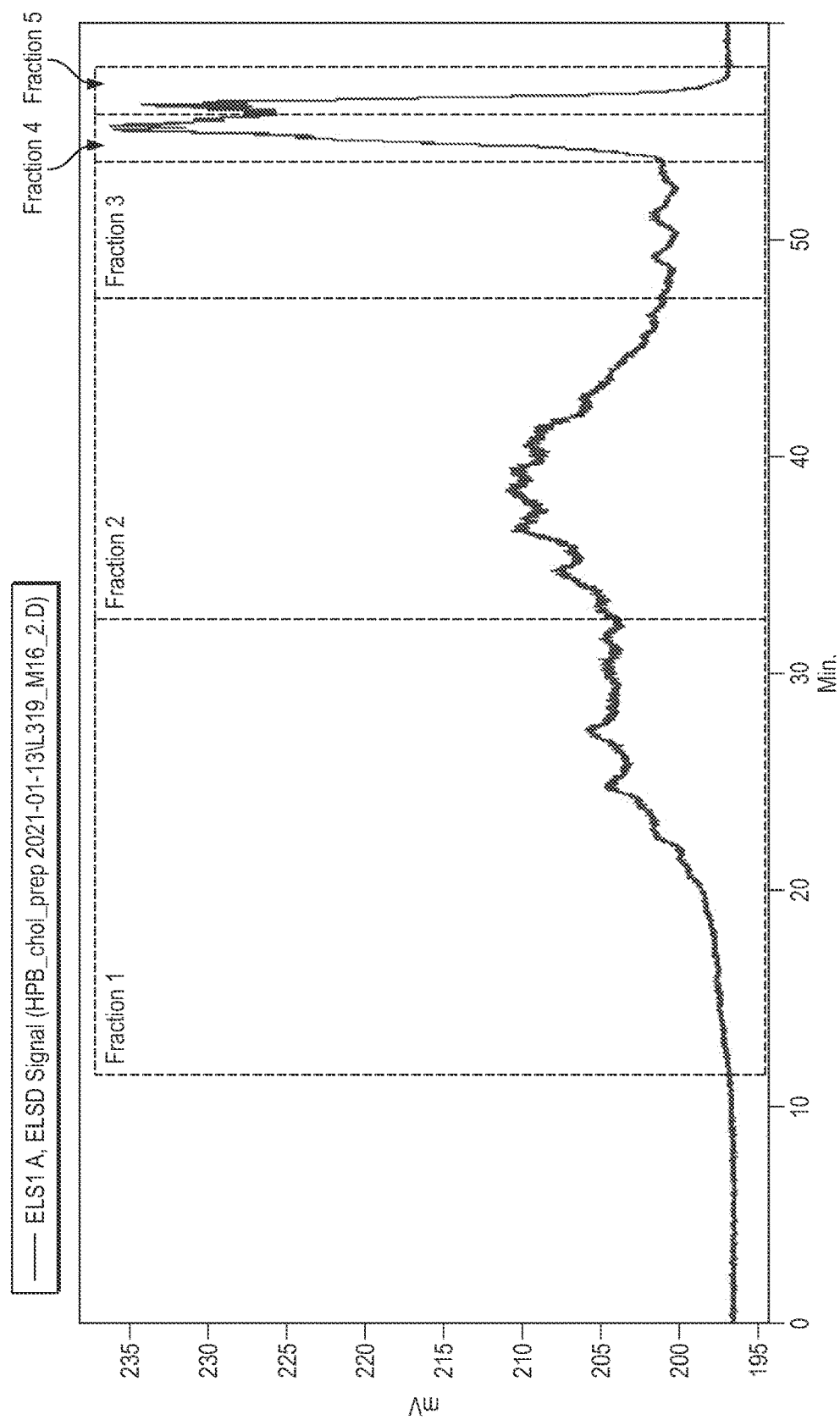
FIG. 33 is an HPLC chromatogram of the mixture of hydroxypropyl-β-cyclodextrins, wherein no fraction was collected. The chromatogram shows when each fraction elutes from the HPLC Cholester column.

If no fraction was collected, the chromatography run and the profile of the sample could be directly monitored with the connected CAD or ELSD detector. An exemplary chromatogram wherein no fraction was collected is shown in FIG. 33.

NMR Methods $^1$H, $^{13}$C, 2D $^1$H-$^1$H (COSY) and 2D $^1$H-$^{13}$C (DEPT-ed HSQC) NMR spectra were recorded on a Bruker BioSpin GmbH 300 mHz, equipped with a 5 mm PABBI 1H/D-BB Z-GRID Z-GRD 59201/0029 probe. Standard pulse sequences and processing routines available in Vnmr J 3.2C/Chempack 5.1 were used, using residual solvent signals (HDO at 4.79 ppm) as an internal reference. The studied samples were dissolved in D$_2$O (5 mg/0.7 mL) for the structure elucidation. The FID signals were recorded at 298 K with at least 16 scans to obtain a spectral window comprised, at least, between 0 ppm and +10 ppm. All spectra were processed using MestReNova v.9.0.1. Automatic baseline correction (polynomial fit) and auto phasing were performed before integration. For the quantitative NMR measurements (quantification of DS) the spectra were processed and evaluated as described in the European Pharmacopeial 10.0 Monograph of Hydroxypropylbetadex.

MALDI-TOF-MS Method

MALDI-TOF-MS spectra were recorded on a Bruker Microflex LRF system. The Microflex LRF operated in positive ion mode using the linear detector. Ion generation was achieved using a 60 Hz N$_2$-Cartridge-Laser including variable power attenuator and UV optics. The laser operated at 337 nm and 2,5-dihydroxybenzoic acid (DHB) was used as matrix.

The matrix stock solution was prepared by measuring 100 mg DHB into a 5 mL volumetric flask and filling up to the calibration mark with 50% ethanol:purified water. The sample stock solution was prepared by measuring 2 mg hydroxypropyl-β-cyclodextrin into the vial and dissolving in 1 mL of purified water. Ten μL of the sample stock solution, 25 μL of the matrix stock solution, and 65 μL of 50% ethanol:purified water were mixed, then 2 μL of the resulting solution was applied to the sample plate and allowed to dry at room temperature.

Results

By applying the semi-preparative HPLC method in loops, isolation of 5 different hydroxypropyl-β-cyclodextrin was achieved in 5 mg scale. The isolated fractions were remeasured by HPLC-CAD and HPLC-ESI-MS on cholester column, by 1 D and 2D NMR experiments, and by MALDI-TOF-MS in order to quantify DS values and to gain structural information about the separated fractions.

HPLC-CAD/MS Analysis

Figure 9:
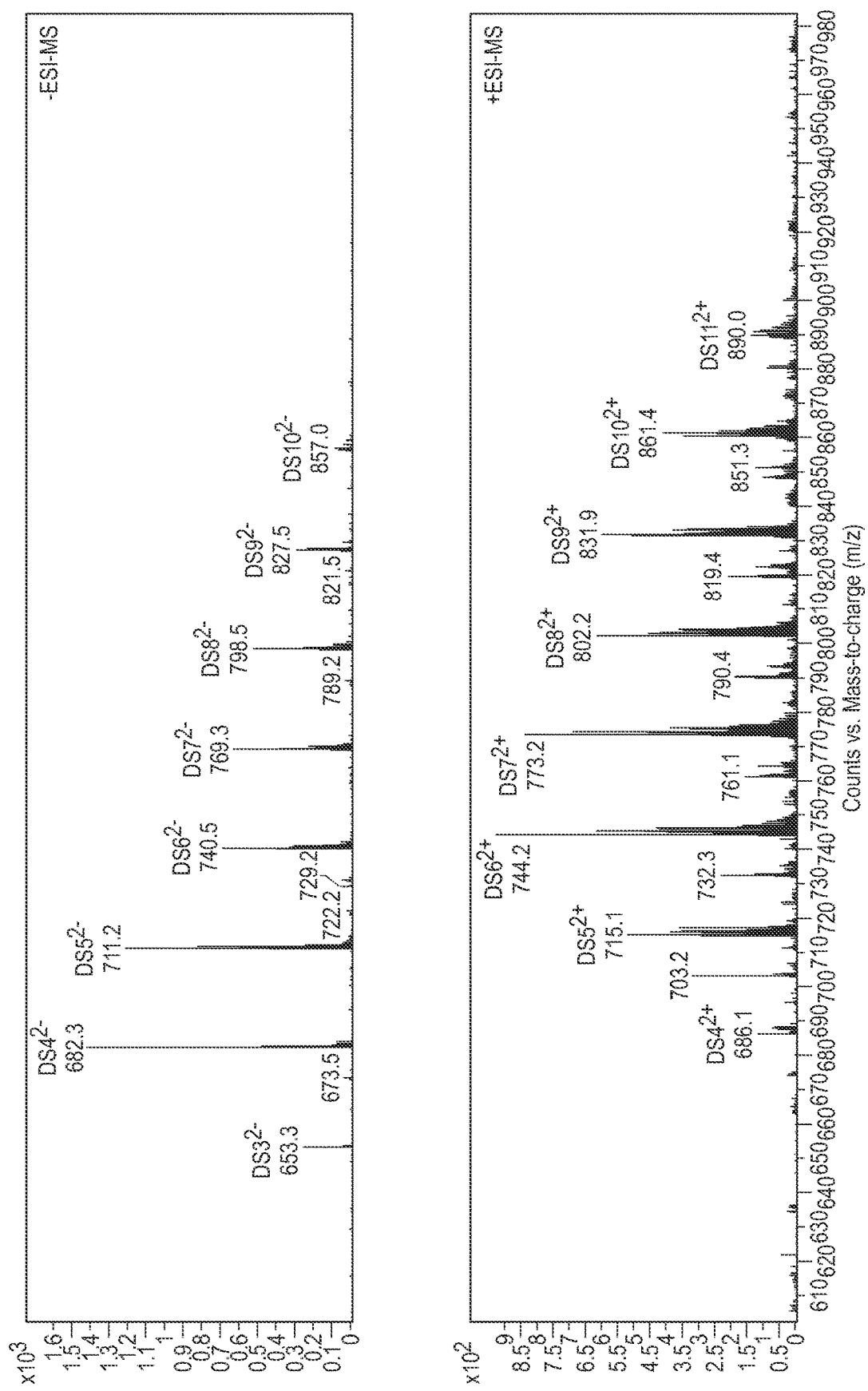
FIG. 9 is an ESI-MS spectrum of the first HDS fraction of a mixture of hydroxypropyl-β-cyclodextrins of the present disclosure.

Fraction 1: HPLC-CAD fingerprint analysis of Fraction 1 compared to unfractionated hydroxypropyl-β-cyclodextrin indicates that Fraction 1 contains the early eluting components of hydroxypropyl-β-cyclodextrin, with a mean retention time at 10.070 minutes. The HPLC-CAD chromatogram of Fraction 1 is shown in FIG. 8. The ESI-MS spectra of Fraction 1 both in negative and positive mode are shown in FIG. 9.

In both ESI-MS spectra, the double charged molecular ions (without any adducts) may be detected. Interestingly in negative mode, the intensities are in a 1-fold higher range ($\times 10^3$ vs. $\times 10^2$) than in positive mode. For this reason the negative spectrum is more reliable for molecular weight determination of the components. Nevertheless, as the components might differ in ionization properties, none of the ESI-MS spectra is recommended for the average molecular weight determination, these serve only as an identification for the components.

In negative mode, the most intense peak has an m/z value of (M−2)/2=682.3. This value corresponds to the structure with formula weight 1366.6 g/mol, which is the hydroxypropyl-β-cyclodextrin with 4 hydroxypropyl side chains (DS-4). The rest of the peak follows the 29 m/z difference pattern—therefore, these components may also be assigned to hydroxypropyl-β-cyclodextrin components with increasing or decreasing degree of hydroxypropylation. In negative mode, the detected DS range is 3-10.

In positive mode, the most intensive peak has an m/z value of (M+2)/2=744.2. This value corresponds to the structure with formula weight 1486.2 g/mol, which is the hydroxypropyl-β-cyclodextrin with 6 hydroxypropyl side chains (DS-6). In positive mode, the detected DS range is slightly shifted toward higher DS values; here, 4-11.

The different intensities of the peaks and the different detected DS ranges between the two modes of detections may be explained by the different protonation/deprotonation characteristics (e.g., different pKa profiles) of the components under the used detection mode. Based on the higher intensities observed in negative ionization mode, components in Fraction 1 are more prone to lose than to gain a proton.

Figure 14:
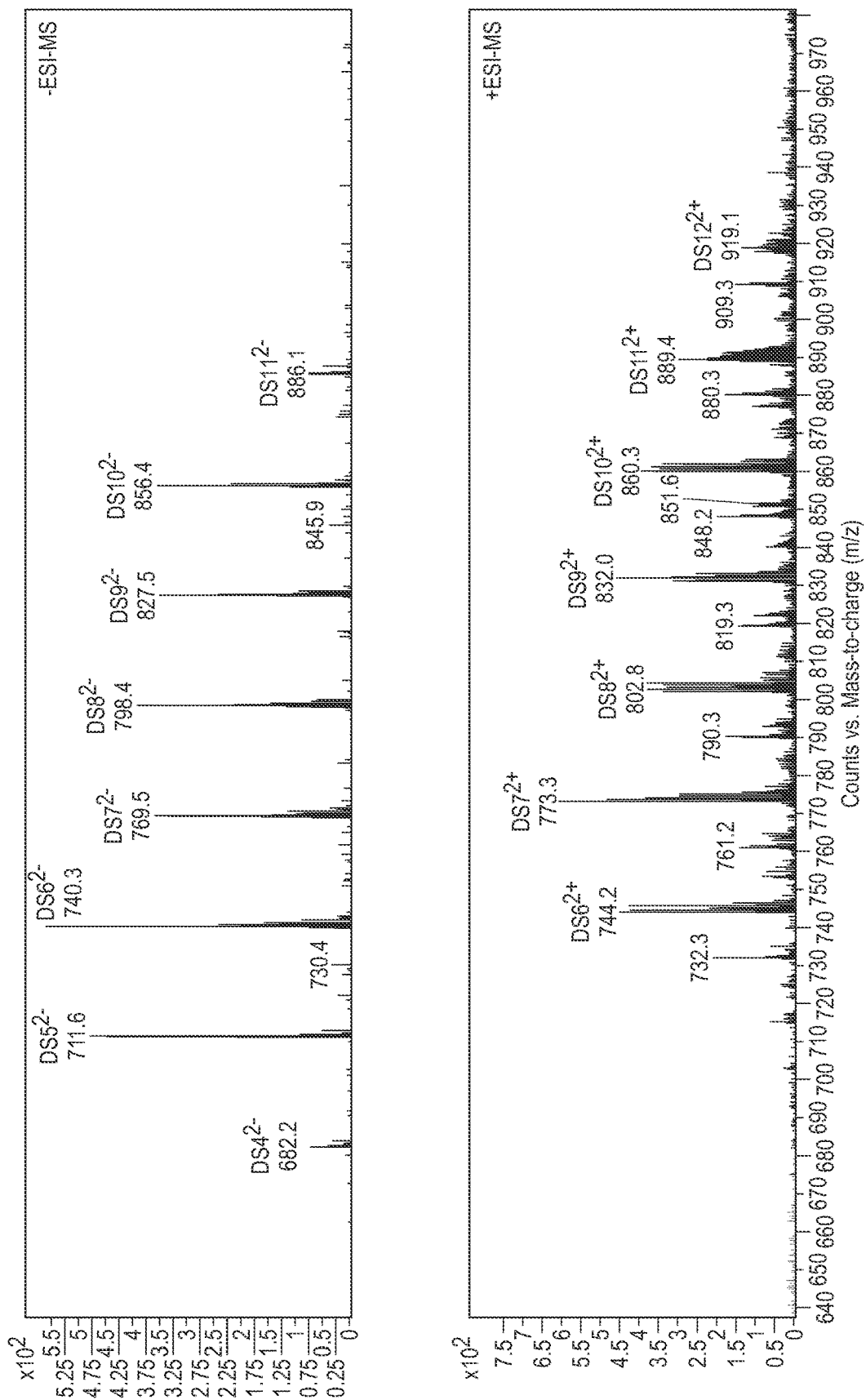
FIG. 14 is an ESI-MS spectrum of the second HDS fraction of a mixture of hydroxypropyl-β-cyclodextrins of the present disclosure.

Fraction 2: HPLC-CAD fingerprint analysis of fraction 2 compared to unfractionated hydroxypropyl-β-cyclodextrin indicates that Fraction 2 has a narrower isomer/DS distribution than unfractionated hydroxypropyl-β-cyclodextrin, and that components of Fraction 2 are identical to the most abundant components in unfractionated hydroxypropyl-β-cyclodextrin. Consequently, the DS value of Fraction 2 must also resemble the DS value of unfractionated hydroxypropyl-β-cyclodextrin. Fraction 2 has a mean retention time at the early eluting components of the unfractionated hydroxypropyl-β-cyclodextrin minute, with a mean retention time at 11.911 minutes. The HPLC-CAD chromatogram of Fraction 2 is shown in FIG. 13. The ESI-MS spectra of Fraction 2 both in negative and positive mode are shown in FIG. 14.

In negative mode, the most intensive peak has an m/z value of (M−2)/2=740.3. This value corresponds to the structure with formula weight: 1483.46 g/mol, which is the hydroxypropyl-β-cyclodextrin with 6 hydroxypropyl side chains (DS-6). The rest of the peak follows the 29 m/z difference pattern—therefore these components may be also assigned to the hydroxypropyl-β-cyclodextrin with increasing or decreasing degree of hydroxypropylation. In negative mode, the detected DS range is 4-11.

In positive mode, the most intensive peak has an m/z value of (M+2)/2=773.3. This value corresponds to the structure with formula weight 1541.54 g/mol, which is the hydroxypropyl-β-cyclodextrin with 7 hydroxypropyl side chains (DS-7). In positive mode, the detected DS range was 6-12.

Figure 19:
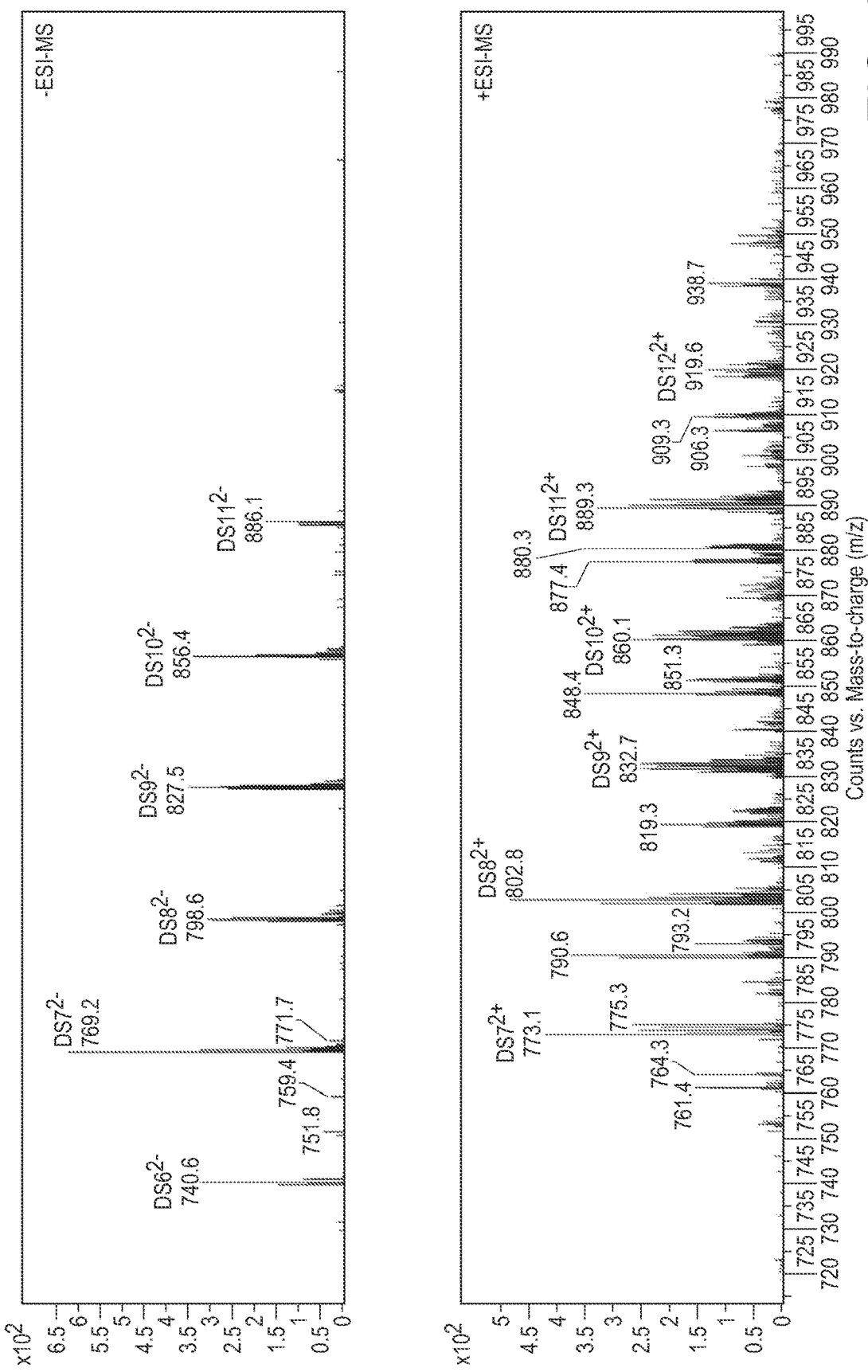
FIG. 19 is an ESI-MS spectrum of the third HDS fraction of a mixture of hydroxypropyl-β-cyclodextrins of the present disclosure.

Fraction 3: The HPLC-CAD chromatogram of Fraction 3 is shown in FIG. 18. The mean retention time of Fraction 3, which may be used for identification of the fraction, was 13.539 minutes. The ESI-MS spectra of Fraction 3 both in negative and positive mode are shown in FIG. 19.

In negative mode the most intensive peak had an m/z value of (M−2)/2=769.2. This value corresponds to the structure with formula weight 1541.54 g/mol, which is the hydroxypropyl-β-cyclodextrin with 7 hydroxypropyl side chains (DS-7). the rest of the peaks follow the 29 m/z difference pattern; therefore, these components may be also assigned to the hydroxypropyl-β-cyclodextrin components with increasing or decreasing degree of hydroxypropylation. In negative mode, the DS range is 6-11.

In positive mode, the most intensive peak has an m/z value of (M+2)/2=802.8. This value corresponds to the structure with formula weight 1599.62 g/mol, which is the hydroxypropyl-β-cyclodextrin with 8 hydroxypropyl side chains (DS-8). In positive mode, the DS range is 7-12.

Figure 24:
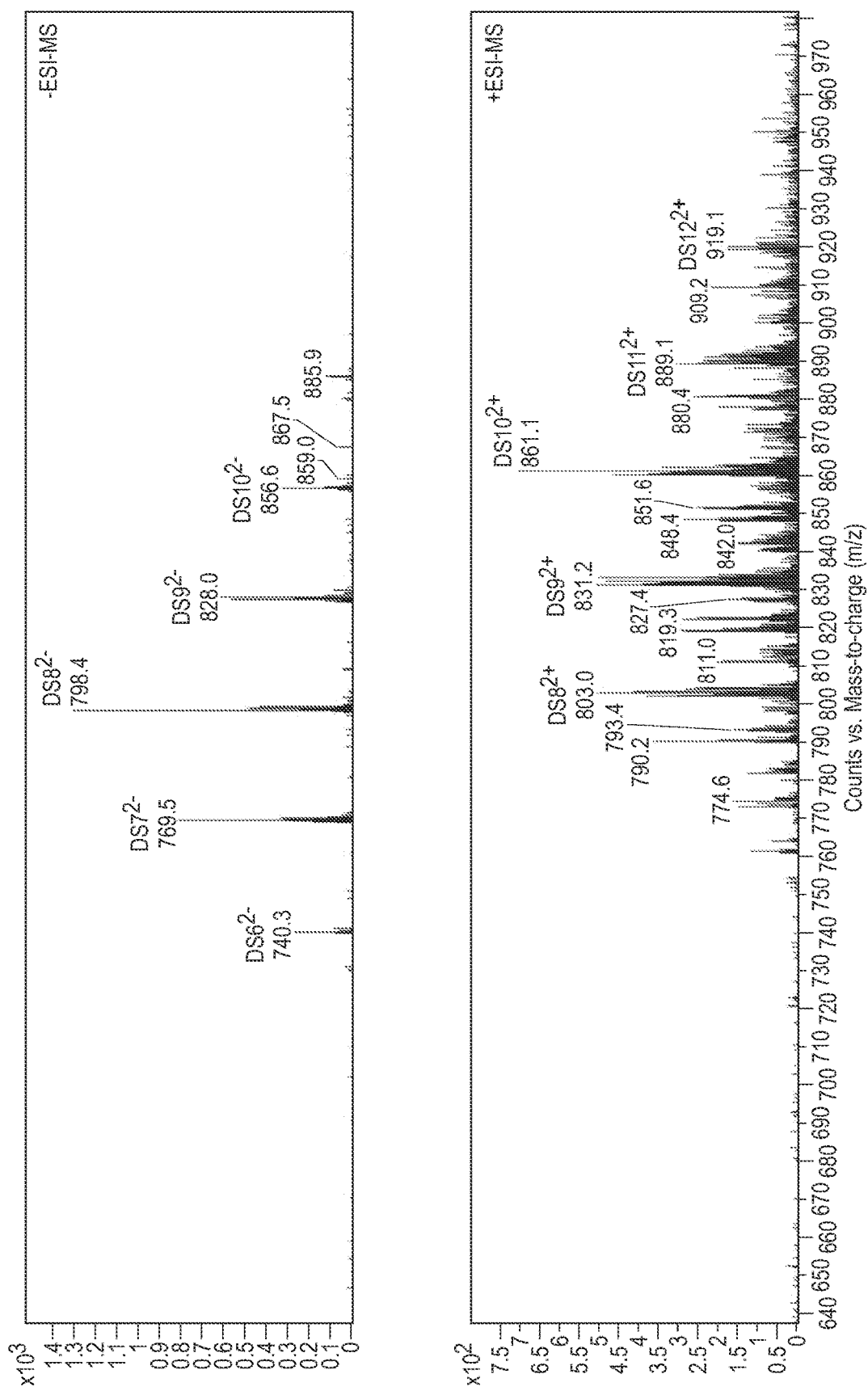
FIG. 24 is an ESI-MS spectrum of the fourth HDS fraction of a mixture of hydroxypropyl-β-cyclodextrins of the present disclosure.

Fraction 4: The HPLC-CAD chromatogram of Fraction 4 is shown in FIG. 23. The mean retention time of Fraction 4, which may be used for identification of the fraction, was 14.267 minutes. Similar to Fraction 3, Fraction 4 had a very narrow component distribution profile, giving a sharp, easily detectable peak in the chromatogram. The ESI-MS spectra of Fraction 3 both in negative and positive mode are shown in FIG. 24.

In negative mode, the most intensive peak has an m/z value of (M−2)/2=798.4. This value corresponds to the structure with formula weight: 1599.62 g/mol, which is the hydroxypropyl-β-cyclodextrin with 8 hydroxypropyl side chains (DS-8). The rest of the peaks follow the 29 m/z difference pattern; therefore, these components may be also assigned to the hydroxypropyl-β-cyclodextrin components with increasing or decreasing degree of hydroxypropylation. In negative mode, the DS range is 6-10.

In positive mode, the most intensive peak has an m/z value of (M+2)/2=861.1. This value corresponds to the structure with formula weight 1715.62 g/mol, which is the hydroxypropyl-β-cyclodextrin with 10 hydroxypropyl side chains (DS-10). In positive mode the DS range is 8-12.

Figure 29:
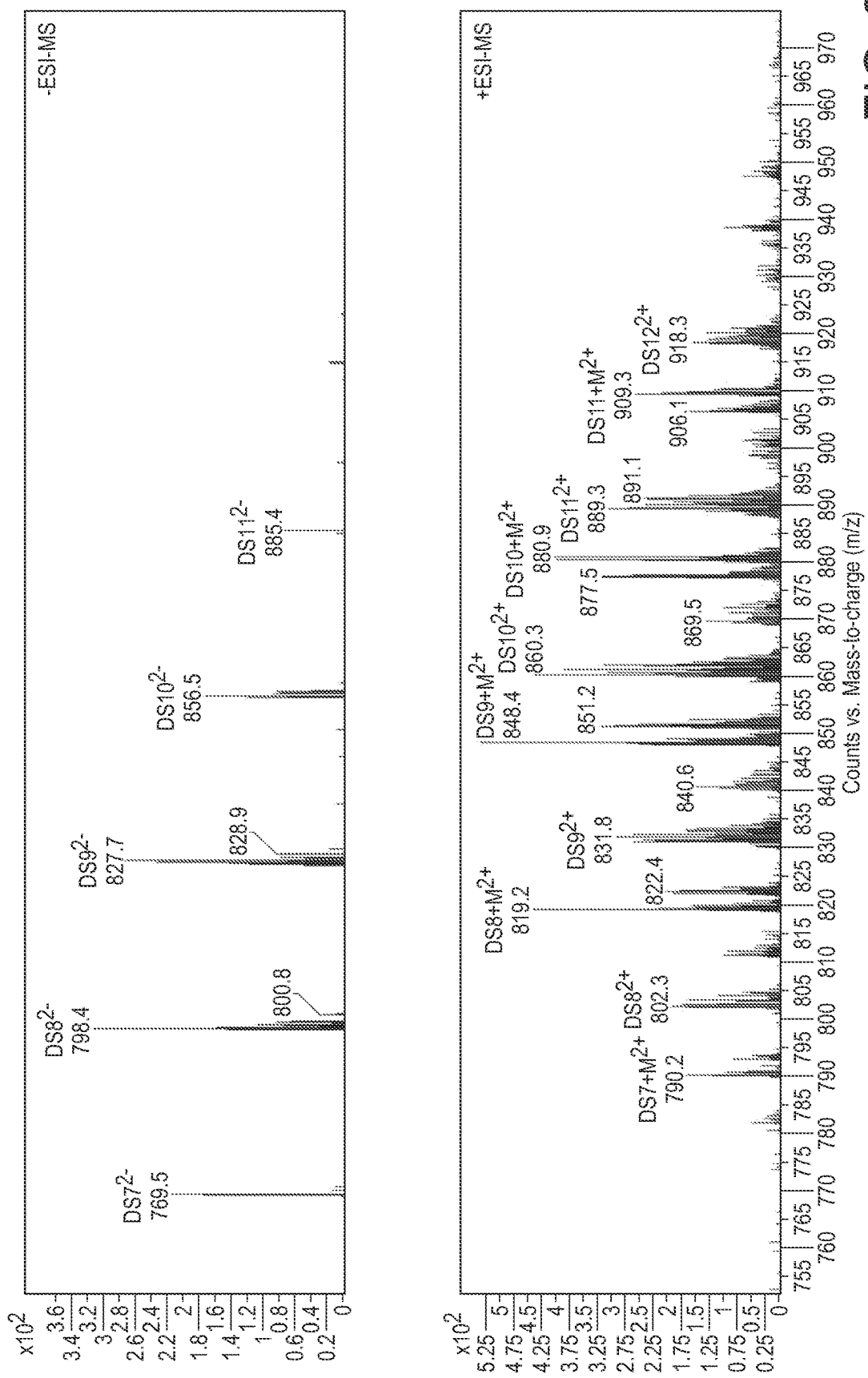
FIG. 29 is an ESI-MS spectrum of the fifth HDS fraction of a mixture of hydroxypropyl-β-cyclodextrins of the present disclosure.

Fraction 5: The HPLC-CAD chromatogram of Fraction 5 is shown in FIG. 28. The mean retention time of Fraction 5, which may be used for identification of the fraction, was 15.428 minutes. Similar to Fraction 3, Fraction 4, and Fraction 5 had a very narrow component distribution profile, giving a sharp, easily detectable peak in the chromatogram. Fraction 5 corresponds to the latest eluting fragments in the unfractionated hydroxypropyl-β-cyclodextrin molecules; therefore, it may be anticipated that Fraction 5 has the highest cholesterol affinity. The ESI-MS spectra of Fraction 3 both in negative and positive mode are shown in FIG. 29.

In negative mode, the most intensive peak has an m/z value of (M−2)/2=798.4. This value corresponds to the structure with formula weight: 1599.62 g/mol, which is the hydroxypropyl-β-cyclodextrin with 8 hydroxypropyl side chains (DS-8). The rest of the peaks follow the 29 m/z difference pattern; therefore, these components may also be assigned to hydroxypropyl-β-cyclodextrin components with increasing or decreasing degree of hydroxypropylation. In negative mode, the DS range is 7-11.

In positive mode, the most intensive peak has an m/z value of (M+2)/2=848.4. This value corresponds to the double charged adduct of hydroxypropyl-β-cyclodextrin with 9 hydroxypropyl side chains (DS-9). In positive mode, the DS range is 7-12.

Moreover, in the positive ESI-MS spectrum of Fraction 5, the adducts [(M+adduct ion)$^{2+}$/2] of all of the components gave more intense peaks than the double charged mother ions [(M+2H)$^{2+}$/2]. Without being bound by theory, it is speculated that Fraction 5 has a specific chelating property towards a selected ion. Based on the m/z differences between (M+adduct ion)$^{2+}$/2 and (M+2H)$^{2+}$/2, this ion may be Ca$^{2+}$ forming the M+Ca$^{2+}$ adducts or K$^+$ forming (M+H$^+$+K$^+$)$^{2+}$ adduct. this phenomenon was also apparent in the +ESI-MS spectrum of Fraction 3, although in that case the adduct ions have much lower intensities compared to the double charged molecular ions.

Determination of the Molecular Weight Distributions by MALDI-TOF-MS

Unfractionated: In FIG. 1, the MALDI-TOF spectrum of the unfractionated hydroxypropyl-β-cyclodextrin sample is shown. The weights distribute around the DS-8 isomer and the weights profile almost assumes a Gaussian shape of a randomly substituted cyclodextrin derivative. Unfractionated hydroxypropyl-β-cyclodextrin is a composite material in which DS-8 is the major representative.

Figure 10:
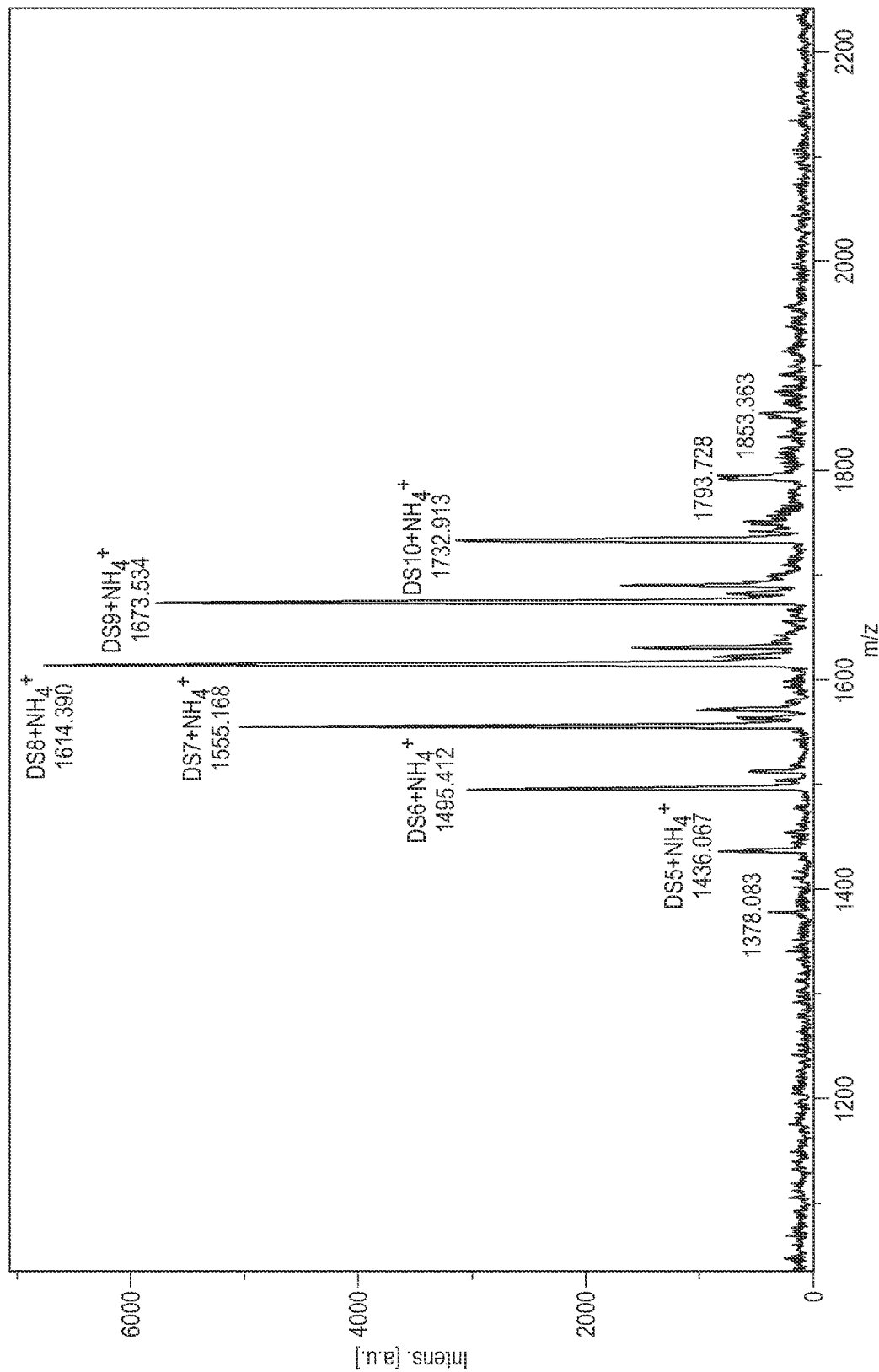
FIG. 10 is a MALDI-TOF spectrum of the first HDS fraction of a mixture of hydroxypropyl-β-cyclodextrins of the present disclosure.

Fraction 1: In FIG. 10, the MALDI-TOF spectrum of the Fraction 1 sample is shown. The weights distribute around the DS-8 isomer and the weights profile almost assumes a Gaussian shape of a randomly substituted cyclodextrin derivative. Fraction 1 is a composite material in which DS-8 is the major representative.

Figure 15:
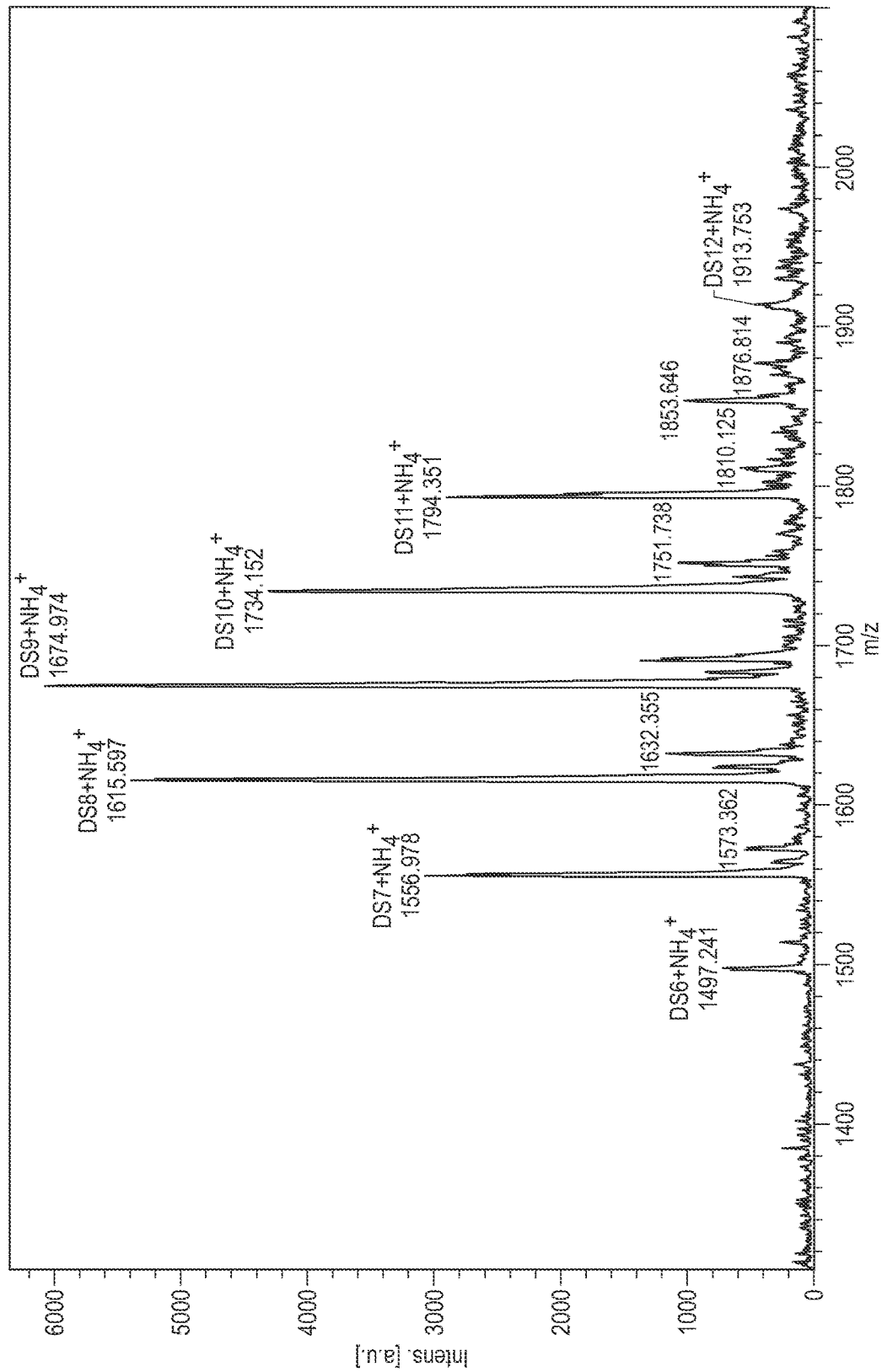
FIG. 15 is a MALDI-TOF spectrum of the second HDS fraction of a mixture of hydroxypropyl-β-cyclodextrins of the present disclosure.

Fraction 2: In FIG. 15, the MALDI-TOF spectrum of the Fraction 2 sample is shown. The weights distribute around the DS-9 isomer and the weights profile almost assumes a Gaussian shape of a randomly substituted cyclodextrin derivative. Fraction 2 is a composite material in which DS-9 is the major representative.

Figure 20:
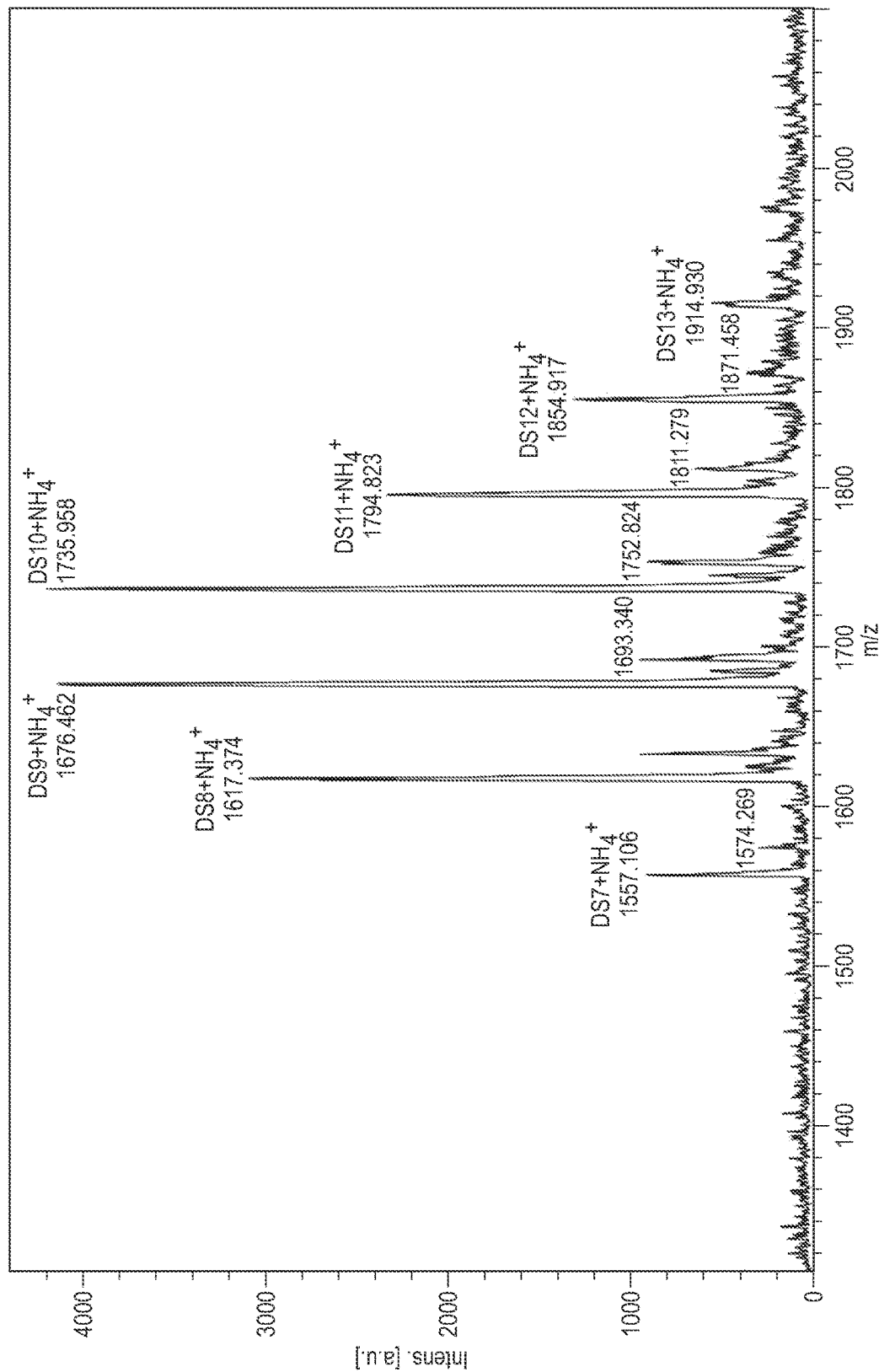
FIG. 20 is a MALDI-TOF spectrum of the third HDS fraction of a mixture of hydroxypropyl-β-cyclodextrins of the present disclosure.

Fraction 3: In FIG. 20, the MALDI-TOF spectrum of the Fraction 3 sample is shown. The weights distribute around the DS-9 and DS-10 isomers and the weights profile almost assumes a Gaussian shape of a randomly substituted cyclodextrin derivative. Fraction 3 is a composite material in which DS-9 and DS-10 are the major representatives.

Figure 25:
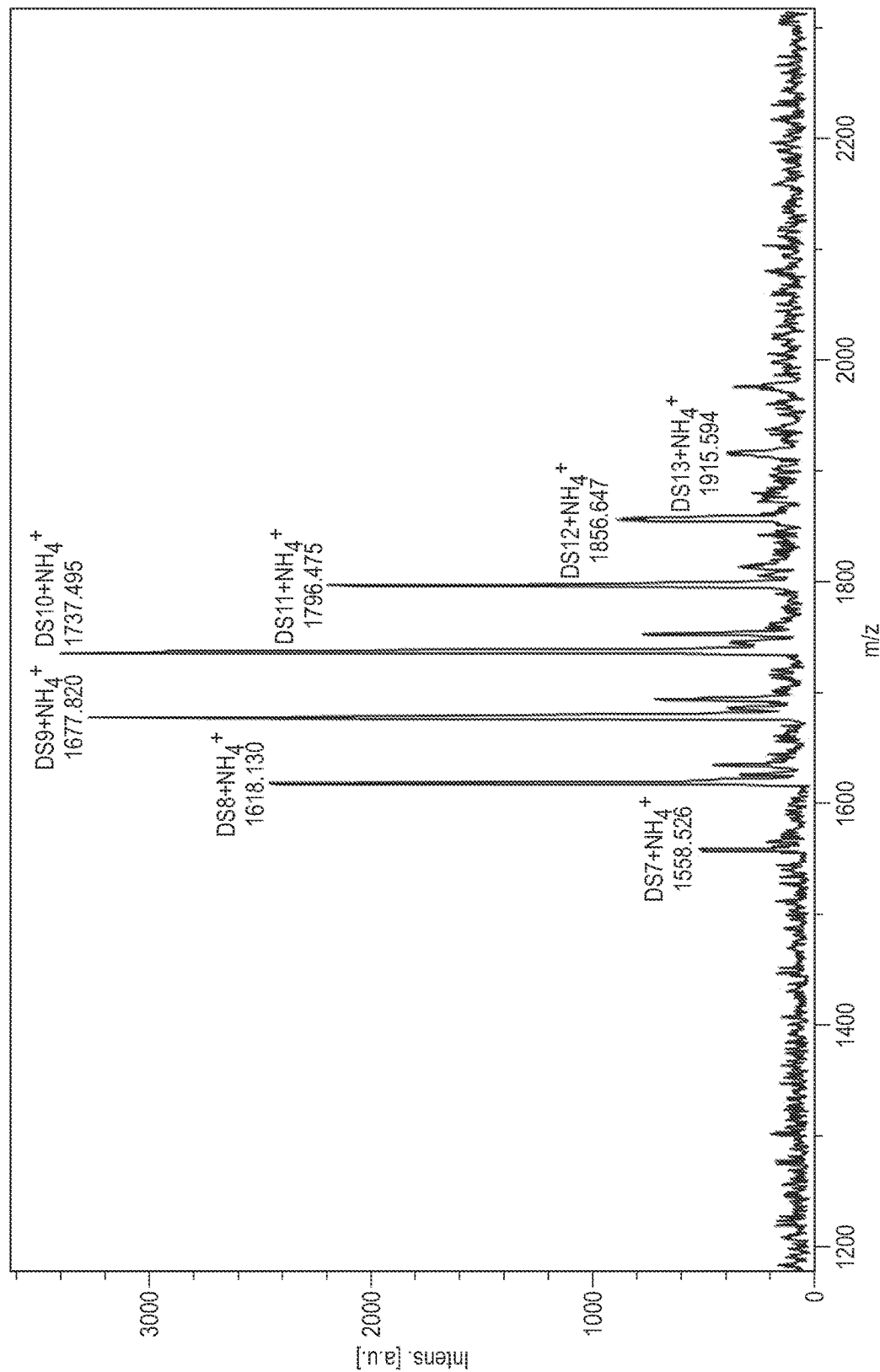
FIG. 25 is a MALDI-TOF spectrum of the fourth HDS fraction of a mixture of hydroxypropyl-β-cyclodextrins of the present disclosure.

Fraction 4: In FIG. 25, the MALDI-TOF spectrum of the Fraction 4 sample is shown. The weights distribute around the DS-9 and DS-10 isomers and the weights profile almost assumes a Gaussian shape of a randomly substituted cyclodextrin derivative. Fraction 4 is a composite material in which DS-9 and DS-10 are the major representatives.

Figure 30:
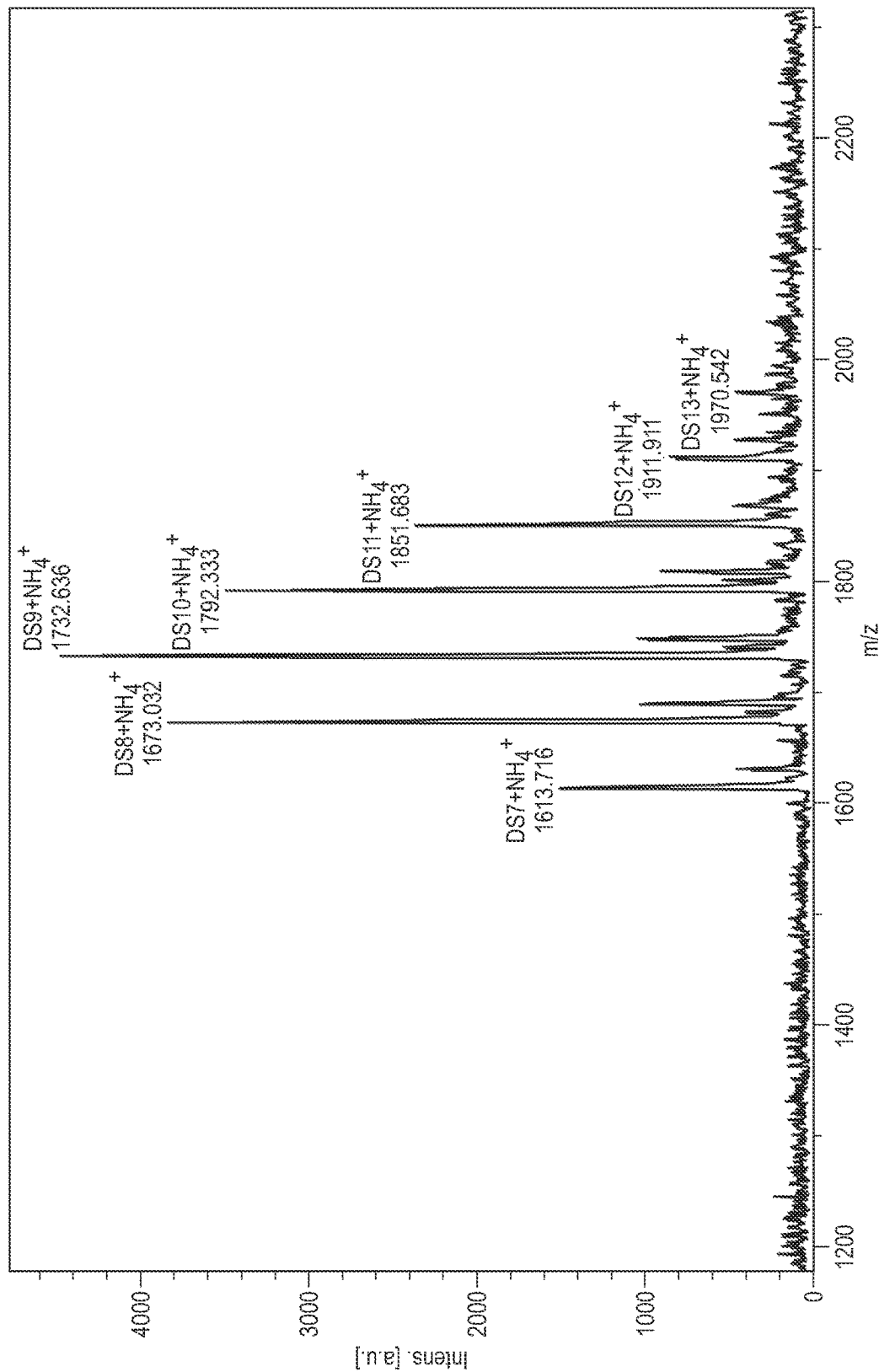
FIG. 30 is a MALDI-TOF spectrum of the fifth HDS fraction of a mixture of hydroxypropyl-β-cyclodextrins of the present disclosure.

Fraction 5: In FIG. 30, the MALDI-TOF spectrum of the Fraction 5 sample is shown. The weights distribute around the DS-9 isomer and the weights profile almost assumes a Gaussian shape of a randomly substituted cyclodextrin derivative. Fraction 5 is a composite material in which DS-10 is the major representative.

Table 5 provides the data obtained by integration of the MALDI spectrum. The spectrum was evaluated by collecting the peak-areas of the assigned DS+Na$^+$ adducts and by calculating the corresponding area percentage values. It may be stated that in Fraction 1 the most abundant isomer is DS-8, in Fractions 2 and 3 the most abundant isomer is DS-9, and in Fractions 4 and 5 the most abundant isomer is DS-10. Although the starting material used for the fractionation contained the DS-4 isomer, this has been, most probably, removed during the fractionation process, as it may not be detected in any of the fractions. Also, while the starting material did not contain any detectable DS-14 isomer, this is clearly present in Fractions 4 and 5.

TABLE 5

% Area of each isomer of hydroxypropyl-β-cyclodextrin
Area %

|  | DS4 | DS5 | DS6 | DS7 | DS8 | DS9 | DS10 | DS11 | DS12 | DS13 | DS14 |
|---|---|---|---|---|---|---|---|---|---|---|---|
| Unfractionated | 0.73 | 3.49 | 10.66 | 24.10 | 26.43 | 18.09 | 9.39 | 4.58 | 1.84 | 0.70 | 0.00 |
| Fraction 1 | 0.00 | 2.83 | 10.64 | 19.30 | 29.30 | 25.30 | 14.30 | 0.00 | 0.00 | 0.00 | 0.00 |
| Fraction 2 | 0.00 | 0.00 | 2.91 | 10.93 | 22.52 | 26.42 | 20.35 | 12.02 | 4.85 | 0.00 | 0.00 |
| Fraction 3 | 0.00 | 0.00 | 0.00 | 3.92 | 18.65 | 25.45 | 22.37 | 17.41 | 8.01 | 4.20 | 0.00 |
| Fraction 4 | 0.00 | 0.00 | 0.00 | 3.16 | 16.44 | 25.24 | 25.52 | 15.10 | 10.03 | 4.50 | 2.67 |
| Fraction 5 | 0.00 | 0.00 | 0.00 | 0.00 | 8.53 | 21.33 | 26.58 | 20.90 | 13.31 | 6.74 | 2.60 |

Figure 34A:
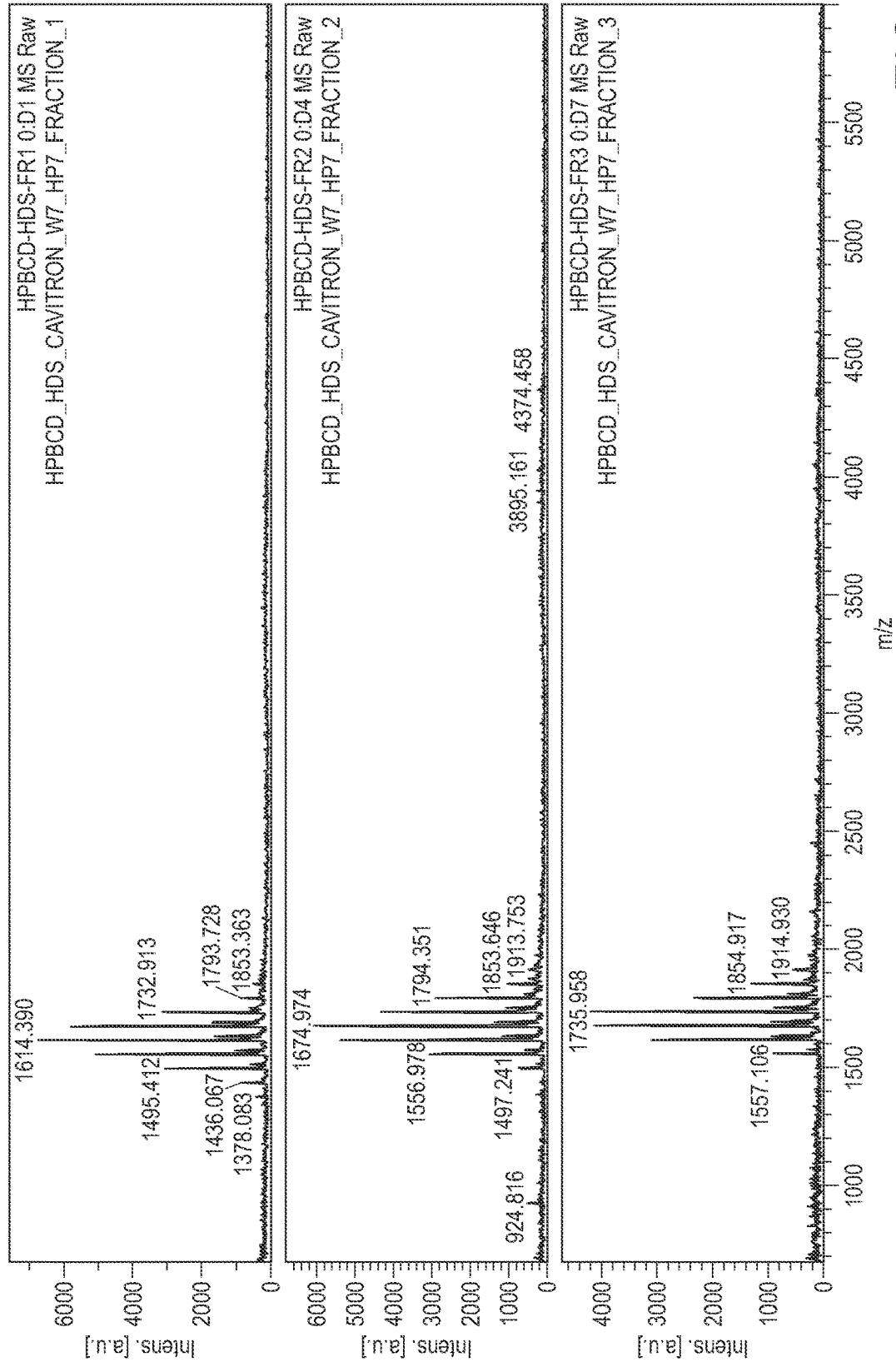
FIGS. 34A-34B shows overlaid MALDI-TOF spectra for HDS fractions 1-5.
Figure 34B:
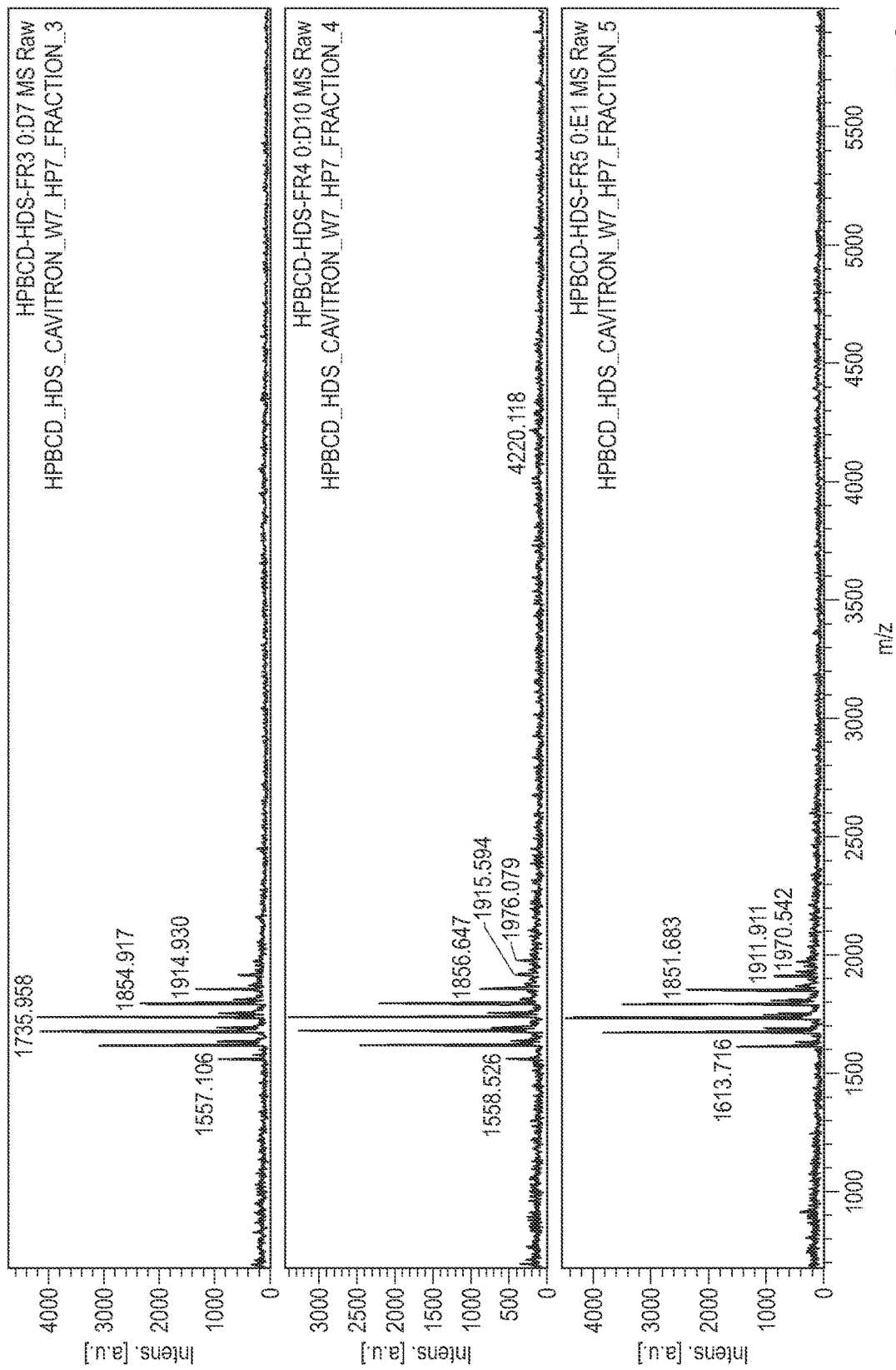

Another difference which maybe immediately spotted by looking at the numeric values or at the overlaid spectra shown in FIGS. 34A-34B is the presence or absence of the DS-5 and DS-6 isomers. Fractions 3-5 lack DS-5 and DS-6 isomers, whereas Fractions 1-2 contain these isomers.

Although MALDI-TOF-MS gives fast and reliable results about the DS distribution, it does not give the necessary information needed to distinguish between the early eluting Fractions 1 and 2 or the later eluting Fractions 3-5, as they have nearly identical MALDI-TOF-MS spectra. Besides these, no other differences may be found when the DS distribution profiles of the five fractions are compared. Fractions 3-5 have almost identical profiles, yet they have substantially different elution profiles on Cholesterol columns. This contradicts previous theories, stating that the mechanism of the hydroxypropyl-β-cyclodextrin fractionation is driven only by the DS value. The retention time of the fractions is likely a function of another characteristic, such as the pattern of substitution (PS).

PS (i.e., the regioisomeric profile of a randomly substituted cyclodextrin) is a property which determines how the substituents are positioned on the cyclodextrin ring, and what is the ratio between cyclodextrins having substituted and unsubstituted 2-O—, 3-O—, and 6-O— positions. For hydroxypropyl-β-cyclodextrin, a qualitative answer is provided by 2D DEPT-ed HSQC NMR experiments.

NMR Structure Elucidation of the Fractions

As unfractionated hydroxypropyl-β-cyclodextrin is not a single chemical entity, but a randomly substituted derivative, it comprises a mixture of isomers differing in the DS and PS, which has a consequence of broad, remarkably overlapping ¹H NMR signals. The inconvenience of the same resonances of side chain atoms (α and β) with the core region (protons of the glucopyranose unit besides the protons of the anomers) also arises, making it difficult to distinguish the corresponding correlations and therefore to determine the locations of the substituents.

Figure 2:
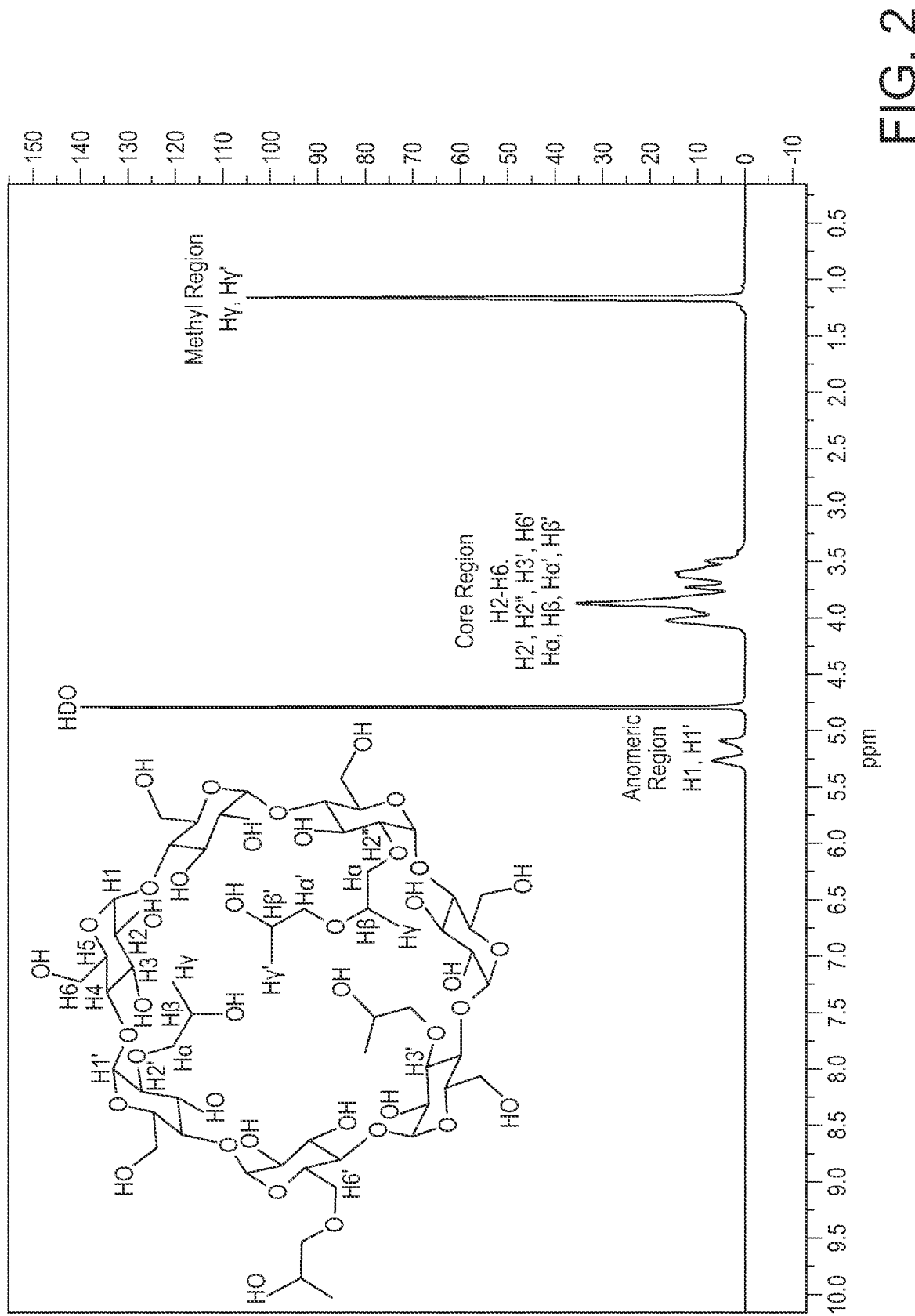
FIG. 2 is a ¹H NMR spectrum (D₂O, 298 K, 600 MHz) of an unfractionated mixture of hydroxypropyl-β-cyclodextrins of the present disclosure. The figure also includes an exemplary hydroxypropyl-β-cyclodextrin molecule with the atom labeling used for structure elucidation.

Signals of hydroxypropyl-β-cyclodextrin constitute three well-separated regions in the ¹H NMR spectrum (see, e.g., FIG. 2). The anomeric protons are generally found between $\delta_{1H}$=5.0-5.4 ppm, while the core region (comprising all the protons of the glucopyranose unit besides the anomer) is generally placed between $\delta_{1H}$=3.2-4.2 ppm. In case of randomly substituted derivatives, protons of the glucose moiety close to the site of substitution may have two separated signals: 1) the substituted type (labelled with '), involved in a glucopyranose unit bearing a side chain at least at one position, which may be the position 2-O—, the position 3-O—, or the position 6-O—; and 2) the unsubstituted type (without '), representing the lack of any substituent, therefore the corresponding atom bearing OH groups.

Substituted and unsubstituted type signals are often overlapping in the core region, while usually well-separated in the anomeric region. In the case of hydroxypropyl-β-cyclodextrin, the α and β protons of the side chain are also found in the core region which makes direct determination of the location of substituent through HMBC spectra impossible. Thus, for elucidation the detailed analysis of DEPT-ed HSQC is the only choice. In this experiment, the methylene units (α, α', C6 and C6') are distinguishable from the methine units (β, β', C2, C2', C3, C3', C4, C5), making the assignment of the core region more straightforward.

The methyl (γ and γ') protons of the side chains represent the third group of signal of hydroxypropyl-β-cyclodextrin around $\delta_{1H}$=1.0-1.2 ppm.

The DS may be determined according to the pharmacopeial methods as the methyl region and the anomeric region are well-separated. EP and USP of Hydroxypropylbetadex for the determination of DS (or molar substitution) describes the integration of the anomeric region, setting the integral value to 7 (number of glucopyranose moieties, number of anomeric hydrogens in hydroxypropyl-β-cyclodextrin). The value of the methyl region will change according to the ratio between anomeric protons and methyl protons. Since methyl protons are located only on the hydroxypropyl side chains and their number per side chain is constantly 3, dividing the integral value of the methyl region by 3, will result in the value of DS.

In theory, the hydroxypropyl side chains may be located at 4 different positions: 2-O—, 3-O—, 6-O— positions of the cyclodextrin or at the β-O— position of the side chain (side chain oligomerization). Substitution at the 2-O— position causes an upfield chemical shift change (towards lower ppm values) of the signal of H2' compared to the signal of the unsubstituted H2. These two signals, however, are not distinguishable solely based on the ¹H NMR spectrum, because of the overlapping H4, H5, and Hα protons in the very same region where this substitution-induced chemical shift change occurs.

On the other hand, in the DEPT-ed HSQC spectrum (see FIG. 3) the signals of 2 and 2' are clearly separated because, upon substitution, the carbon resonances are influenced as well (they undergo a 10 ppm chemical shift change) which enables the resolution of 2 and 2' signals in the DEPT-ed HSQC spectrum. By following a similar approach, the 3 and 3', 6 and 6', and α and α' signals may be differentiated which allow the determination of a semi-quantitative PS for hydroxypropyl-β-cyclodextrin.

Thus, according to the data for unfractionated hydroxypropyl-β-cyclodextrin, the positions 2-O, 3-O—, and 6-O— of the cyclodextrin are substituted in 46%, 54%, and 10% of the hydroxypropyl-β-cyclodextrin molecules, respectively. Besides the determination of the ratio of the substituted positions, extent of side-chain oligomerization was also estimated. Based on the comparison of α and α' signals, 7% of the hydroxypropyl substituents were found to be present in the oligomerized state. The integral values obtained from the DEPT-ed HSQC spectrum of the unfractionated hydroxypropyl-β-cyclodextrin for the semi-quantitative determination of PS are shown in Table 6.

TABLE 6

Integral values of unfractionated hydroxypropyl-β-cyclodextrin
Unfractionated hydroxypropyl-β-cyclodextrin DS = 7.7

| Unit | HSQC Integral | Sum/Integral Position | Substituted % | Substituted unit/molecule |
|---|---|---|---|---|
| 2 | 0.94 | 1.73 | 46% | 3.2 |
| 2' | 0.79 | | | |
| 3 | 0.68 | 1.47 | 54% | 3.8 |
| 3' | 0.79 | | | |
| 6 | 3.97 | 4.43 | 10% | 0.7 |
| 6' | 0.46 | | | |
| α | 4.68 | 5.03 | 7% | — |
| α' | 0.35 | | | |

Figure 35:
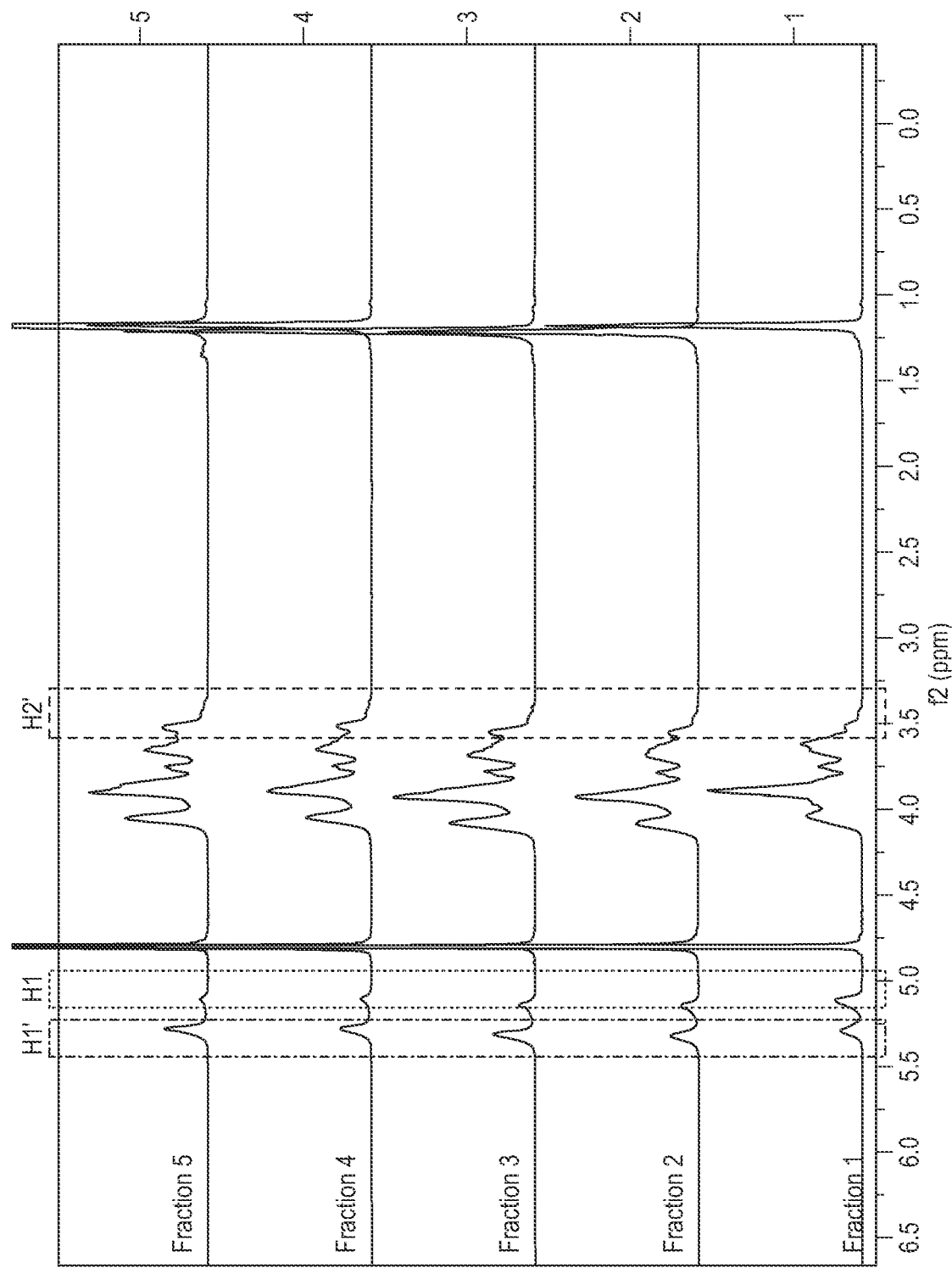
FIG. 35 shows overlaid ¹H NMR spectra for HDS fractions 1-5.

The $^1$H NMR spectra for Fractions 1-5 are shown in FIGS. 6, 11, 16, 21, and 26. By comparing the $^1$H NMR spectra of the five fractions (see overlaid $^1$H NMR spectra in FIG. 35), two important trends may be seen. The first trend is the continuous and unambiguous change between the intensities of the two anomeric signals H1' and H1. While H1' intensity gradually increases from Fraction 1 to Fraction 5, H1 decreases. The second trend is the continuous increase in the intensity of signal H2' from Fraction 1 to Fraction 5. Previous work proved that the H1' signal belongs to anomeric protons of glucose units bearing the hydroxypropyl side chain at position 2-O—; thus, these two above mentioned phenomena are interconnected: as the substitution at position 2-O— is more pronounced, the ratio between H1' and H1 protons increases. From these observations it is evident that while in Fraction 1 the substituted and unsubstituted 2-O— positions are present almost in the same amount, in Fraction 5 the majority of the 2-O— positions are occupied by HP moieties.

Since H1 and H1' protons are well-separated from each other, by integrating separately the peak of H1 (δ=5.0 ppm) and the peak of H1' (δ=5.4 ppm) and based on the fact that each hydroxypropyl-β-cyclodextrin contains seven anomeric protons in total, a quantitative data may be obtained about the number of substituted 2-O— positions (equal to the integrated value of the H1') and about the number of unsubstituted 2-OH positions (equal to the integrated value of H1). Table 7 provides the integral values obtained form the 1H NMR spectra of Fractions 1-5 for the quantitative determination of DS and PS.

TABLE 7

Integral values of HDS Fractions 1-5

| Fraction | DS | H1' peak area (H1 + H1' = 7.00) | H1 peak area (H1 + H1' = 7.00) | PS (from H1/H1' integrals) (%) | | |
|---|---|---|---|---|---|---|
| | | | | 2-O-HP | 3-O-HP | 6-O-HP |
| 1 | 6.69 | 3.12 | 3.88 | 44.57 | 55.43 | 0 |
| 2 | 7.42 | 4.28 | 2.73 | 61.14 | 39.00 | 0 |
| 3 | 8.53 | 4.96 | 2.04 | 70.86 | 29.14 | 0 |
| 4 | 8.08 | 5.28 | 1.72 | 75.43 | 24.57 | 0 |
| 5 | 9.65 | 5.77 | 1.23 | 82.43 | 17.57 | 0 |

Figure 36:
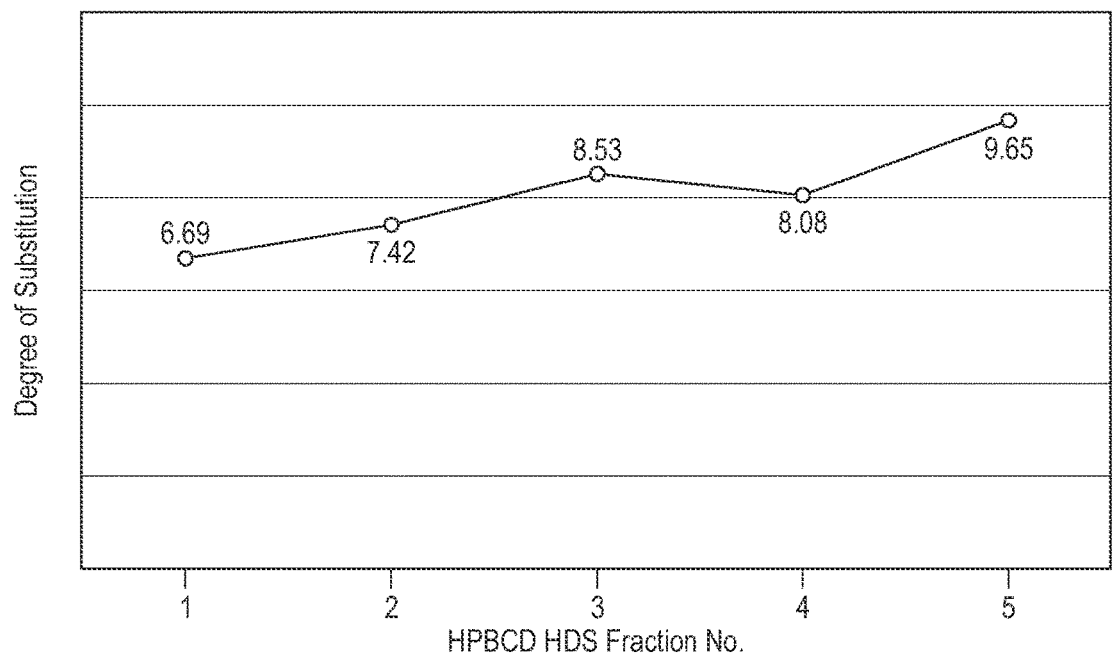
FIG. 36 shows the trend of the average degree of substitution in HDS fractions 1-5.

Interestingly, the DEPT-ed HSQC spectra of the fractions proved that none of the materials contain substituents on the primary side (lack of 6' signals). Based on this, PS may be directly calculated from the H1/H1' ratios, since the 6-O—HP % value in all the fractions is 0. This gives the PS results as shown in Table 7 and in FIG. 36. By summarizing the DS data obtained in NMR measurements, it may be stated that the DS value increases gradually from Fractions 1 to 5 with a plateau between Fractions 3 and 5. Surprisingly, Fraction 4 has a lower DS value than the earlier eluting Fraction 3, which is another confirmation that retention time of hydroxypropyl-β-cyclodextrin is not only a function of DS.

Figure 37:
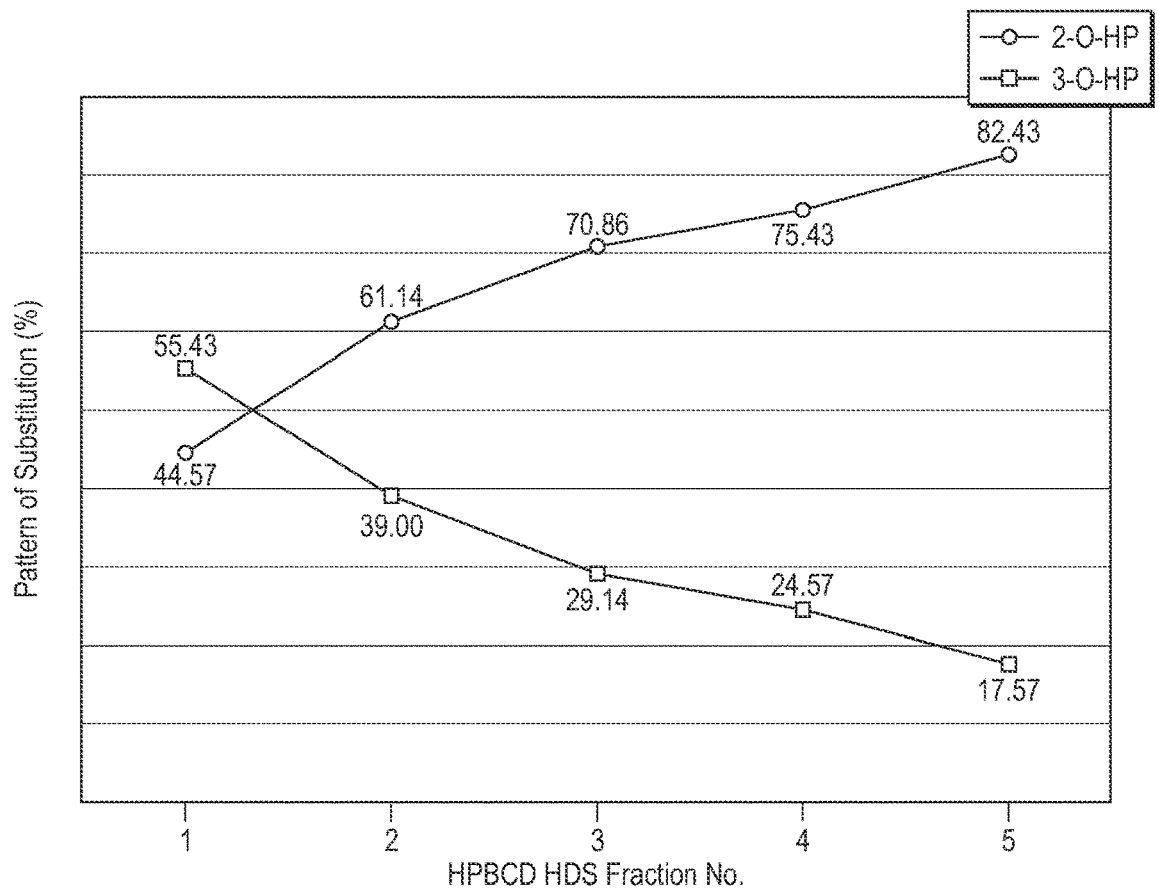
FIG. 37 shows the trend of the pattern of substitution (%) in HDS fractions 1-5.
Figure 38:
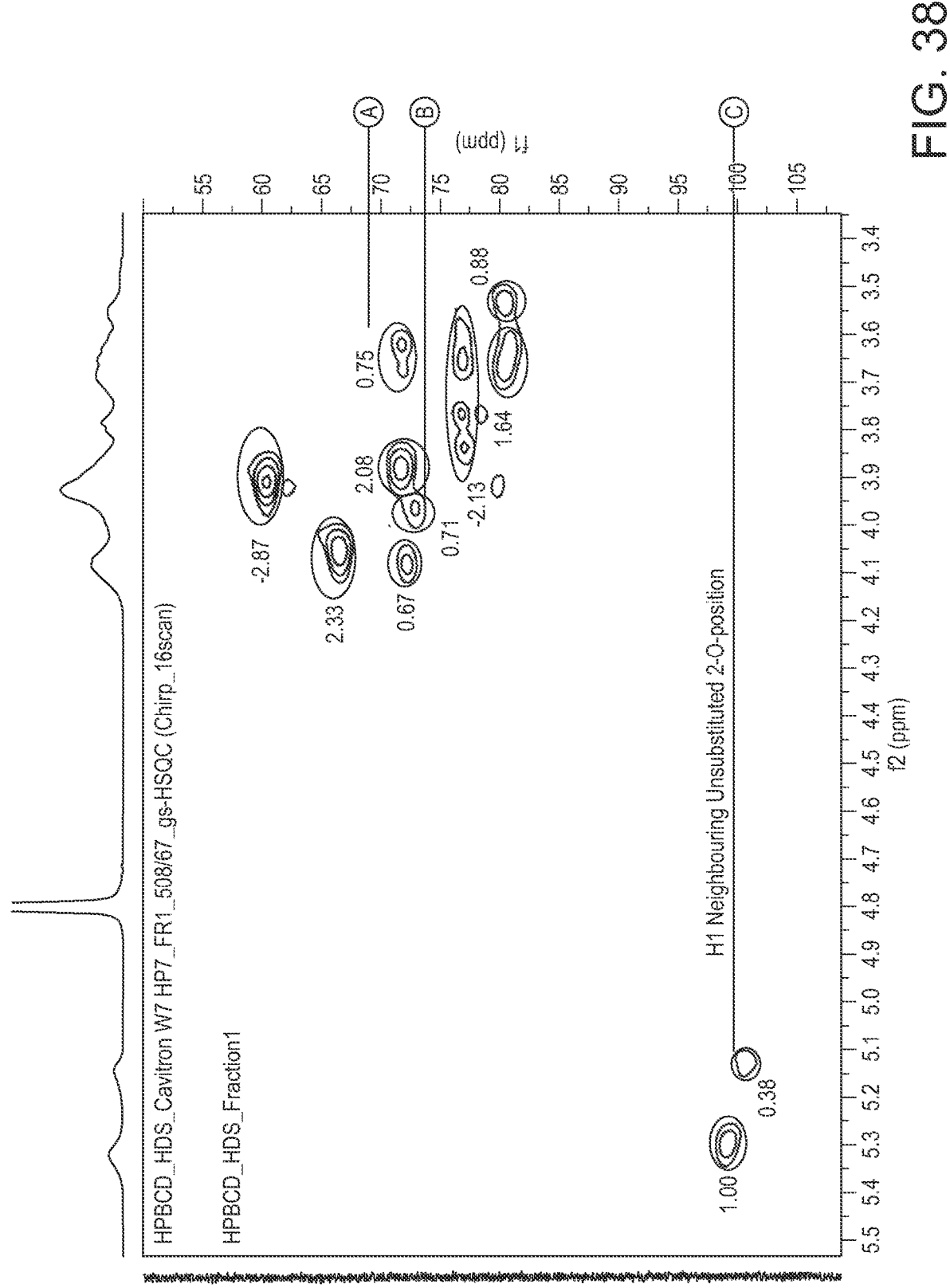
FIG. 38 shows differences between the DEPT-ed HSQC spectra for HDS fractions 1 and 5, which are used to elucidate the pattern of substitution.

By summarizing the PS values obtained from NMR measurements, it may be stated that PS has a clear trend when comparing the different fractions, as shown in FIG. 37. The 2-O— substitution increases while the 3-O— substitution decreases going from Fraction 1 towards Fraction 5. The very same trend may be seen from the comparison of the DEPT-ed HSQC spectra of the different fractions. The DEPT-ed HSQC spectra for Fractions 1-5 are shown in FIGS. 7, 12, 17, 22, and 27. As the fraction number increases, the intensities of the signals corresponding to 2-O— substitution (2', H1') increase and, simultaneously, the signals which are indicative for the 3-O— substitution (3') or for the unsubstituted 2-O— position (2, H1) decrease as fraction number increases and completely diminish from the spectrum of Fraction 5. The aspect of the DEPT-ed HSQC spectrum of Fraction 5 is almost symmetric and resembles that of a single isomer hydroxypropyl-β-cyclodextrin. The diffusion of the signals of the methylene units composing hydroxypropyl side chains (α-protons) are most probably consequences of both intra and/or intermolecular inclusion phenomena and minor substitution on the O3 positions. A comparison of the DEPT-ed HSQC spectra of Fractions 1 and 5 highlighting these trends is shown in FIG. 38.

Based on the summarized results from the NMR experiments, it may be stated that retention on Cholester columns is caused by 2-O-hydroxypropylation, while 3-O-hydroxypropylation causes earlier elution from the column. If the structure modification of cholesterol by the flexible linker used for the grafting is not considered substantial for the interaction with the hydroxypropyl-β-cyclodextrin isomer, it is possible to correlate the elution order with cholesterol affinity and reasonably conclude that 2-O-hydroxypropylation of β-cyclodextrin leads to higher cholesterol affinity than 3-O-hydroxypropylation.

According to $^1$H NMR evaluation, Fraction 5 has an average degree of substitution of 9.65 and based on MALDI-TOF-MS results, the main components are those containing 10 hydroxypropyl units. Based on $^1$H NMR PS elucidation in hydroxypropyl-β-cyclodextrin HDS fraction 5, 82% of the hydroxypropyl-β-cyclodextrin species carry the side chain exclusively at positions 2-O—. Since in the β-cyclodextrin molecule there are only seven 2-O— positions available for substitution, the remaining 3 substituents must be (mostly) located on the side chains.

Figure 39:
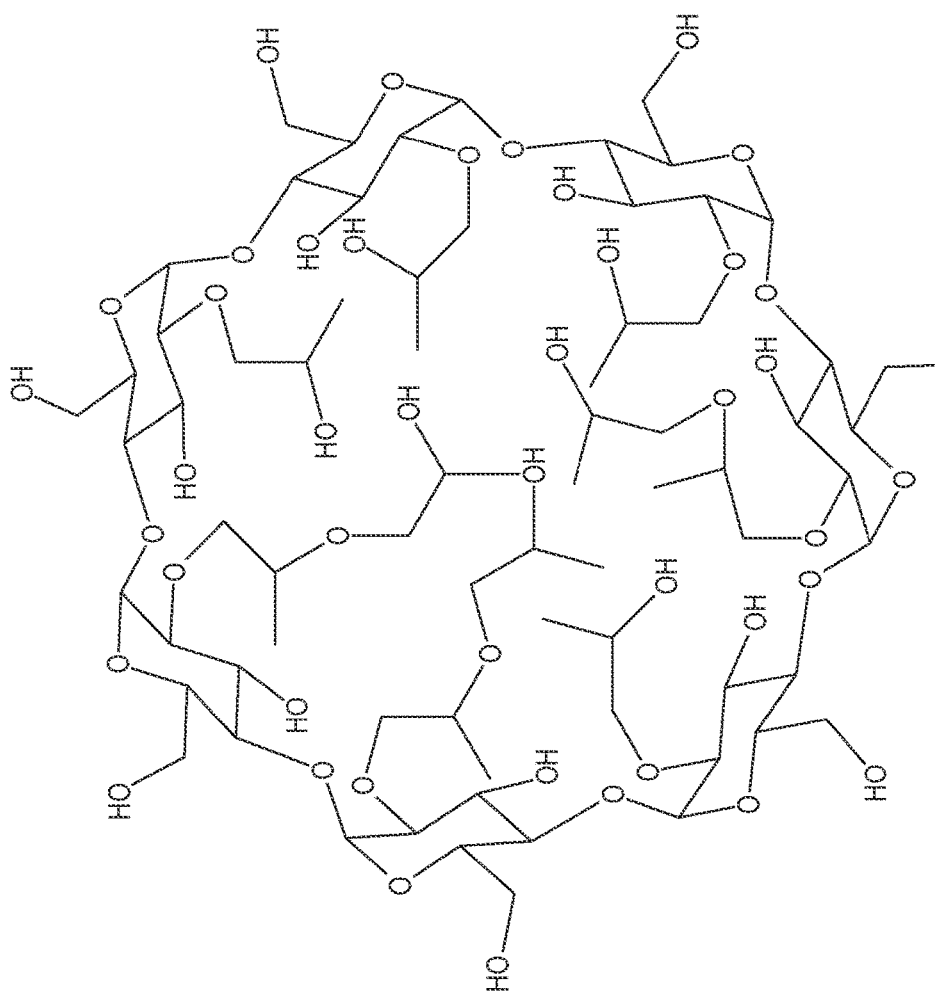
FIG. 39 shows the predicted structure of the most cholesterol affine isomer of hydroxypropyl-β-cyclodextrin.

Based on these facts, a proposed structure for the most cholesterol affine component of hydroxypropyl-β-cyclodextrin is depicted in FIG. 39.

The proposed structure may be synthesized through a selectively 2,6-silylated β-cyclodextrin intermediate. Silyl ether protection is fully compatible with strong basic conditions, necessary for the complete substitution of the secondary side by protecting groups (allyl, benzyl or acetyl groups) or by alkylating agents (preparation of per-2-O-alkylated cyclodextrins).

Silylated-cyclodextrins also tolerate phase transfer conditions (PTC) for alkylation furthermore when alkylation of per (2,6-di-O-tert-butydimethylsilyl)-β-cyclodextrin occurs in basic conditions, migration of protecting groups from 2-O— to 3-O-positions occur, enabling the preparation of the per-2-O-alkylated-β-cyclodextrins. After the secondary side derivatization, the silyl ether protecting groups may be easily removed using tetrabutylammonium fluoride (TBAF) or by acid hydrolysis, which generates the desired per-2-O-alkyl-β-cyclodextrins.

Since the targeted compound contains hydroxyalkyl moieties with different lengths, two different alkylating reagents must be used in a consecutive manner.

Figure 40:
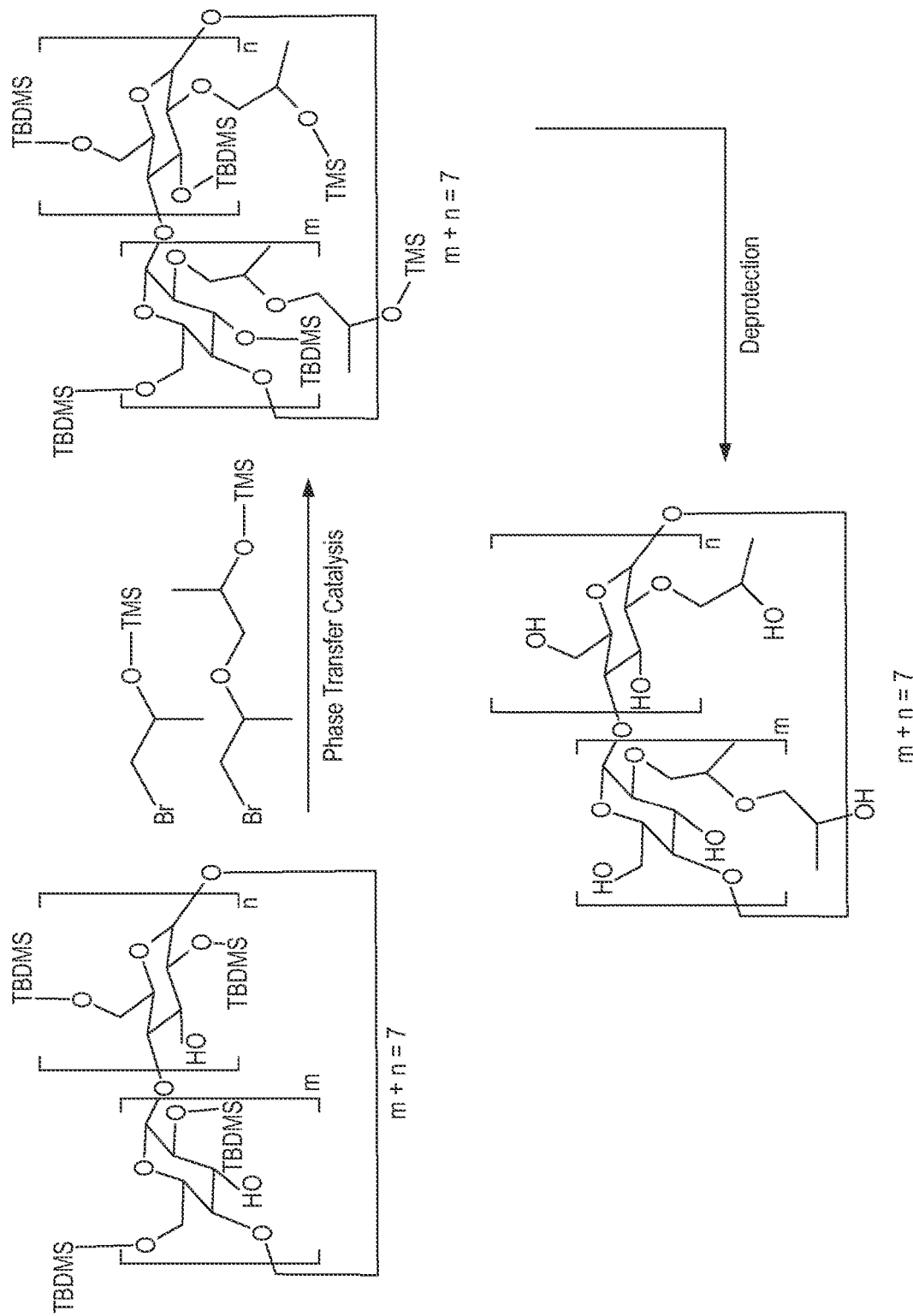
FIG. 40 shows a possible reaction scheme for producing the most cholesterol affine isomer of hydroxypropyl-β-cyclodextrin.

In order to avoid reaction between the two reagents and in order to simplify the terminal deprotection step, the silyl ether protection group chemistry is advised also for the reagents. Considering the atom economy, the use of trimethylsilyl (TMS) instead of the tert-butyldimethylsilyl (TBDMS) groups may be envisaged for these reagents. A proposed reaction scheme is shown in FIG. 40.

Example 2: Solubility Test of Cholesterol and Hydroxypropyl-β-Cyclodextrin HDS Fractions 1-5 and Hydroxypropyl-β-Cyclodextrin LDS Fractions 1-5

It was aimed to investigate the solubility of Cholesterol in the presence of different 2-hydroxypropyl beta cyclodextrins (HPBCD) and their fractions obtained from preparative chromatography on Cholester columns (Cholesterol immobilized on the surface of silica gel). The solubility tests were performed with fractions 1-5 of low degree of substitution HPBCD (HPBCD LDS) and with fractions of high degree of substitution HPBCD (HPBCD HDS). The solubility samples were HPLC analyzed to determine the Cholesterol and the HPBCD content.

Cholesterol Content Determination in Cholesterol-HPBCD Phase Solubility Samples

The HPLC instrument included an Agilent 1260 quarterner pumping system, and Agilent 1260 autosampler, an Agilent 1260 thermostatted column compartment, an Agilent 1200 Diode array detector (DAD), and an OpenLab CDS ChemStation Rev. C.01.07.SR1 [113] Agilent ChemStation for LC 3D. The column was a Zorbax Eclipse XDB-C8 column (5 μm, 4.6×150 mm). The column temperature was 40° C. The mobile phase eluent A was acetonitrile:purified water (90:10+0.05% FA) and eluent B was acetonitrile+0.05% FA. The gradient program is shown in Table 8 below.

TABLE 8

Gradient profile for cholesterol-HPBCD phase solubility test.

| t/min | "A" eluent % | "B" eluent % | flow |
|---|---|---|---|
| 0 | 100 | 0 | 1.5 mL/min |
| 5 | 0 | 100 | 1.5 mL/min |

Stop Time: 15 min
Post Time: 4 min.

The sample volume was 10 μL. Detection was accomplished with DAD (210 nm BW4, Ref: 360 nm BW100). The spectrum included apx+slopes+baselines from 200 nm to 350 nm.

Reagents and chemical included acetonitrile for chromatography, isopropyl alcohol for chromatography, and purified water. The cholesterol standard was provided by Sigma-Aldrich Chemie GmbH.

A cholesterol standard stock solution for calibration (CLS-SSS-1) was prepared by measuring 10 mg of cholesterol standard into a 10 mL graduated glass flask. 2.5 mL isopropyl alcohol was pipetted into the graduated glass flask, and the solution was mixed thoroughly with inversion until the cholesterol dissolved and made up to the mark with acetonitrile before mixing thoroughly with inversion again. The final concentration of CLS-SSS-1 was 1 mg/mL.

Cholesterol reference standard solutions for calibration (RSS-1-5) was prepared according to Table 9 below.

TABLE 9

Reference standard solutions for calibration

| Calibration level | CLS-SSS/ μL | PW/ μl | Dilution/- fold | Comment | Concentration/ (mg/mL) |
|---|---|---|---|---|---|
| RSS-1 | 50 | 4950 | 100 | Final | 0.020 |
| RSS-2 | 100 | 4900 | 50 | volume: 5 | 0.010 |
| RSS-3 | 125 | 4875 | 40 | mL | 0.008 |
| RSS-4 | 200 | 4800 | 25 | | 0.005 |
| RSS-5 | 500 | 4500 | 10 | | 0.002 |

A second cholesterol standard stock solution for calibration (CLS-SSS-2) was prepared using the same procedure described above. The CLS-SSS-2 was diluted 40 fold with eluent A to form a cholesterol solution for control calibration (CLS-CCAL) (125 μL CLS-SSS-2 were pipetted into a 5 mL graduated glass flask and made up to the volume with eluent A). The final concentration of the CLS-CCAL was 0.008 mg/mL.

The samples obtained from phase-solubility study were measured after filtration (0.22 μm nominal pore size syringe filter) and appropriate dilution with acetonitrile to meet the linearity criteria of the method.

The linearity of the method was tested in a concentration range of 0.002 mg/mL to 0.02 mg/mL. The linear model is valid in the tested concentration range, the correlation coefficient was higher than 0.999. Acceptance criteria for the calibration curve was a regression coefficient ($R_2$)≥0.99 and that the Y-axis intercept should be maximum±15.0% of the area of the RSS-3 sample. The obtained concentration was always corrected with dilution.

Because of the linear characteristic of the DAD detection, linear type function was fitted. The OpenLab CDS ChemStation software was used for the evaluation of the Cholesterol content in the samples (in concentration, mg/mL) using ESTD report.

HPBCD Content Determination in Cholesterol-HPBCD Phase Solubility Samples

The HPLC instrument included an Agilent 1260 quarterner pumping system, and Agilent 1260 autosampler, an Agilent 1260 thermostatted column compartment, an Agilent 1200 Diode array detector (DAD), an evaporative light-scattering detector, and an OpenLab CDS ChemStation Rev. C.01.07.SR1 [113] Agilent ChemStation for LC 3D. The column was a ACE UltraCore 2.5 SuperPhenylHexyl column (4.6×150 mm). The column temperature was 30° C. The mobile phase eluent A was purified water and eluent B was methanol:purified water (90:10). The gradient program is shown in Table 10 below.

TABLE 10

Gradient profile for cholesterol-HPBCD phase solubility samples

| t/min | "A" eluent % | "B" eluent % | flow |
|---|---|---|---|
| 0 | 100 | 0 | 1 mL/min |
| 2 | 100 | 0 | 1 mL/min |
| 3 | 30 | 70 | 1 mL/min |
| 10 | 30 | 70 | 1 mL/min |
| 10.1 | 100 | 0 | 1 mL/min |
| 16 | 100 | 0 | 1 mL/min |

Stop Time: 16 min

The sample volume was 5 μL-4 μL-3 μL-2 μL-1 μL in case of calibration samples, and 3 μL in case of sample solutions. Detection by ELSD was performed at 55, gain 1, 30 Hz, filter 3, and $N_2$ at 3.2 bar.

Reagents and chemicals included methanol for chromatography, purified water, and β-cyclodextrin.

During the measurements the calibration solutions was prepared from the different HPBCD HDS and LDS fractions. The materials used are shown in Table 11.

TABLE 11

Materials used in cholesterol-HPBCD phase solubility tests

| Compound name | | Producer/LOT No. |
|---|---|---|
| Fractions of HPBCD HDS (Wacker Cavitron W7 HP7 A2002A0134) | HPBCD HDS Fr. 1. | CycloLab/L1/107/I-X/Fr.1. |
| | HPBCD HDS Fr. 2. | CycloLab/L1/107/I-X/Fr.2. |
| | HPBCD HDS Fr. 3. | CycloLab/L1/107/I-X/Fr.3. |
| | HPBCD HDS Fr. 4. | CycloLab/L1/107/I-X/Fr.4. |
| | HPBCD HDS Fr. 5. | CycloLab/L1/107/I-X/Fr.5. |
| Fractions of HPBCD LDS (Wacker Cavitron W7 HP5 A2002A0038) | HPBCD LDS Fr. 1. | CycloLab/L1/137/1 |
| | HPBCD LDS Fr. 2. | CycloLab/L1/137/2 |
| | HPBCD LDS Fr. 3. | CycloLab/L1/137/3 |
| | HPBCD LDS Fr. 4. | CycloLab/L1/137/4 |
| | HPBCD LDS Fr. 5. | CycloLab/L1/137/5 |

Standard stock solutions of the HPBCD fractions (HPBCD-HDS-SSS-FR1-FR5 or HPBCD-LDS-SSS-FR1-FR5) were prepared by weighing 5 mg of HPBCD-HDS or HPBCD-LDS fraction into a 1 mL graduated glass flask and making up to the mark with purified water, followed by thorough mixing with inversion. The final concentration of the standard stock solutions was 5 mg/mL.

Because of few amounts of the fractions the HPBCD-HDS-SSS-FR1-FR5 or HPBCD-LDS-SSS-FR1-FR5 sample was measured and the injection volume was changed during the measurement of the calibration curve. The injection volumes were the following: 5 μL-4 μL-3 μL-2 μL-1 μL. The obtained results were used to plot the calibration curves.

The samples obtained from phase-solubility study were measured after filtration (0.22 μm nominal pore size syringe filter). The samples were diluted 10-fold with acetonitrile to meet the linearity criteria of the method. 500 μL Cholesterol-HPBCD phase solubility solution was transferred into a 5 mL volumetric flask and filled up to about ⅓ full with acetonitrile and mixed thoroughly to homogenize. Made to volume and mixed thoroughly by inversion. Concentration of the Test solution is 3.2 mg/mL.

Figure 41:
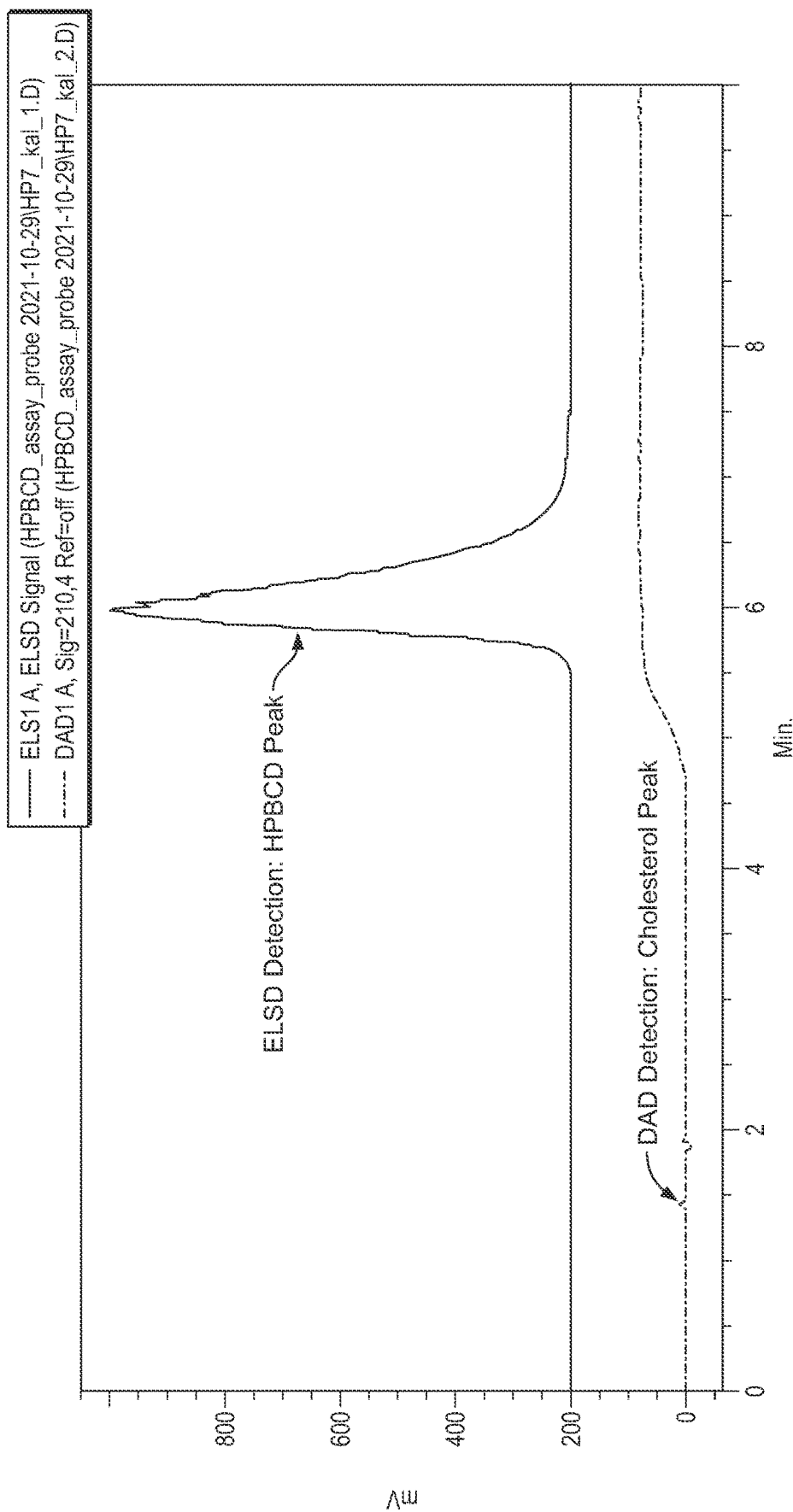
FIG. 41 is an overlaid HPLC chromatogram showing the elution of a mixture of hydroxypropyl-β-cyclodextrins and the elution of cholesterol.

The purpose was to prove that the HPBCD may be detected selectively in the Cholesterol—HPBCD phase solubility test solution in the presence of Cholesterol. According to the overlayed chromatogram in FIG. 41, it may be observed that the HPBCD peak eluate at later retention time than the Cholesterol peak. In the applied conditions there was no interference between the Cholesterol and the peaks of the HPBCD fractions.

The linearity of the method was tested in a concentration range of 1 mg/mL to 5 mg/mL. The linear model was valid in the tested concentration range, the correlation coefficient was higher than 0.999.

Because of the non-linear characteristic of the ELS detection, a power type function is fitted. The OpenLab CDS ChemStation software was used for the evaluation of the HPBCD content in the samples (in concentration, mg/mL) using ESTD report.

Experimental Part of the Solubility Test

Phase solubility studies were performed in aqueous media at 37° C. temperature, wherein cyclodextrin solutions of discrete concentrations were weighed and excess amount of Cholesterol was added. The samples were protected from light during the experiment. Each experimental condition repeated in triplicate. After 24 hours equilibration time at 37±1° C. (using magnetic stirrer at 500 RPM), the dissolved Cholesterol concentrations were determined by HPLC after filtration through a syringe filter having polyethylene sulfone membrane of 0.22 micron nominal pore size. The HPBCD content of the phase solubility samples were also measured.

First, the solubility of Cholesterol was studied in HPBCD HDS and LDS 20% (w/w) solutions. Excess amount of Cholesterol was added to the CD solutions in aqueous media at 37° C. temperature. Five parallel phase solubility sample were prepared and during the HPLC analysis every sample was injected in triplicate.

The solubility of Cholesterol was studied in 5% (w/w) solutions of the fractions of HPBCD HDS and LDS. Excess amount of Cholesterol was added to the CD solutions in aqueous media at 37° C. temperature. Three parallel phase solubility sample were prepared and during the HPLC analysis every sample was injected in triplicate.

Results

Figure 42:
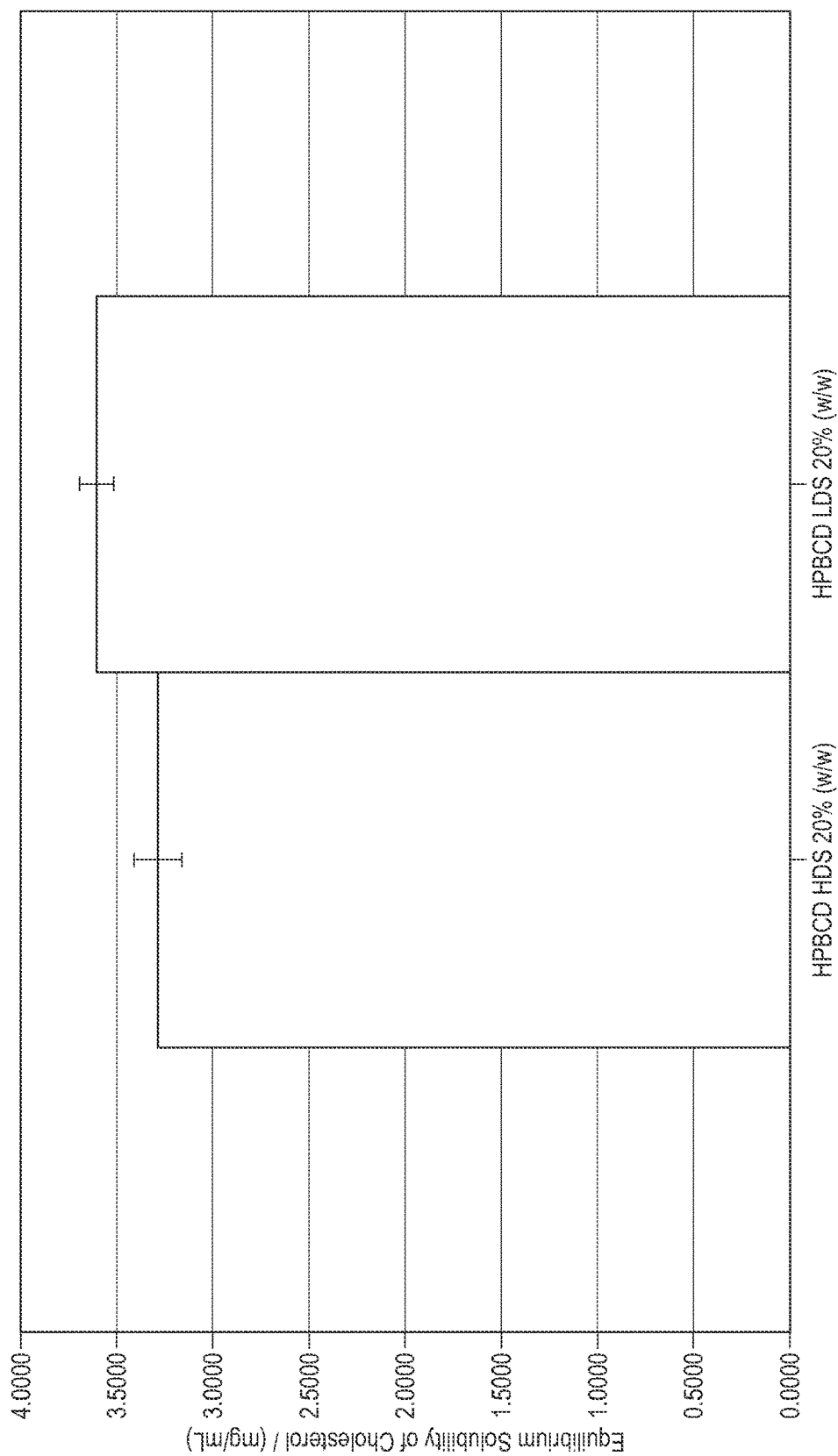
FIG. 42 shows the equilibrium solubility of cholesterol in the presence of HDS hydroxypropyl-β-cyclodextrins and LDS hydroxypropyl-β-cyclodextrins.

Results of the solubility isotherms with HPBCD HP5 and HP7: The solubility results are plotted in FIG. 42. In the presence of HPBCD HDS (20% (w/w), the aqueous solubility of Cholesterol was lower than in the presence of HPBCD LDS (20% (w/w). This experiment was not carried out in the presence of 5% (w/w) HPBCD HDS/LDS. As a next step in the project, the Cholesterol solubility potential of the fractions of the HPBCD HDS and LDS were studied.

Figure 43:
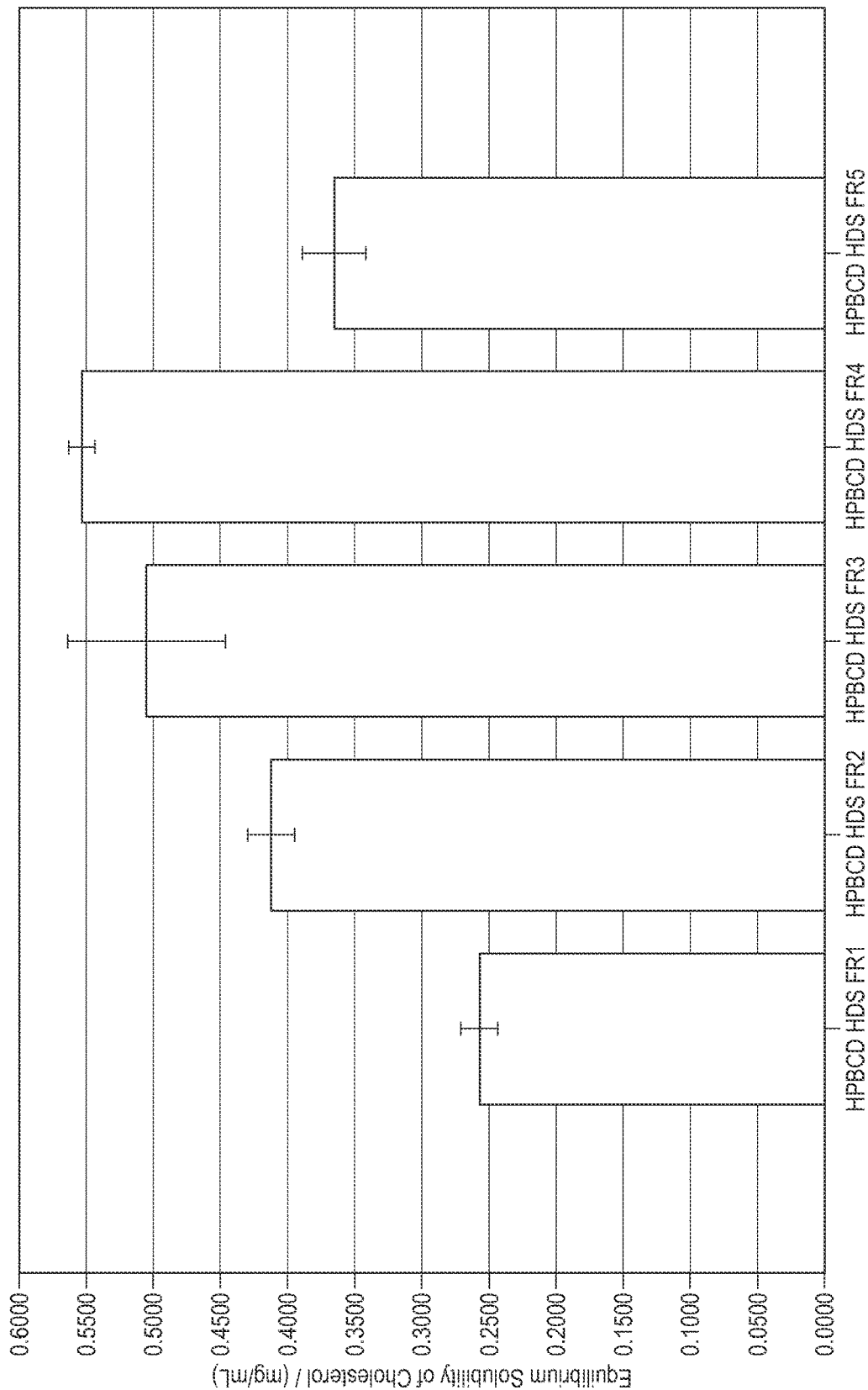
FIG. 43 shows the equilibrium solubility of cholesterol in the presence of the HDS fractions 1-5 of hydroxypropyl-β-cyclodextrin.

Results of the solubility isotherms with HPBCD HDS and LDS fractions: The solubility results, which were obtained with fractions of the HPBCD HDS, are plotted in FIG. 43. AN interesting trend may be observed on the graph: the Cholesterol solubility potential GROWS from the HPBCD HDS FR-1 (0.26 mg/mL) to the HPBCD HDS FR-4 (0.55 mg/mL), but the Cholesterol solubilizing potential of HPBCD HDS FR-5 is well behind of the expected value (only 0.37 mg/mL) in case of 5% (w/w) HPBCD HDS FR-5 solution.

During the preparative chromatography the HPBCD HDS FR-5 fraction showed the strongest interaction with the Cholesterol HPLC column. After the elution from the preparative HPLC column the liquid sample was evaporated and the HPBCD HDS FR-5 may form a different structure (arrangement of the side chains, orientation of the glucose subunits) in solid form, than it was present in the methanol-water (mobile phase)/cholesterol (stationary phase) environment during the chromatography. Most probably this new arrangement causes the lower apparent solubility and hence the out of trend results in terms of Cholesterol solubilizing potential. This theory must be verified with further measurements (solution NMR host-guest interaction studies with HPBCD HDS FR-5 and Cholesterol, powder X-ray analysis of the HPBCD HDS FR-5 and HPBCD HDS FR-5/Cholesterol complex, solid phase NMR analysis of HPBCD HDS FR-5 and HPBCD HDS FR-5/Cholesterol complex).

The HPBCD HDS FR-5 feature was different during the phase solubility test than the other HPBCD HDS fractions. The HPBCD HDS FR5 was not soluble in water in 5% (w/w) concentration, but after the 24 hours equilibration time at 37° C. with Cholesterol the whole amount (5% (w/w)) of HPBCD HDS FR5 was dissolved. It may be assumed that the cholesterol may improve the HPBCD HDS FR5 solubility in water.

To prove this hypothesis, an experiment was executed with HPBCD HDS FR5. The solubility of HPBCD HDS FR5 was tested in water without Cholesterol in the same circumstances as the previous experiment. According to the result 41.95 mg/mL was the concentration of the HPBCD HDS FR5 sample. This result is nearly 9 mg/mL less. In the light of the result, we may say that the Cholesterol improve the HPBCD HDS FR5 solubility in water.

Figure 44:
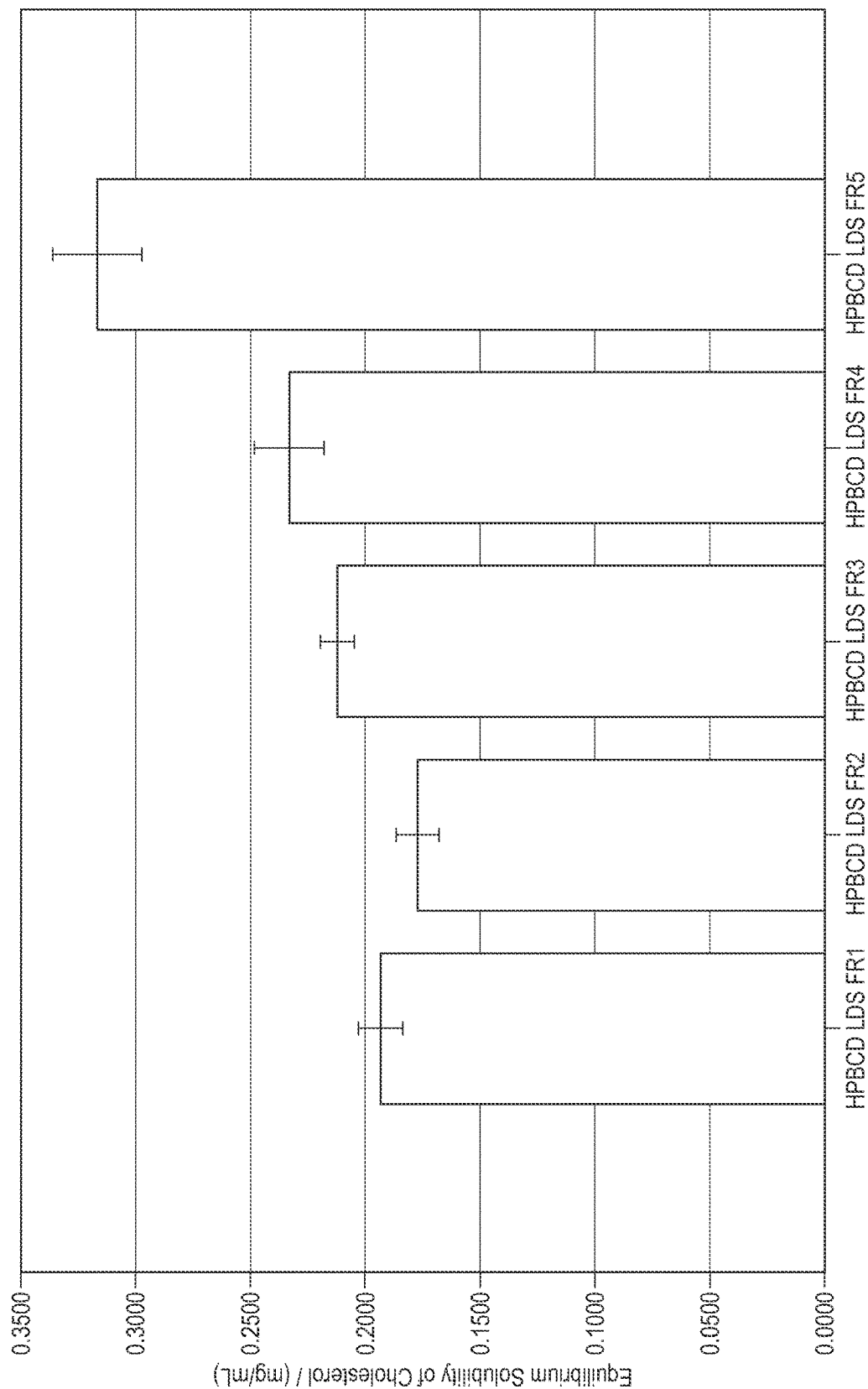
FIG. 44 shows the equilibrium solubility of cholesterol in the presence of the LDS fractions 1-5 of hydroxypropyl-β-cyclodextrin.

The solubility results, which were obtained with fractions of the HPBCD LDS, are plotted in FIG. 44. In case of HPBCD LDS fractions the results meet with the hypothetic trend. The Cholesterol solubility potential is growing from fraction 1 to fraction 5. The HPBCD LDS fraction 5 has better Cholesterol binding affinity then the HPBCD LDS fraction 1. These results are in agreement with the elution order from the preparative HPLC column.

According to the data obtained from the fractions all the HPBCD HDS fractions have better Cholesterol solubilizing ability than the HPBCD LDS fractions.

CONCLUSIONS

Phase-solubility studies were performed to study the interaction between different HPBCDs (LDS and HDS) and their fractions obtained from the preparative Cholester columns. The results show that there is a trend in the Cholesterol solubilizing in case of fractions of HPBCD LDS. The solubilizing potential of the fractions is increasing from HPBCD LDS fraction 1 to fraction 5. These results are in a line with the elution order from the Cholester HPLC column.

On the other hand, there is an unexpected trend in the results which were obtained with the fractions of HPBCD HDS. The HPBCD HDS FR5 is out of the trend.

Because of the interesting solubility behavior of the HPBCD HDS FR5 further experiments are planned. According to the result we may say that the HPBCD HDS FR5 has better solubility in water in the presence of cholesterol. To find out the cause of this unexpected phenomenon further experiments are required in particular about the solid phase structure of HPBCD HDS FR5 compared with other fractions. Comparison of the structure of HPBCD HDS FR5 alone and in the presence of Cholesterol, might also reveal explanation for this unusual behavior.

Example 3: Nanofiltered Compositions

Twenty compositions comprising purified mixtures of β-cyclodextrin molecules were prepared according to the nanofiltration methods of the present disclosure (see Nanofiltration section above). The mixtures of β-cyclodextrin molecules were not isomerically-purified according to the present disclosure. Each batch of the compositions was assigned a number from 1-20. Each of the batches is described in Table 12 below.

TABLE 12

| Batch # | Diluent | pH | Buffer | Concentration of Buffer |
|---|---|---|---|---|
| 1 | WFI | not measured | none | none |
| 2 | Saline | not measured | none | none |
| 3 | Saline | 7.40 | none | none |
| 4 | Saline | 7.00 | none | none |
| 5 | WFI | 7.00 | Potassium phosphate | 10 mM |
| 6 | WFI | 7.00 | Potassium phosphate | 5 mM |
| 7 | WFI | 7.40 | Potassium phosphate | 10 mM |
| 8 | WFI | 7.40 | Potassium phosphate | 5 mM |
| 9 | Saline | 7.00 | Potassium phosphate | 10 mM |
| 10 | Saline | 7.00 | Potassium phosphate | 5 mM |
| 11 | Saline | 7.40 | Potassium phosphate | 10 mM |
| 12 | Saline | 7.40 | Potassium phosphate | 5 mM |
| 13 | WFI | 7.00 | Sodium phosphate | 10 mM |
| 14 | WFI | 7.00 | Sodium phosphate | 5 mM |
| 15 | WFI | 7.40 | Sodium phosphate | 10 mM |
| 16 | WFI | 7.40 | Sodium phosphate | 5 mM |
| 17 | Saline | 7.00 | Sodium phosphate | 10 mM |
| 18 | Saline | 7.00 | Sodium phosphate | 5 mM |
| 19 | Saline | 7.40 | Sodium phosphate | 10 mM |
| 20 | Saline | 7.40 | Sodium phosphate | 5 mM |

WFI = sterile water for injection

The batches were then sterilized. The appearance of the batch, pH, osmolality, density, content, β-cyclodextrin content, impurities, and PGL were measured before and after sterilization. These values are provided in Tables 13A to 13C.

TABLE 13A

| | pH | | Osm. (mosmol/kg) | | Density (g/cm$^3$) | |
|---|---|---|---|---|---|---|
| Batch # | Before Steril. | After Steril. | Before Steril. | After Steril. | Before Steril. | After Steril. |
| 1 | 6.32 | 4.99 | 641 | 648 | 1.0964 | 1.0964 |
| 2 | 4.88 | 4.55 | 1188 | 1164 | 1.1035 | 1.1033 |

TABLE 13A-continued

| Batch # | pH Before Steril. | pH After Steril. | Osm. (mosmol/kg) Before Steril. | Osm. (mosmol/kg) After Steril. | Density (g/cm³) Before Steril. | Density (g/cm³) After Steril. |
|---|---|---|---|---|---|---|
| 3 | 6.23 | 5.70 | 1180 | 1170 | 1.1028 | 1.1030 |
| 4 | 6.06 | 5.40 | 1143 | 1201 | 1.0178 | 1.1026 |
| 5 | 6.91 | 6.83 | 1053 | 1030 | 1.1009 | 1.1019 |
| 6 | 7.01 | 6.93 | 1045 | 1034 | 1.1010 | 1.1017 |
| 7 | 7.32 | 7.25 | 1183 | 966 | 1.1069 | 1.0970 |
| 8 | 7.33 | 7.22 | 1063 | 1064 | 1.1006 | 1.1017 |
| 9 | 7.04 | 7.00 | 686 | 671 | 1.0956 | 1.0862 |
| 10 | 7.04 | 6.97 | 658 | 656 | 1.0965 | 1.0966 |
| 11 | 7.40 | 7.36 | 695 | 699 | 1.0967 | 1.0974 |
| 12 | 7.40 | 7.37 | 668 | 664 | 1.0971 | 1.0971 |
| 13 | 6.96 | 6.95 | 1058 | 1003 | 1.1000 | 1.1010 |
| 14 | 6.96 | 6.97 | 1048 | 1035 | 1.1007 | 1.1014 |
| 15 | 7.27 | 7.29 | 1095 | 1084 | 1.1021 | 1.1020 |
| 16 | 7.28 | 7.27 | 1142 | 1064 | 1.1015 | 1.1021 |
| 17 | 7.01 | 6.99 | 636 | 617 | 1.0925 | 1.0932 |
| 18 | 7.05 | 7.00 | 696 | 669 | 1.0972 | 1.0968 |
| 19 | 7.41 | 7.37 | 713 | 684 | 1.0957 | 1.0963 |
| 20 | 7.40 | 7.33 | 670 | 684 | 1.0965 | 1.0972 |

TABLE 13B

| Batch # | Content (%) Before Steril. | Content (%) After Steril. | BCD (%) Before Steril. | BCD (%) After Steril. | Impurities (%) Before Steril. | Impurities (%) After Steril. |
|---|---|---|---|---|---|---|
| 1 | 101.3 | 103.0 | <LOD | <LOD | <LOD | 0.01 |
| 2 | 101.4 | 98.0 | <LOD | <LOD | <LOD | 0.02 |
| 3 | 98.6 | 99.8 | <LOD | <LOD | <LOD | <LOD |
| 4 | 98.6 | 96.2 | <LOD | <LOD | <LOD | <LOD |
| 5 | 104.7 | 99.0 | <LOD | <LOD | <LOD | <LOD |
| 6 | 101.4 | 97.2 | <LOD | <LOD | <LOD | <LOD |
| 7 | 103.7 | 102.4 | <LOD | <LOD | <LOD | <LOD |
| 8 | 100.7 | 96.8 | <LOD | <LOD | <LOD | <LOD |
| 9 | 98.5 | 94.9 | <LOD | <LOD | <LOD | <LOD |
| 10 | 103.7 | 101.1 | <LOD | <LOD | <LOD | <LOD |
| 11 | 100.6 | 97.5 | <LOD | <LOD | <LOD | <LOD |
| 12 | 99.1 | 99.0 | <LOD | <LOD | <LOD | <LOD |
| 13 | 99.9 | 97.9 | <LOD | <LOD | <LOD | <LOD |
| 14 | 98.7 | 99.1 | <LOD | <LOD | <LOD | <LOD |
| 15 | 98.0 | 98.1 | <LOD | <LOD | <LOD | <LOD |
| 16 | 99.1 | 97.5 | <LOD | <LOD | <LOD | <LOD |
| 17 | 94.1 | 96.8 | <LOD | <LOD | <LOD | <LOD |
| 18 | 100.0 | 99.6 | <LOD | <LOD | <LOD | <LOD |
| 19 | 100.4 | 97.0 | <LOD | <LOD | <LOD | <LOD |
| 20 | 97.4 | 98.4 | <LOD | <LOD | <LOD | <LOD |

<LOD = below level of detection

TABLE 13C

| Batch # | PGL (%) Before Steril. | PGL (%) After Steril. |
|---|---|---|
| 1 | 0.010 | 0.013 |
| 2 | 0.009 | 0.011 |
| 3 | 0.011 | 0.012 |
| 4 | 0.014 | 0.011 |
| 5 | 0.010 | 0.010 |
| 6 | 0.012 | 0.014 |
| 7 | 0.012 | 0.015 |
| 8 | 0.010 | 0.012 |
| 9 | 0.009 | 0.011 |
| 10 | 0.008 | 0.012 |
| 11 | 0.010 | 0.010 |
| 12 | 0.013 | 0.010 |
| 13 | 0.011 | 0.011 |
| 14 | 0.009 | 0.010 |
| 15 | 0.011 | 0.010 |
| 16 | 0.009 | 0.010 |
| 17 | 0.015 | 0.010 |
| 18 | 0.017 | 0.010 |
| 19 | 0.013 | 0.012 |
| 20 | 0.010 | 0.013 |

Portions of each of the batches were stored for 28 days. One portion of the batches was stored at 5° C. Another portion of the batches was stored at 40° C. Similar measurements were collected for these batches after 28 days.

Example 4: Nanofiltration Testing

Analytical Methods

HPLC with ELSD detector: The HPLC method using an ELSD detector that was developed for characterizing materials here. Method details (Table 14A) and retention times (Table 14B) are summarized below.

TABLE 14A

| | |
|---|---|
| Mobile phase A | MilliQ water |
| Mobile phase B | Methanol:MilliQ water 9:1 |
| Column | CD Screen I column, 250 × 4 mm from Cyclo Therapeutics Inc |
| Column temperature | 30° C. |
| Flow rate | 1 mL/min |
| Injection volume | 10 μL |
| ELSD Detector | Lamp on, Temperature: 40° C.; Gain: 3(×4); Filter: 1 sec; Sampling rate: 2.5 Hz |
| Run time | 30 min |

| | Time (min) | % B |
|---|---|---|
| Gradient program | 0 | 48 |
| | 5 | 48 |
| | 15 | 100 |
| | 20 | 100 |
| | 20.1 | 48 |
| | 30 | 48 |

TABLE 14B

| Compound | Retention time (min) | Relative Retention time (RRT) |
|---|---|---|
| β-cyclodextrin | 5.446 | 0.446 |
| Hydroxypropyl-β-cyclodextrin | 12.203 | 1 |

GC Method: A gas chromatography method was established for measuring the concentration of propylene glycol (Table 15). The approximate limit of detection of the method is 2 mg/mL.

TABLE 15

| | |
|---|---|
| Gas Chromatograph | Agilent 6890N Gas Chromatograph with FID detector |
| Column | Restek Rtx-Wax Column, 30 m × 0.25 mm ID × 0.25 μm film thickness |
| Injection Liner | Restek P/N 23305, Topaz linear, split precision linear w/wool |
| Injection Temperature | 250° C. |
| Injection Volume | 1 μL |

TABLE 15-continued

| | |
|---|---|
| Syringe Volume | 10 μL |
| Oven Temperature Profile | Initial temperature: 40° C. (Hold 1 min) 30° C./min ramp to 250° C. (2 minute hold) |
| Column Flow | 1.7 mL/min Helium (constant flow) |
| Detector | FID |
| Detector Temperature | 250° C. |
| Detector Gas Flow | Air (Oxidizer): 360 mL/min Hydrogen (Fuel): 40 mL/min |
| Split Ratio | 50:1 |
| Carrier Gas | Helium |
| Data Acquisition Time | 10 min |

Process Development

Feedstock Solution and Preparation: The feedstocks were commercial-grade HPBCD materials. Solutions were prepared by dilution with either deionized or 18.2 MΩ water. Initial screening was carried out using Cavitron HP7 Pharma materials. Feedstocks are summarized in Table 16.

TABLE 16

| Vendor | Grade | Quantity |
|---|---|---|
| Wacker/Ashland | Cavitron W7 HP7 Pharma | 5 kg |
| Wacker/Ashland | Cavitron W7 HP5 Pharma | 5 kg |
| Alcami/Roquette | Kleptose | 3.8 kg |

Flatsheet Membrane Screening: Flatsheet membranes were evaluated using custom process skids equipped with a SEPA CF Cell under constant volume mode. Permeate generation was monitored using a mass flow meter, and diafiltration water was added at a rate equivalent to the permeate removal. Partway through, the experiments were transferred to a new equivalent skid. The SEPA CF Cell and membrane press were identical in both setups. The membrane surface area used during these experiments had 140 cm² surface area.

The first phase of this project involved evaluating flat sheet membranes that had the highest flux and complete rejection of HPBCD product. XN45 Trisep, TS40 Trisep, and Synder NFX membranes were analyzed for the process. These membranes were selected on the basis of molecular weight cutoff, flux, and sodium chloride removal efficiency. The membrane active area on the SEPA CF cell is 140 cm². The experiment's flux was hence calculated by dividing the flow rate of the permeate by the active area.

Screening experiments were done at room temperature and a feed pressure of 300 psi. Diafiltration water, a total of 3-5 volumes (300-500 mL) were collected. Samples of the retentate were analyzed by both ELSD (HPBCD) and GC (propylene glycol). Generally, propylene glycol was detectable in the first diafiltration volume at concentrations of ~2.4 g/L but not in subsequent samples. A summary of membrane performance from the screened membranes appears in Table 17. The Trisep XN45 membrane gave good flux and was the only membrane that didn't have detectable product in the permeate. This membrane was selected as the preferred membrane for additional work.

TABLE 17

| Membrane | LNB # | Flux (KMH, 10 wt % feed) | Flux (KMH, 30 wt % feed) | HPBCD in permeate |
|---|---|---|---|---|
| Trisep TS40 | RS02-23 (10 wt %)/ RS02-27 (30 wt %) | 18.5 | 5.1 | Yes |
| Trisep XN45 | RS02-17 (10 wt %)/ RS02-20 (30 wt %) | 13.7 | 5.2 | No |
| Synder NFX | RS02-28 (10 wt %)/ RS02-29 (30wt %) | 11.8 | 4.1 | Yes |

XN45 Flux Evaluation in Flatsheet Systems: Flux of the XN45 membrane as a function of feedstock concentration was evaluated at 200 psig and room temperature under a recycle mode whereby the permeate was sent back to the feed vessel. Starting from a 40 wt % feed, permeate was sent back and MilliQ water was added manually to evaluate flux at different weight percentages of feedstock. The flux was found to fit a power law with intercept quite close to previous clean water flux values (~100 KMH). Going to higher concentrations reduces the amount of diafiltration water required to achieve the same level of purification, as rejection of propylene glycol or sodium chloride is not expected to change as a function of concentration.

Surprisingly, the length of time required to turn over the tank was relatively invariant of concentration. Specifically, operating at a higher concentration with a lower flux would require the same amount of run time but less water than operating at a lower concentration with a higher flux. Table 18 summarizes the average flux obtained for each of the feedstock weight percentages evaluated.

TABLE 18

| Feedstock concentration (wt %) | Average Flux (KMH) | L soln/kg HPBCD | Hours per DV (kg soln/m²-hr/ L soln) | Diafiltration water for 5 DV (L/kg HPBCD) |
|---|---|---|---|---|
| 10 | 10.4 | 10.0 | 1.04 | 50 |
| 15 | 7.6 | 6.7 | 1.14 | 33 |
| 20 | 6.0 | 5.0 | 1.19 | 25 |
| 25 | 4.8 | 4.0 | 1.20 | 20 |
| 30 | 3.9 | 3.3 | 1.18 | 17 |
| 35 | 3.3 | 2.9 | 1.16 | 14 |
| 40 | 2.8 | 2.5 | 1.14 | 13 |

XN45 Flux evaluation in spiral wound systems: Flux of the XN45 membrane as a function of temperature, pressure, and recirculation rate was evaluated under a recycle mode whereby the permeate was sent back to the feed vessel. The feedstock was Cavitron HP7 Pharma I at 10 wt % using a 1.8" diameter×12" length (1812) spiral wound membrane with 0.23 m² surface area. Increasing the temperature, pressure, and recirculation rate all had positive impacts on flux, and the normalized flux was increased 2.8× from baseline material at 50° C., 200 psig back pressure, and with the recirculation pump set to 20 Hz (~2 GPM). The feedstock was discharged and frozen after the test. Samples of permeate from each test were analyzed by ELSD for the presence of HPBCD, and no HPBCD was detected in any sample. Performance is summarized in Table 19.

TABLE 19

| Sample ID | Nominal temperature (° C.) | Nominal pressure (° C.) | Recirc pump rate (Hz) | Actual temperature (° C.) | Actual pressure (psig) | Permeate flow rate (g/min) | Flux (KMH) | Normalized flux |
|---|---|---|---|---|---|---|---|---|
| 1 | 20 | 100 | 15 | 20.6 | 103 | 131.6 | 34 | 1.0 |
| 2 | 20 | 200 | 15 | 21.3 | 203 | 178.0 | 46 | 1.4 |
| 3 | 30 | 100 | 15 | 29.2 | 100 | 160 | 42 | 1.2 |
| 4 | 30 | 200 | 15 | 29.6 | 200 | 214 | 56 | 1.6 |
| 5 | 40 | 100 | 15 | 40.0 | 100 | 219 | 57 | 1.7 |
| 6 | 40 | 200 | 15 | 41.1 | 210 | 270 | 70 | 2.1 |
| 7 | 50 | 100 | 15 | 47.2 | 104 | 233 | 61 | 1.8 |
| 8 | 50 | 200 | 15 | 48.8 | 211 | 308 | 80 | 2.3 |
| 9 | 50 | 200 | 10 | 49.5 | 207 | 252 | 66 | 1.9 |
| 10 | 50 | 200 | 20 | 49.0 | 216 | 366 | 95 | 2.8 |

Estimation of diafiltration volume requirements: The XN45 membrane has a molecular weight cutoff (MWCO) of 500 Da and a 10-30% rejection coefficient of sodium chloride. As the molecular weight cutoff is generally defined as a rejection coefficient of 90% at the specified molecular weight (MW), estimated rejection coefficients were calculated according to Equation 1 below.

$$R = 0.9 \frac{MW}{MWCO} = 0.0018 \, MW \quad \text{(Equation 1)}$$

Despite having the same molecular weight as propylene oxide, sodium chloride was assumed to have a slightly higher rejection coefficient (R) of 20%. Using the assumed rejection coefficients, the amount of diafiltration to achieve a specific removal level were estimated by Equation 2.

$$DV = -\frac{\ln(1-R)}{1-RE} \quad \text{(Equation 2)}$$

The results indicate that nearly 99% removal efficiency (RE) of propylene oxide and propylene glycol could be achieved in around 5 diafiltration volumes, and that PO-dimer and PO-trimer would be removed at up to 95%. Tetramers and larger oligomers might require more diafiltration water for >95%, but it is anticipated that the amount of PO-trimer and higher oligomers will be a quite small fraction of the overall impurities. Based on these calculations, an optimal amount of diafiltration water of 5 DV was assumed as shown in Table 20.

TABLE 20

| Species | MW (g/mol) | Assumed rejection (R, %) | #DV to achieve removal efficiency (RE, %) | | | |
|---|---|---|---|---|---|---|
| | | | 90 | 95 | 99 | 99.9 |
| Sodium chloride | 58 | 20 | 2.9 | 3.7 | 5.8 | 8.6 |
| Propylene glycol | 58 | 10 | 2.6 | 3.3 | 5.1 | 7.7 |
| PO1 (Propylene oxide) | 76 | 14 | 2.7 | 3.5 | 5.3 | 8.0 |
| PO2 (PO-dimer) | 134 | 24 | 3.0 | 3.9 | 6.1 | 9.1 |
| PO3 (PO-trimer) | 210 | 38 | 3.7 | 4.8 | 7.4 | 11.1 |
| PO4 (PO-tetramer) | 344 | 62 | 6.0 | 7.9 | 12.1 | 18.1 |

Effect of Upconcentration on Overall Water Removal: an upconcentration stage was added as a final unit operation after purification prior to final recovery. This process entailed continuing to remove water from the process without addition of diafiltration water. Increasing the concentration from 20 wt % solids to 30 wt % solids resulted in removal of nearly 40% of the water in the system, which resulted in significantly reduced evaporation requirements in spray drying or lyophilization unit operations. Example water removal calculations are presented in Table 21.

TABLE 21

| kg HPBCD | kg water | Brix (wt % solids) | Water removed (%) |
|---|---|---|---|
| 2 | 8 | 20.0 | 0.0 |
| 2 | 7 | 22.2 | 12.5 |
| 2 | 6 | 25.0 | 25.0 |
| 2 | 5 | 28.6 | 37.5 |
| 2 | 4 | 33.3 | 50.0 |
| 2 | 3 | 40.0 | 62.5 |
| 2 | 2 | 50.0 | 75.0 |

Demo Run of Cavitron W7 HP7 using 1812 Spiral Wound Membrane: A 1 kg demonstration run was carried out using a 1812 membrane. Feedstock was prepared at 30 wt % by dissolving 1001.2 g of Cavitron HP7 into 2330 g of 18.2 MΩ water. The material was measured as 29 Brix.

Figure 58:
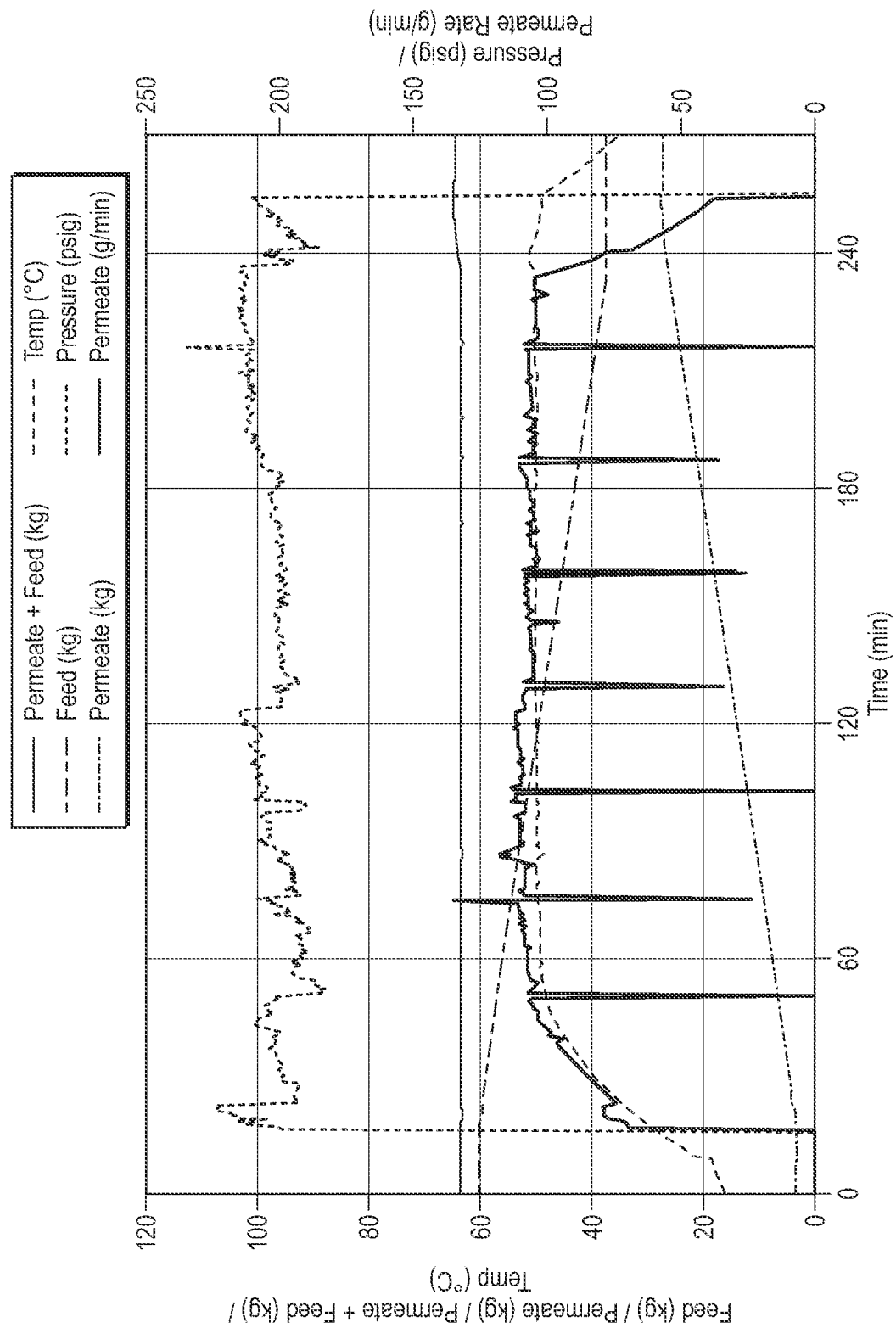
FIG. 58 shows process data from the nanofiltration of Cavitron HP7, including the permeate mass, the permeate mass flow rate, the feed mass, the combined permeate and feed mass, the temperature, and the pressure.

The nanofiltration skid was thoroughly cleaned by recirculating 8.0 L of 18.2 MΩ water through the skid for at least 5 minutes and then draining the skid. The process was repeated five times. Some carryover of water occurred in the membrane casing. After loading the material into the nanofiltration skid, the measured Brix had decreased to 18.2 due to the residual water, indicating a total volume of around 5.3 L. Diafiltration was started during the heating process with a removal of ~100 g/min (26 KMH) of permeate at a back pressure of ~200 psig and temperature of 50° C. The material was washed with ~4.5 diafiltration volumes generating a total permeate weight of 24 kg. Process data is provided in FIG. 58.

Figure 59:
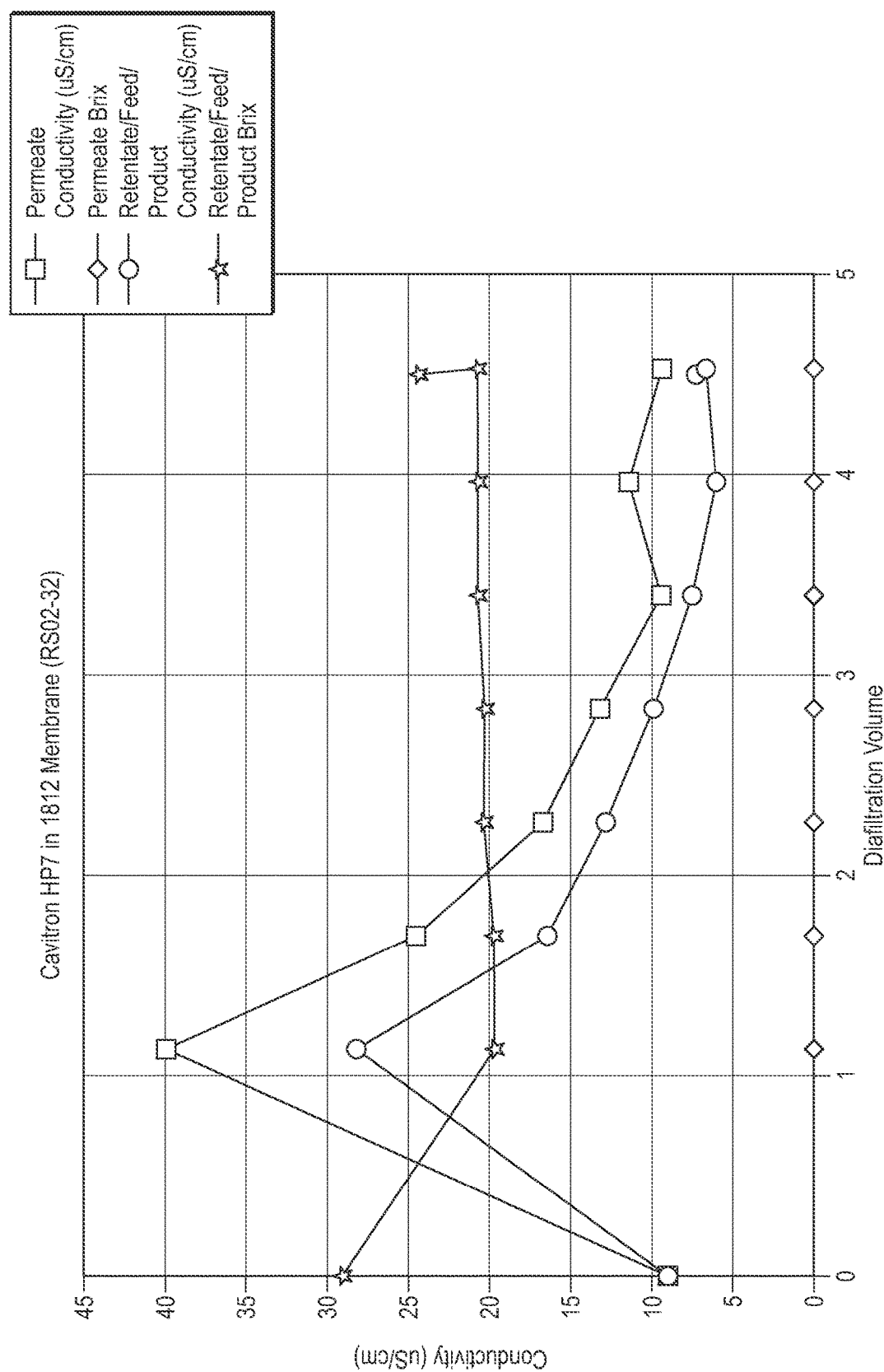
FIG. 59 shows the conductivity of the permeate, the permeate brix, the retentate/feed/product, and the retentate/feed/product brix for the purification of Cavitron HP7.

Samples were collected at roughly each diafiltration volume, and the conductivity of the permeate and retentate decreased over the course of the purification. No HPBCD was detected in the permeate. After the completion of the diafiltration process, a small amount of additional water was taken out to upconcentrate the final product to 24.3 Brix. The process resulted in recovering a total of 2.65 kg of material, corresponding to 0.64 kg HPBCD. The balance of material was presumed to be in the aqueous hold up/dead volume of the system. The data is shown in Table 22. The conductivity of the brix, permeate, and retentate during the diafiltration of Cavitron HP7 at 1.0 kg scale using an 1812 (0.23 m²) membrane is shown in FIG. 59.

TABLE 22

| Description | # DV | Permeate weight (kg) | Permeate Conductivity (uS/cm) | Permeate Brix | Retentate/ Feed/ Product Conductivity (uS/cm) | Retentate/ Feed/ Product Brix | Mass (kg) | HPBCD (kg) |
|---|---|---|---|---|---|---|---|---|
| Feed starting material | 0 | | 9 | | 9.0 | 29.0 | 3.3 | 0.97 |
| Sample 1 | 1.1 | 6 | 40 | 0 | 28.2 | 19.7 | | |
| Sample 2 | 1.7 | 9 | 24.5 | 0 | 16.4 | 19.7 | | |
| Sample 3 | 2.3 | 12 | 16.7 | 0 | 12.8 | 20.3 | | |
| Sample 4 | 2.8 | 15 | 13.2 | 0 | 9.9 | 20.3 | | |
| Sample 5 | 3.4 | 18 | 9.5 | 0 | 7.5 | 20.7 | | |
| Sample 6 | 4.0 | 21 | 11.4 | 0 | 6.0 | 20.7 | | |
| Sample 7 | 4.5 | 24 | 9.4 | 0 | 6.7 | 20.7 | | |
| Final product | 4.5 | | | | 7.2 | 24.3 | 2.65 | 0.64 |

Spiral Wound Membrane Production Runs

Figure 45:
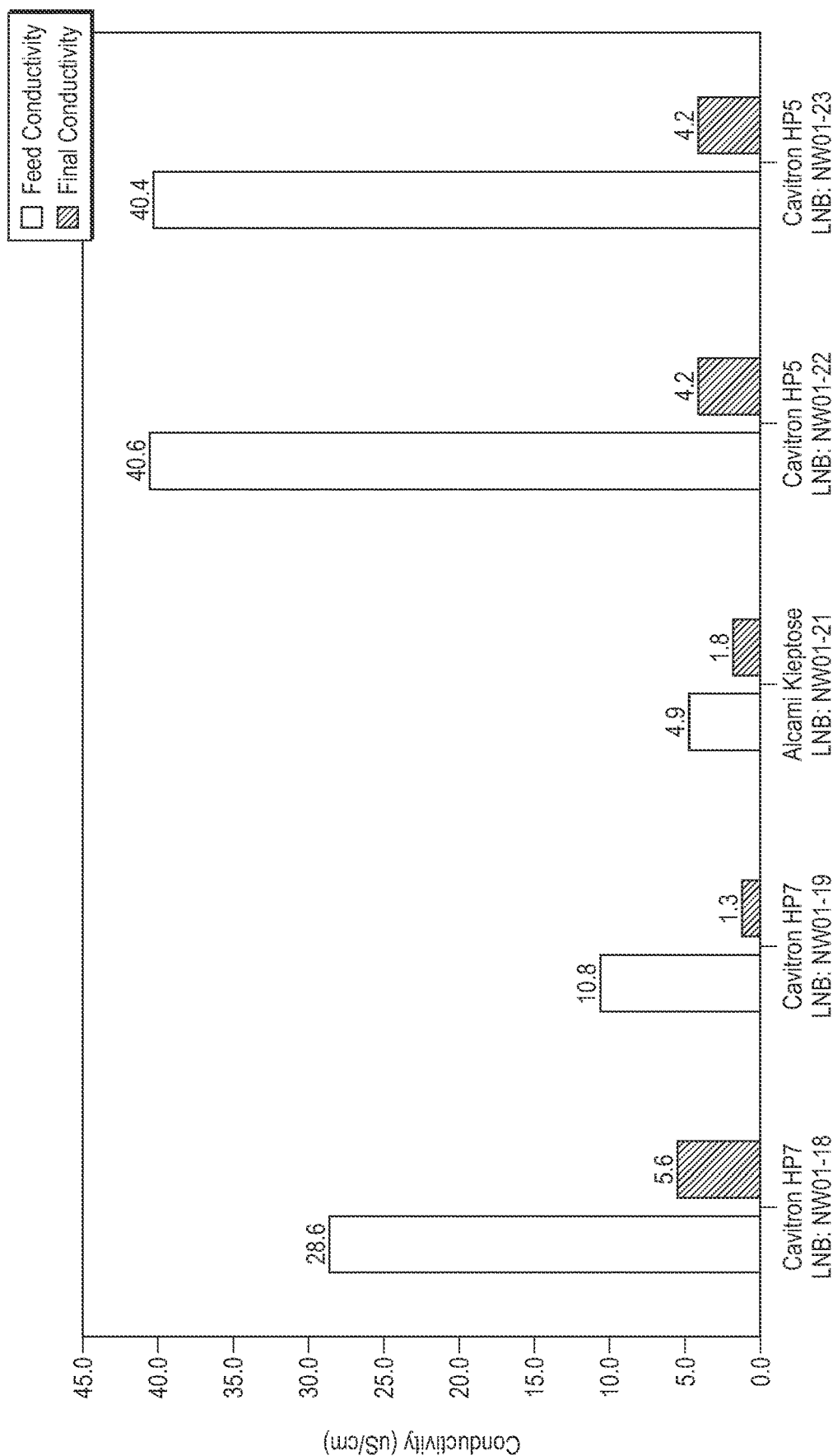
FIG. 45 shows the conductivity of Cavitron HP7, Alcami Kleptose, and Cavitron HP5 before and after nanofiltration using the methods described herein.

Bulk purification was carried out using a 2.5" diameter × 40" length (2540) membrane with 2.3 m² surface area, an order of magnitude higher than in the 1 kg demonstration run. The increase in flux from the additional surface area generally resulted in needing to carry out the filtration at lower than entitlement conditions in order to work with the existing equipment. Specifically, the operating pressure was tuned to maintain a flux of ~500 g/min and was generally quite low, no more than 100 psig. Samples of the permeate and retentate were taken at each diafiltration volume, and no HPBCD was detected in any of the permeates. The conductivity of the final product was always lower than the feedstock, indicating removal of inorganic impurities. As the feedstock was quite pure from going through the manufacturer's purification process, the total conductivity of both feed and purified product was always quite low. A summary of the conductivity of the HPBCD is shown in FIG. 45.

Feedstocks and purified products were analyzed by HPLC and ELSD detector. No difference was observed between the feedstock and purified products, which indicates that impurity removal was not impacting the main HPBCD molecule.

Feedstock and purified products were analyzed by NMR. Some very slight differences were observed.

Samples of permeate from Cavitron HP7 (NW01-19) purification were analyzed by ELSD, and no HPBCD was found in the permeate.

Purification of Cavitron W7 HP7 Pharma: Purification of Cavitron W7 HP7 Pharma material was carried out in two experiments. Feedstock was prepared at 20 wt % by dissolving Cavitron HP7 into 18.2 MΩ water. The material was measured as 20.2 (LNB: NW01-18) and 19.5 (LNB: NW01-19) Brix. Material was diafiltered using 5 volumes of 18.2 MΩ water and subjected to a final upconcentration before being discharged. Final Brix upon discharge was 24.2 and 27.0. The two lots were blended together to give a single final product. The results for the NW-01-18 and the NW01-19 runs are shown in Tables 23A and 231B, respectively.

TABLE 23A

| Description | # DV | Permeate Conductivity (μS/cm) | Permeate Brix | Retentate/ Feed/ Product Conductivity (μS/cm) | Retentate/ Feed/ Product Brix | Mass (kg) | HPBCD (kg) |
|---|---|---|---|---|---|---|---|
| Feed | 0 | | | 28.6 | 20.2 | 10.0 | 2.02 |
| Sample 1 | 1 | 7.2 | 0 | 12.1 | 20.3 | | |
| Sample 2 | 2 | 6.52 | 0 | 8.5 | 19.9 | | |
| Sample 3 | 3 | 3.15 | 0 | 6.3 | 19.4 | | |
| Sample 4 | 4 | 2.02 | 0 | 3.1 | 20.2 | | |
| Sample 5 | 5 | 1.92 | 0 | 4.6 | 19.1 | | |
| Final product | 5 | | | 5.6 | 24.2 | 9.13 | 2.21 |

TABLE 23B

| Description | # DV | Permeate Conductivity (μS/cm) | Permeate Brix | Retentate/ Feed/ Product Conductivity (μS/cm) | Retentate/ Feed/ Product Brix | Mass (kg) | HPBCD (kg) |
|---|---|---|---|---|---|---|---|
| Feed | 0 | | | 10.8 | 19.5 | 8.12 | 1.58 |
| Sample 1 | 1 | 5.94 | 0 | 6.1 | 19.9 | | |
| Sample 2 | 2 | 3.7 | 0 | 4.3 | 20.0 | | |
| Sample 3 | 3 | 2.1 | 0 | 3.4 | 20.1 | | |

TABLE 23B-continued

| Description | # DV | Permeate Conductivity (μS/cm) | Permeate Brix | Retentate/ Feed/ Product Conductivity (μS/cm) | Retentate/ Feed/ Product Brix | Mass (kg) | HPBCD (kg) |
|---|---|---|---|---|---|---|---|
| Sample 4 | 4 | 1.96 | 0 | 3.2 | 20.1 | | |
| Sample 5 | 5 | 1.15 | 0 | 2.8 | 20.3 | | |
| Final product | 5 | NA | | 1.3 | 27.0 | 4.82 | 1.30 |

Figure 46:
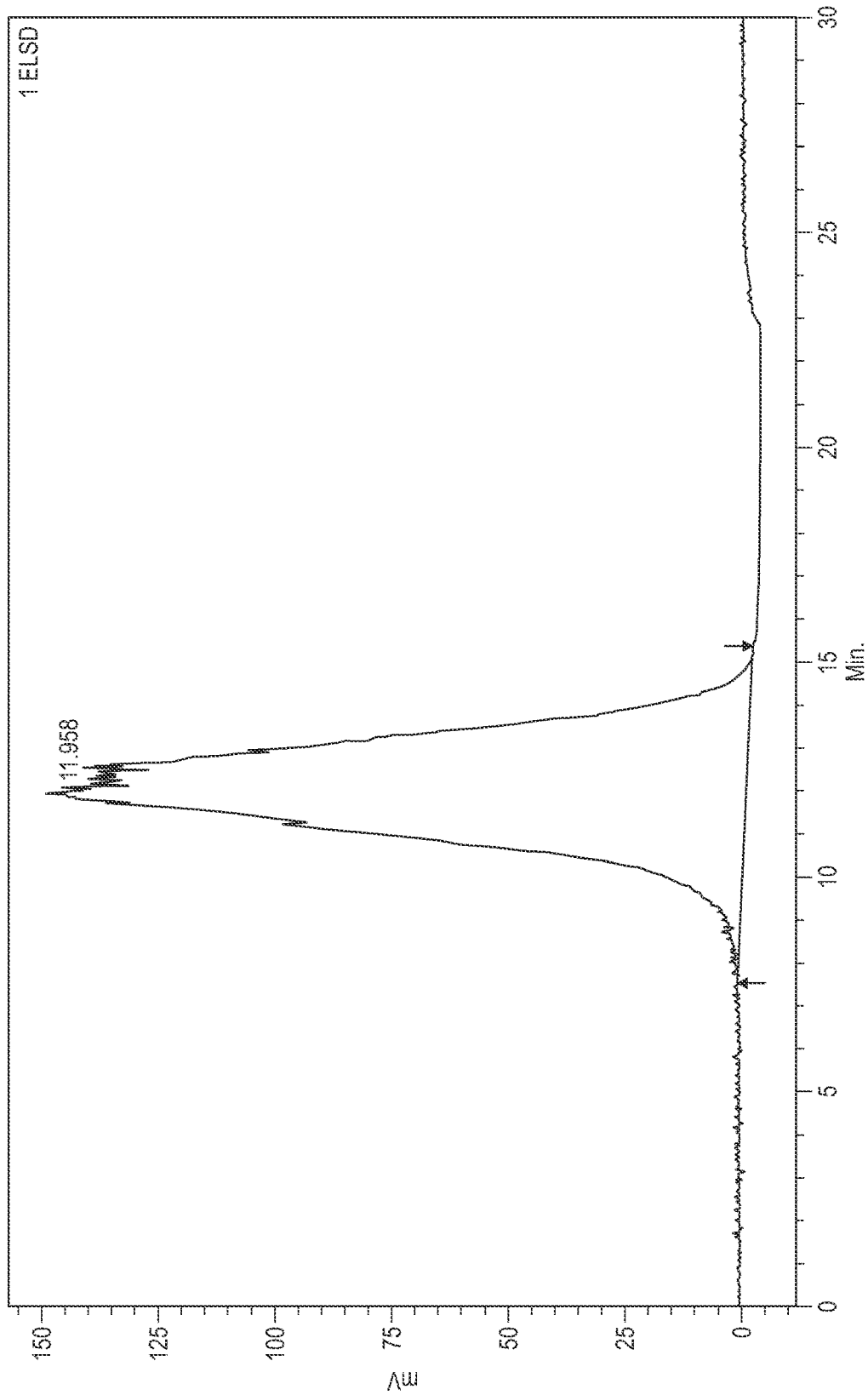
FIG. 46 shows a HPLC-ELSD spectrum of Cavitron HP7 before nanofiltration using the methods described herein.
Figure 48:
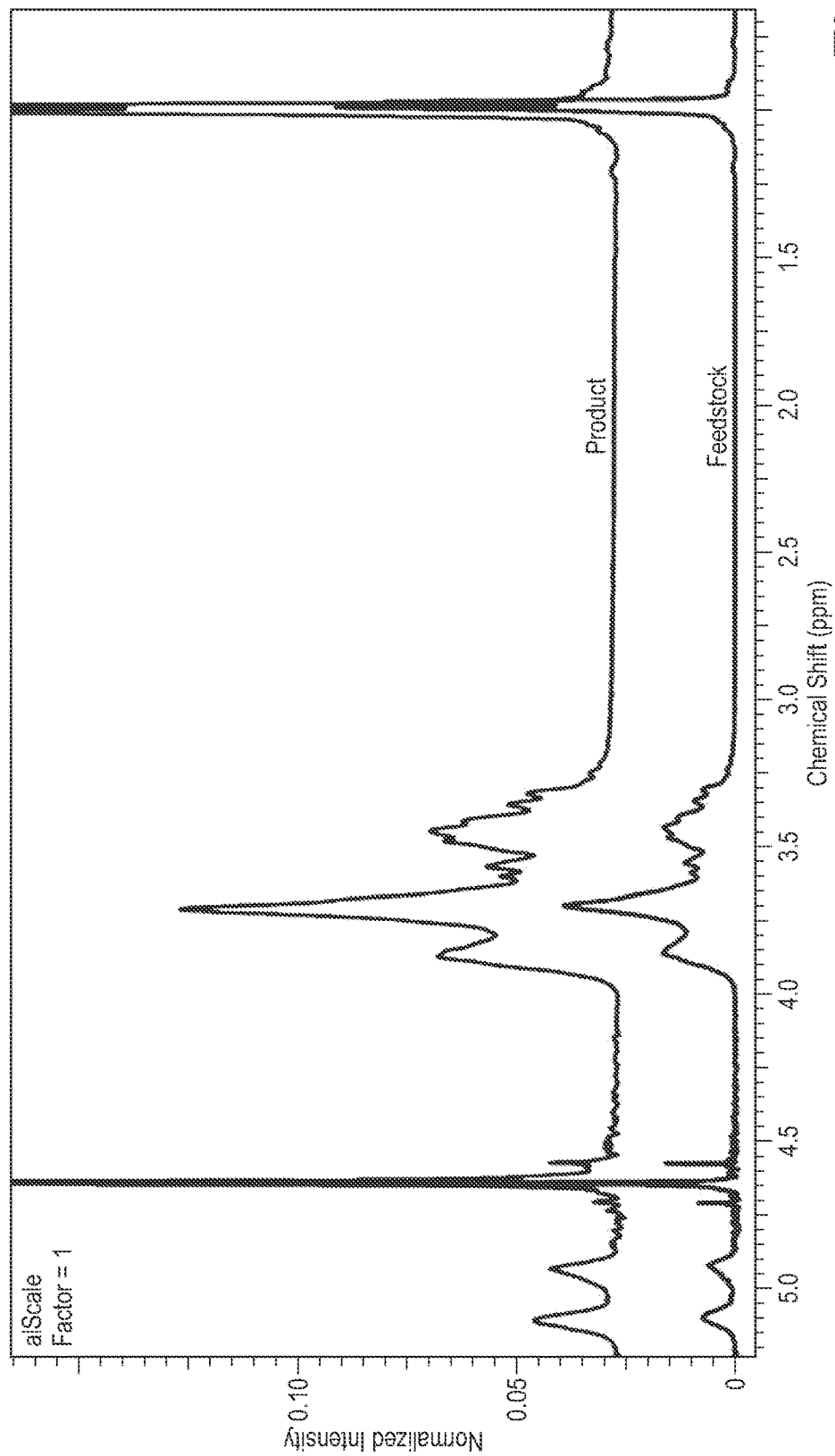
FIG. 48 shows $^1$H-NMR spectra of Cavitron HP7 before and after nanofiltration using the methods described herein.
Figure 49:
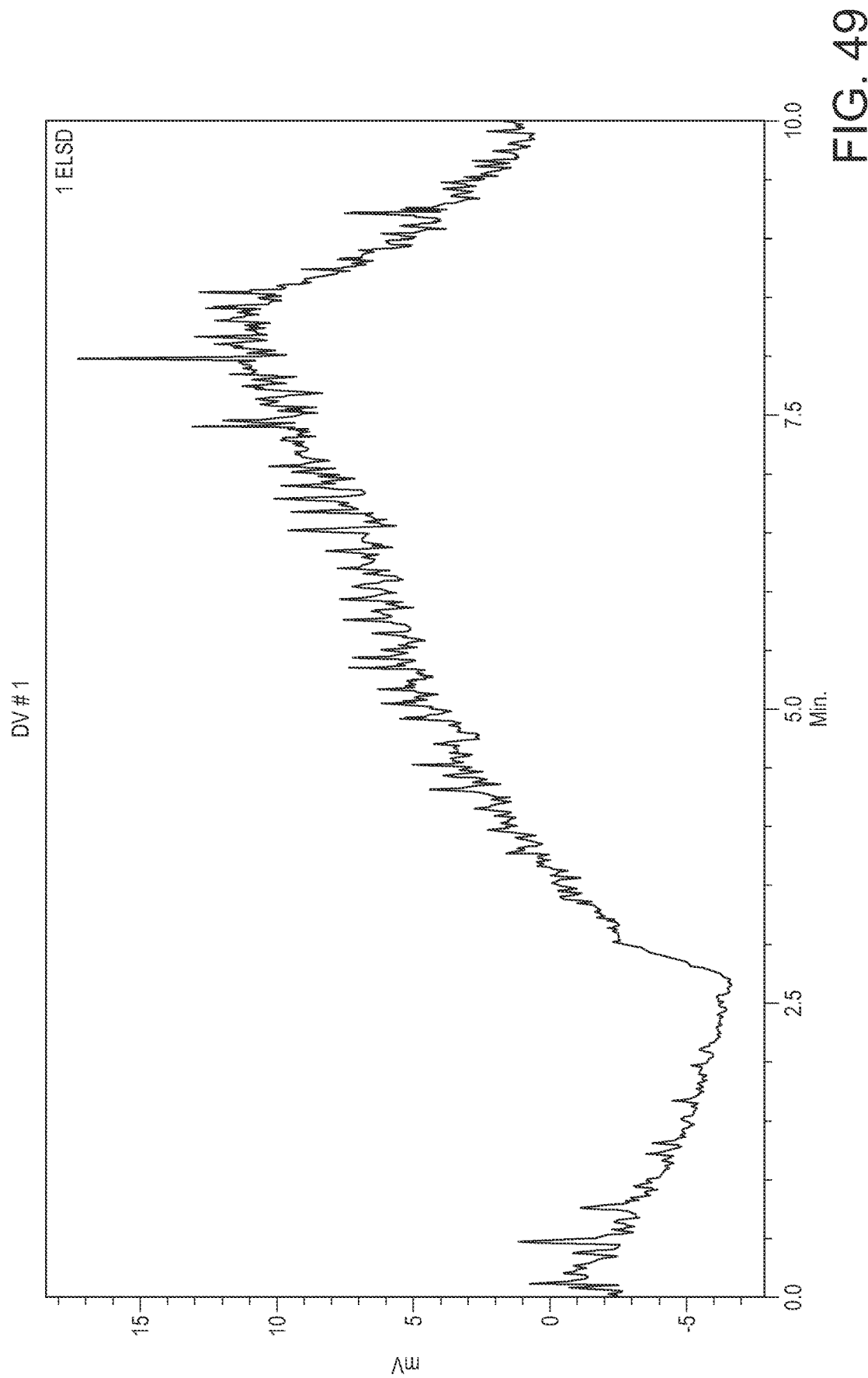
FIG. 49 shows a HPLC-ELSD spectrum of the permeate of the first diafiltration volume of Cavitron HP7.
Figure 50:
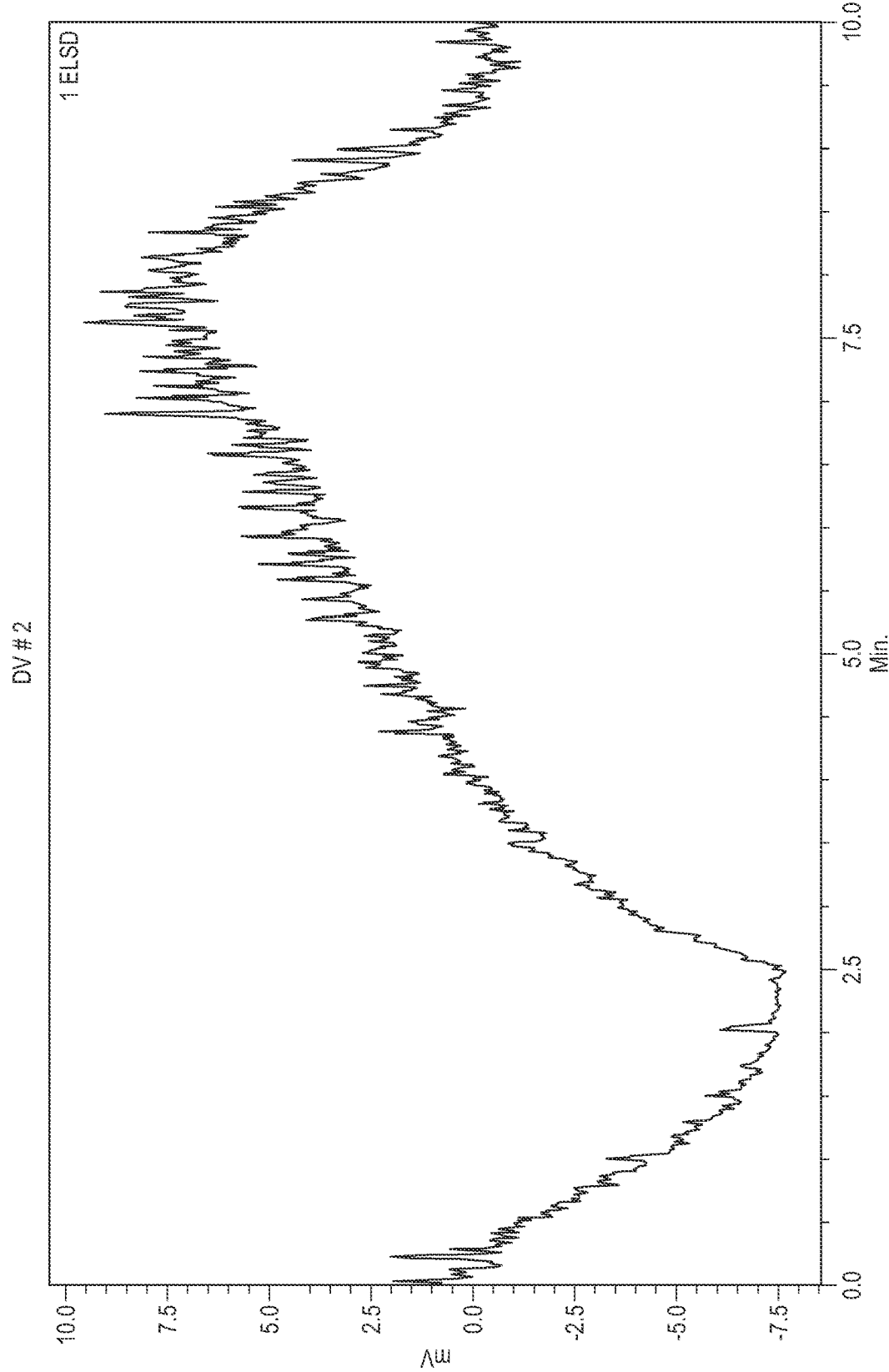
FIG. 50 shows a HPLC-ELSD spectrum of the permeate of the second diafiltration volume of Cavitron HP7.
Figure 51:
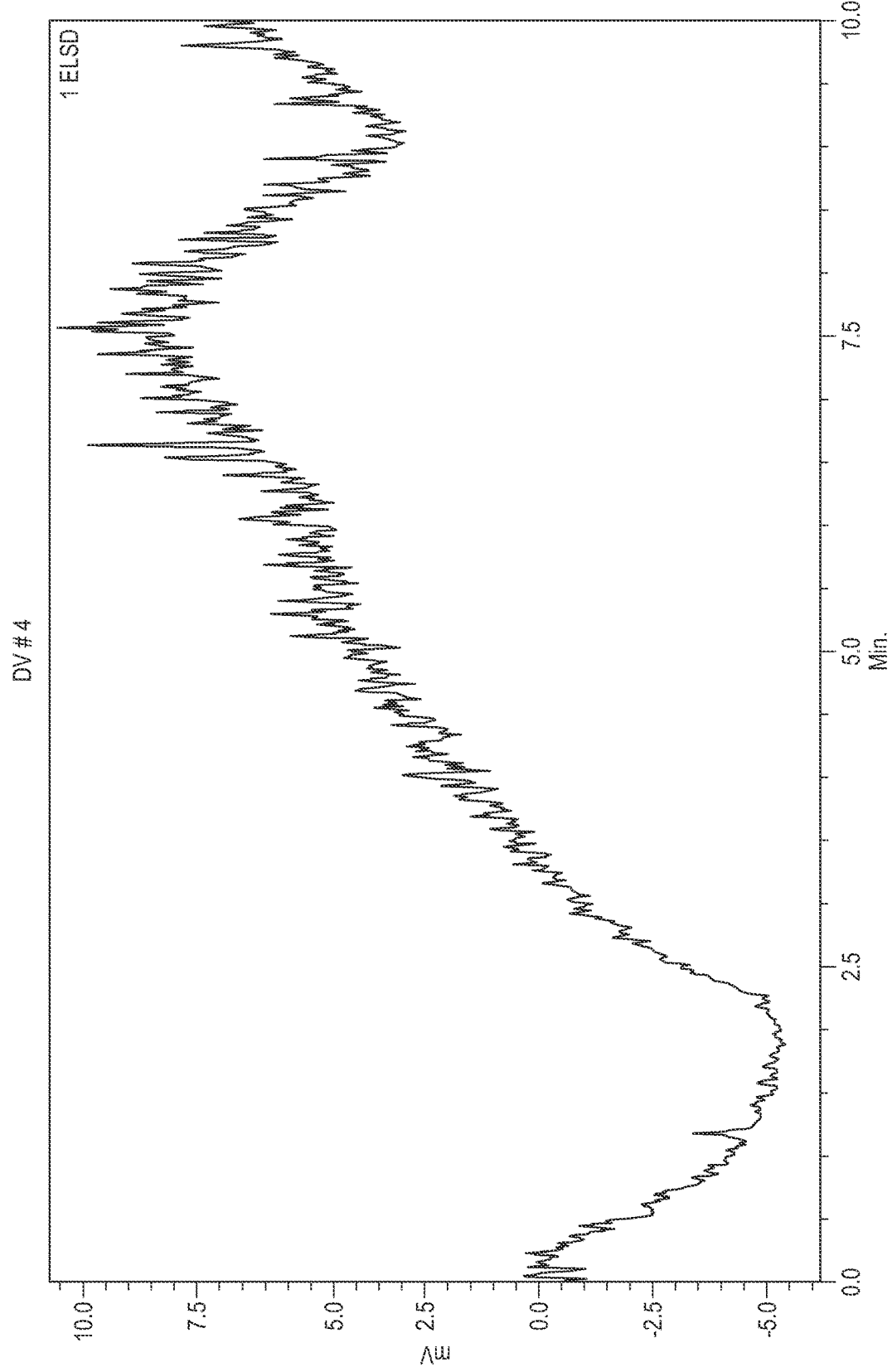
FIG. 51 shows a HPLC-ELSD spectrum of the permeate of the fourth diafiltration volume of Cavitron HP7.
Figure 52:
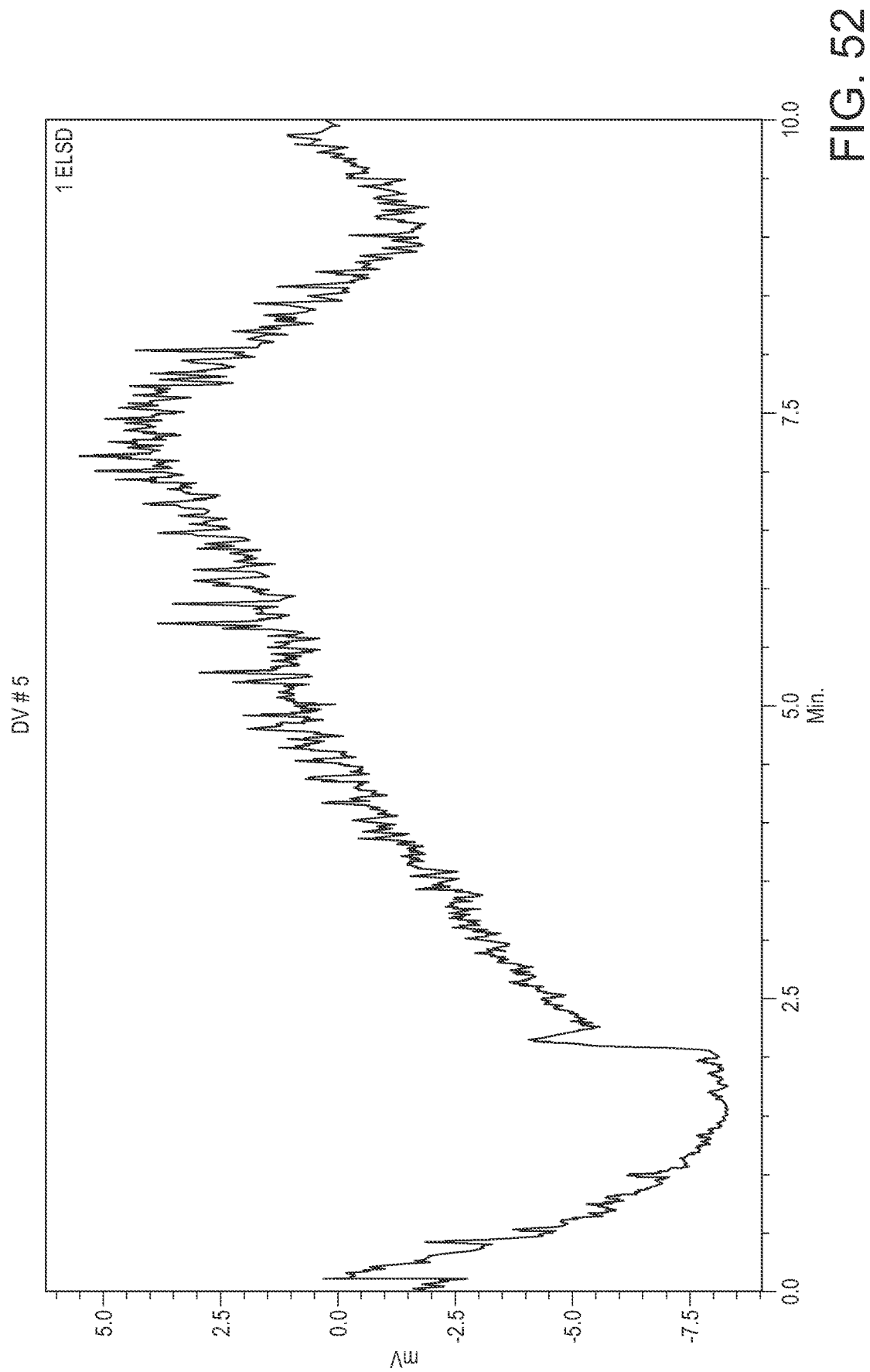
FIG. 52 shows a HPLC-ELSD spectrum of the permeate of the fifth diafiltration volume of Cavitron HP7.

Samples of permeate and retentate from each diafiltration volume from NW01-19 were analyzed by HPLC-ELSD and were found to not have any HPBCD present. HPLC-ELSD spectra for the gross mixture of Cavitron HP7 are shown in FIG. 46 (before filtration) and FIG. 47 (after filtration). The HPLC-ELSD spectra for four of the diafiltration volumes are shown in FIGS. 49-52 (permeate) and FIGS. 53-57 (retentate). Note that the HPLC-ELSD spectra for diafiltration volume #3 permeate is not included. The $^1$H-NMR spectra before (feedstock) and after (product) purification is shown in FIG. 48.

Figure 60:
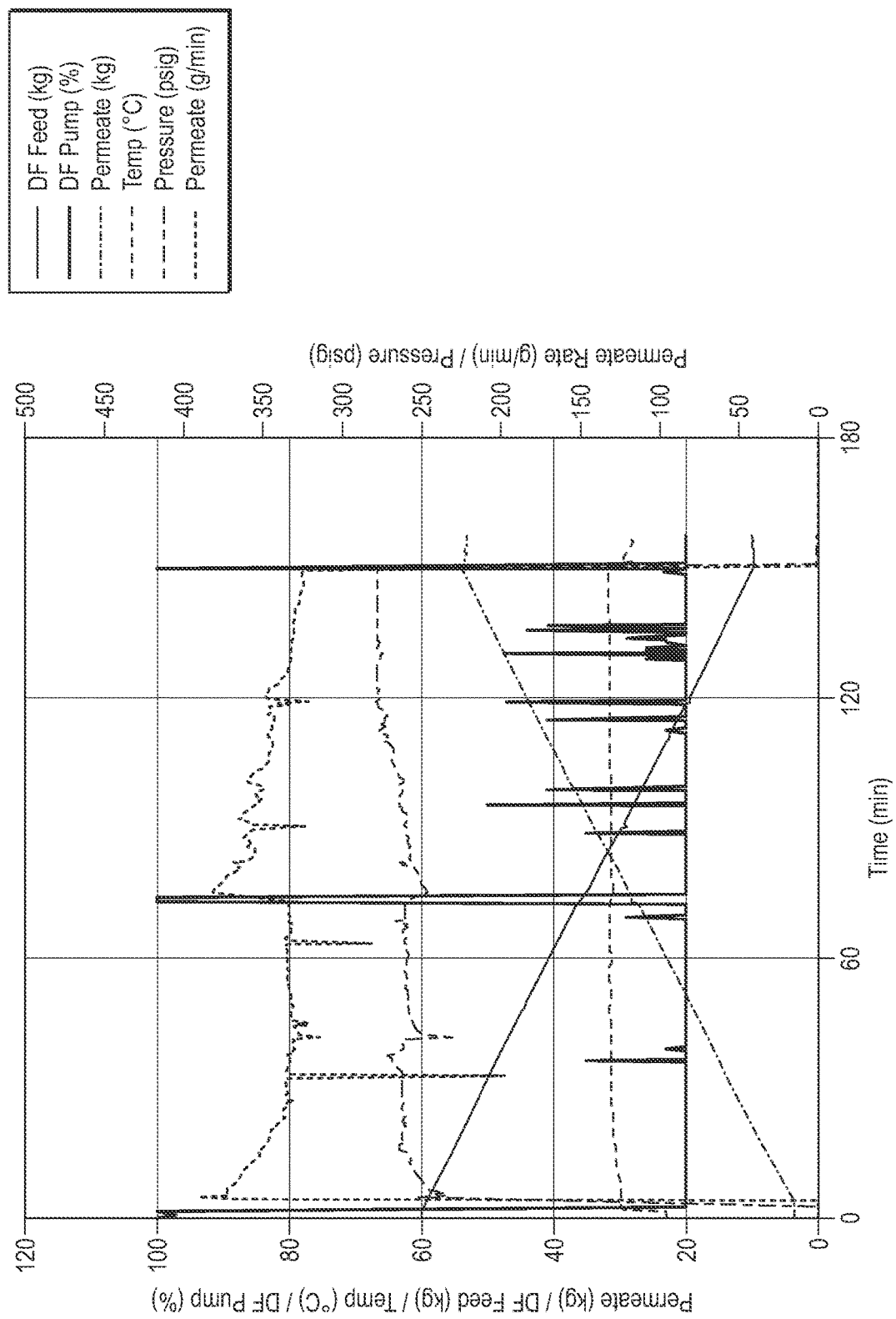
FIG. 60 shows process data from the nanofiltration of Cavitron HP5, including the permeate mass, the permeate mass flow rate, the feed mass, the temperature, the pressure, and the pump.

Purification of Cavitron HP5 Pharma: Purification of Cavitron HP5 Pharma material was carried out in two experiments. Feedstock was prepared by dissolving Cavitron HP5 into 18.2 MΩ water. The material was measured as 24.5 (LNB: NW01-22) and 27.1 (LNB: NW01-23) Brix. Material was diafiltered using 5 volumes of 18.2 MΩ water and subjected to a final upconcentration before being discharged. No cleaning was done between runs, and the mass balance on the second run was very good due to recovery of the retained material. The final Brix upon discharge was 31 and 28. The two lots were blended together to give a single final product. The flux at the higher concentration was lower compared to other experiments due to the higher viscosity, which resulted in operating at higher back pressure. The additional pressure requirements were not problematic, and the overall run was quite smooth. The results for the NW01-22 and the NW01-23 are shown in Tables 24A and 24B, respectively. The data from the experiment is shown in FIG. 60.

TABLE 24A

| Description | # DV | Permeate Conductivity (μS/cm) | Permeate Brix | Retentate/ Feed/ Product Conductivity (μS/cm) | Retentate/ Feed/ Product Brix | Mass (kg) | HPBCD (kg) |
|---|---|---|---|---|---|---|---|
| Feed | 0 | | | 40.6 | 24.5 | 10.0 | 2.45 |
| Sample 1 | 1 | 22.33 | 0 | 17.7 | 23.5 | | |
| Sample 2 | 2 | 11.14 | 0 | 9.5 | 23.4 | | |
| Sample 3 | 3 | 9.23 | 0 | 6.8 | 24.7 | | |
| Sample 4 | 4 | 6.46 | 0 | 4.6 | 25.2 | | |
| Sample 5 | 5 | 3.17 | 0 | 4.5 | 26.0 | | |
| Final product | 5 | | | 4.2 | 31 | 6.66 | 2.06 |

TABLE 24B

| Description | # DV | Permeate Conductivity (μS/cm) | Permeate Brix | Retentate/ Feed/ Product Conductivity (μS/cm) | Retentate/ Feed/ Product Brix | Mass (kg) | HPBCD (kg) |
|---|---|---|---|---|---|---|---|
| Feed | 0 | | | 40.4 | 27.1 | 10 | 2.71 |
| Sample 1 | 1 | 27.22 | 0 | 15.2 | 29.0 | | |
| Sample 2 | 2 | 14.1 | 0 | 12.8 | 29.3 | | |
| Sample 3 | 3 | 9.58 | 0 | 5.2 | 28.5 | | |
| Sample 4 | 4 | 8.76 | 0 | 4.9 | 29.2 | | |
| Sample 5 | 5 | 8.28 | 0 | 4.2 | 30.3 | | |
| Final product | 5 | | | 4.2 | 27.9 | 9.16 | 2.56 |

Figure 61:
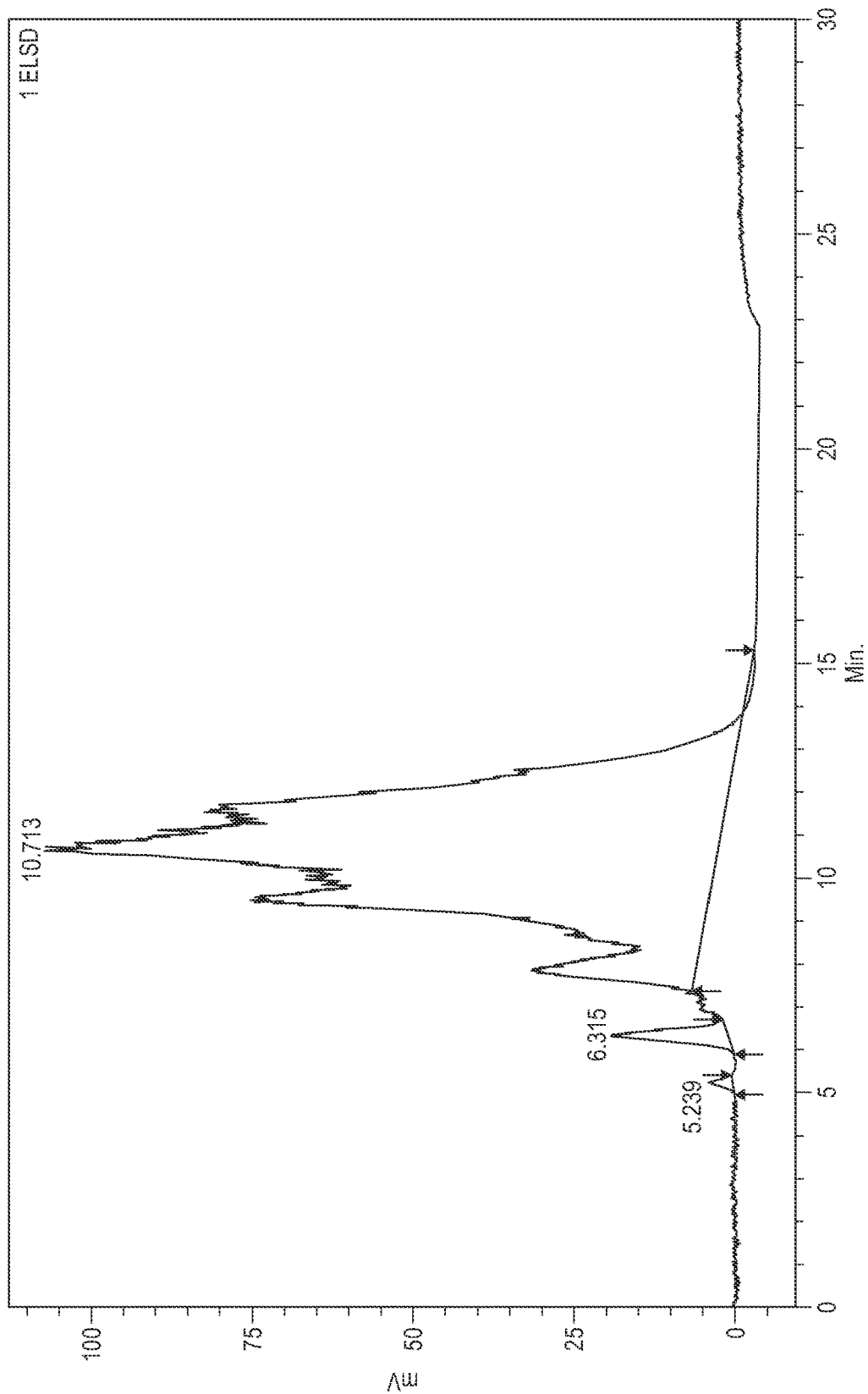
FIG. 61 shows a HPLC-ELSD spectrum of Cavitron HP5 before nanofiltration using the methods described herein.
Figure 62:
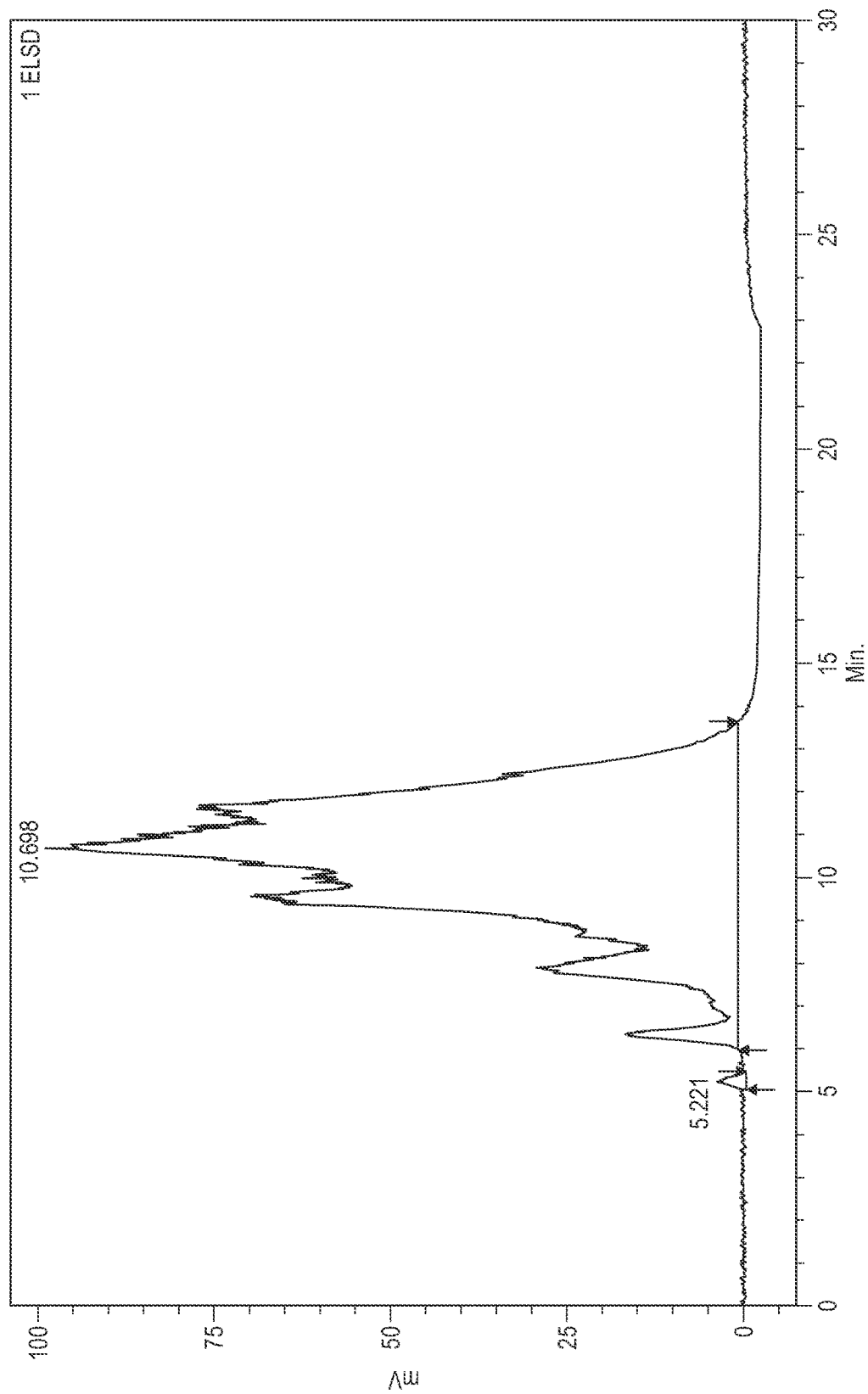
FIG. 62 shows a HPLC-ELSD spectrum of Cavitron HP5 after nanofiltration using the methods described herein.
Figure 63:
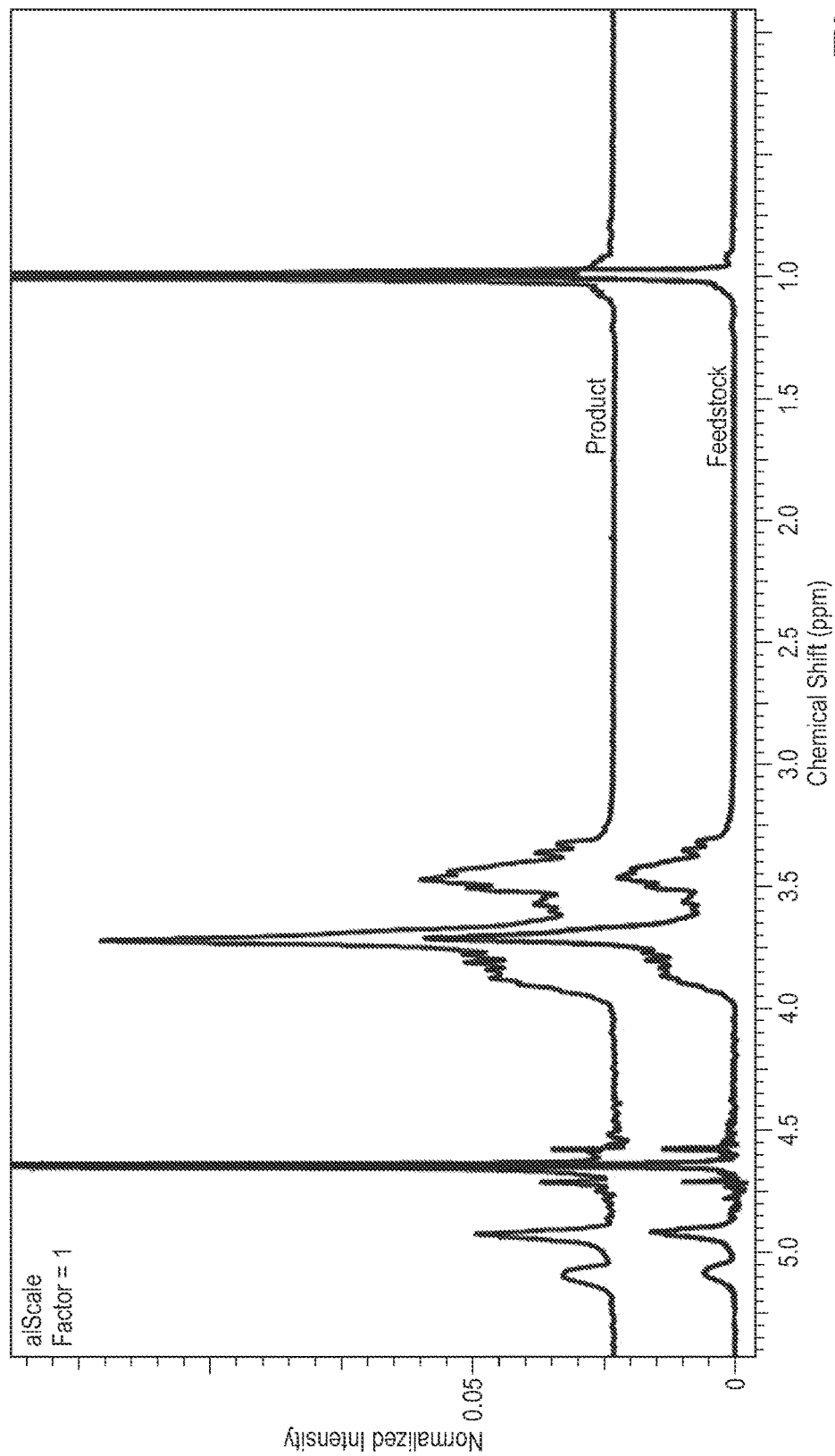
FIG. 63 shows $^1$H-NMR spectra of Cavitron HP5 before and after nanofiltration using the methods described herein.
Figure 64:
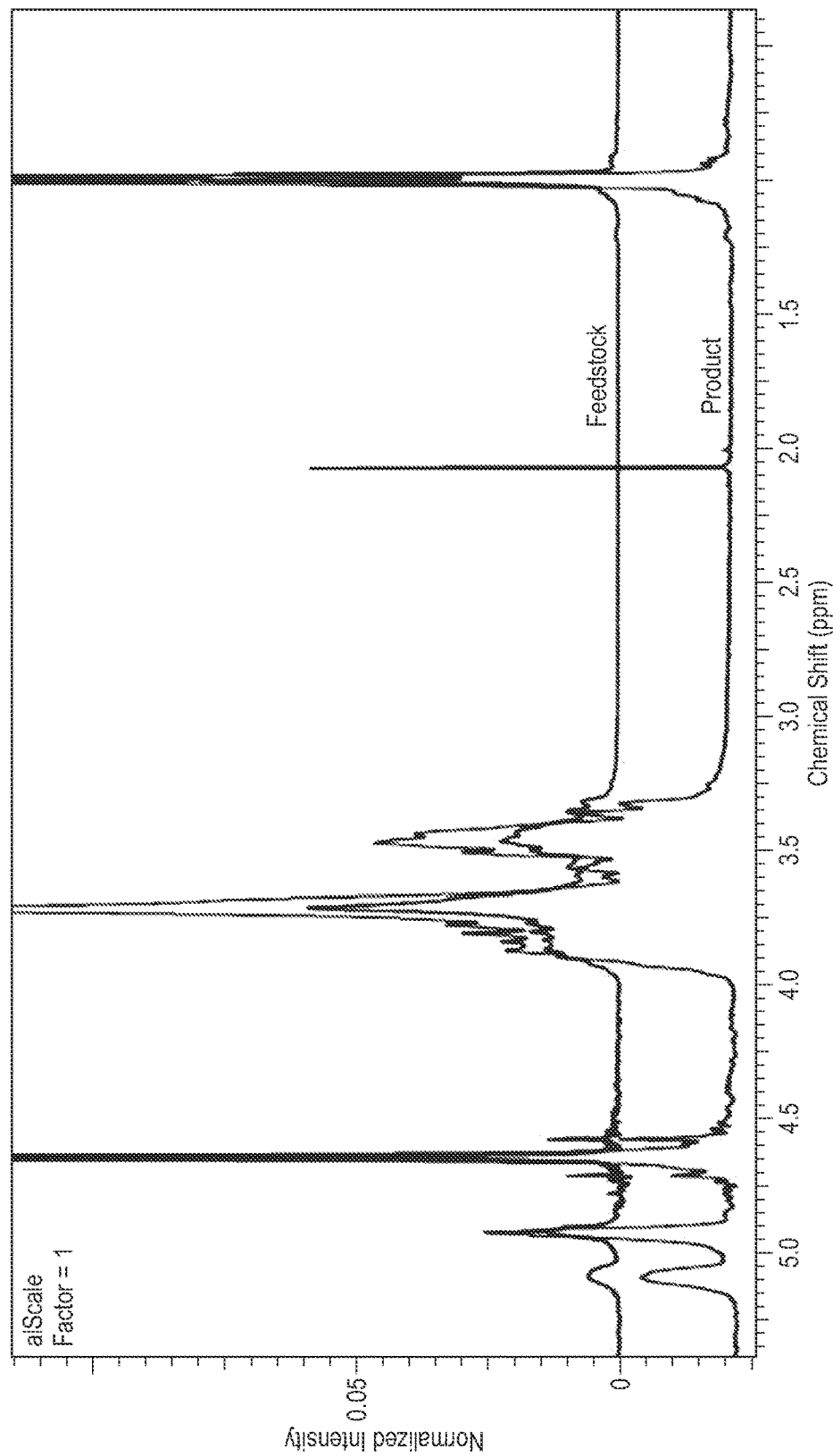
FIG. 64 shows another $^1$H-NMR spectra of Cavitron HP5 before and after nanofiltration using the methods described herein.

The HPLC-ELSD spectra for the composition before and after purification are shown in FIGS. 61 and 62, respectively. The HNMR spectra for the NW01-22 and NW01-23 runs are shown in FIGS. 63 and 64, respectively.

Figure 65:
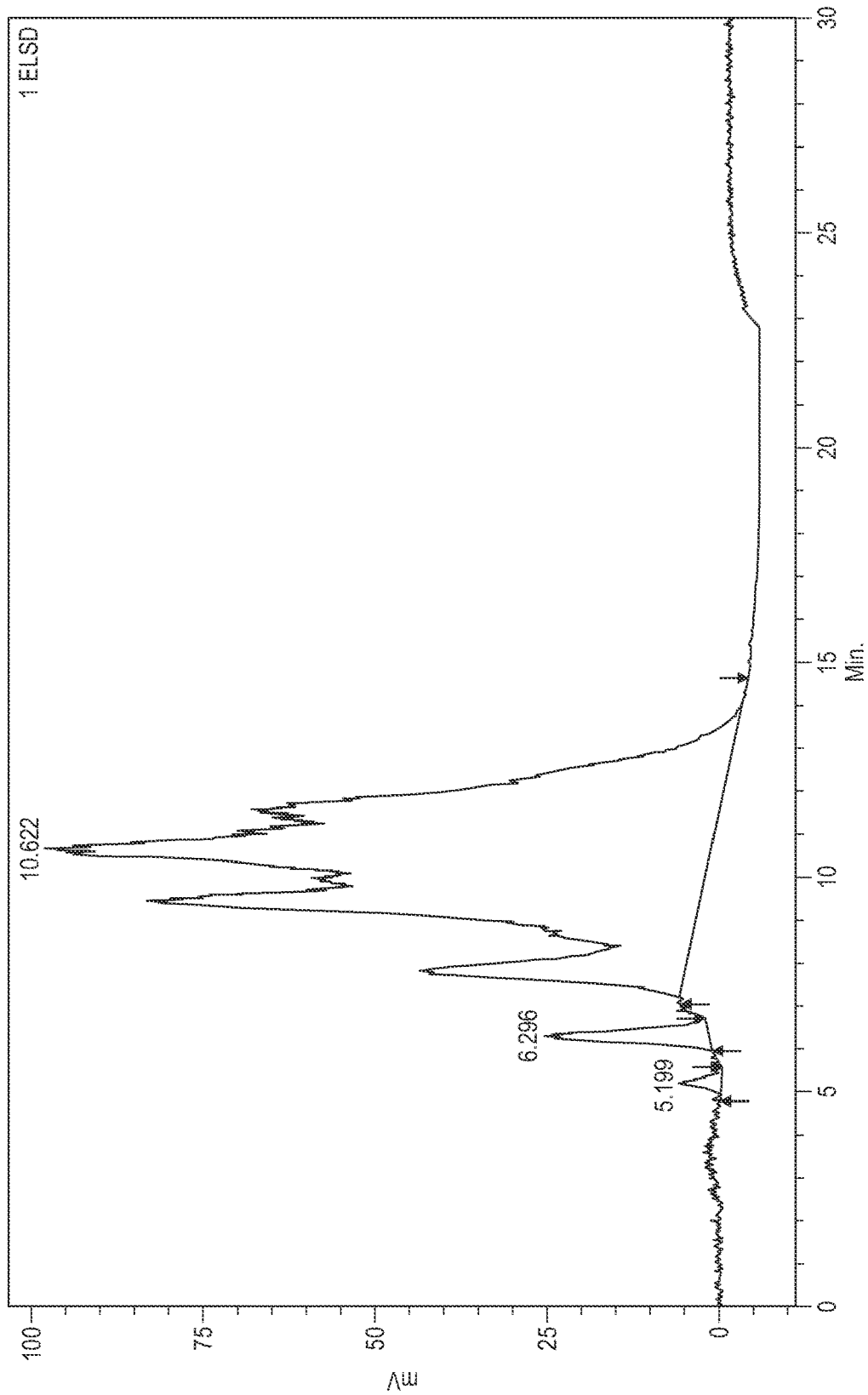
FIG. 65 shows a HPLC-ELSD spectrum of Alcami Kleptose before nanofiltration using the methods described herein.
Figure 66:
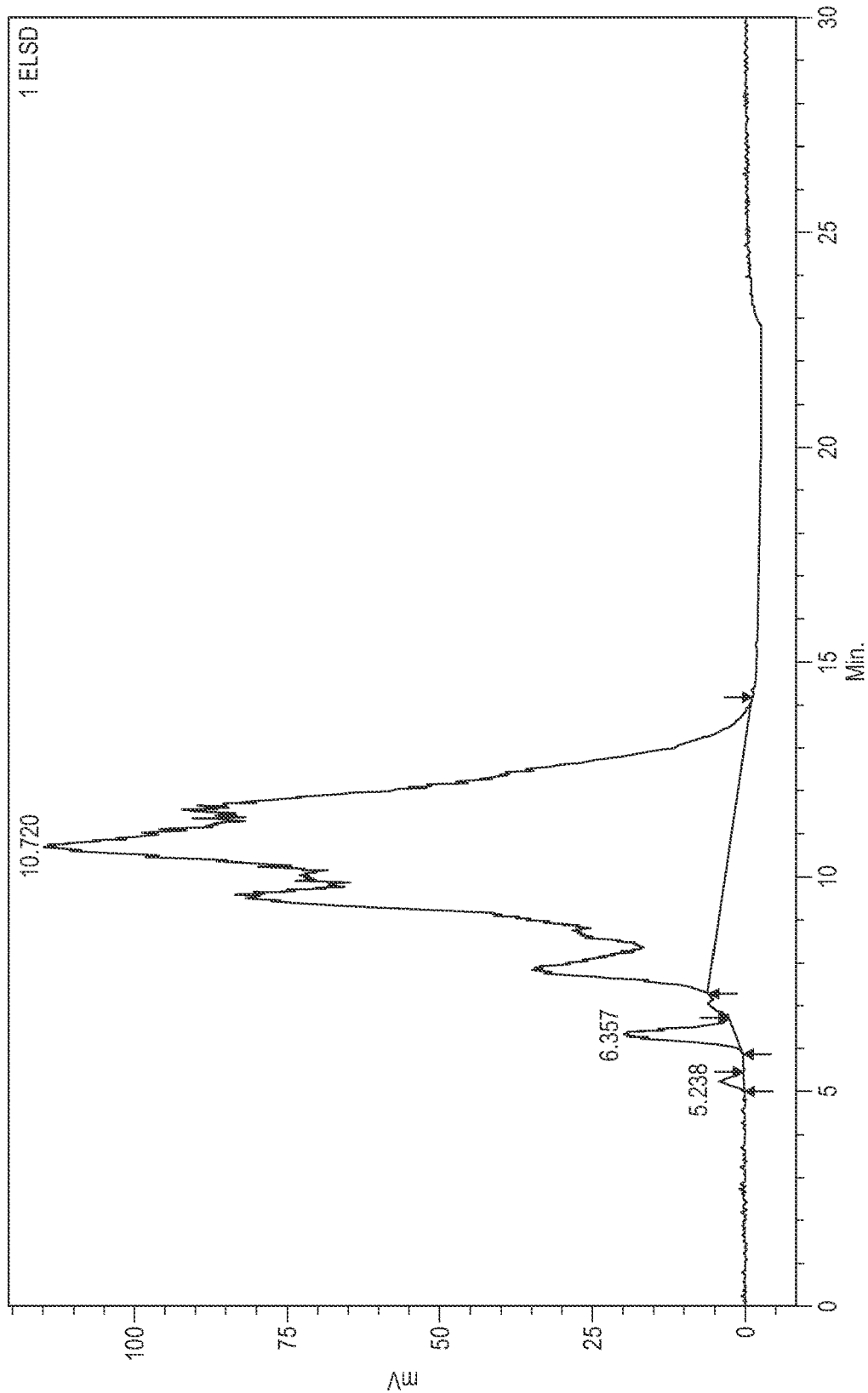
FIG. 66 shows a HPLC-ELSD spectrum of Alcami Kleptose after nanofiltration using the methods described herein.
Figure 67:
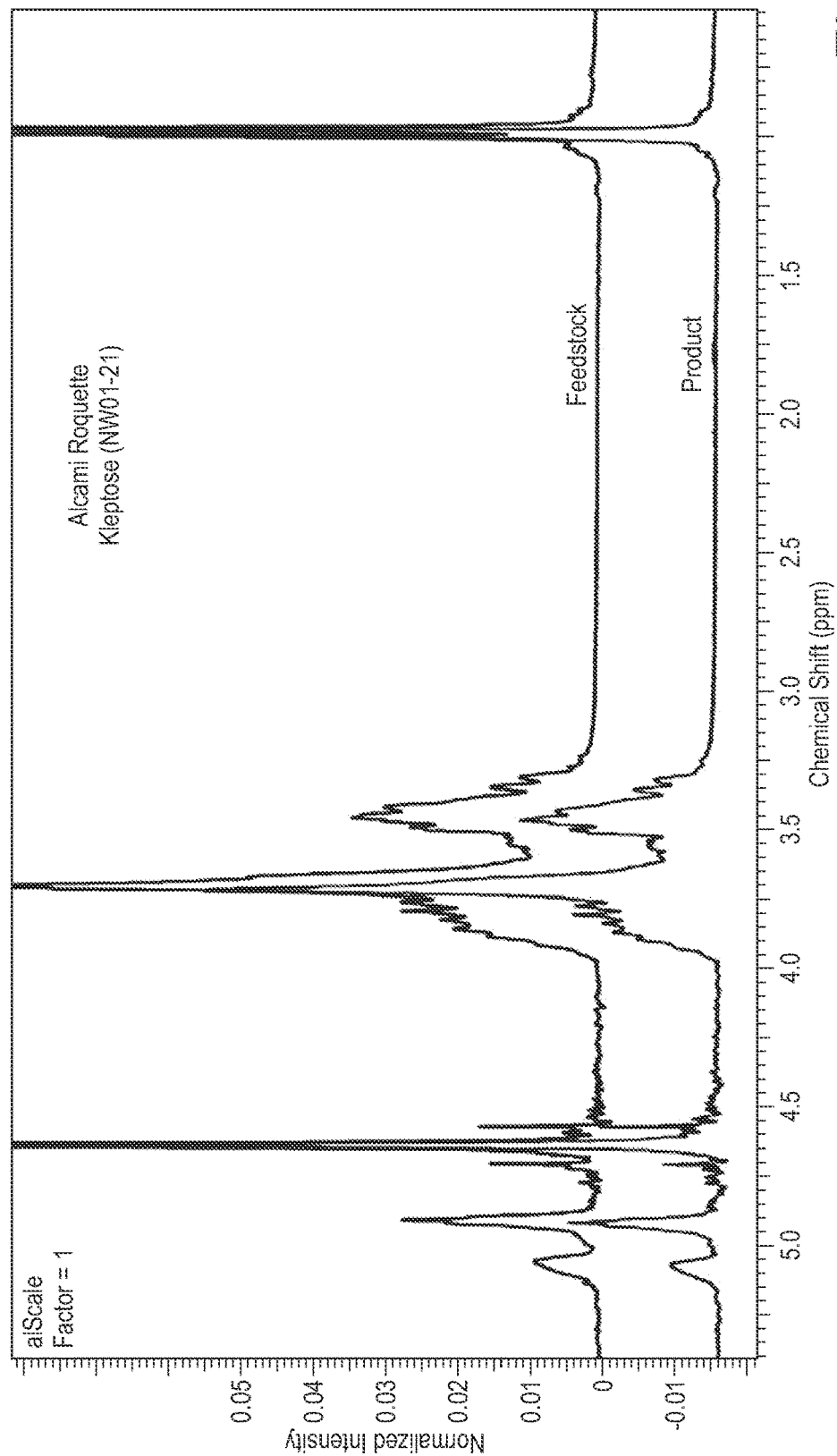
FIG. 67 shows $^1$H-NMR spectra of Alcami Kleptose before and after nanofiltration using the methods described herein.

Purification of Alcami Roquette Kleptose: Purification of Alcami Roquette Kleptose was carried out in one experiment. Feedstock was prepared by dissolving the Kleptose into 18.2 MΩ water. The material was measured as 19.3 (LNB: NW1-21) Brix. Material was diafiltered using 5× volumes of 18.2 MΩ water and subjected to a final upconcentration before being discharged. No cleaning was done between runs, and the mass balance on the second run was very good due to recovery of the retained material. The final Brix upon discharge was 25.6. The experimental results appear in Table 25. The HPLC-ELSD spectra for the composition before and after purification are shown in FIGS. 65 and 66, respectively. The HNMR spectra for the composition before (feedstock) and after (product) is shown in FIG. 67.

TABLE 25

| Description | # DV | Permeate Conductivity (uS/cm) | Permeate Brix | Retentate/ Feed/ Product Conductivity (uS/cm) | Retentate/ Feed/ Product Brix | Mass (kg) | HPBCD (kg) |
|---|---|---|---|---|---|---|---|
| Feed | 0 | | | 4.9 | 19.3 | 9.5 | 1.83 |
| Sample 1 | 1 | 2.9 | 0 | 3.1 | 18.9 | | |
| Sample 2 | 2 | 1.5 | 0 | 1.9 | 19.0 | | |
| Sample 3 | 3 | 1.39 | 0 | 1.8 | 18.9 | | |
| Sample 4 | 4 | 1.15 | 0 | 1.3 | 19.1 | | |
| Sample 5 | 5 | 1.04 | 0 | 1.2 | 19.1 | | |
| Final product | 5 | | | 1.8 | 25.6 | 5.23 | 1.34 |

Commercial Manufacturing Sizing Calculations

Commercial sizing estimates were made for a batch-based process using the fluxes obtained, notably 26 KMH at a feed concentration of 20 wt % and 5 diafiltration volumes to achieve the required purity. Further assumptions include 24/7 operations with 18 hours of diafiltration, 2 hours of upconcentration, and 4 hours of membrane CIP/material prep. The resulting product stream would be ~29 wt % solids, which should be readily processable and suitable for either antisolvent crystallization or spray drying. It is anticipated that the CIP can be done less frequently.

For a throughput of 1000 kg HPBCD per day (~365 ton/year), the quantity of diafiltration water required is 25000 kg/day with permeate being generated at a rate of ~1400 kg/hour and diafiltration water being added at an equivalent rate. The required membrane surface area is 53.4 m², which is 79% of surface area present in 2×8040 Trisep XN45 membranes. During upconcentration, it is assumed that the average flux reduces to 15 KMH due to the increased viscosity of the solution at the higher concentration. Over two hours of ontime, an additional 1603 kg of water is purged from the system, which results in a final solution mass of 3397 kg and a solution concentration of 29.4 wt % solids. With a properly designed system, it is anticipated for a holdup volume to be on the order of ~60 kg (2%), and if the membrane is cleaned after each batch, this material would be lost. Subsequent batch processing would result in this material being recovered. The feed vessel for a process would be roughly 6 m³ (1584 gal) and should be well agitated with a mixing time on the order of 5 minutes or less. More advanced designs, such as multiple continuous loops, could be implemented which could result in slightly smaller feed tanks at the expense of a more complicated process.

Wastewater Analysis from purification of commercial HPBCD (Wacker Cavitron HP5): During the purification of Wacker Cavitron HP5 in test NW01-23, the first diafiltration volume of permeate was sampled and submitted to a third-party lab for wastewater analysis. The first volume would have the highest fraction of sodium chloride and impurities and represents a worst case scenario. The material was found to have a chemical oxygen demand of 229 mg/L with a biochemical oxygen demand less than the detectable limit of 44 mg/L. Nitrogen was not detected, total suspended solids (TSS), and total solids (TS) were quite low. Discharge from a manufacturing plant would be even lower than what is indicated here by blending more dilute permeate from later diafiltration volumes with the first diafiltration volume.

Having described several embodiments, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present systems and methods, which, as a matter of language, might be said to fall therebetween.

What is claimed is:

1. A composition comprising a mixture of isomerically-purified hydroxypropyl β-cyclodextrin molecules comprising: β-cyclodextrin substituted with seven hydroxypropyl groups ("DS-7"); wherein the mixture further comprises less than 1% by mass β-cyclodextrin substituted with five hydroxypropyl groups ("DS-5"), and wherein the mixture has an average degree of substitution of 6.02-7.98, and wherein the total amount of impurities are measured to be less than or equal to 0.05% by HPLC.

2. The composition of claim 1, wherein the mixture further comprises less than 1% by mass β-cyclodextrin substituted with four hydroxypropyl groups ("DS-4").

3. The composition of claim 1, wherein the mixture further comprises less than 1% by mass β-cyclodextrin substituted with three hydroxypropyl groups ("DS-3").

4. The composition of claim 1, wherein the mixture further comprises less than 0.05% by mass unsubstituted beta-cyclodextrin ("DS-0") and less than 0.05% by mass β-cyclodextrin substituted with one hydroxypropyl group ("DS-1").

5. The composition of claim 1, wherein the mixture further comprises less than 1% by mass β-cyclodextrin substituted with eight hydroxypropyl groups ("DS-8").

6. The composition of claim 1, wherein the mixture further comprises less than 1% by mass β-cyclodextrin substituted with nine hydroxypropyl groups ("DS-9").

7. The composition of claim 1, wherein the mixture further comprises less than 1% by mass β-cyclodextrin substituted with ten hydroxypropyl groups ("DS-10").

8. The composition of claim 1, wherein the mixture further comprises less than 1% by mass β-cyclodextrin substituted with eleven hydroxypropyl groups ("DS-11").

9. The composition of claim 1, wherein the mixture further comprises less than 1% by mass β-cyclodextrin substituted with twelve hydroxypropyl groups ("DS-12").

10. The composition of claim 1, wherein the mixture further comprises less than 1% by mass β-cyclodextrin substituted with thirteen hydroxypropyl groups ("DS-13").

11. The composition of claim 1, wherein the mixture further comprises less than 1% by mass β-cyclodextrin substituted with fourteen hydroxypropyl groups ("DS-14").

12. The mixture of claim 1, wherein the composition has an HPLC-CAD mean retention time of about 10.1 minutes.

13. The composition of claim 1, wherein the osmolality of the composition is about 635-695 mOs/kg; and/or wherein the true density of the composition is about 1.096-1.098 g/cm$^3$.

14. The composition of claim 1, wherein the composition further comprises no more than 10 ppb of propylene glycol as measured by HPLC.

15. The composition of claim 1, wherein the composition further comprises no more than 10 ppb propylene glycol as measured by gas chromatography.

16. The composition of claim 1, wherein the composition further comprises no more than 10 ppb propylene glycol as measured by PG/EG-ratio of propylene glycol to ethylene glycol.

17. The composition of claim 1, wherein the composition further comprises no more than 1 ppm propylene oxide.

18. The composition of claim 1, wherein the composition further comprises between 0 and 10 ppm chloride.

19. The composition of claim 1, wherein the composition has a conductivity between 0 and 8 μS/cm.

20. A composition comprising a mixture of isomerically-purified hydroxypropyl β-cyclodextrin molecules comprising: β-cyclodextrin substituted with seven hydroxypropyl groups ("DS-7"); wherein the mixture further comprises less than 1% by mass β-cyclodextrin substituted with four hydroxypropyl groups ("DS-4"), and wherein the composition has an average degree of substitution of 6.02-7.98, and wherein the total amount of impurities are measured to be less than or equal to 0.05% by HPLC.

21. The mixture further of claim 20, wherein the composition comprises less than 1% by mass β-cyclodextrin substituted with three hydroxypropyl groups ("DS-3").

22. The composition of claim 20, wherein the mixture further comprises less than 0.05% by mass unsubstituted beta-cyclodextrin ("DS-0") and less than 0.05% by mass β-cyclodextrin substituted with one hydroxypropyl group ("DS-1").

23. A composition comprising a mixture of isomerically-purified hydroxypropyl β-cyclodextrin molecules comprising: β-cyclodextrin substituted with seven hydroxypropyl groups ("DS-7"); wherein the mixture further comprises less than 1% by mass β-cyclodextrin substituted with five hydroxypropyl groups ("DS-5"), and wherein the mixture has an average degree of substitution of 6.02-7.98 and the mixture is determined by MALDI-TOF mass spectrometry.

24. The composition of claim 23, wherein the percentage of DS-5 is determined by MALDI-TOF mass spectrometry.

25. The composition of claim 23, wherein the composition is suitable for administration to a human patient in need thereof.

26. A composition comprising a mixture of isomerically-purified hydroxypropyl β-cyclodextrin molecules comprising: β-cyclodextrin substituted with seven hydroxypropyl groups ("DS-7"); wherein the mixture further less than 1% by mass β-cyclodextrin substituted with four hydroxypropyl groups ("DS-4"), and wherein the mixture has an average degree of substitution of 6.02-7.98 and the mixture is determined by MALDI-TOF mass spectrometry.

27. The composition of claim 26, wherein the percentage of DS-4 is determined by MALDI-TOF mass spectrometry.

28. The composition of claim 26, wherein the composition is suitable for administration to a human patient in need thereof.

* * * * *

UNITED STATES PATENT AND TRADEMARK OFFICE
CERTIFICATE OF CORRECTION

PATENT NO. : 12,215,174 B2
APPLICATION NO. : 18/633063
DATED : February 4, 2025
INVENTOR(S) : Pfeiffer et al.

Page 1 of 1

It is certified that error appears in the above-identified patent and that said Letters Patent is hereby corrected as shown below:

In the Claims

Column 247, Claim 12, Lines 25-26:
"12. The mixture of claim 1, wherein the composition has an HPLC-CAD mean retention time of about 10.1 minutes." should be --12. The composition of claim 1, wherein the mixture has an HPLC-CAD mean retention time of about 10.1 minutes.--

Column 248, Claim 21, Lines 10-13:
"21. The mixture further of claim 20, wherein the composition comprises less than 1% by mass β-cyclodextrin substituted with three hydroxypropyl groups ("DS-3")." should be --21. The composition of claim 20, wherein the mixture further comprises less than 1% by mass β-cyclodextrin substituted with three hydroxypropyl groups ("DS-3").--

Column 248, Claim 26, Lines 32-39:
"26. A composition comprising a mixture of isomerically-purified hydroxypropyl β-cyclodextrin molecules comprising: β-cyclodextrin substituted with seven hydroxypropyl groups ("DS-7"); wherein the mixture further less than 1% by mass β-cyclodextrin substituted with four hydroxypropyl groups ("DS-4"), and wherein the mixture has an average degree of substitution of 6.02-7.98 and the mixture is determined by MALDI-TOF mass spectrometry." should be --26. A composition comprising a mixture of isomerically-purified hydroxypropyl β-cyclodextrin molecules comprising: β-cyclodextrin substituted with seven hydroxypropyl groups ("DS-7"); wherein the mixture further comprises less than 1% by mass β-cyclodextrin substituted with four hydroxypropyl groups ("DS-4"), and wherein the mixture has an average degree of substitution of 6.02-7.98 and the mixture is determined by MALDI-TOF mass spectrometry.--

Signed and Sealed this
Eighth Day of April, 2025

Coke Morgan Stewart
*Acting Director of the United States Patent and Trademark Office*